US012583839B2

(12) United States Patent
Yu et al.

(10) Patent No.: US 12,583,839 B2
(45) Date of Patent: *Mar. 24, 2026

84

(54) PD-L1 ANTAGONIST COMPOUND

(71) Applicant: ADLAI NORTYE BIOPHARMA CO., LTD., Zhejiang (CN)

(72) Inventors: Zhiyong Yu, Zhejiang (CN); Pan Li, Zhejiang (CN); Beidi Xu, Zhejiang (CN); Yu Zhou, Zhejiang (CN); Wei Pang, Zhejiang (CN); Qiaodong Wen, Zhejiang (CN); Yongqiang Shi, Zhejiang (CN); Zhao Sun, Zhejiang (CN); Meng Lv, Zhejiang (CN)

(73) Assignee: ADLAI NORTYE BIOPHARMA CO., LTD., Zhejiang (CN)

( * ) Notice: Subject to any disclaimer, the term of this patent is extended or adjusted under 35 U.S.C. 154(b) by 864 days.

This patent is subject to a terminal disclaimer.

(21) Appl. No.: 17/780,979

(22) PCT Filed: Dec. 22, 2020

(86) PCT No.: PCT/CN2020/138157

§ 371 (c)(1),
(2) Date: May 28, 2022

(87) PCT Pub. No.: WO2021/129584

PCT Pub. Date: Jul. 1, 2021

(65) Prior Publication Data

US 2023/0054028 A1 Feb. 23, 2023

(30) Foreign Application Priority Data

Dec. 26, 2019 (CN) ......................... 201911368320.1

(51) Int. Cl.

| | |
|---|---|
| ***C07D 403/12*** | (2006.01) |
| ***C07D 401/12*** | (2006.01) |
| ***C07D 401/14*** | (2006.01) |
| ***C07D 403/10*** | (2006.01) |
| ***C07D 403/14*** | (2006.01) |
| ***C07D 405/14*** | (2006.01) |
| *A61K 31/416* | (2006.01) |
| *A61K 31/4439* | (2006.01) |
| *A61K 31/5377* | (2006.01) |
| *A61P 29/00* | (2006.01) |
| *A61P 31/12* | (2006.01) |
| *A61P 35/00* | (2006.01) |
| *A61P 37/00* | (2006.01) |
| *A61P 37/02* | (2006.01) |

(52) U.S. Cl.

CPC ......... *C07D 403/12* (2013.01); *C07D 401/12* (2013.01); *C07D 401/14* (2013.01); *C07D 403/10* (2013.01); *C07D 403/14* (2013.01); *C07D 405/14* (2013.01)

(58) Field of Classification Search

CPC .. C07D 403/12; C07D 401/12; C07D 401/14; C07D 403/10; C07D 403/14; C07D 405/14

See application file for complete search history.

(56) References Cited

U.S. PATENT DOCUMENTS

| | | | | |
|---|---|---|---|---|
| 7,928,140 | B2 * | 4/2011 | Booker | A61P 35/00 548/161 |
| 12,091,398 | B2 * | 9/2024 | Li | C07D 405/14 |
| 2015/0291549 | A1 | 10/2015 | Chupak et al. | |
| 2016/0194307 | A1 | 7/2016 | Chupak et al. | |
| 2019/0185450 | A1 | 6/2019 | Yeung et al. | |
| 2022/0227733 | A1 | 7/2022 | Li et al. | |

FOREIGN PATENT DOCUMENTS

| | | | |
|---|---|---|---|
| CN | 105705489 | A | 6/2016 |
| CN | 106536515 | A | 3/2017 |
| CN | 109665968 | A | 4/2019 |
| CN | 109689640 | A | 4/2019 |
| CN | 112313220 | A | 2/2021 |
| EP | 3929188 | A1 | 12/2021 |

(Continued)

OTHER PUBLICATIONS

Wu X, Gu Z, Chen Y, Chen B, Chen W, Weng L, Liu X. Application of PD-1 Blockade in Cancer Immunotherapy. Comput Struct Biotechnol J. May 23, 2019;17:661-674. doi: 10.1016/j.csbj.2019.03.006. PMID: 31205619; PMCID: PMC6558092. (Year: 2019).*

(Continued)

*Primary Examiner* — Bruck Kifle
*Assistant Examiner* — Kevin S Martin
(74) *Attorney, Agent, or Firm* — Yue (Robert) Xu; Apex Attorneys at Law, LLP

(57) ABSTRACT

Provided are a compound of Formula (I) and a pharmaceutical composition thereof, as well as a method for using the compounds of Formula (I) to prevent and/or treat immune-related disorders.

Formula (I)

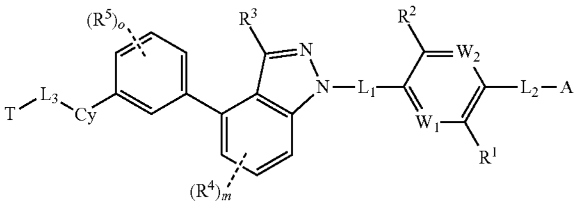

19 Claims, No Drawings

(56) References Cited

FOREIGN PATENT DOCUMENTS

| | | | |
|---|---|---|---|
| WO | 2018195321 | A1 | 10/2018 |
| WO | 2020169058 | A1 | 8/2020 |

OTHER PUBLICATIONS

International Search Report for PCT/CN2020/138157 mailed Mar. 22, 2021, ISA/CN.
The 1st Office Action dated May 31, 2023 for the Chinese Patent Application No. CN202080079596.2.
The 1st Office Action dated Jun. 1, 2023 for the Japanese Patent Application No. JP2022-522850.

* cited by examiner

PD-L1 ANTAGONIST COMPOUND

CROSS REFERENCE OF RELATED APPLICATION

This application is a U.S. National Phase application based upon PCT Application No. PCT/CN2020/138157, which claims the priority to Chinese Patent Application No. 201911368320.1, titled "PD-L1 ANTAGONIST COMPOUND", filed on Dec. 26, 2019 with the China National Intellectual Property Administration, which is incorporated herein by reference in entirety.

FIELD

The present invention relates to a PD-L1 antagonist compound and a method of using the same for treating/preventing immune-related conditions.

BACKGROUND

Because of its excellent efficacy and innovation, cancer immunotherapy was named the most important scientific breakthrough of the year by Science magazine in 2013. Cancer immunotherapy is expected to become an innovation in the field of tumor therapy after surgery, chemotherapy, radiotherapy and targeted therapy. According to cancer immunotherapy, the immunogenicity of tumor cells and the sensitivity to effector cell killing are improved, and the body's anti-tumor immune response is stimulated and enhanced through the application of immunological principles and methods; and tumors are killed and tumor growth is inhibited by using immune cells and effector molecules to infuse the host in vivo, and cooperating with the body's immune system. Cancer immunotherapy has attracted much attention recently and is the focus of tumor therapy. In recent years, the good news of cancer immunotherapy has continued. At present, it has shown strong anti-tumor activity in the treatment of some tumor types such as melanoma and non-small cell lung cancer, and cancer immunotherapy drugs have been approved by the U.S. FDA (Food and Drug Administration, FDA) for clinical use.

PD-1 (programmed death 1) is a member of the CD28 superfamily. Immunomodulation targeting PD-1 is of great significance in anti-tumor, anti-infection, anti-autoimmune diseases and survival of organ transplant. Its ligand PD-L1 can also serve as a target and the corresponding antibody can also play the same role. PD-L1 (programmed cell death-Ligand 1) is a first type transmembrane protein of 40 kDa in size. Under normal circumstances, the immune system will respond to foreign antigens that accumulate in the lymph nodes or spleen, and promote the proliferation of antigen-specific T cells. The binding of PD-1 to PD-L1 can transmit inhibitory signals and reduce the proliferation of T cells.

One way for tumor cells to evade destruction by T cells is to produce PD-L1 on the surface of T cells. When PD-1 on the surface of immune T cells recognizes PD-L1, inhibitory signals can be transmitted, and T cells is not able to detect tumor cells and send out attack signals to the tumor cells. PD-1 is a novel immunotherapy that evades the immune system the depletion of tumor cells. The mechanism of PD-1 immunotherapy is to design specific protein antibodies against PD-1 or PD-L1, prevent the recognition process of PD-1 and PD-L1, and partially restore T cell function, so that T cells can kill tumor cells.

PD-1 is expressed in activated T cells, B cells and myeloid cells with two ligands, PD-L1 and PD-L2. PD-L1/L2 is expressed in antigen presenting cells, and PD-L1 is also expressed in various tissues. The binding of PD-1 to PD-L1 mediates co-inhibitory signaling of T cell activation, regulates T cell activation and proliferation, and plays a negative regulatory role similar to CTLA-4. Chinese scientist Chen Lieping's laboratory first discovered that PD-L1 is highly expressed in tumor tissues and regulates the function of tumor infiltrating CD8 T cells. Therefore, the immunoregulation targeting PD-1/PD-L1 is of great significance against tumors.

A number of therapeutic monoclonal antibodies (mAbs) targeting the PD-1/PD-L1 interaction have been approved by the U.S. FDA for marketing. In addition to the development of related monoclonal antibodies, the search for oral small molecule compounds that are convenient for cancer patients to target inhibition of immune checkpoints is also a frontier domain of cancer immunotherapy. Small molecule compounds can pass through the cell membrane and act on intracellular targets, so they have a wide range of applications. Secondly, small molecules often have good bioavailability and compliance after chemical modification, effectively avoiding the decomposition and inactivation of enzymes in the digestive intestine. Finally, the research on small molecules is also quite mature in many aspects such as production process, dosage form design and administration mode.

Most monoclonal antibodies (mAbs) are administered by high-dose intravenous injection. Small molecule drugs, which are more suitable for oral administration, can reduce serious immune-related adverse events. Compared with monoclonal antibodies, small molecule drug inhibitors have many other benefits, such as more economical and stable manufacturing costs, and better permeability to organs and tumors. Given the numerous advantages of small molecule pharmacokinetic properties, it will exhibit dose flexibility in monotherapy or other combination schemes. The small molecule compounds of the present invention may provide an attractive treatment option for patients and physicians.

SUMMARY

The present invention provides a compound of Formula (I) or a pharmaceutically acceptable salt thereof, a prodrug, an isotopic derivative, an isomer, a solvate, or a metabolite thereof.

Formula (I)

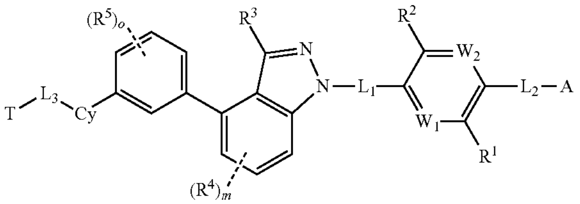

wherein $L_1$ is selected from —$CR^AR^B$— and —C(O)—;

$L_2$, $L_3$ is selected from —$(CR^CR^D)_p$, —$(CR^CR^D)_p$—$NR^a$—$(CR^CR^D)_q$—, —$(CR^CR^D)_p$—O—$(CR^CR^D)_q$ and —C(O)—;

$W_1$, $W_2$ each independently represent $CR^L$ or N;

$R^1$ each independently represent hydrogen, halogen, nitro, cyano or —$NR^aR^b$ or $C_1$-$C_6$ alkyl, $C_3$-$C_6$ cycloalkyl, —O($C_1$-$C_6$ alkyl), —O($C_0$-$C_6$ alkylene)($C_5$-$C_{10}$ aryl), —O($C_0$-$C_6$ alkylene)(5-10 membered heteroaryl), —$O(C_0$-$C_6$ alkylene)($C_3$-$C_6$ cycloalkyl) or —$O(C_0$-$C_6$ alkylene)(3-6 membered heterocycloalkyl) substituted with 0, 1, 2 or 3 substituents; wherein the substituents are selected from —$OR^a$, cyano, oxo, halogen, $C_1$-$C_6$ alkyl, —($C_1$-$C_6$ alkylene)$OR^a$, cyano $C_1$-$C_6$ alkyl, $C_1$-$C_6$ haloalkyl, $C_3$-$C_8$ cycloalkyl, —$C(O)R^a$, —($C_1$-$C_6$ alkylene)$C(O)R^a$, —$C(O)OR^a$, —($C_1$-$C_6$ alkyl)C(O)$OR^a$, —$NR^aR^b$, —($C_1$-$C_6$ alkylene)$NR^aR^b$, —C(O)$NR^aR^b$, —$SO_2R^a$, —C(O)$NR^aSO_2R^b$ and —$NR^aC(O)R^b$;

$R^2$, $R^3$, $R^4$, $R^5$ each independently represent hydrogen, halogen, nitro, cyano, —$NR^aR^b$, —$SO_2R^a$, —$S(O)R^a$, —$P(O)R^aR^b$, $C_1$-$C_6$ alkyl, —O($C_1$-$C_6$ alkyl), —O($C_3$-$C_6$ cycloalkyl), halo($C_1$-$C_6$ alkyl) or $C_3$-$C_6$ cycloalkyl;

Cy represents benzene ring or six-membered heteroaryl substituted by 0, 1, 2 or 3 $R^6$ wherein the six-membered heteroaryl may optionally contain 1 or 2 nitrogen atoms; wherein the $R^6$ represents hydrogen, halogen, nitro, cyano, —$NR^aR^b$, —$SO_2R^a$, —$S(O)R^a$ or —P(O)$R^aR^b$ or $C_1$-$C_6$ alkyl, $C_3$-$C_6$ cycloalkyl, —O($C_1$-$C_6$ alkyl), —O($C_0$-$C_6$ alkylene)($C_5$-$C_{10}$ aryl), —O($C_0$-$C_6$ alkylene)(5-10 membered heteroaryl), —O($C_0$-$C_6$ alkylene)($C_3$-$C_6$ cycloalkyl) or —O($C_0$-$C_6$ alkylene)(3-6 membered heterocycloalkyl) substituted with 0, 1, 2 or 3 substituents; wherein the substituents are selected from —$OR^a$, cyano, oxo, halogen, $C_1$-$C_6$ alkyl, —($C_1$-$C_6$ alkylene)$OR^a$, cyano $C_1$-$C_6$ alkyl, $C_1$-$C_6$ haloalkyl, $C_3$-$C_8$ cycloalkyl, —$C(O)R^a$, —($C_1$-$C_6$ alkylene)$C(O)R^a$, —$C(O)OR^a$, —($C_1$-$C_6$ alkylene) C(O)$OR^a$, —$NR^aR^b$, —($C_1$-$C_6$ alkylene)$NR^aR^b$, —C(O)$NR^aR^b$, —$SO_2R^a$, —C(O)$NR^aSO_2R^b$ or —$NR^aC(O)R^b$;

wherein $R^L$ represents hydrogen, $C_1$-$C_6$ alkyl, —O($C_1$-$C_6$ alkyl), —O($C_3$-$C_6$ cycloalkyl), halogen, nitro, cyano, —$NR^aR^b$, halo($C_1$-$C_6$ alkyl) or $C_3$-$C_6$ cycloalkyl;

T, A each independently represent —($C_1$-$C_6$ alkyl), —($C_0$-$C_6$ alkylene)-($C_3$-$C_{12}$ cycloalkyl), —($C_0$-$C_6$ alkylene)-(3-12 membered heterocycloalkyl), —($C_0$-$C_6$ alkylene)-($C_6$-$C_{10}$ aryl) or —($C_0$-$C_6$ alkylene)-(5-10 membered heteroaryl) substituted with 0, 1, 2 or 3 substituents, wherein the substituents are selected from: cyano, oxo, halogen, $C_1$-$C_6$ alkyl, —($C_0$-$C_6$ alkylene) $OR^a$, cyano $C_1$-$C_6$ alkyl, halo($C_1$-$C_6$ alkyl), $C_3$-$C_8$ cycloalkyl, —($C_0$-$C_6$ alkylene)$C(O)R^a$, —($C_0$-$C_6$ alkylene)$C(O)OR^a$, —($C_0$-$C_6$ alkenyl)$C(O)OR^a$, —($C_0$-$C_6$ alkylene)$NR^aR^b$, —C(O)$NR^aR^b$, —$NR^aSO_2R^b$, —C(O)$NR^aSO_2R^b$ and —$NR^aC(O)R^b$;

wherein $R^A$, $R^B$ each independently represent hydrogen, $C_1$-$C_6$ alkyl, —($C_0$-$C_3$ alkylene)($C_3$-$C_{12}$ cycloalkyl), —($C_0$-$C_3$ alkylene)(3-12 membered heterocycloalkyl), halo($C_1$-$C_6$ alkyl) or halogen, or $R^A$ and $R^B$ together with their co-attached carbon atoms form a 3-6 membered ring;

$R^C$, $R^D$ each independently represent: hydrogen, $C_1$-$C_6$ alkyl, —($C_0$-$C_3$ alkylene)($C_3$-$C_{12}$ cycloalkyl), —($C_0$-$C_3$ alkylene)(3-12 membered heterocycloalkyl), halo ($C_1$-$C_6$ alkyl) or halogen, or $R^C$ and $R^D$ together with their co-attached carbon atom form a 3-6 membered ring;

$R^a$, $R^b$ each independently represent hydrogen, $C_1$-$C_6$ alkyl, halo($C_1$-$C_6$ alkyl), —($C_0$-$C_6$ alkylene)OH, —($C_0$-$C_3$ alkylene)($C_3$-$C_{12}$ cycloalkyl), —($C_0$-$C_3$ alkylene)(3-12 membered heterocycloalkyl), —($C_0$-$C_3$ alkylene)($C_6$-$C_{10}$ aryl), —($C_0$-$C_3$ alkylene)(5-10 membered heteroaryl) or halo($C_1$-$C_6$ alkyl), or $R^a$ and $R^b$ together with their co-attached atom form a 3-6 membered ring;

wherein m, o each independently represent 0, 1 or 2;

wherein p, q each independently represent 0, 1, 2 or 3.

Preferably, the formula (I) compound having the following structure of Formula (II):

Formula (II)

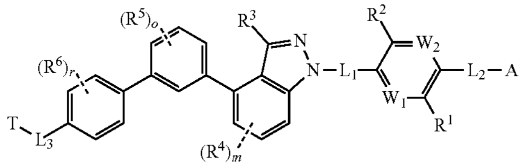

wherein $R^1$, $R^2$, $R^3$, $R^4$, $R^5$, $R^6$, $L_1$, $L_2$, $L_3$, T, A, $W_1$, $W_2$, m, o as defined by formula (I);

wherein r represents 0, 1, 2 or 3.

Preferably, the formula (I) compound has the following formula (III) structure:

Formula (III)

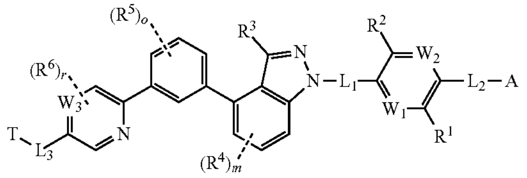

wherein $R^1$, $R^2$, $R^3$, $R^4$, $R^5$, $R^6$, $L_1$, $L_2$, $L_3$, T, A, $W_1$, $W_2$, m, o as defined by formula (I);

wherein $W_3$ represents $CR^M$ or N;

wherein $R^M$ represents hydrogen, $C_1$-$C_6$ alkyl, —O($C_1$-$C_6$ alkyl), —O($C_3$-$C_6$ cycloalkyl), halogen, nitro, cyano, —$NR^aR^b$, halo($C_1$-$C_6$ alkyl) or $C_3$-$C_6$ cycloalkyl;

wherein r represents 0, 1 or 2.

Preferably, the formula (I) compound has the following formula (IV) structure:

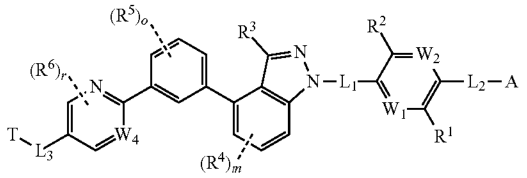

wherein $R^1$, $R^2$, $R^3$, $R^4$, $R^5$, $R^6$, $L_1$, $L_2$, $L_3$, T, A, $W_1$, $W_2$, m, o as defined by formula (I);

wherein $W_4$ represents $CR^N$ or N;

wherein $R^N$ represents hydrogen, $C_1$-$C_6$ alkyl, —O($C_1$-$C_6$ alkyl), —O($C_3$-$C_6$ cycloalkyl), halogen, nitro, cyano, —$NR^aR^b$, halo($C_1$-$C_6$ alkyl) or $C_3$-$C_6$ cycloalkyl;

wherein r represents 0, 1 or 2.

In the compounds of the present invention, $L_1$ is preferably selected from —$CR^AR^B$, wherein $R^A$, $R^B$ are each independently selected from hydrogen, halogen, $C_1$-$C_6$ alkyl and halo($C_1$-$C_6$ alkyl), preferably are hydrogen.

In the compounds of the present invention, $L_2$ and $L_3$ are preferably independently selected from —$CR^CR^D$— and —$CR^CR^D$—$NR^a$— $(CR^CR^D)_q$—, wherein q is selected from 0, 1 or 2, wherein $R^C$, $R^D$ are each independently selected from hydrogen, halogen, $C_1$-$C_6$ alkyl and halo($C_1$-$C_6$ alkyl), preferably are hydrogen; $R^a$ is each independently selected from hydrogen, $C_1$-$C_6$ alkyl, halo($C_1$-$C_6$ alkyl) and —($C_0$-$C_3$ alkylene)$C_3$-$C_{12}$ cycloalkyl.

In the compounds of the present invention, $W_1$, $W_2$ each preferably independently represents CH or N.

In the compounds of the present invention, $W_3$ preferably represents CH or N.

In the compounds of the present invention, $W_4$ preferably represents CH or N.

In the compounds of the present invention, T, A each preferably independently represents —($C_1$-$C_6$ alkyl), —($C_0$-$C_6$ alkylene)-($C_3$-$C_{12}$ cycloalkyl) or —($C_0$-$C_6$ alkylene)-(3-12 membered heterocycloalkyl) substituted with 0, 1, 2 or 3 substituents, wherein the substituents are selected from cyano, oxo, halogen, $C_1$-$C_6$ alkyl, —($C_0$-$C_6$ alkylene)$OR^a$, cyano $C_1$-$C_6$ alkyl, halo($C_1$-$C_6$ alkyl), $C_3$-$C_8$ cycloalkyl, —($C_0$-$C_6$ alkylene)C(O)$R^a$, —($C_0$-$C_6$ alkylene)C(O)O$R^a$, —($C_0$-$C_6$ alkenyl)C(O)O$R^a$, —($C_0$-$C_6$ alkylene)N$R^a$$R^b$, —C(O)N$R^a$$R^b$, —N$R^a$$SO_2$$R^b$, —C(O)N$R^a$$SO_2$$R^b$ and —N$R^a$C(O)$R^b$, wherein $R^a$ and $R^b$ each independently represent hydrogen, $C_1$-$C_6$ alkyl or halo($C_1$-$C_6$ alkyl).

In the compounds of the present invention, T, A each preferably independently represents $C_1$-$C_6$ alkyl, $C_3$-$C_{12}$ cycloalkyl or 3-12 membered heterocycloalkyl substituted with 0, 1 or 2 substituents, wherein the substituents are selected from cyano, oxo, —O$R^a$, —($C_0$-$C_6$ alkylene)C(O)O$R^a$, —($C_0$-$C_6$ alkenyl)C(O)O$R^a$, —N$R^a$C(O)$R^b$, —N$R^a$$SO_2$$R^b$ and —C(O)N$R^a$$SO_2$$R^b$, wherein $R^a$ and $R^b$ each independently represent hydrogen, $C_1$-$C_6$ alkyl or halo ($C_1$-$C_6$ alkyl).

In the compounds of the present invention, T, A each preferably independently represents the following groups

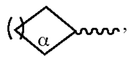, 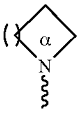

optionally substituted with 0, 1 or 2 substituents, wherein the substituents are selected from $C_1$-$C_6$ alkyl, —O$R^a$, —($C_0$-$C_6$ alkylene)C(O)O$R^a$ and —($C_0$-$C_6$ alkenyl)C(O)O$R^a$, wherein $R^a$ represents hydrogen or $C_1$-$C_6$ alkyl, preferably are hydrogen, wherein α represents 1, 2 or 3.

In the compounds of the present invention, T, A each preferably independently represents the following groups:

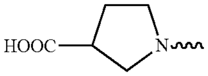
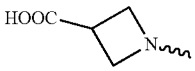
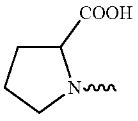
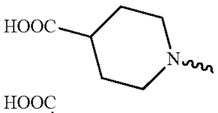
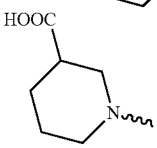
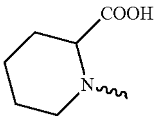
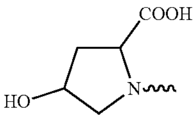
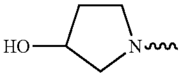

-continued

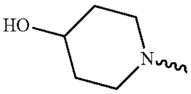
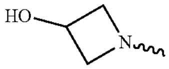
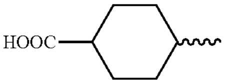
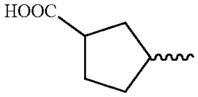
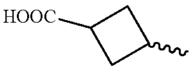
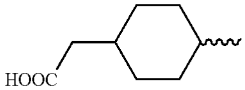
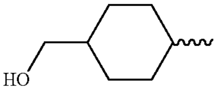
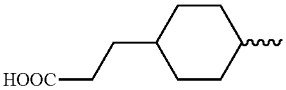
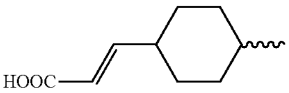
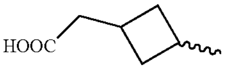
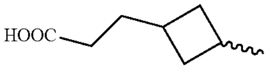
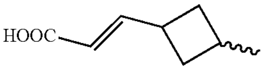
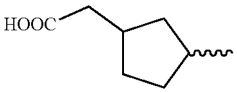
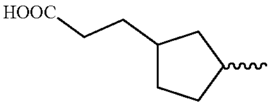
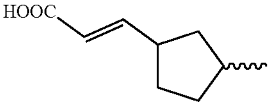.

In the compounds of the present invention, T, A each preferably independently represents the following groups

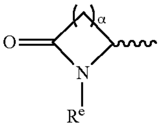

optionally substituted with 0, 1 or 2 substituents, wherein the substituents are selected from $C_1$-$C_6$ alkyl, —O$R^a$ and halogen, wherein $R^e$, $R^a$ each independently represent hydrogen or $C_1$-$C_6$ alkyl; wherein α represents 1, 2, 3 or 4.

In the compounds of the present invention, T, A each preferably independently represents

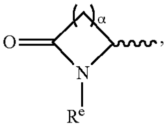, wherein $R^e$ represents hydrogen or $C_1$-$C_6$ alkyl; wherein α represents 1, 2, 3 or 4.

In the compounds of the present invention, T, A each preferably independently represents:

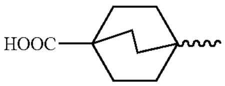
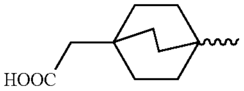
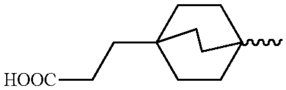
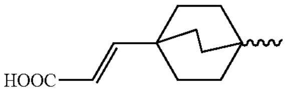
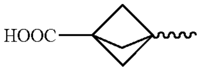
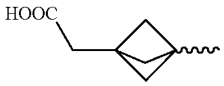
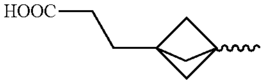
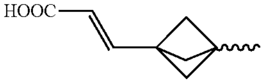
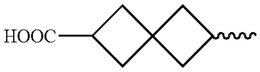
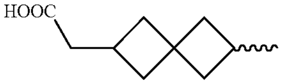
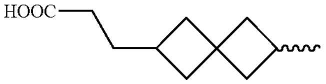
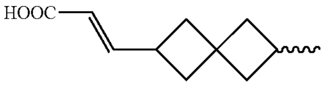
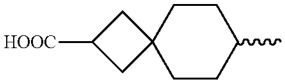
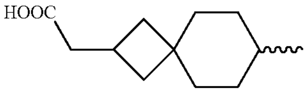
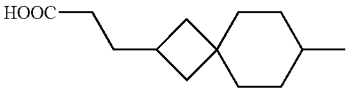
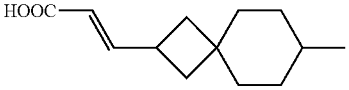
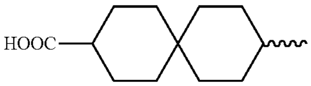
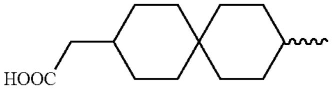
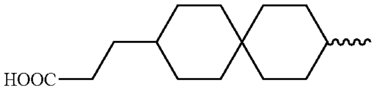
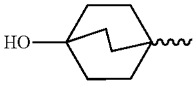

-continued

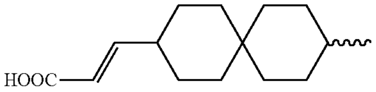
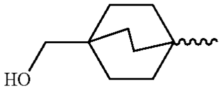
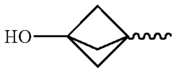
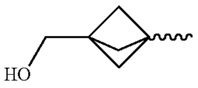
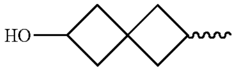
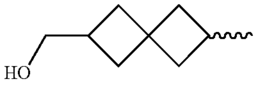
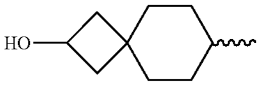
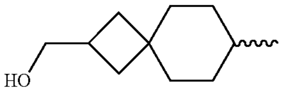
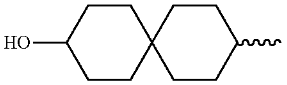
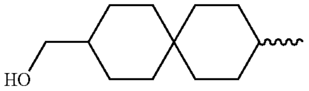

In the compounds of the present invention, $R^1$ preferably represents —O($C_1$-$C_6$ alkyl), —O($C_0$-$C_6$ alkylene)($C_5$-$C_{10}$ aryl), —O($C_0$-$C_6$ alkylene)(5-10 membered heteroaryl), —O($C_0$-$C_6$ alkylene)($C_3$-$C_6$ cycloalkyl) or —O($C_0$-$C_6$ alkylene)(3-6 membered heterocycloalkyl) substituted with 0, 1, 2 or 3 substituents; wherein the substituents are selected from: cyano, oxo, halogen, cyano $C_1$-$C_6$ alkyl and $C_1$-$C_6$ haloalkyl.

In the compounds of the present invention, $R^2$ preferably represents hydrogen, halogen, nitro, cyano, —$SO_2R^a$, $C_1$-$C_6$ alkyl, halo($C_1$-$C_6$ alkyl) or $C_3$-$C_6$ cycloalkyl; wherein $R^a$ represents hydrogen, $C_1$-$C_6$ alkyl or halo($C_1$-$C_6$ alkyl).

In the compounds of the present invention, $R^3$, $R^4$ each preferably independently represents hydrogen, halogen, nitro or cyano.

In the compounds of the present invention, $R^5$ preferably represents hydrogen, halogen, nitro, cyano, $C_1$-$C_6$ alkyl, halo($C_1$-$C_6$ alkyl) or $C_3$-$C_6$ cycloalkyl.

In the compounds of the present invention, $R^6$ preferably represents hydrogen, halogen, nitro, cyano, —$SO_2R^a$, $C_1$-$C_6$ alkyl, halo($C_1$-$C_6$ alkyl) or $C_3$-$C_6$ cycloalkyl or —O($C_1$-$C_6$ alkyl), —O($C_0$-$C_6$ alkylene)($C_5$-$C_{10}$ aryl), —O($C_0$-$C_6$ alkylene)(5-10 membered heteroaryl), —O($C_0$-$C_6$ alkylene) ($C_3$-$C_6$ cycloalkyl) or —O($C_0$-$C_6$ alkylene)(3-6 membered heterocycloalkyl) substituted with 0, 1, 2 or 3 substituents; wherein the substituents are selected from: cyano, oxo, halogen, cyano $C_1$-$C_6$ alkyl and $C_1$-$C_6$ haloalkyl.

In the compounds of the present invention, $R^L$ preferably represents hydrogen or halogen.

In the compounds of the present invention, $R^M$, $R^N$ each preferably independently represents hydrogen.

DETAILED DESCRIPTION
Specifically, the present invention provides compounds with the following structures:
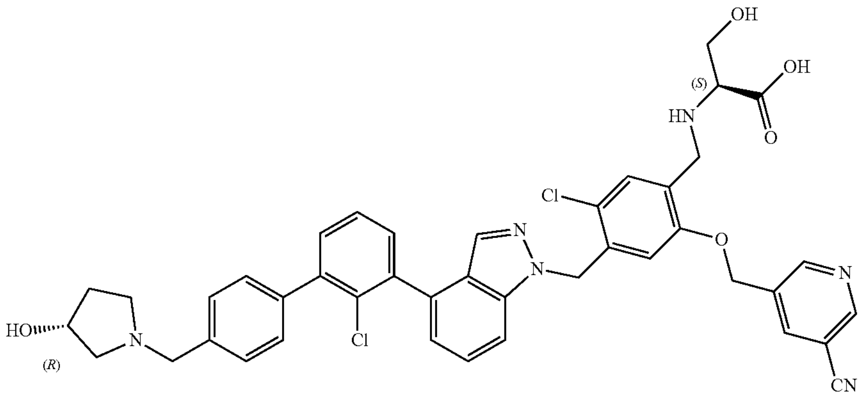
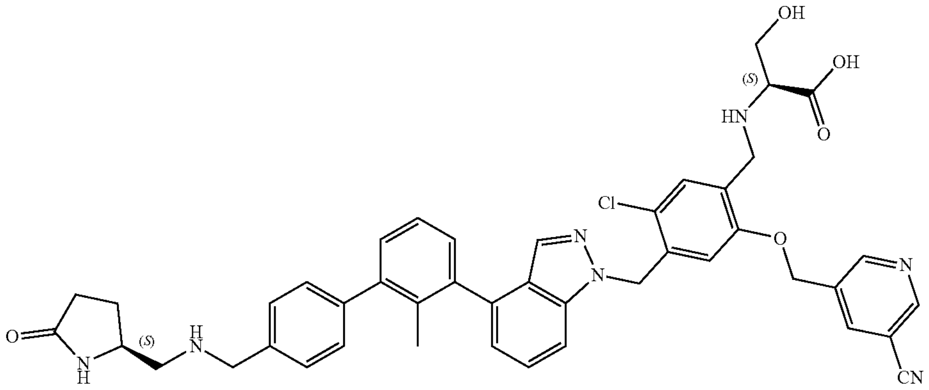
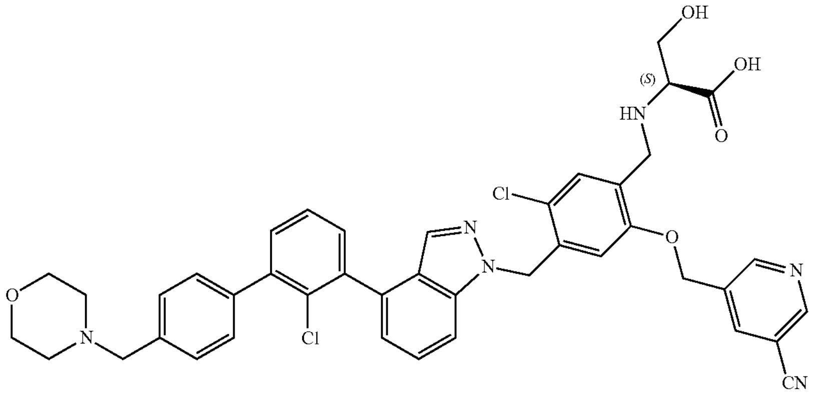
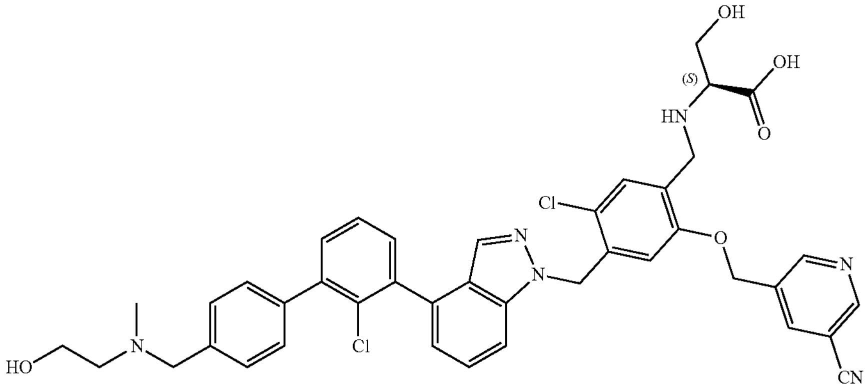

-continued
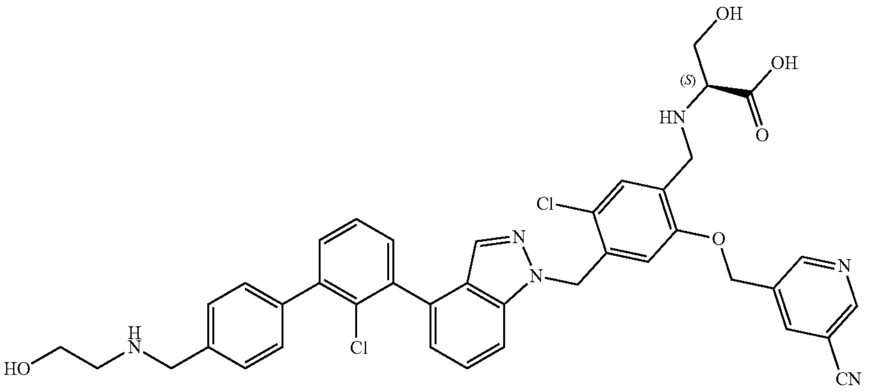
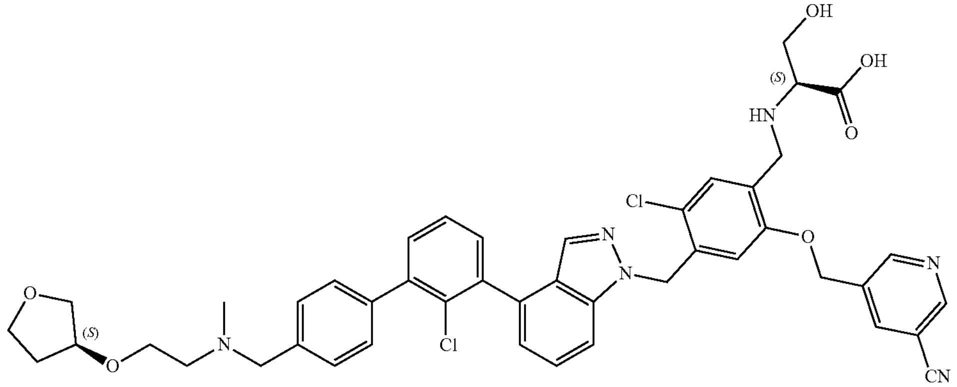
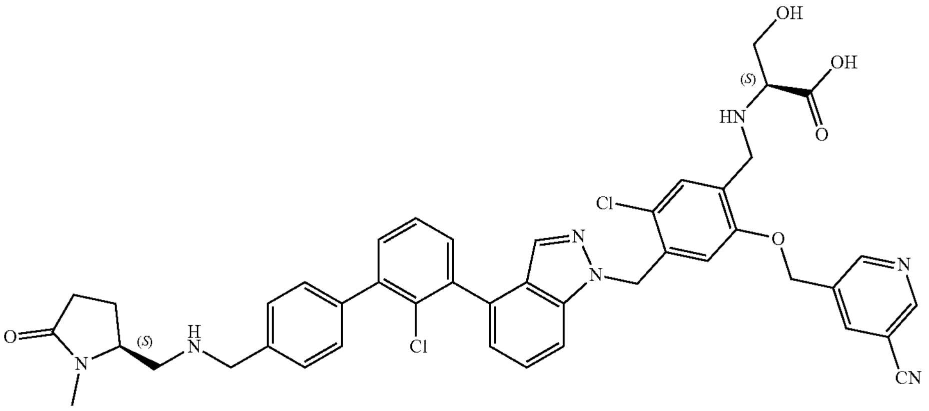
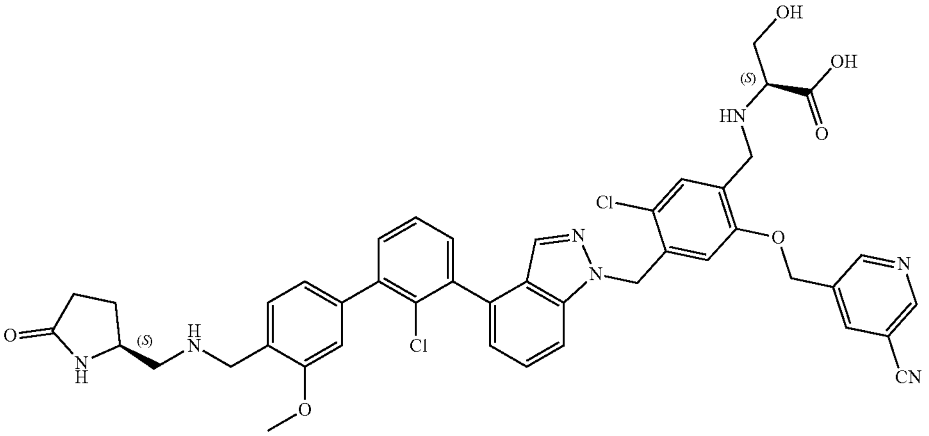

-continued
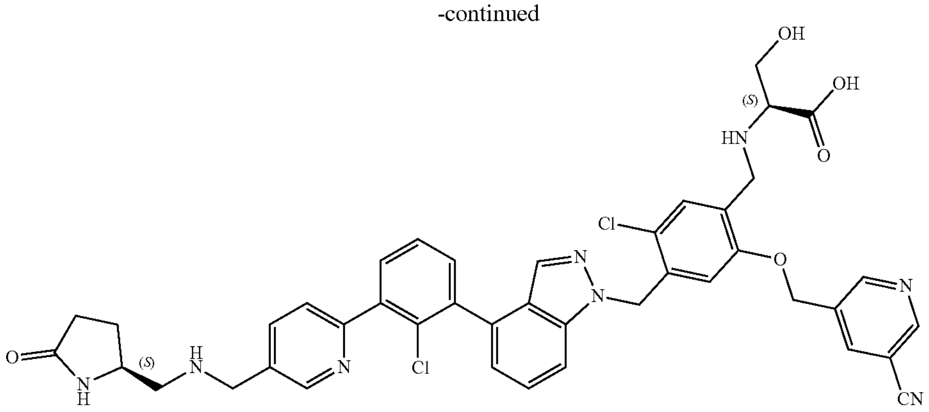
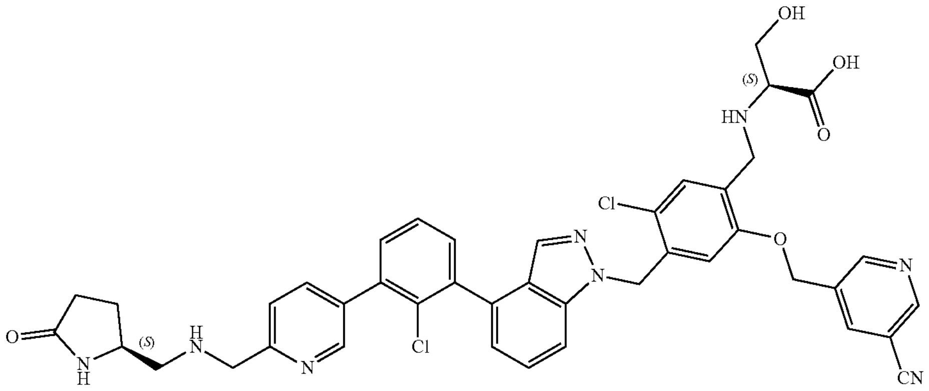
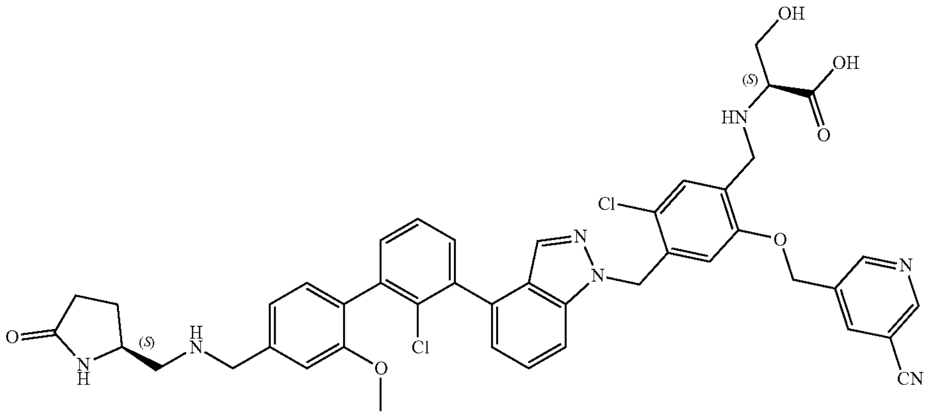
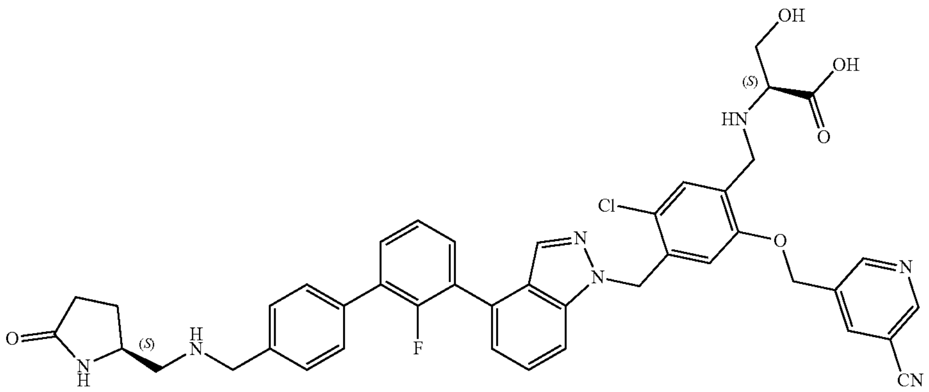

-continued
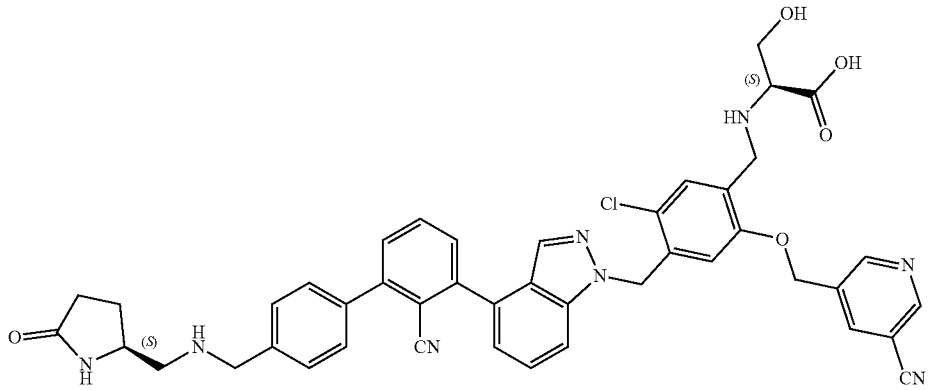
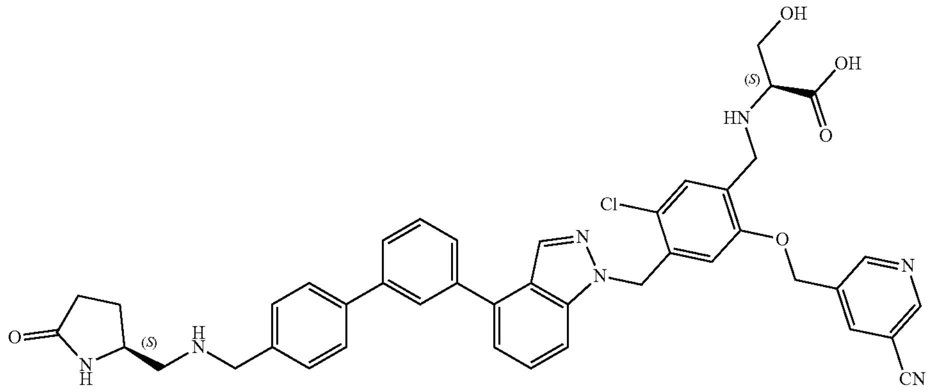
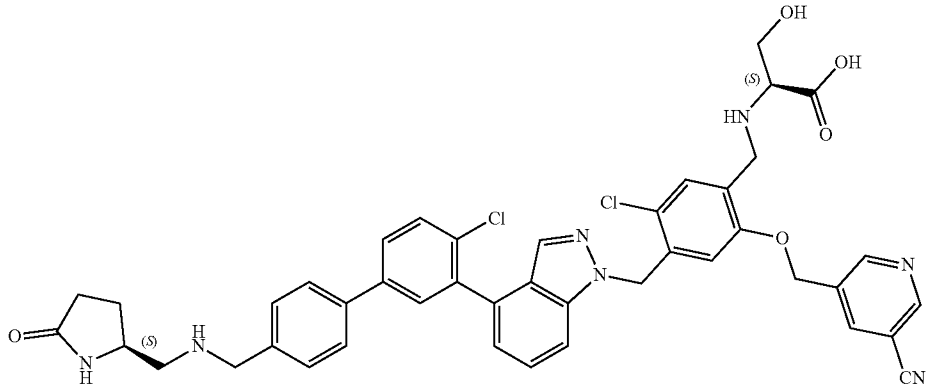
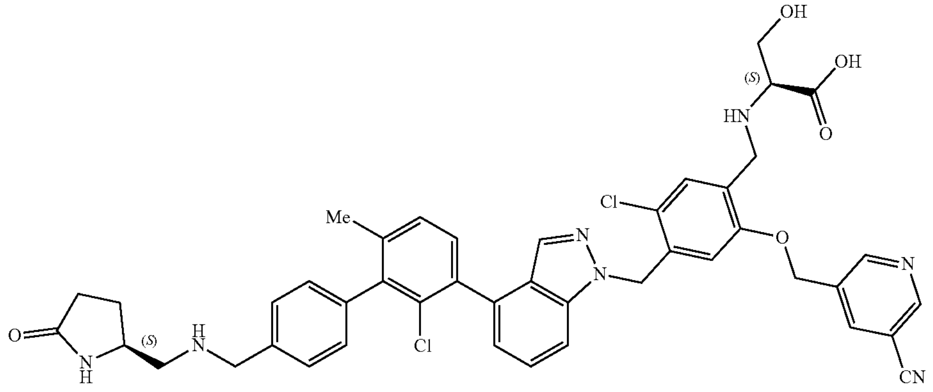

-continued
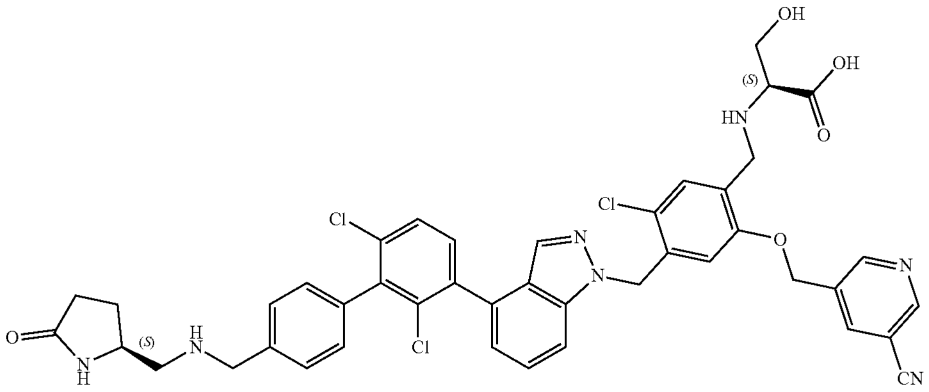
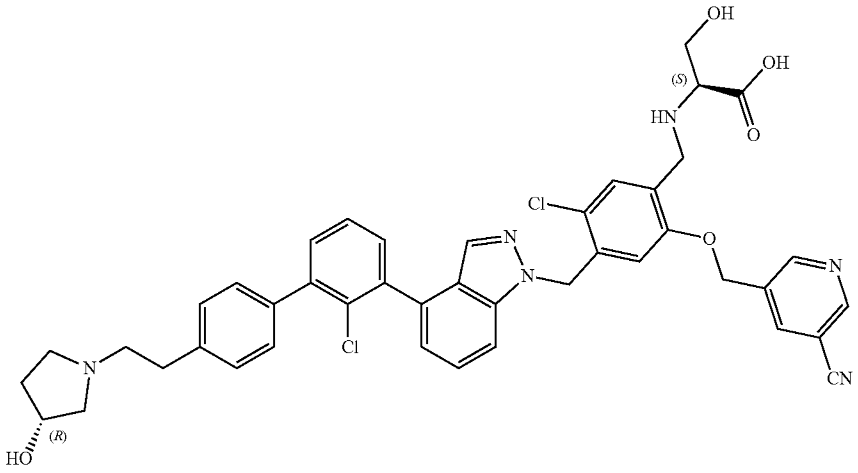
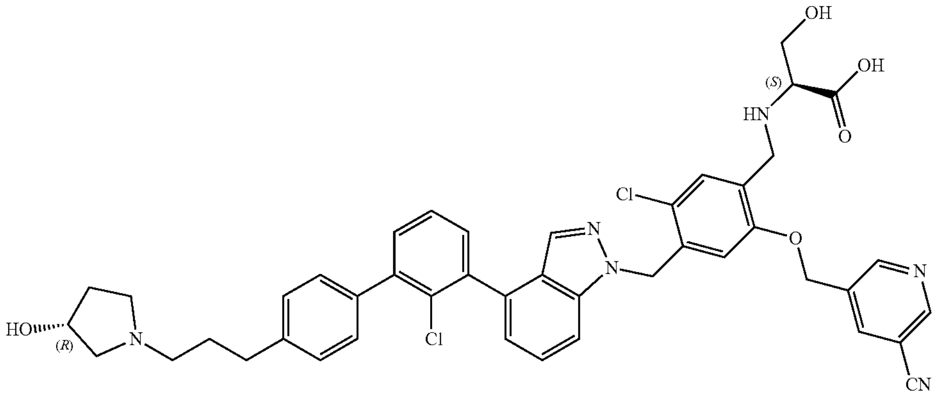
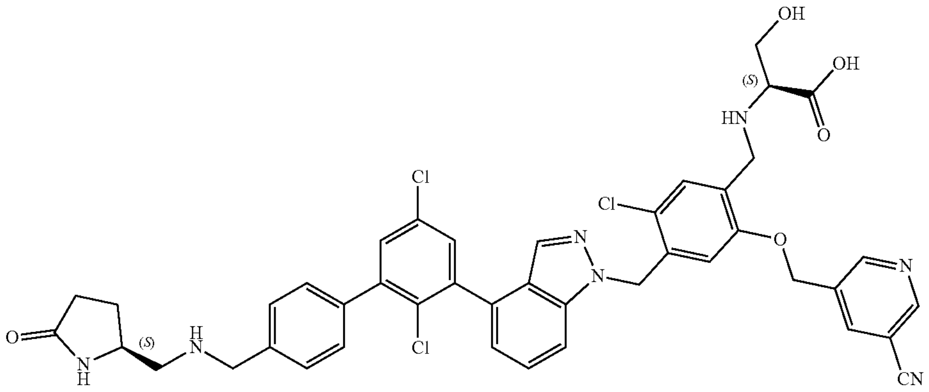

-continued
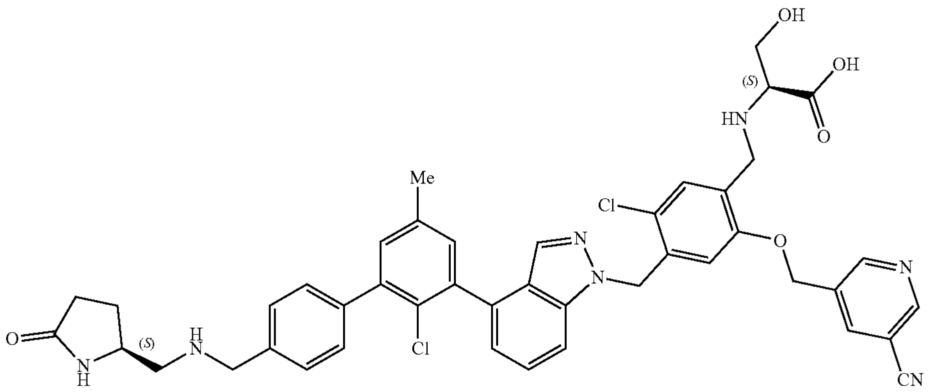
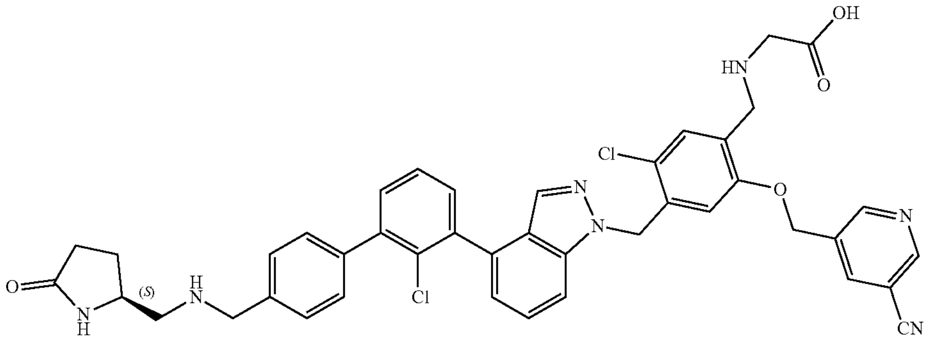
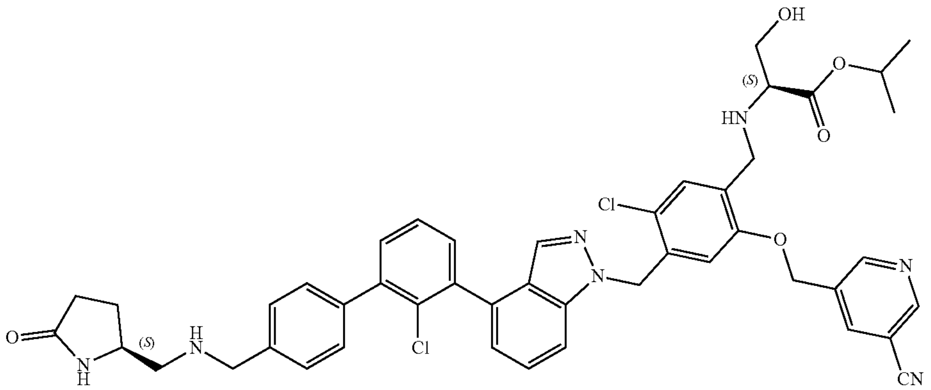
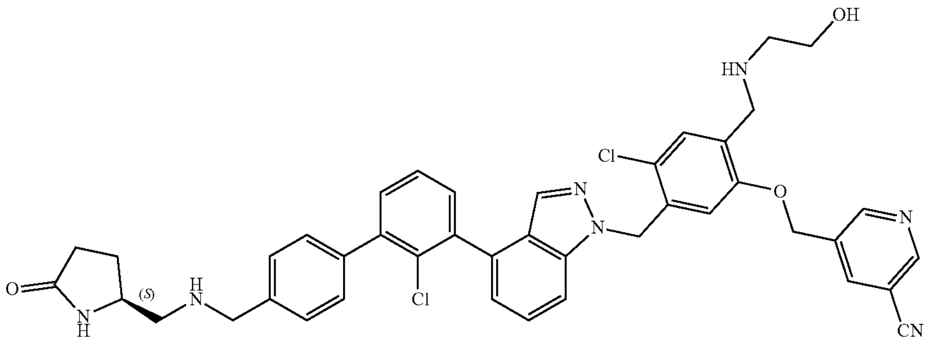

-continued
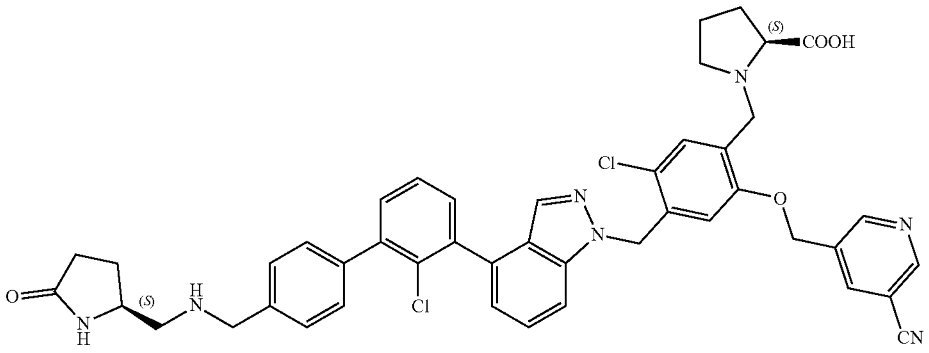
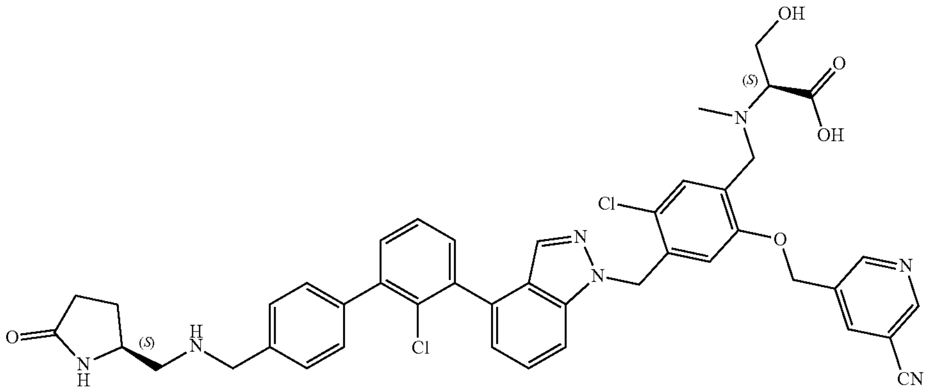
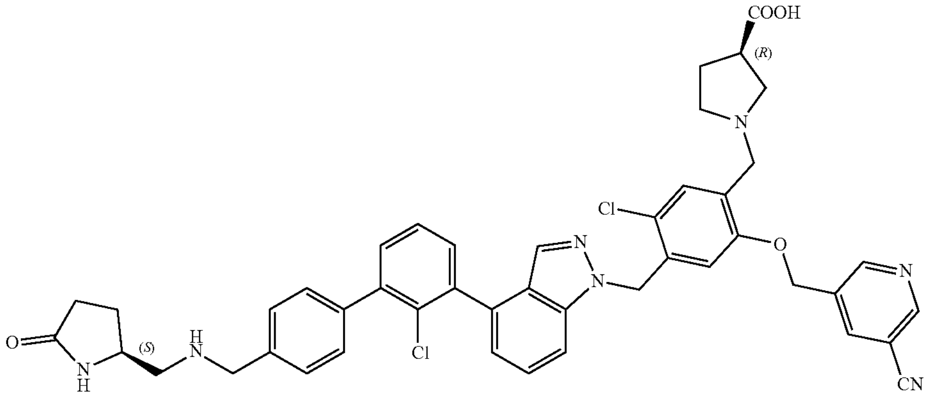
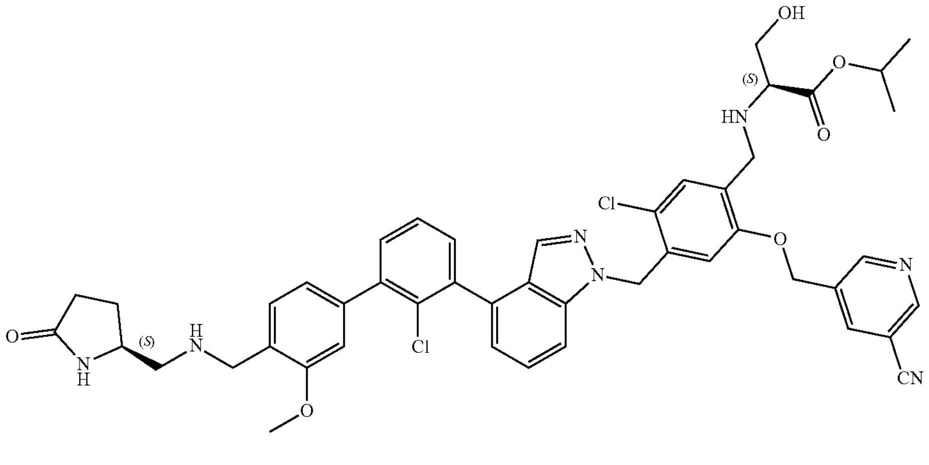

-continued
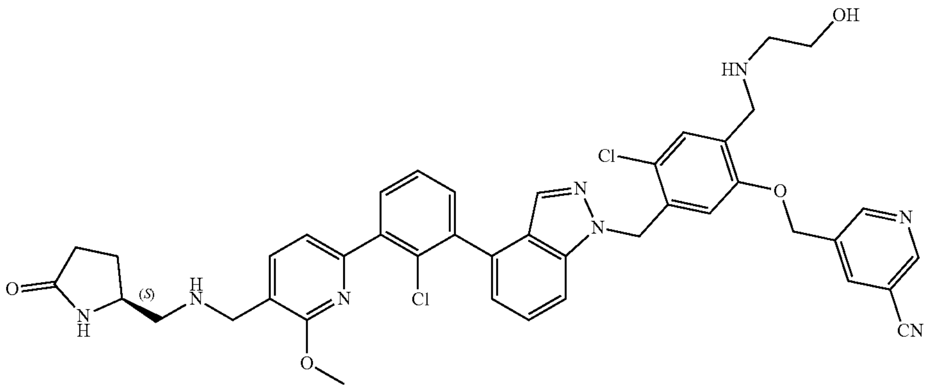
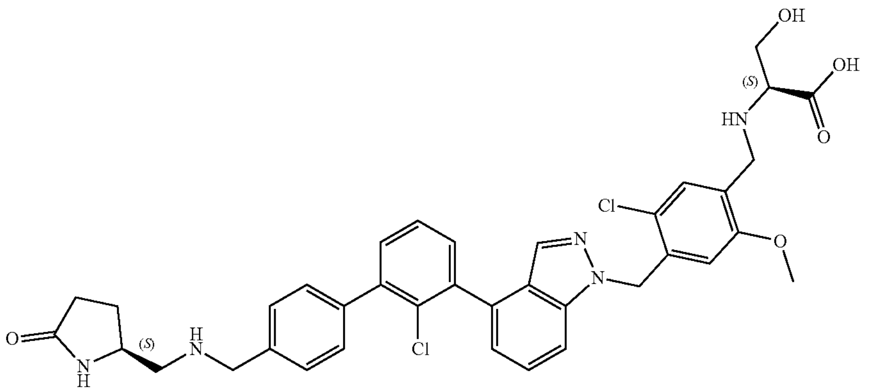
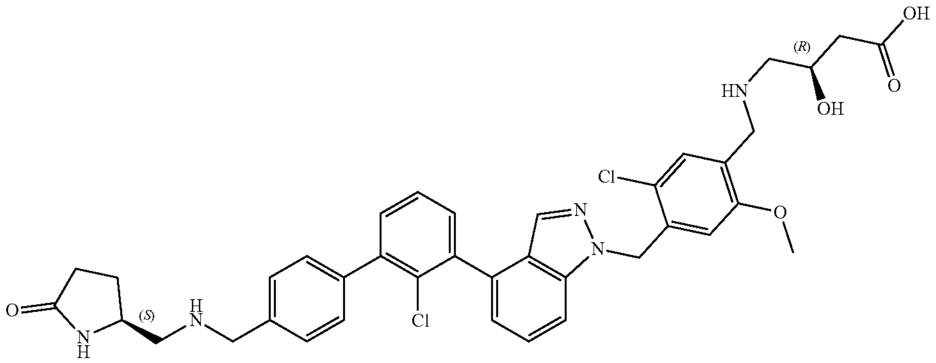
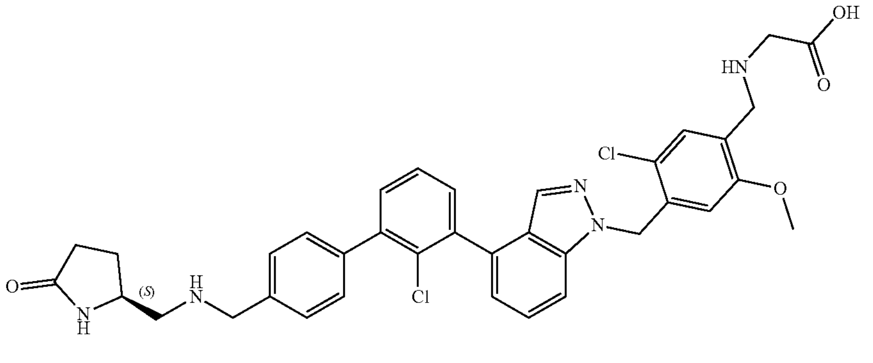

-continued
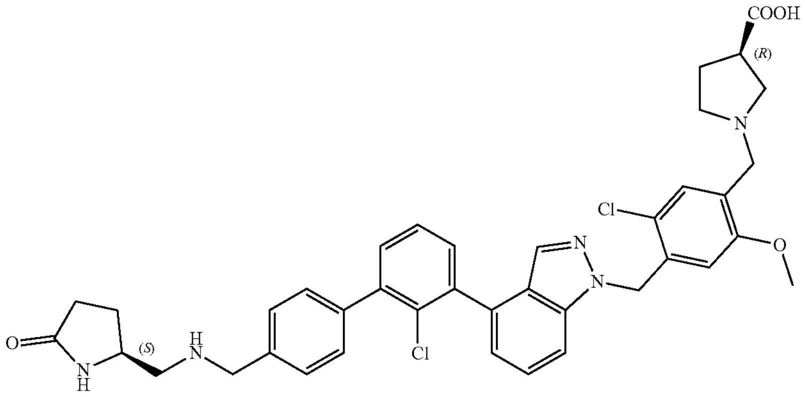
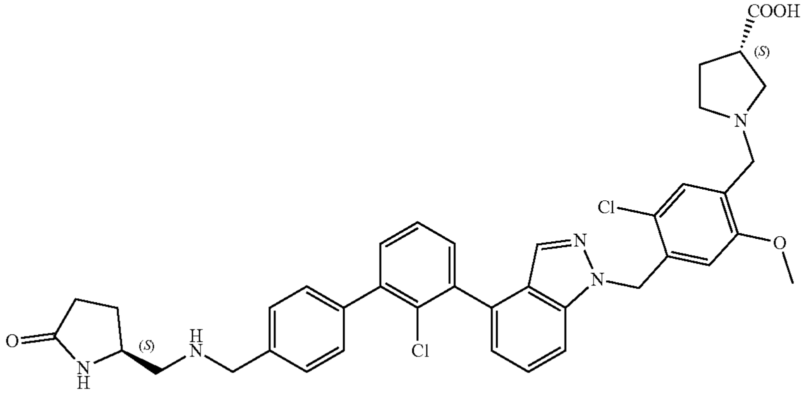
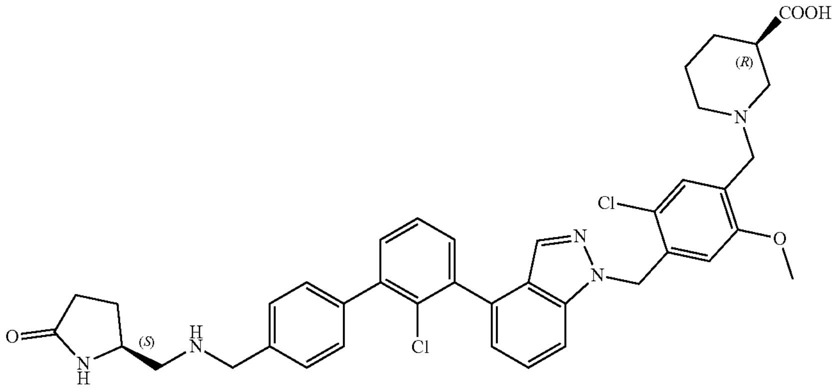
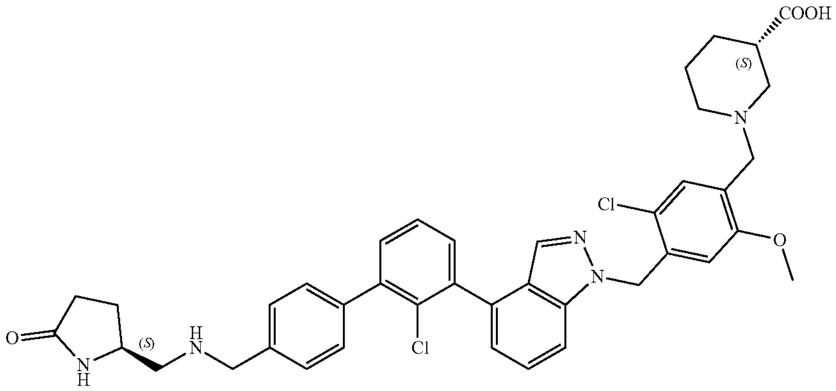

-continued
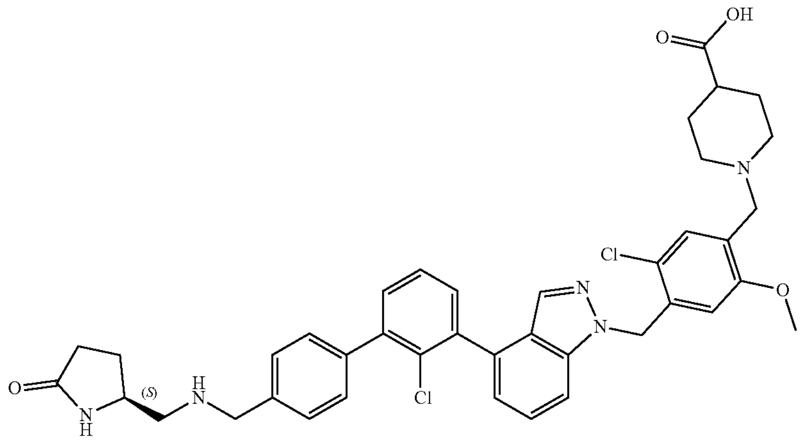
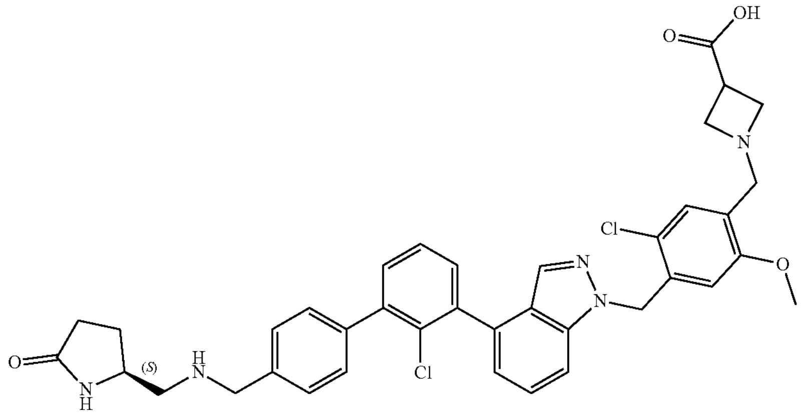
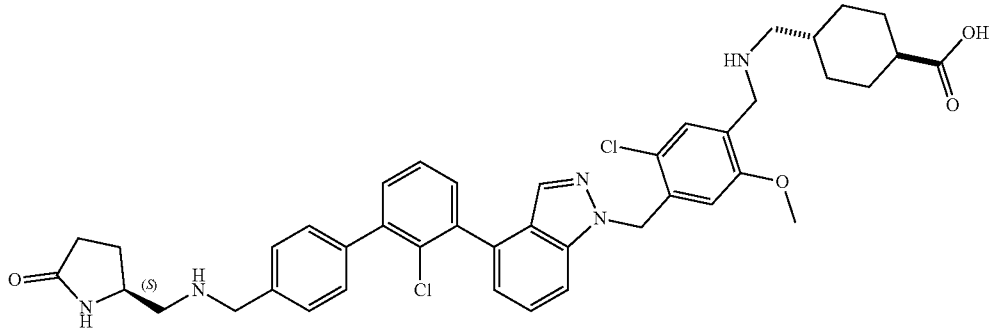
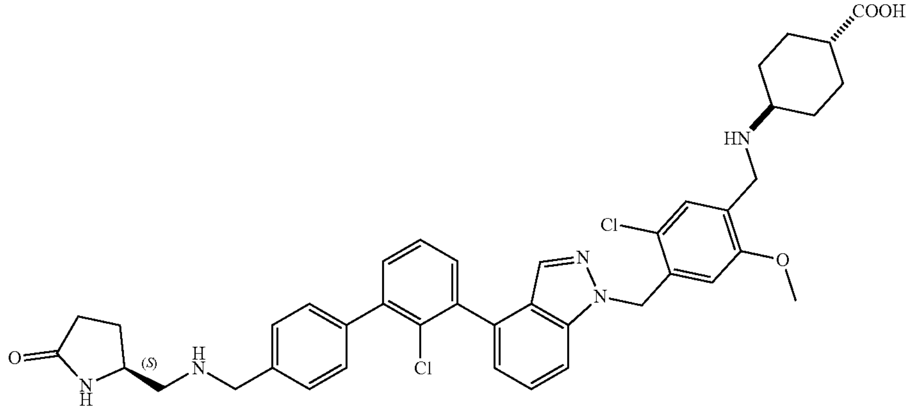

-continued
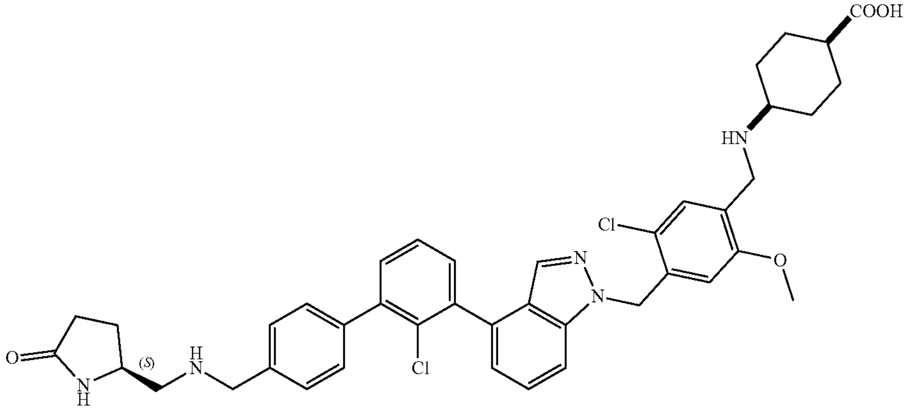
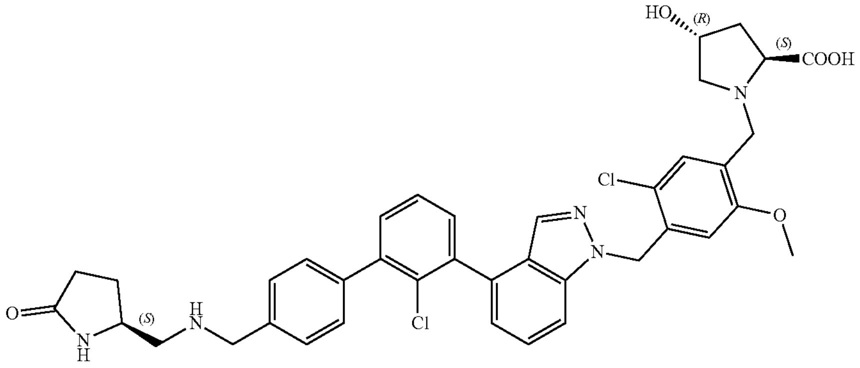
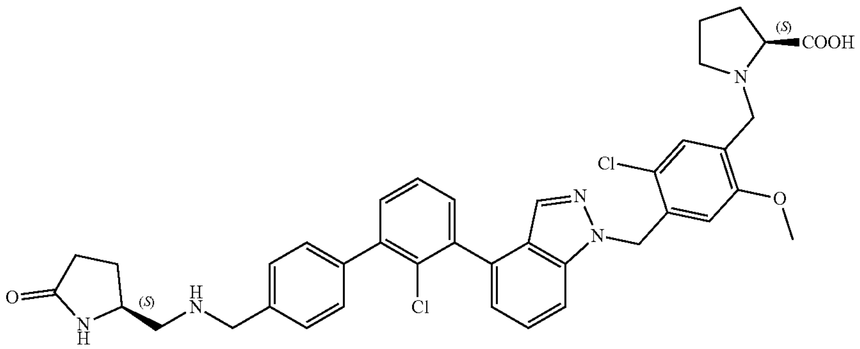
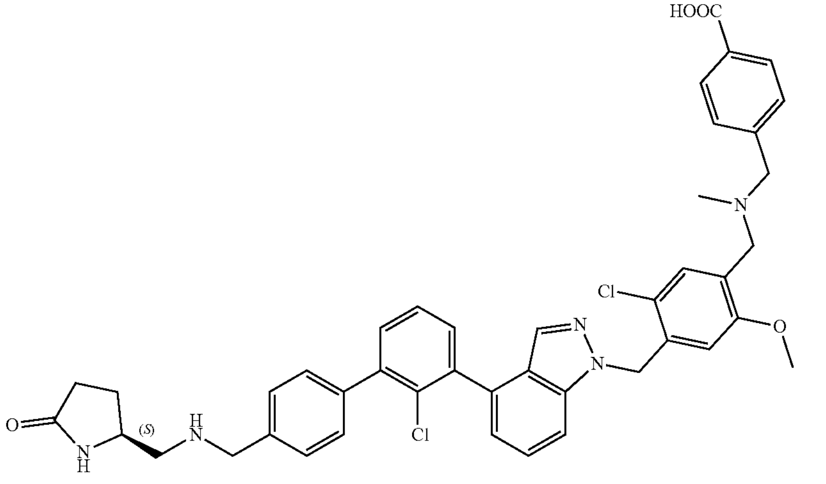

-continued
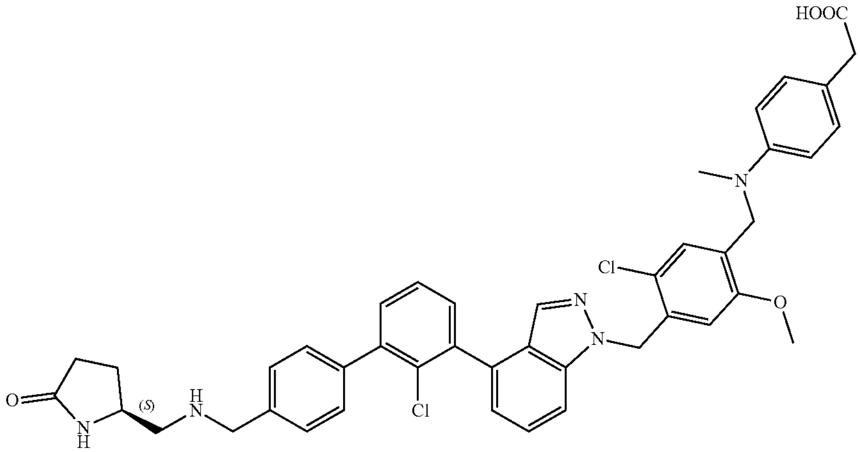
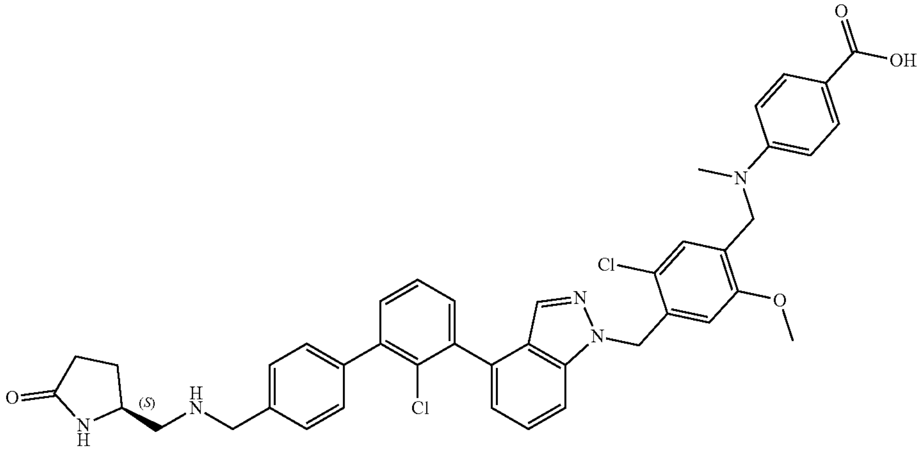
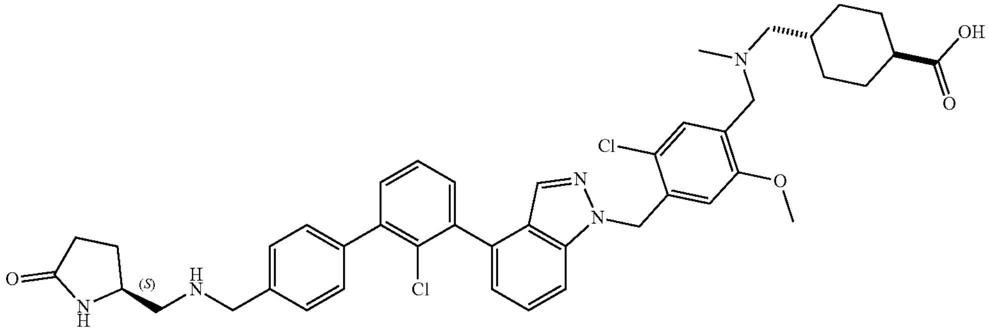
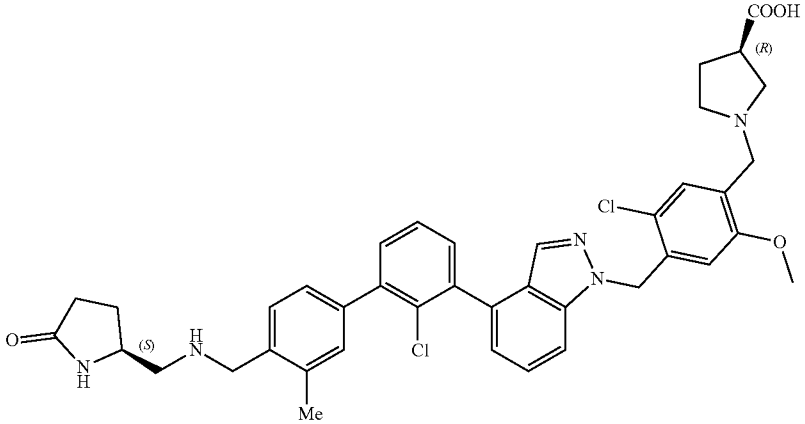

-continued
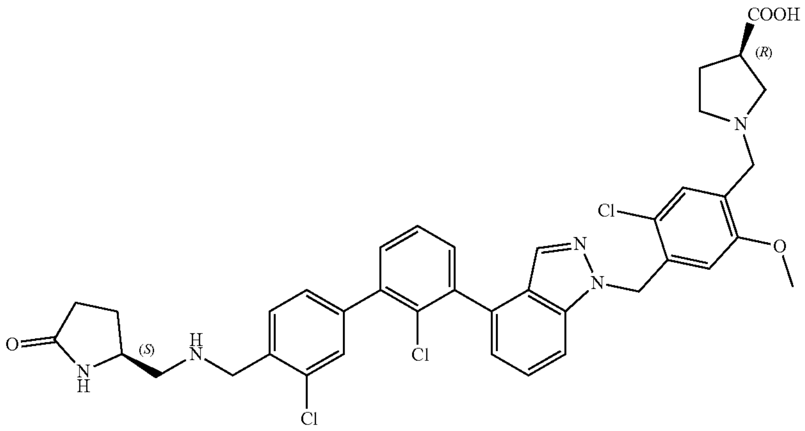
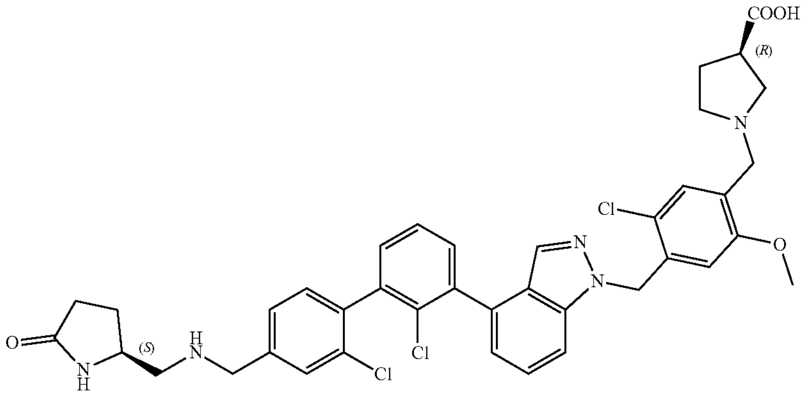
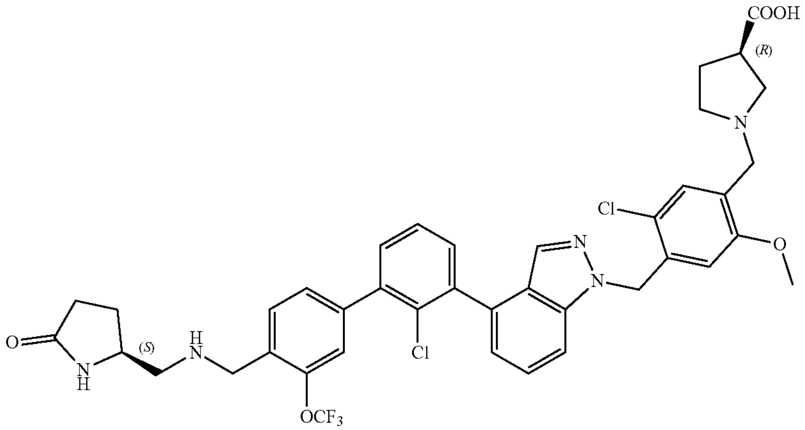
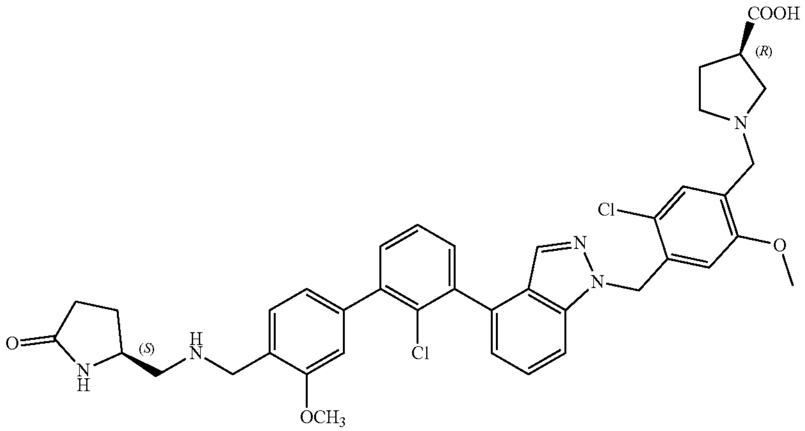

-continued
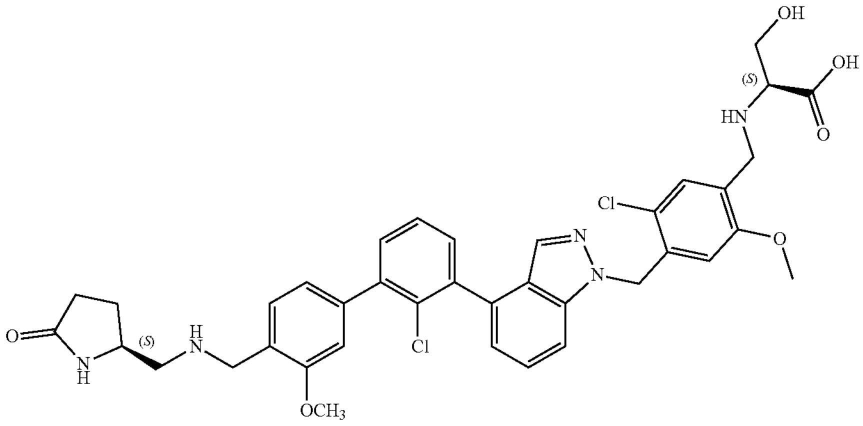
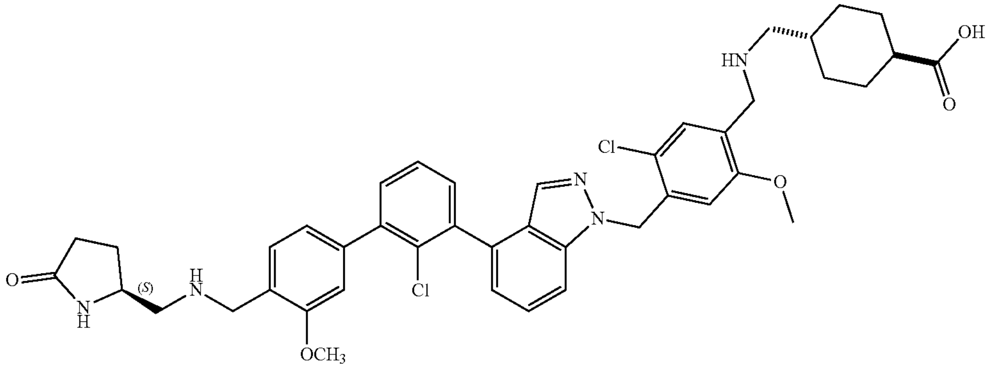
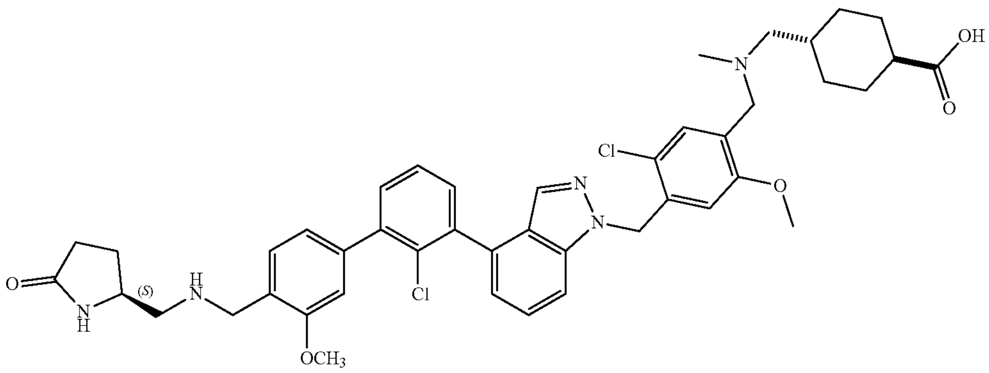
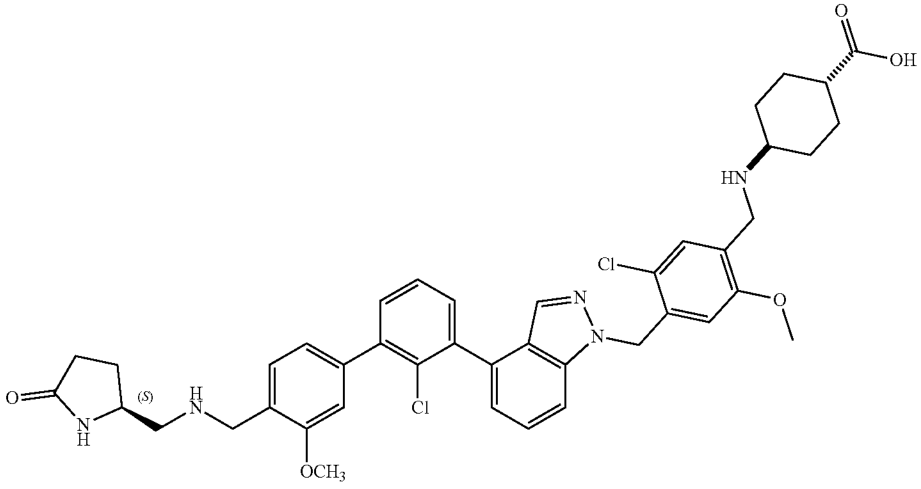

-continued
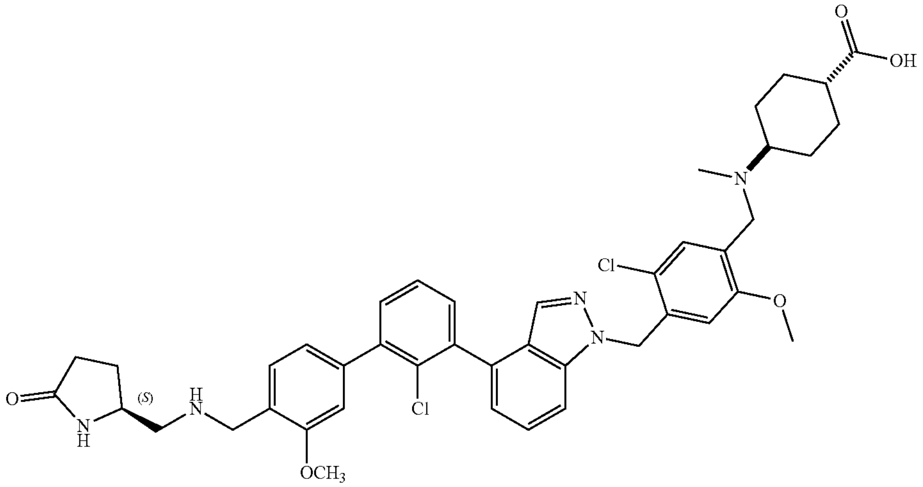
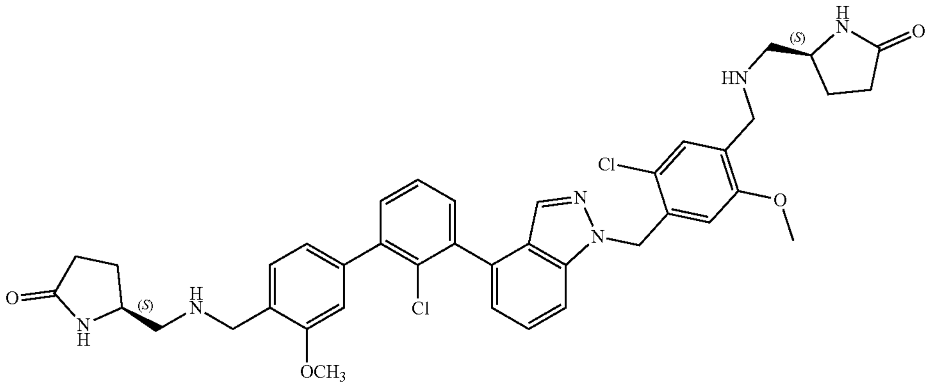
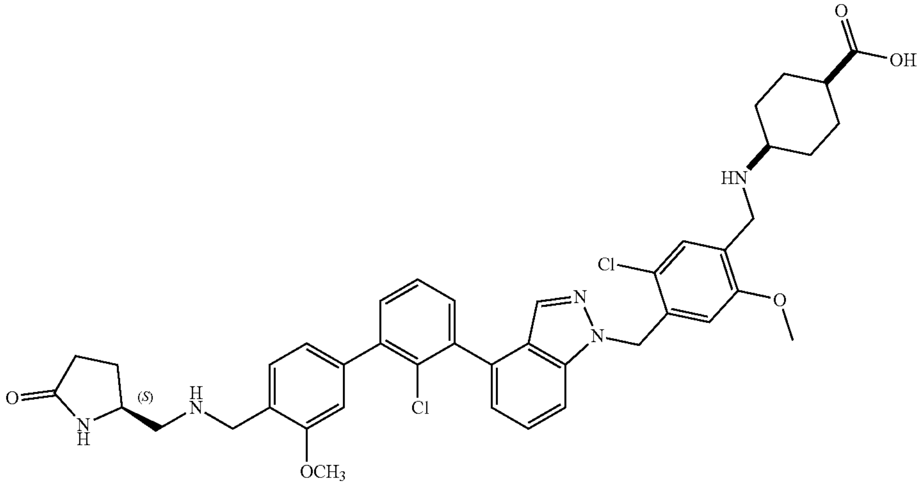

-continued
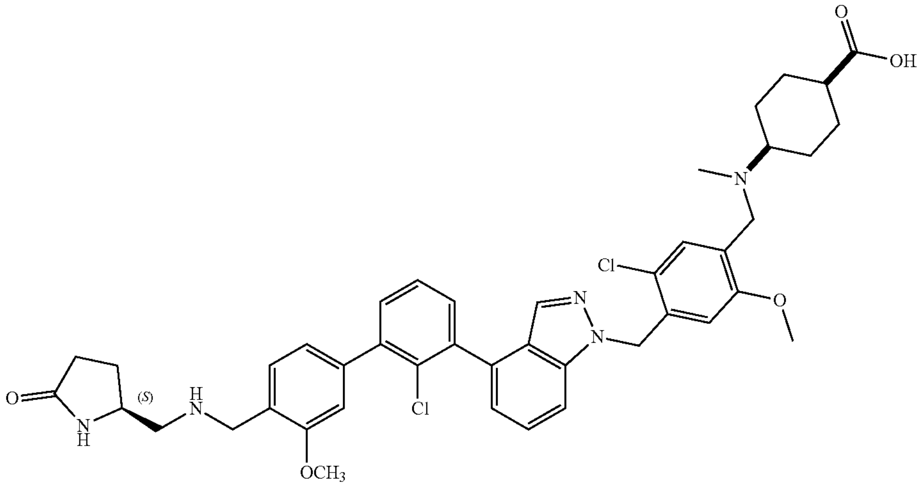
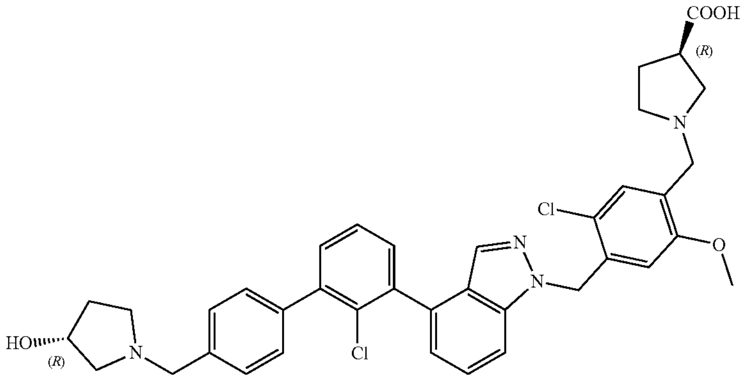
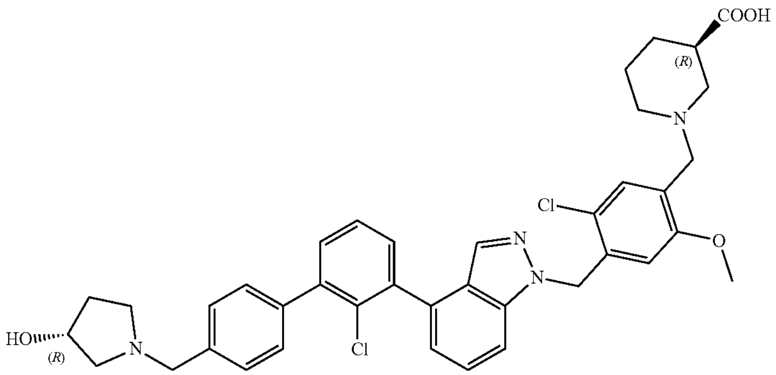
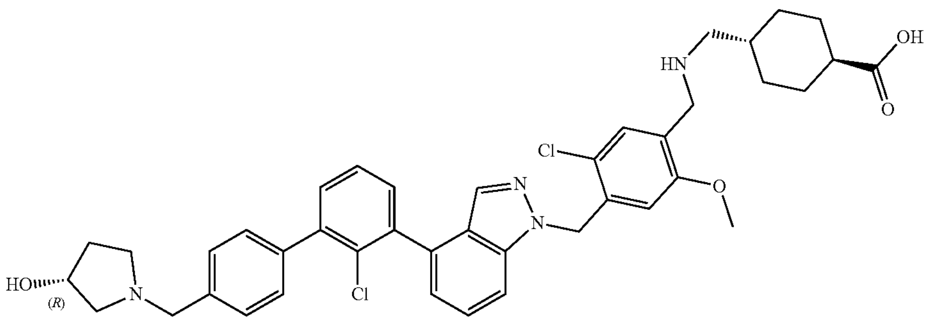

-continued
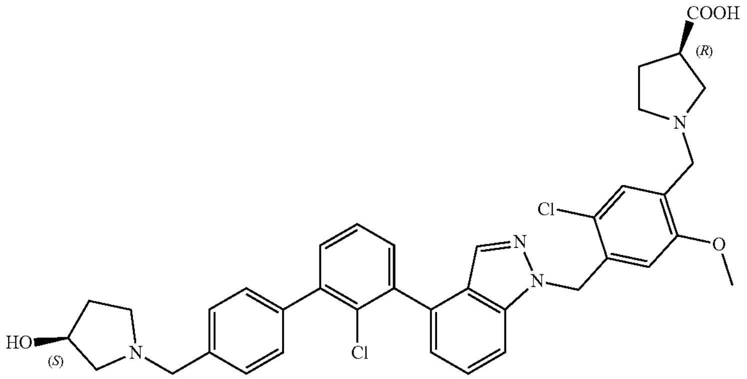
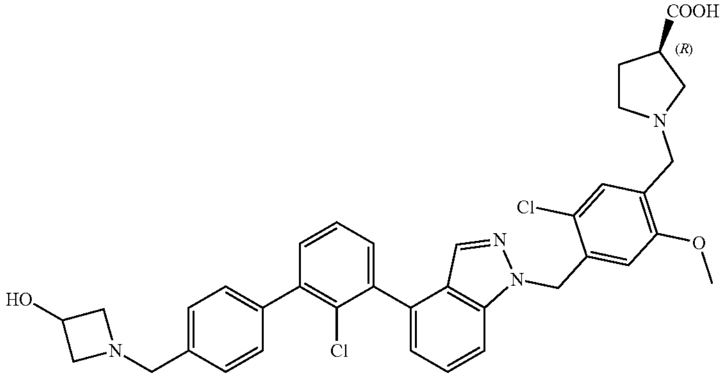
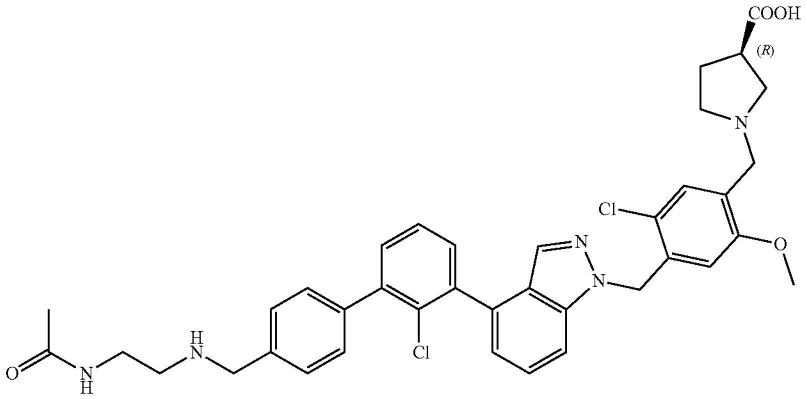
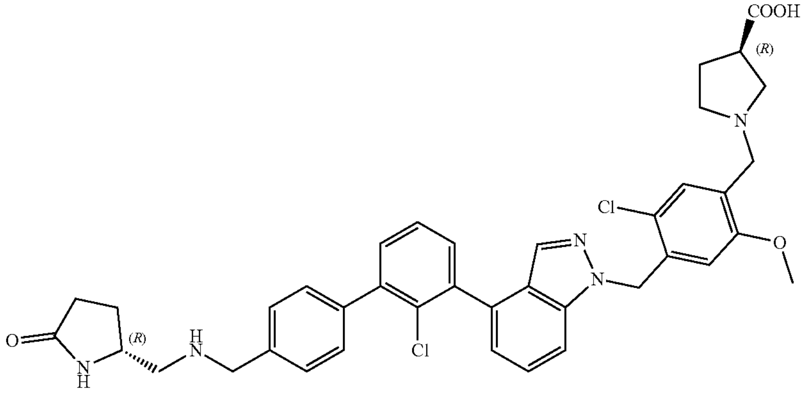

-continued
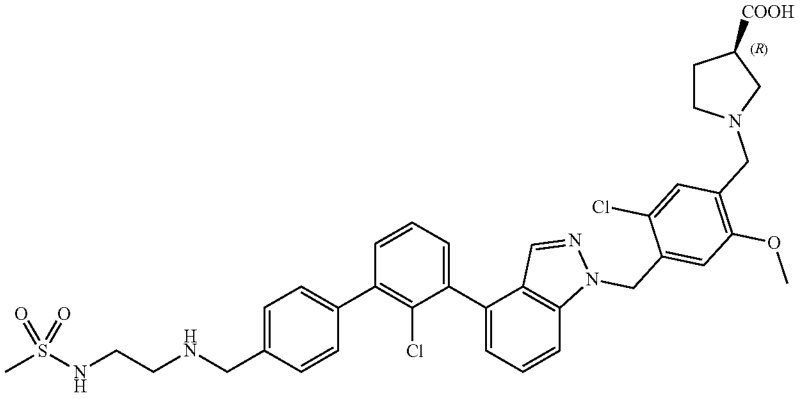
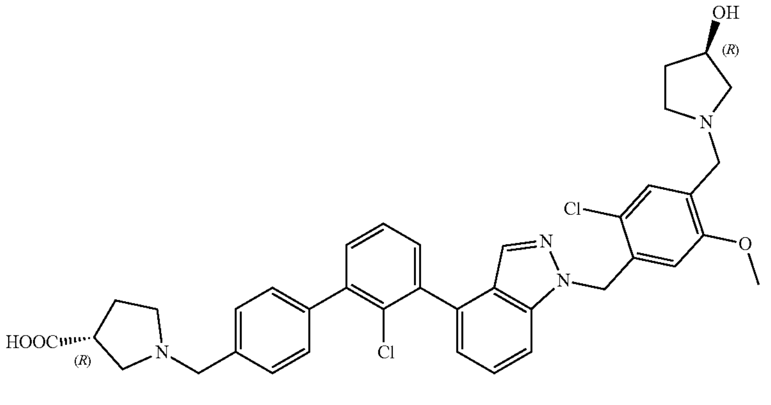
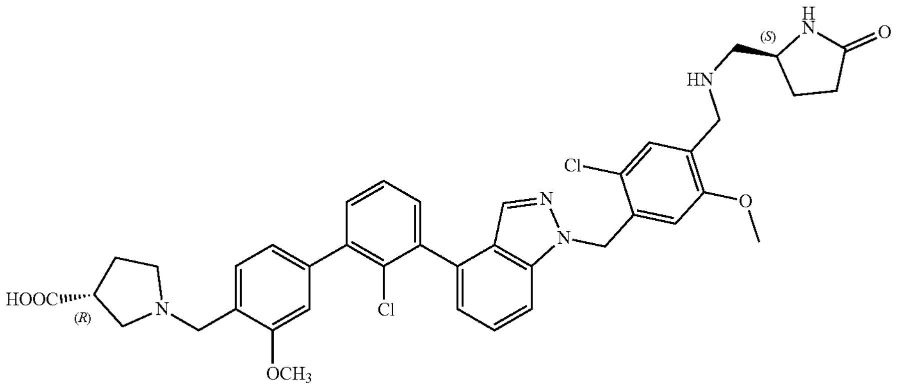
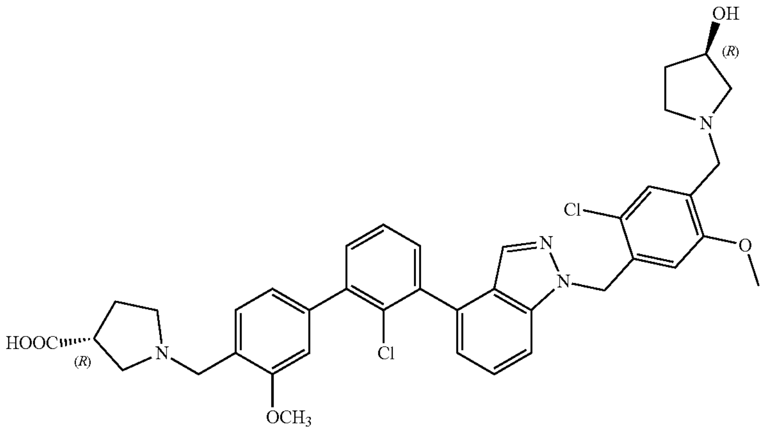

-continued
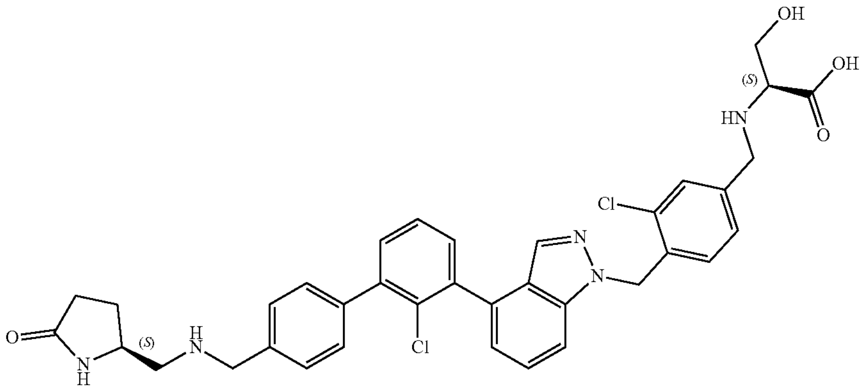
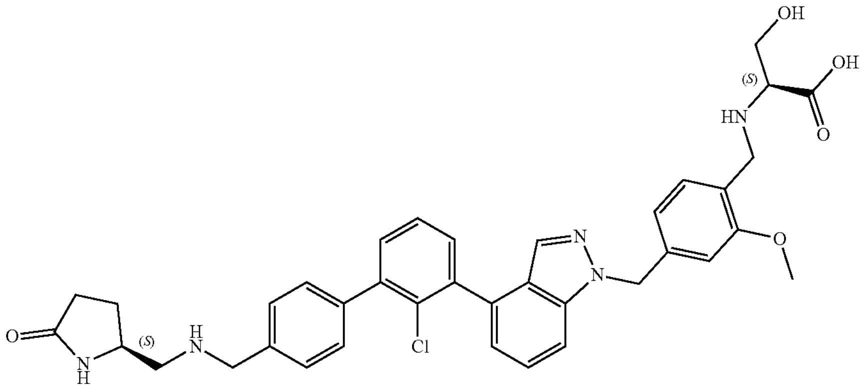
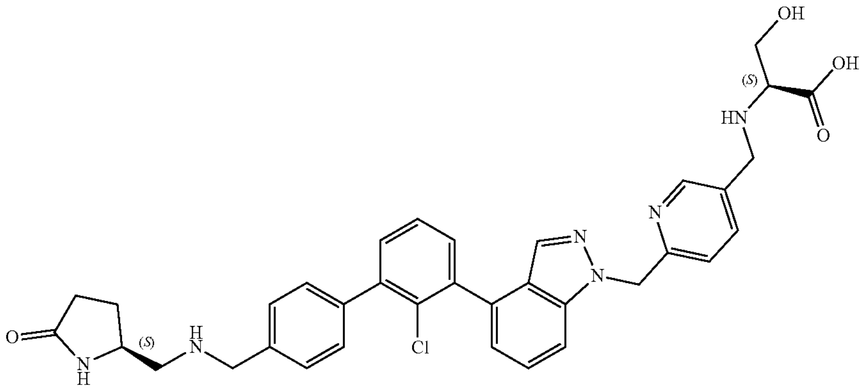
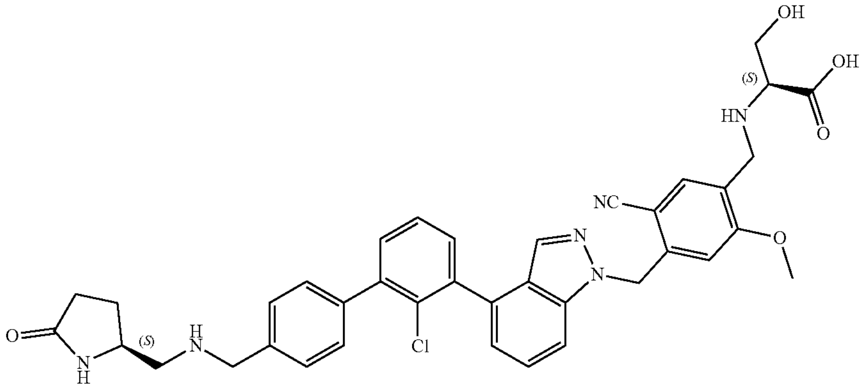

-continued
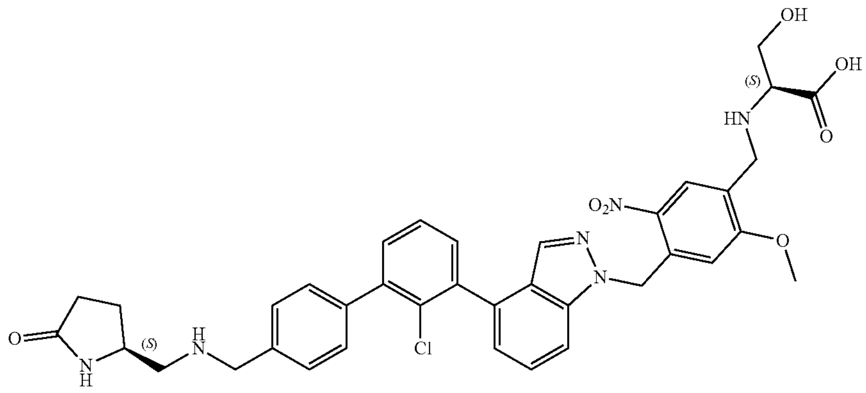
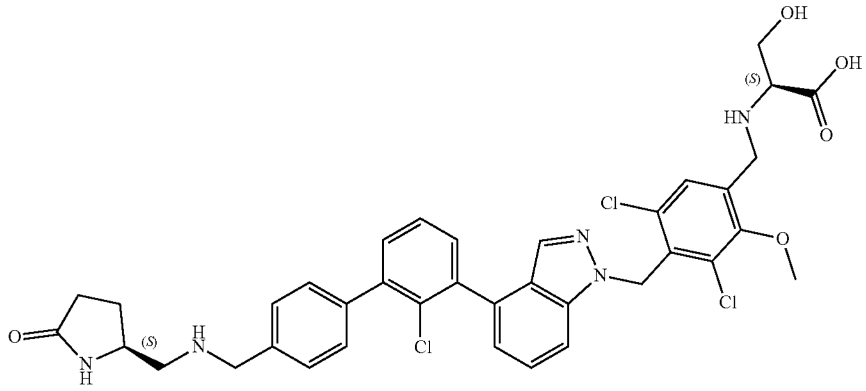
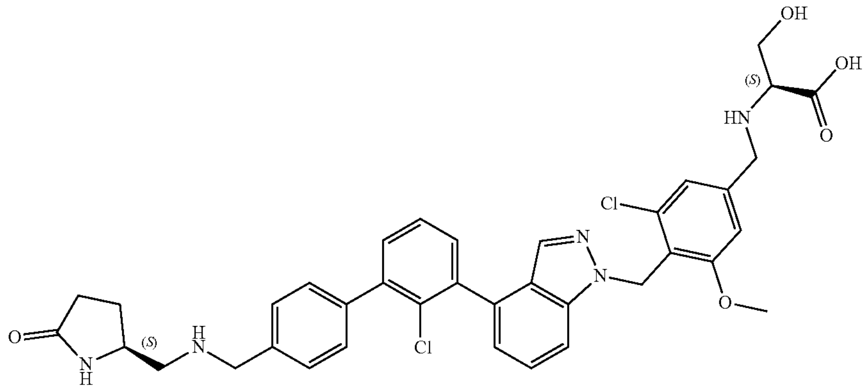
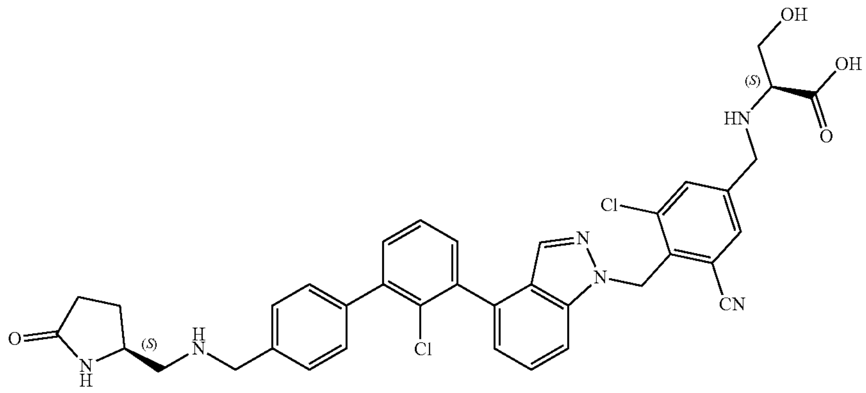

-continued
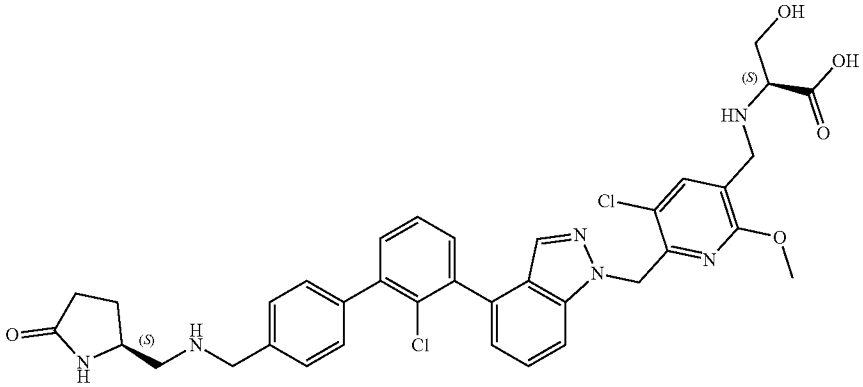
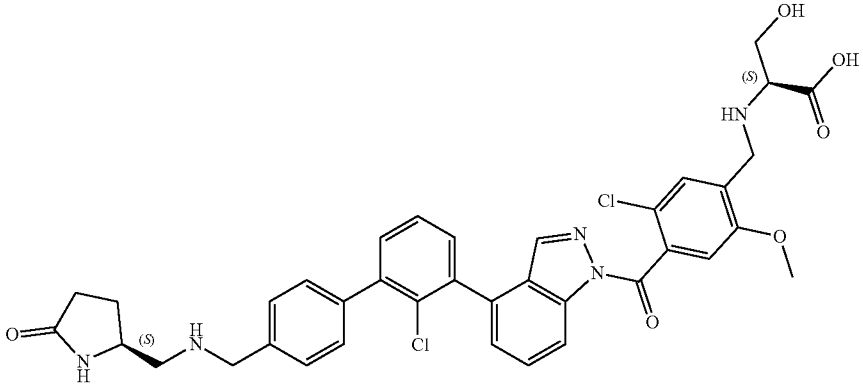
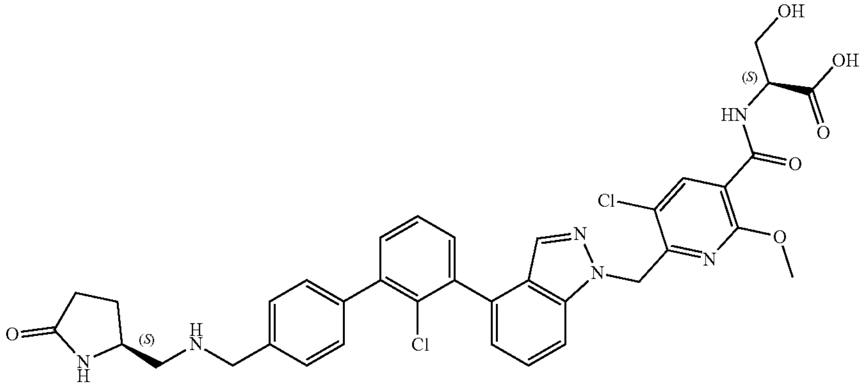
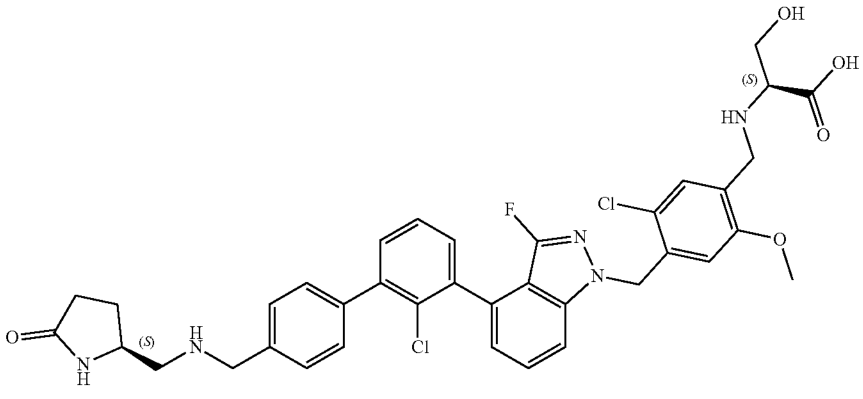

-continued
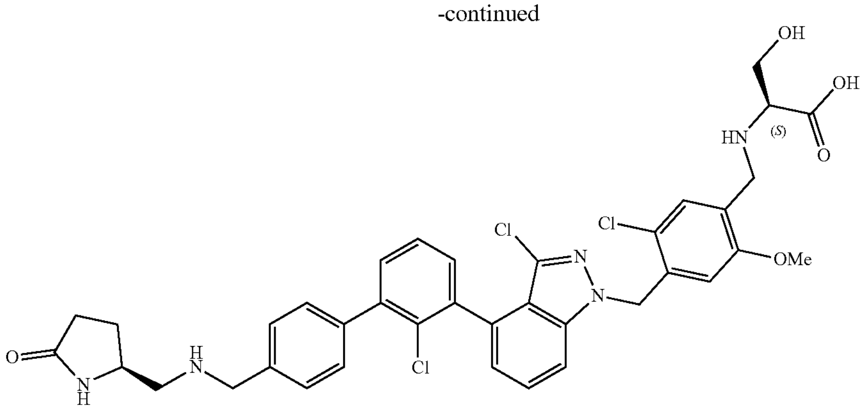
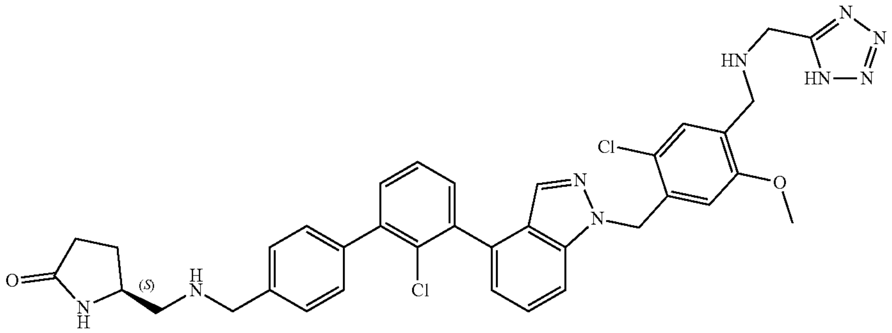
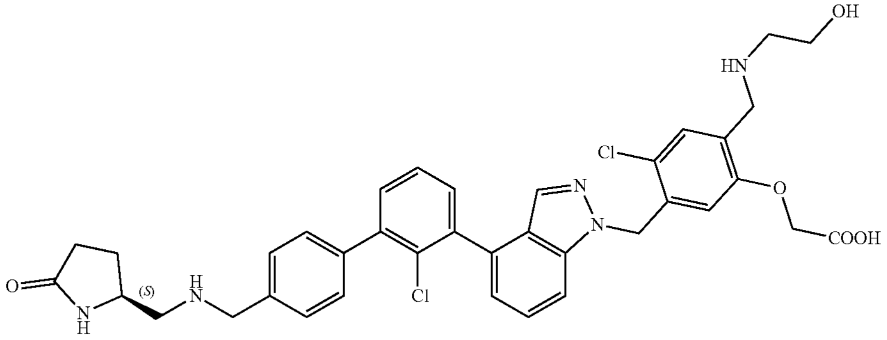
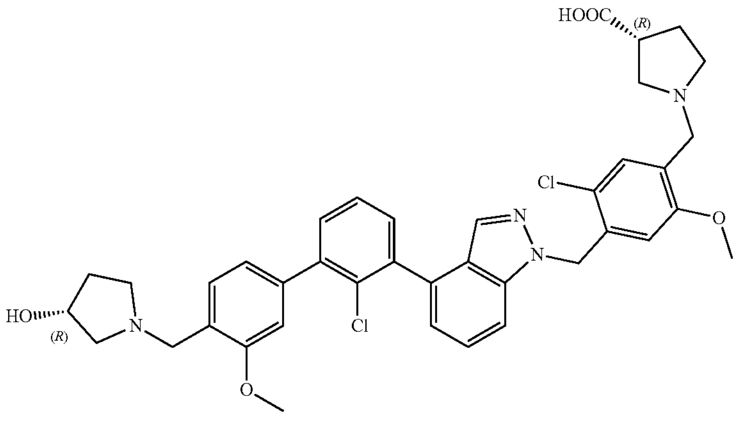

-continued
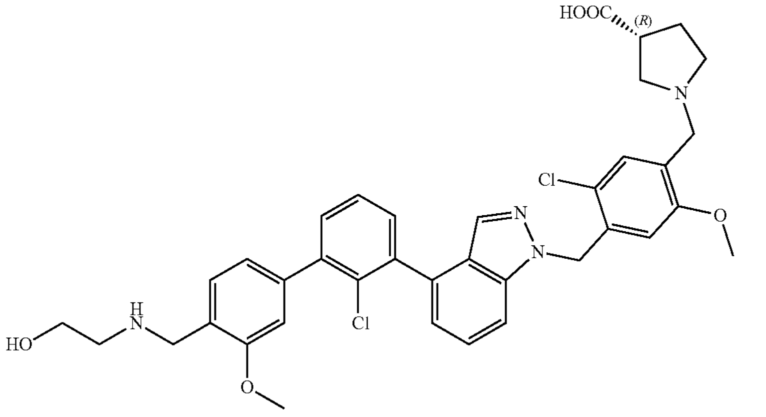
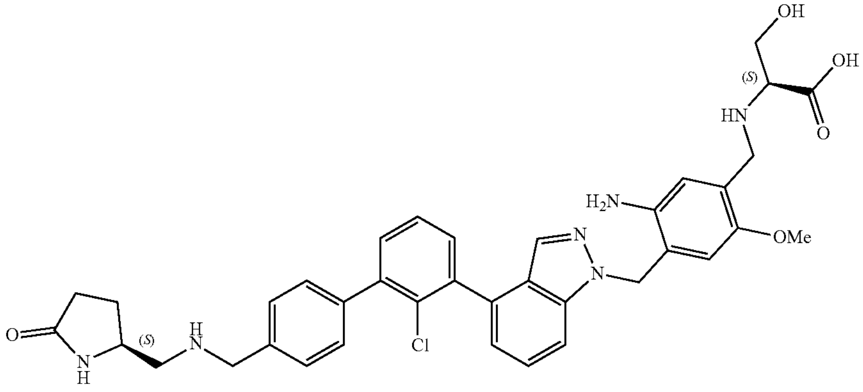
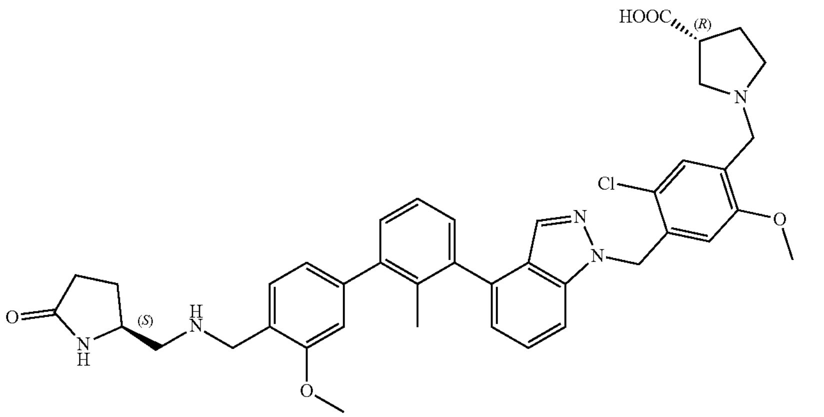
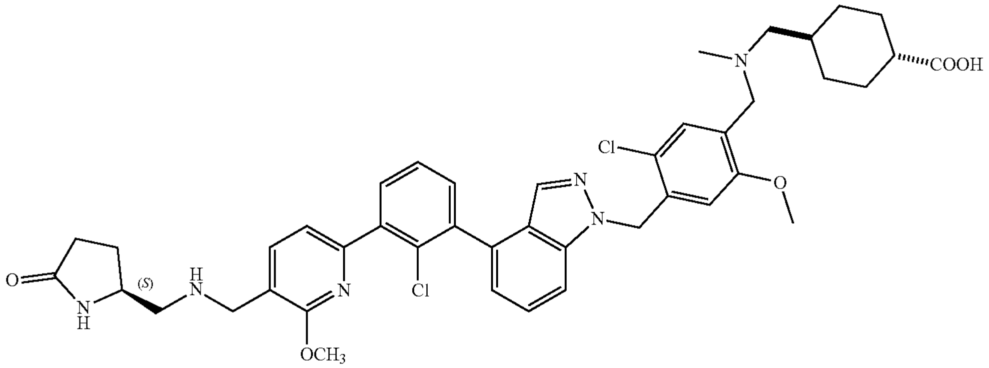

-continued
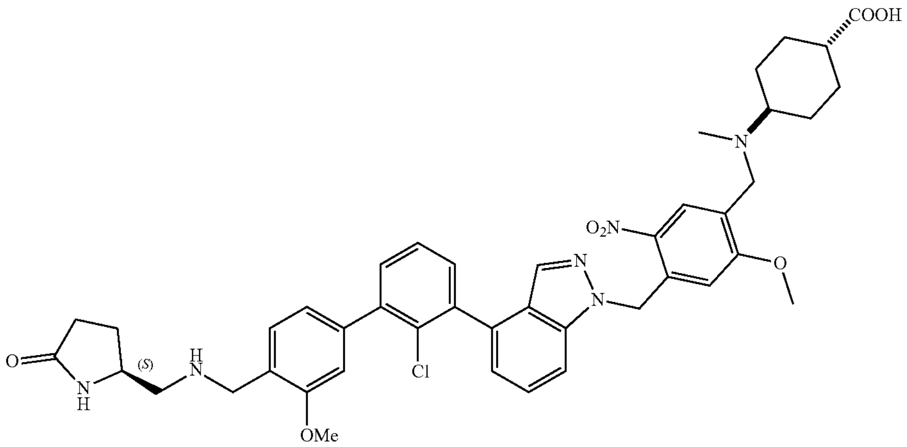
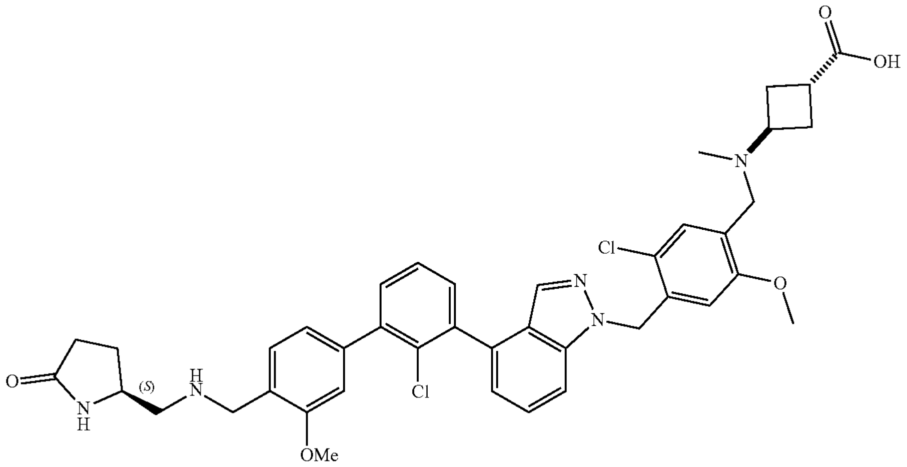
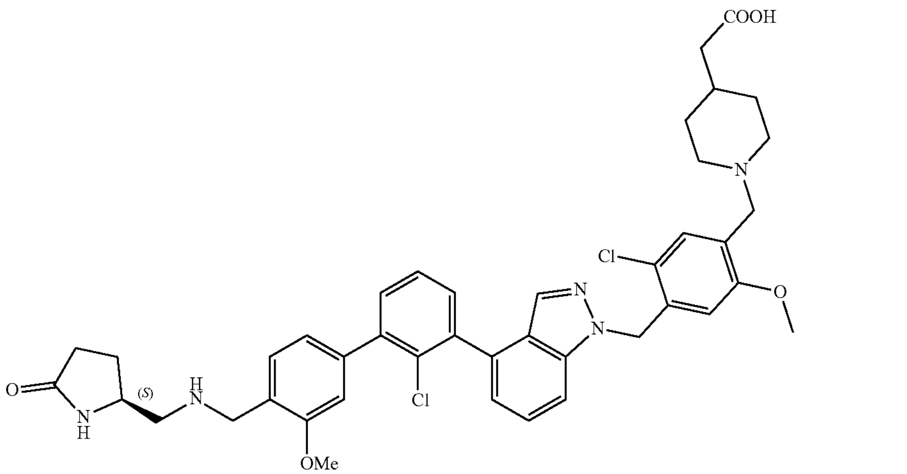

-continued
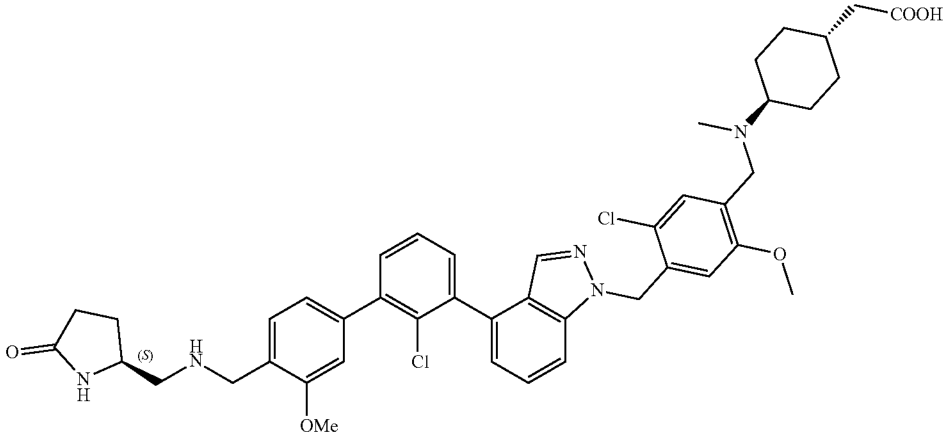
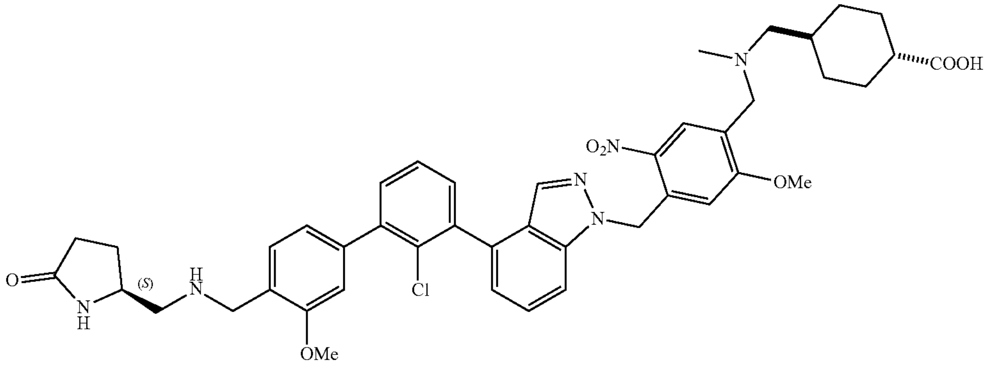
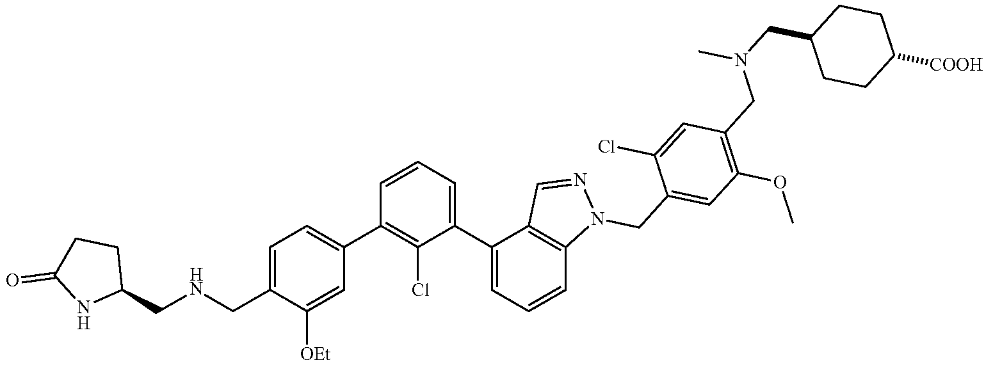
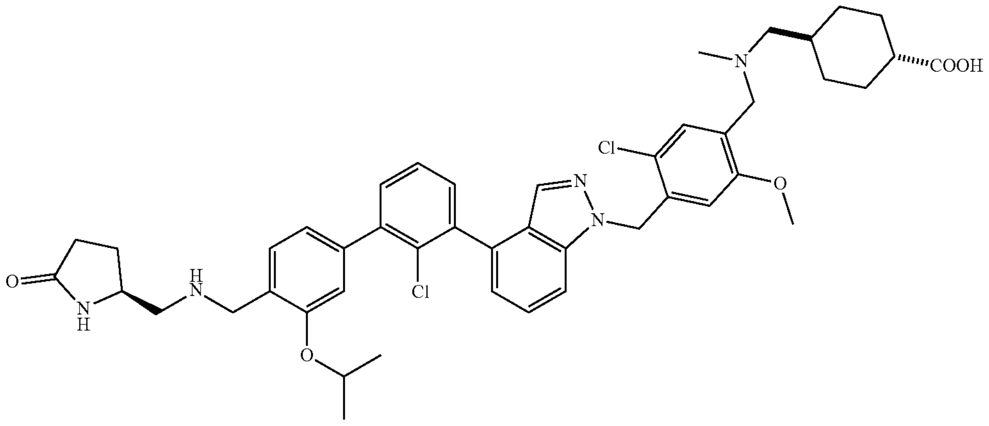

-continued
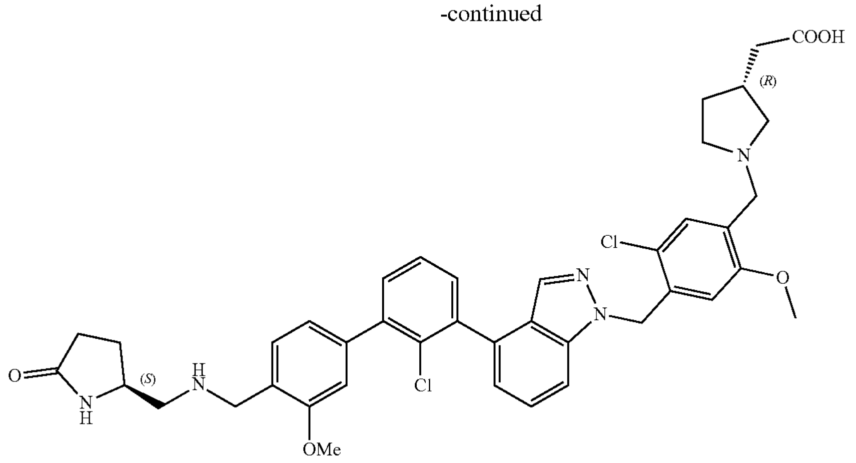
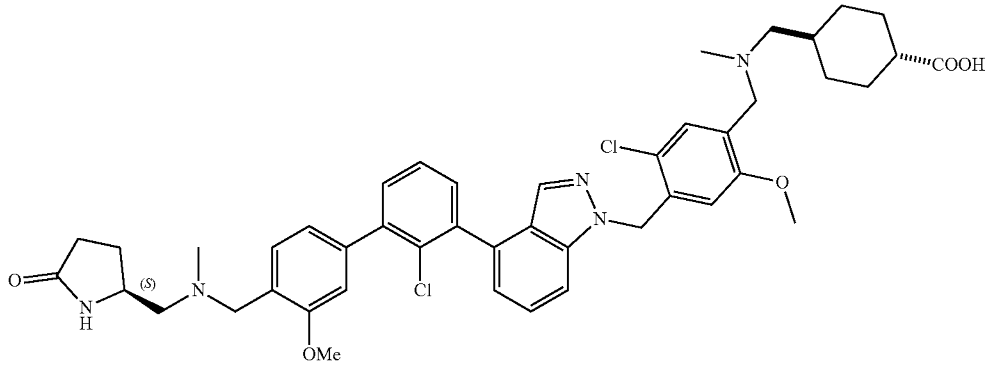
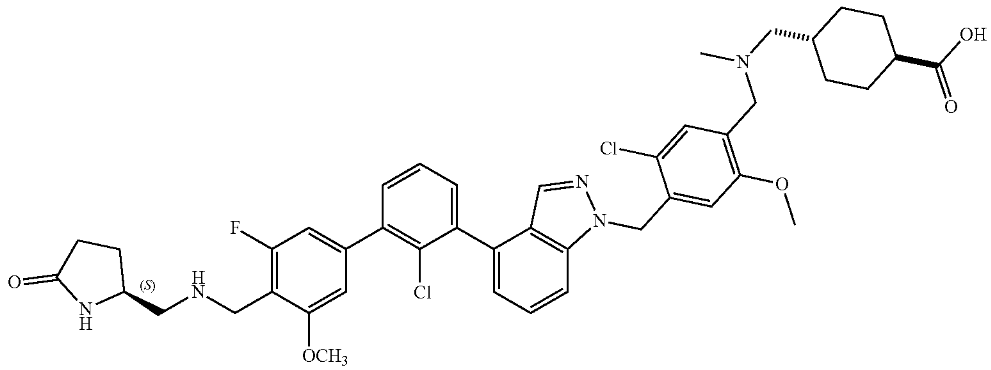
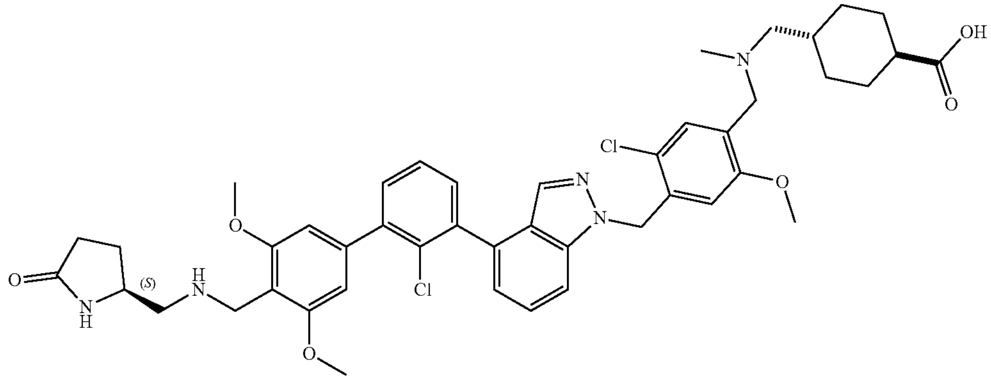

-continued
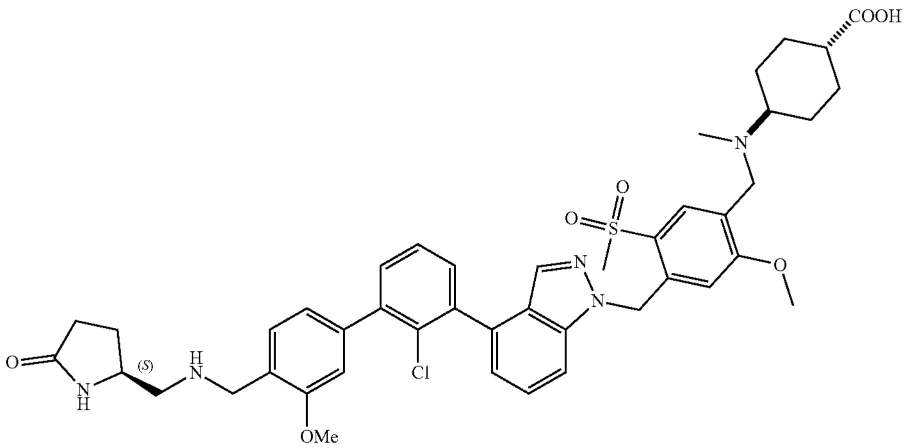
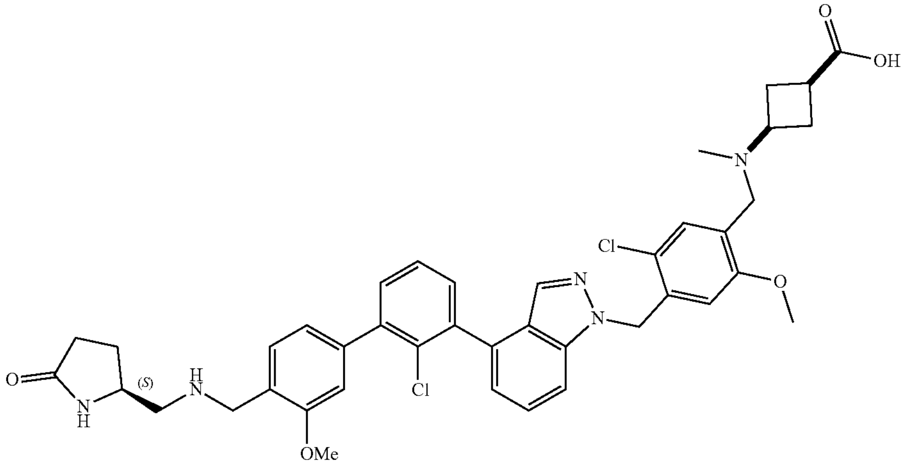
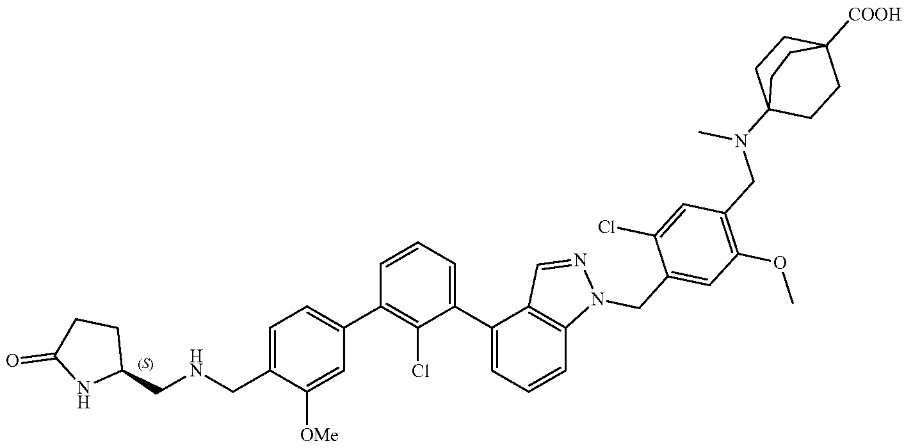

-continued
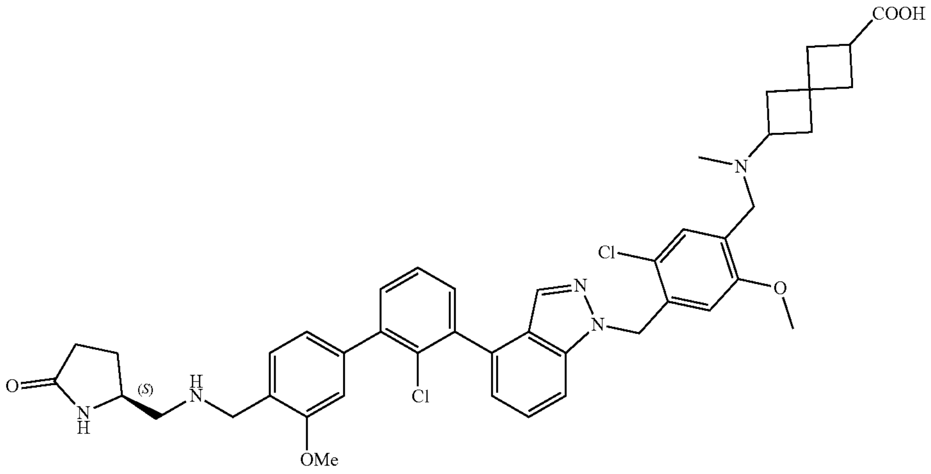
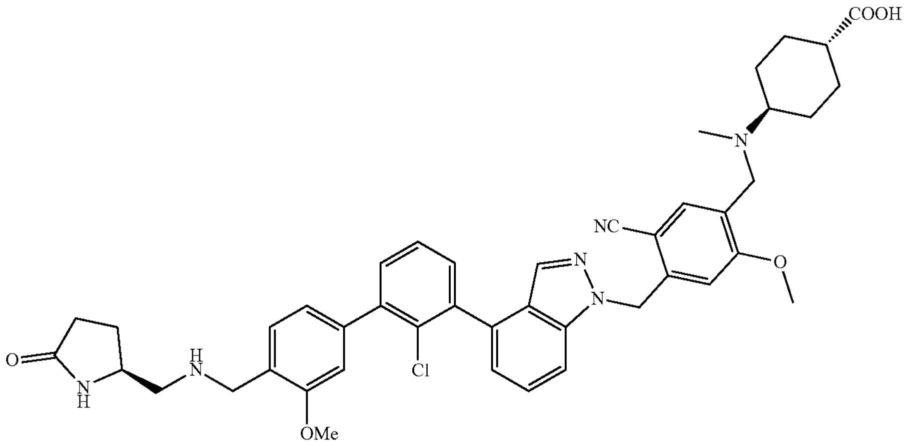
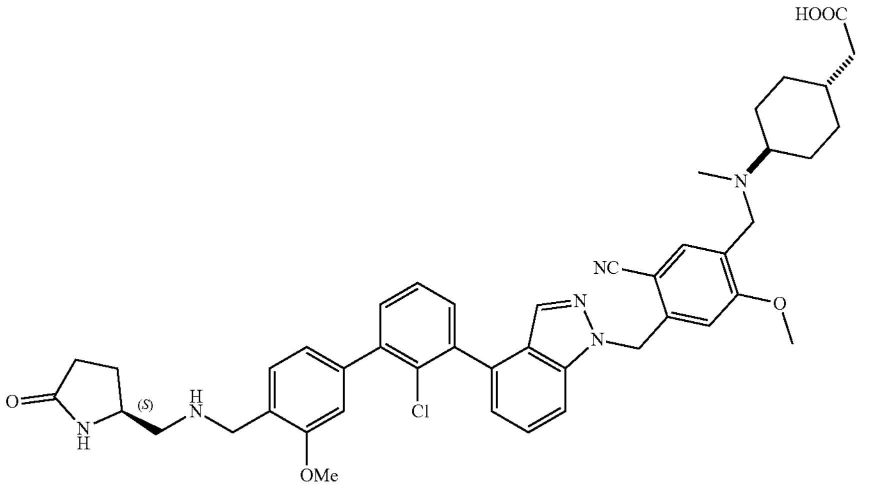

-continued
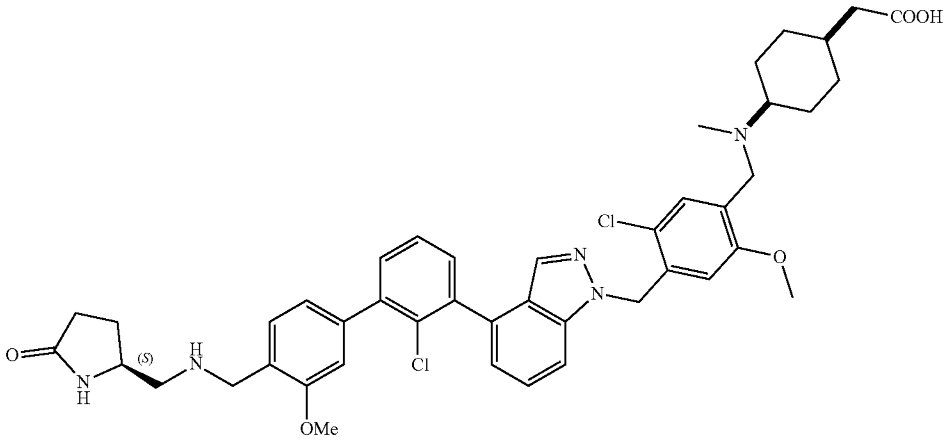
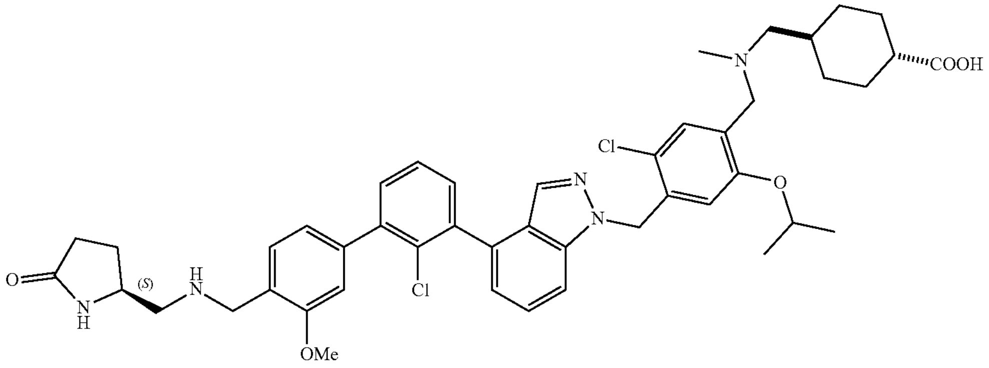
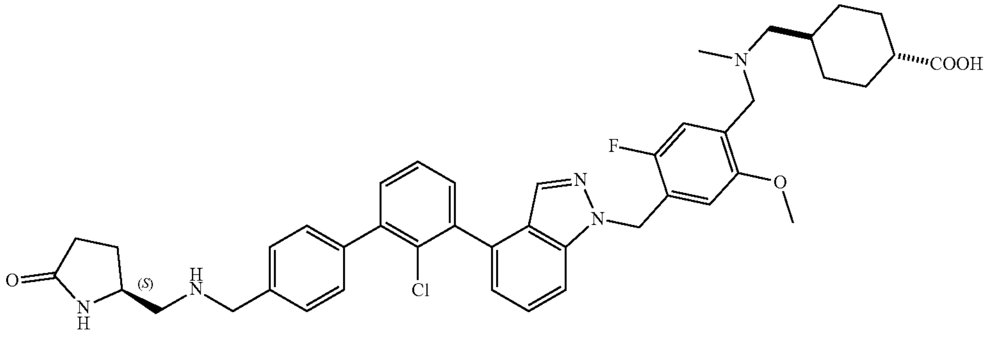
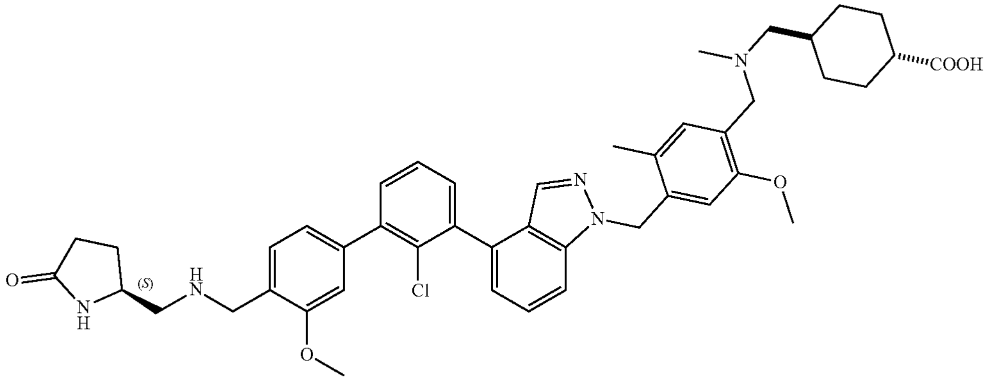

-continued
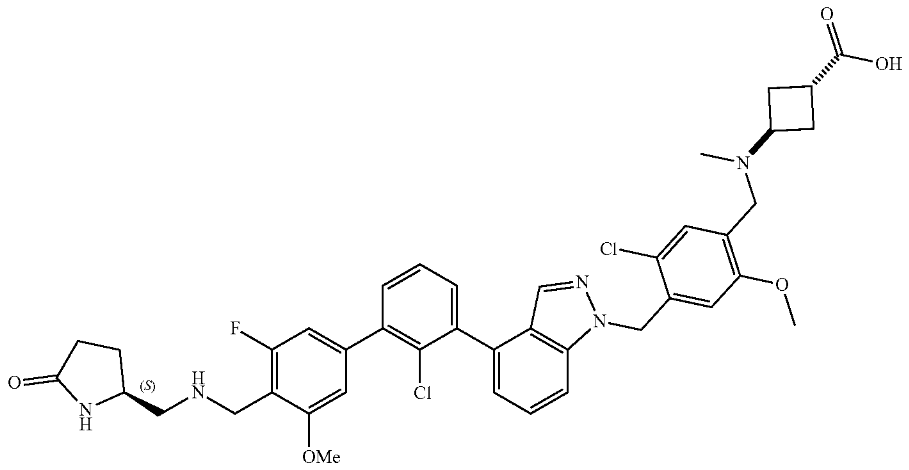
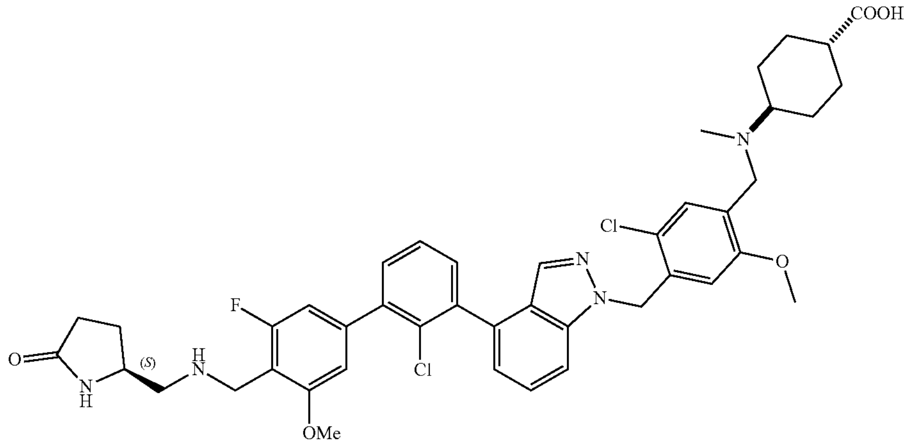
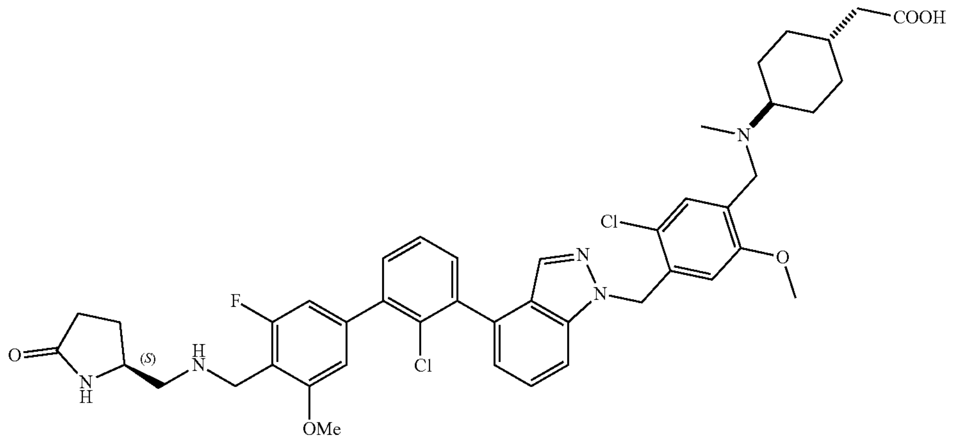

-continued
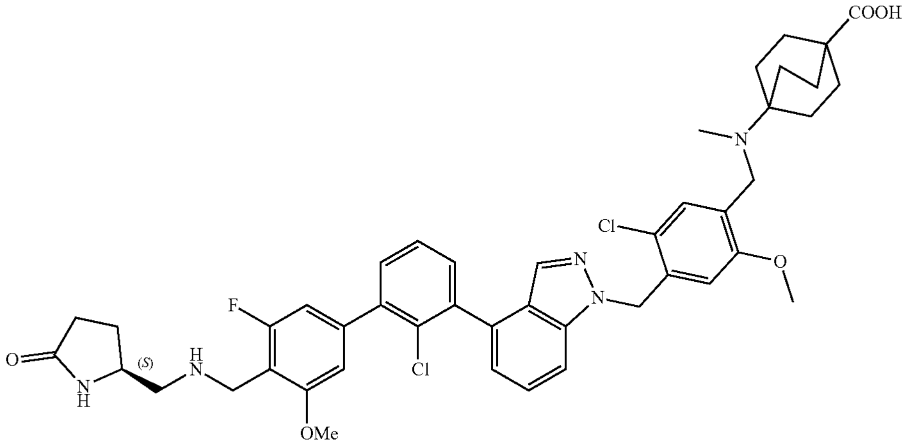
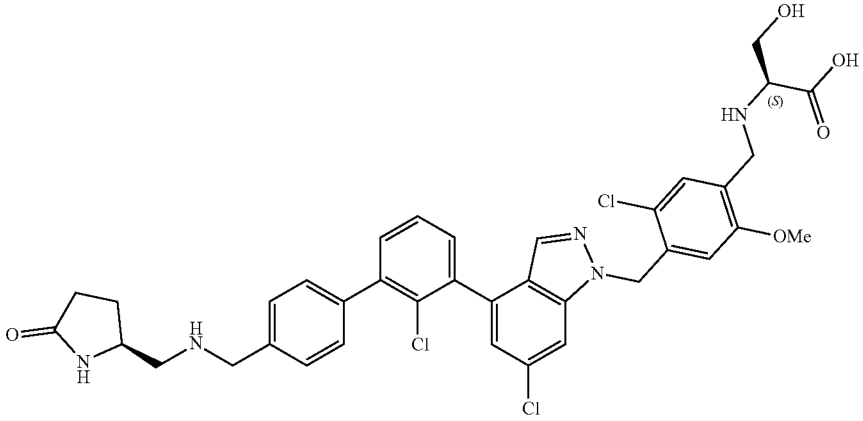
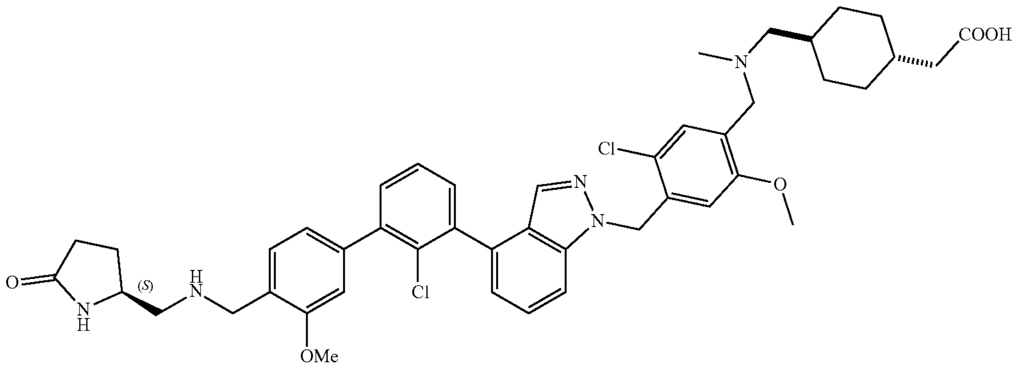
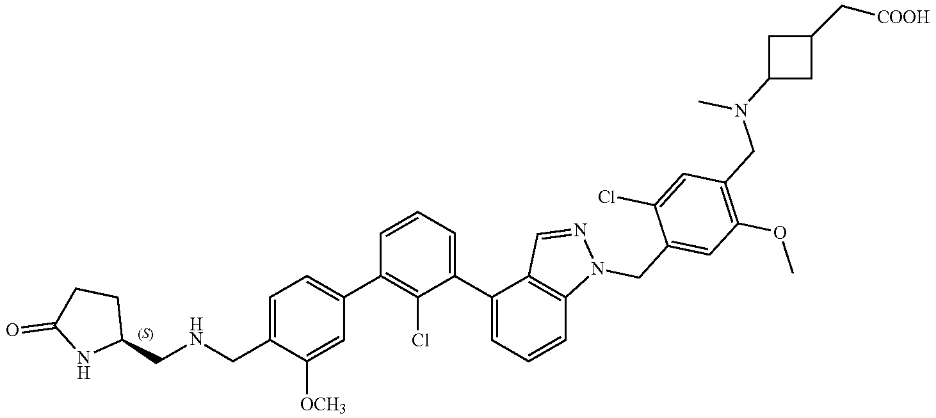

-continued
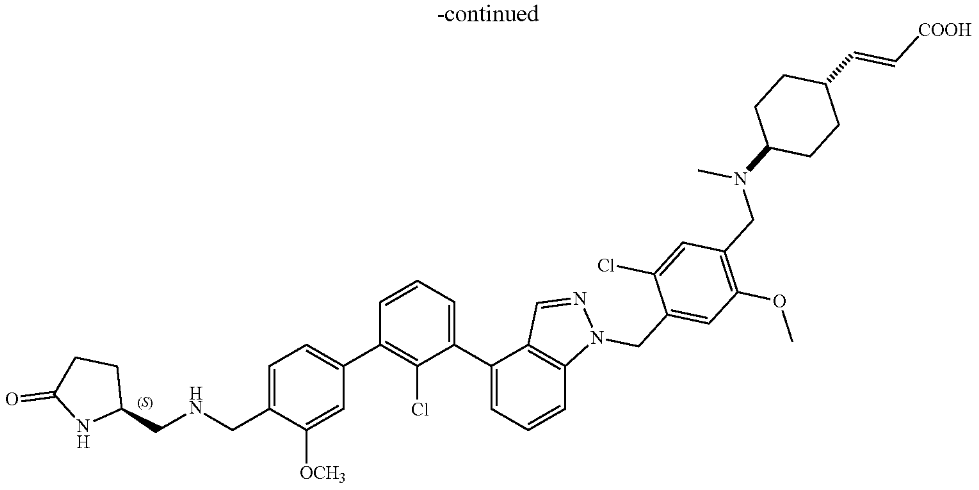
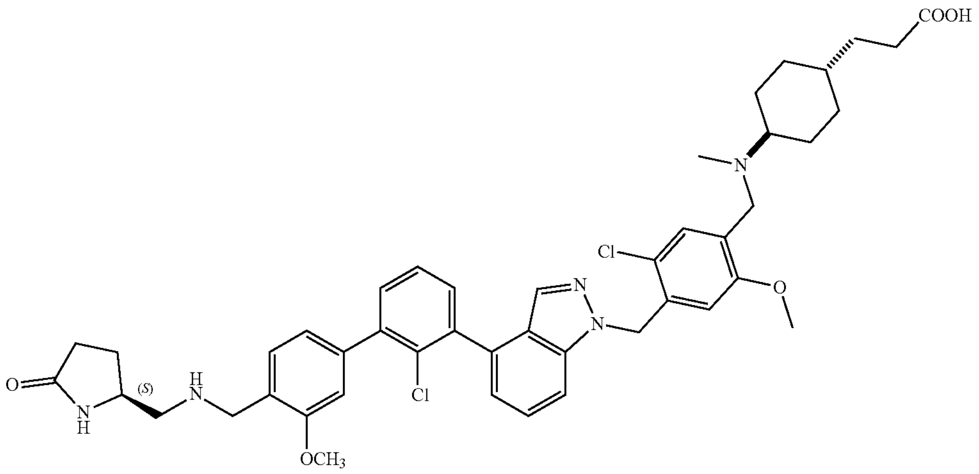
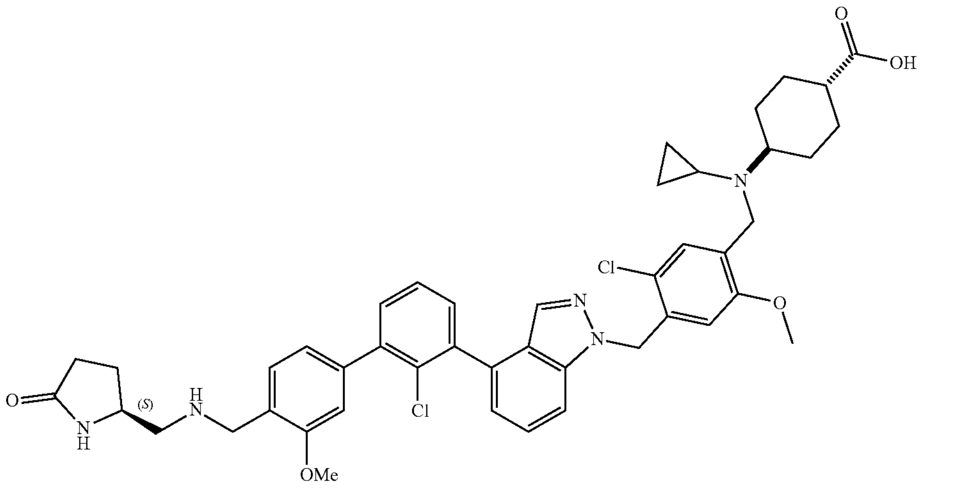

-continued
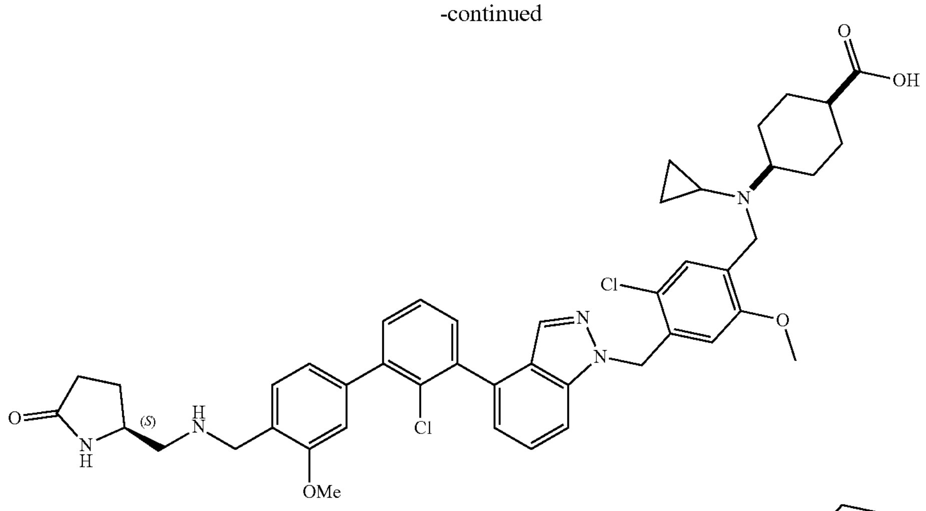
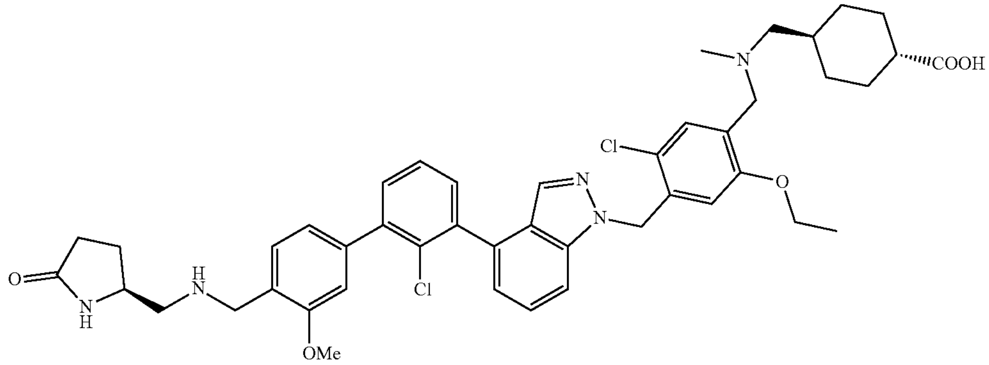
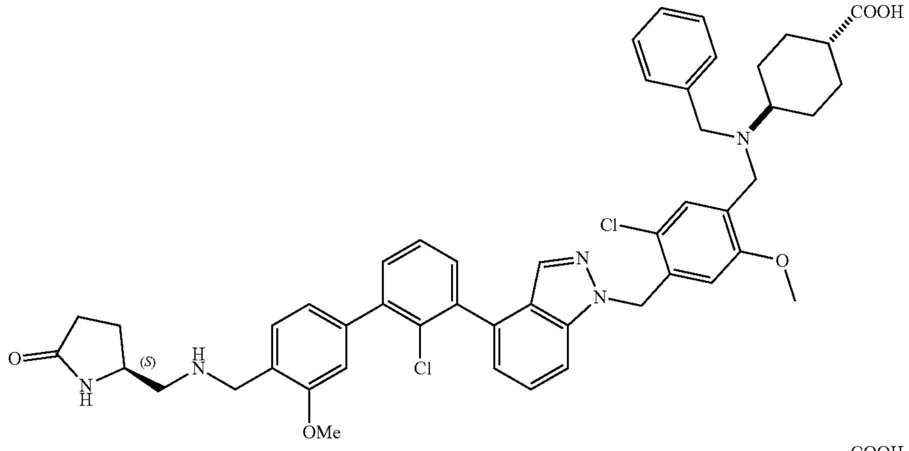
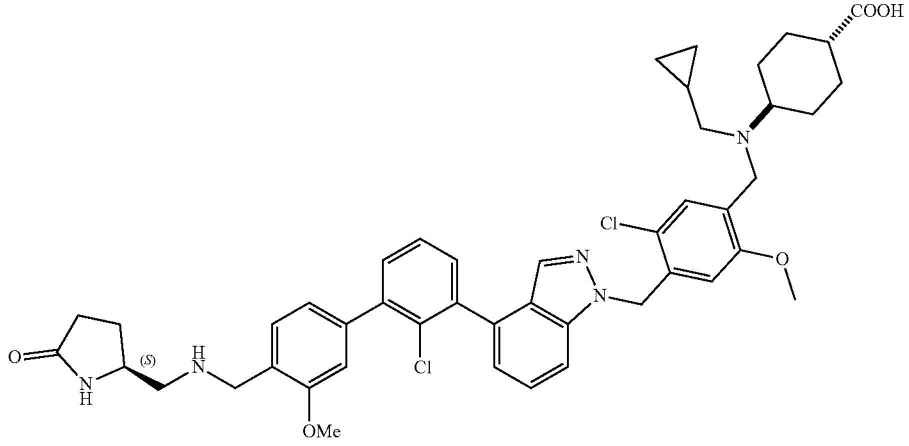

-continued
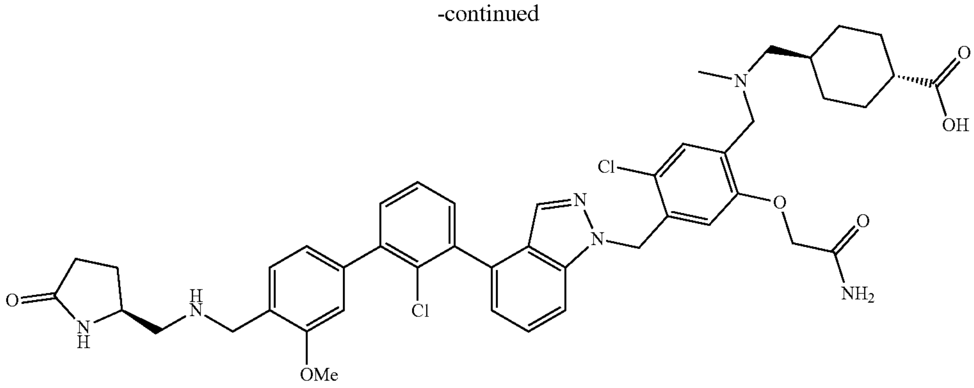
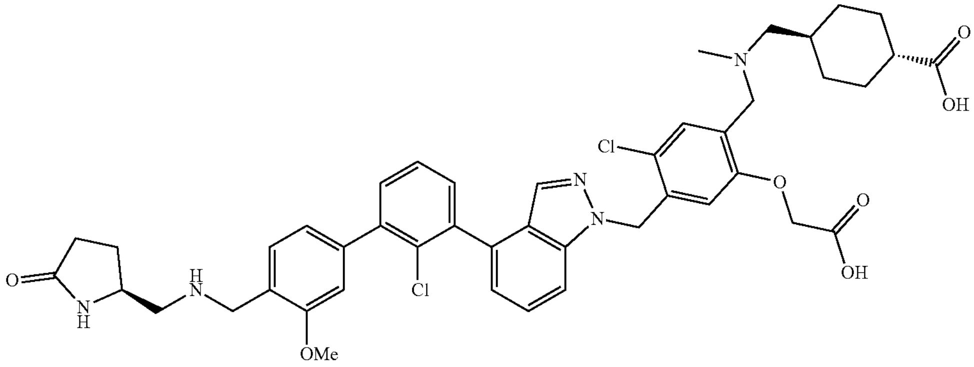
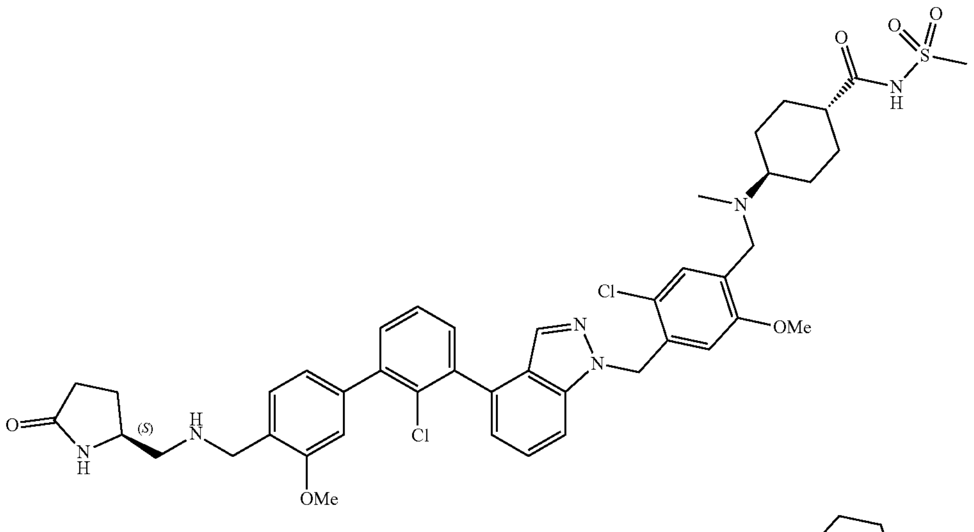
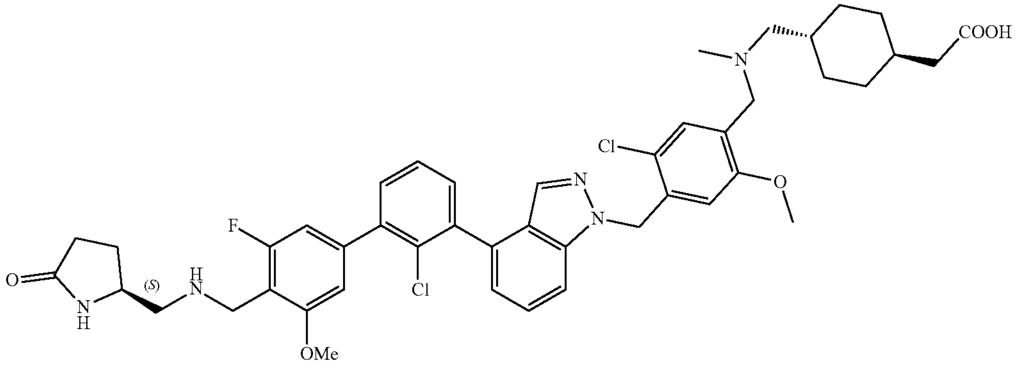

-continued
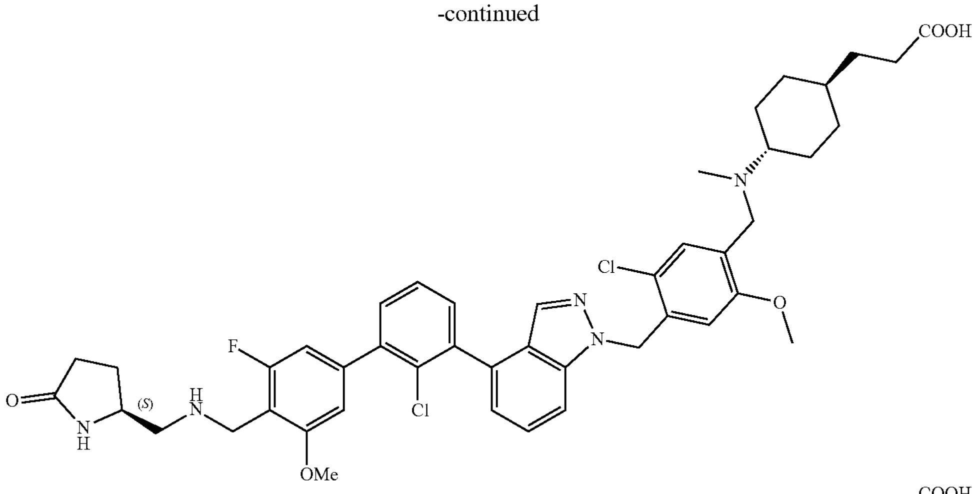
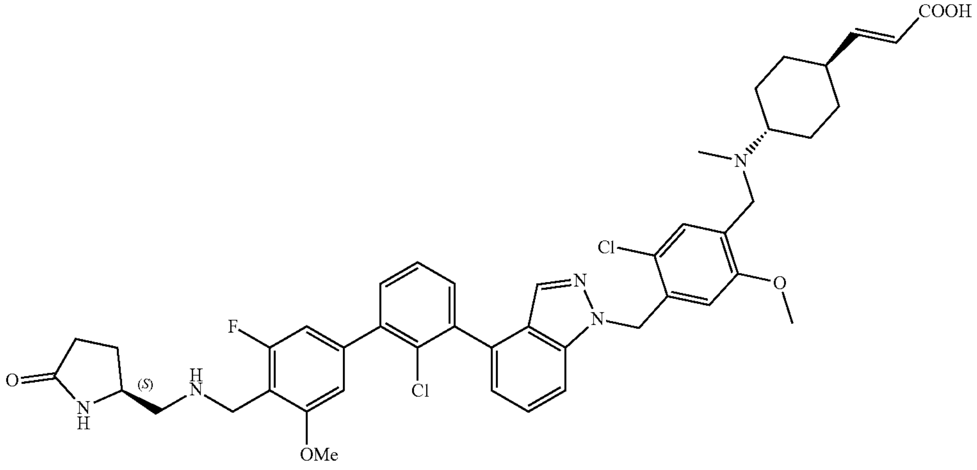
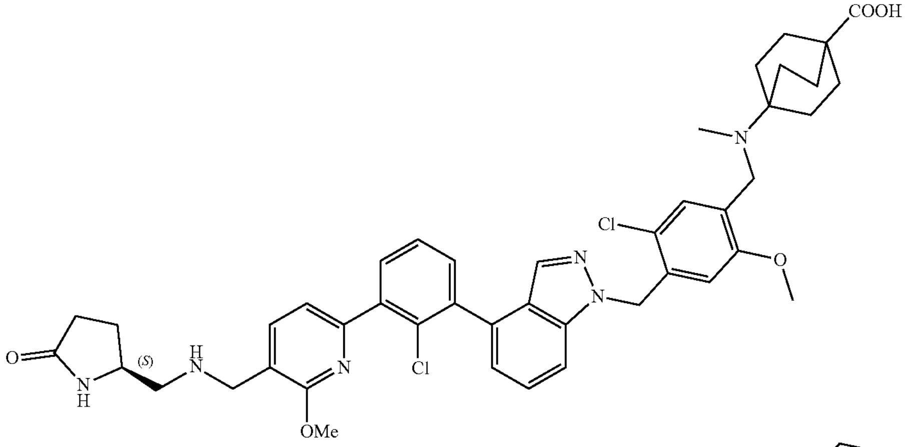
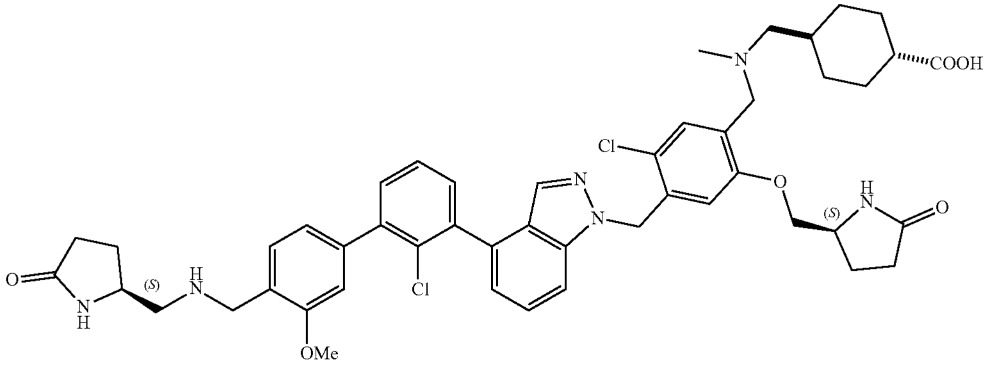

-continued
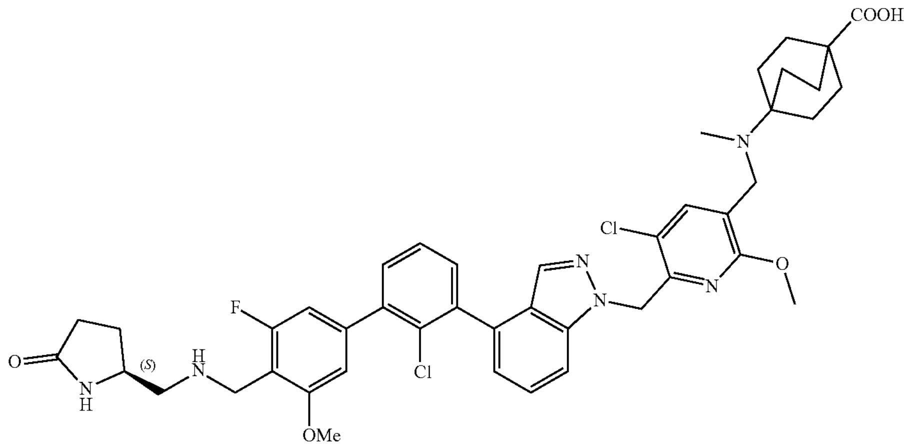
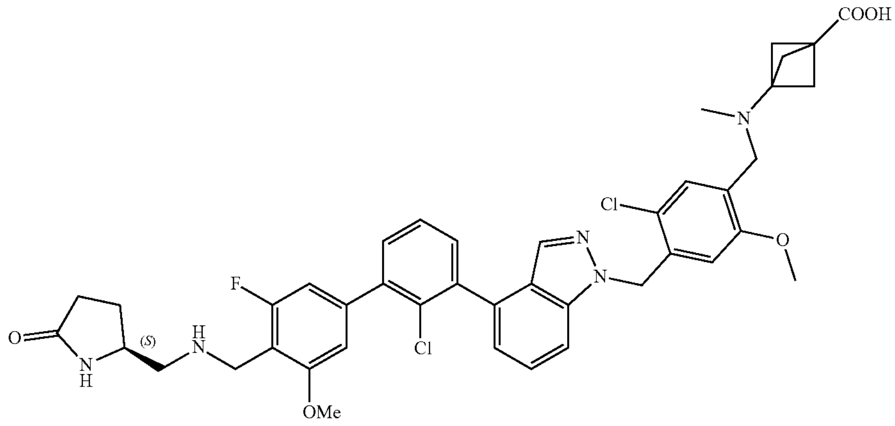
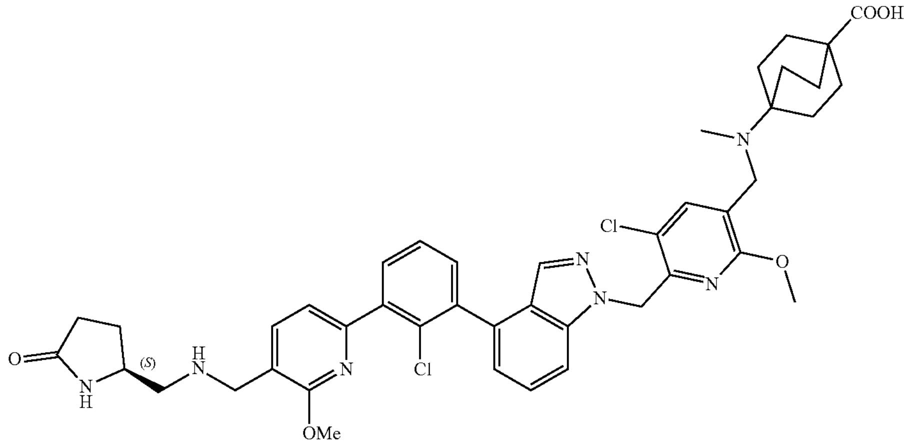

-continued
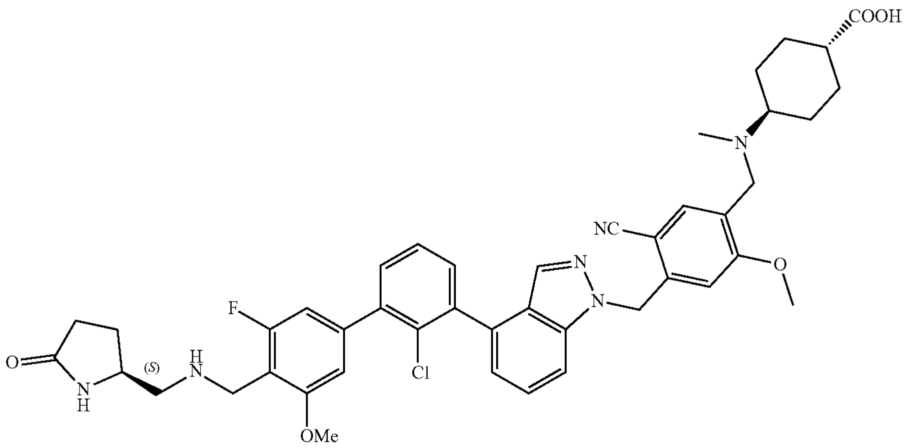
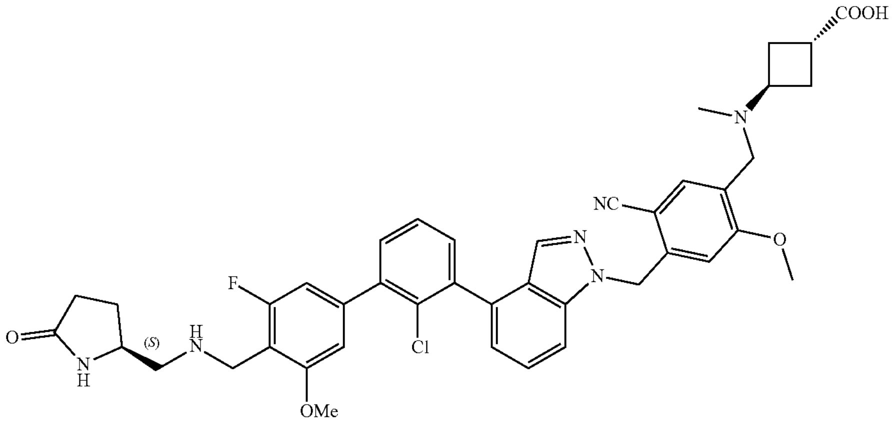
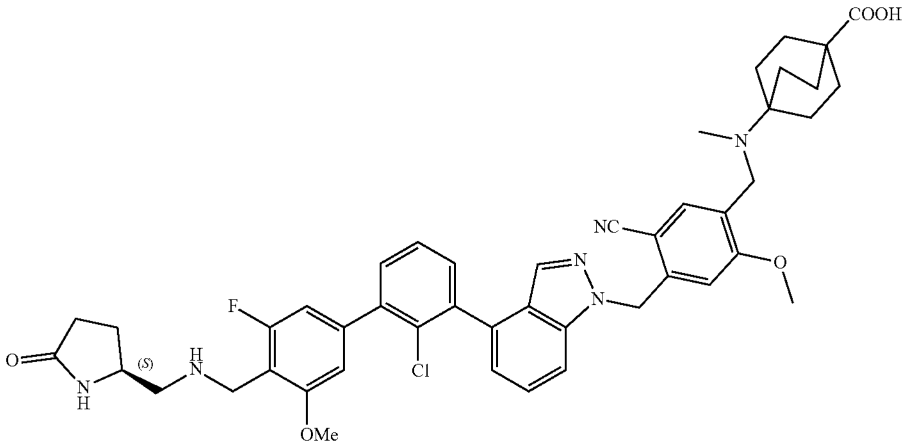

-continued
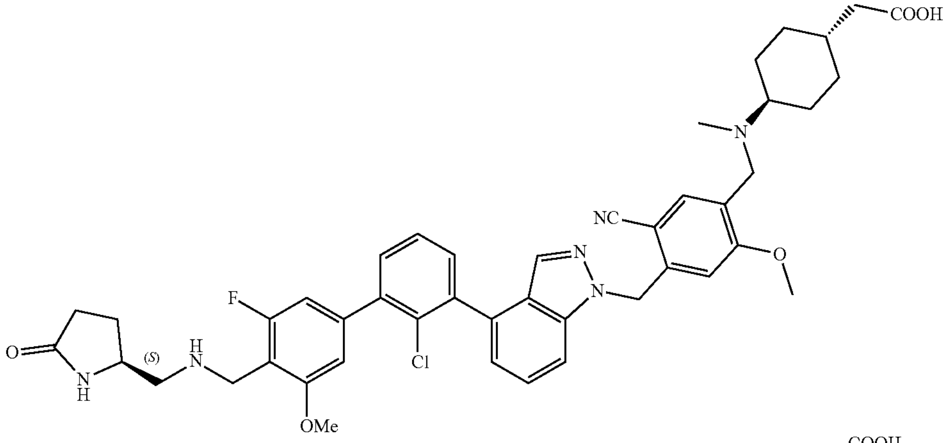
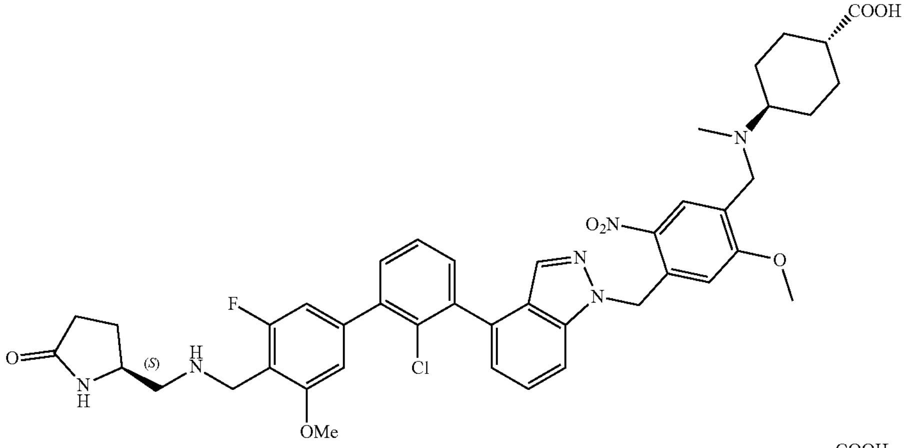
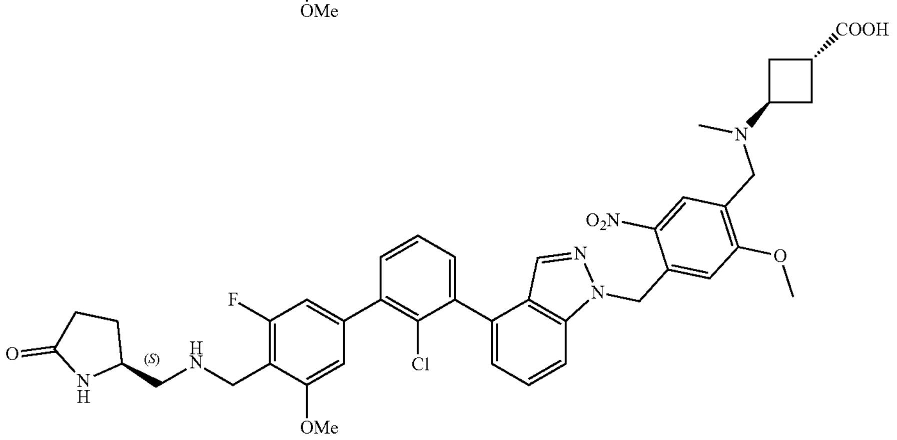
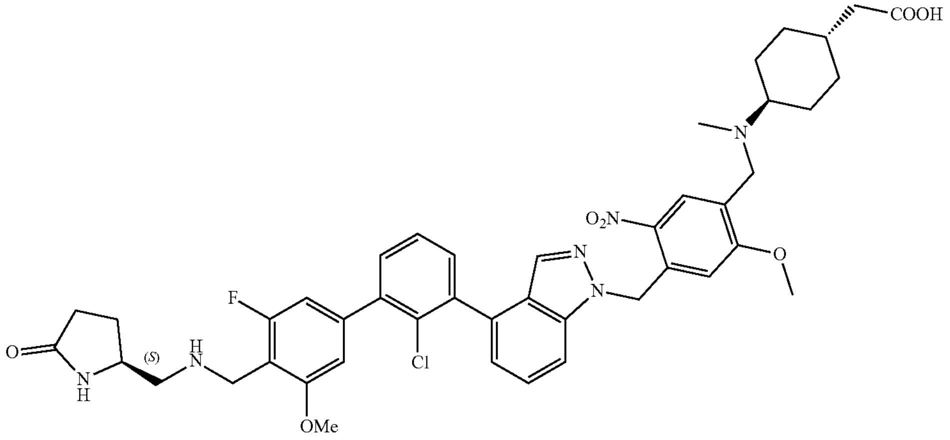

-continued
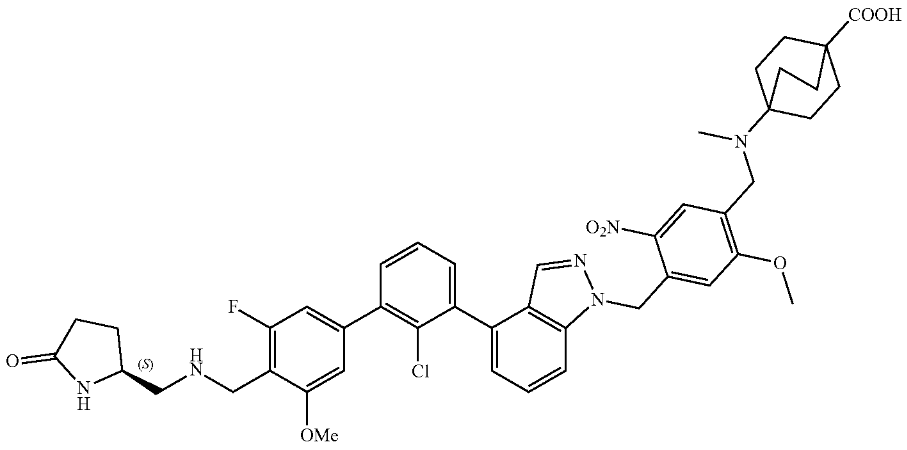
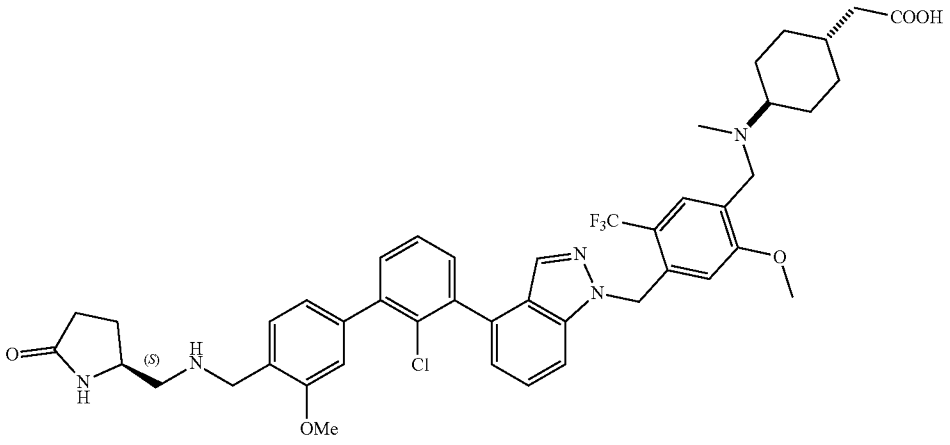
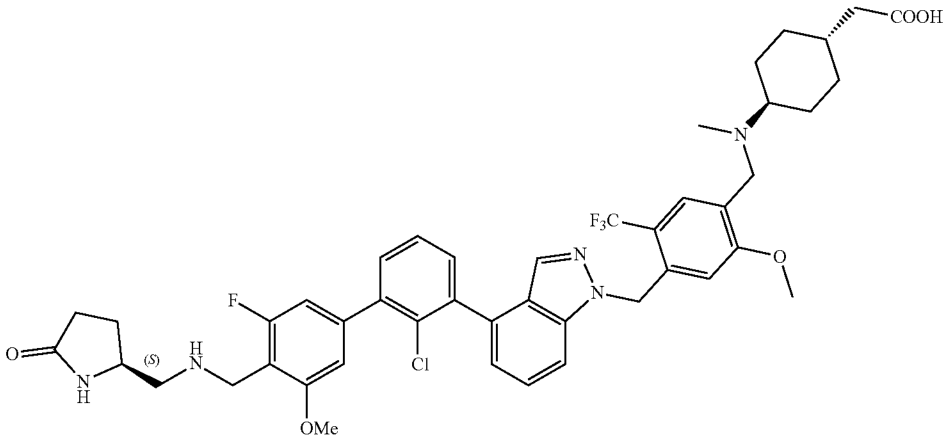

-continued
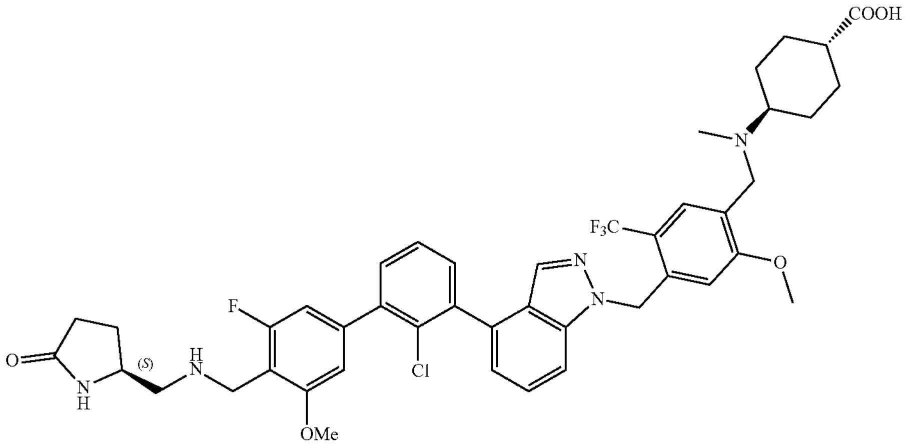
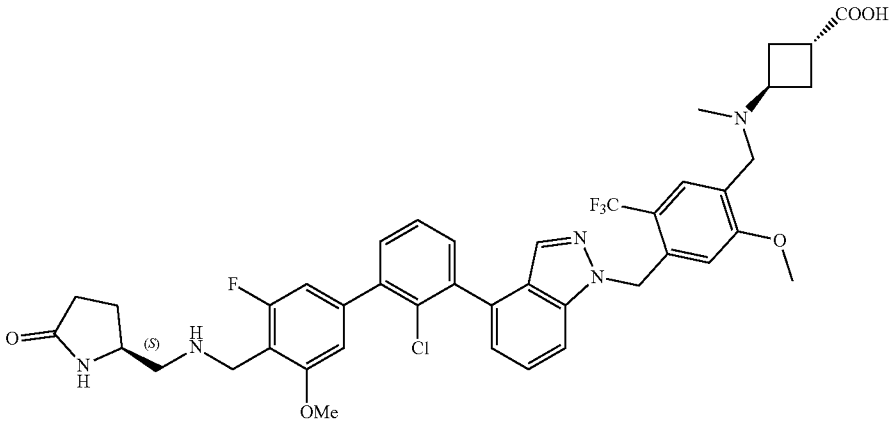
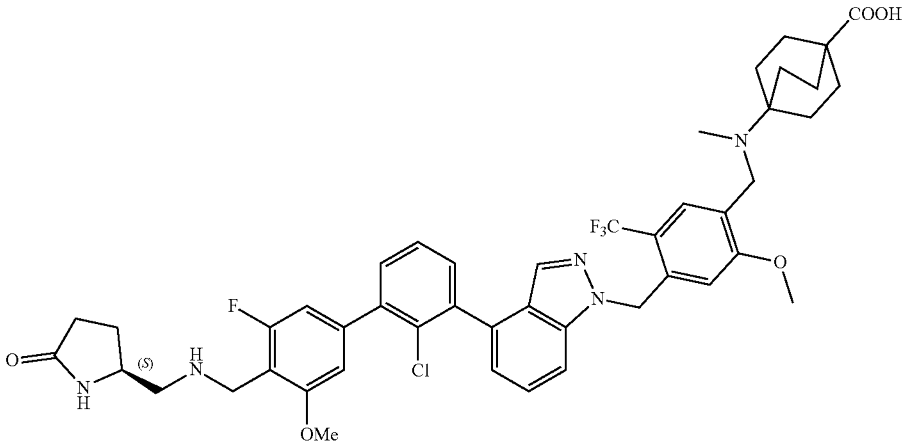

-continued
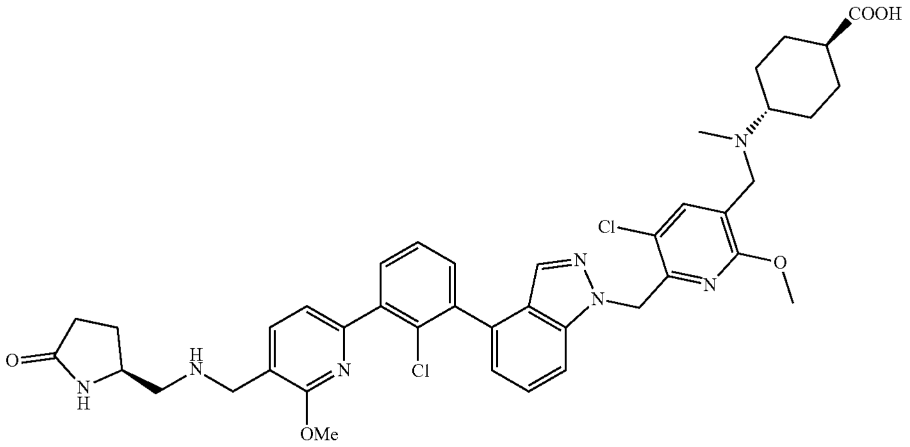
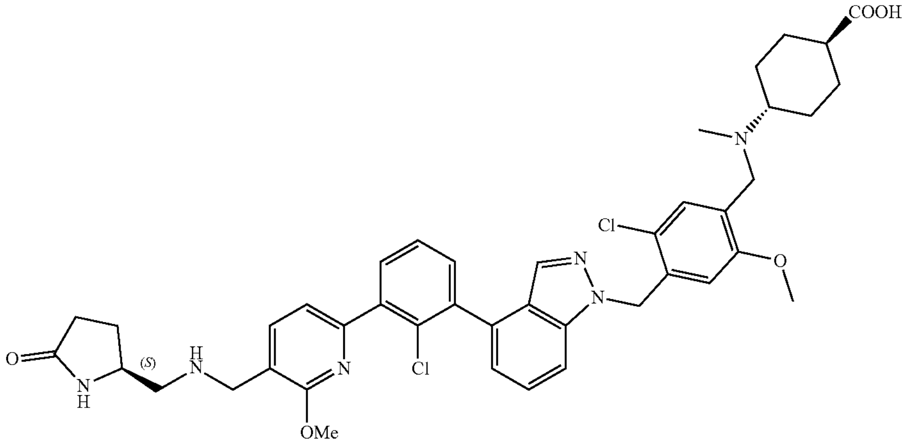
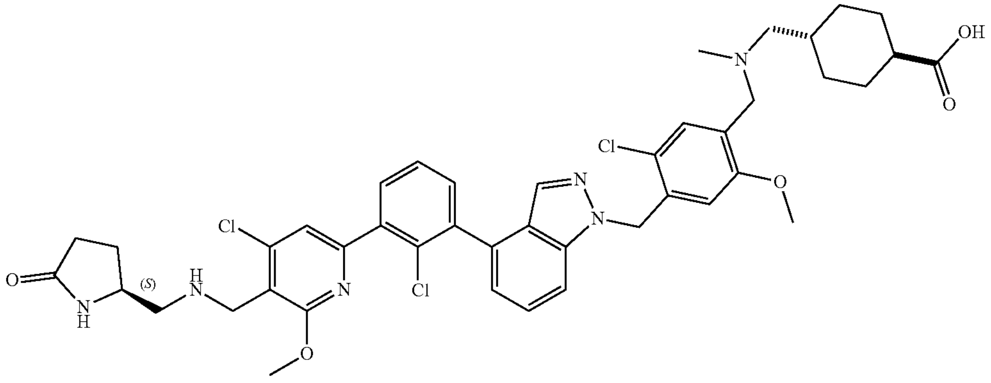
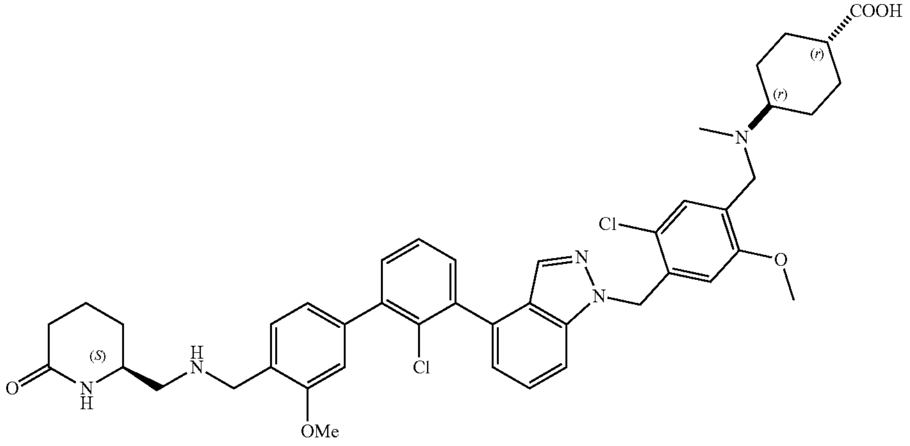

-continued
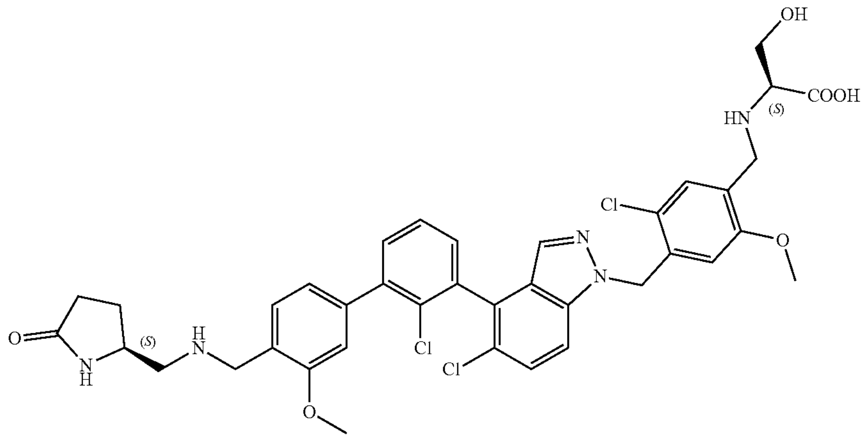
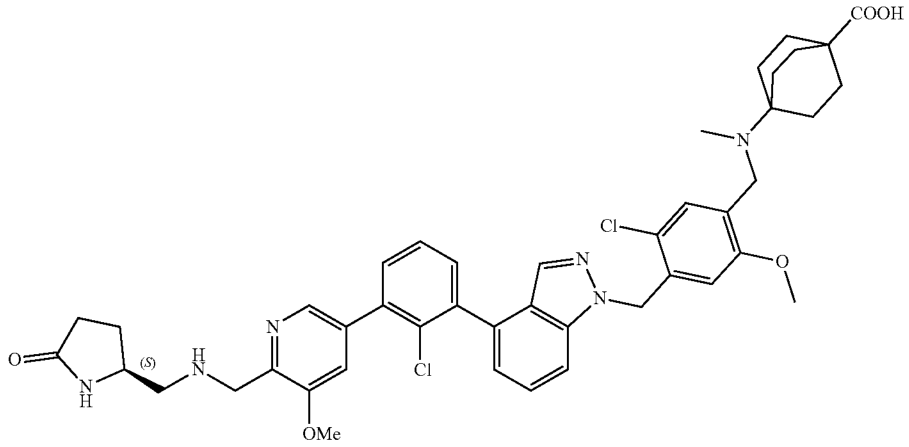
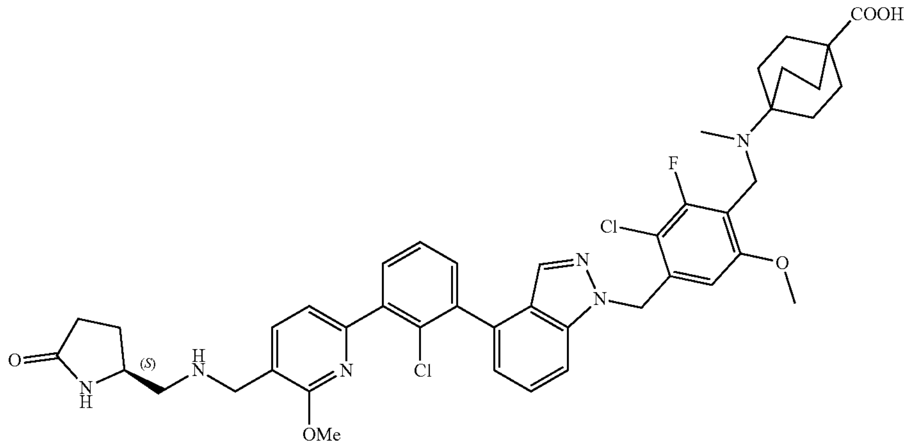

-continued
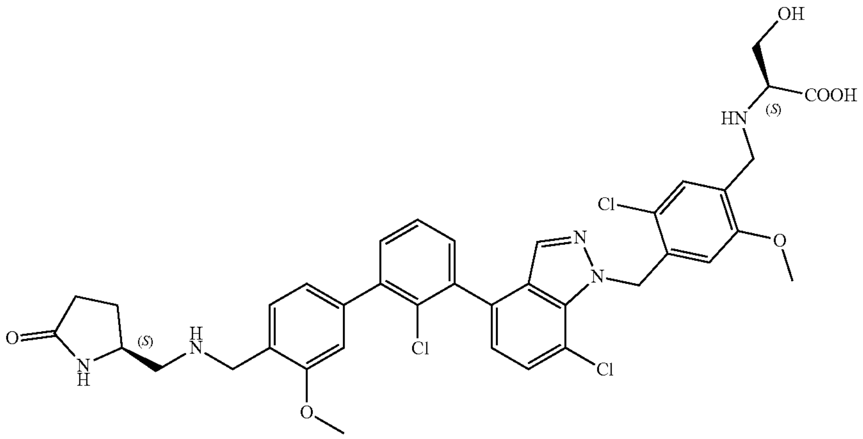
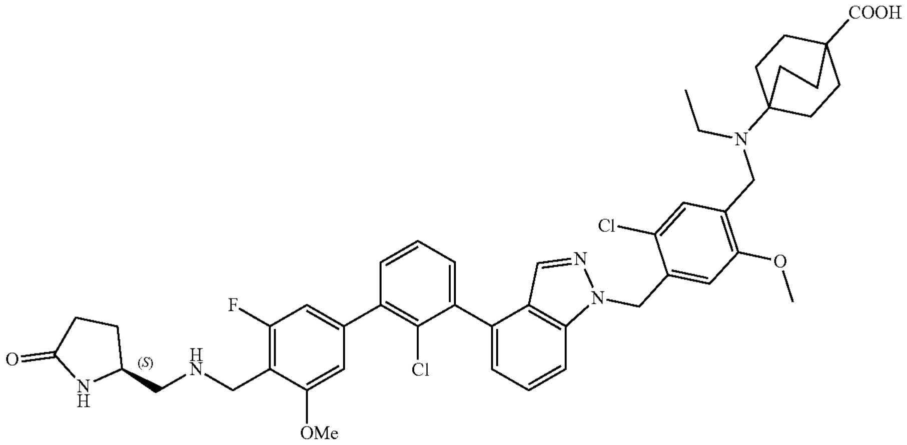
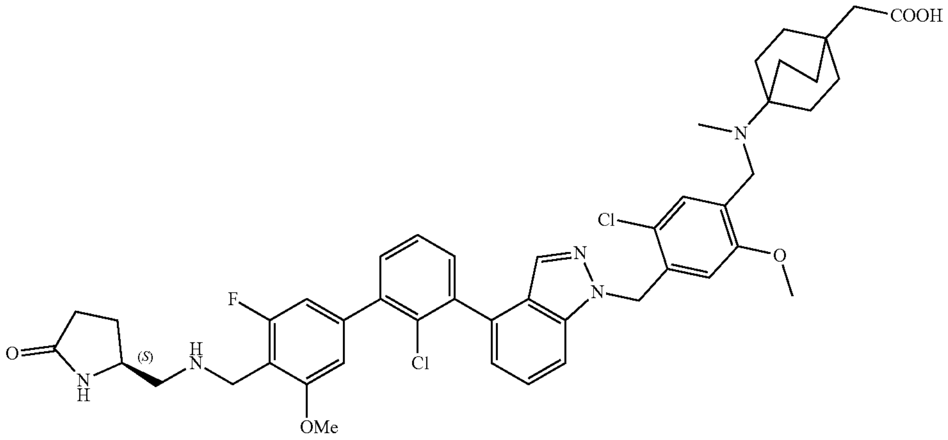

-continued
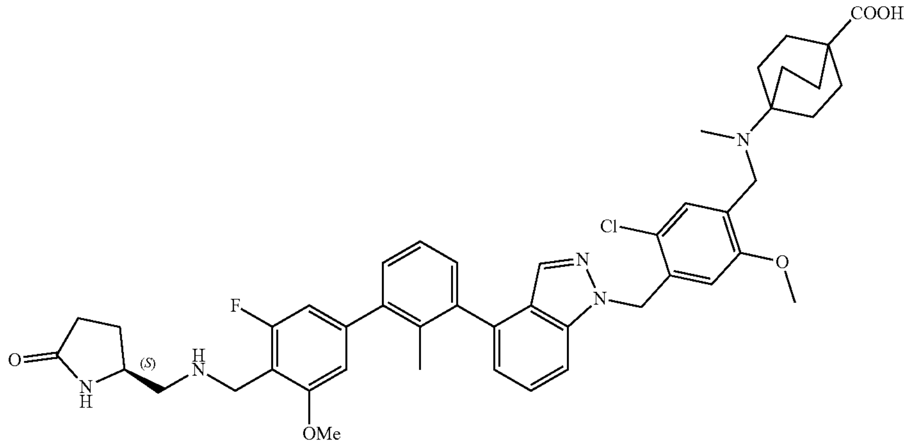
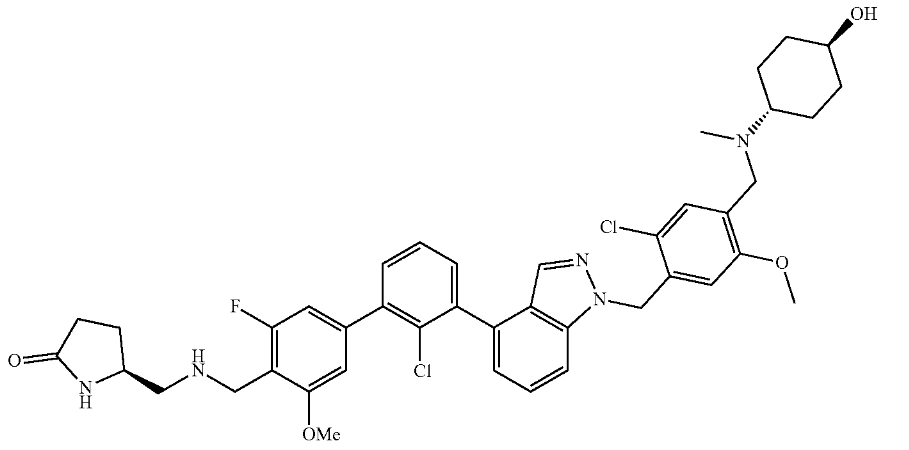
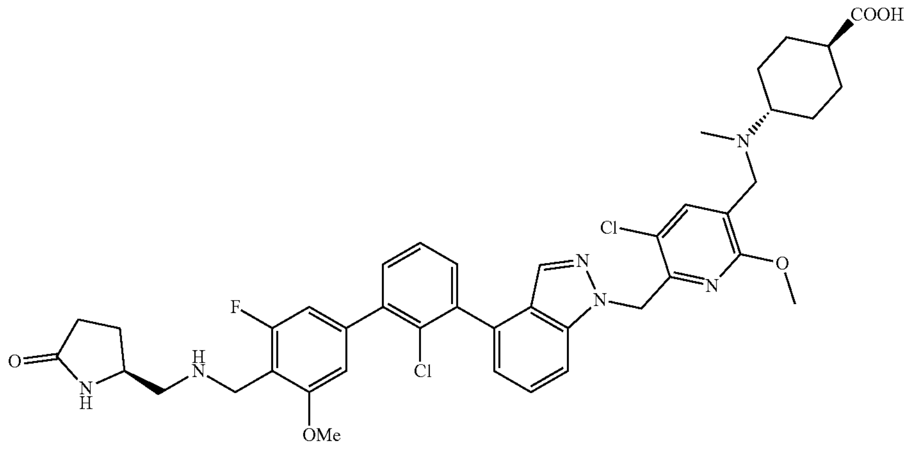

-continued
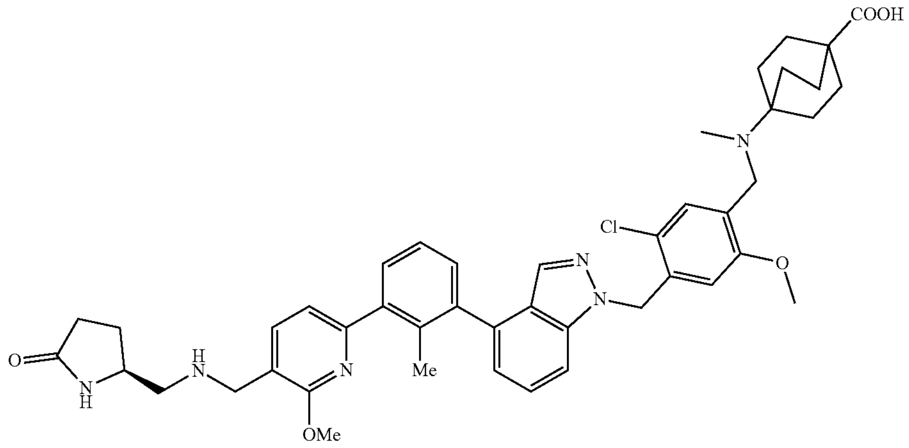
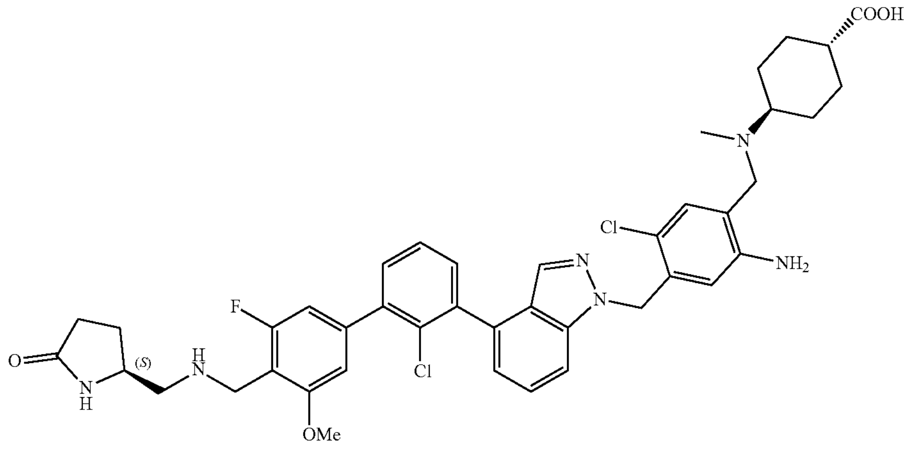
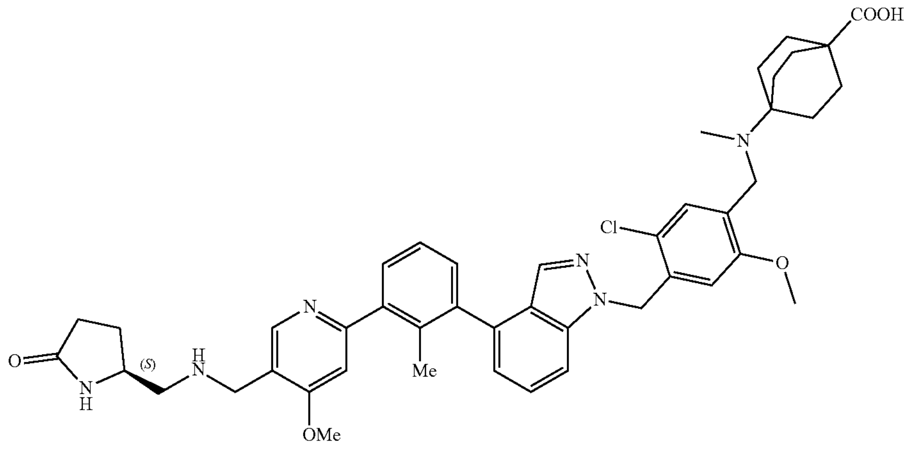

-continued
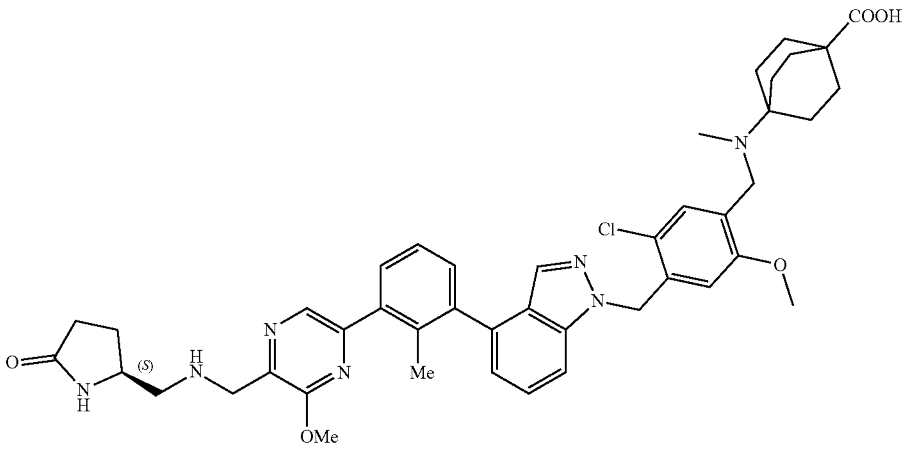
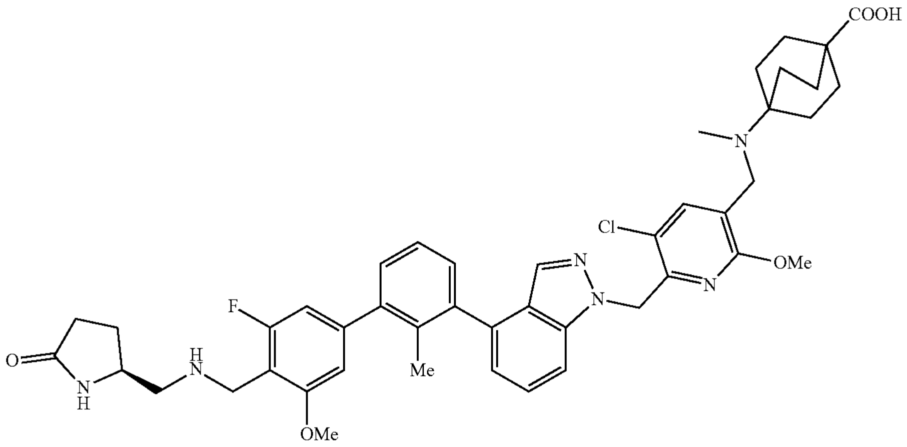
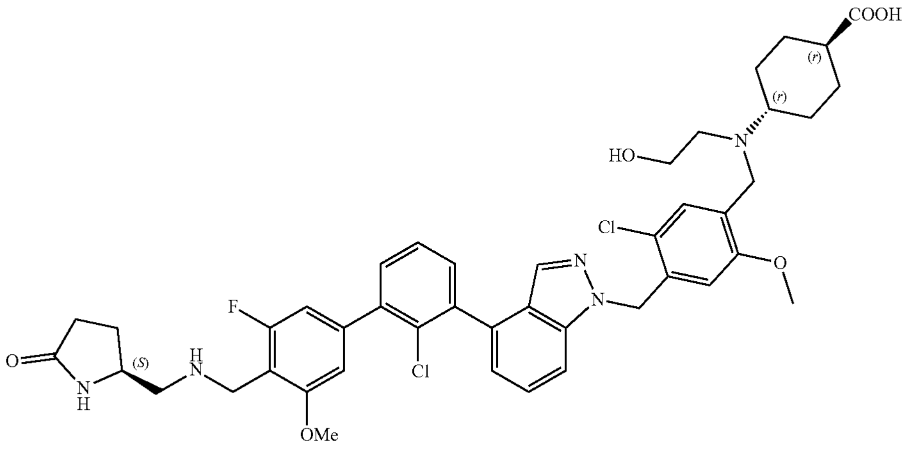

-continued
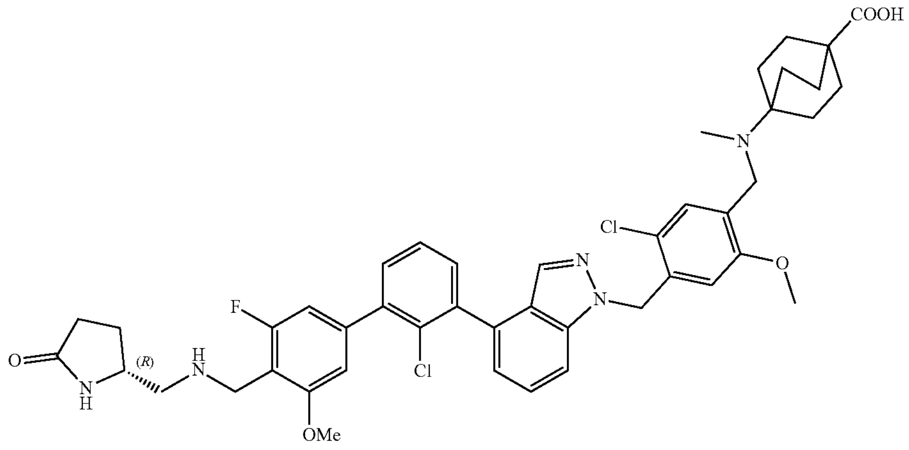
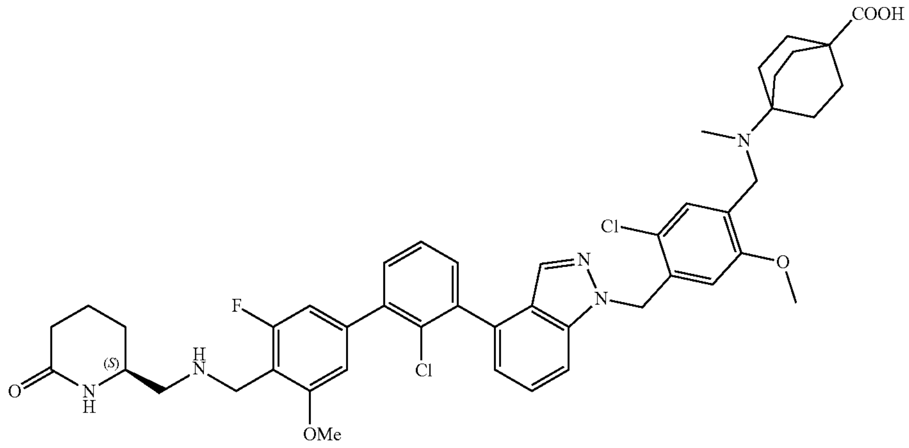
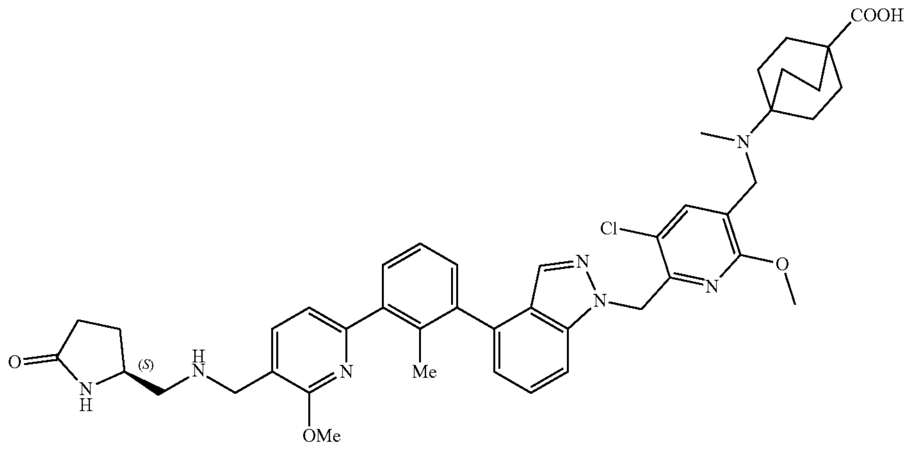

-continued

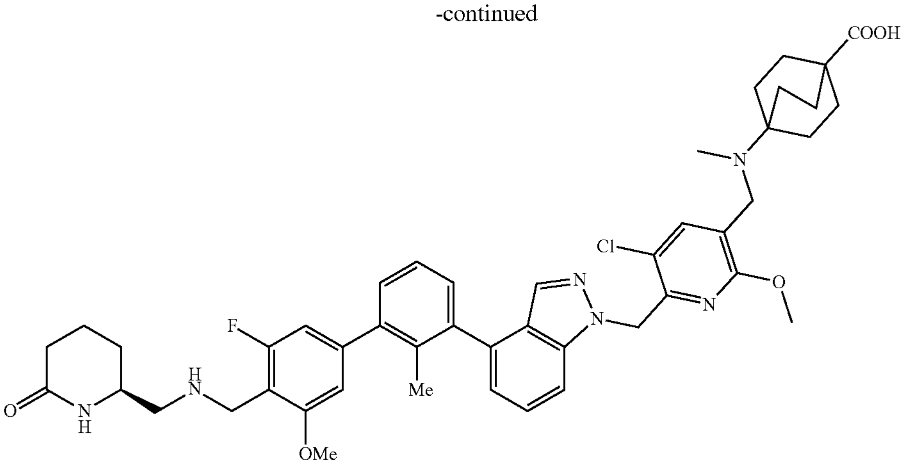

In addition, the present invention also provides a pharmaceutical composition including a compound of the present invention, and optionally further including an additional therapeutic agent and/or an immune checkpoint inhibitor. The pharmaceutical compositions of the present invention may include a pharmaceutically acceptable carrier.

In addition, the present invention also provides the use of a compound of the present invention or a pharmaceutical composition containing the compound of the present invention in the preparation of a medicament for the treatment of a disease or condition that can be treated by the inhibition of PD-L1 binding to PD-1. Preferably, the disease is selected from the group consisting of tumors, cancers, viral infections, inflammation-related diseases and autoimmune diseases.

The present invention also provides the use of a compound of the present invention or a pharmaceutical composition containing the compound of the present invention in the preparation of a medicament for the treatment of a disease or condition responsive to the inhibition of PD-L1 binding to PD-1. Preferably, the disease or condition is selected from the group consisting of tumors, cancers, viral infections, inflammation-related diseases and autoimmune diseases.

In addition, the present invention also provides a method for the treatment of a disease or condition (preferably tumors, cancers, viral infections, inflammation-related diseases, and autoimmune diseases) that can be treated by the inhibition of PD-L1 binding to PD-1, including administering to a mammal in need thereof a compound or a pharmaceutical composition of the present invention.

The present invention also provides a method for the treatment of a disease or condition responsive to the inhibition of PD-L1 binding to PD-1, including administering to a mammal in need thereof a compound or a pharmaceutical composition of the present invention. The term "disease or condition responsive to the inhibition of PD-L1 binding to PD-1" means any disease or condition in which: the disease progression may be altered by the inhibition of PD-L1 binding to PD-1, or may result in alleviation, inhibition, elimination, and amelioration of diseases, conditions, and disorders, or may prevent such diseases or conditions. Preferably, the disease or condition responsive to the inhibition of PD-L1 binding to PD-1 is selected from the group consisting of tumors, cancers, viral infections, inflammation-related diseases, and autoimmune diseases.

The present invention also provides a method for the inhibition of PD-L1 binding to PD-1, including exposing the compound or the pharmaceutical composition of the present invention to the PD-L1 and/or PD-1.

In the above-mentioned embodiments related to the compounds, pharmaceutical compositions and uses and methods of using the compounds or pharmaceutical compositions of the present invention, the compound of the present invention especially includes the form of a pharmaceutically acceptable salt thereof.

Representative examples of inflammatory diseases, autoimmune diseases, and immune-mediated diseases may include, but are not limited to, arthritis, rheumatoid arthritis, spondyloarthritis, gouty arthritis, osteoarthritis, juvenile arthritis, other arthritic conditions, lupus, systemic lupus erythematosus (SLE), skin-related diseases, psoriasis, eczema, dermatitis, allergic dermatitis, pain, lung disease, lung Inflammation, adult respiratory distress syndrome (ARDS), pulmonary sarcoidosis, chronic pulmonary inflammatory disease, chronic obstructive pulmonary disease (COPD), cardiovascular disease, atherosclerosis, myocardial infarction, congestive heart failure, myocardial ischemia-reperfusion injury, inflammatory bowel disease, Crohn's disease, ulcerative colitis, irritable bowel syndrome, asthma, Sjogren's syndrome, autoimmune thyroid disease, urticaria (rubella), multiple sclerosis, scleroderma, organ transplant rejection, xenotransplantation, idiopathic thrombocytopenic purpura (ITP), Parkinson's disease, Alzheimer's disease, diabetes-related diseases, inflammation, pelvic inflammatory diseases, allergic rhinitis, allergic bronchitis, allergic sinusitis, leukemia, lymphoma, B-cell lymphoma, T-cell lymphoma, myeloma, acute lymphocytic leukemia (ALL), chronic lymphocytic leukemia (CLL), acute myelogenous leukemia (AML), chronic myelogenous leukemia (CML), hairy cell leukemia, Hodgkin's disease, non-Hodgkin's lymphoma, multiple myeloma, myelodysplastic syndrome (MDS), myeloproliferative tumor (MPN), diffuse large B-cell lymphoma, and follicular lymphoma.

Representative examples of cancers or tumors may include, but are not limited to, skin cancer, bladder cancer, ovarian cancer, breast cancer, gastric cancer, pancreatic cancer, prostate cancer, colon cancer, lung cancer, bone cancer, brain cancer, neurocytoma, rectal cancer, colon cancer, familial adenomatous polyposis cancer, hereditary nonpolyposis colorectal cancer, esophageal cancer, lip cancer, laryngeal cancer, hypopharyngeal cancer, tongue cancer, salivary gland cancer, gastric cancer, adenocarcinoma, medullary thyroid cancer, papillary thyroid cancer, renal cancer, carcinoma of renal parenchyma, ovarian cancer, cervical cancer, corpus carcinoma, endometrial cancer, choriocarcinoma, pancreatic cancer, prostate cancer, testicular cancer, carcinoma of urinary system, melanoma, brain tumors such as glioblastoma, astrocytoma, meningioma, medulloblastoma and peripheral neuroectodermal tumors, Hodgkin's lymphoma, non-Hodgkin's lymphoma, Burkitt's lymphoma, acute lymphoblastic leukemia (ALL), chronic lymphocytic leukemia (CLL), acute myelogenous leukemia (AML), chronic myelogenous leukemia (CML), adult T-cell leukemia lymphoma, diffuse large B-cell lymphoma (DLBCL), hepatocellular carcinoma, gallbladder carcinoma, bronchial carcinoma, small cell lung carcinoma, non-small cell lung carcinoma, multiple myeloma, basal cell tumor, teratoma, retinoblastoma, choroidal melanoma, seminoma, rhabdomyosarcoma, craniopharyngioma, osteosarcoma, chondrosarcoma, myosarcoma, liposarcoma, fibrosarcoma, Ewing's sarcoma, or plasmacytoma.

When a compound of the present invention or a pharmaceutically acceptable salt thereof is administered in combination with another therapeutic agent or immune checkpoint inhibitor for the treatment of cancer or tumors, the compound of the present invention or a pharmaceutically acceptable salt thereof may provide an enhanced anticancer effect.

Representative examples of therapeutic agent for the treatment of a cancer or tumor may include, but are not limited to, cell signal transduction inhibitors, Chlorambucil, Melphalan, Cyclophosphamide, Ifosfamide, Busulfan, Carmustine, Lomustine, Streptozotocin, Cisplatin, Carboplatin, Oxaliplatin, Dacarbazine, Temozolomide, Procarbazine, Methotrexate, Fluorouracil, Cytarabine, Gemcitabine, Mercaptopurine, Fludarabine, Vinblastine, Vincristine, Vinorelbine, Paclitaxel, Docetaxel, Topotecan, Irinotecan, Etoposide, Trabectedin, Dactinomycin, Doxorubicin, Epirubicin, Daunorubicin, Mitoxantrone, Bleomycin, Mitomycin C, Ixabepilone, Tamoxifen, Flutamide, Gonadorelin Analogs, Megestrol, Prednisone, Dexamethasone, Methylprednisolone, Thalidomide, Interferon A, Calcium Folinate, Sirolimus, Sirolimus Lipide, Everolimus, Afatinib, Alisertib, Amuvatinib, Apatinib, Axitinib, Bortezomib, Bosutinib, Brivanib, Cabozantinib, Cediranib, Crenolanib, Crizotinib, Dabrafenib, Dacomitinib, Danusertib, Dasatinib, Dovitinib, Erlotinib, Foretinib, Ganetespib, Gefitinib, Ibrutinib, Icotinib, Imatinib, Iniparib, Lapatinib, Lenvatinib, Linifanib, Linsitinib, Masitinib, Momelotinib, Motesanib, Neratinib Nilotinib, Niraparib, Oprozomib, Olaparib, Pazopanib, Pictiliisib, Ponatinib, Quizartinib, Regorafenib, Rigosertib, Rucaparib, Ruxolitinib, Saracatinib, Saridegib, Sorafenib, Sunitinib, Telatinib, Tivantinib, Tivozanib, Tofacitinib, Trametinib, Vandetanib, Veliparib, Vemurafenib, Erivedge, Volasertib, Alemtuzumab, Bevacizumab, Brentuximab Vedotin, Catumaxomab, Cetuximab, Denosumab, Gemtuzumab, Ipilimumab, Nimotuzumab, Ofatumumab, Panitumumab, Rituximab, Tositumomab, Trastuzumab, PI3K inhibitors, CSF1R inhibitors, A2A and/or A2B receptor antagonists, IDO inhibitors, anti-PD-1 antibodies, LAG3 antibodies, TIM-3 antibodies, and anti-CTLA-4 antibodies, or any combination thereof.

When a compound of the present invention or a pharmaceutically acceptable salt thereof is administered in combination with another therapeutic agent for the treatment of inflammatory diseases, autoimmune diseases and immune-mediated diseases, the compound of the present invention or a pharmaceutically acceptable salt thereof may provide an enhanced therapeutic effect.

Representative examples of therapeutic agents for the treatment of inflammatory diseases, autoimmune diseases, and immune-mediated diseases may include, but are not limited to, steroidal drugs (e.g., prednisone, prednisolone, methylprednisolone, cortisone, hydroxycortisone, betamethasone, dexamethasone, etc.), methotrexate, leflunomide, anti-TNF a agents (e.g., etanercept, infliximab, adalimumab, etc.), calcineurin inhibitors (e.g., tacrolimus, pimecrolimus, etc.), and antihistamines (e.g., diphenhydramine, hydroxyzine, loratadine, ebastine, ketotifen, cetirizine, levocetirizine, fexofenadine, etc.), and at least one therapeutic agent selected therefrom may be included in the pharmaceutical compositions of the present invention.

The compound of the present invention or a pharmaceutically acceptable salt thereof can be administered orally or parenterally as an active ingredient in an effective amount ranging from 0.1 mg/kg body weight/day to 2,000 mg/kg body weight/day, preferably 1 mg/kg body weight/day to 1,000 mg/kg body weight/day in the case of mammals including humans (body weight about 70 kg), and administered in a single or four divided doses per day, or following/not following a predetermined time. The dosage of the active ingredient may be adjusted according to a number of relevant factors, such as the condition of the subject to be treated, the type and severity of the disease, the frequency of administration and the opinion of the physician). In some cases, amounts less than the above doses may be suitable. If it does not cause harmful side effects, an amount larger than the above dose can be used and the amount can be administered in divided doses per day.

In addition, the present invention also provides a method for the inhibition of PD-L1 binding to PD-1, including exposing the compound of the present invention, the pharmaceutically acceptable salt thereof or the pharmaceutical composition of the present invention to the PD-L1 and/or PD-1.

Definition of Terms:

It should be noted that, when reference is made herein to a "compound" having a specific structural formula, stereoisomers, diastereomers, enantiomers, racemic mixtures, and isotopic derivatives thereof, as well as pharmaceutically acceptable salts, solvates, and hydrates as alternative forms, are also generally contemplated. It is well known to those skilled in the art that a salt, solvate, hydrate of a compound is an alternative form of the compound that can be converted to the compound under conditions such that, as used herein, reference to a compound generally includes pharmaceutically acceptable salts thereof, and further includes solvates and hydrates thereof.

Similarly, when a compound is referred to herein, prodrugs, metabolites, and nitrogen oxides thereof are also generally included.

The pharmaceutically acceptable salt of the present invention may be formed using the an inorganic acid or an organic acid, the "pharmaceutically acceptable salt" means a salt that is, within the scope of sound medical judgment, suitable for use in contact with the tissues of humans and lower animals without undue toxicity, irritation, and allergic response, commensurate with a reasonable benefit/risk ratio. As outlined below, the salts may be prepared in situ during the final isolation and purification of the compounds of the present invention, or prepared by reacting the free base or free acid with a suitable reagent separately. For example, the free base may be reacted with a suitable acid. In addition, when the compounds of the present invention carry an acidic moiety, suitable pharmaceutically acceptable salts thereof may include metal salts, such as alkali metal salts (e.g., sodium or potassium salts); and alkaline earth metal salts (e.g., calcium or magnesium salts). Examples of pharmaceutically acceptable non-toxic acid addition salts are salts formed by amino groups with inorganic acids (e.g., hydrochloric acid, hydrobromic acid, phosphoric acid, sulfuric acid, and perchloric acid) or organic acids (e.g., acetic acid, oxalic acid, maleic acid, tartaric acid, citric acid, succinic acid, or malonic acid), or formed by using other methods known in the prior art such as ion exchange. Other pharmaceutically acceptable salts include adipate, sodium alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfonate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectate, persulfate, 3-phenylpropionate, phosphate, picrate, pivalate, propionate, stearate, succinate, sulfate, tartrate, thiocyanate, p-toluenesulfonate, undecanoate, and valerate. Representative alkali metal or alkaline earth metal salts include salts of sodium, lithium, potassium, calcium, and magnesium. Other pharmaceutically acceptable salts include, nontoxic ammonium salts (where appropriate), quaternary ammonium salts, and ammonium cations formed with counterions, for example, halides, hydroxides, carboxylates, sulfates, phosphates, nitrates, lower alkyl sulfonates, and aryl sulfonates.

The pharmaceutically acceptable salts of the present invention may be prepared by a conventional method, for example, by dissolving the compound of the present invention in a water-miscible organic solvent (e.g., acetone, methanol, ethanol, and acetonitrile), adding an excess of an aqueous organic or inorganic acid thereto to precipitate the salt from the resulting mixture, removing the solvent and remaining free acid therefrom, and then isolating the precipitated salt.

The precursors or metabolites of the present invention may be those known in the art as long as the precursors or metabolites are converted into compounds by metabolism in vivo. For example, "prodrugs" refer to those of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use. The term "prodrugs" refer to compounds which yield the parent compounds of the above-mentioned formulae rapidly through transformation in vivo, for example, through metabolism in vivo, or N-demethylation of a compound of the present invention.

"Solvate" of the present invention means a physical association of a compound of the present invention with one or more solvent molecules (whether organic or inorganic). The physical association includes hydrogen bonding. In some cases, for example when one or more solvent molecules are incorporated in the crystal lattice of the crystalline solid, the solvate will be capable of being isolated. The solvent molecules in the solvate may be present in a regular and/or disordered arrangement. Solvates may include stoichiometric or non-stoichiometric solvent molecules. "Solvate" encompasses both solution-phase and isolatable solvates. Exemplary solvates include, but are not limited to, hydrates, ethanolates, methanolates, and isopropanolates. Methods of solvation are well known in the art.

The "stereoisomerism" of the present invention is divided into conformational isomerism and configurational isomerism, and the configurational isomerism can also be divided into cis-trans isomerism and optical isomerism (i.e., optical isomerism). The conformational isomerism refers to a stereoisomerism phenomenon in which the rotation or distortion of the carbon-carbon single bond of an organic molecule with a certain configuration makes the atoms or atomic groups of the molecule produce different arrangements in space, and common examples include the structures of alkanes and cycloalkanes, such as chair and boat conformations as found in the cyclohexane structure. "Stereoisomers" means when the compounds of the present invention contain one or more asymmetric centers, thus they can be served as racemates and racemic mixtures, single enantiomers, diastereomeric mixtures, and single diastereomers. The compounds of the present invention may have asymmetric centers, each of which produces two optical isomers, and the scope of the present invention includes all possible optical isomers and diastereomeric mixtures and pure or partially pure compounds. The compounds of the present invention may exist in the form of tautomers, which have different linking points of hydrogen through the displacement of one or more double bonds. For example, ketone and its enol form are keto-enol tautomers. Each tautomer and mixtures thereof are included in the compounds of the present invention. All enantiomers, diastereomers, racemates, mesomers, cis-trans-isomers, tautomers, geometric isomers, epimers, and mixtures thereof of the compounds of Formula (I) are included within the scope of the present invention.

An "isotopic derivative" of the present invention refers to a molecule in which a compound is labeled with an isotope in this patent. Isotopes commonly used as isotopic labels are: hydrogen isotopes, $^{2}H$ and $^{3}H$; carbon isotope: $^{11}C$, $^{13}C$ and $^{14}C$; chlorine isotope: $^{35}Cl$ and $^{37}Cl$; fluorine isotope: $^{18}F$; iodine isotope: $^{123}I$ and $^{125}I$; nitrogen isotopes: $^{13}N$ and $^{15}N$; oxygen isotopes: $^{15}O$, $^{17}O$ and $^{18}O$ and sulfur isotope $^{35}S$. These isotopically labeled compounds can be used to study the distribution of pharmaceutical molecules in tissues. Deuterium $^{2}H$ and carbon $^{13}C$, in particular, are more widely used due to their ease of labeling and ease of detection. Substitution of certain heavy isotopes, such as heavy hydrogen ($^{2}H$), may enhance metabolic stability, prolong the half-life, and provide therapeutic advantages resulting from reduced dosage. Generally, starting from the labeled starting materials, isotopically-labeled compounds are synthesized by using known synthesis techniques in the same way as the synthesis of non-isotopically labeled compounds.

The compound or pharmaceutical compositions of the present invention may be formulated into dosage forms, such as tablets, granules, powders, capsules, syrups, emulsions, microemulsions, solutions or suspensions, for oral or parenteral administration (including intramuscular, intravenous and subcutaneous routes, and intratumoral injection) according to any of the conventional methods.

The pharmaceutical compositions of the present invention for oral administration may be prepared by mixing the active ingredient with carriers such as: cellulose, calcium silicate, corn starch, lactose, sucrose, dextrose, calcium phosphate, stearic acid, magnesium stearate, calcium stearate, gelatin, talc, surfactants, suspending agents, emulsifying agents, and diluents. Examples of carriers employed in the injectable compositions of the present invention consist of water, saline solutions, dextrose solutions, glucose-like solutions, alcohols, glycols, ethers (e.g., polyethylene glycol 400), oils, fatty acids, fatty acid esters, glycerides, surfactants, suspending agents, and emulsifying agents.

Additional features of the present invention will become apparent from the description of exemplary embodiments of the present invention which are presented for purposes of illustration and are not intended to be limiting thereof, and the following examples are prepared, isolated and characterized using the methods disclosed herein.

Terms used in the present invention, including the specification and claims, are defined as follows, unless otherwise indicated. It must be noted that, in the description and the appended claims, the singular forms "a", "an", and "the" include plural referents unless the context clearly dictates otherwise. If not stated otherwise, conventional methods of mass spectrometry, nuclear magnetic, HPLC, protein chemistry, biochemistry, recombinant DNA techniques and pharmacology are used. In this use, the use of "or" or "and" means "and/or" if not stated otherwise.

Throughout the specification and claims, a given chemical formula or name shall encompass all stereo and optical isomers and racemates in which such isomers exist. Unless otherwise indicated, all chiral (enantiome and diastereoisomer) and racemic forms are within the scope of the present invention. Many geometric isomers of C═C double bonds, C═N double bonds, and ring systems may also be present in the compounds, and all the above-mentioned stable isomers are encompassed in the present invention. Cis- and trans- (or E- and Z-) geometric isomers of the compounds of the present invention are described herein and may be isolated as mixtures of isomers or as separated isomeric forms. The compounds of the present invention may be isolated in optically active or racemic forms. All methods for preparing the compounds of the present invention and intermediates prepared therein are considered part of the present invention. In preparing enantiomeric or diastereomeric products, they can be isolated by conventional methods, for example, by chromatography or fractional crystallization. Depending on the process conditions, the final products of the present invention are obtained in free (neutral) or salt form. Both the free forms and salts of these end products are within the scope of the present invention. If desired, one form of the compound may be converted to another form. The free base or acid may be converted to a salt; the salt may be converted to the free compound or another salt; mixtures of isomeric compounds of the present invention may be isolated into the individual isomers. The compounds, free forms and salts thereof of the present invention, may exist in a variety of tautomeric forms in which hydrogen atoms are transposed onto other parts of the molecule and the chemical bonds between the atoms of the molecule are thus rearranged. It is to be understood that all tautomeric forms which may exist are included in the present invention.

Unless otherwise defined, the definitions of substituents of the present invention are each independent and not interrelated, e.g., for $R^a$ (or $R^b$) in substituents, they are each independent in the definition of different substituents. Specifically, when a definition of $R^a$ (or $R^b$) is selected in a substituent, it does not mean that $R^a$ (or $R^b$) has the same definition in other substituents. More specifically, for example (a non-exhaustive list) for $NR^aR^b$, when the definition of $R^a$ (or $R^b$) is selected from hydrogen, it does not mean that in —C(O)—$NR^aR^b$, $R^a$ (or $R^b$) must be hydrogen.

Unless otherwise defined, when a substituent is labeled "optionally substituted", the substituent is selected from, for example, the following substituents consisting of alkyl, cycloalkyl, aryl, heterocyclyl, halogen, hydroxy, alkoxy, oxo, alkanoyl, aryloxy, alkanoyloxy, amino, alkylamino, arylamino, arylalkylamino, disubstituted amine group (in which two amino substituents are selected from alkyl, aryl or arylalkyl), alkanoylamino, aroylamino, aralkanoylamino, substituted alkanoylamino, substituted arylamino, substituted aralkanoylamino, thio, alkylthio, arylthio, arylalkylthio, arylthiocarbonyl, arylalkylthiocarbonyl, alkylsulfonyl, arylsulfonyl, arylalkylsulfonyl, sulfonamido such as —$SO_2NH_2$, substituted sulfonamido, nitro, cyano, carboxy, carbamoyl such as —$CONH_2$, substituted carbamoyl such as —CONH alkyl, —CONH aryl, —CONH arylalkyl or the case where there are two substituents selected from alkyl, aryl or arylalkyl on the nitrogen, alkoxycarbonyl, aryl, substituted aryl, guanidino, heterocyclyl such as indolyl, imidazolyl, furanyl, thienyl, thiazolyl, pyrrolidinyl, pyridyl, pyrimidinyl, pyrrolidinyl, piperidinyl, morpholinyl, piperazinyl, and homopiperazinyl, and substituted heterocyclyl.

As used herein, the term "alkyl" or "alkylene" is intended to include both branched and straight chain saturated aliphatic hydrocarbon groups having the specified number of carbon atoms. For example, "C1-C6 alkyl" denotes an alkyl group having 1 to 6 carbon atoms. Examples of alkyl groups include, but are not limited to, methyl (Me), ethyl (Et), n-propyl, isopropyl, n-butyl, isobutyl, tert-butyl, n-pentyl, isopentyl, and neopentyl.

The term "alkenyl" denotes a straight or branched chain hydrocarbon group containing one or more double bonds and typically 2 to 20 carbon atoms in length. For example, "C2-C6 alkenyl" contains 2 to 6 carbon atoms. Alkenyl groups include, but are not limited to, for example, ethenyl, propenyl, butenyl, and 1-methyl-2-buten-1-yl.

The term "alkynyl" denotes a straight or branched chain hydrocarbon group containing one or more triple bonds and typically 2 to 20 carbon atoms in length. For example, "C2-C6 alkynyl" contains 2 to 6 carbon atoms. Representative alkynyl groups include, but are not limited to, for example, ethynyl, 1-propynyl, and 1-butynyl.

The term "alkoxy" or "alkyloxy" refers to —O-alkyl. "C1-C6 alkoxy" (or alkyloxy) is intended to include C1, C2, C3, C4, C5, and C6 alkoxy. Examples of alkoxy groups include, but are not limited to, methoxy, ethoxy, propoxy (e.g., n-propoxy and isopropoxy), and t-butoxy. Similarly, "alkylthio" or "thioalkoxy" means an alkyl group, as defined above, with the specified number of carbon atoms linked via a sulfur bridge; for example, methyl-S- and ethyl-S—.

The term "carbonyl" refers to an organic functional group (C═O) composed of two carbon and oxygen atoms linked by a double bond.

The term "aryl", alone or as part of a larger moiety such as "aralkyl", "aralkoxy", or "aryloxyalkyl", refers to a monocyclic, bicyclic, or tricyclic ring system having a total of 5 to 12 ring members, where at least one ring in the system is aromatic and where each ring in the system contains 3 to 7 ring members. In certain embodiments of the present invention, "aryl" refers to an aromatic ring system including, but not limited to, phenyl, biphenyl, indanyl, 1-naphthyl, 2-naphthyl, and tetrahydronaphthyl. The term "aralkyl" or "arylalkyl" refers to an alkyl residue attached to an aryl ring. Non-limiting examples include benzyl, and phenethyl. The fused aryl group may be attached to another group at a suitable position on the cycloalkyl ring or the aromatic ring. For example, a dashed line drawn from a ring system indicates that the bond may be attached to any suitable ring atom.

The term "cycloalkyl" refers to a monocyclic or bicyclic alkyl group. Monocyclic alkyl refers to C3-C8 cyclic alkyl including, but not limited to, cyclopropyl, cyclobutyl, cyclopentyl, cyclohexyl, and norbornyl. Branched cycloalkyl such as 1-methylcyclopropyl and 2-methylcyclopropyl are included in the definition of "cycloalkyl". Bicyclic alkyl includes bridged, spiro, or fused cycloalkyl.

The term "cycloalkenyl" refers to a monocyclic or bicyclic alkenyl group. Monocyclic alkenyl refers to C3-C8 cyclic alkenyl including, but not limited to, cyclopropenyl, cyclobutenyl, cyclopentenyl, cyclohexenyl, and norbornenyl. Branched cycloalkenyl such as 1-methylcyclopropenyl and 2-methylcyclopropenyl are included in the definition of "cycloalkenyl". Bicyclic alkenyl includes bridged, spiro or fused cyclic alkenyl.

"Halo" or "halogen" includes fluoro, chloro, bromo and iodo. "Haloalkyl" is intended to include both branched and straight-chain saturated aliphatic hydrocarbon groups having the specified number of carbon atoms and substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" groups intended to include branched and straight chain saturated aliphatic hydrocarbon groups having the specified number of carbon atoms and substituted with one or more fluorine atoms.

"Haloalkoxy" or "haloalkyloxy" denotes a haloalkyl group, as defined above, having the indicated number of carbon atoms linked via an oxygen bridge. For example, "C1-C6 haloalkoxy" is intended to include C1, C2, C3, C4, C5, and C6 haloalkoxy. Examples of haloalkoxy include, but are not limited to, trifluoromethoxy, 2,2,2-trifluoroethoxy, and pentafluoroethoxy. Similarly, "haloalkylthio" or "thiohaloalkoxy" denotes a haloalkyl group, as defined above, having the indicated number of carbon atoms linked via a sulfur bridge; for example, trifluoromethyl-S- and pentafluoroethyl-S—.

In the present disclosure, the expression Cx1-Cx2 is used when referring to some substituent groups, which means that the number of carbon atoms in the substituent group may be x1 to x2. For example, C0-C8 means that the group contains 0, 1, 2, 3, 4, 5, 6, 7 or 8 carbon atoms, C1-C8 means that the group contains 1, 2, 3, 4, 5, 6, 7 or 8 carbon atoms, C2-C8 means that the group contains 2, 3, 4, 5, 6, 7 or 8 carbon atoms, C3-C8 means that the group contains 3, 4, 5, 6, 7 or 8 carbon atoms, C4-C8 means that the group contains 4, 5, 6, 7 or 8 carbon atoms, C0-C6 means that the group contains 0, 1, 2, 3, 4, 5 or 6 carbon atoms, $C_1$-$C_6$ means that the group contains 1, 2, 3, 4, 5 or 6 carbon atoms, $C_2$-$C_6$ means that the group contains 2, 3, 4, 5 or 6 carbon atoms, and $C_3$-$C_6$ means that the group contains 3, 4, 5 or 6 carbon atoms.

In the present disclosure, the expression "x1-x2 membered ring" is used when referring to cyclic groups such as aryl, heteroaryl, cycloalkyl and heterocycloalkyl, which means that the number of ring atoms of the group may be x1 to x2. For example, the 3- to 12-membered cyclic group may be a 3, 4, 5, 6, 7, 8, 9, 10, 11, or 12 membered ring, the number of ring atoms of which may be 3, 4, 5, 6, 7, 8, 9, 10, 11, or 12; the 3- to 6-membered ring means that the cyclic group may be a 3, 4, 5 or 6 membered ring, the number of ring atoms of which may be 3, 4, 5 or 6; the 3- to 8-membered ring means that the cyclic group may be a 3, 4, 5, 6, 7 or 8 membered ring, the number of ring atoms of which may be 3, 4, 5, 6, 7 or 8; the 3- to 9-membered ring means that the cyclic group may be a 3, 4, 5, 6, 7, 8 or 9 membered ring, the number of ring atoms of which may be 3, 4, 5, 6, 7, 8 or 9; the 4- to 7-membered ring means that the cyclic group may be a 4, 5, 6 or 7 membered ring, the number of ring atoms of which may be 4, 5, 6 or 7; the 5- to 8-membered ring means that the cyclic group may be a 5, 6, 7 or 8 membered ring, the number of ring atoms of which may be 5, 6, 7 or 8; the 5- to 12-membered ring means that the cyclic group may be a 5, 6, 7, 8, 9, 10, 11 or 12 membered ring, the number of ring atoms of which may be 5, 6, 7, 8, 9, 10, 11 or 12; and the 6- to 12-membered ring means that the cyclic group may be a 6, 7, 8, 9, 10, 11 or 12 membered ring, the number of ring atoms of which may be 6, 7, 8, 9, 10, 11 or 12. The ring atom may be a carbon atom or a heteroatom, for example, a heteroatom selected from N, O and S. When the ring is a heterocycle, the heterocycle may contain 1, 2, 3, 4, 5, 6, 7, 8, 9, 10 or more ring heteroatoms, for example, a heteroatom selected from N, O and S.

In the present invention, one or more halogens may each independently be selected from fluorine, chlorine, bromine, and iodine.

The term "heteroaryl" means a stable 3-, 4-, 5-, 6-, or 7-membered aromatic monocyclic or aromatic bicyclic or 7-, 8-, 9-, 10-, 11-, 12-membered aromatic polycyclic heterocycle, which is fully unsaturated, partially unsaturated, and contains carbon atoms and 1, 2, 3 or 4 heteroatoms independently selected from N, O and S; and includes any polycyclic group in which any heterocycle defined above is fused to a benzene ring. The nitrogen and sulfur heteroatoms may optionally be oxidized. The nitrogen atom is substituted or unsubstituted (i.e., N or NR, where R is H or another substituent if defined). The heterocycle may be attached to its pendant group at any heteroatom or carbon atom that results in a stable structure. If the resulting compound is stable, the heterocyclyl groups described herein may be substituted on a carbon or nitrogen atom. The nitrogen in the heterocycle may be optionally quaternized. Preferably, when the total number of S and O atoms in the heterocycle exceeds 1, then these heteroatoms are not adjacent to each other. Preferably, the total number of S and O atoms in the heterocycle is not greater than 1. When the term "heterocycle" is used, it is intended to include heteroaryl. Examples of heteroaryls include, but are not limited to, acridinyl, azetidinyl, azocinyl, benzimidazolyl, benzofuranyl, benzothiofuranyl, benzothienyl, benzoxazolyl, benzoxazolinyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1,5,2-dithiazinyl, dihydrofuro [2,3-b]tetrahydrofuranyl, furanyl, furazanyl, imidazolidinyl, imidazolinyl, imidazolyl, 1H-indazolyl, imidazopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinyl, perimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridyl, thienothiazolyl, thienooxazolyl, thienoimidazolyl, thienyl, triazinyl, 1,2,3-triazolyl, 1,2,4-triazolyl, 1,2,5-triazolyl, 1,3,4-triazolyl and xanthenyl, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl and 1,2,3,4-tetrahydro-quinazolinyl. The term "heteroaryl" may also include biaryl structures formed from "aryl" and monocyclic "heteroaryl" as defined above, for example, but not limited to "-phenylbipyridyl-", "-phenylbipyrimidinyl", "-pyridylbiphenyl", "-pyridylbipyrimidinyl-", "-pyrimidinylbiphenyl-"; where the present invention also includes fused and spiro compounds containing, for example, the above-mentioned heterocycles.

As used herein, the term "heterocycloalkyl" refers to a monocyclic heterocycloalkyl system, or a bicyclic heterocycloalkyl system, and also includes spiroheterocycles or bridged heterocycloalkyl groups. The monocyclic heterocycloalkyl refers to a saturated or unsaturated but not aromatic 3- to 8-membered cyclic alkyl system containing at least one heteroatom selected from O, N, S, or P. The bicyclic heterocycloalkyl system refers to a heterocycloalkyl fused with a phenyl, or a cycloalkyl, or a cycloalkenyl, or a heterocycloalkyl, or a heteroaryl.

As used herein, the term "bridged cycloalkyl" refers to polycyclic compounds that share two or more carbon atoms, including bicyclic bridged cyclic hydrocarbons and polycyclic bridged cyclic hydrocarbons. The former are composed of two alicyclic rings sharing more than two carbon atoms; the latter are a bridged cyclic hydrocarbons consisting of more than three rings.

As used herein, the term "spirocycloalkyl" refers to polycyclic hydrocarbons that share one carbon atom (referred to as a spiro atom) between single rings.

As used herein, the term "bridged cycloheteryl" refers to polycyclic compounds that share two or more carbon atoms, and contain at least one atom selected from O, N, or S. including bicyclic bridged heterocycles and polycyclic bridged heterocycles.

As used herein, the term "heterospirocyclyl" refers to polycyclic hydrocarbons that share one carbon atom (referred to as a spiro atom) between single rings, and contain at least one heteroatom selected from O, N, or S.

As used herein, the term "substituted" means that at least one hydrogen atom is replaced with a non-hydrogen group, provided that normal valency is maintained and that the substitution results in a stable compound. As used herein, the ring double bond is a double bond (e.g., C═C, C═N, or N═N) formed between two adjacent ring atoms.

In the case where nitrogen atoms (e.g., amines) are present on the compounds of the present invention, these nitrogen atoms may be converted to N-oxides by treatment with an oxidizing agent (e.g., mCPBA and/or hydrogen peroxide) to obtain other compounds of the present invention. Thus, the nitrogen atoms shown and claimed are considered to encompass both the nitrogen shown and its N-oxides to obtain the derivatives of the present invention.

When any variable occurs more than once in any composition or formula of a compound, its definition at each occurrence is independent of its definition at every other occurrence. Thus, for example, if a group is shown to be substituted with 0-3 R, the group may be optionally substituted with up to three R groups, and at each occurrence R is independently selected from the definition of R. Furthermore, combinations of substituents and/or variables are permissible only if such combinations result in stable compounds.

As used herein, the term "patient" refers to an organism treated by the methods of the present invention. Such organisms preferably include, but are not limited to, mammals (e.g., murine, ape/monkey, equine, bovine, swine, canine, feline, etc.) and most preferably refer to humans.

As used herein, the term "effective amount" means an amount of a drug or pharmaceutical agent (i.e., a compound of the present invention) that will elicit the biological or medical response of a tissue, system, animal or human that is being sought, for example, by a researcher or clinician. Furthermore, the term "therapeutically effective amount" means an amount results in an improved treatment, cure, prevention or alleviation of a disease, condition or side effect, or a reduction in the rate of progression of a disease or condition, as compared to a corresponding subject not receiving such an amount. An effective amount can be administered in one or more dosing, administrations, or dosages and is not intended to be limited by the particular formulation or route of administration. The term also includes an amount effective that enhances normal physiological function within its scope.

As used herein, the term "treatment" includes its broad meaning and encompasses therapeutic and/or prophylactic treatment of a subject. Specifically, the term "treatment" includes any treatment that results in the alleviation, inhibition, elimination, and amelioration, and/or prevention of conditions, diseases, disorders, etc., such as the alleviation, reduction, modulation, amelioration, elimination, prevention, or amelioration of the symptoms thereof. The therapeutic treatment include alleviating, inhibiting, or ameliorating the symptoms or conditions of a disease; inhibiting the generation of complications; ameliorating potential metabolic syndrome; inhibiting the development of a disease or condition, such as controlling the development of a disease or condition; alleviating a disease or condition; reducing the disease or symptoms; alleviating complications resulting from the disease or condition, or treating symptoms resulting from the disease or condition. The prophylactic treatment includes prior treatment to prevent, block or delay, slow the occurrence or development of, or lessen the severity of the disease or condition.

Likewise, a "therapeutic agent" also includes a medicament or reagent that has a therapeutic and/or prophylactic treatment on a subject.

The term "medicinal" or "pharmaceutically acceptable" is used herein to refer to those compounds, materials, compositions, and/or dosage forms as follows: within the scope of sound medical judgment, suitable for use in contact with the tissues of humans and animals without undue toxicity, irritation, allergic response, and/or other problems or complications, commensurate with a reasonable benefit/risk ratio.

Specific Pharmaceutical and Medical Terms

The term "cancer", as used herein, refers to an uncontrolled abnormal growth of cells and is capable of metastasis (transmission) under certain conditions. This type of cancer includes, but is not limited to, solid tumors (e.g., bladder, bowel, brain, chest, uterus, heart, kidney, lung, lymphoid tissue (lymphoma), ovary, pancreas, or other endocrine organs (e.g., thyroid), prostate, skin (melanoma), or hematological tumors (e.g., aleukemic leukemia).

The term "administered in combination" or similar terms, as used herein, refers to the administration of several selected therapeutic agents to a patient in the same or different modes of administration at the same or different times.

The term "enhance" or "can enhance", as used herein, means that the desired result can be increased or prolonged in potency or duration. Thus, in enhancing the therapeutic effect of a drug, the term "can enhance" refers to the ability of the drug to increase or prolong potency or duration in the system. "Synergistic value", as used herein, refers to the ability to maximize the ability of another therapeutic agent in an ideal system.

The term "immunological disease" refers to a disease or condition that responds adversely or deleteriously to endogenous or exogenous antigens. The result is often a dysfunction of the cells, or thus destruction and dysfunction, or destruction of organs or tissues that may produce immune symptoms.

The term "kit" is synonymous with "product package".

The term "object", "subject" or "patient" includes mammals and non-mammals. Mammals include, but are not limited to, mammals: human, non-human primates such as chimpanzees, apes and monkeys; agricultural animals such as bovines, equines, goats, sheep, swines; domestic animals such as rabbits, canines; experimental animals include rodents, such as rats, mice, and guinea pigs. Non-mammalian animals include, but are not limited to, birds, and fish. In a preferred embodiment, the selected mammal is a human.

As used herein, a compound or pharmaceutical composition, upon administration, may result in amelioration of a disease, symptom, or condition, particularly amelioration of the severity, delay of the onset, alleviation of the progression, or reduction of the duration of the condition. Regardless of fixed administration or temporary administration, continuous administration or intermittent administration, it may be attributed to or related to the administration.

Route of Administration

Suitable routes of administration include, but are not limited to, oral, intravenous, rectal, aerosol, parenteral, ophthalmic, pulmonary, transdermal, vaginal, aural, nasal, and topical administration. In addition, by way of example only, parenteral administration includes intramuscular, subcutaneous, intravenous, intramedullary, ventricular, intraperitoneal, intralymphatic, and intranasal injections.

The compounds of the present invention may be administered topically. In particular embodiments, the prolonged action preparation is administered by implantation (e.g., subcutaneously or intramuscularly) or by intramuscular injection. Further, in another embodiment, the drug is administered by a targeted drug delivery system, for example, liposomes encapsulated by organ-specific antibodies. In this particular embodiment, the liposomes are selectively targeted to specific organs and absorbed.

Pharmaceutical Compositions and Dosages

As used herein, the phrase "pharmaceutically acceptable carrier" means a pharmaceutical material, composition or vehicle, such as a liquid or solid filler, diluent, excipient, manufacturing adjuvant (e.g., lubricant, talc, magnesium stearate, calcium stearate or zinc stearate or stearic acid), or solvent encapsulating material, which refers to carrying or transporting the subject compound from one organ or portion of the body to another organ or portion of the body. Each carrier must be "acceptable" in the sense of being compatible with the other ingredients of the formulation and not deleterious to the patient.

The term "pharmaceutical composition" means a composition including a compound of the present invention and optionally other pharmaceutically acceptable carrier. "Pharmaceutically acceptable carrier" means a medium generally accepted in the art for the delivery of a biologically active agent to an animal, particularly a mammal, and includes, i.e., adjuvants, excipients, or vehicles such as diluents, preservatives, fillers, flow regulating agents, disintegrating agents, wetting agents, emulsifying agents, suspending agents, sweetening agents, flavoring agents, perfuming agents, antibacterial agents, antifungal agents, lubricating agents, and dispersing agents. This depends on the mode of administration and the nature of the dosage form.

The pharmaceutical compositions of the present invention may include a therapeutically effective amount of one or more compounds of the present invention formulated together with optionally one or more pharmaceutically acceptable carriers (additives) and/or diluents, and optionally one or more of the other therapeutic agents described above. The compounds of the present invention may be administered for any of the above-mentioned uses by any suitable means, for example by orally, such as in the form of tablets, pills, powders, granules, elixirs, tinctures, suspensions (including nanosuspensions, microsuspensions, spray-dried dispersions), syrups and emulsions; by sublingually; by buccally; by parenterally, such as by subcutaneous, intravenous, intramuscular or intrasternal injection or infusion techniques (e.g., in the form of sterile injectable aqueous or nonaqueous solutions or suspensions); by nasally, including administration to the nasal mask, such as by inhalation spray; by topically, such as in the form of a cream or ointment; or by rectally, such as in the form of suppositories; or by intratumoral injection. They may be administered alone, but are generally administered using pharmaceutical acceptable carriers selected based on the chosen route of administration and standard pharmaceutical practice.

The pharmaceutical acceptable carriers are formulated according to a number of factors within the knowledge of those skilled in the art. These factors include, but are not limited to: types and properties of the formulated active agents; a subject to be administered the composition containing the active agent; the intended route of administration of the composition; and targeted therapeutic indications. The pharmaceutically acceptable carriers include aqueous and non-aqueous liquid media and various solid and semi-solid dosage forms.

The above-mentioned carrier may include many different ingredients and additives in addition to the active agent, and the above-mentioned other ingredients, for example, stabilizing active agent and binder, are included in the formulation for various reasons known to those skilled in the art. For a description of suitable pharmaceutical acceptable carriers and factors involved in the selection of carrier, see a number of readily available sources, such as Allen L. V. Jr. et al. Remington: The Science and Practice of Pharmacy (2 Volumes), 22nd Edition (2012), Pharmaceutical Press.

The dosage regimen for the compounds of the present invention will, of course, vary depending upon known factors such as the pharmacodynamic characteristics of the particular agent and its mode and route of administration; species, age, sex, health, medical condition and weight of the recipient; the nature and extent of symptoms; kind of concurrent treatment; treatment frequency; routes of administration, renal and hepatic function and desired effects in patients. According to general guidelines, when used for a given effect, the daily oral dosage of each active ingredient should be from about 0.001 mg/day to about 10-5000 mg/day, preferably from about 0.01 mg/day to about 1000 mg/day, and most preferably from about 0.1 mg/day to about 250 mg/day. During constant infusion, the most preferred intravenous dose should be from about 0.01 mg/kg/min to about 10 mg/kg/min. The compounds of the present invention may be administered in a single daily dose, or the total daily dose may be administered in divided doses of two, three or four times daily.

The compounds are generally administered in the form of a mixture of suitable pharmaceutical diluents, excipients, or carriers (collectively referred to herein as pharmaceutical acceptable carriers) suitably selected with respect to the intended form of administration (e.g., oral tablets, capsules, elixirs, and syrups) and consistent with conventional pharmaceutical practice.

Dosage forms (pharmaceutical compositions) suitable for administration may contain from about 1 mg to about 2000 mg of active ingredient per dosage unit. In these pharmaceutical compositions, the active ingredient will generally be present in an amount of about 0.1-95% by weight, based on a total weight of the composition.

Typical capsules for oral administration contain at least one compound of the present invention (250 mg), lactose (75 mg) and magnesium stearate (15 mg). The mixture was processed through a 60 meshes screen and packaged into No. 1 gelatin capsules.

A typical injectable formulation may be prepared as follows: at least one compound of the present invention (250 mg) was placed in a vial in a sterile manner, and lyophilized and sealed in a sterile manner. For use, the contents in the vial were mixed with 2 mL of normal saline to produce an injectable formulation.

The scope of the present invention includes (alone or in combination with a pharmaceutical acceptable carrier) pharmaceutical compositions containing a therapeutically effective amount of at least one compound of the present invention as an active ingredient. Optionally, the compounds of the present invention may be used alone, in combination with other compounds of the present invention, or in combination with one or more other therapeutic agents (e.g., anticancer agents or other pharmaceutically active agents).

Regardless of the selected route of administration, the compounds of the present invention (which may be used in suitable hydrated forms) and/or the pharmaceutical compositions of the present invention are formulated into pharmaceutically acceptable dosage forms by conventional methods known to those skilled in the art.

The actual dosage level of the active ingredient in the pharmaceutical compositions of the present invention may be varied so as to obtain an amount of the active ingredient that is effective to achieve the desired therapeutic response, composition, and mode of administration for a particular patient without being toxic to the patient.

The selected dosage level will depend upon a variety of factors, including the factors well known in the medical field such as the activity of the employed specific compound of the present invention, or an ester, salt or amide thereof, routes of administration; administration time; the discharge rate of the employed specific compound; the absorption rate and extent; duration of treatment; other drugs, compounds and/or substances used in combination with the employed specific compounds; the age, sex, weight, condition, general health and prior medical history of the patient being treated.

A physician or veterinarian having ordinary skill in the art can readily determine and prescribe an effective amount of the desired pharmaceutical composition. For example, to achieve the desired therapeutic effect, the physician or veterinarian may start a relatively small amount of the compound of the present invention used in the pharmaceutical composition below the desired level and gradually increase the dosage until the desired effect is achieved. In general, a suitable daily dose of a compound of the present invention will be that amount of the compound that is the lowest dose effective to produce a therapeutic effect. Such an effective dose will generally depend on such factors. In general, oral, intravenous, intracerebroventricular, and subcutaneous doses of a compound of the present invention for a patient range from about 0.01 to about 50 mg/kg body weight/day. If desired, an effective daily dose of the active compound may be administered in two, three, four, five, six or more sub-doses respectively at appropriate intervals throughout the day, optionally in unit dosage form. In certain aspects of the present invention, the medication is administered once a day.

Although the compound of the present invention may be administered alone, it is preferably administered in the form of a pharmaceutical preparation (composition).

Pharmaceutical Compositions and Dosages

As used herein, the phrase "pharmaceutically acceptable carrier" means a pharmaceutical material, composition or vehicle, such as a liquid or solid filler, diluent, excipient, manufacturing adjuvant (e.g., lubricant, talc, magnesium stearate, calcium stearate or zinc stearate or stearic acid), or solvent encapsulating material, which refers to carrying or transporting the subject compound from one organ or portion of the body to another organ or portion of the body. Each carrier must be "acceptable" in the sense of being compatible with the other ingredients of the formulation and not deleterious to the patient.

The term "pharmaceutical composition" means a composition including a compound of the present invention and optionally other pharmaceutically acceptable carrier. "Pharmaceutically acceptable carrier" means a medium generally accepted in the art for the delivery of a biologically active agent to an animal, particularly a mammal, and includes, i.e., adjuvants, excipients, or vehicles such as diluents, preservatives, fillers, flow regulating agents, disintegrating agents, wetting agents, emulsifying agents, suspending agents, sweetening agents, flavoring agents, perfuming agents, antibacterial agents, antifungal agents, lubricating agents, and dispersing agents. This depends on the mode of administration and the nature of the dosage form.

The pharmaceutical compositions of the present invention may include a therapeutically effective amount of one or more compounds of the present invention formulated together with optionally one or more pharmaceutically acceptable carriers (additives) and/or diluents, and optionally one or more of the other therapeutic agents described above. The compounds of the present invention may be administered for any of the above-mentioned uses by any suitable means, for example by orally, such as in the form of tablets, pills, powders, granules, elixirs, tinctures, suspensions (including nanosuspensions, microsuspensions, spray-dried dispersions), syrups and emulsions; by sublingually; by buccally; by parenterally, such as by subcutaneous, intravenous, intramuscular or intrasternal injection or infusion techniques (e.g., in the form of sterile injectable aqueous or nonaqueous solutions or suspensions); by nasally, including administration to the nasal mask, such as by inhalation spray; by topically, such as in the form of a cream or ointment; or by rectally, such as in the form of suppositories; or by intratumoral injection. They may be administered alone, but are generally administered using pharmaceutical acceptable carriers selected based on the chosen route of administration and standard pharmaceutical practice.

The pharmaceutical acceptable carriers are formulated according to a number of factors within the knowledge of those skilled in the art. These factors include, but are not limited to: types and properties of the formulated active agents; a subject to be administered the composition containing the active agent; the intended route of administration of the composition; and targeted therapeutic indications. The pharmaceutically acceptable carriers include aqueous and nonaqueous liquid media and various solid and semi-solid dosage forms.

The above-mentioned carrier may include many different ingredients and additives in addition to the active agent, and the above-mentioned other ingredients, for example, stabilizing active agent and binder, are included in the formulation for various reasons known to those skilled in the art. For a description of suitable pharmaceutical acceptable carriers and factors involved in the selection of carrier, see a number of readily available sources, such as Allen L. V. Jr. et al. Remington: The Science and Practice of Pharmacy (2 Volumes), 22nd Edition (2012), Pharmaceutical Press.

The dosage regimen for the compounds of the present invention will, of course, vary depending upon known factors such as the pharmacodynamic characteristics of the particular agent and its mode and route of administration; species, age, sex, health, medical condition and weight of the recipient; the nature and extent of symptoms; kind of concurrent treatment; treatment frequency; routes of administration, renal and hepatic function and desired effects in patients. According to general guidelines, when used for a given effect, the daily oral dosage of each active ingredient should be from about 0.001 mg/day to about 10-5000 mg/day, preferably from about 0.01 mg/day to about 1000 mg/day, and most preferably from about 0.1 mg/day to about 250 mg/day. During constant infusion, the most preferred intravenous dose should be from about 0.01 mg/kg/min to about 10 mg/kg/min. The compounds of the present invention may be administered in a single daily dose, or the total daily dose may be administered in divided doses of two, three or four times daily.

The compounds are generally administered in the form of a mixture of suitable pharmaceutical diluents, excipients, or carriers (collectively referred to herein as pharmaceutical acceptable carriers) suitably selected with respect to the intended form of administration (e.g., oral tablets, capsules, elixirs, and syrups) and consistent with conventional pharmaceutical practice.

Dosage forms (pharmaceutical compositions) suitable for administration may contain from about 1 mg to about 2000 mg of active ingredient per dosage unit. In these pharmaceutical compositions, the active ingredient will generally be present in an amount of about 0.1-95% by weight, based on a total weight of the composition.

Typical capsules for oral administration contain at least one compound of the present invention (250 mg), lactose (75 mg) and magnesium stearate (15 mg). The mixture was processed through a 60 meshes screen and packaged into No. 1 gelatin capsules.

A typical injectable formulation may be prepared as follows: at least one compound of the present invention (250 mg) was placed in a vial in a sterile manner, and lyophilized and sealed in a sterile manner. For use, the contents in the vial were mixed with 2 mL of normal saline to produce an injectable formulation.

The scope of the present invention includes (alone or in combination with a pharmaceutical acceptable carrier) pharmaceutical compositions containing a therapeutically effective amount of at least one compound of the present invention as an active ingredient. Optionally, the compounds of the present invention may be used alone, in combination with other compounds of the present invention, or in combination with one or more other therapeutic agents (e.g., anticancer agents or other pharmaceutically active agents).

Regardless of the selected route of administration, the compounds of the present invention (which may be used in suitable hydrated forms) and/or the pharmaceutical compositions of the present invention are formulated into pharmaceutically acceptable dosage forms by conventional methods known to those skilled in the art.

The actual dosage level of the active ingredient in the pharmaceutical compositions of the present invention may be varied so as to obtain an amount of the active ingredient that is effective to achieve the desired therapeutic response, composition, and mode of administration for a particular patient without being toxic to the patient.

The selected dosage level will depend upon a variety of factors, including the factors well known in the medical field such as the activity of the employed specific compound of the present invention, or an ester, salt or amide thereof, routes of administration; administration time; the discharge rate of the employed specific compound; the absorption rate and extent; duration of treatment; other drugs, compounds and/or substances used in combination with the employed specific compounds; the age, sex, weight, condition, general health and prior medical history of the patient being treated.

A physician or veterinarian having ordinary skill in the art can readily determine and prescribe an effective amount of the desired pharmaceutical composition. For example, to achieve the desired therapeutic effect, the physician or veterinarian may start a relatively small amount of the compound of the present invention used in the pharmaceutical composition below the desired level and gradually increase the dosage until the desired effect is achieved. In general, a suitable daily dose of a compound of the present invention will be that amount of the compound that is the lowest dose effective to produce a therapeutic effect. Such an effective dose will generally depend on such factors. In general, oral, intravenous, intracerebroventricular, and subcutaneous doses of a compound of the present invention for a patient range from about 0.01 to about 50 mg/kg body weight/day. If desired, an effective daily dose of the active compound may be administered in two, three, four, five, six or more sub-doses respectively at appropriate intervals throughout the day, optionally in unit dosage form. In certain aspects of the present invention, the medication is administered once a day.

Although the compound of the present invention may be administered alone, it is preferably administered in the form of a pharmaceutical preparation (composition).

Kit/Product Package

Kits/product packages are also described herein for the treatment of the above-mentioned indications. These kits may be composed of a conveyor, a medicine pack or a container box. The container box can be divided into multiple compartments to accommodate one or more containers, such as vials, and test tubes, where each container contains all a single component in the method. Suitable containers consist of bottles, vials, syringes, and test tubes. The container is made of an acceptable glass or plastic material.

For example, the container may contain one or more of the compounds described herein; the compound may exist either in the form of a pharmaceutical composition or may exist as a mixture with other ingredients described herein. The container may have a sterile outlet (e.g., the container may be an intravenous infusion bag or bottle and the stopper may be pierced by a hypodermic needle). Such kits may contain a compound and descriptions, labels or instructions for the method of use described herein.

A typical kit may include one or more containers, each containing one or more materials (e.g., reagents, concentrated stock solutions, and/or equipment) to accommodate commercial promotions and the needs of the user for the use of compounds. Such materials include, but are not limited to, buffers, diluents, filters, needles, syringes, conveyors, bags, containers, bottles, and/or tubes, with a list of contents and/or instructions for use, and with a build-in package. The entire set of instructions must be included.

The label may be displayed on or closely related to the container. The appearance of the label on the container means that the label letters, numbers or other features are pasted, molded, or engraved on the container; the label can also appear in the container box or shipping box containing a variety of containers, such as in the product insert. A label may be used to indicate a particular therapeutic use of the contents. The label may also indicate directions for the use of contents, such as described in the methods described above.

All of the features described in this specification (including any accompanying claims, abstract and drawings), and/or all of the steps involved in any method or process, may be present in any combination unless some features or steps are mutually exclusive in the same combination.

The features mentioned above, or the features mentioned in the embodiments mentioned herein, may be combined in any combination. All of the features disclosed in this specification may be combined in any combination, and each feature disclosed in this specification may be replaced by any alternative feature serving the same, equivalent or similar purpose. Thus, unless otherwise specified, the features disclosed are only general examples of equivalent or similar features.

The present invention will be described in detail below in connection with specific examples. It should be understood that these examples are only used to describe the present invention and are not intended to limit the scope of the present invention. The experimental methods in the following examples which are not specified with specific conditions are generally carried out according to conventional conditions or according to the conditions recommended by the manufacturer. All percentages, ratios, ratios, or parts are calculated by weight, unless otherwise stated.

The units in weight-volume percent in the present invention are well known to those skilled in the art and refer, for example, to the weight of solute in a 100 milliliters of solution. Unless otherwise defined, all professional and scientific terms used in the text have the same meaning as those familiar to those skilled in the art. In addition, any methods and materials similar or equivalent to those described can be used in the methods of the present invention. The preferred embodiments and materials described herein are exemplary only.

EXAMPLES

When no preparation route is mentioned, the relevant intermediates are commercially available (eg from Sigma Aldrich, Alfa).

Generic Process

Commercially available reagents were used without further purification. $^1$H-NMR spectra were recorded on a Bruker instrument at 500 MHz. Chemical shift values are represented in parts per million, ie, delta values. The following abbreviation is used for the multiplicity of NMR signals: s=singlet, brs=broad, d=doublet, t=triplet, m=multiplet. Coupling constants are listed in J values, measured in Hz. NMR and mass spectral results are corrected for background peaks. Chromatograms refer to 100 mesh Column chromatography performed on silica gel and performed under nitrogen pressure (flash chromatography). TLC used to monitor the reaction refers to TLC performed using a specific mobile phase and silica gel F254 from Merck as stationary phase.

LC-MS Experiments were measured under the following conditions:

Apparatus: Thermo U3000, ALLtech ELSD, MSQ, UV detector combined ELSD and MSD (elution ratio 4:1). Column: Waters X-Bridge C-18, 3.5 μm, 4.6×50 mm; Column temperature: 30° C. Gradient [time] (min)/solvent B in A (%)]: 0.00/5.0, 0.70/95, 1.40/95, 1.41/5, 1.50/5. (Solvent A=0.01% trifluoroacetic acid in water; Solvent B=0.01% trifluoroacetic acid in acetonitrile). UV detection: 214/254/280/300 nm; DAD detection: 200-400 nm; flow rate: 4 mL/min; MS: ESI, 100-1500 m/z Preparative HPLC usually uses basic methods (gradient of acetonitrile and water with 10 mM ammonium bicarbonate in water); Thermo U3000 AFC-3000; Column: Globalsil C-18 12 nm, 250×20 mm, 10 μm, or equivalent; Flow rate: 20 mL/min for separation.

The Synthesis of Intermediate

The Preparation of Compound INT-1:

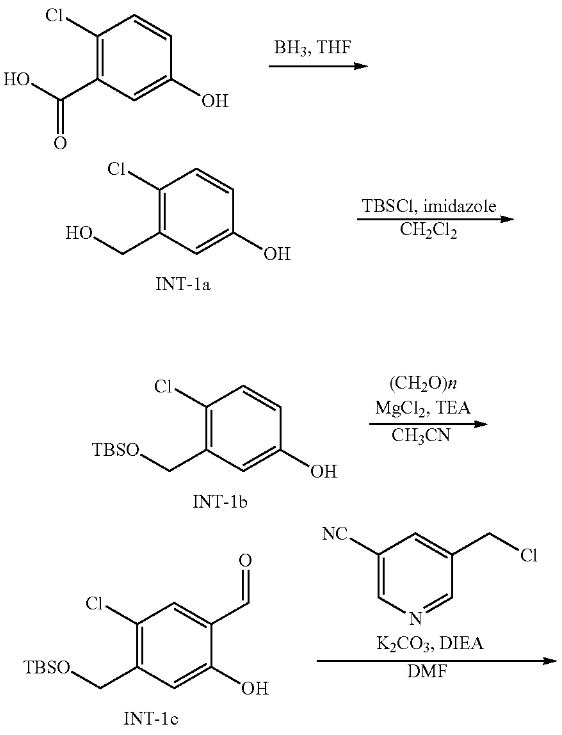

INT-1a
INT-1b
INT-1c

-continued

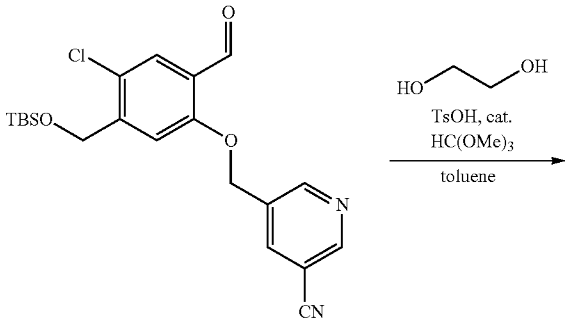

INT-1d

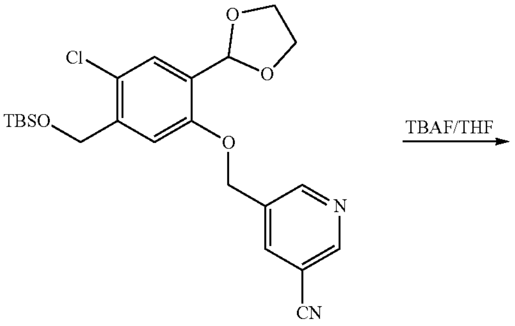

INT-1e

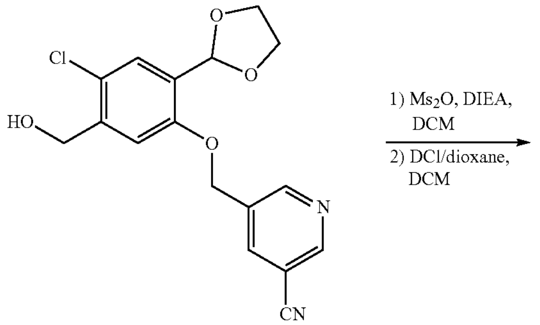

INT-1f

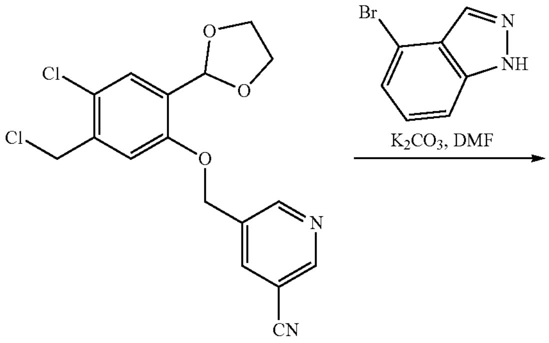

INT-1g

-continued

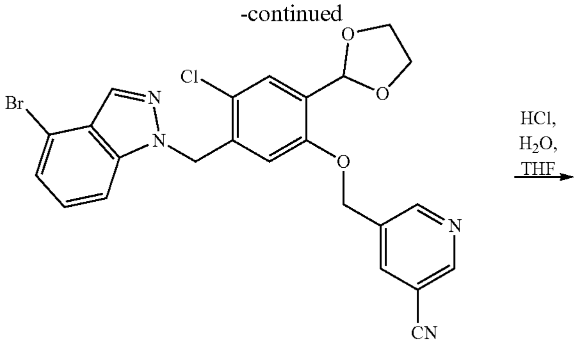

INT-1h

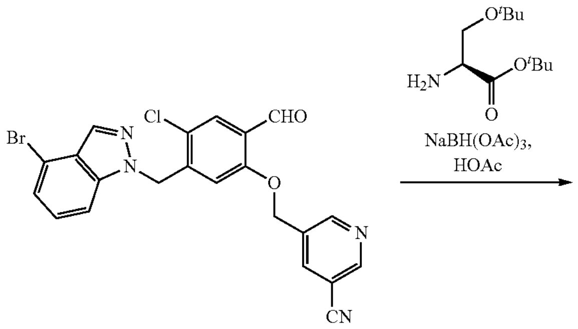

INT-1i

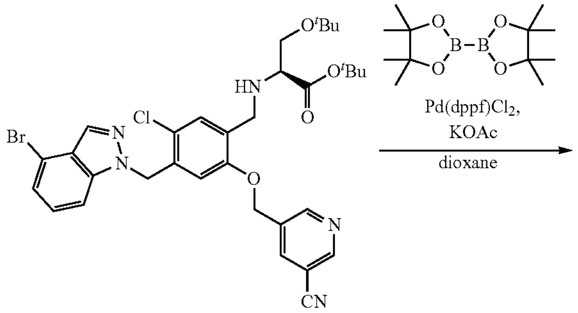

INT-1j

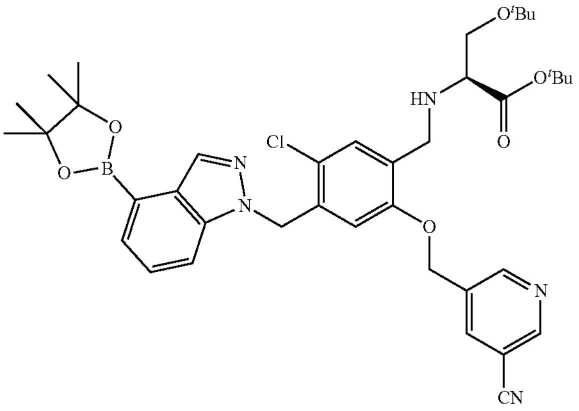

INT-1

2-chloro-5-hydroxybenzoic acid (29.0 g, 168 mmol) was dissolved in tetrahydrofuran (100 mL), under nitrogen atmosphere and ice bath borane (1.0 M in tetrahydrofuran solution, 336 mL) was added dropwise. After dripping completed, the reaction solution was raised to room temperature and stirred for 16 hours. TLC detected that the raw material was completely consumed. Methanol was added dropwise to the reaction solution under ice bath to quench the reaction until no more bubbles emerged. Solvent was concentrated to obtain light yellow solid INT-1a (26.6 g, yield: 99.8%).

Compound INT-1a (26.6 g, 168 mmol) and imidazol (11.5 g, 169 mmol) were dissolved in dichloromethane (300 mL). At 0° C. tert-butyldimethylsilyl chloride (25.5 g, 169 mmol) predissolved in dichloromethane (100 mL) solution was in batches added. The mixture was heated to 30° C. and stirred for 16 hours. The reaction was quenched with water (100 mL). The aqueous phase was extracted with dichloromethane (100 mL×2). The combined organic phase was washed with saturated salt solution (500 mL), dried with anhydrous sodium sulfate, filtered, and concentrated. The residue was separated with silica gel column chromatography to obtain light yellow liquid INT-1b (33.4 g, yield: 73%).

Compound INT-1b (8.0 g, 29.3 mmol) was dissolved in acetonitrile (100 mL), triethylamine (14.8 g, 147 mmol), magnesium chloride (5.58 g, 58.6 mmol) and paraformaldehyde (8.80 g, 293 mmol) were then added. The mixture was heated to 90° C. in a nitrogen atmosphere and was stirred vigorously for 20 hours. The reaction solution was diluted by water (100 mL). Adjusting pH=3-4 with saturated aqueous citric acid solution. The solution was extracted with ethyl acetate (200 mL×2). The combined organic phase was washed with saturated salt solution (300 mL), dried with anhydrous sodium sulfate, filtered, and concentrated. The residue was separated by silica gel column chromatography to obtain a white solid INT-1c (5.0 g, yield: 56.7%). $^1$H NMR (500 MHz, DMSO-d6) δ 10.97 (s, 1H), 10.23 (s, 1H), 7.58 (s, 1H), 7.25 (s, 1H), 4.72 (s, 2H), 0.96 (s, 9H), 0.14 (s, 6H).

5-chloromethyl-3-cyano pyridine hydrochloride (3.20 g, 17.0 mmol) was dissolved in N,N-dimethylformamide (20 mL), under ice bath N,N-diisopropylethylamine (5.48 g, 42.4 mmol) and potassium carbonate (5.86 g, 42.4 mmol) were added. After stirring for 10 minutes, to the reaction solution INT-1c (4.25 g, 14.1 mmol) and potassium iodide (234 mg, 1.41 mmol) were added. The reaction solution in ice bath was stirred for half an hour, and then heated to 50° C. and stirred for 16 hours. The reaction solution was cooled down in ice bat. After adding 100 mL solid precipitated. Solid was filtered, washed with water, dried, and then solid crude was separated by silica gel column chromatography to obtain a white solid INT-1d (5.00 g, yield: 84.9%). MS (ESI): m/z 417.2 $(M+H)^+$.

Compound INT-1d (5.0 g, 12.0 mmol) was dissolved in toluene (10 mL), ethylene glycol (14.9 g, 240 mmol) and p-toluenesulfonic acid (228 mg, 1.20 mmol) were added, and trimethyl orthoformate (2.55 g, 24.0 mmol) was added dropwise. The mixture was heated to 80° C. in a nitrogen atmosphere and was stirred for 16 hours. The reaction solution was cooled down in ice bath, and was quenched with saturated sodium bicarbonate aqueous solution (50 mL), aqueous phase was extracted with ethyl acetate (100 mL×2). The combined organic phase was washed with saturated salt solution (200 mL), dried with anhydrous sodium sulfate, filtered, and concentrated. The residue was separated by silica gel column chromatography to obtain a white solid INT-1e (5.50 g, yield: 99.5%). MS (ESI): m/z 461.2 $(M+H)^+$.

Compound INT-1e (2.20 g, 4.77 mmol) was dissolved in tetrahydrofuran (10 mL), and tetrabutylammonium fluoride in a tetrahydrofuran solution (1 M, 7.16 mL) was added. The reaction solution was stirred for half an hour at 30° C., and was diluted by water (30 mL). The aqueous phase was extracted with ethyl acetate (50 mL×2). The combined organic phase was washed with saturated salt solution (50 mL), dried with anhydrous sodium sulfate, filtered, and concentrated. The residue was slurried with a mixture of ethyl acetate and petroleum ether (v/v=3/100, 20 mL), and filtered to obtain light yellow solid INT-if (1.58 g, yield: 95.5%). MS (ESI): m/z 347.2 $(M+H)^+$.

Compound INT-if (1.50 g, 4.33 mmol) was dissolved in dichloromethane (30 mL), N, N-diisopropylethylamine (1.68 g, 13.0 mmol) was added, and under 0° C. and nitrogen atmosphere methanesulfonic anhydride (1.51 g, 8.65 mmol) was added. Then The a mixture of N,N-diisopropylethylamine (1.68 g, 13.0 mmol) and hydrochloric acid dioxane (4 M, 1.62 mL) in dichloromethane (10 mL) was added. The reaction solution was stirred for 16 hours at 25° C. The reaction was quenched with water (30 mL). Aqueous phase was extracted with dichloromethane (50 mL×2). The combined organic phase was washed with saturated salt solution (50 mL), dried with anhydrous sodium sulfate, filtered, and concentrated. The residue was separated by silica gel column chromatography to obtain a light-yellow solid INT-1g (1.40 g, yield: 88.6%). MS (ESI): m/z 365.2 $(M+H)^+$.

Compound INT-1g (1.36 g, 3.72 mmol), 4-bromo-1H-indazole (734 mg, 3.72 mmol) and potassium carbonate (1.03 g, 7.45 mmol) were dissolved in N, N-dimethylformamide (10 mL). The mixture was stirred for 16 hours at 50° C. The reaction solution was cooled in ice bath. Upon adding 100 mL water, solid precipitated, filtered, washed with water, and dried. Thus obtained solid crude was separated by silica gel column chromatography to obtain a light yellow solid INT-1h (1.08 g, yield: 55.2%). $^1$H NMR (500 MHz, DMSO-d6) δ 8.96 (d, J=2.0 Hz, 1H), 8.82 (s, 1H), 8.27 (s, 1H), 8.05 (s, 1H), 7.70 (d, J=8.5 Hz, 1H), 7.45 (s, 1H), 7.40 (d, J=7.5 Hz, 1H), 7.32 (t, J=7.5 Hz, 1H), 6.91 (s, 1H), 6.04 (s, 1H), 5.71 (s, 2H), 5.16 (s, 2H), 4.04-4.01 (m, 2H), 3.97-3.89 (m, 2H); MS (ESI): m/z 525.0 $(M+H)^+$.

Compound INT-1h (1.00 g, 1.90 mmol) was dissolved in tetrahydrofuran (20 mL), and hydrochloric acid (4.0 M aqueous solution, 5.0 mL). The reaction solution was stirred for 1 hour at 30° C., then was neutralized with saturated sodium bicarbonate aqueous solution. The aqueous phase was extracted with ethyl acetate (50 mL×2). The combined organic phase was washed with saturated salt solution (100 mL), dried with anhydrous sodium sulfate, filtered, and concentrated to obtain light yellow solid INT-1i (900 mg, yield: 98.2%). MS (ESI): m/z 481.0 $(M+H)^+$.

Compound INT-1i (840 mg, 1.74 mmol) was dissolved in N,N-dimethylformamide (5 mL), O-isopropyl-L-serine tert-butyl ester (418 mg, 1.92 mmol) and acetic acid (209 mg, 3.48 mmol) were added, and the reaction solution was stirred for 1 hour at 30° C. Then to the reaction solution sodium triacetoxyborohydride (1.48 g, 6.96 mmol) was added. The reaction was stirred for 1 hour at 30° C., and then was quenched with water (50 mL). The aqueous phase was extracted with ethyl acetate (50 mL×2). The combined organic phase was washed with saturated salt solution (50 mL), dried with anhydrous sodium sulfate, filtered, and concentrated. The residue was separated by silica gel column chromatography to obtain a light-yellow solid INT-1j (720 mg, yield: 60.5%). MS (ESI): m/z 682.1 $(M+H)^+$.

Intermediate INT-1j (1.00 g, 1.46 mmol), pinacol diboronate (558 mg, 2.20 mmol), potassium acetate (431 mg, 4.39 mmol) and Pd(dppf)$Cl_2$ (107 mg, 0.15 mmol) were dissolved in dioxane (15 mL). The reaction solution was heated to 90° C. stirred overnight in a nitrogen atmosphere. After the reaction solution was cooled to room temperature, it was diluted with ethyl acetate (100 mL), filtered with diatomite, and washed with 100 mL ethyl acetate. The obtained filtrate was concentrated. The residue was separated by silica gel column chromatography (dichloromethane/methanol, v/v=20/1) to obtain light yellow solid INT-1 (600 mg, yield: 56.1%). MS (ESI): m/z 730.7 $(M+H)^+$.

The Preparation of Compound INT-2:

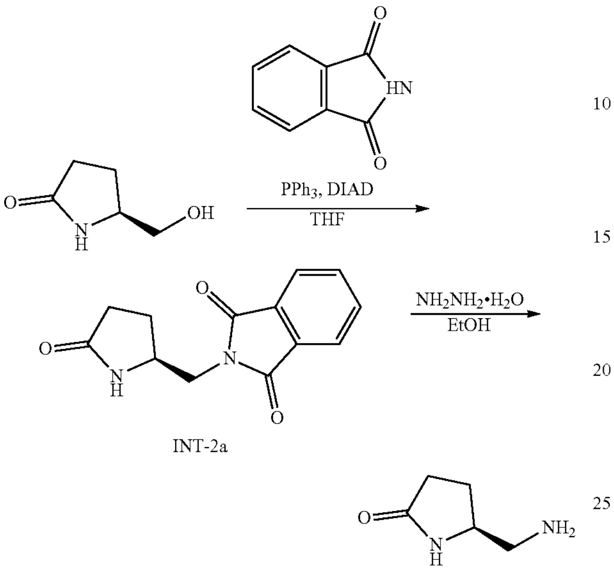

INT-2a

INT-2

(S)-5-hydroxymethyl-2-pyrrolidone (10.0 g, 86.9 mmol) was dissolved in anhydrous tetrahydrofuran (200 mL), phthalimide (12.8 g, 86.9 mmol) and triphenylphosphine (34.2 g, 130 mmol) were added. Under ice bath and nitrogen atmosphere to the reaction solution diisopropyl azodicarboxylate (26.4 g, 130 mmol) was slowly added dropwise. The reaction solution was raised to room temperature and stirred overnight. The resulting precipitate was filtered and dried to obtain white solid INT-2a (11.4 g, yield: 53.7%). MS (ESI): m/z 245.1 $(M+H)^+$.

Compound INT-2a (1.0 g, 4.09 mmol) was dissolved in ethanol (20 mL), 80% hydrazine hydrate (512 mg, 8.19 mmol) was added. The reaction solution was heated to 85° C. and stirred for 2 hours. After the reaction was cooled to room temperature, the resulting precipitate was filtered. The filtrate was concentrated and then dichloromethane (50 mL) was added. The filtrate was further filtered and concentrated to obtain yellow oily liquid INT-2 (430 mg, yield: 92.0%). $^1H$ NMR (500 MHz, DMSO-$d_6$) δ 7.65 (s, 1H), 3.43-3.37 (m, 1H), 2.47-2.42 (m, 2H), 2.12-2.04 (m, 2H), 2.03-1.96 (m, 1H), 1.66-1.60 (m, 1H), 1.58 (s, 2H).

The Preparation of Compound INT-3:

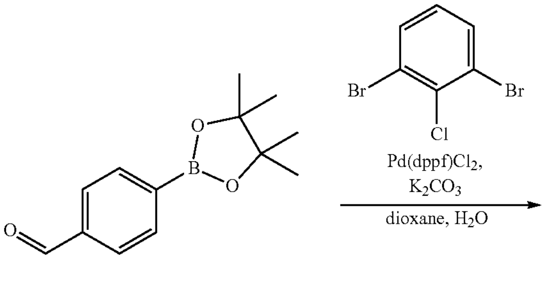

-continued

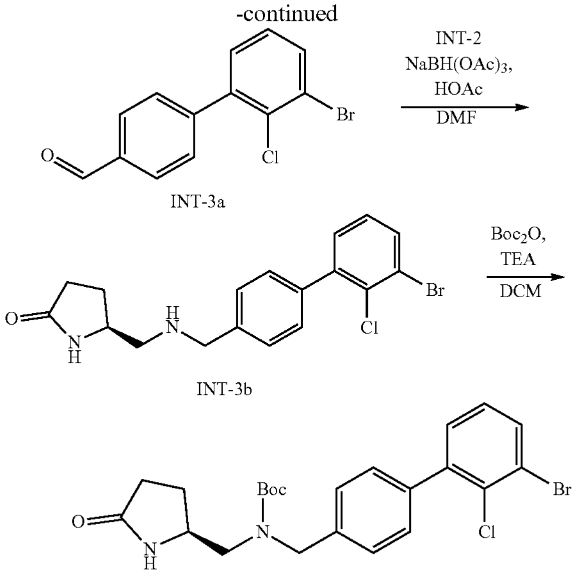

INT-3a

INT-3b

INT-3

4-formylphenylboronic acid pinacol ester (4.50 g, 19.4 mmol) and 1,3-dibromo-2-chlorobenzene (10.5 g, 38.8 mmol) were dissolved in a mixture of dioxane and water (60 mL, v/v=5/1), and potassium carbonate (8.04 g, 58.2 mmol) and Pd(dppf)$Cl_2$ (1.42 g, 1.94 mmol). The reaction solution in a nitrogen atmosphere was heated to 80° C. and stirred for 3 hours. The reaction was quenched with water (100 mL). The aqueous phase was extracted with ethyl acetate (200 mL×2). The combined organic phase was washed with saturated salt solution (200 mL), dried by anhydrous sodium sulfate, filtered, and concentrated. The residue was separated by silica gel column chromatography (petroleum ether/ethyl acetate, v/v=4/1) to obtain white solid INT-3a (3.7 g, yield: 64.6%).

Compound INT-3a (1.00 g, 3.38 mmol) was dissolved in N,N-dimethylformamide (10 mL), and compound INT-2 (541 mg, 4.74 mmol) and acetic acid (203 mg, 3.38 mmol) were sequentially added. The resulting reaction solution was stirred for 1 hour at room temperature, and then sodium triacetoxyborohydride (2.87 g, 13.5 mmol) was added. The resulting reaction solution was further stirred overnight at room temperature, and the reaction was quenched with saturated sodium bicarbonate aqueous solution (50 mL). The aqueous phase was extracted with ethyl acetate (50 mL×3). The combined organic phase was washed with water (100 mL) and saturated salt solution (100 mL) sequentially, dried by anhydrous sodium sulfate, filtered, and concentrated to obtain yellow solid INT-3b (1.41 g, yield: 99.5%). MS (ESI): m/z 393.3 $(M+H)^+$.

Compound INT-3b (1.41 g, 3.58 mmol) was dissolved in dichloromethane (15 mL), sequentially added triethylamine (725 mg, 7.16 mmol) and di-tert-butyl decarbonate (860 mg, 3.94 mmol). The reaction solution at room temperature was stirred for 2 hours, and the was diluted by 200 mL dichloromethane. The organic phase was sequentially washed with water (100 mL) and saturated salt solution (100 mL), dried with anhydrous sodium sulfate, filtered, and concentrated. The residue was separated by silica gel column chromatography (dichloromethane/methanol, v/v=20/1) to obtain white solid INT-3 (1.55 g, yield: 87.6%). $^1H$ NMR (500 MHz, DMSO-$d_6$) δ 7.78 (dd, J=7.8 Hz, 1H), 7.69 (s, 1H), 7.44-7.25 (m, 6H), 4.53-4.39 (m, 2H), 3.80-3.70 (m, 1H), 3.26-3.10 (m, 2H), 2.17-1.99 (m, 3H), 1.76-1.66 (m, 1H), 1.38 (s, 9H); MS (ESI): m/z 493.3 $(M+H)^+$.

The Preparation of Compound INT-4:

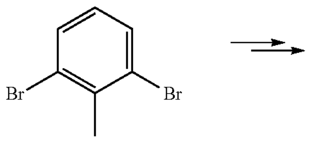

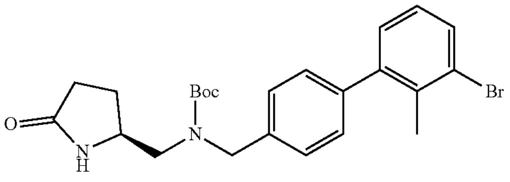

INT-4

Starting from 1,3-dibromo-2-toluene, referring to the synthesis of compound INT-3, thus obtained white solid INT-4. $^1H$ NMR (500 MHz, Chloroform-d) δ 7.76 (d, J=7.2 Hz, 1H), 7.28-7.22 (m, 7H), 4.53 (s, 2H), 4.05-3.67 (m, 1H), 3.42-3.20 (m, 2H), 2.40 (s, 3H), 2.01-1.90 (m, 3H), 1.82-1.71 (m, 1H), 1.36 (s, 9H); MS (ESI): m/z 473.4 $(M+H)^+$.

The Preparation of Compound INT-5:

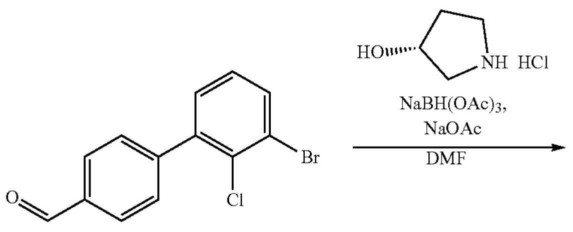

INT-3a

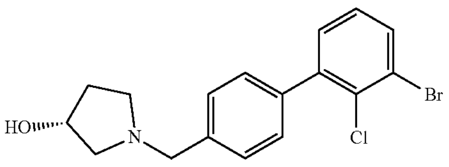

INT-5

Compound INT-3a (1.50 g, 5.08 mmol) was dissolved in N,N-dimethylformamide (20 mL), and sequentially (R)-3-hydroxypyrrolidine hydrochloride (1.88 g, 15.2 mmol) and anhydrous sodium acetate (1.25 g, 15.2 mmol) were added. The reaction solution was stirred overnight at room temperature. Then sodium triacetoxyborohydride (4.31 g, 20.3 mmol) was added. The reaction solution at room temperature was further stirred for 2 hours, and the reaction was quenched with saturated sodium bicarbonate aqueous solution (100 mL). Aqueous phase was extracted with ethyl acetate (100 mL×2). The combined organic phase was washed with saturated salt solution (100 mL), dried with anhydrous sodium sulfate, filtered, and concentrated. The residue was separated by silica gel column chromatography (dichloromethane/methanol, v/v=20/1) to obtain light yellow solid INT-5 (1.60 g, yield: 80.6%). $^1H$ NMR (500 MHz, Methanol-$d_4$) δ 7.71-7.67 (m, 1H), 7.46-7.41 (m, 2H), 7.38-7.33 (m, 2H), 7.32 (d, J=7.8 Hz, 1H), 7.25 (t, J=7.8 Hz, 1H), 4.41-4.31 (m, 1H), 3.81-3.66 (m, 2H), 2.88-2.83 (m, 1H), 2.83-2.76 (m, 1H), 2.64-2.58 (m, 1H), 2.56-2.51 (m, 1H), 2.22-2.12 (m, 1H), 1.79-1.70 (m, 1H); MS (ESI): m/z 366.1 $(M+H)^+$.

The Preparation of Compound INT-6:

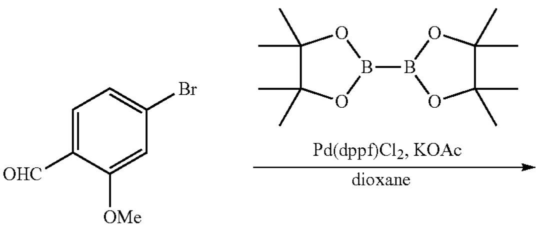

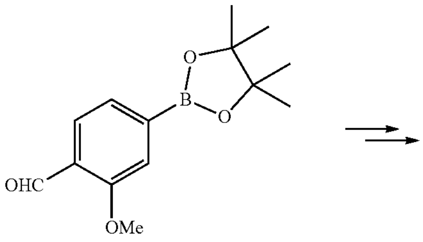

INT-6a

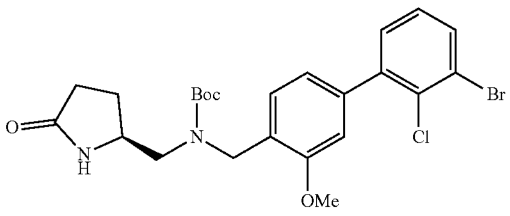

INT-6

Starting from 4-bromo-2-methoxybenzaldehyde, referring to last step Suzuki boron esterification reaction of compound INT-1, compound is obtained INT-6a.

Starting from compound INT-6a, referring to the synthesis of compound INT-3, thus obtained compound INT-6. $^1H$ NMR (500 MHz, DMSO-$d_6$) δ 7.78 (d, J=8.0 Hz, 1H), 7.70 (s, 1H), 7.42-7.38 (m, 1H), 7.33 (t, J=7.5 Hz, 1H), 7.11-7.03 (m, 1H), 7.02-7.00 (m, 1H), 6.98-6.93 (m, 1H), 4.47-4.34 (m, 2H), 3.81 (s, 3H), 3.77-3.71 (m, 1H), 3.26-3.17 (m, 2H), 2.18-2.10 (m, 1H), 2.09-2.00 (m, 2H), 1.74-1.64 (m, 1H), 1.47-1.26 (m, 9H). MS (ESI): m/z 523.2 $(M+H)^+$.

The Preparation of Compound INT-7:

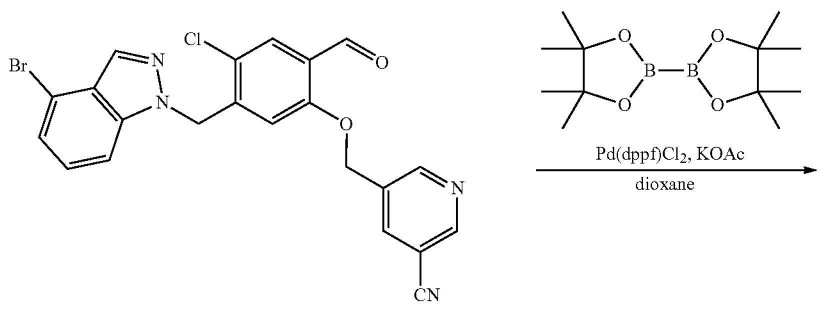

INT-1i

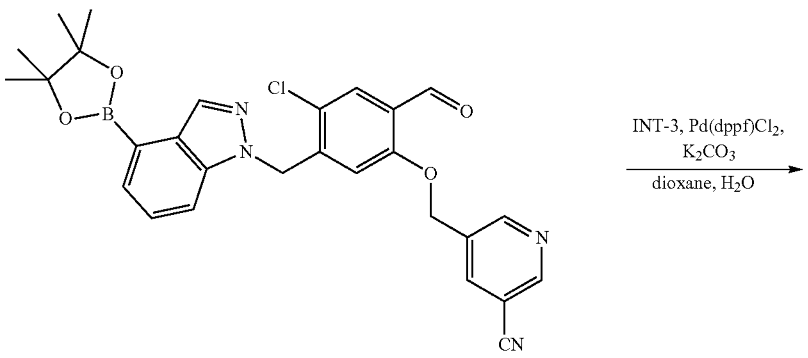

INT-7a

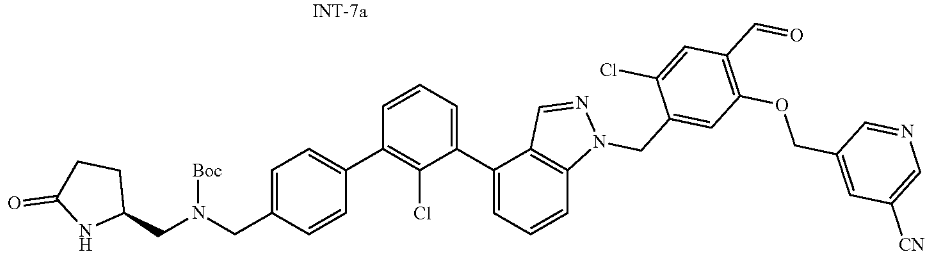

INT-7

Intermediate INT-1i (1.00 g, 2.08 mmol), bis(pinacolato) diboron (635 mg, 2.50 mmol), potassium acetate (612 mg, 6.24 mmol) and Pd(dppf)$Cl_2$ (152 mg, 0.21 mmol) were dissolved in dioxane (20 mL) solution. The reaction solution was heated to 90° C. stirred overnight in a nitrogen atmosphere. The reaction solution was cooled to room temperature, and then diluted with ethyl acetate (100 mL), filtered with diatomite, and the filter cake was further washed with ethyl acetate (100 mL). The obtained filtrate was concentrated under reduced pressure. The residue was separated by silica gel column chromatography (petroleum ether/ethyl acetate, v/v=1/1) to obtain light yellow solid INT-7a (940 mg, yield: 85.5%). MS (ESI): m/z 529.2 $(M+H)^+$.

Compound INT-7a (96.4 mg, 0.18 mmol) and compound INT-3 (75.0 mg, 0.15 mmol) were dissolved in a mixed solvent of dioxane and water (11 mL, v/v=10/1), potassium carbonate (63.0 mg, 0.46 mmol) and Pd(dppf)$Cl_2$ (11.1 mg, 0.015 mmol) were added. The mixture was heated to 80° C. and stirred for 3 hours in a nitrogen atmosphere. Then the reaction was quenched with water (50 mL). The aqueous phase was extracted with ethyl acetate (50 mL×2). The combined organic phase was washed with saturated salt solution (50 mL), dried with anhydrous sodium sulfate, filtered, and concentrated. The residue was separated by preparative thin layer chromatography (dichloromethane/methanol, v/v=95/5) to obtain light yellow solid INT-7 (120 mg, yield: 96.9%). MS (ESI): m/z 815.2 $(M+H)^+$.

The Preparation of Compound INT-8:

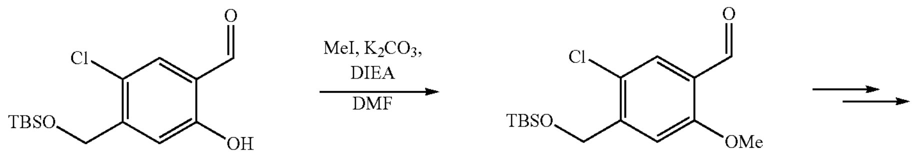

INT-1c

INT-8a

-continued

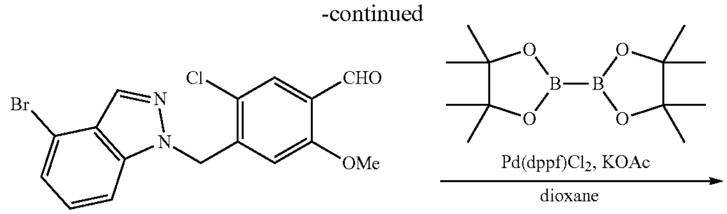

INT-8b

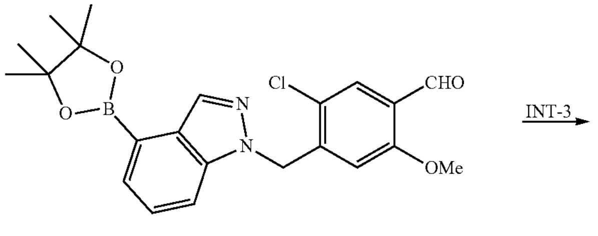

INT-8c

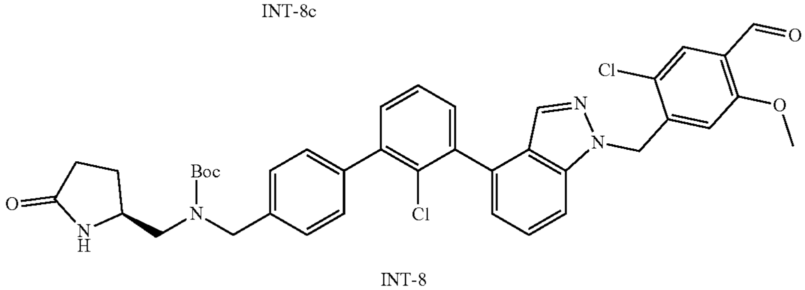

INT-8

Starting from compound INT-1c and iodomethane, referring to the synthesis of INT-1i, compound INT-8b is obtained. MS (ESI): m/z 379.1 (M+H)$^+$.

Starting from compound INT-8b, referring to the synthesis of compound INT-7, compound INT-8c and compound INT-8 are obtained. Their spectral information is as follows:

INT-8c: $^1$H NMR (500 MHz, Chloroform-d) δ 10.31 (s, 1H), 8.50 (s, 1H), 7.83 (s, 1H), 7.69 (d, J=7.0 Hz, 1H), 7.47 (d, J=8.5 Hz, 1H), 7.44-7.37 (m, 1H), 6.42 (s, 1H), 5.73 (s, 2H), 3.60 (s, 3H), 1.42 (s, 12H); MS (ESI): m/z 427.3 (M+H)$^+$.

INT-8: MS (ESI): m/z 713.5 (M+H)$^+$.

The Preparation of Compound INT-9:

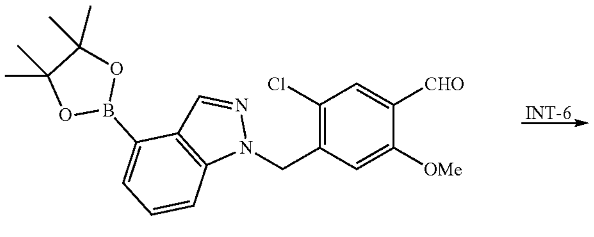

INT-8c

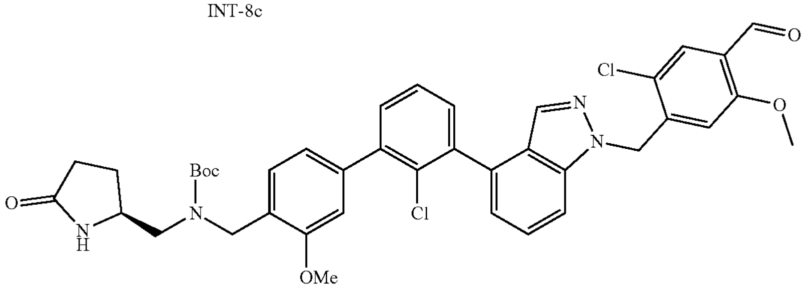

INT-9

Starting from compound INT-8c and compound INT-6, referring to the synthesis of compound INT-8, compound INT-9 is obtained. MS (ESI): m/z 743.6 $(M+H)^+$.

The Preparation of Compound INT-10:

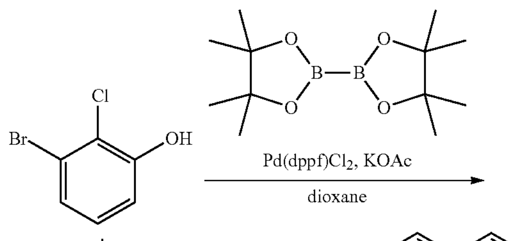

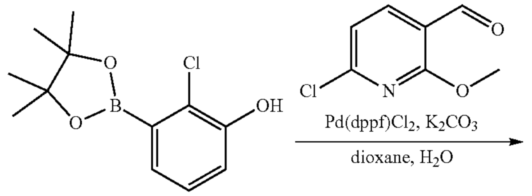

INT-10a

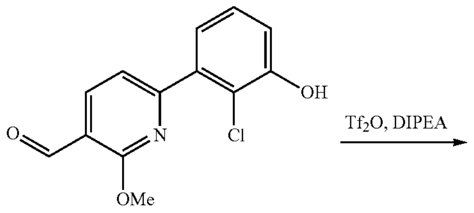

INT-10b

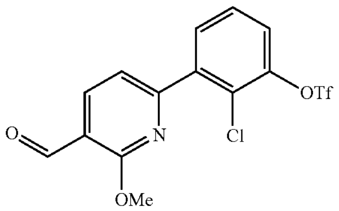

INT-10

Starting from 3-bromo-2-chlorophenol, referring to the synthesis of compound INT-7a, compound INT-10a is obtained. MS (ESI): m/z 253.3 $(M-H)^-$.

Starting from compound INT-10a and 6-Chloro-2-methoxy-3-pyridinecarbaldehyde, referring to the synthesis of compound INT-3a, compound INT-10b is obtained. MS (ESI): m/z 262.0 $(M-H)^-$.

Compound INT-10b (500 mg, 1.90 mmol) was dissolved in anhydrous dichloromethane (10 mL), N,N-diisopropylethylamine (490 mg, 3.80 mmol) was added, and in ice bath was cooled to 0° C., subsequently trifluoromethanesulfonic anhydride (804 mg, 2.85 mmol) was slowly added dropwise. The reaction solution was gradually warmed to room temperature, further stirred for 2 hours. The reaction was quenched with 50 mL saturated ammonium chloride aqueous solution. The aqueous phase was extracted with ethyl acetate (30 mL×2). The combined organic phase was washed with 50 mL saturated salt solution, dried with anhydrous sodium sulfate, filtered, and concentrated. The residue was separated by silica gel column chromatography to obtain orange oily matter INT-10 (482 mg, yield: 64.2%). MS (ESI): m/z 396.2 $(M+H)^+$.

The Preparation of Compound INT-11:

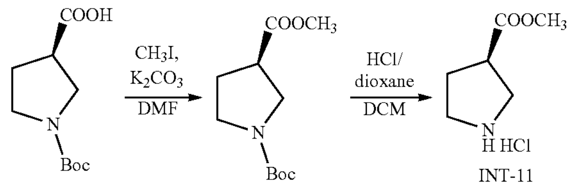

INT-11b INT-11a INT-11

At 25° C., a reaction solution of N'N-dimethylformamide (3 mL) with (R)-1-Boc-3-carboxypyrrolidine (1.00 g, 4.65 mmol), iodomethane (1.00 g, 7.05 mmol) and potassium carbonate (2.00 g, 14.5 mmol) dissolved was stirred for 3 hours. Subsequently the reaction solution was diluted with (50 mL), extracted with ethyl acetate (50 mL×2). The combined organic phase, was washed with 50 mL saturated salt solution, dried with anhydrous sodium sulfate, filtered, and concentrated to obtain yellow oily matter INT-11a (1.00 g, yield: 93.9%).

In dichloromethane (2 mL) solution with compound INT-11a (1.00 g, 4.36 mmol) dissolved hydrochloric acid (4 M in 1,4-dioxane solution, 5 mL) was added. The reaction solution was stirred for 3 hours at 25° C. The resulting reaction solution was concentrated to obtain yellow solid INT-11 (700 mg, yield: 96.9%). $^1H$ NMR (500 MHz, DMSO-d6) δ 9.70 (brs, 2H), 3.66 (s, 3H), 3.42-3.35 (m, 1H), 3.30-3.22 (m, 2H), 3.19-3.13 (m, 2H), 2.22-2.14 (m, 1H), 2.06-1.99 (m, 1H).

The Preparation of Compound INT-12:

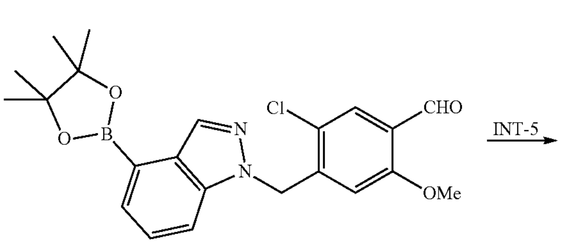

INT-8c

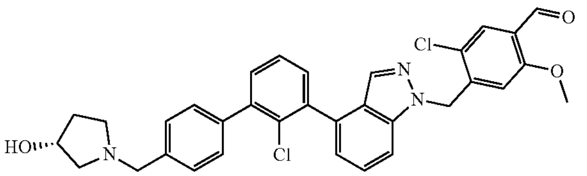

INT-15

Starting from compound INT-8c and compound INT-5, referring to the synthesis of compound INT-8, compound INT-12 is obtained. MS (ESI): m/z 586.4 $(M+H)^+$.

The Preparation of Compound INT-13:

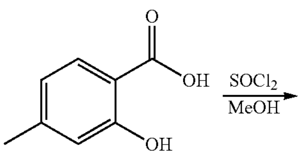

-continued

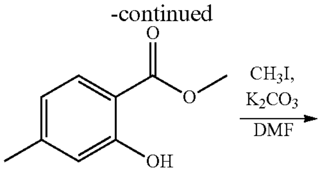

INT-13a

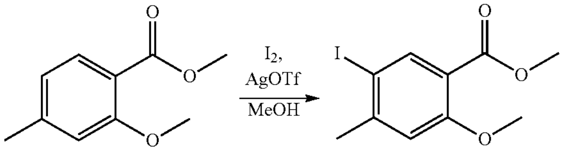

INT-13b INT-13

Under ice bath conditions, thionyl chloride (11.7 g, 98.6 mmol) was added to methanol (20 mL) solution with 2-hydroxy-4-methylbenzoic acid (5.0 g, 32.9 mmol) dissolved. The reaction solution was stirred for 16 hours at 65° C. The reaction solution was concentrated, and to the residue ethyl acetate (100 mL) and water (100 mL) were added. The organic phase was washed with saturated sodium bicarbonate solution (100 mL), saturated salt solution (100 mL), dried with anhydrous sodium sulfate, filtered, and concentrated to obtain yellow oily matter INT-13a (5.25 g, yield: 96.1%).

In N, N-dimethylformamide (30 mL) with compound INT-13a (5.25 g, 31.6 mmol) dissolved iodomethane (5.83 g, 41.1 mmol) and potassium carbonate (8.73 g, 63.2 mmol) were added. The reaction solution was stirred for 6 hours at 25° C. The reaction solution was concentrated, and to the residue ethyl acetate (100 mL) and water (100 mL) were added. The organic phase was washed with saturated salt solution (100 mL), dried with anhydrous sodium sulfate, filtered, and concentrated to obtain yellow oily matter INT-13b (5.6 g, yield: 98.4%).

In methanol (15 mL) solution with compound INT-13b (1.0 g, 5.55 mmol) dissolved silver triflate (1.57 g, 6.10 mmol) and iodine (1.55 g, 6.10 mmol) were added. The reaction solution was stirred for 2 hours at 25° C., subsequently was filtered, and the filtrate was diluted with ethyl acetate (50 mL), and was washed with sodium sulfite aqueous solution (5% w/w, 50 mL) and saturated salt solution (100 mL), dried with anhydrous sodium sulfate, filtered, and concentrated to obtain orange solid INT-13 (1.6 g, yield: 94.2%). $^{1}$H NMR (500 MHz, Chloroform-d) δ 8.20 (s, 1H), 6.86 (s, 1H), 3.88 (s, 3H), 3.87 (s, 3H), 2.45 (s, 3H); MS (ESI): m/z 306.9 $(M+H)^+$.

The Preparation of Compound INT-14:

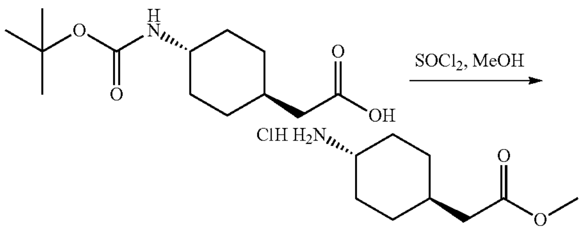

INT-14

Thionyl chloride (185 mg, 1.55 mol) was added to methanol (3 mL) solution with trans-(N-Boc-4-aminocyclohexyl) acetic acid (100 mg, 0.39 mmol) dissolved. The reaction solution was stirred for 3 hours at 70° C. The reaction solution was concentrated to obtain white solid INT-14 (70 mg, yield: 86.7%). $^{1}$H NMR (500 MHz, DMSO-d6) δ 8.15-7.92 (m, 3H), 3.56 (s, 3H), 2.87 (s, 1H), 2.21-2.15 (m, 2H), 1.95-1.87 (m, 2H), 1.74-1.66 (m, 2H), 1.63-1.53 (m, 1H), 1.35-1.25 (m, 2H), 1.06-0.95 (m, 2H).

The Preparation of Compound INT-15:

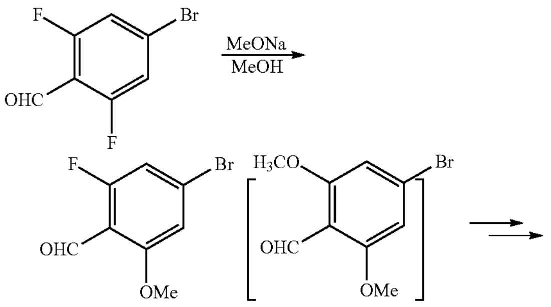

INT-15a INT-15b

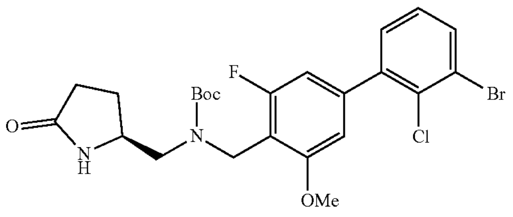

INT-15

Under ice bath conditions, to methanol (10 mL) solution with 4-bromo-2, 6-difluorobenzaldehyde (1.10 g, 4.98 mmol) dissolved sodium methoxide (5.4 M in methanol solution, 1.11 mL) was added dropwise. The reaction solution under the same conditions was stirred for 3 hours. The reaction solution was quenched with hydrochloric acid (1 M aqueous solution, 12 mL) and was stirred for 10 minutes. The obtained solution was further diluted with water (100 mL), and extracted with ethyl acetate (100 mL×2). The combined organic phase was washed with saturated salt solution (150 mL), dried with anhydrous sodium sulfate, and concentrated. The residue was separated by silica gel column chromatography (petroleum ether/ethyl acetate, v/v=10/1) to obtain white solid INT-15a (660 mg, yield: 56.9%) and white solid INT-15b (204 mg, yield: 16.7%).

Compound INT-15a: $^{1}$H NMR (500 MHz, Chloroform-d) δ 10.36 (s, 1H), 6.97-6.93 (m, 2H), 3.94 (s, 3H).

Compound INT-15b: $^{1}$H NMR (500 MHz, Chloroform-d) δ 10.42 (s, 1H), 6.76 (s, 2H), 3.90 (s, 6H).

Starting from compound INT-15a, referring to the synthesis of compound INT-6, compound INT-15 is obtained. $^{1}$H NMR (500 MHz, DMSO-d6) δ 7.83 (d, J=8.0 Hz, 1H), 7.71 (s, 1H), 7.45 (d, J=7.8 Hz, 1H), 7.37 (t, J=7.8 Hz, 1H), 6.90-6.86 (m, 2H), 4.54-4.50 (m, 2H), 3.84 (s, 3H), 3.77-3.73 (m, 1H), 3.17 (d, J=5.3 Hz, 2H), 2.12-2.02 (m, 3H), 1.71-1.65 (m, 1H), 1.40-1.32 (m, 9H); MS (ESI): m/z 541.5 $(M+H)^+$.

The Preparation of Compound INT-16:

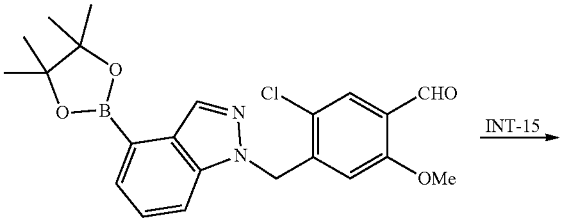

INT-8c

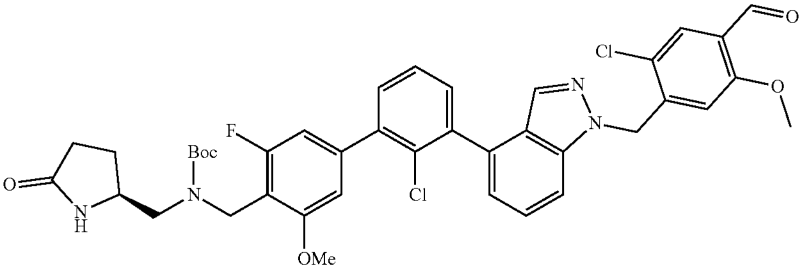

Starting from compound INT-8c and compound INT-15, referring to the synthesis of compound INT-8, compound INT-16 is obtained. MS (ESI): m/z 761.7 $(M+H)^+$.

The Preparation of Compound INT-17:

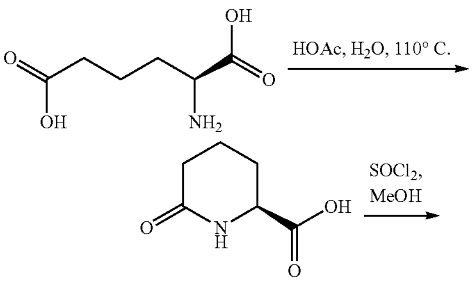

INT-17a

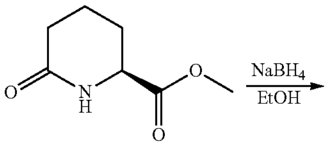

INT-17b

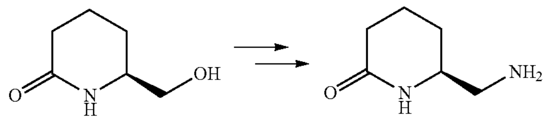

INT-17c INT-17

At 110° C., a solution of acetic acid and water (25 mL, v/v=1/4) with S-2-aminoadipic acid (5 g, 31 mmol) dissolved was stirred for 16 hours. The reaction solution was concentrated. The obtained residue was dissolved by ethanol, wherein the unreacted starting materials will not be dissolved by ethanol. The filtrate was concentrated to obtain white solid INT-17a (3 g, yield: 67.6%). MS (ESI): m/z 142.1 $(M-H)^-$.

Starting from compound INT-17a, referring to the synthesis of compound INT-13a, thus obtained colorless oily matter INT-17b.

At 0° C., sodium borohydride (433 mg, 11.5 mmol) was added to ethanol (10 mL) solution with compound INT-17b (450 mg, 2.9 mmol) dissolved. The obtained mixture was stirred for 16 hours at room temperature. The reaction was quenched with small amount of acetic acid, and the resulting reaction solution was concentrated. The obtained residue was dissolved with dichloromethane. The organic phase was washed with saturated salt solution, dried with anhydrous sodium sulfate, and concentrated to obtain colorless oily matter INT-17c (369 mg, yield: 99.8%). MS (ESI): m/z 130.2 $(M+H)^+$.

Starting from compound INT-17c, referring to the synthesis of compound INT-2, thus obtained light yellow oily matter INT-17. $^1H$ NMR (500 MHz, DMSO-d6) δ 7.34 (s, 1H), 3.22-3.06 (m, 1H), 2.59-2.42 (m, 2H), 2.18-1.98 (m, 2H), 1.75 (brs, 2H), 1.64-1.50 (m, 2H), 1.37-1.18 (m, 2H).

The Preparation of Compound INT-18:

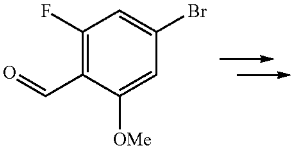

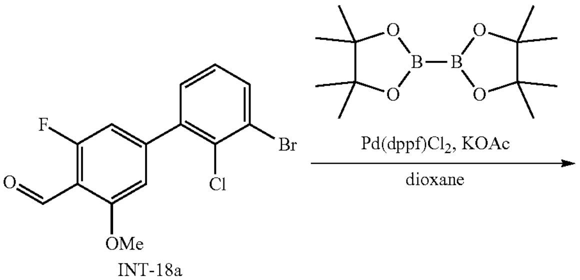

INT-18a

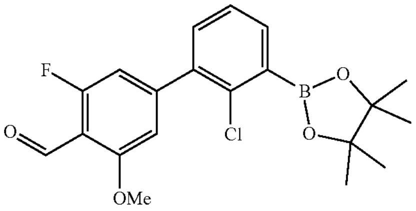

INT-18

Starting from compound INT-15a, referring to last step Suzuki boron esterification reaction of compound INT-1 and the synthesis of compound INT-3a, thus obtained compound INT-18a. $^1$H NMR (500 MHz, DMSO-d6) δ 10.34 (s, 1H), 7.91-7.87 (m, 1H), 7.52-7.48 (m, 1H), 7.44-7.38 (m, 1H), 7.13-7.10 (m, 1H), 7.04-7.00 (m, 1H), 3.96 (s, 3H).

Starting from compound INT-18a, referring to last step Suzuki boron esterification reaction of compound INT-1, thus obtained compound INT-18. $^1$H NMR (500 MHz, DMSO-d6) δ 10.31 (s, 1H), 7.68-7.64 (m, 1H), 7.55-7.51 (m, 1H), 7.44 (t, J=7.5 Hz, 1H), 7.05 (s, 1H), 6.97-6.89 (m, 1H), 3.93 (s, 3H), 1.31 (s, 12H); MS (ESI): m/z 391.7 $(M+H)^+$.

The Synthesis of Example Compound

Example 1

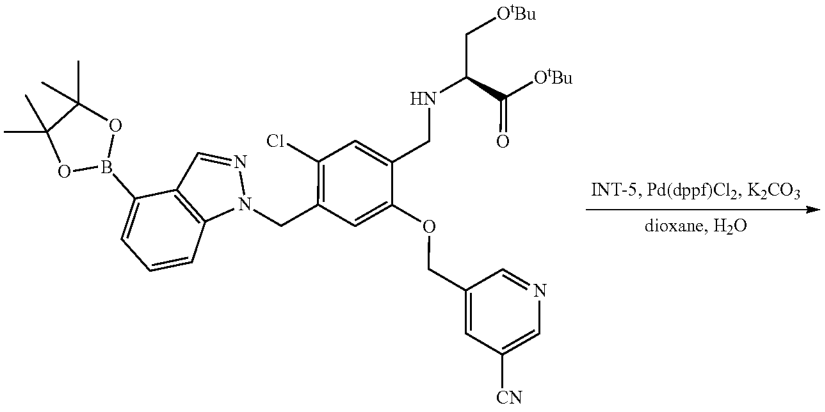

INT-1

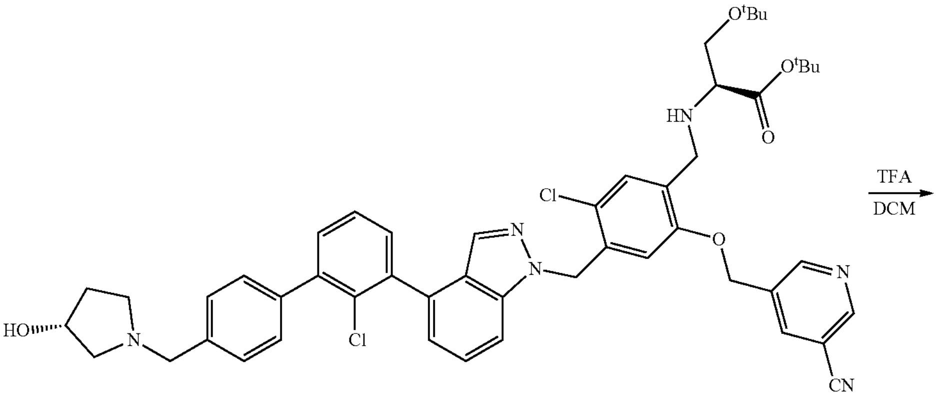

1a

-continued

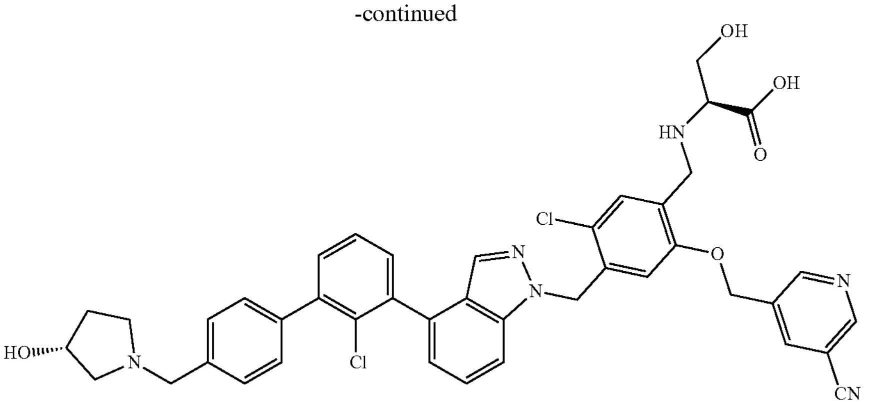

1

Starting from compound INT-1 and compound INT-5, referring to the synthesis of compound INT-7, compound 1a is obtained. MS (ESI): m/z 889.9 $(M+H)^+$.

Compound 1a (20 mg, 0.022 mmol) was dissolved in dichloromethane (2 mL), trifluoroacetic acid (2 mL) was added, and the reaction solution was stirred at 25° C. for 6 hours. After the reaction solution was concentrated, the residue was purified by preparative high performance liquid chromatography to obtain a white solid 1 (6.5 mg, yield: 37.4%). $^1H$ NMR (500 MHz, DMSO-d6) δ 8.95 (s, 1H), 8.84 (s, 1H), 8.33 (s, 1H), 7.87 (s, 1H), 7.72-7.67 (m, 1H), 7.55-7.45 (m, 7H), 7.40 (d, J=8.0 Hz, 2H), 7.18-7.15 (m, 1H), 6.83 (s, 1H), 5.74-5.69 (m, 2H), 5.11-5.05 (m, 2H), 4.24-4.18 (m, 1H), 3.93 (d, J=14.5 Hz, 1H), 3.85 (d, J=14.5 Hz, 1H), 3.65 (d, J=13.0 Hz, 1H), 3.61-3.55 (m, 2H), 3.12-3.07 (m, 1H), 2.72-2.68 (m, 1H), 2.65-2.58 (m, 2H), 2.38-2.32 (m, 2H), 2.05-1.97 (m, 1H), 1.59-1.52 (m, 1H); MS (ESI): m/z 777.8 $(M+H)^+$.

Example 2

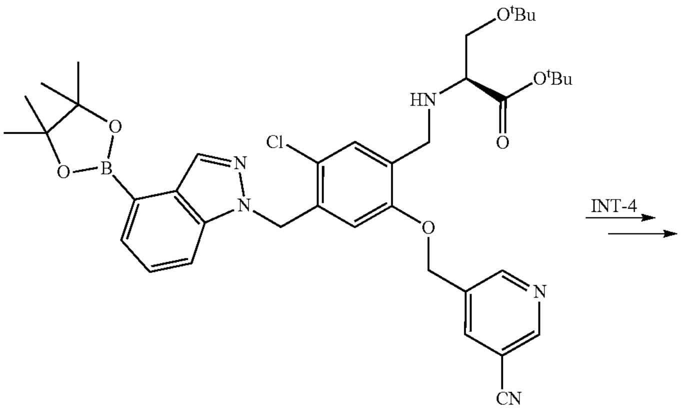

INT-1

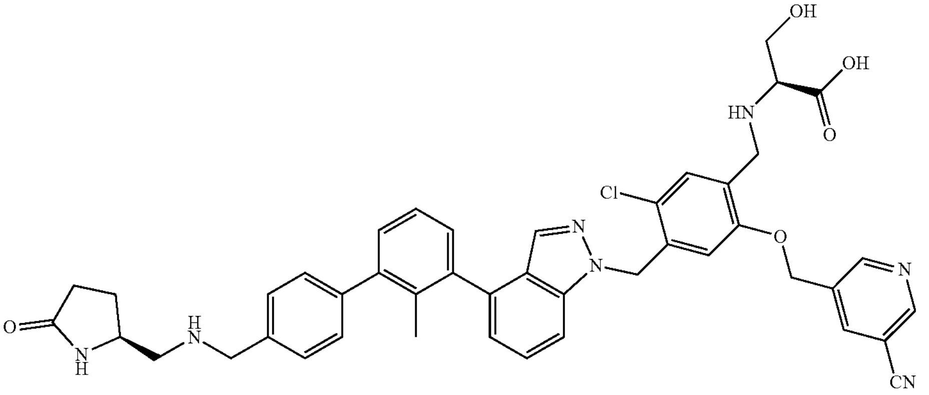

2

Starting from compound INT-1 and compound INT-4, referring to the synthesis of compound 1, compound 2 is obtained. $^1H$ NMR (500 MHz, DMSO-d6) δ 8.95 (d, J=2.0 Hz, 1H), 8.84 (d, J=2.0 Hz, 1H), 8.34 (t, J=2.0 Hz, 1H), 7.84 (s, 1H), 7.71-7.64 (m, 2H), 7.55 (s, 1H), 7.46-7.37 (m, 6H), 7.34-7.31 (m, 1H), 7.28 (d, J=7.5, 1H), 7.09 (d, J=7.0 Hz, 1H), 6.86 (s, 1H), 5.71 (s, 2H), 5.14-5.08 (m, 2H), 3.96-3.84 (m, 2H), 3.79-3.74 (m, 2H), 3.64-3.57 (m, 3H), 3.13-3.09 (m, 1H), 2.55 (d, J=6.0 Hz, 2H), 2.15-2.05 (m, 3H), 1.99 (s, 3H), 1.73-1.67 (m, 1H); MS (ESI): m/z 784.3 $(M+H)^+$.
Example 3
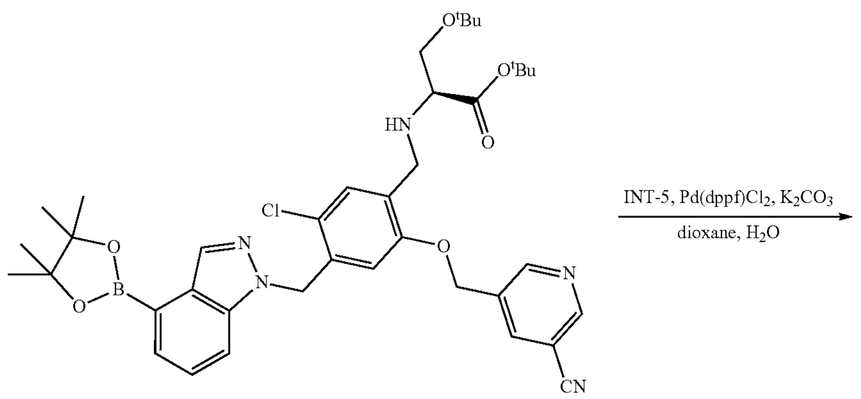
INT-1
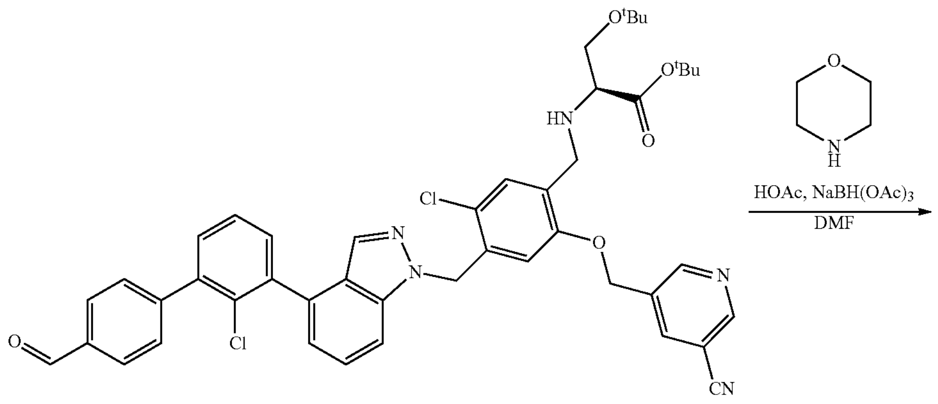
3a
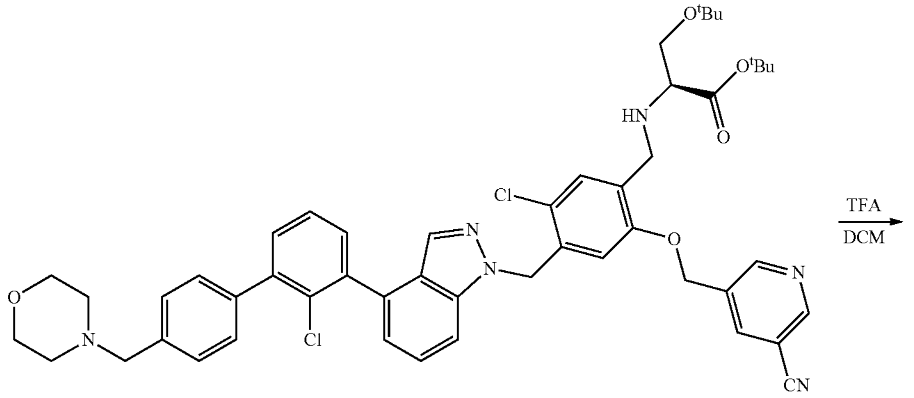
3b -continued

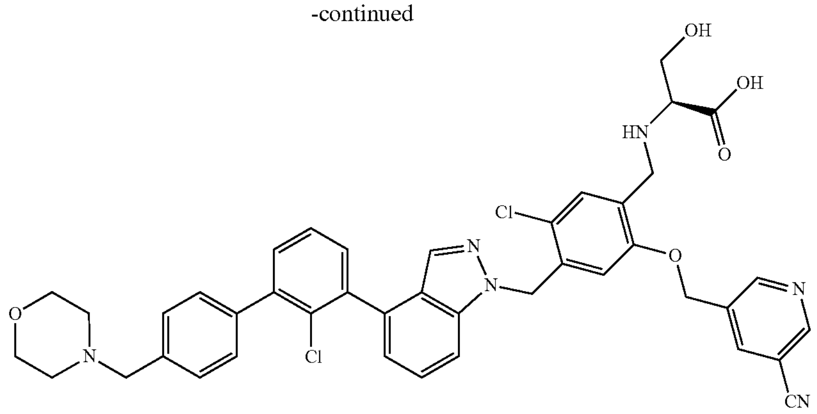

3

Starting from compound INT-1 and compound INT-3a, referring to the synthesis of compound INT-7, compound 3a is obtained. MS (ESI): m/z 818.4 $(M+H)^+$.

Starting from compound 3a and morpholine, referring to compound INT-3b in the synthesis process of reductive amination step, compound 3b is obtained. MS (ESI): m/z 889.9 $(M+H)^+$.

Starting from compound 3b, referring to last step Boc deprotection step in the synthesis of compound 1, compound 3 is obtained. $^1$H NMR (500 MHz, DMSO-d6) δ 8.95 (s, 1H), 8.84 (s, 1H), 8.33 (s, 1H), 7.86 (s, 1H), 7.72-7.67 (m, 1H), 7.56-7.45 (m, 7H), 7.41 (d, J=7.5 Hz, 2H), 7.17 (d, J=7.0 Hz, 1H), 6.83 (s, 1H), 5.72 (s, 2H), 5.13-5.05 (m, 2H), 3.92 (d, J=14.0 Hz, 1H), 3.85 (d, J=14.0 Hz, 1H), 3.63-3.56 (m, 6H), 3.52 (s, 2H), 3.13-3.06 (m, 1H), 2.40 (s, 4H); MS (ESI): m/z 777.6 $(M+H)^+$.

Example 4

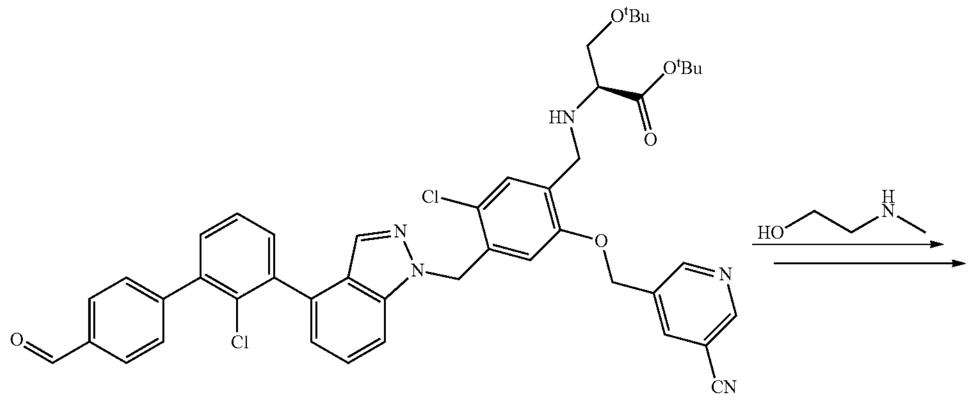

3a

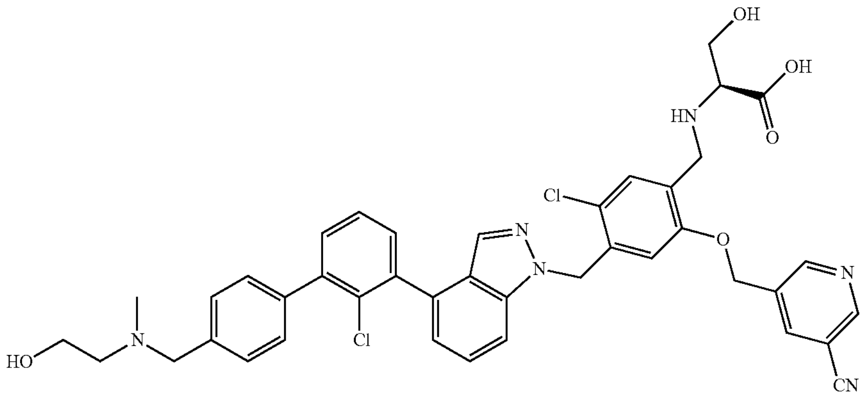

4

Starting from compound 3a and N-methylethanolamine, referring to the synthesis of compound 3, compound 4 is obtained. $^1$H NMR (500 MHz, DMSO-d6) δ 8.95 (d, J=2.0 Hz, 1H), 8.84 (d, J=2.0 Hz, 1H), 8.33 (d, J=2.5 Hz, 1H), 7.87 (s, 1H), 7.71 (d, J=8.5 Hz, 1H), 7.56 (s, 1H), 7.55-7.46 (m, 6H), 7.41 (d, J=8.0 Hz, 2H), 7.17 (d, J=7.0 Hz, 1H), 6.84 (s, 1H), 5.72 (s, 2H), 5.14-5.06 (m, 2H), 3.96 (d, J=14.0 Hz, 1H), 3.88 (d, J=14.0 Hz, 1H), 3.69-3.63 (m, 1H), 3.61-3.58 (m, 1H), 3.57 (s, 2H), 3.54 (t, J=6.5 Hz, 2H), 3.18-3.14 (m, 1H), 2.55-2.53 (m, 2H), 2.20 (s, 3H); MS (ESI): m/z 765.7 (M+H)$^+$.
Example 5
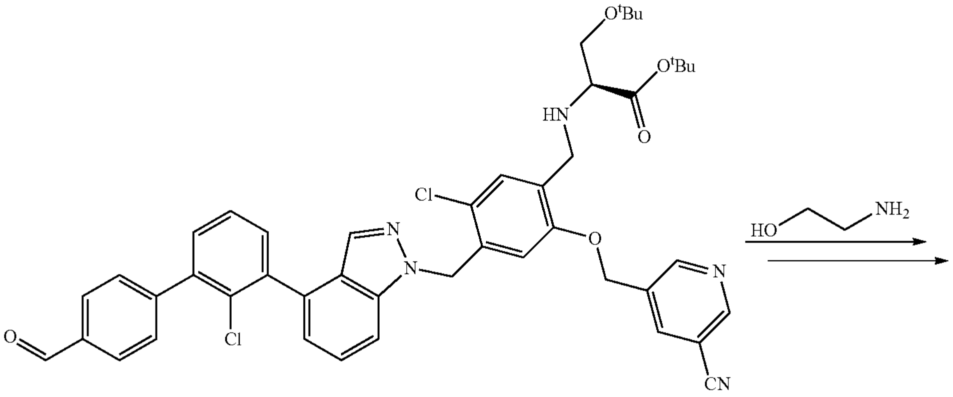
3a
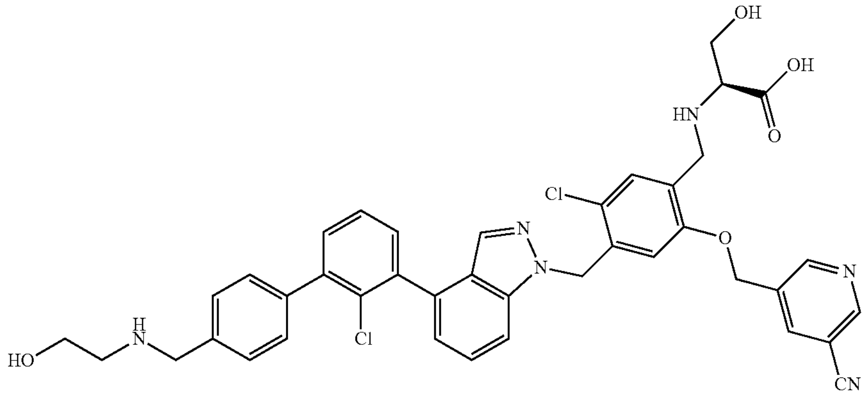
5

Starting from compound 3a and ethanolamine, referring to the synthesis of compound 3, compound 5 is obtained. $^1$H NMR (500 MHz, DMSO-d6) δ 8.94 (s, 1H), 8.83 (s, 1H), 8.32 (s, 1H), 7.86 (s, 1H), 7.70 (d, J=8.5 Hz, 1H), 7.56-7.50 (m, 3H), 7.49-7.43 (m, 6H), 7.17 (d, J=7.0 Hz), 1-56.83 (s, 1H), 5.72 (s, 2H), 5.13-5.05 (m, 2H), 3.90 (d, J=14.0 Hz, 1H), 3.86-3.80 (m, 3H), 3.60-3.54 (m, 2H), 3.51 (t, J=6.0 Hz, 2H), 3.10-3.05 (m, 1H), 2.65 (t, J=6.0 Hz, 2H); MS (ESI): m/z 751.4 $(M+H)^+$.

Example 6

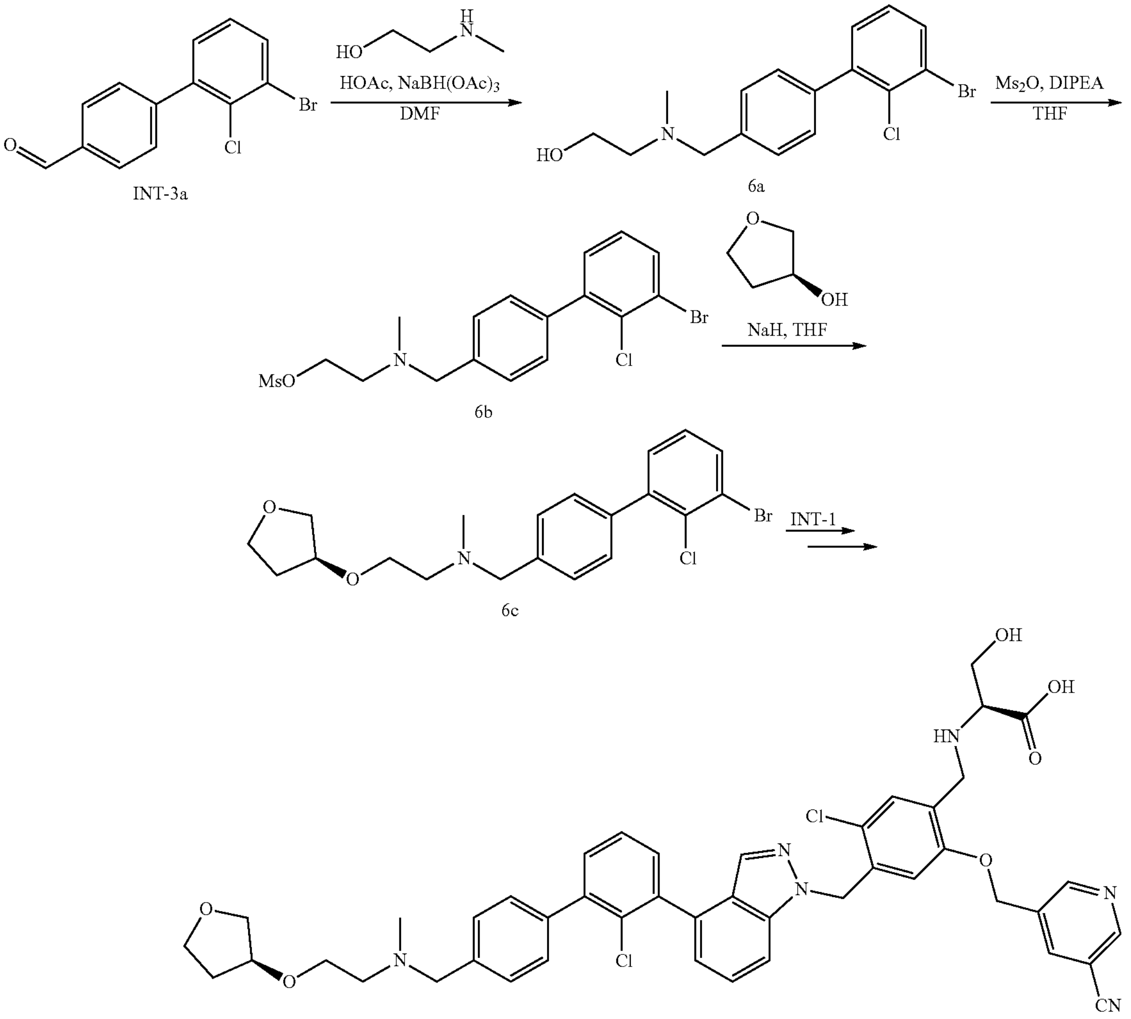

INT-3a

6a

6b

6c

6

Starting from compound INT-3a and N-methylethanolamine, referring to reductive amination step in the synthesis of compound INT-3b, compound 6a is obtained. MS (ESI): m/z 354.2 $(M+H)^+$.

Under ice bath conditions, in tetrahydrofuran (5 mL) solution with compound 6a (207 mg, 0.58 mmol) dissolved N,N-diisopropylethylamine (226 mg, 1.75 mmol) and methanesulfonic anhydride (203 mg, 1.17 mmol) were sequentially added. The reaction solution was stirred for half an hour in ice bath and was warmed to 25° C., and was at the same temperature stirred for 2 hours. The reaction solution was diluted with water (20 mL). The aqueous phase was extracted with dichloromethane (20 mL×2). The combined organic phase was dried with anhydrous sodium sulfate, filtered, and concentrated, thus compound 6b is obtained. Under ice bath and nitrogen atmosphere, in tetrahydrofuran (5 mL) with (R)-(−)-3-hydroxytetrahydrofuran (103 mg, 1.17 mmol) dissolved sodium hydride (60% w/w in kerosene, 46.8 mg) was added. The reaction solution was stirred for half an hour in ice bath, and the obtained compound 6b was added. The resulting reaction solution was heated to 50° C. and stirred overnight. After cooling down to room temperature, the reaction solution was quenched with water (20 mL). The aqueous phase was extracted with ethyl acetate (20 mL×2). The combined organic phase was washed with saturated salt solution (30 mL), dried with anhydrous sodium sulfate, filtered, and concentrated. The residue was separated by preparative thin layer chromatography (dichloromethane/methanol, v/v=15/1) to obtain yellow oily matter 6c (110 mg, yield: 44.4%). MS (ESI): m/z 424.3 $(M+H)^+$.

Starting from compound INT-1 and compound 6c, referring to the synthesis of compound 1, compound 6 is obtained. $^1H$ NMR (500 MHz, DMSO-d6) δ 8.94 (d, J=2.0 Hz, 1H), 8.84 (d, J=2.0 Hz, 1H), 8.34-8.32 (m, 1H), 7.86 (s, 1H), 7.70 (d, J=8.5 Hz, 1H), 7.55-7.45 (m, 7H), 7.40 (d, J=8.0 Hz, 2H), 7.20-7.15 (m, 1H), 6.81 (s, 1H), 5.72 (s, 2H), 5.12-5.05 (m, 2H), 4.12-4.08 (m, 1H), 3.89-3.77 (m, 2H), 3.73-3.68 (m, 1H), 3.67-3.62 (m, 3H), 3.57 (s, 2H), 3.55-3.48 (m, 4H), 3.02-2.94 (m, 1H), 2.55 (t, J=6.0 Hz, 2H), 2.20 (s, 3H), 1.94-1.83 (m, 2H); MS (ESI): m/z 835.7 $(M+H)^+$.

Example 7

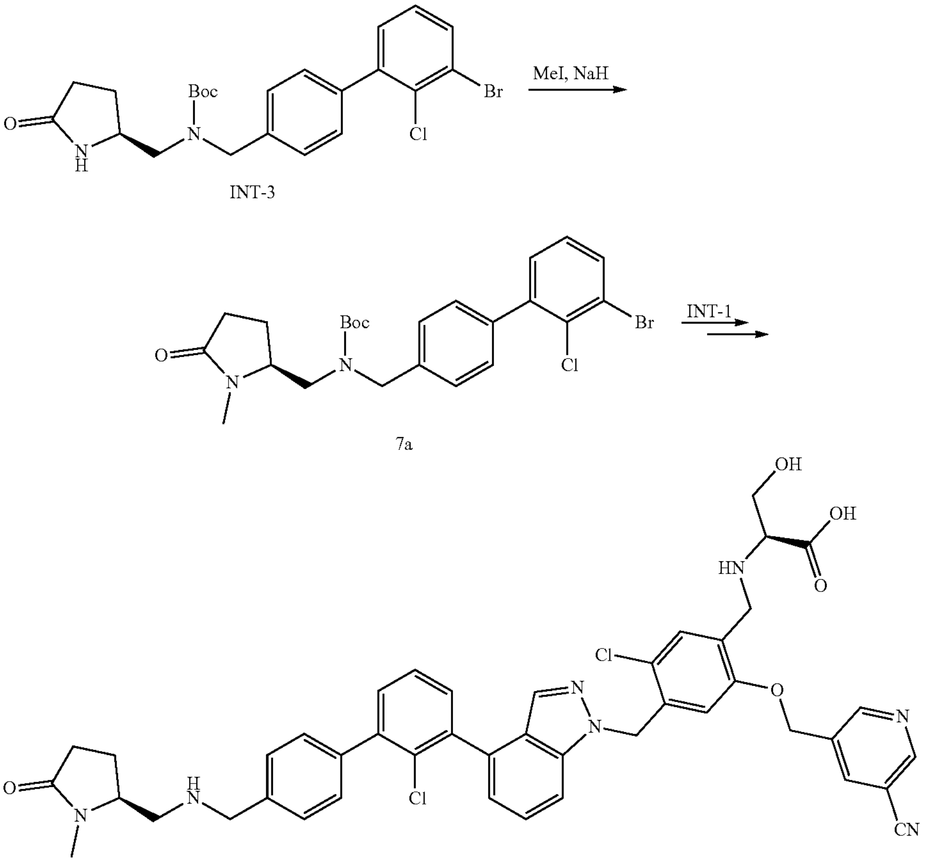

INT-3

7a

7

Under ice bath conditions, in tetrahydrofuran (2 mL) with compound INT-3 (200 mg, 0.40 mmol) dissolved sodium hydride (60% w/w in kerosene, 32.4 mg) was added. The reaction solution was under ice bath condition stirred for half an hour. Subsequently, at room temperature in the reaction solution iodomethane (86 mg, 0.61 mmol) was added. The resulting reaction solution was at room temperature stirred overnight. The reaction solution was quenched with water (20 mL). Aqueous phase was extracted with ethyl acetate (20 mL×2). The combined organic phase was washed with saturated brine (30 mL), dried over anhydrous sodium sulfate, filtered, and concentrated. The residue was separated by silica gel column chromatography (dichloromethane/methanol, v/v=10/1) to obtain a yellow oil 7a (200 mg, yield: 97%). MS (ESI): m/z 507.4 $(M+H)^+$.

Starting from compound INT-1 and compound 7a, referring to the synthesis of compound 1, compound 7 is obtained. $^1H$ NMR (500 MHz, DMSO-d6) δ 8.99-8.90 (m, 1H), 8.90-8.79 (m, 1H), 8.32 (s, 1H), 7.86 (s, 1H), 7.70 (d, J=8.5 Hz, 1H), 7.57-7.43 (m, 9H), 7.17 (d, J=7.0 Hz, 1H), 6.83 (s, 1H), 5.72 (s, 2H), 5.15-5.05 (m, 2H), 3.97-3.91 (m, 1H), 3.89-3.83 (m, 1H), 3.78 (s, 2H), 3.68-3.52 (m, 3H), 3.18-3.10 (m, 1H), 2.73-2.63 (m, 5H), 2.33-2.22 (m, 1H), 2.18-2.08 (m, 1H), 2.06-1.98 (m, 1H), 1.87-1.77 (m, 1H); MS (ESI): m/z 818.6 $(M+H)^+$.

Example 8
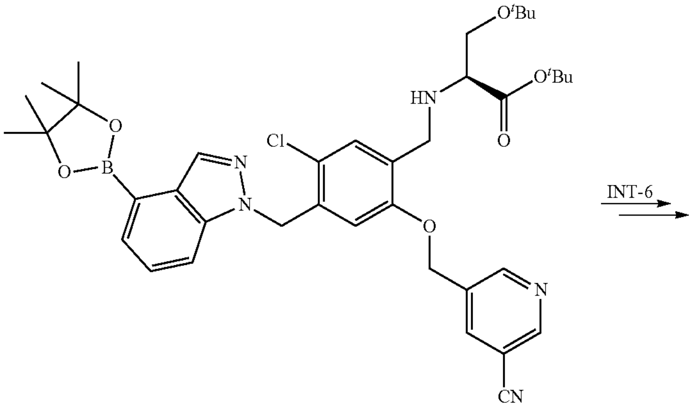
INT-1
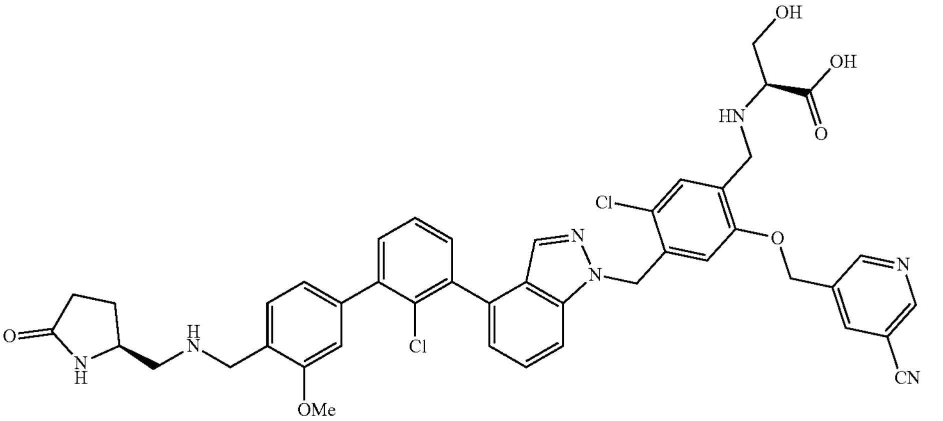
8
Starting from compound INT-1 and compound INT-6, referring to the synthesis of compound 1, compound 8 is obtained. $^1$H NMR (500 MHz, DMSO-d6) δ 8.95 (d, J=2.0 Hz, 1H), 8.84 (d, J=2.0 Hz, 1H), 8.34 (d, J=2.0 Hz, 1H), 7.88 (s, 1H), 7.74-7.68 (m, 2H), 7.57-7.49 (m, 4H), 7.48-7.45 (m, 1H), 7.42 (d, J=8.0 Hz, 1H), 7.19-7.15 (m, 1H), 7.11-7.04 (m, 2H), 6.85 (s, 1H), 5.72 (s, 2H), 5.15-5.06 (m, 2H), 3.95 (d, J=14.5 Hz, 1H), 3.87 (d, J=14.5 Hz, 1H), 3.83 (s, 3H), 3.76-3.73 (m, 2H), 3.66-3.62 (m, 2H), 3.61-3.55 (m, 1H), 3.15-3.11 (m, 1H), 2.58-2.54 (m, 2H), 2.14-2.06 (m, 3H), 1.74-1.66 (m, 1H); MS (ESI): m/z 834.7 $(M+H)^+$.
Example 9
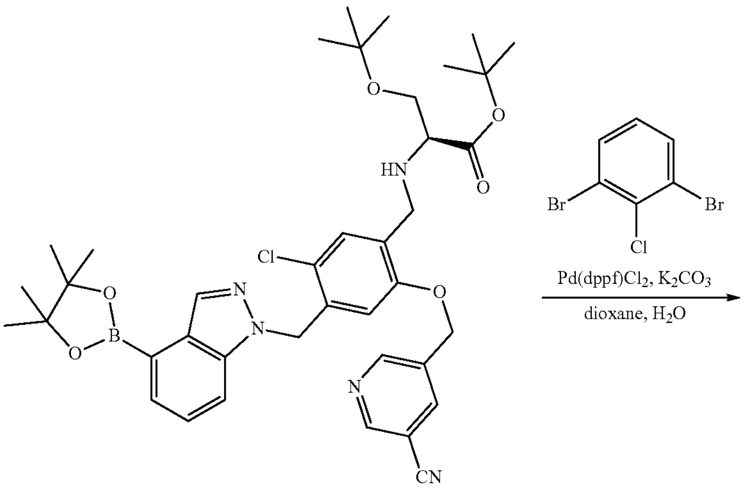
INT-1

-continued
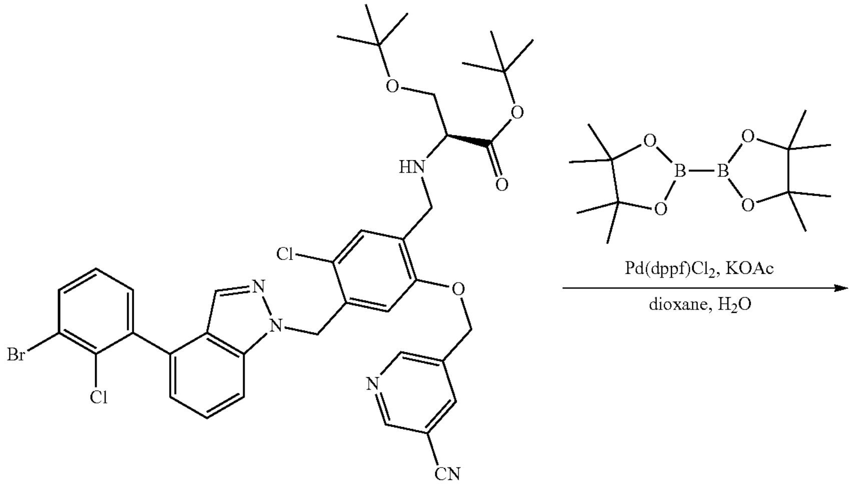
9a
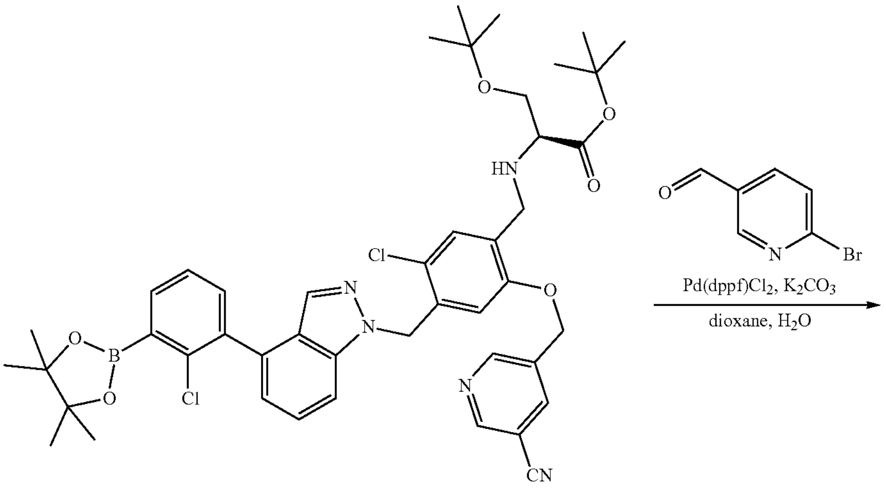
9b
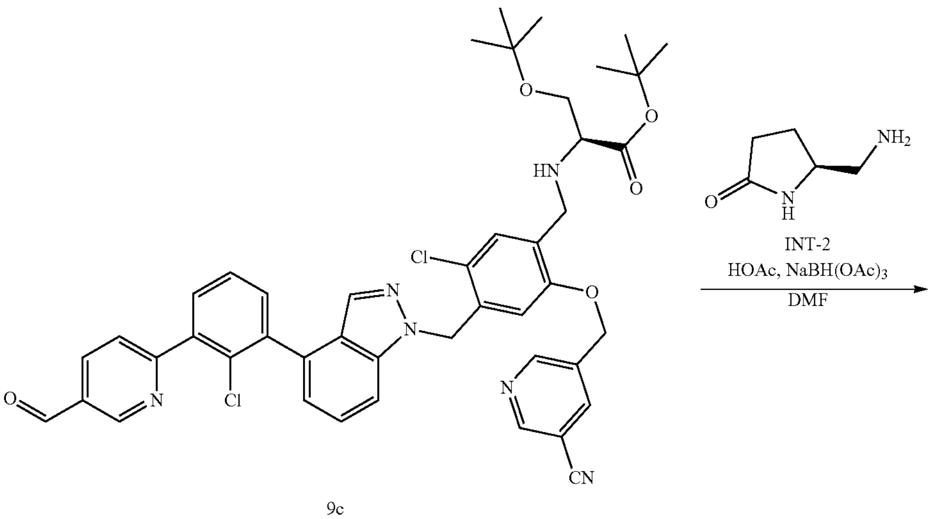
9c

-continued
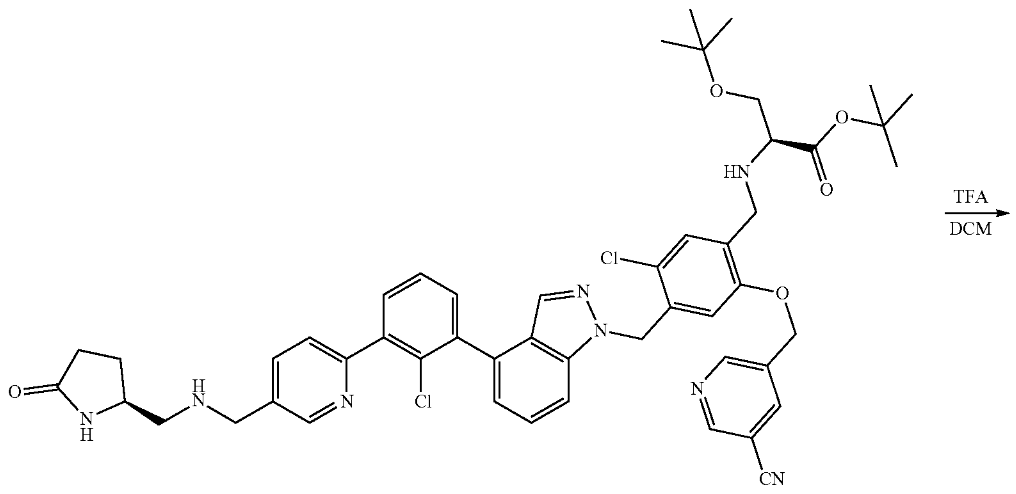
9d
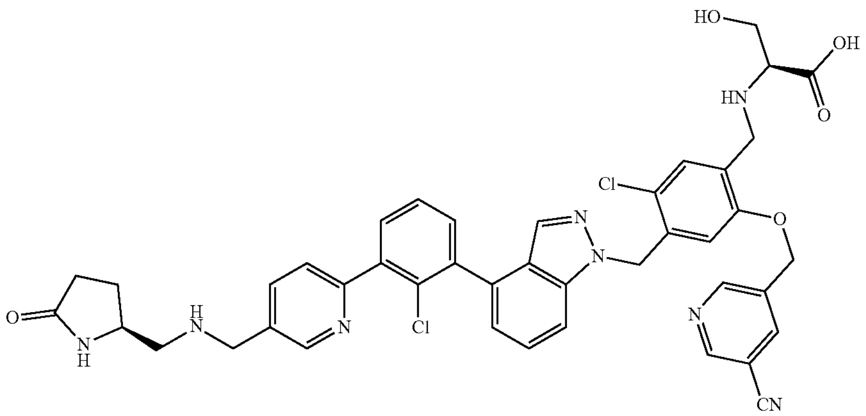
9

Starting from compound INT-1 and 1,3-dibromo-2-chlorobenzene, referring to last step Suzuki reaction in the synthesis of compound INT-7, compound 9a is obtained. MS (ESI): m/z 792.6 $(M+H)^+$.

Starting from compound 9a, referring to the synthesis of compound INT-7a, compound 9b is obtained. MS (ESI): m/z 840.6 $(M+H)^+$.

Starting from compound 9b and 2-bromo-5-aldehyde pyridine, referring to last step Suzuki reaction in the synthesis of compound INT-7, compound 9c is obtained. MS (ESI): m/z 819.4 $(M+H)^+$.

Starting from compound 9c and compound INT-2, referring to compound INT-3b in the synthesis of reductive amination step, compound 9d is obtained. MS (ESI): m/z 917.8 $(M+H)^+$.

Starting from compound 9d, referring to last step Boc deprotection step in the synthesis of compound 1, compound 9 is obtained. $^1H$ NMR (500 MHz, DMSO-d6) δ 8.96 (d, J=2.0 Hz, 1H), 8.84 (d, J=2.0 Hz, 1H), 8.65 (d, J=2.0 Hz, 1H), 8.33 (s, 1H), 7.92-7.83 (m, 2H), 7.75-7.66 (m, 3H), 7.65-7.55 (m, 3H), 7.52-7.44 (m, 1H), 7.21-7.14 (m, 1H), 6.86 (s, 1H), 5.73 (s, 2H), 5.15-5.05 (m, 2H), 3.99-3.73 (m, 4H), 3.69-3.55 (m, 3H), 3.21-3.15 (m, 1H), 2.58-2.52 (m, 2H), 2.18-2.03 (m, 3H), 1.75-1.64 (m, 1H); MS (ESI): m/z 805.8 $(M+H)^+$.

Example 10

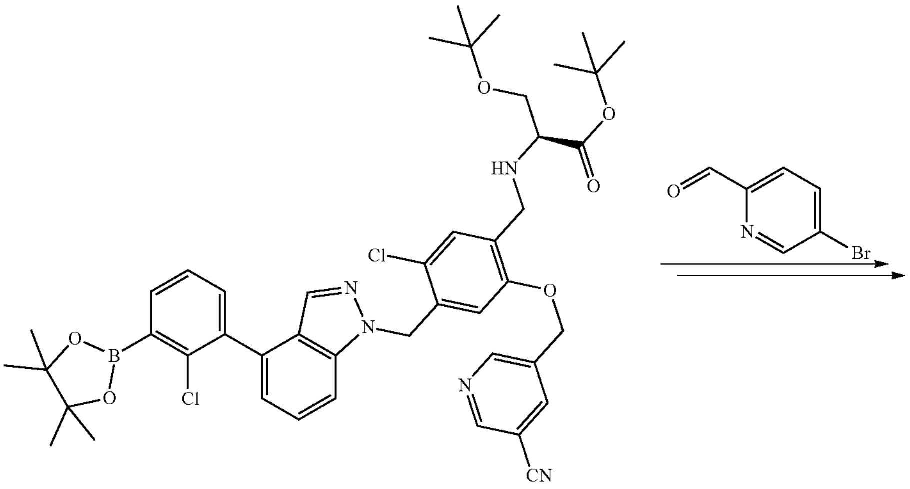

9b

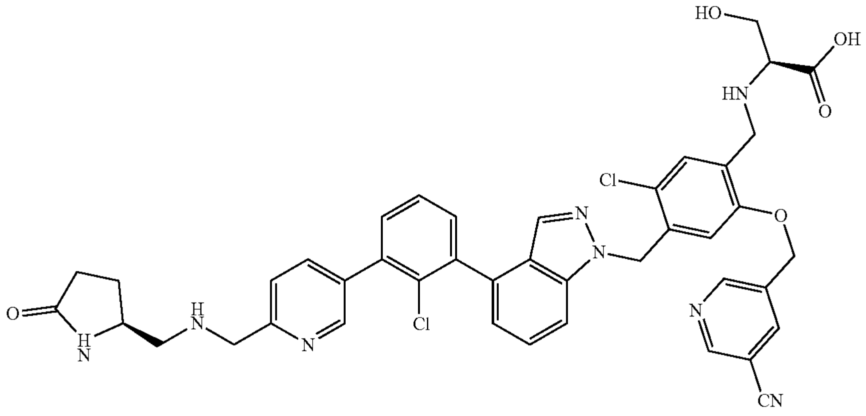

10

Starting from compound 9b and 5-bromo-2-pyridinecarboxaldehyde, referring to the synthesis of compound 9, compound 10 is obtained. $^{1}$H NMR (500 MHz, DMSO-d6) δ 8.95 (s, 1H), 8.84 (s, 1H), 8.64 (s, 1H), 8.33 (s, 1H), 7.96 (d, J=8.0 Hz, 1H), 7.90 (s, 1H), 7.74-7.69 (m, 2H), 7.62-7.44 (m, 6H), 7.18 (d, J=7.0 Hz, 1H), 6.83 (s, 1H), 5.72 (s, 2H), 5.14-5.05 (m, 2H), 3.93-3.73 (m, 4H), 3.68-3.50 (m, 3H), 3.03-2.94 (m, 1H), 2.58 (d, J=6.2 Hz, 2H), 2.16-2.05 (m, 3H), 1.75-1.66 (m, 1H); MS (ESI): m/z 805.3 $(M+H)^{+}$.
Example 11
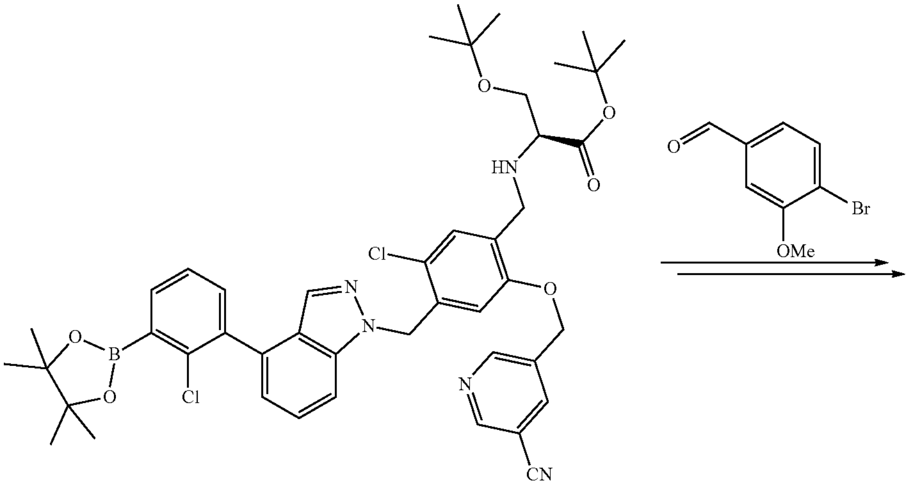
9b
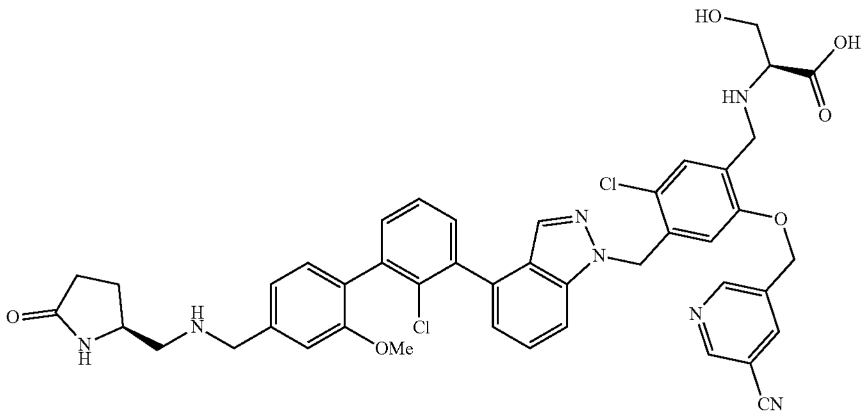
11

Starting from compound 9b and 4-bromo-3-methoxybenzaldehyde, referring to the synthesis of compound 9, compound 11 is obtained. $^1$H NMR (500 MHz, DMSO-d6) δ 8.88 (d, J=2.0 Hz, 1H), 8.77 (d, J=2.0 Hz, 1H), 8.27-8.25 (m, 1H), 7.73 (s, 1H), 7.66-7.59 (m, 2H), 7.47 (s, 1H), 7.45-7.37 (m, 3H), 7.32-7.28 (m, 1H), 7.15-7.08 (m, 2H), 7.05 (s, 1H), 6.93 (d, J=7.7 Hz, 1H), 6.78 (s, 1H), 5.64 (s, 2H), 5.06-5.00 (m, 2H), 3.87-3.82 (m, 1H), 3.80-3.75 (m, 1H), 3.74-3.67 (m, 6H), 3.58-3.56 (m, 1H), 3.51-3.50 (m, 1H), 3.04-2.99 (m, 1H), 2.51-2.47 (m, 2H), 2.08-1.99 (m, 3H), 1.68-1.59 (m, 1H); MS (ESI): m/z 834.7 $(M+H)^+$.

Example 12

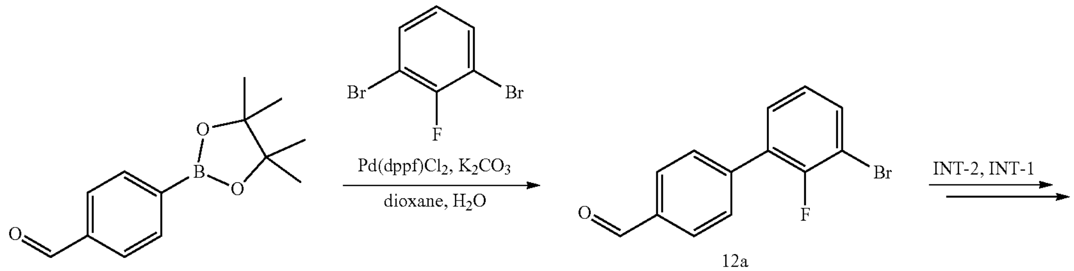

12a

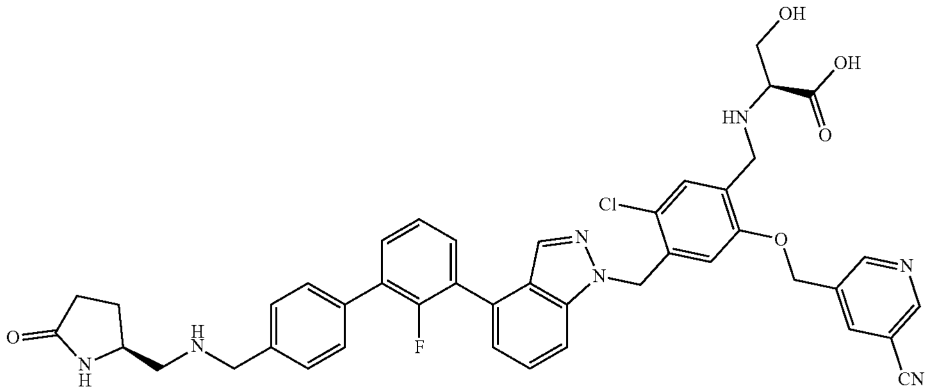

12

Starting from 4-formylphenylboronic acid pinacol ester and 1,3-dibromo-2-fluorobenzenefluorobenzene, referring to the synthesis of compound INT-3a, compound is obtained 12a. $^1$H NMR (500 MHz, Chloroform-d) δ 10.08 (s, 1H), 7.97 (d, J=8.0 Hz, 2H), 7.70 (d, J=8.0 Hz, 2H), 7.61 (t, J=7.0 Hz, 1H), 7.40 (t, J=7.0 Hz, 1H), 7.14 (t, J=7.5 Hz, 1H).

Starting from compound 12a, compound INT-2 and compound INT-1, referring to the synthesis of compound INT-3 and compound 1, compound 12 is obtained. $^1$H NMR (500 MHz, DMSO-d6) δ 8.93 (d, J=2.0 Hz, 1H), 8.84 (d, J=2.0 Hz, 1H), 8.34-8.32 (m, 1H), 8.02 (d, J=2.5 Hz, 1H), 7.72 (d, J=8.5 Hz, 1H), 7.68 (s, 1H), 7.64-7.57 (m, 4H), 7.53 (s, 1H), 7.51-7.42 (m, 4H), 7.30-7.26 (m, 1H), 6.85 (s, 1H), 5.72 (s, 2H), 5.15-5.07 (m, 2H), 3.90 (d, J=14.5 Hz, 1H), 3.85-3.72 (m, 3H), 3.65-3.60 (m, 1H), 3.56 (d, J=5.5 Hz, 2H), 3.07-2.99 (m, 1H), 2.54-2.52 (m, 2H), 2.14-2.05 (m, 3H), 1.73-1.64 (m, 1H); MS (ESI): m/z 788.3 $(M+H)^+$.

Example 13

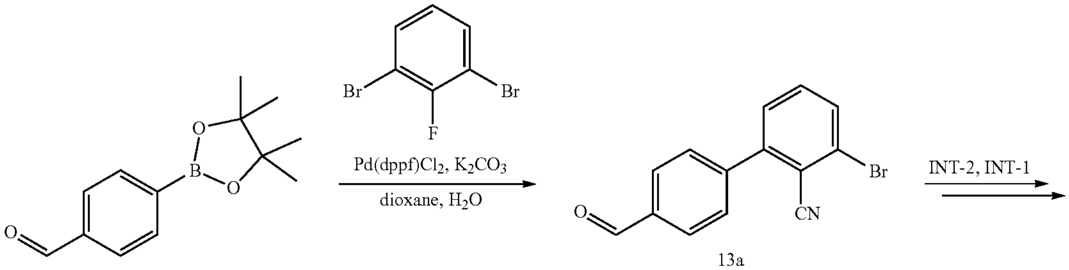

13a

-continued

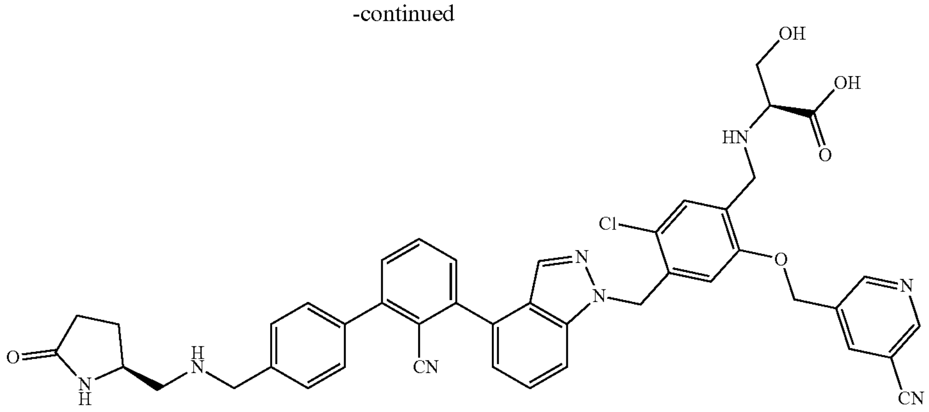

13

Starting from 4-formylphenylboronic acid pinacol ester and 2,6-dibromo-benzonitrile, referring to the synthesis of compound INT-3a, compound 13a is obtained. $^1H$ NMR (500 MHz, Chloroform-d) δ 10.11 (s, 1H), 8.02 (d, J=8.0 Hz, 1H), 7.76 (d, J=8.0 Hz, 1H), 7.71 (d, J=8.0 Hz, 2H), 7.54 (t, J=8.0 Hz, 1H), 7.47 (d, J=8.0 Hz, 1H).

Starting from compound 13a, compound INT-2 and compound INT-1, referring to the synthesis of compound INT-3 and compound 1, compound 13 is obtained. $^1H$ NMR (500 MHz, DMSO-d6) δ 8.94 (d, J=2.0 Hz, 1H), 8.81 (d, J=2.0 Hz, 1H), 8.31-8.29 (m, 1H), 8.07 (d, J=2.5 Hz, 1H), 7.93-7.87 (m, 1H), 7.80-7.72 (m, 2H), 7.70-7.63 (m, 4H), 7.56-7.45 (m, 4H), 7.37-7.33 (m, 1H), 6.70 (s, 1H), 5.78-5.73 (m, 2H), 5.06-4.99 (m, 2H), 3.90 (d, J=15.0 Hz, 1H), 3.84-3.75 (m, 3H), 3.71 (d, J=15.0 Hz, 1H), 3.66-3.61 (m, 1H), 3.58-3.54 (m, 1H), 3.09-3.02 (m, 1H), 2.56-2.53 (m, 2H), 2.14-2.05 (m, 3H), 1.73-1.65 (m, 1H); MS (ESI): m/z 795.7 $(M+H)^+$.

Example 14

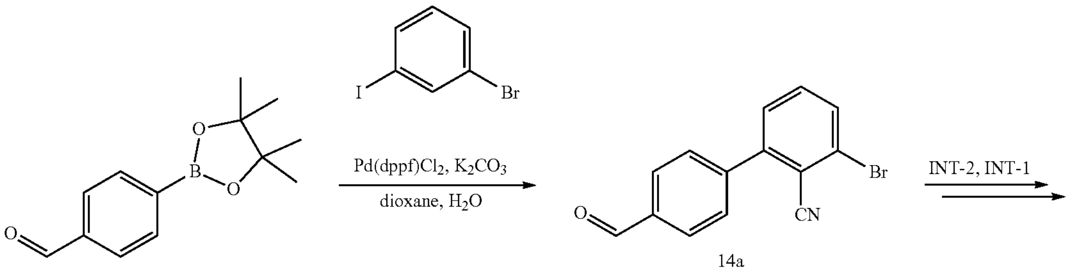

14a

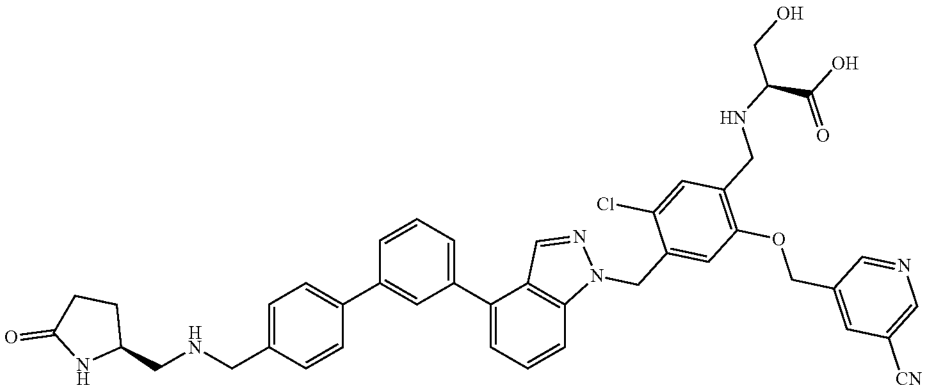

14

Starting from 4-formylphenylboronic acid pinacol ester and 1-bromo-3-r benzene, referring to the synthesis of compound INT-3a, compound 14a is obtained.

Starting from compound 14a, compound INT-2 and compound INT-1, referring to the synthesis of compound INT-3 and compound 1, compound 14 is obtained. $^1$H NMR (500 MHz, DMSO-d6) δ 8.91 (d, J=2.0 Hz, 1H), 8.83 (d, J=2.0 Hz, 1H), 8.32-8.30 (m, 1H), 8.21-8.18 (m, 1H), 7.96-7.94 (m, 1H), 7.76-7.71 (m, 4H), 7.69-7.62 (m, 3H), 7.55 (s, 1H), 7.51-7.44 (m, 3H), 7.38 (d, J=7.0 Hz, 1H), 6.83 (s, 1H), 5.76-5.70 (m, 2H), 5.16-5.08 (m, 2H), 3.94 (d, J=14.0 Hz, 1H), 3.87 (d, J=14.0 Hz, 1H), 3.79 (d, J=14.0 Hz, 1H), 3.75 (d, J=14.0 Hz, 1H), 3.66-3.61 (m, 2H), 3.61-3.55 (m, 1H), 3.15-3.12 (m, 1H), 2.54-2.52 (m, 2H), 2.13-2.04 (m, 3H), 1.72-1.64 (m, 1H); MS (ESI): m/z 770.7 (M+H)$^+$.

Example 15

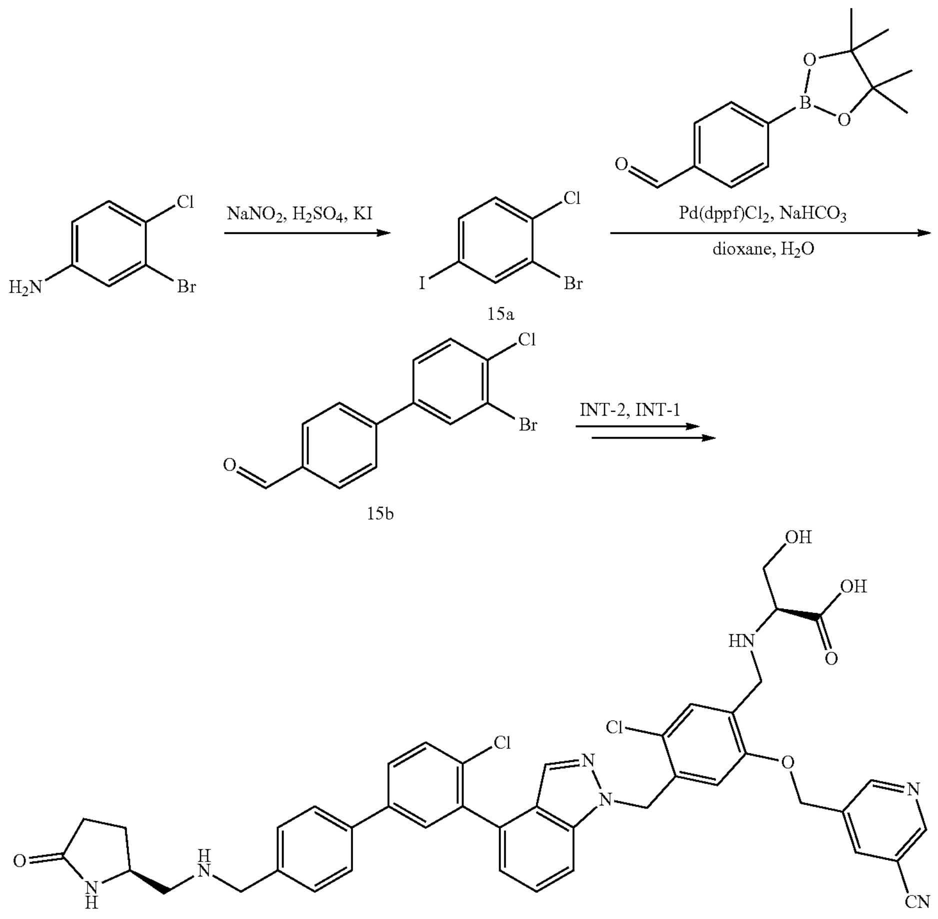

15a

15b

15

At room temperature, 3-bromo-4-chloroaniline (2.06 g, 9.98 mmol) was dissolved in sulfuric acid (25% w/w aqueous solution, 40 mL), and was stirred for half an hour. Then the reaction solution was cooled to −5° C., aqueous (10 mL) solution with sodium nitrite (826 mg, 12.0 mmol) predissolved was slowly added dropwise. After the dropping is completed, the reaction solution was further stirred for 1 hour at −5° C. Subsequently a mixed solution of ethyl acetate and water (50 mL, v/v=3/2) with potassium iodide (3.31 g, 20.0 mmol) predissolved was added dropwise, during which the reaction temperature is ensured below −5° C. Aqueous phase was further extracted with ethyl acetate (50 mL×2). The combined organic phase was sequentially washed with saturated sodium thiosulfate solution (100 mL×2) and saline (100 mL), dried with anhydrous sodium sulfate, filtered, and concentrated. The residue was separated by silica gel column chromatography to obtain a light yellow solid 15a (2.05 g, yield: 64.7%). $^1$H NMR (500 MHz, $CDCl_3$) δ 7.95 (d, J=2.0 Hz, 1H), 7.57-7.53 (m, 1H), 7.17 (d, J=8.5 Hz, 1H).

4-formylphenylboronic acid pinacol ester (439 mg, 1.89 mmol) and compound 15a (500 mg, 1.58 mmol) were dissolved in a mixture of dioxane and water (10 mL, v/v=4/1), sodium bicarbonate (397 mg, 4.73 mmol) and Pd(dppf)$Cl_2$ (58 mg, 0.079 mmol) were added. The reaction solution in a nitrogen atmosphere was heated to 80° C. and stirred for 3 hours. The reaction was quenched with water (50 mL), and the aqueous phase was extracted with ethyl acetate (50 mL×2). The combined organic phase was washed with saturated salt solution (100 mL), dried with anhydrous sodium sulfate, filtered, and concentrated. The residue was separated by silica gel column chromatography (petroleum ether/ethyl acetate, v/v=10/1) to obtain yellow oily matter 15b (271 mg, yield: 58.2%).

Starting from compound 15b, compound INT-2 and compound INT-1, referring to the synthesis of compound INT-3 and compound 1, compound 15 is obtained. $^1$H NMR (500 MHz, DMSO-d6) δ 8.93 (s, 1H), 8.84 (s, 1H), 8.34 (s, 1H), 7.85 (s, 1H), 7.81-7.76 (m, 2H), 7.74-7.65 (m, 5H), 7.55-7.40 (m, 4H), 7.25-7.19 (m, 1H), 6.81 (s, 1H), 5.72 (s, 2H), 5.13-5.04 (m, 2H), 3.90-3.83 (m, 1H), 3.78-3.69 (m, 3H), 3.63-3.53 (m, 3H), 3.06-2.97 (m, 1H), 2.57-2.55 (m, 2H), 2.13-2.03 (m, 3H), 1.70-1.63 (m, 1H); MS (ESI): m/z 804.7 $(M+H)^+$.

Example 16

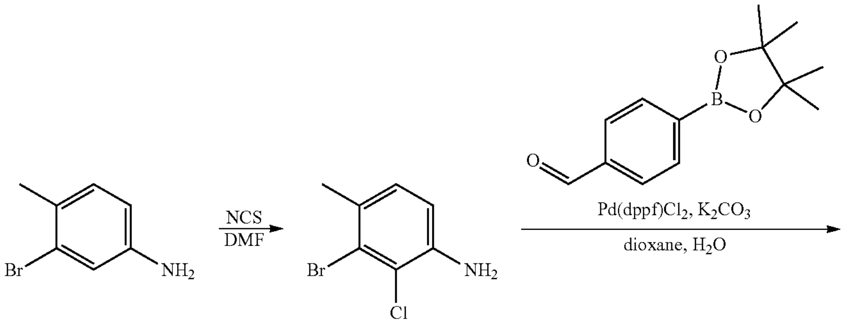

16a

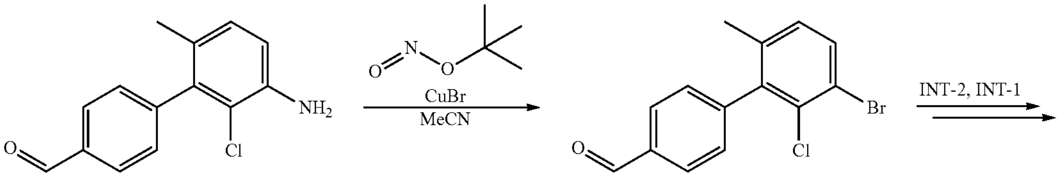

16b 16c

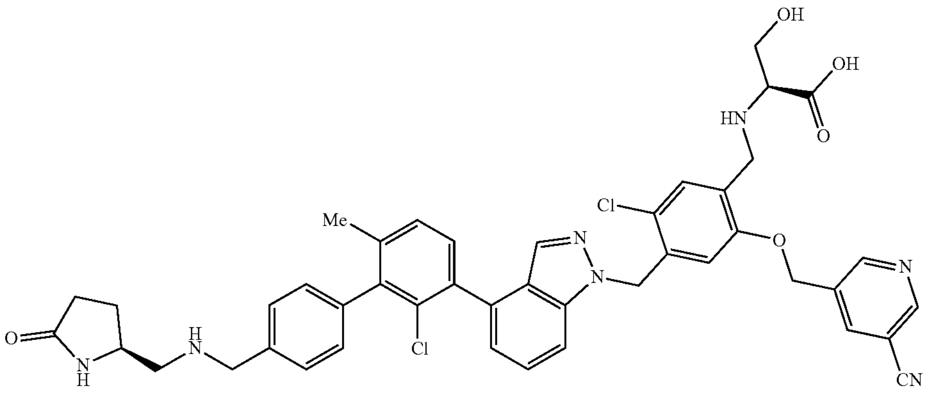

16

At room temperature, in N, N-dimethylformamide (3 mL) solution with 3-bromo-4-methylaniline (584 mg, 3.14 mmol) dissolved N-chlorosuccinimide (419 mg, 3.14 mmol) was added. The reaction solution was heated to 80° C. and was stirred for 1 hour at the same temperature. The reaction was quenched with (50 mL), and the aqueous phase was extracted with ethyl acetate (50 mL×2). The combined organic phase was washed with saturated salt solution (100 mL), dried with anhydrous sodium sulfate, filtered, and concentrated. The residue was separated by silica gel column chromatography (petroleum ether/ethyl acetate, v/v=10/1) to obtain white solid 16a (292 mg, yield: 42.2%). $^1$H NMR (500 MHz, DMSO-$d_6$) δ 6.97 (d, J=8.2 Hz, 1H), 6.70 (d, J=8.2 Hz, 1H), 5.41 (s, 2H), 2.22 (s, 3H).

Starting from 4-formylphenylboronic acid pinacol ester and compound 16a, referring to the synthesis of compound INT-3a, compound 16b is obtained.

At room temperature, in acetonitrile (1 mL) solution with compound 16b (100 mg, 0.41 mmol) dissolved tert-butyl nitrite (50 mg, 0.49 mmol) and copper(I) bromide (91 mg, 0.63 mmol) were added. The reaction solution was heated to 60° C., and was stirred for 1 hour at the same temperature. The reaction was quenched with water (20 mL), aqueous phase was extracted with ethyl acetate (20 mL×2). The combined organic phase was saturated salt solution (50 mL) washed with, dried with anhydrous sodium sulfate, filtered, concentrated. The residue was separated by silica gel column chromatography (petroleum ether/ethyl acetate, v/v=10/1) to obtain white solid 16c (28 mg, yield: 22.2%). $^1$H NMR (500 MHz, Chloroform-d) δ 10.09 (s, 1H), 8.02-7.95 (m, 2H), 7.56 (d, J=8.2 Hz, 1H), 7.35 (d, J=8.0 Hz, 2H), 7.08 (d, J=8.2 Hz, 1H), 2.01 (s, 3H).

Starting from compound 16c, compound INT-2 and compound INT-1, referring to the synthesis of compound INT-3 and compound 1, compound 16 is obtained. $^1$H NMR (500 MHz, DMSO-d6) δ 8.98-8.88 (m, 1H), 8.85-8.77 (m, 1H), 8.32-8.23 (m, 1H), 7.81 (s, 1H), 7.67-7.63 (m, 2H), 7.53 (s, 1H), 7.47-7.42 (m, 3H), 7.42-7.39 (m, 2H), 7.27-7.21 (m, 2H), 7.14-7.09 (m, 1H), 6.82 (s, 1H), 5.69 (s, 2H), 5.11-5.04 (m, 2H), 3.95-3.82 (m, 2H), 3.82-3.75 (m, 2H), 3.66-3.61 (m, 2H), 3.59-3.55 (m, 1H), 3.17-3.13 (m, 1H), 2.62-2.56 (m, 2H), 2.14-2.10 (m, 1H), 2.08 (s, 3H), 2.08-2.04 (m, 1H), 2.02-1.92 (m, 1H), 1.74-1.64 (m, 1H); MS (ESI): m/z 818.5 $(M+H)^+$.

Example 17

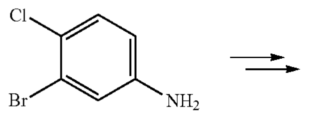

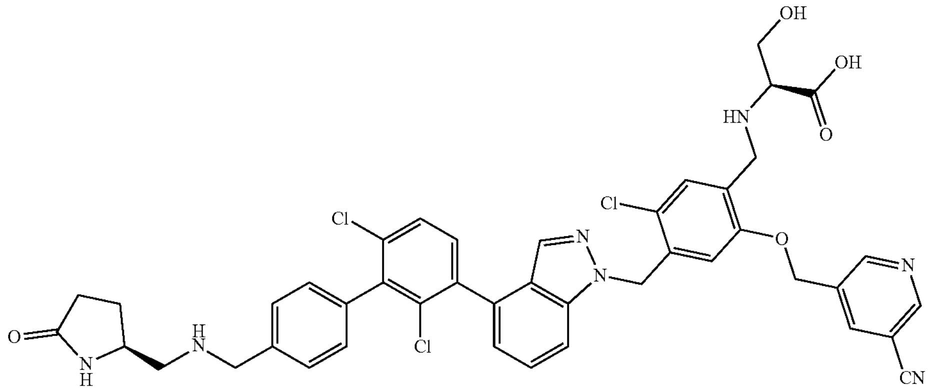

17

Starting from 3-bromo-4-chloroaniline, referring to the synthesis of compound 16, compound 17 is obtained. $^1$H NMR (500 MHz, DMSO-d6) δ 8.95-8.88 (m, 1H), 8.85-8.76 (m, 1H), 8.34-8.27 (m, 1H), 7.90-7.84 (m, 1H), 7.72-7.64 (m, 3H), 7.54 (d, J=8.3 Hz, 1H), 7.49-7.40 (m, 4H), 7.29 (d, J=7.7 Hz, 2H), 7.14 (d, J=7.0 Hz, 1H), 6.73 (s, 1H), 5.68 (s, 2H), 5.09-4.99 (m, 2H), 3.80-3.71 (m, 2H), 3.66 (s, 2H), 3.63-3.57 (m, 1H), 3.42-3.34 (m, 2H), 3.21-3.16 (m, 1H), 2.56-2.52 (m, 2H), 2.13-2.04 (m, 3H), 1.70-1.64 (m, 1H); MS (ESI): m/z 838.2 $(M+H)^+$.
Example 18
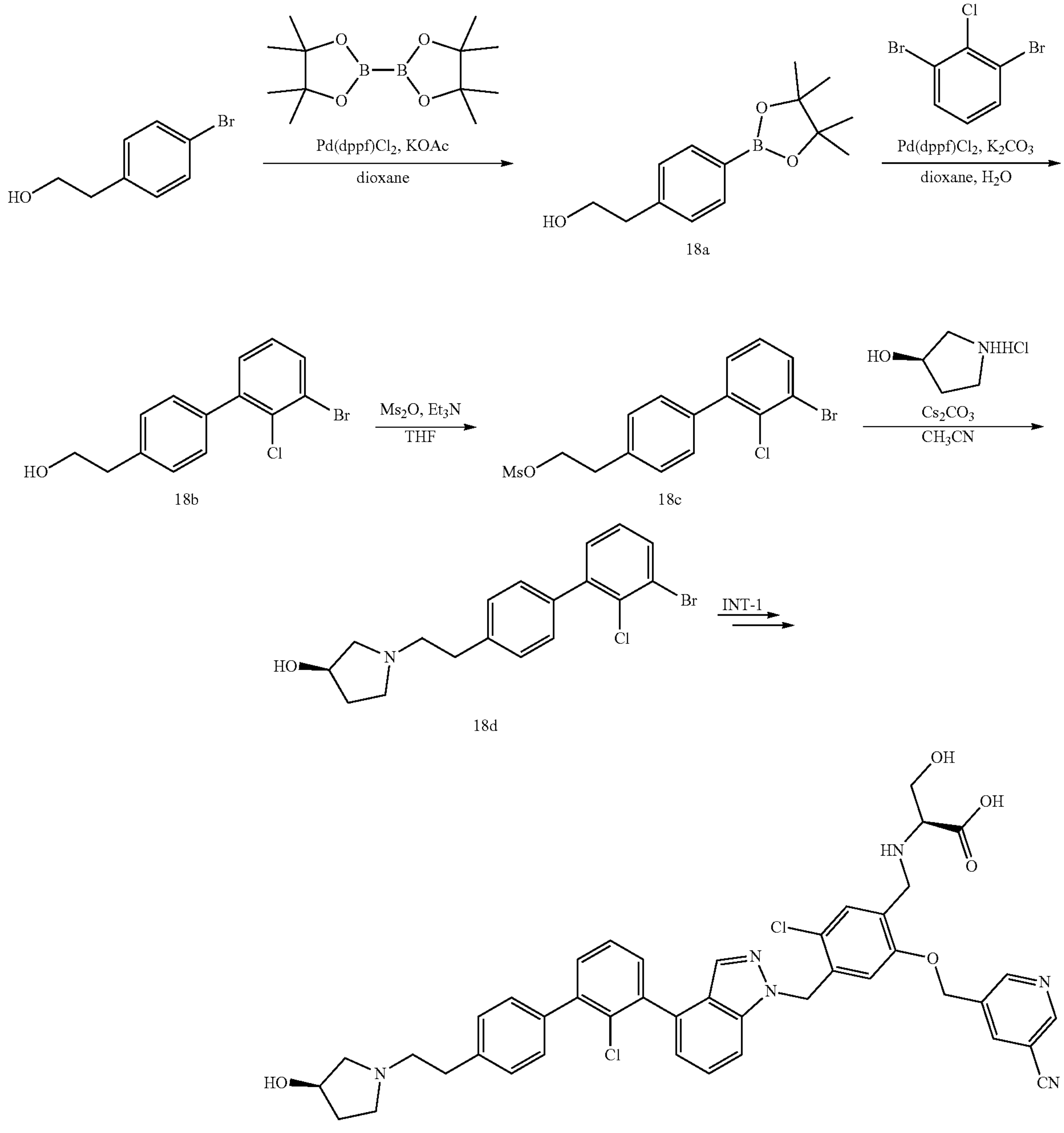

Starting from 4-bromophenethyl alcohol, referring to the synthesis of compound INT-7a, compound 18a is obtained. MS (ESI): m/z 249.1 $(M+H)^+$.

Starting from compound 18a and 1,3-dibromo-2-toluene, referring to compound INT-3a the synthesis of, compound is obtained 18b. MS (ESI): m/z 311.0 $(M+H)^+$.

Starting from compound 18b, referring to the synthesis of compound 6b, compound 18c is obtained. MS (ESI): m/z 389.0 $(M+H)^+$.

At 50° C., acetonitrile (10 mL) solution with compound 18c (290 mg, 0.74 mmol), (R)-3-hydroxypyrrolidine hydrochloride (138 mg, 1.12 mmol) and cesium carbonate (727 mg, 2.23 mmol) mixed was stirred for 16 hours. The reaction was quenched with water (30 mL). Aqueous phase was extracted with ethyl acetate (30 mL×2). The combined organic phase was washed with saturated salt solution (50 mL), dried with anhydrous sodium sulfate, filtered, and concentrated. The residue was separated by silica gel column chromatography (dichloromethane/methanol, v/v=10/1) to obtain yellow oily matter 18d (140 mg, yield: 49.0%). MS (ESI): m/z 380.2 $(M+H)^+$.

Starting from compound 18d and compound INT-1, referring to the synthesis of compound 1, compound 18 is obtained. $^1$H NMR (500 MHz, DMSO-d6) δ 8.93 (d, J=2.0 Hz, 1H), 8.83 (d, J=2.0 Hz, 1H), 8.33-8.31 (m, 1H), 7.86 (s, 1H), 7.69 (d, J=8.5 Hz, 1H), 7.53-7.51 (m, 2H), 7.48-7.45 (m, 2H), 7.44-7.41 (m, 2H), 7.34-7.32 (m, 3H), 7.16 (d, J=7.0 Hz, 1H), 6.79 (s, 1H), 5.71 (s, 2H), 5.08 (d, J=3.0 Hz, 2H), 4.20-4.18 (m, 1H), 3.86-3.81 (m, 2H), 3.53-3.51 (m, 2H), 2.97 (t, J=6.0 Hz, 1H), 2.80-2.76 (m, 4H), 2.68-2.63 (m, 4H), 2.00-1.96 (m, 1H), 1.57-1.53 (m, 1H); MS (ESI): m/z 791.5 $(M+H)^+$.

Example 19

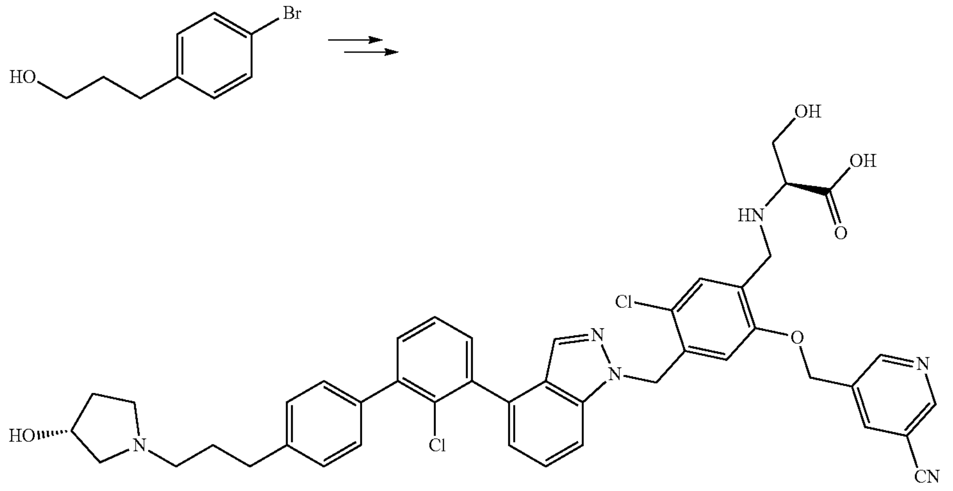

19

4-bromo phenylpropanol, referring to the synthesis of compound 18, compound 19 is obtained. $^1$H NMR (500 MHz, DMSO-d6) δ 8.94 (d, J=2.0 Hz, 1H), 8.84 (d, J=2.0 Hz, 1H), 8.54 (s, 1H), 8.35-8.33 (m, 1H), 7.86 (s, 1H), 7.69 (d, J=8.5 Hz, 1H), 7.55-7.51 (m, 2H), 7.49-7.42 (m, 5H), 7.30 (d, J=8.0 Hz, 2H), 7.16 (d, J=7.0 Hz, 1H), 6.75 (s, 1H), 5.70 (s, 2H), 5.13-4.98 (m, 2H), 4.22-4.15 (m, 2H), 3.71-3.64 (m, 2H), 3.24-3.17 (m, 3H), 2.71-2.63 (m, 3H), 2.56-2.53 (m, 1H), 2.42-2.38 (m, 3H), 2.30-2.27 (m, 1H), 2.01-1.93 (m, 1H), 1.79-1.73 (m, 2H), 1.56-1.50 (m, 1H); MS (ESI): m/z 805.7 $(M+H)^+$.

Example 20

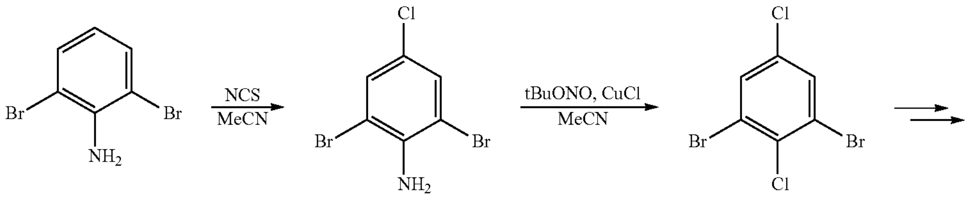

20a

20b

-continued

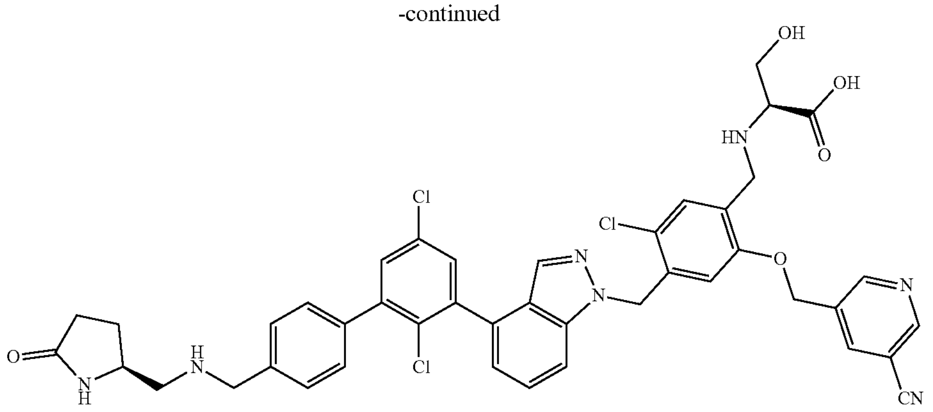

20

At 25° C., N-chlorosuccinimide (639 mg, 4.78 mmol) was in batches added to acetonitrile (20 mL) solution with 2, 6-dibromoaniline (1.00 g, 3.99 mmol) dissolved. The resulting reaction solution was stirred at the same temperature for 16 hours. After adding water to the reaction solution, solid is precipitated. Thus obtained solid was further washed with water, and dried to obtain white solid 20a (1.10 g, yield: 96.7%). $^1$H NMR (500 MHz, DMSO-d6) δ 7.53 (s, 2H), 5.48 (s, 2H).

Starting from compound 20a, referring to the synthesis of compound 16c, wherein copper(I) bromide is replaced with cuprous chloride, compound 20b is obtained. $^1$H NMR (500 MHz, DMSO-d6) δ 8.00 (s, 2H).

Starting from compound 20b, referring to the synthesis of compound 12, compound 20 is obtained. $^1$H NMR (500 MHz, DMSO-d6) δ 8.95-8.88 (m, 1H), 8.83-8.76 (m, 1H), 8.32-8.23 (m, 1H), 7.90 (s, 1H), 7.70 (d, J=8.5 Hz, 1H), 7.68-7.64 (m, 1H), 7.61-7.58 (m, 1H), 7.56-7.41 (m, 7H), 7.21-7.14 (m, 1H), 6.79-6.66 (m, 1H), 5.70 (s, 2H), 5.13-5.01 (m, 2H), 3.83-3.70 (m, 4H), 3.61 (t, J=6.5 Hz, 1H), 3.51-3.47 (m, 1H), 3.44-3.41 (m, 1H), 2.86 (s, 1H), 2.53-2.52 (m, 2H), 2.16-2.00 (m, 3H), 1.73-1.63 (m, 1H); MS (ESI): m/z 838.3 (M+H)$^+$.

Example 21

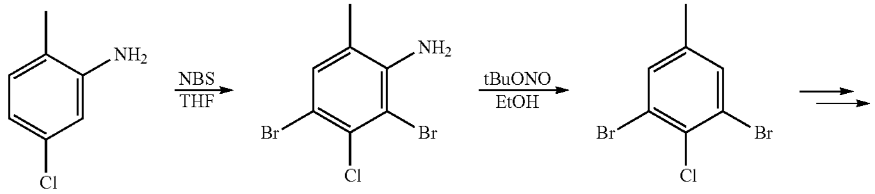

21a 21b

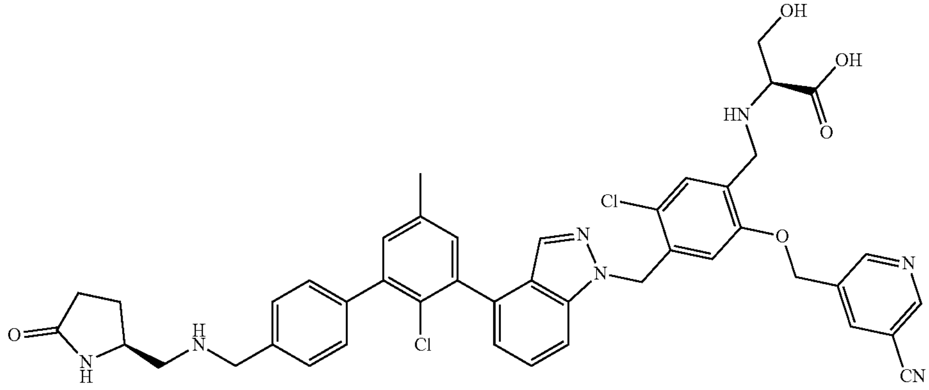

21

At 25° C., N-bromosuccinimide (6.28 g, 35.3 mmol) was in batches added to acetonitrile (30 mL) solution with 5-chloro-2-methylaniline (2.00 g, 14.1 mmol) dissolved. The resulting reaction solution was stirred at the same temperature for 16 hours. The reaction was quenched with water (100 mL), and the aqueous phase was extracted with ethyl acetate (100 mL×3). The combined organic phase was washed with saturated salt solution (200 mL), dried with anhydrous sodium sulfate, filtered, and concentrated. The residue was separated by silica gel column chromatography to obtain dark red solid 21a (4.00 g, yield: 94.6%). $^1$H NMR (500 MHz, Chloroform-d) δ 7.27 (s, 1H), 4.25 (s, 2H), 2.18 (s, 3H).

At 25° C. and nitrogen atmosphere, tert-butyl nitrite (3.91 g, 33.4 mmol) was slowly added dropwise to ethanol (30 mL) solution with compound 21a (4.00 g, 13.4 mmol) dissolved. The reaction solution was stirred for 2 hours at 50° C. The reaction solution was concentrated after being cooled down. The resulting residue was separated by silica gel column chromatography to obtain white solid 21b (2.1 g, yield: 55.3%). $^1$H NMR (500 MHz, Chloroform-d) δ 7.41 (s, 2H), 2.29 (s, 3H).

Starting from compound 21b, referring to the synthesis of compound 12, compound 21 is obtained. $^1$H NMR (500 MHz, DMSO-d6) δ 8.93 (d, J=2.0 Hz, 1H), 8.82 (d, J=2.0 Hz, 1H), 8.31-8.29 (m, 1H), 7.84 (s, 1H), 7.72-7.63 (m, 2H), 7.53 (s, 1H), 7.48-7.39 (m, 5H), 7.33-7.25 (m, 2H), 7.13 (d, J=7.0 Hz, 1H), 6.82 (s, 1H), 5.70 (s, 2H), 5.14-5.04 (m, 2H), 3.93 (d, J=14.5 Hz, 1H), 3.85 (d, J=14.5 Hz, 1H), 3.80-3.73 (m, 2H), 3.67-3.54 (m, 3H), 3.14 (t, J=5.5 Hz, 1H), 2.54-2.53 (m, 2H), 2.38 (s, 3H), 2.12-2.04 (m, 3H), 1.72-1.64 (m, 1H); MS (ESI): m/z 818.8 (M+H)$^+$.

Example 22

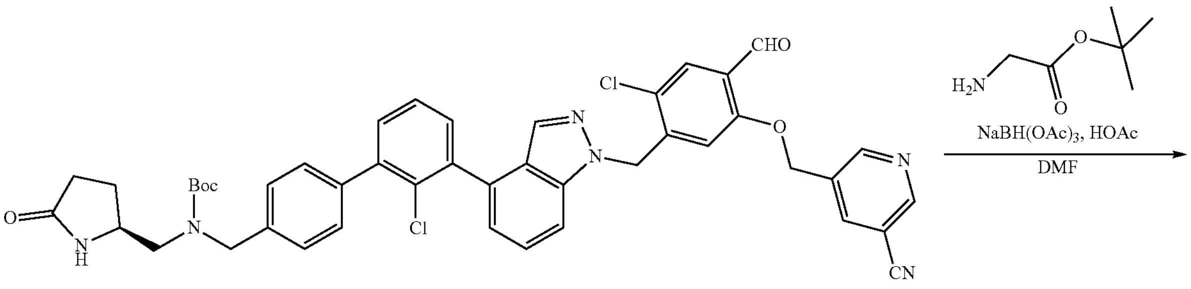

INT-7

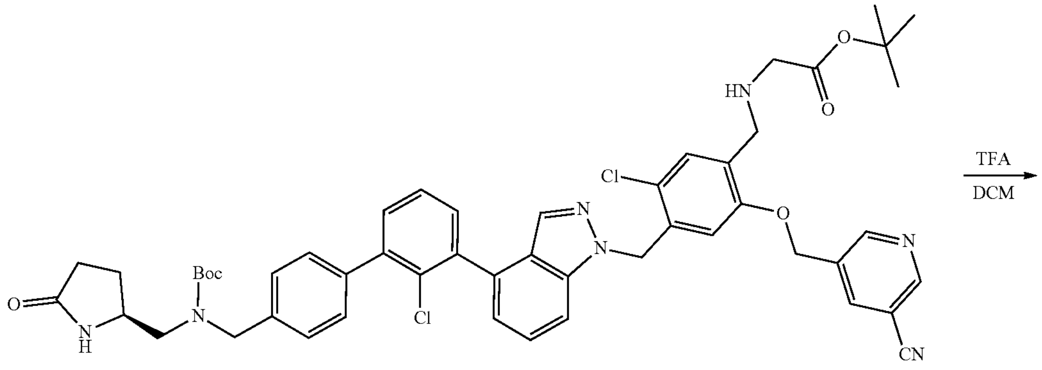

22a

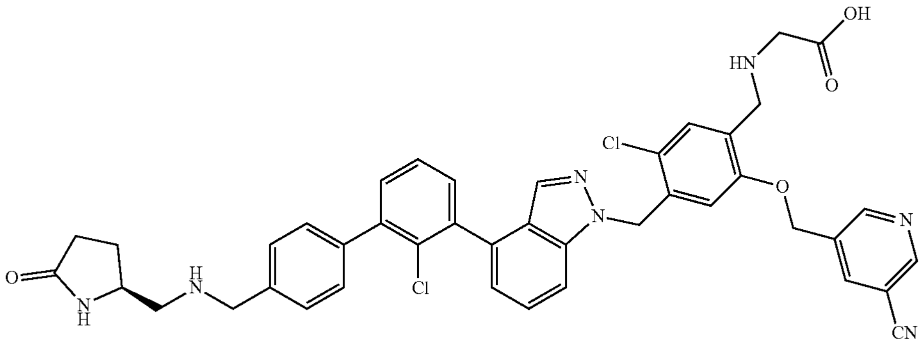

22

Starting from compound INT-7 and glycine tert-butyl ester, referring to reductive amination in the synthesis of compound INT-1j and Boc deprotecting group step in the synthesis of compound 1, compound 22 is obtained. $^{1}$H NMR (500 MHz, DMSO-d6) δ 8.95 (d, J=2.0 Hz, 1H), 8.84 (d, J=2.0 Hz, 1H), 8.34-8.32 (m, 1H), 7.87 (s, 1H), 7.71 (d, J=8.5 Hz, 1H), 7.67 (s, 1H), 7.56-7.46 (m, 9H), 7.17 (d, J=7.0 Hz, 1H), 6.86 (s, 1H), 5.73 (s, 2H), 5.11 (s, 2H), 3.93 (s, 2H), 3.90-3.82 (m, 2H), 3.71-3.67 (m, 1H), 3.18 (s, 2H), 2.73-2.61 (m, 2H), 2.17-2.09 (m, 3H), 1.75-1.69 (m, 1H); MS (ESI): m/z 774.7 $(M+H)^{+}$.

Example 23

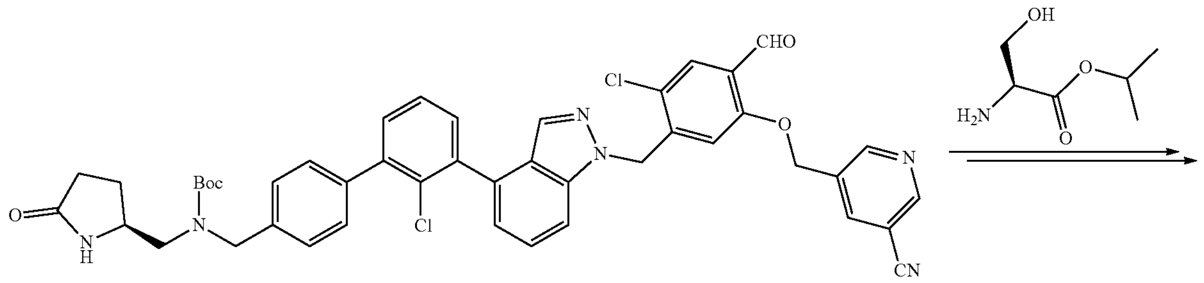

INT-7

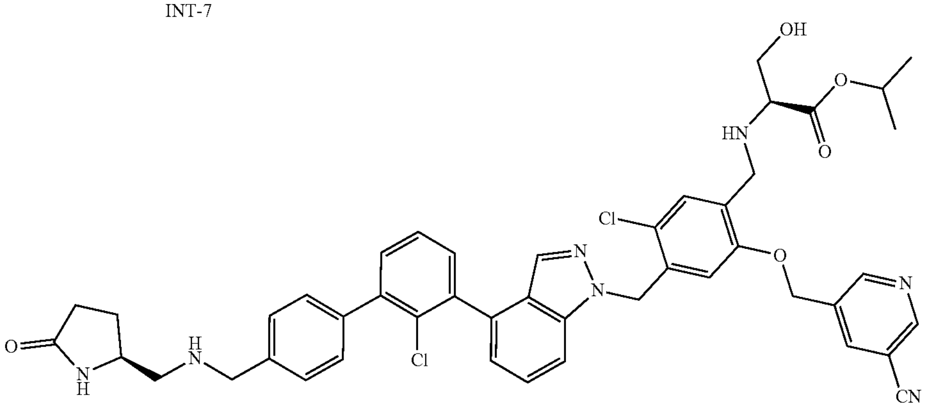

23

Starting from compound INT-7 and serine isopropyl ester, referring to the synthesis of compound 22, compound 23 is obtained. $^{1}$H NMR (500 MHz, DMSO-d6) δ 8.97 (d, J=1.9 Hz, 1H), 8.83 (d, J=1.9 Hz, 1H), 8.30 (d, J=1.9 Hz, 1H), 7.87 (s, 1H), 7.74-7.68 (m, 2H), 7.55-7.43 (m, 9H), 7.17 (d, J=7.0 Hz, 1H), 6.85 (s, 1H), 5.71 (s, 2H), 5.09 (s, 2H), 4.86-4.80 (m, 1H), 3.81-3.72 (m, 3H), 3.66-3.60 (m, 2H), 3.54 (d, J=5.0 Hz, 2H), 3.19 (t, J=5.0 Hz, 1H), 2.56-2.54 (m, 2H), 2.14-2.07 (m, 3H), 1.74-1.65 (m, 1H), 1.11 (d, J=6.0 Hz, 3H), 1.08 (d, J=6.5 Hz, 3H); MS (ESI): m/z 846.7 $(M+H)^{+}$.

Example 24

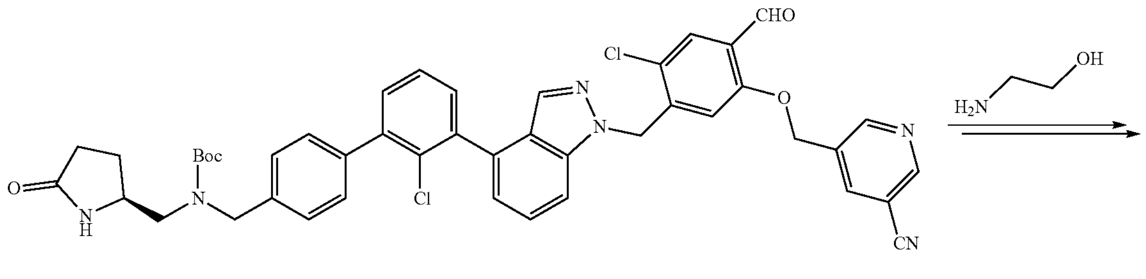

INT-7

-continued
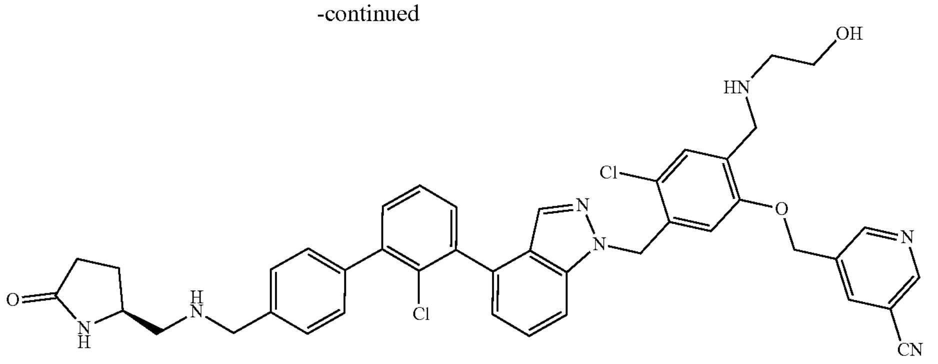
24
Starting from compound INT-7 and ethanolamine, referring to the synthesis of compound 22, compound 24 is obtained. $^1$H NMR (500 MHz, DMSO-d6) δ 8.96 (d, J=2.0 Hz, 1H), 8.83 (d, J=2.0 Hz, 1H), 8.29 (s, 1H), 7.87 (s, 1H), 7.71 (d, J=9.5 Hz, 2H), 7.54 (t, J=7.5 Hz, 1H), 7.52-7.43 (m, 8H), 7.17 (d, J=7.0 Hz, 1H), 6.84 (s, 1H), 5.72 (s, 2H), 5.09 (s, 2H), 3.79 (d, J=13.5 Hz, 1H), 3.77-3.73 (m, 3H), 3.66-3.61 (m, 1H), 3.47 (t, J=5.5 Hz, 2H), 2.59 (t, J=5.5 Hz, 2H), 2.57-2.54 (m, 2H), 2.15-2.06 (m, 3H), 1.72-1.66 (m, 1H); MS (ESI): m/z 760.6 $(M+H)^+$.
Example 25
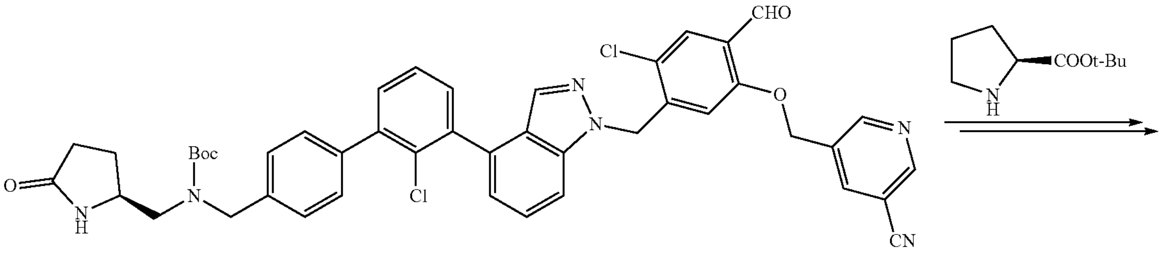
INT-7
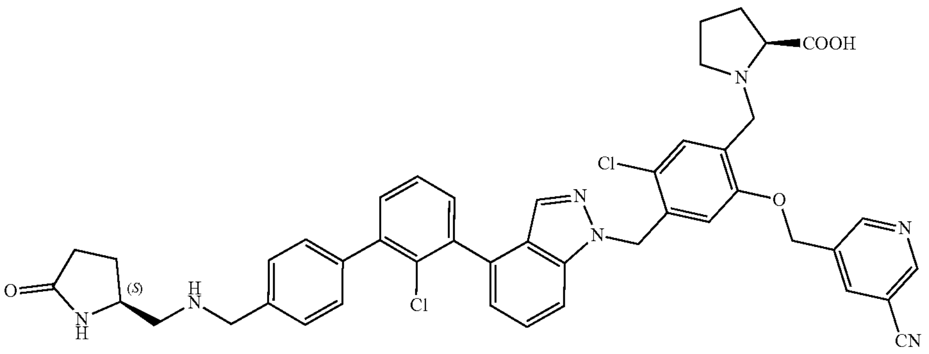
25

Starting from compound INT-7 and proline tert-butyl ester, referring to the synthesis of compound 22, compound 25 is obtained. $^1$H NMR (500 MHz, DMSO-d6) δ 8.95 (d, J=2.0 Hz, 1H), 8.82 (d, J=2.0 Hz, 1H), 8.35-8.33 (m, 1H), 7.88 (s, 1H), 7.72-7.68 (m, 2H), 7.55-7.44 (m, 9H), 7.17 (d, J=7.0 Hz, 1H), 6.82 (s, 1H), 5.72 (s, 2H), 5.14-5.06 (m, 2H), 3.98 (d, J=14.0 Hz, 1H), 3.82 (d, J=14.0 Hz, 1H), 3.77 (d, J=7.5 Hz, 2H), 3.65-3.62 (m, 1H), 3.05-3.02 (m, 1H), 2.56-2.54 (m, 2H), 2.15-2.03 (m, 5H), 1.90-1.84 (m, 1H), 1.81-1.65 (m, 4H); MS (ESI): m/z 814.8 (M+H)$^+$.
Example 26
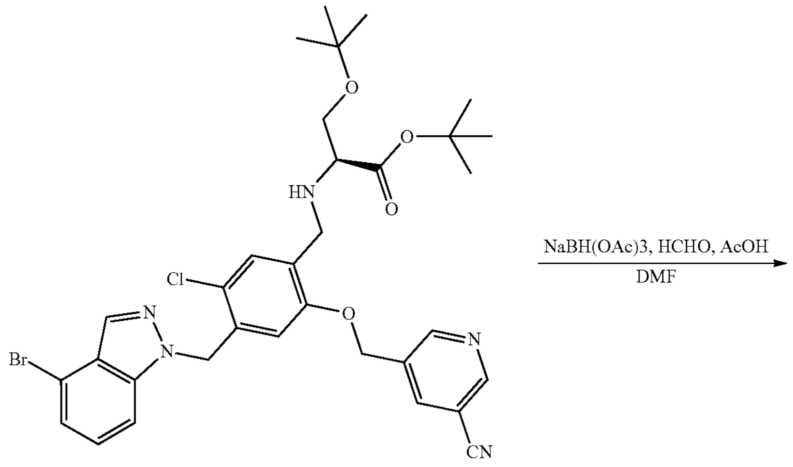
INT-1j
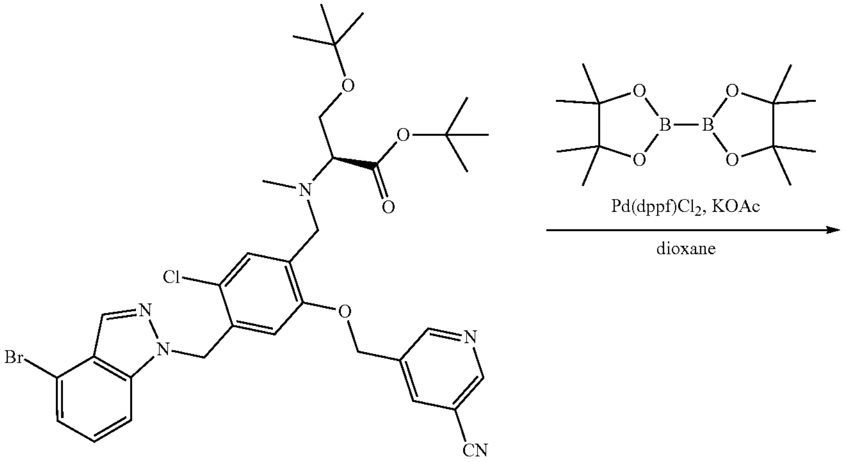
26a -continued

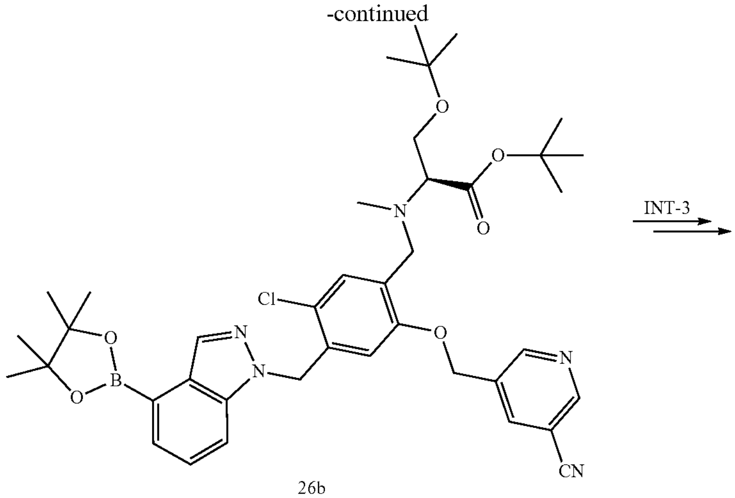

26b

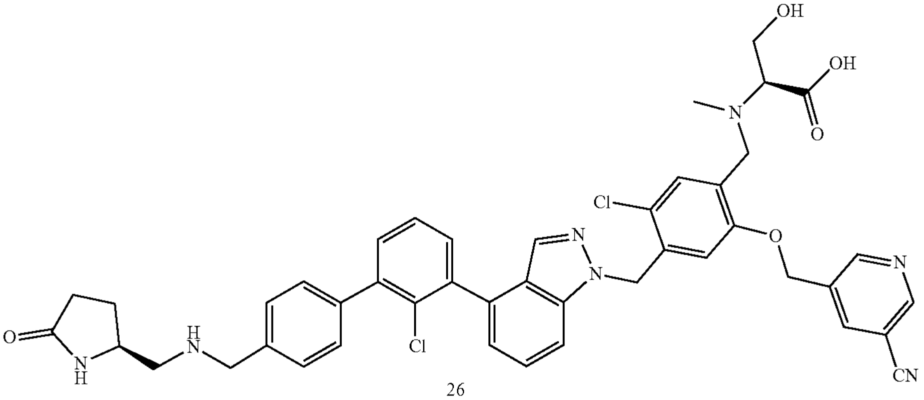

26

Starting from compound INT-1j, referring to reductive amination in the synthesis of compound INT-1j and boron esterification step in the synthesis of compound INT-1, compound 26b is obtained. MS (ESI): m/z 744.6 $(M+H)^+$.

Starting from compound 26b and compound INT-3, referring to the synthesis of compound 1, compound 26 is obtained. $^1$H NMR (500 MHz, DMSO-d6) δ 8.94 (d, J=2.0 Hz, 1H), 8.80 (d, J=2.0 Hz, 1H), 8.27 (s, 1H), 7.87 (s, 1H), 7.72-7.68 (m, 2H), 7.57-7.43 (m, 9H), 7.17 (d, J=7.0 Hz, 1H), 6.80 (s, 1H), 5.71 (s, 2H), 5.09 (s, 2H), 3.82-3.69 (m, 6H), 3.66-3.58 (m, 2H), 2.55 (d, J=6.0 Hz, 2H), 2.28 (s, 3H), 2.14-2.07 (m, 3H), 1.74-1.66 (m, 1H); MS (ESI): m/z 818.8 $(M+H)^+$.

Example 27

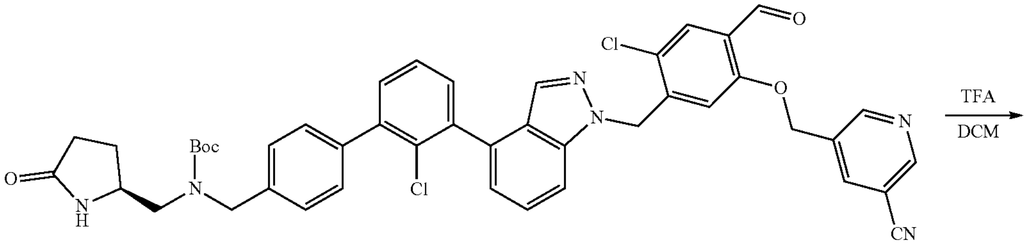

INT-7

-continued

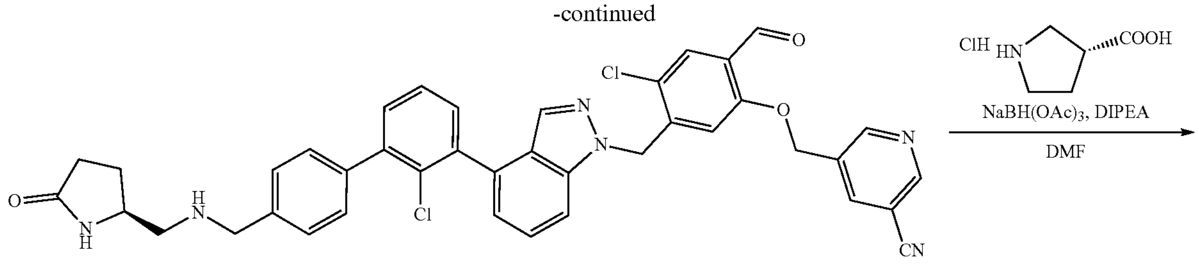

27a

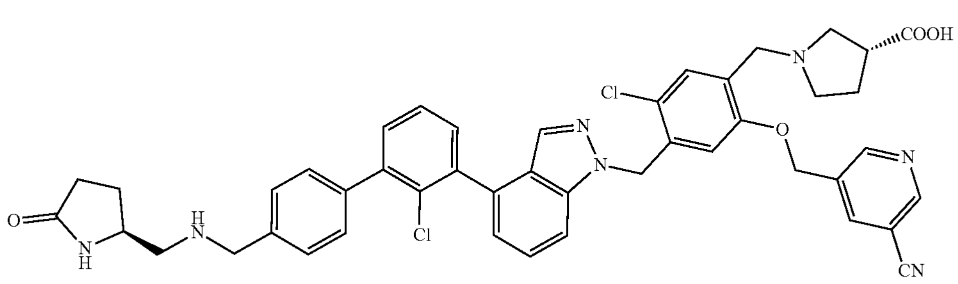

27

Starting from compound INT-7, referring to Boc deprotecting group step in the synthesis process of compound 1, compound 27a is obtained. MS (ESI): m/z 715.5 $(M+H)^+$.

At 25° C., in N'N-dimethylformamide (2 mL) with compound 27a (45 mg, 0.054 mmol) dissolved (R)-3-hydroxypyrrolidine hydrochloride (21 mg, 0.14 mmol) and N,N-diisopropylethylamine (70 mg, 0.54 mmol) were added. The resulting reaction solution was stirred for 1 hour at the same temperature, and then sodium triacetate borohydride (58 mg, 0.27 mmol) was added. The reaction solution was further stirred for 16 hours at 25° C. after adding water (20 mL) to the reaction solution, it was extracted with ethyl acetate (15 mL×2). Organic phase was concentrated, and the residue was separated by preparative high performance liquid chromatography to obtain white solid 27 (10 mg, yield: 22.6%). $^1$H NMR (500 MHz, DMSO-d6) δ 8.93 (d, J=2.0 Hz, 1H), 8.79 (d, J=2.0 Hz, 1H), 8.26-8.24 (m, 1H), 7.85 (s, 1H), 7.71-7.65 (m, 2H), 7.52-7.40 (m, 9H), 7.15 (d, J=6.9 Hz, 1H), 6.80 (s, 1H), 5.69 (s, 2H), 5.07 (s, 2H), 3.77 (d, J=12.5 Hz, 1H), 3.74 (d, J=12.5 Hz, 1H), 3.62-3.56 (m, 3H), 2.92-2.86 (m, 1H), 2.69-2.61 (m, 2H), 2.54-2.52 (m, 4H), 2.11-2.05 (m, 3H), 1.95-1.90 (m, 2H), 1.70-1.64 (m, 1H); MS (ESI): m/z 814.8 $(M+H)^+$.

Example 28

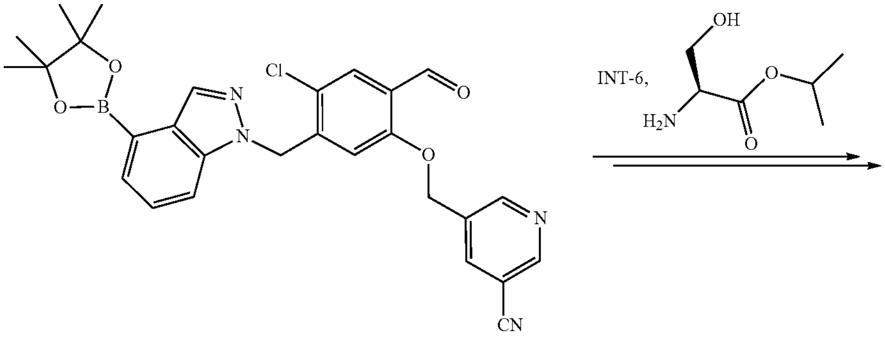

INT-7a

-continued
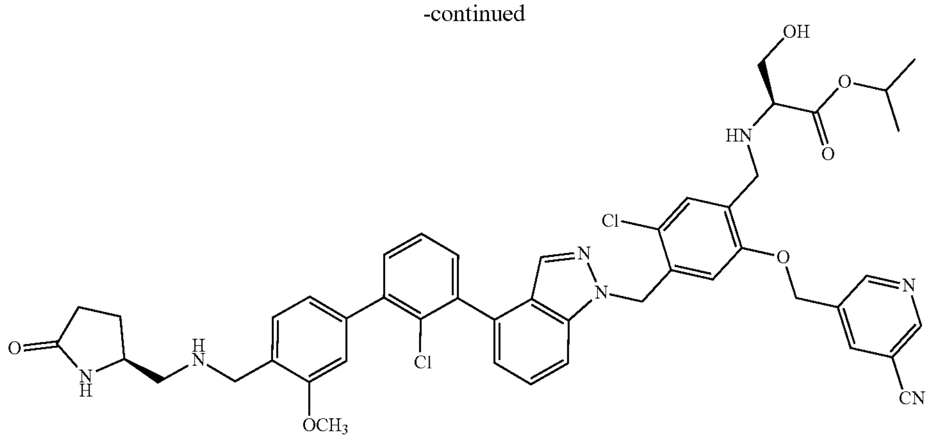
28
Starting from compound INT-7a, compound INT-6 and serine isopropyl ester, referring to the synthesis of compound INT-7 and compound 23, compound 28 is obtained. $^1$H NMR (500 MHz, DMSO-d6) δ 8.96 (d, J=2.0 Hz, 1H), 8.82 (d, J=2.0 Hz, 1H), 8.30-8.28 (m, 1H), 7.88 (s, 1H), 7.71 (d, J=8.6 Hz, 1H), 7.68 (s, 1H), 7.56-7.47 (m, 4H), 7.46 (s, 1H), 7.42 (d, J=7.7 Hz, 1H), 7.17 (d, J=7.1 Hz, 1H), 7.09 (d, J=1.6 Hz, 1H), 7.08-7.04 (m, 1H), 6.84 (s, 1H), 5.71 (s, 2H), 5.09 (s, 2H), 4.87-4.81 (m, 1H), 4.78 (t, J=5.8 Hz, 1H), 3.83 (s, 3H), 3.77 (d, J=14.7 Hz, 1H), 3.75-3.73 (m, 1H), 3.66-3.60 (m, 2H), 3.54 (t, J=5.6 Hz, 2H), 3.30-3.28 (m, 1H), 3.19 (t, J=5.3 Hz, 1H), 2.56 (d, J=6.0 Hz, 2H), 2.16-2.05 (m, 3H), 1.75-1.64 (m, 1H), 1.11 (d, J=6.2 Hz, 3H), 1.09 (d, J=6.2 Hz, 3H); MS (ESI): m/z 876.2 $(M+H)^+$.
Example 29
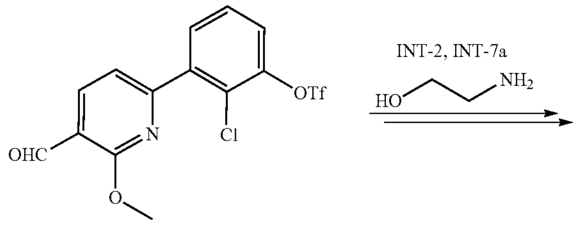
INT-10
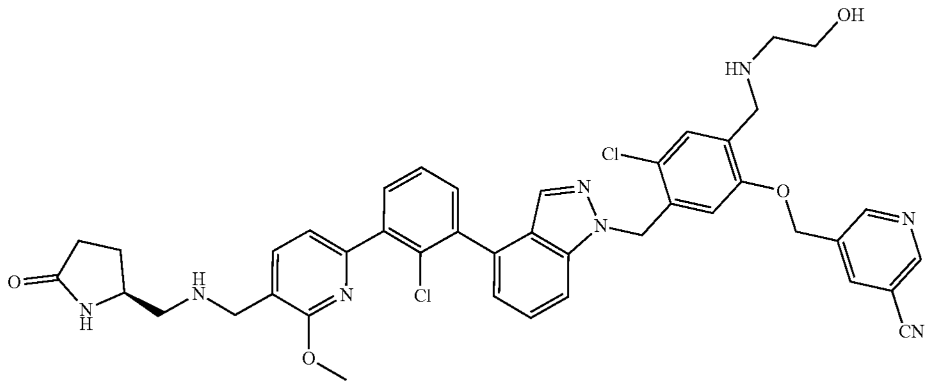
29

Starting from compound INT-10, compound INT-2, compound INT-7a and ethanolamine, referring to the synthesis of compound INT-3, compound INT-7 and compound 23, compound 29 is obtained. $^1$H NMR (500 MHz, DMSO-d6) δ 8.97 (d, J=2.0 Hz, 1H), 8.84 (d, J=2.0 Hz, 1H), 8.33-8.31 (m, 1H), 7.85 (s, 1H), 7.83 (d, J=7.5 Hz, 1H), 7.73 (d, J=9.0 Hz, 1H), 7.72 (s, 1H), 7.69-7.65 (m, 1H), 7.60-7.54 (m, 2H), 7.52-7.47 (m, 2H), 7.32 (d, J=7.5 Hz, 1H), 7.18 (d, J=7.0 Hz, 1H), 6.87 (s, 1H), 5.72 (s, 2H), 5.11 (s, 2H), 3.92 (s, 3H), 3.80 (s, 2H), 3.72 (d, J=4.0 Hz, 2H), 3.66-3.62 (m, 1H), 3.48 (t, J=5.5 Hz, 2H), 2.64 (t, J=5.5 Hz, 2H), 2.56 (d, J=6.0 Hz, 2H), 2.14-2.07 (m, 3H), 1.74-1.66 (m, 1H); MS (ESI): m/z 791.6 $(M+H)^+$.

Example 30

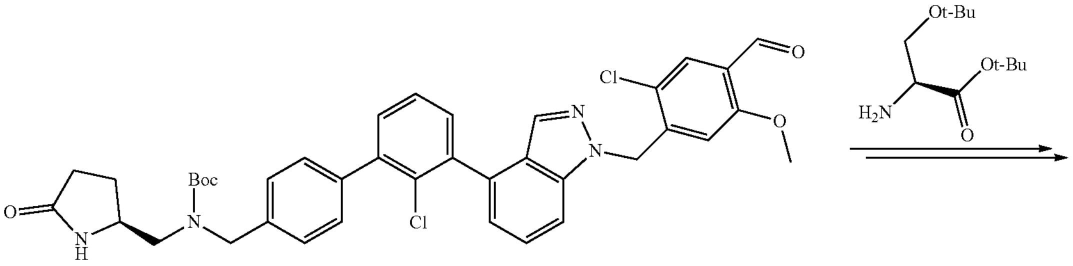

INT-8

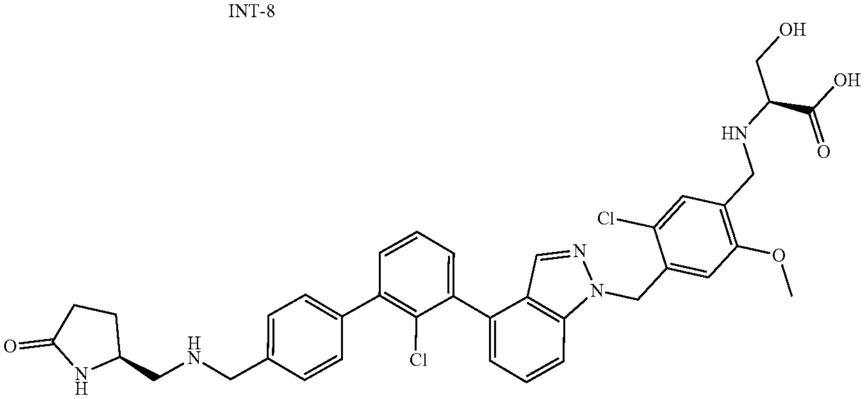

30

Starting from compound INT-8 and O-isopropyl-L-serine tert-butyl ester, referring to the synthesis of compound 22, compound 30 is obtained. $^1$H NMR (500 MHz, DMSO-d6) δ 7.91 (s, 1H), 7.78 (d, J=8.5 Hz, 1H), 7.69 (s, 1H), 7.56-7.44 (m, 9H), 7.17 (d, J=7.0 Hz, 1H), 6.72 (s, 1H), 5.75 (s, 2H), 3.89 (d, J=14.5 Hz, 1H), 3.83-3.75 (m, 3H), 3.68-3.63 (m, 2H), 3.61 (s, 3H), 3.60-3.57 (m, 1H), 3.14 (t, J=5.5 Hz, 1H), 2.57 (d, J=6.5 Hz, 2H), 2.16-2.07 (m, 3H), 1.74-1.67 (m, 1H); MS (ESI): m/z 702.5 $(M+H)^+$.

Example 31

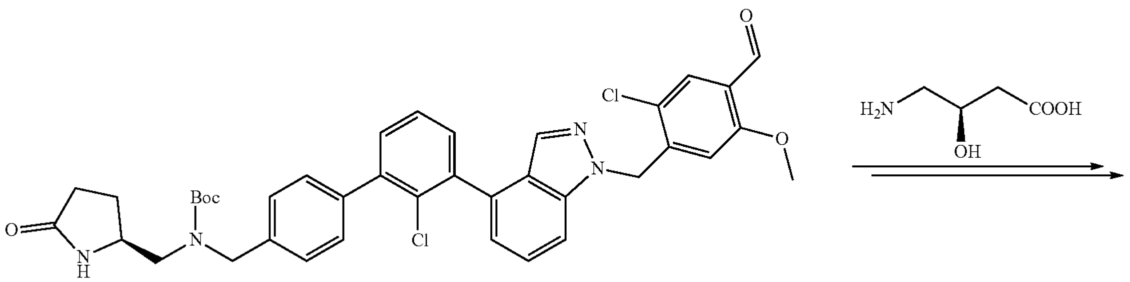

INT-8

-continued
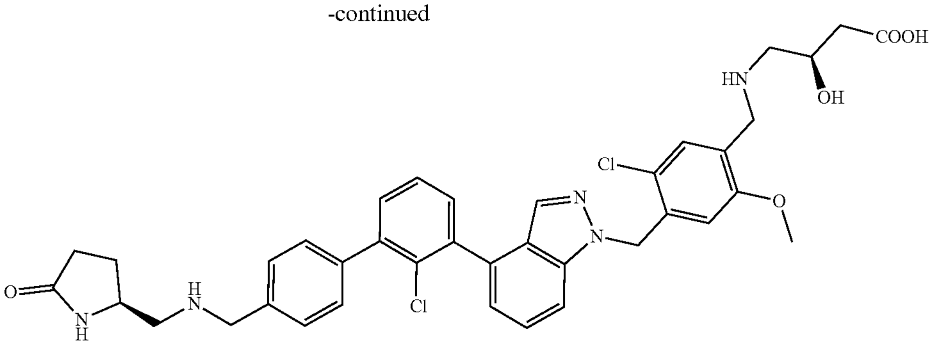
31
Starting from compound INT-8 and (R)-(−)-4-amino-3-hydroxybutyric acid, referring to the synthesis of compound 27, compound 31 is obtained. $^1$H NMR (500 MHz, DMSO-d6) δ 7.90 (s, 1H), 7.77 (d, J=8.5 Hz, 1H), 7.67 (s, 1H), 7.55-7.50 (m, 2H), 7.49-7.43 (m, 7H), 7.17 (d, J=7.0 Hz, 1H), 6.69 (s, 1H), 5.74 (s, 2H), 3.94-3.90 (m, 1H), 3.80-3.77 (m, 2H), 3.69-3.68 (m, 2H), 3.65-3.63 (m, 1H), 3.60 (s, 3H), 2.57-2.53 (m, 4H), 2.45-2.39 (m, 1H), 2.28-2.22 (m, 1H), 2.13-2.05 (m, 3H), 1.75-1.65 (m, 1H); MS (ESI): m/z 716.7 (M+H)$^+$.
Example 32
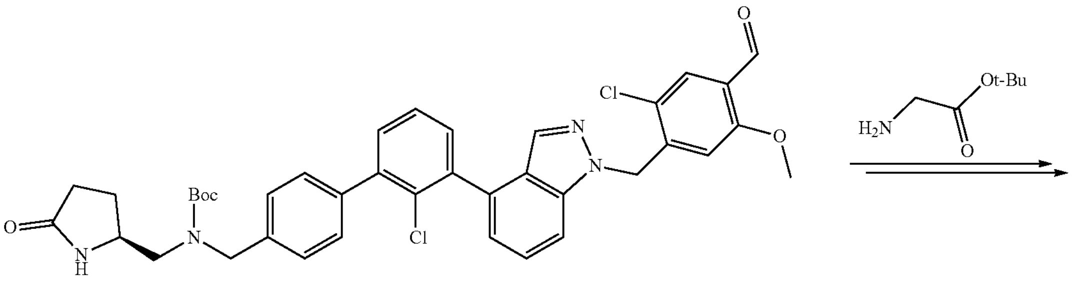
INT-8
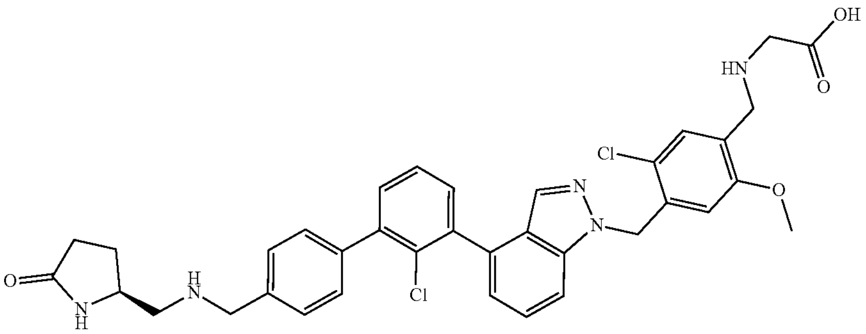
32

Starting from compound INT-8 and glycine tert-butyl ester, referring to the synthesis of compound 22, compound 32 is obtained. $^1H$ NMR (500 MHz, DMSO-d6) δ 7.90 (s, 1H), 7.77 (d, J=9.0 Hz, 1H), 7.67 (s, 1H), 7.55-7.50 (m, 2H), 7.49-7.42 (m, 7H), 7.17 (d, J=7.0 Hz, 1H), 6.70 (s, 1H), 5.74 (s, 2H), 3.80-3.72 (m, 4H), 3.65-3.62 (m, 1H), 3.60 (s, 3H), 3.07 (s, 2H), 2.55-2.53 (m, 2H), 2.14-2.07 (m, 3H), 1.72-1.66 (m, 1H); MS (ESI): m/z 672.6 $(M+H)^+$.

Example 33

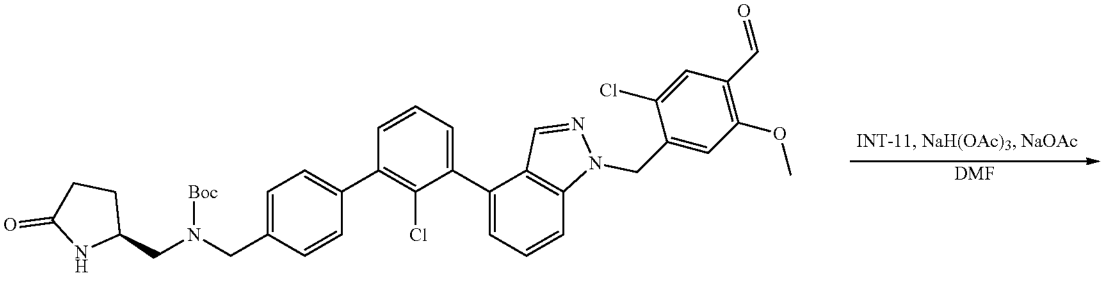

INT-8

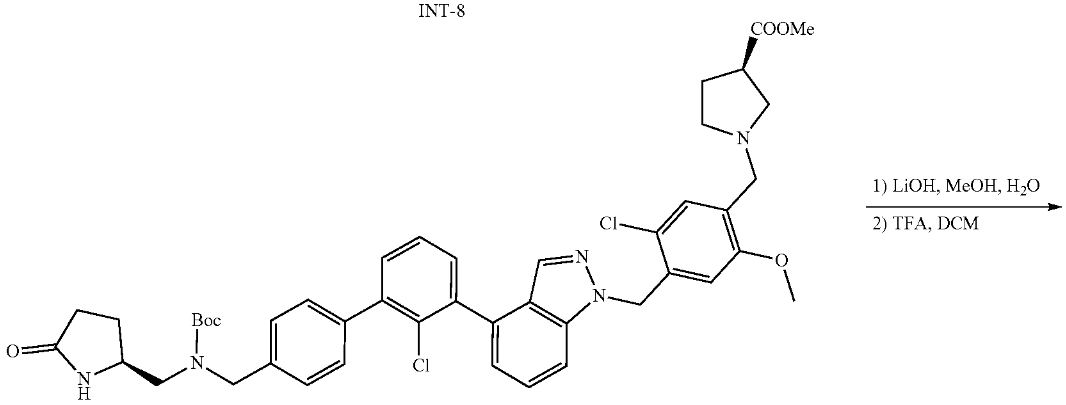

33a

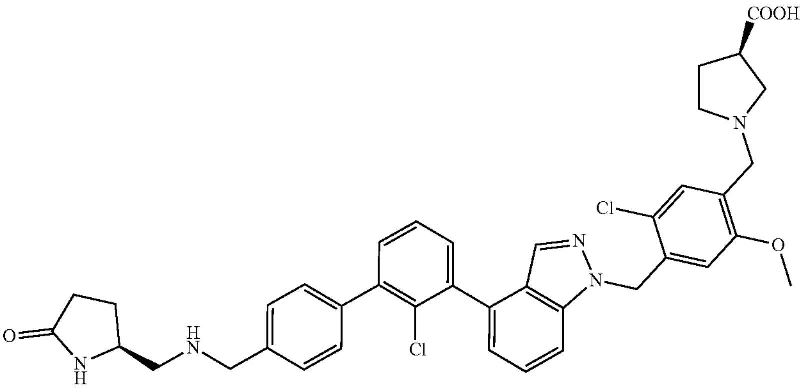

33

Starting from compound INT-8 and compound INT-11, referring to the synthesis of compound INT-5, compound 33a is obtained. MS (ESI): m/z 826.7 $(M+H)^+$.

At 25° C., In the mixed solution of methanol and washer (9 mL, v/v=8/1) with compound 33a (90 mg, 0.11 mmol) dissolved lithium hydroxide (10 mg, 0.42 mmol) was added. The reaction solution was stirred for 1 hour at the same temperature. The reaction solution was concentrated and then diluted with saturated ammonium chloride. Aqueous phase was extracted with ethyl acetate (10 mL×2). The combined organic phase was concentrated. The residue was dissolved in mixed solution of dichloromethane and trifluoroacetic acid (4 mL, v/v=3/1), and further reacted for 2 hours at 25° C. After the reaction solution was concentrated, the residue was separated by preparative high performance liquid chromatography to obtain white solid 33 (10.3 mg, yield: 23.5%). $^1$H NMR (500 MHz, DMSO-d6) δ 7.91 (s, 1H), 7.77 (d, J=8.5 Hz, 1H), 7.69 (s, 1H), 7.55-7.50 (m, 2H), 7.49-7.43 (m, 6H), 7.37 (s, 1H), 7.17 (d, J=7.0 Hz, 1H), 6.68 (s, 1H), 5.73 (s, 2H), 3.83-3.74 (m, 2H), 3.67-3.62 (m, 1H), 3.58 (s, 3H), 3.56-3.48 (m, 2H), 2.95-2.88 (m, 1H), 2.68-2.64 (m, 2H), 2.59-2.54 (m, 2H), 2.54-2.51 (m, 1H), 2.15-2.06 (m, 3H), 1.98-1.90 (m, 2H), 1.74-1.66 (m, 1H); MS (ESI): m/z 712.7 (M+H)$^+$.

Example 34

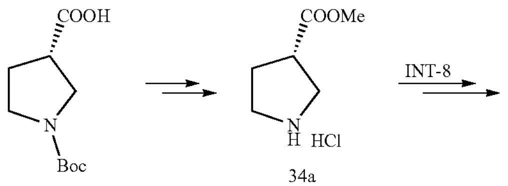

34a

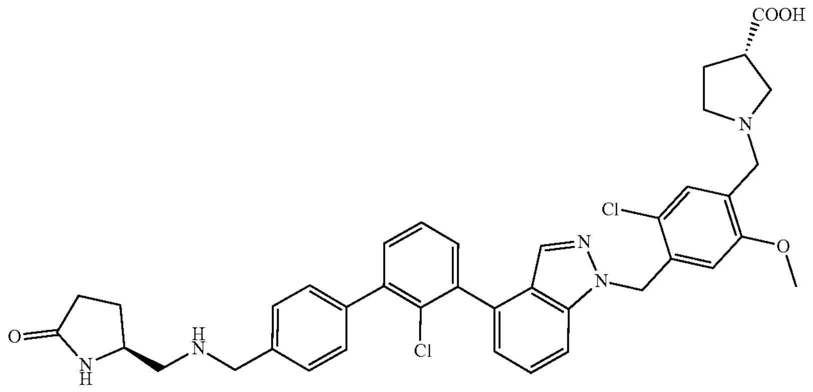

34

Starting from (R)-1-Boc-3-carboxypyrrolidine, referring to the synthesis of compound INT-11, compound 34a is obtained.

Starting from compound 34a and compound INT-8, referring to the synthesis of compound 33, compound 34 is obtained. $^1$H NMR (500 MHz, DMSO-d6) δ 7.91 (s, 1H), 7.77 (d, J=8.5 Hz, 1H), 7.68 (s, 1H), 7.55-7.43 (m, 8H), 7.37 (s, 1H), 7.17 (d, J=7.0 Hz, 1H), 6.67 (s, 1H), 5.73 (s, 2H), 3.81-3.73 (m, 2H), 3.66-3.61 (m, 1H), 3.58 (s, 3H), 3.56-3.47 (m, 2H), 2.92-2.86 (m, 1H), 2.69-2.62 (m, 2H), 2.56-2.53 (m, 2H), 2.49-2.46 (m, 1H), 2.14-2.07 (m, 3H), 1.96-1.90 (m, 2H), 1.74-1.66 (m, 1H); MS (ESI): m/z 712.7 (M+H)$^+$.

Example 35

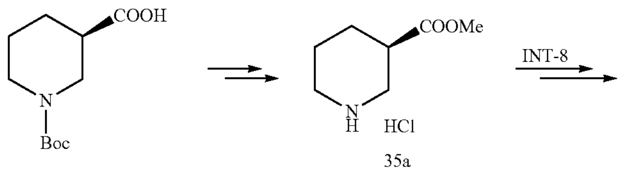

35a

-continued
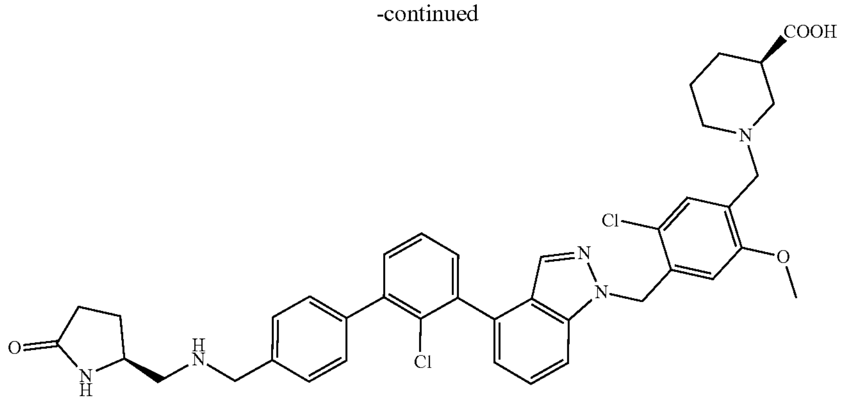
35
Starting from (R)-1-Boc-piperidine-3-carboxylic acid, referring to the synthesis of compound INT-11, compound is obtained 35a.
Starting from compound 35a and compound INT-8, referring to the synthesis of compound 33, compound is obtained 35. $^{1}H$ NMR (500 MHz, DMSO-d6) δ 7.91 (s, 1H), 7.77 (d, J=8.5 Hz, 1H), 7.68 (s, 1H), 7.55-7.42 (m, 8H), 7.39 (s, 1H), 7.17 (d, J=7.0 Hz, 1H), 6.68 (s, 1H), 5.73 (s, 2H), 3.80-3.73 (m, 2H), 3.65-3.61 (m, 1H), 3.58 (s, 3H), 3.41 (s, 2H), 2.78-2.72 (m, 1H), 2.59-2.53 (m, 3H), 2.44-2.40 (m, 1H), 2.24-2.18 (m, 1H), 2.13-2.04 (m, 4H), 1.79-1.73 (m, 1H), 1.72-1.67 (m, 1H), 1.64-1.59 (m, 1H), 1.50-1.42 (m, 1H), 1.40-1.33 (m, 1H); MS (ESI): m/z 726.7 $(M+H)^+$.
Example 36
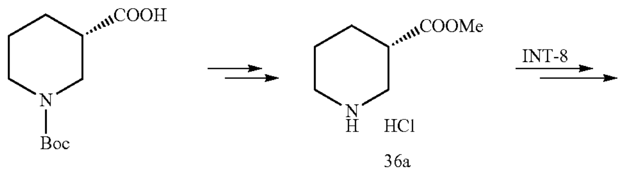
36a
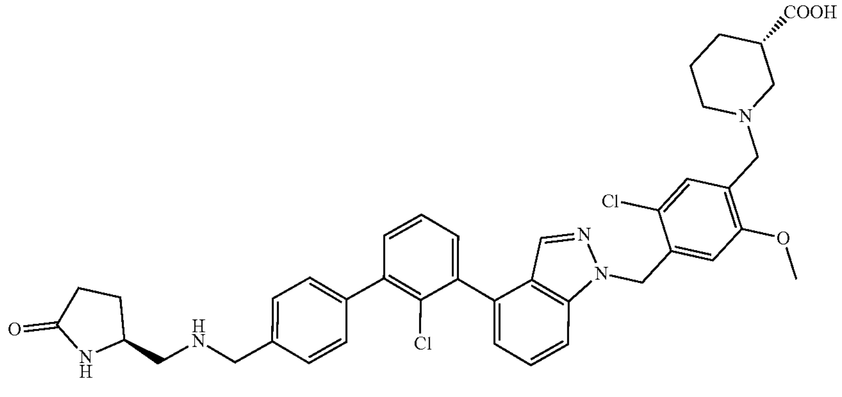
36

Starting from (S)-1-Boc-piperidine-3-carboxylic acid, referring to the synthesis of compound INT-11, compound 36a is obtained.

Starting from compound 36a and compound INT-8, referring to the synthesis of compound 33, compound 36 is obtained. $^1$H NMR (500 MHz, DMSO-d6) δ 7.91 (s, 1H), 7.77 (d, J=8.5 Hz, 1H), 7.68 (s, 1H), 7.55-7.50 (m, 2H), 7.49-7.43 (m, 6H), 7.39 (s, 1H), 7.17 (d, J=7.0 Hz, 1H), 6.68 (s, 1H), 5.73 (s, 2H), 3.83-3.74 (m, 2H), 3.66-3.63 (m, 1H), 3.58 (s, 3H), 3.42 (s, 2H), 2.77-2.73 (m, 1H), 2.56 (m, 3H), 2.45-2.39 (m, 1H), 2.23-2.16 (m, 1H), 2.15-2.04 (m, 4H), 1.79-1.73 (m, 1H), 1.72-1.66 (m, 1H), 1.64-1.59 (m, 1H), 1.50-1.42 (m, 1H), 1.41-1.33 (m, 1H); MS (ESI): m/z 726.7 $(M+H)^+$.

Example 37

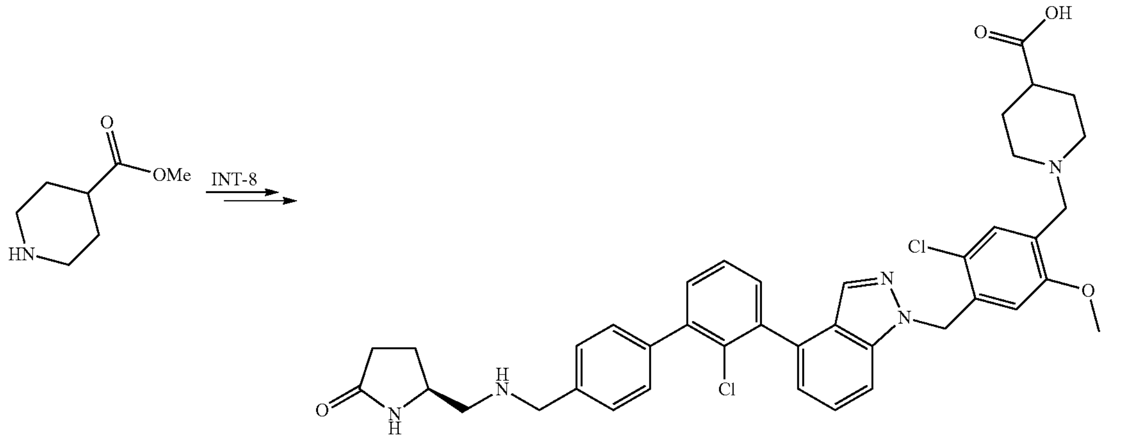

37

Starting from methyl 4-piperidinecarboxylate and compound INT-8, referring to the synthesis of compound 33, compound 37 is obtained. $^1$H NMR (500 MHz, DMSO-d6) δ 7.90 (s, 1H), 7.78-7.76 (m, 1H), 7.67 (s, 1H), 7.53-7.46 (m, 7H), 7.35 (s, 1H), 7.32 (s, 1H), 7.17 (d, J=7.0 Hz, 1H), 6.69 (s, 1H), 5.73 (s, 2H), 3.81-3.73 (m, 2H), 3.65-3.62 (m, 1H), 3.58 (s, 3H), 3.52-3.50 (m, 2H), 2.80-2.77 (m, 1H), 2.74-2.70 (m, 1H), 2.20-2.15 (m, 1H), 2.13-2.08 (m, 3H), 2.02-1.98 (m, 4H), 1.78-1.74 (m, 2H), 1.72-1.67 (m, 1H), 1.56-1.52 (m, 2H); MS (ESI): m/z 726.7 $(M+H)^+$.

Example 38

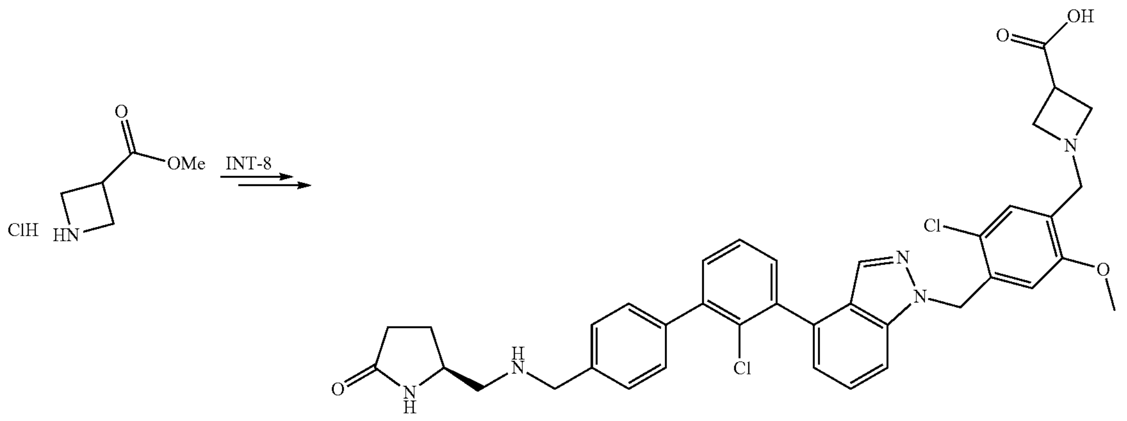

38

Starting from methyl 3-carboxylate azetidine hydrochloride and compound INT-8, referring to the synthesis of compound 33, compound 38 is obtained. $^1$H NMR (500 MHz, DMSO-d6) δ 7.90 (s, 1H), 7.77 (d, J=8.5 Hz, 1H), 7.68 (s, 1H), 7.55-7.44 (m, 8H), 7.27 (s, 1H), 7.17 (d, J=7.0 Hz, 1H), 6.67 (s, 1H), 5.72 (s, 2H), 3.84-3.77 (m, 2H), 3.68-3.63 (m, 1H), 3.58 (s, 3H), 3.47 (s, 2H), 3.42-3.38 (m, 2H), 3.23-3.17 (m, 3H), 2.58 (d, J=6.0 Hz, 2H), 2.16-2.06 (m, 3H), 1.74-1.66 (m, 1H); MS (ESI): m/z 698.7 (M+H)$^+$.

Example 39

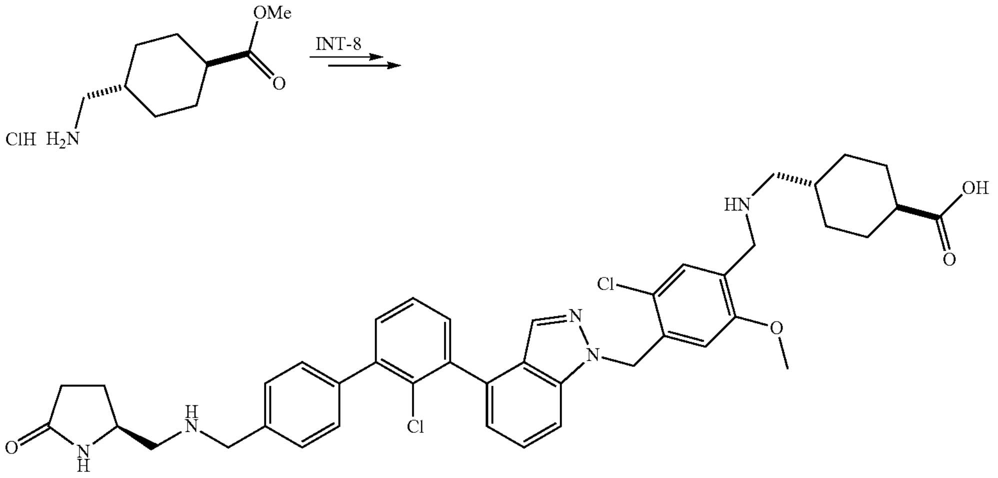

39

Starting from methyl 4-aminomethyl-cyclohexanecarboxylate hydrochloride and compound INT-8, referring to the synthesis of compound 33, compound 39 is obtained. $^1$H NMR (500 MHz, DMSO-d6) δ 7.91 (s, 1H), 7.77 (d, J=8.5 Hz, 1H), 7.69 (s, 1H), 7.55-7.50 (m, 2H), 7.48-7.41 (m, 7H), 7.17 (d, J=7.0 Hz, 1H), 6.70 (s, 1H), 5.74 (s, 2H), 3.83-3.75 (m, 2H), 3.68 (s, 2H), 3.67-3.62 (m, 1H), 3.60 (s, 3H), 2.57 (d, J=6.0 Hz, 2H), 2.40 (d, J=6.5 Hz, 2H), 2.15-2.06 (m, 4H), 1.88 (d, J=11.0 Hz, 2H), 1.80 (d, J=11.0 Hz, 2H), 1.74-1.67 (m, 1H), 1.43-1.37 (m, 1H), 1.32-1.22 (m, 2H), 0.94-0.84 (m, 2H); MS (ESI): m/z 754.8 (M+H)$^+$.

Example 40

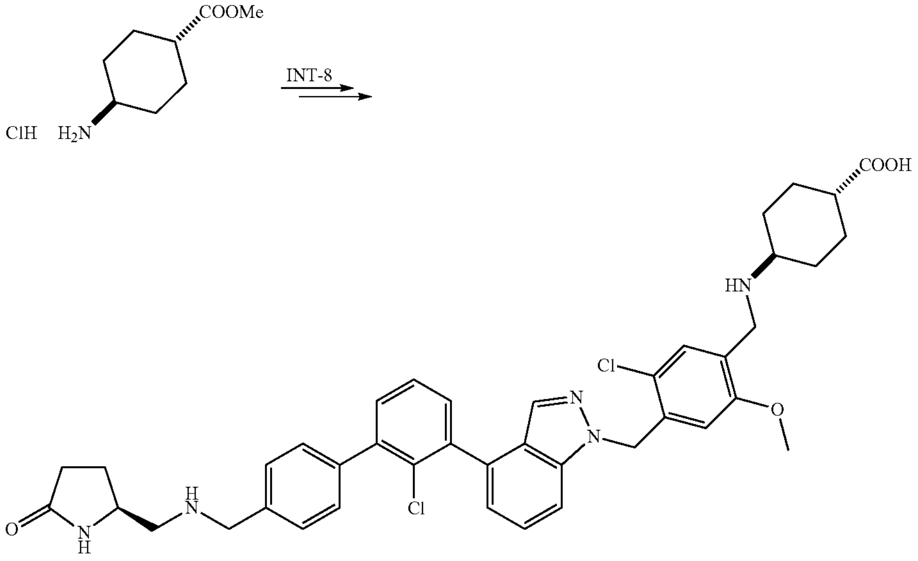

40

Starting from trans-4-methyl aminocyclohexanate hydrochloride and compound INT-8, referring to the synthesis of compound 33, compound 40 is obtained. $^{1}$H NMR (500 MHz, DMSO-d6) δ 7.91 (s, 1H), 7.79 (d, J=8.5 Hz, 1H), 7.67 (s, 1H), 7.56-7.51 (m, 3H), 7.50-7.45 (m, 6H), 7.18 (d, J=7.0 Hz, 1H), 6.78 (s, 1H), 5.76 (s, 2H), 3.95 (s, 2H), 3.88-3.80 (m, 2H), 3.69-3.65 (m, 1H), 3.64 (s, 3H), 2.81 (s, 1H), 2.62 (d, J=6.5 Hz, 2H), 2.18-2.09 (m, 4H), 2.04 (d, J=11.0 Hz, 2H), 1.94 (d, J=11.0 Hz, 2H), 1.75-1.67 (m, 1H), 1.37-1.22 (m, 4H); MS (ESI): m/z 740.7 (M+H)$^{+}$.

Example 41

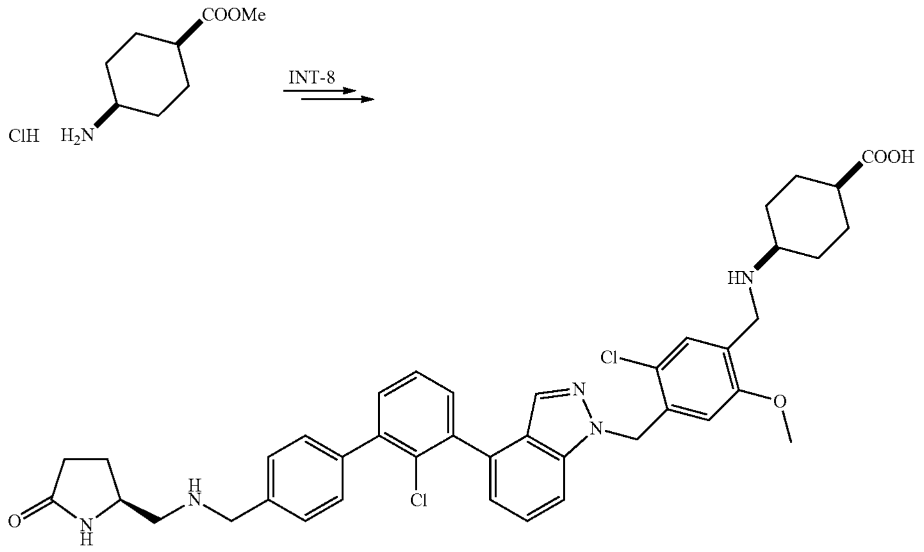

41

Starting from cis-4-methyl aminocyclohexanate hydrochloride and compound INT-8, referring to the synthesis of compound 33, compound 41 is obtained. $^{1}$H NMR (500 MHz, DMSO-d6) δ 7.91 (s, 1H), 7.78 (d, J=8.5 Hz, 1H), 7.67 (s, 1H), 7.56-7.51 (m, 3H), 7.50-7.45 (m, 6H), 7.18 (d, J=7.0 Hz, 1H), 6.76 (s, 1H), 5.76 (s, 2H), 3.92-3.78 (m, 4H), 3.69-3.66 (m, 1H), 3.63 (s, 3H), 2.87-2.83 (m, 1H), 2.61 (d, J=6.0 Hz, 2H), 2.46-2.44 (m, 1H), 2.15-2.07 (m, 3H), 2.00-1.92 (m, 2H), 1.81-1.67 (m, 3H), 1.53-1.44 (m, 4H); MS (ESI): m/z 740.7 (M+H)$^{+}$.

Example 42

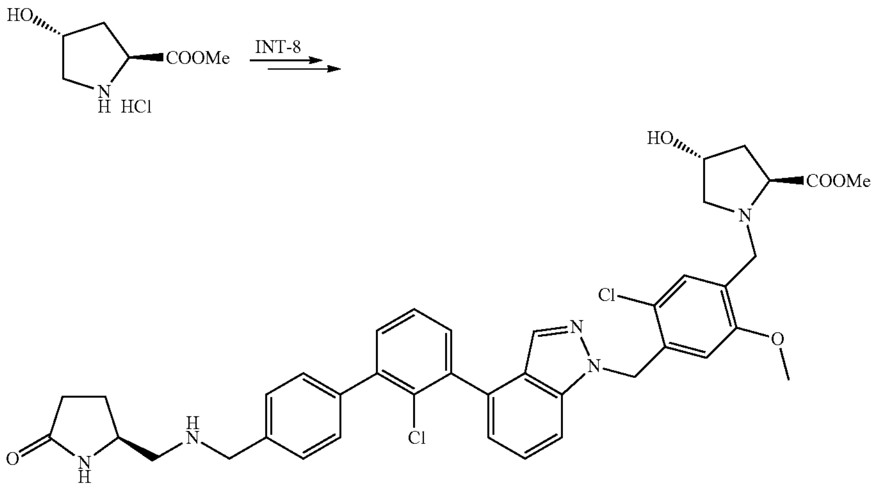

42

Starting from trans-4-hydroxy-L-proline methyl ester hydrochloride and compound INT-8, referring to the synthesis of compound 33, compound 42 is obtained. $^1H$ NMR (500 MHz, DMSO-d6) δ 7.91 (s, 1H), 7.77 (d, J=8.5 Hz, 1H), 7.67 (s, 1H), 7.55-7.50 (m, 2H), 7.49-7.43 (m, 7H), 7.17 (d, J=7.0 Hz, 1H), 6.69 (d, J=7.0 Hz, 1H), 5.74 (s, 2H), 4.21-4.15 (m, 1H), 3.87-3.82 (m, 1H), 3.80-3.76 (m, 2H), 3.67-3.62 (m, 2H), 3.61-3.57 (m, 3H), 3.50-3.45 (m, 1H), 3.21-3.19 (m, 1H), 2.58-2.53 (m, 3H), 2.13-2.07 (m, 3H), 2.02-1.90 (m, 1H), 1.81-1.75 (m, 1H), 1.73-1.67 (m, 1H); MS (ESI): m/z 728.7 $(M+H)^+$.

Example 43

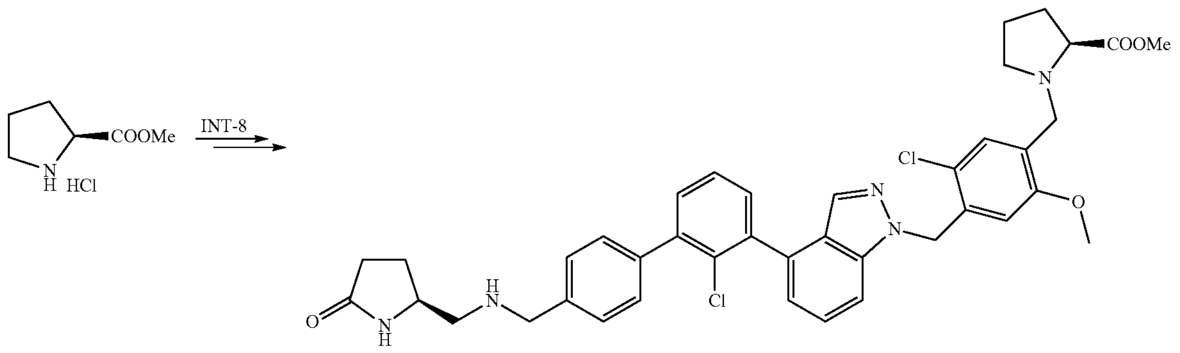

42

Starting from methyl L-proline hydrochloride and compound INT-8, referring to the synthesis of compound 33, compound 43 is obtained. $^1H$ NMR (500 MHz, DMSO-d6) δ 7.91 (s, 1H), 7.78 (d, J=8.5 Hz, 1H), 7.69 (s, 1H), 7.55-7.43 (m, 10H), 7.17 (d, J=7.0 Hz, 1H), 6.70 (s, 1H), 5.75 (s, 2H), 3.93 (d, J=14.0 Hz, 1H), 3.84-3.77 (m, 3H), 3.67-3.62 (m, 1H), 3.60 (s, 3H), 3.37-3.33 (m, 1H), 3.10-3.04 (m, 1H), 2.59-2.52 (m, 3H), 2.14-2.05 (m, 4H), 1.90-1.83 (m, 1H), 1.80-1.74 (m, 1H), 1.73-1.66 (m, 2H); MS (ESI): m/z 712.7 $(M+H)^+$.

Example 44

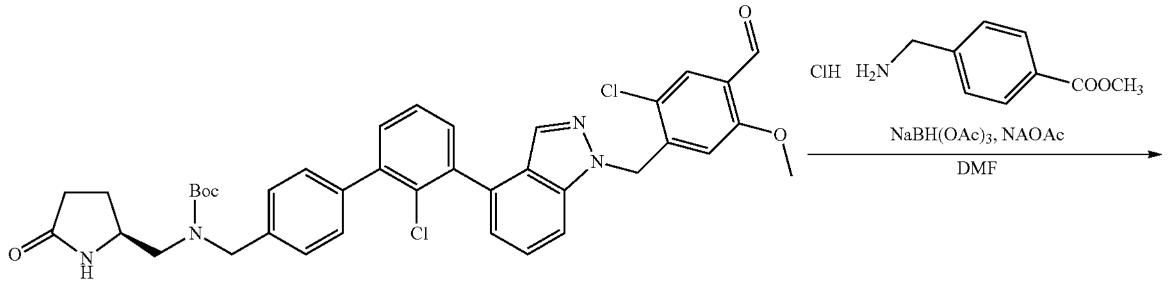

INT-8

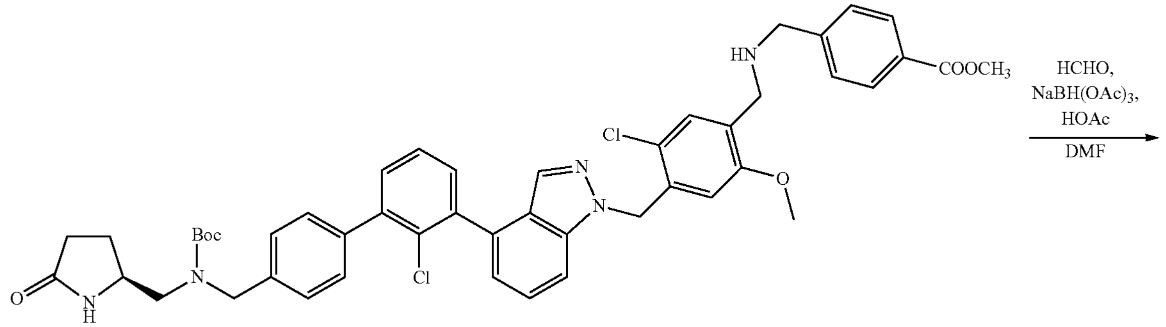

44a

-continued

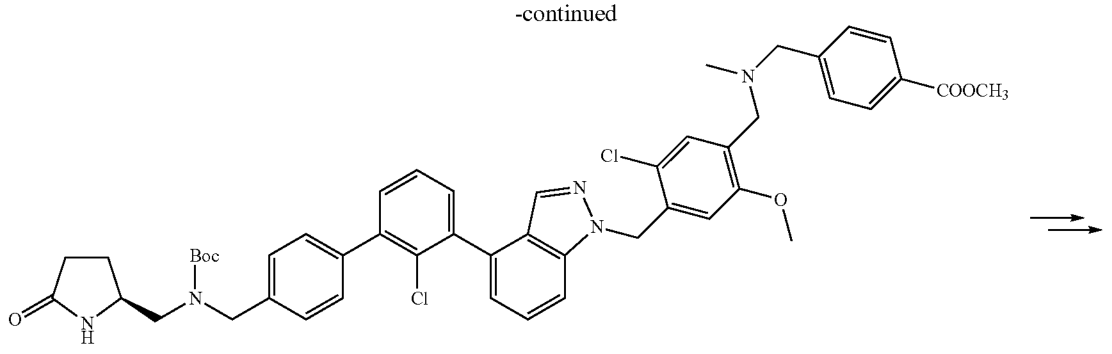

44b

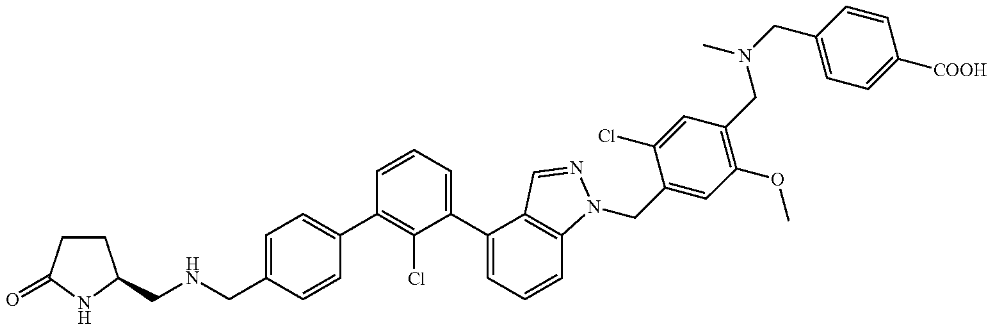

44

Starting from compound INT-8 and methyl 4-aminomethylbenzoate hydrochloride, referring to the synthesis of compound INT-5, compound 44a is obtained. MS (ESI): m/z 862.7 $(M+H)^+$.

Starting from compound 44a, referring to reductive amination step in the synthesis of compound INT-1j, compound 44b is obtained. MS (ESI): m/z 876.8 $(M+H)^+$.

Starting from compound 44b, referring to last two steps in the synthesis of compound 33, compound 44 is obtained. $^1H$ NMR (500 MHz, DMSO-d6) δ 7.90 (s, 1H), 7.88 (d, J=8.0 Hz, 2H), 7.77 (d, J=8.5 Hz, 1H), 7.68 (s, 1H), 7.54-7.50 (m, 2H), 7.49-7.44 (m, 7H), 7.40 (d, J=7.5 Hz, 2H), 7.17 (d, J=7.0 Hz, 1H), 6.68 (s, 1H), 5.74 (s, 2H), 3.81-3.73 (m, 2H), 3.66-3.62 (m, 1H), 3.59-3.53 (m, 2H), 3.57 (s, 3H), 3.45 (s, 2H), 2.56-2.53 (m, 2H), 2.14-2.07 (m, 6H), 1.72-1.66 (m, 1H); MS (ESI): m/z 762.7 $(M+H)^+$.

Example 45

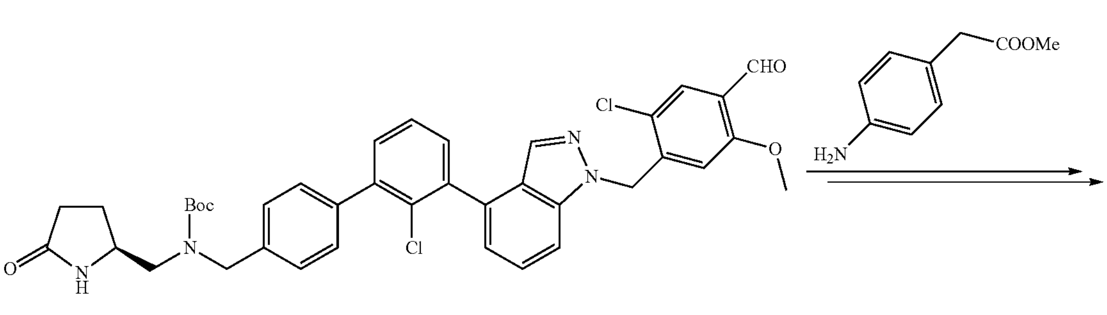

Int-8

-continued
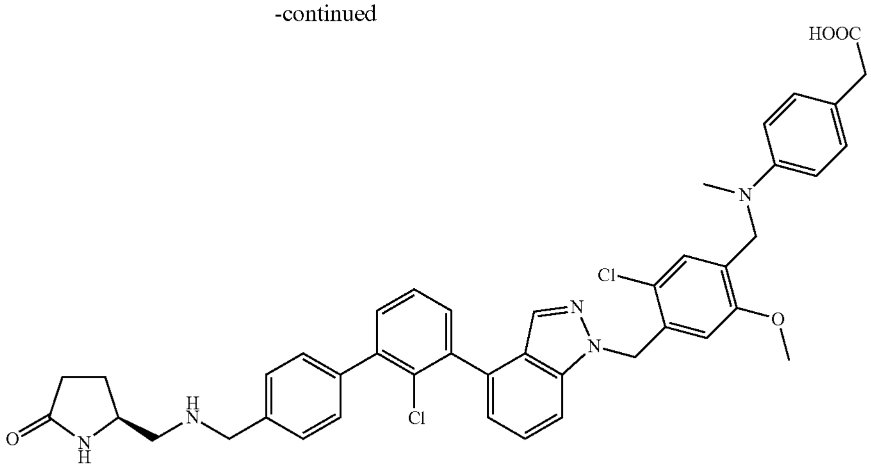
45
Starting from compound INT-8 and methyl p-aminophenylacetate, referring to the synthesis of compound 44, compound 45 is obtained. $^1H$ NMR (500 MHz, DMSO-d6) δ 7.90 (s, 1H), 7.77 (d, J=8.5 Hz, 1H), 7.68 (s, 1H), 7.54-7.50 (m, 2H), 7.49-7.43 (m, 6H), 7.17 (d, J=7.0 Hz, 1H), 7.02 (d, J=8.0 Hz, 2H), 6.92 (s, 1H), 6.75 (s, 1H), 6.55 (d, J=8.0 Hz, 2H), 5.72 (s, 2H), 4.41 (s, 2H), 3.81-3.73 (m, 2H), 3.66-3.61 (m, 4H), 3.35 (s, 2H), 2.98 (s, 3H), 2.58-2.53 (m, 2H), 2.14-2.06 (m, 3H), 1.74-1.66 (m, 1H); MS (ESI): m/z 762.7 $(M+H)^+$.
Example 46
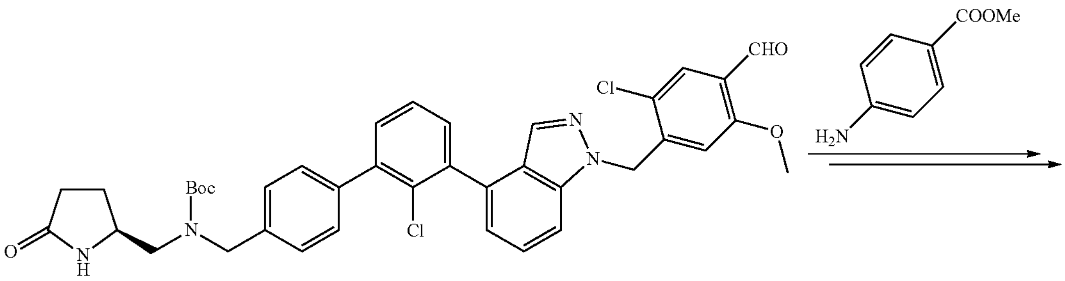
Int-8
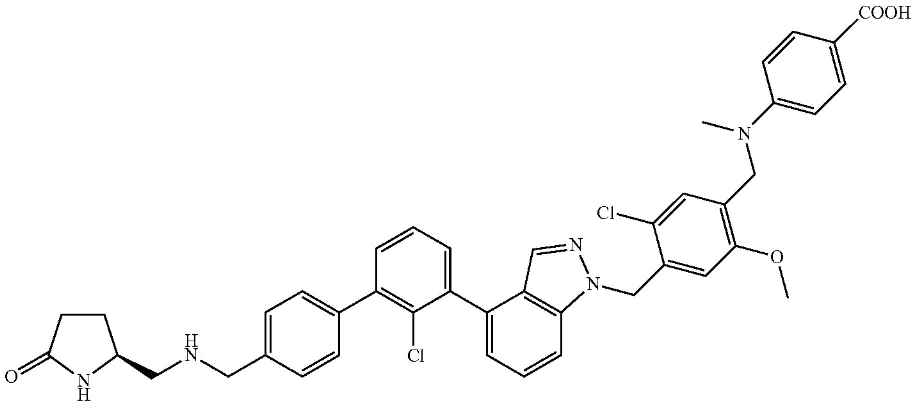
46

Starting from compound INT-8 and methyl p-aminobenzoate, referring to the synthesis of compound 44, compound 46 is obtained. $^1$H NMR (500 MHz, DMSO-d6) δ 7.91 (s, 1H), 7.79 (d, J=8.6 Hz, 1H), 7.74-7.70 (m, 2H), 7.64-7.60 (m, 5H), 7.59-7.50 (m, 3H), 7.50-7.46 (m, 1H), 7.17 (d, J=7.1 Hz, 1H), 6.87 (s, 1H), 6.85-6.81 (m, 1H), 6.68-6.63 (m, 2H), 5.72 (s, 2H), 4.53 (s, 2H), 4.25 (s, 2H), 3.91-3.85 (m, 1H), 3.68 (s, 3H), 3.09 (s, 3H), 2.57-2.53 (m, 2H), 2.23-2.14 (m, 3H), 1.83-1.77 (m, 1H); MS (ESI): m/z 748.7 $(M+H)^+$.

Example 47

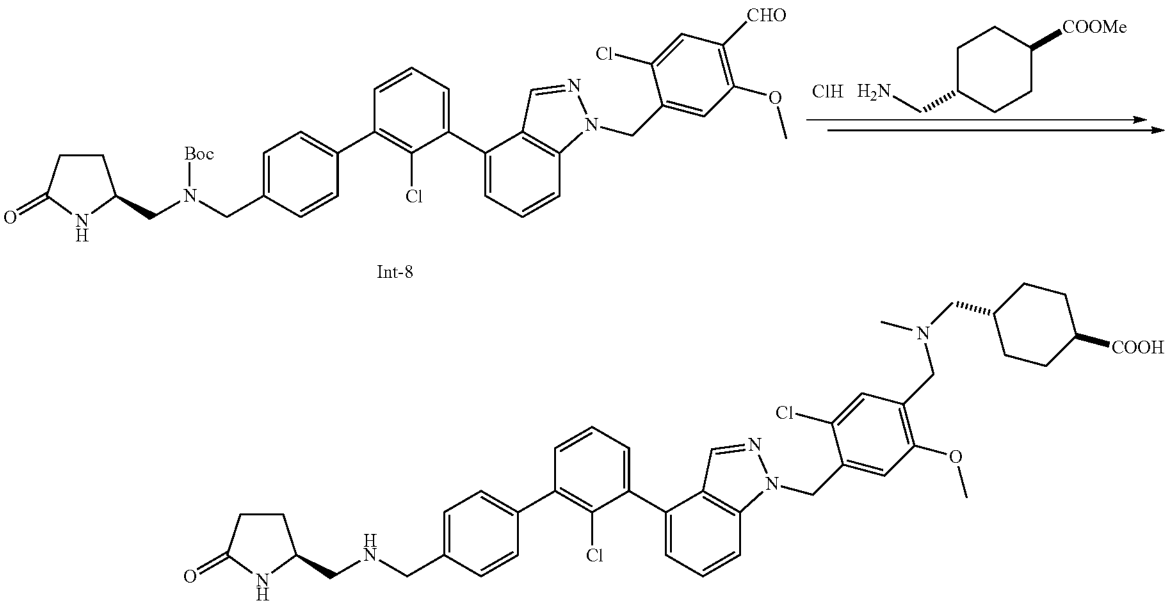

Int-8

47

Starting from compound INT-8 and methyl 4-aminomethyl-cyclohexanecarboxylate hydrochloride, referring to the synthesis of compound 44, compound 47 is obtained. $^1$H NMR (500 MHz, DMSO-d6) δ 7.89 (s, 1H), 7.75 (d, J=8.5 Hz, 1H), 7.67 (s, 1H), 7.53-7.40 (m, 8H), 7.36 (s, 1H), 7.15 (d, J=7.0 Hz, 1H), 6.65 (s, 1H), 5.71 (s, 2H), 3.78-3.71 (m, 2H), 3.64-3.60 (m, 1H), 3.55 (s, 3H), 3.35-3.31 (m, 2H), 2.53-2.51 (m, 2H), 2.13-2.07 (m, 4H), 2.07 (s, 3H), 2.01-1.96 (m, 1H), 1.85-1.76 (m, 4H), 1.71-1.65 (m, 1H), 1.46-1.39 (m, 1H), 1.28-1.17 (m, 3H), 0.82-0.73 (m, 2H); MS (ESI): m/z 768.4 $(M+H)^+$.

Example 48

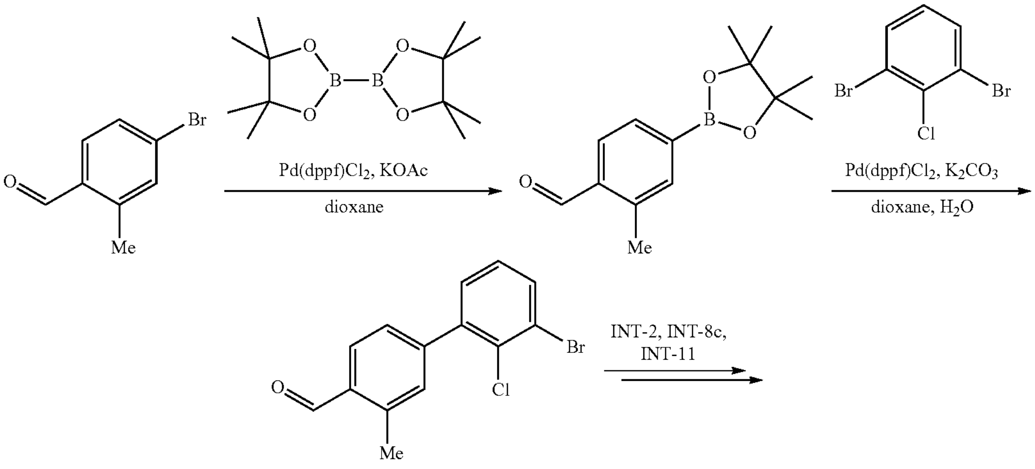

48b

-continued

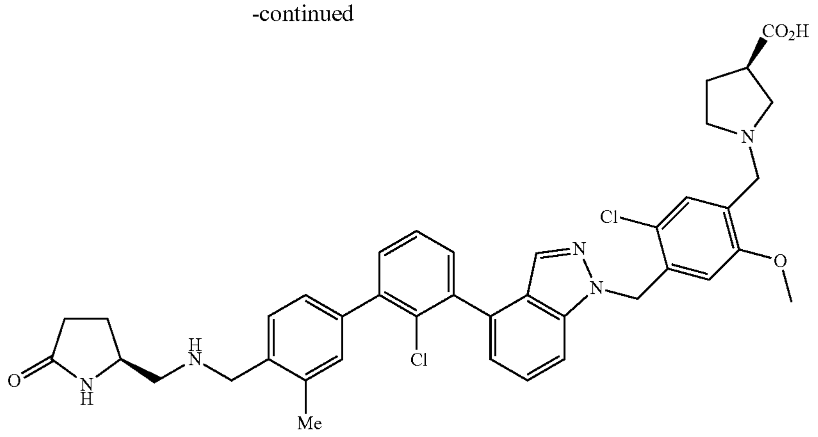

48

Starting from 4-bromo-2-methylbenzaldehyde, referring to boron esterification in the synthesis step of compound INT-7a, compound 48a is obtained. $^1$H NMR (500 MHz, DMSO-d6) δ 10.26 (s, 1H), 7.79 (d, J=7.5 Hz, 1H), 7.66 (d, J=7.5 Hz, 1H), 7.60 (s, 1H), 2.61 (s, 3H), 1.29 (s, 12H).

Starting from compound 48a and 1,3-dibromo-2-chlorobenzene, referring to the synthesis of compound INT-3a, compound 48b is obtained. $^1$H NMR (500 MHz, DMSO-d6) δ 10.27 (s, 1H), 7.89 (d, J=7.9 Hz, 1H), 7.85-7.81 (m, 1H), 7.48-7.34 (m, 4H), 2.66 (s, 3H).

Starting from compound 48b, compound INT-2, compound INT-8c and compound INT-11, referring to the synthesis of compound INT-3, compound INT-8 and compound 33, compound 48 is obtained. $^1$H NMR (500 MHz, DMSO-d6) δ 7.88 (s, 1H), 7.75 (d, J=8.6 Hz, 1H), 7.67 (s, 1H), 7.53-7.38 (m, 5H), 7.35 (s, 1H), 7.30-7.23 (m, 2H), 7.14 (d, J=7.0 Hz, 1H), 6.66 (s, 1H), 5.71 (s, 2H), 3.74-3.67 (m, 2H), 3.65-3.61 (m, 1H), 3.56 (s, 3H), 3.52-3.48 (m, 2H), 2.92-2.85 (m, 1H), 2.64-2.61 (m, 2H), 2.59-2.56 (m, 2H), 2.34 (s, 3H), 2.11-2.05 (m, 3H), 1.94-1.89 (m, 2H), 1.71-1.66 (m, 1H); MS (ESI): m/z 726.2 $(M+H)^+$.

Example 49

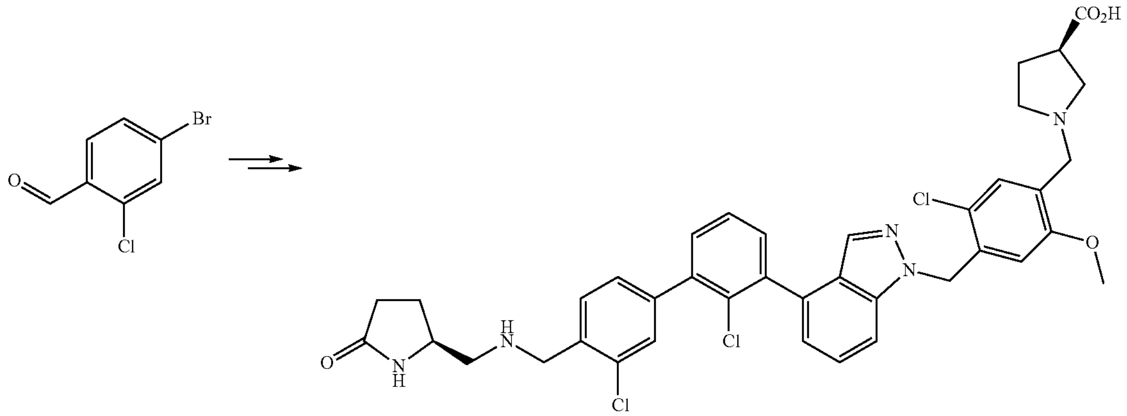

49

Starting from 4-bromo-2-chlorobenzaldehyde, referring to the synthesis of compound 48, compound 49 is obtained. $^1H$ NMR (500 MHz, DMSO-d6) δ 7.94 (s, 1H), 7.77 (d, J=8.5 Hz, 1H), 7.69 (s, 1H), 7.65 (d, J=7.9 Hz, 1H), 7.59 (d, J=1.8 Hz, 1H), 7.57-7.45 (m, 5H), 7.37 (s, 1H), 7.17 (d, J=7.0 Hz, 1H), 6.68 (s, 1H), 5.73 (s, 2H), 3.90-3.80 (m, 2H), 3.70-3.61 (m, 1H), 3.58 (s, 3H), 3.56-3.49 (m, 2H), 2.96-2.86 (m, 1H), 2.69-2.63 (m, 2H), 2.61-2.56 (m, 2H), 2.53-2.50 (m, 2H), 2.17-2.06 (m, 3H), 1.97-1.90 (m, 2H), 1.75-1.66 (m, 1H); MS (ESI): m/z 746.6 $(M+H)^+$.

Example 50

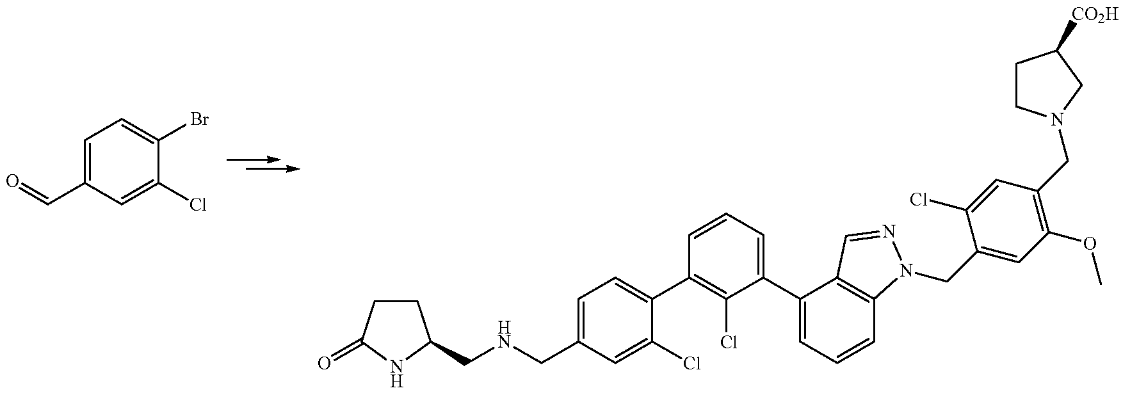

50

Starting from 4-bromo-3-chlorobenzaldehyde, referring to the synthesis of compound 48, compound 50 is obtained. $^1H$ NMR (500 MHz, DMSO-d6) δ 7.80 (s, 1H), 7.76 (d, J=8.5 Hz, 1H), 7.66 (s, 1H), 7.57-7.47 (m, 4H), 7.39-7.38 (m, 3H), 7.34 (s, 1H), 7.16 (d, J=7.0 Hz, 1H), 6.66 (s, 1H), 5.71 (s, 2H), 3.80-3.72 (m, 2H), 3.63-3.60 (m, 1H), 3.56 (s, 3H), 3.53-3.47 (m, 2H), 2.90-2.83 (m, 1H), 2.65-2.59 (m, 2H), 2.55-2.51 (m, 2H), 2.47-2.45 (m, 2H), 2.14-2.03 (m, 3H), 1.95-1.87 (m, 2H), 1.72-1.63 (m, 1H); MS (ESI): m/z 746.5 $(M+H)^+$.

Example 51

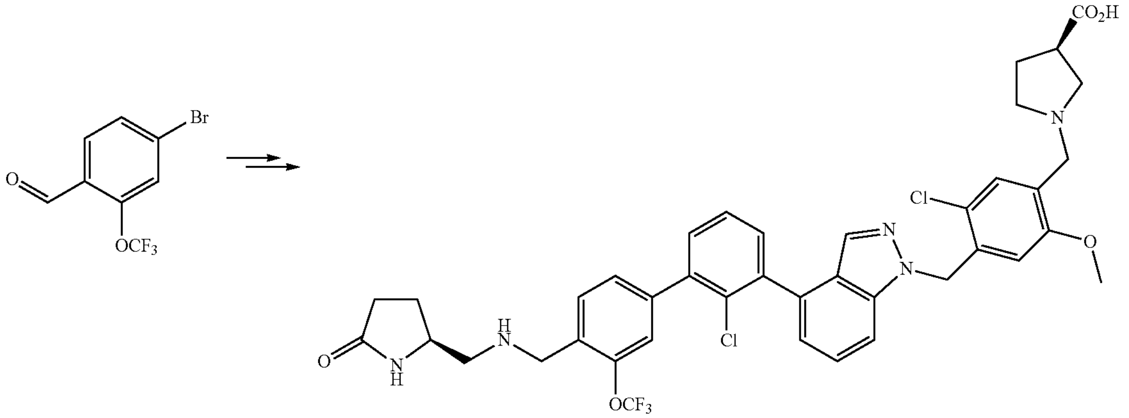

51

Starting from 4-bromo-2-(trifluoromethoxy) benzaldehyde, referring to the synthesis of compound 48, compound 51 is obtained. $^1H$ NMR (500 MHz, DMSO-d6) δ 7.96 (s, 1H), 7.82-7.73 (m, 2H), 7.69 (s, 1H), 7.61-7.50 (m, 5H), 7.51-7.48 (m, 1H), 7.38 (s, 1H), 7.19 (d, J=7.0 Hz, 1H), 6.69 (s, 1H), 5.75 (s, 2H), 3.88-3.80 (m, 2H), 3.65 (t, J=6.5 Hz, 1H), 3.59 (s, 3H), 3.57-3.49 (m, 2H), 2.85-2.75 (m, 1H), 2.70-2.60 (m, 2H), 2.60-2.55 (m, 2H), 2.56-2.53 (m, 1H), 2.50-2.43 (m, 1H), 2.18-2.08 (m, 3H), 1.98-1.85 (m, 2H), 1.77-1.67 (m, 1H); MS (ESI): m/z 796.7 $(M+H)^+$.

Example 52

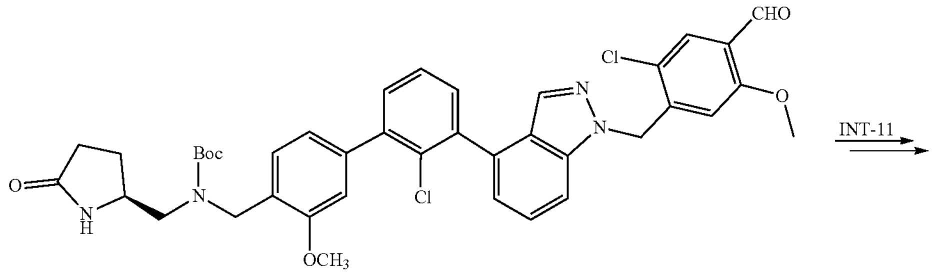

INT-9

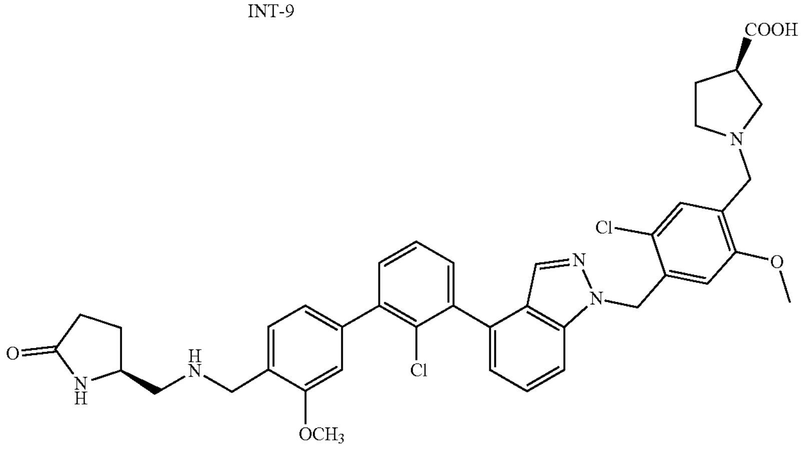

52

Starting from compound INT-9 and compound TNT-1i, referring to the synthesis of compound 33, compound 52 is obtained. $^1H$ NMR (500 MHz, DMSO-d6) δ 7.92 (s, 1H), 7.77 (d, J=8.6 Hz, 1H), 7.68 (s, 1H), 7.57-7.47 (m, 4H), 7.42 (d, J=7.7 Hz, 1H), 7.37 (s, 1H), 7.17 (d, J=7.0 Hz, 1H), 7.09 (d, J=1.7 Hz, 1H), 7.08-7.04 (m, 1H), 6.69 (s, 1H), 5.73 (s, 2H), 3.83 (s, 3H), 3.75-3.72 (m, 2H), 3.66-3.62 (m, 1H), 3.59 (s, 3H), 3.55-3.50 (m, 2H), 2.95-2.87 (m, 1H), 2.70-2.62 (m, 2H), 2.60-2.54 (m, 2H), 2.53-2.51 (m, 2H), 2.17-2.04 (m, 3H), 1.97-1.90 (m, 2H), 1.75-1.65 (m, 1H); MS (ESI): m/z 742.2 $(M+H)^+$.

Example 53

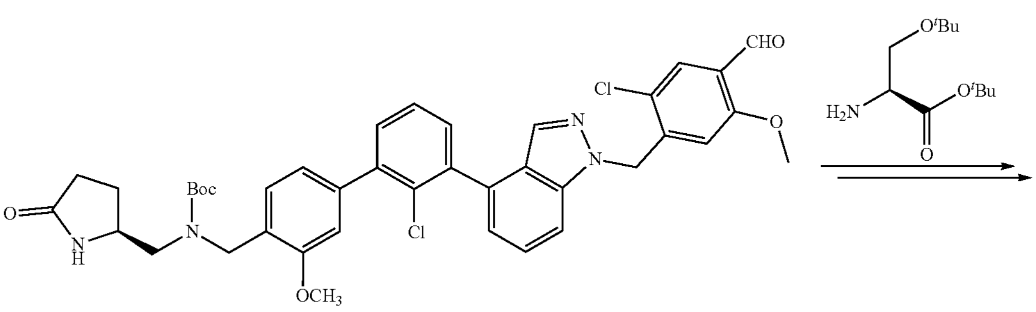

INT-9

-continued
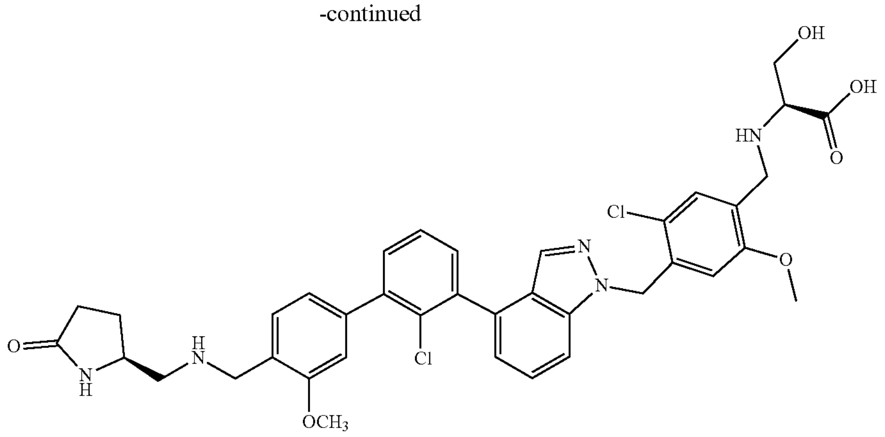
53
Starting from compound INT-9 and O-isopropyl-L-serine tert-butyl ester, referring to the synthesis of compound 22, compound 53 is obtained. $^1$H NMR (500 MHz, DMSO-d6) δ 7.92 (s, 1H), 7.78 (d, J=8.4 Hz, 1H), 7.67 (s, 1H), 7.55-7.48 (m, 5H), 7.42 (d, J=7.7 Hz, 1H), 7.17 (d, J=7.0 Hz, 1H), 7.10 (s, 1H), 7.07 (d, J=8.1 Hz, 1H), 6.73 (s, 1H), 5.74 (s, 2H), 3.88 (d, J=14.6 Hz, 1H), 3.84 (s, 3H), 3.81-3.74 (m, 3H), 3.68-3.63 (m, 2H), 3.61 (s, 3H), 3.60-3.57 (m, 1H), 3.14 (t, J=5.4 Hz, 1H), 2.62-2.57 (m, 2H), 2.18-2.04 (m, 3H), 1.76-1.66 (m, 1H); MS (ESI): m/z 732.6 (M+H)$^+$.
Example 54
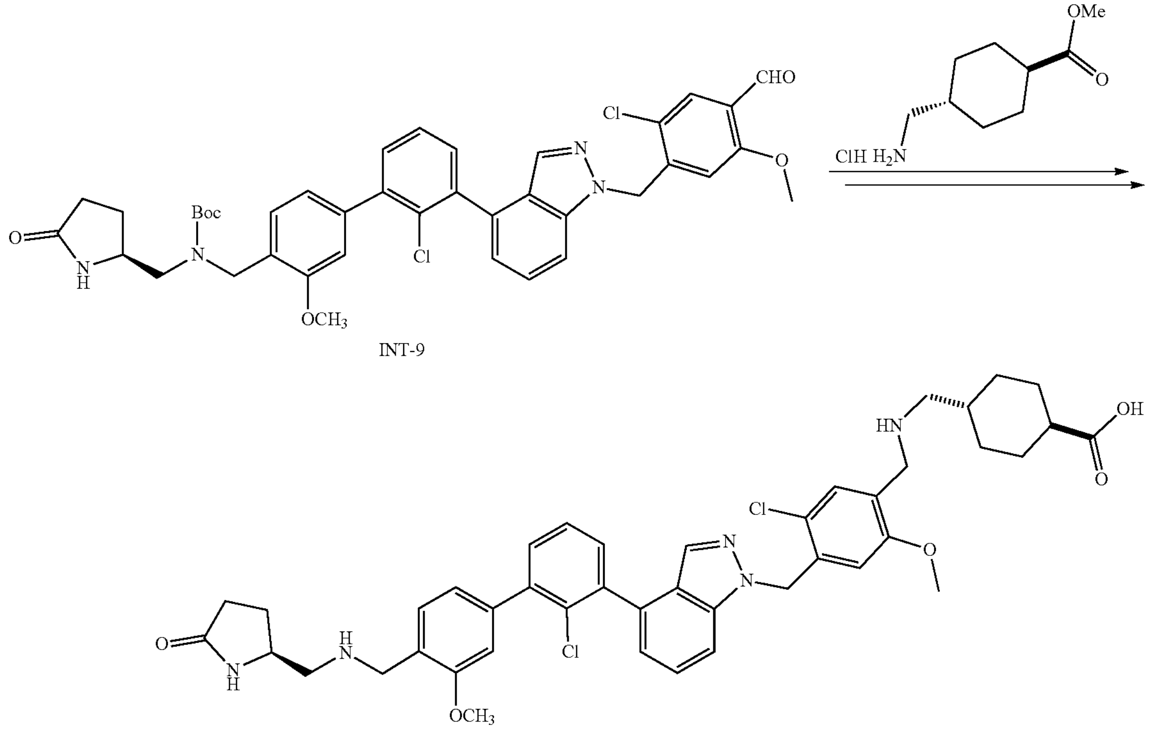
INT-9
54

Starting from compound INT-9 and methyl 4-aminomethyl-cyclohexanecarboxylate hydrochloride, referring to the synthesis of compound 33, compound 54 is obtained. $^1H$ NMR (500 MHz, DMSO-d6) δ 7.91 (s, 1H), 7.77 (d, J=8.6 Hz, 1H), 7.67 (s, 1H), 7.57-7.45 (m, 5H), 7.45-7.39 (m, 2H), 7.17 (d, J=7.0 Hz, 1H), 7.09 (d, J=1.6 Hz, 1H), 7.06 (d, J=7.2 Hz, 1H), 6.70 (s, 1H), 5.73 (s, 2H), 3.83 (s, 3H), 3.75-3.73 (m, 2H), 3.66-3.62 (m, 3H), 3.60 (s, 3H), 2.59-2.54 (m, 2H), 2.37-2.33 (m, 2H), 2.18-2.05 (m, 4H), 1.90-1.84 (m, 2H), 1.82-1.76 (m, 2H), 1.72-1.68 (m, 1H), 1.42-1.32 (m, 1H), 1.32-1.20 (m, 3H), 0.95-0.82 (m, 2H); MS (ESI): m/z 784.7 $(M+H)^+$.

Example 55

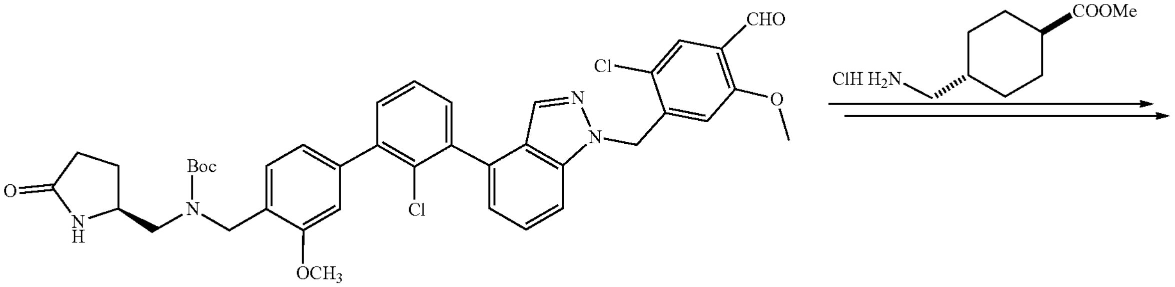

INT-9

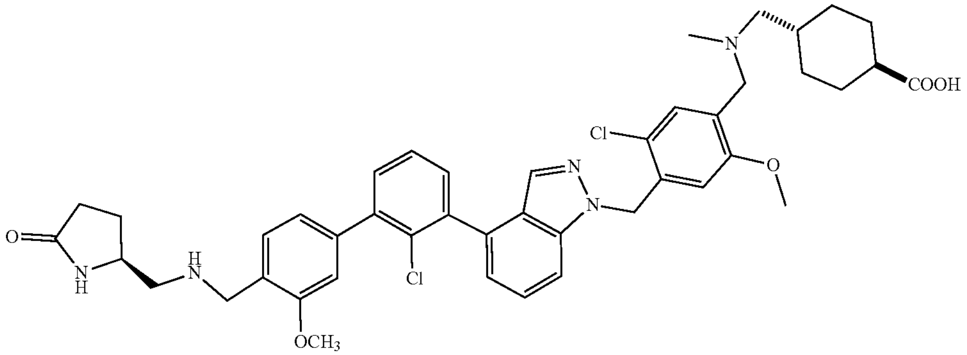

55

Starting from compound INT-9 and methyl 4-aminomethyl-cyclohexanecarboxylate hydrochloride, referring to the synthesis of compound 44, compound 55 is obtained. $^1H$ NMR (500 MHz, DMSO-d6) δ 7.92 (s, 1H), 7.77 (d, J=8.6 Hz, 1H), 7.67 (s, 1H), 7.56-7.46 (m, 4H), 7.42 (d, J=7.7 Hz, 1H), 7.38 (s, 1H), 7.17 (d, J=7.0 Hz, 1H), 7.09 (d, J=1.6 Hz, 1H), 7.08-7.04 (m, 1H), 6.69 (s, 1H), 5.73 (s, 2H), 3.83 (s, 3H), 3.79-3.71 (m, 2H), 3.66-3.62 (m, 1H), 3.58 (s, 3H), 3.36 (s, 2H), 2.58-2.56 (m, 2H), 2.15-2.06 (m, 9H), 1.89-1.80 (m, 4H), 1.74-1.66 (m, 1H), 1.51-1.42 (m, 1H), 1.33-1.23 (m, 2H), 0.88-0.76 (m, 2H); MS (ESI): m/z 798.7 $(M+H)^+$.

Example 56

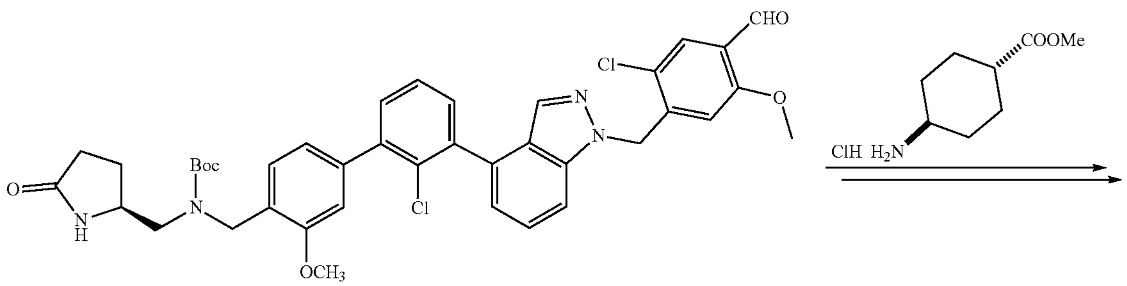

INT-9

-continued
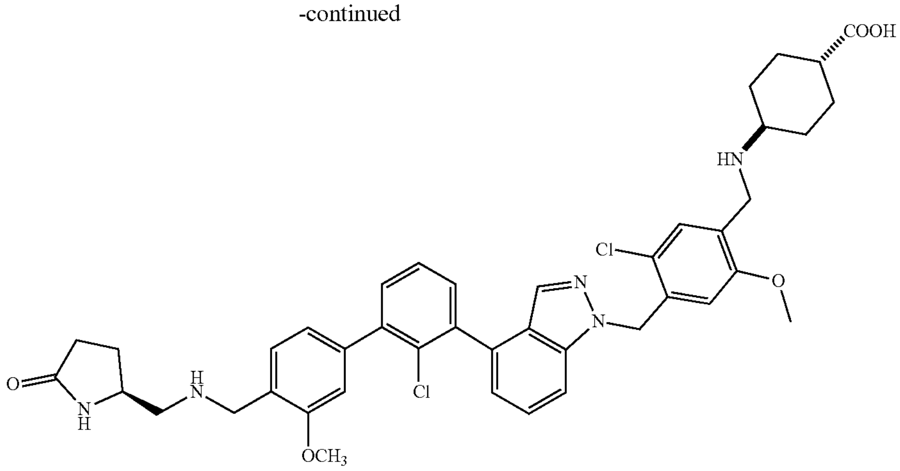
56
Starting from trans-4-methyl aminocyclohexanate hydrochloride and compound INT-9, referring to the synthesis of compound 33, compound 56 is obtained. $^{1}H$ NMR (500 MHz, DMSO-d6) δ 7.89 (s, 1H), 7.74 (d, J=8.5 Hz, 1H), 7.66 (s, 1H), 7.54-7.43 (m, 4H), 7.42 (s, 1H), 7.40 (d, J=8.0 Hz, 1H), 7.15 (d, J=7.0 Hz, 1H), 7.07 (d, J=1.5 Hz, 1H), 7.05-7.01 (m, 1H), 6.67 (s, 1H), 5.71 (s, 2H), 3.81 (s, 3H), 3.75-3.68 (m, 2H), 3.65-3.59 (m, 3H), 3.58 (s, 3H), 2.56-2.52 (m, 2H), 2.32-2.24 (m, 1H), 2.14-2.03 (m, 4H), 1.92-1.80 (m, 4H), 1.72-1.63 (m, 1H), 130-1.18 (m, 2H), 1.05-0.95 (m, 2H); MS (ESI): m/z 770.7 $(M+H)^{+}$.
Example 57
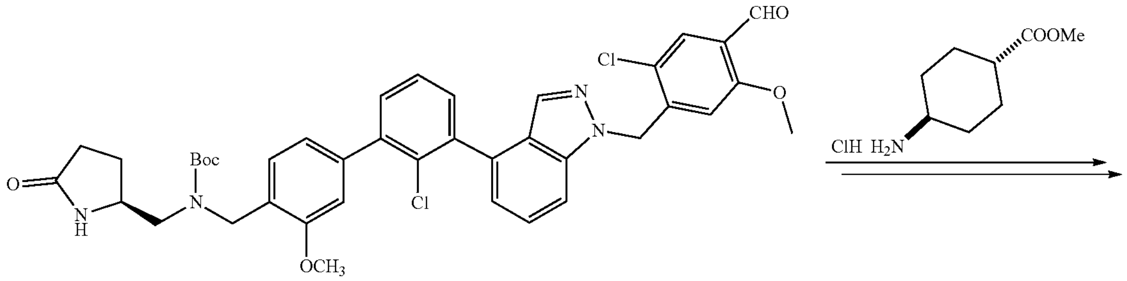
INT-9
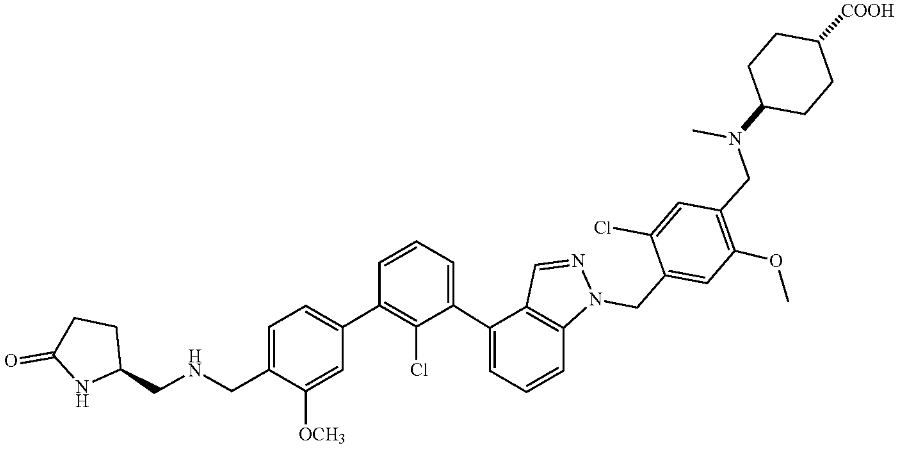
57

Starting from trans-4-methyl aminocyclohexanate hydrochloride and compound INT-9, referring to the synthesis of compound 44, compound 57 is obtained. $^{1}H$ NMR (500 MHz, DMSO-d6) δ 7.89 (s, 1H), 7.75 (d, J=8.5 Hz, 1H), 7.66 (s, 1H), 7.55-7.43 (m, 4H), 7.39 (d, J=8.0 Hz, 1H), 7.36 (s, 1H), 7.15 (d, J=7.0 Hz, 1H), 7.07 (d, J=1.5 Hz, 1H), 7.07-7.01 (m, 1H), 6.67 (s, 1H), 5.71 (s, 2H), 3.81 (s, 3H), 3.75-3.67 (m, 2H), 3.64-3.59 (m, 1H), 3.57 (s, 3H), 3.44 (s, 2H), 2.56-2.52 (m, 2H), 2.39-2.31 (m, 1H), 2.14-2.10 (m, 7H), 1.95-1.86 (m, 2H), 1.81-1.74 (m, 2H), 1.71-1.65 (m, 1H), 1.31-1.23 (m, 4H); MS (ESI): m/z 784.8 $(M+H)^{+}$.

Example 58

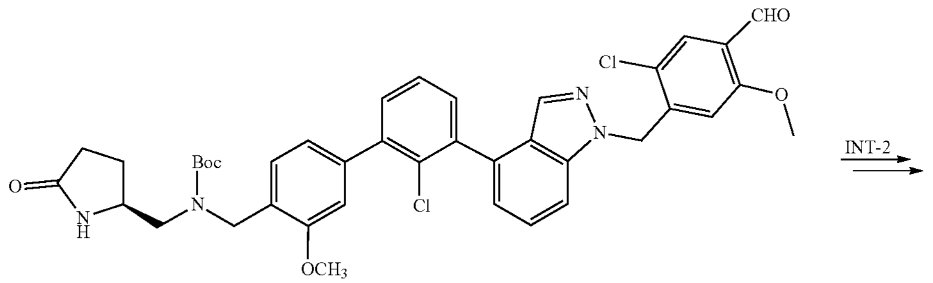

INT-9

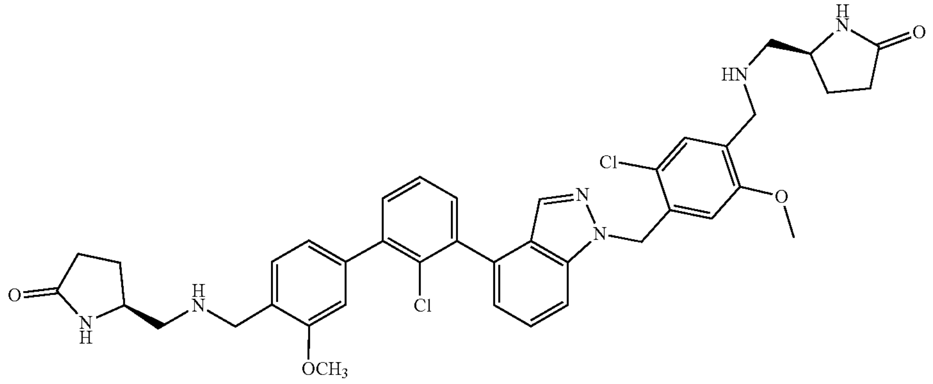

58

Starting from compound INT-9 and compound INT-2, referring to the synthesis of compound 22, compound 58 is obtained. $^{1}H$ NMR (500 MHz, DMSO-d6) δ 7.89 (s, 1H), 7.75 (d, J=8.5 Hz, 1H), 7.66 (s, 1H), 7.63 (s, 1H), 7.53-7.44 (m, 4H), 7.41 (s, 1H), 7.40 (d, J=8.0 Hz, 1H), 7.15 (d, J=7.0 Hz, 1H), 7.06 (s, 1H), 7.04 (d, J=8.0 Hz, 1H), 6.68 (s, 1H), 5.71 (s, 2H), 3.81 (s, 3H), 3.76-3.68 (m, 2H), 3.66-3.59 (m, 4H), 3.58 (s, 3H), 2.56-2.52 (m, 2H), 2.47-2.42 (m, 2H), 2.14-2.03 (m, 6H), 1.70-1.60 (m, 2H); MS (ESI): m/z 741.8 $(M+H)^{+}$.

Example 59

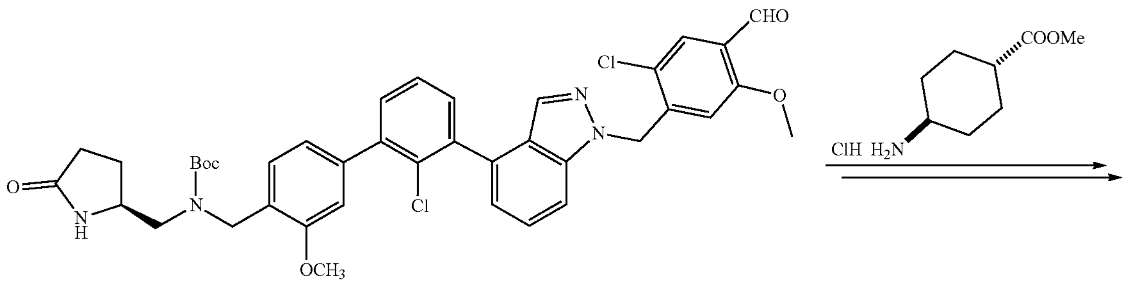

INT-9

-continued
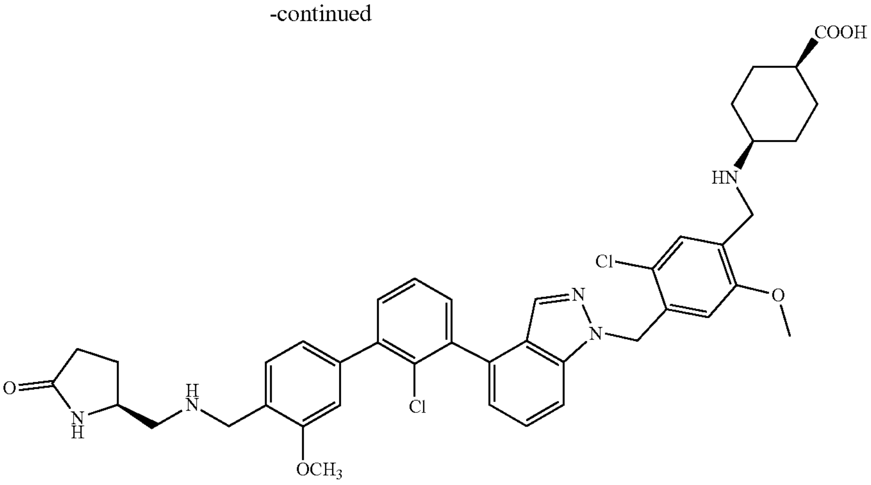
59
Starting from cis-4-methyl aminocyclohexanate hydrochloride and compound INT-9, referring to the synthesis of compound 33, compound 59 is obtained. $^1$H NMR (500 MHz, DMSO-d6) δ 7.89 (s, 1H), 7.74 (d, J=8.5 Hz, 1H), 7.67 (s, 1H), 7.53-7.45 (m, 4H), 7.43 (s, 1H), 7.39 (d, J=7.5 Hz, 1H), 7.15 (d, J=7.0 Hz, 1H), 7.08-7.06 (m, 1H), 7.05-7.02 (m, 1H), 6.67 (s, 1H), 5.70 (s, 2H), 3.81 (s, 3H), 3.75-3.67 (m, 2H), 3.62-3.60 (m, 3H), 3.58 (s, 3H), 2.55-2.52 (m, 3H), 2.31-2.25 (m, 1H), 2.13-2.04 (m, 3H), 1.87-1.79 (m, 2H), 1.72-1.63 (m, 1H), 1.57-1.48 (m, 2H), 1.46-1.37 (m, 4H); MS (ESI): m/z 770.7 $(M+H)^+$.
Example 60
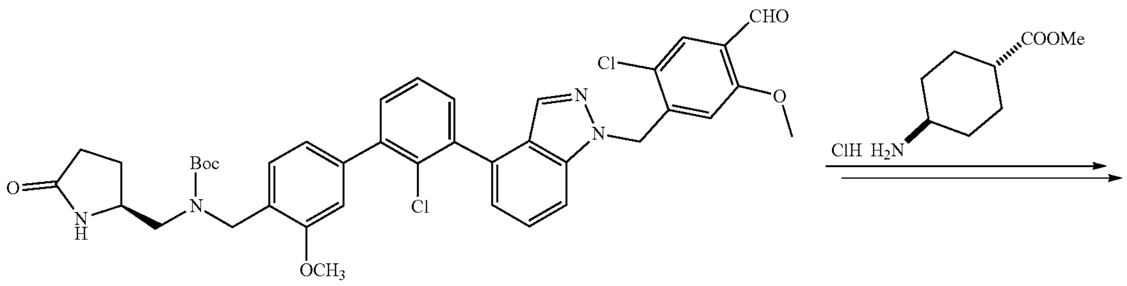
INT-9
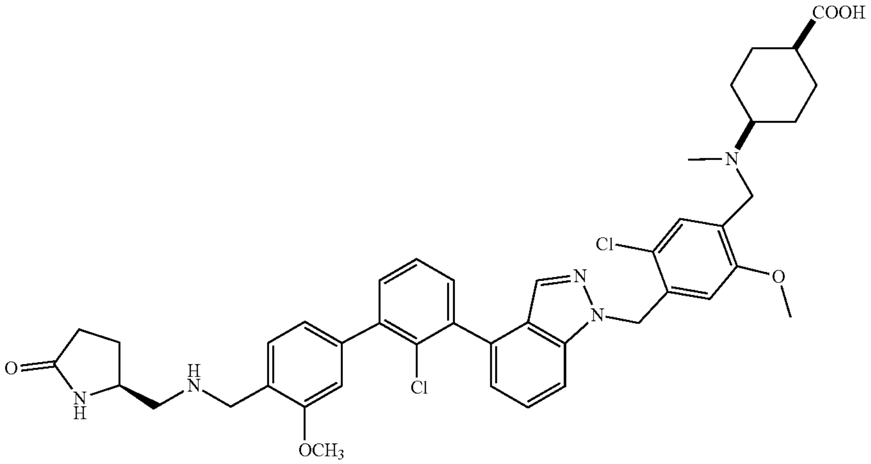
60

Starting from cis-4-methyl aminocyclohexanate hydrochloride and compound INT-9, referring to the synthesis of compound 44, compound 60 is obtained. $^1$H NMR (500 MHz, DMSO-d6) δ 7.89 (s, 1H), 7.75 (d, J=8.5 Hz, 1H), 7.66 (s, 1H), 7.53-7.44 (m, 4H), 7.40 (d, J=7.5 Hz, 1H), 7.35 (s, 1H), 7.15 (d, J=7.0 Hz, 1H), 7.09-7.06 (m, 1H), 7.05-7.01 (m, 1H), 6.67 (s, 1H), 5.71 (s, 2H), 3.81 (s, 3H), 3.75-3.67 (m, 2H), 3.64-3.60 (m, 1H), 3.56 (s, 2H), 3.42-3.35 (m, 3H), 2.57-2.52 (m, 2H), 2.45-2.40 (m, 1H), 2.38-2.31 (m, 1H), 2.14-2.07 (m, 3H), 2.06 (s, 3H), 2.01-1.93 (m, 2H), 1.72-1.63 (m, 1H), 1.60-1.52 (m, 2H), 1.50-1.37 (m, 4H); MS (ESI): m/z 784.7 $(M+H)^+$.

Example 61

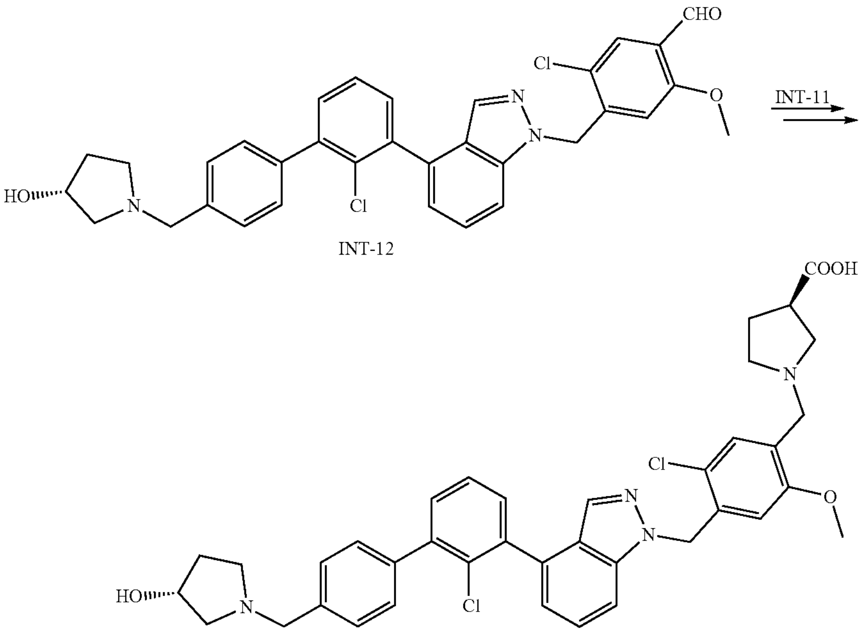

INT-12

61

Starting from compound INT-11 and compound INT-12, referring to the synthesis of compound 33, compound 61 is obtained. $^1$H NMR (500 MHz, DMSO-d6) δ 7.88 (s, 1H), 7.75 (d, J=8.5 Hz, 1H), 7.53-7.48 (m, 2H), 7.48-7.43 (m, 4H), 7.41-7.36 (m, 2H), 7.35 (s, 1H), 7.15 (d, J=7.0 Hz, 1H), 6.65 (s, 1H), 5.71 (s, 2H), 4.21-4.16 (m, 1H), 3.70-3.45 (m, 4H), 3.56 (s, 3H), 2.92-2.85 (m, 1H), 2.72-2.66 (m, 1H), 2.64-2.57 (m, 3H), 2.45-2.40 (m, 3H), 2.36-2.32 (m, 1H), 2.02-1.96 (m, 1H), 1.95-1.88 (m, 2H), 1.58-1.52 (m, 1H); MS (ESI): m/z 685.8 $(M+H)^+$.

Example 62

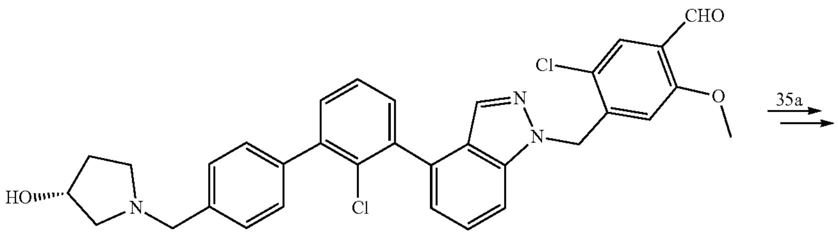

INT-12

-continued
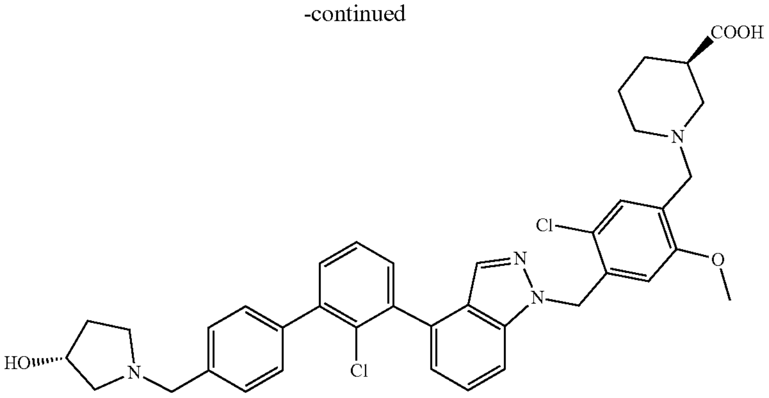
62
Starting from compound INT-12 and compound 35a, referring to the synthesis of compound 33, compound 62 is obtained. $^1$H NMR (500 MHz, DMSO-d6) δ 7.90 (s, 1H), 7.77 (d, J=8.5 Hz, 1H), 7.55-7.50 (m, 2H), 7.49-7.45 (m, 4H), 7.42-7.37 (m, 3H), 7.17 (d, J=7.0 Hz, 1H), 6.67 (s, 1H), 5.73 (s, 2H), 4.24-4.19 (m, 1H), 3.66-3.58 (m, 2H), 3.57 (s, 3H), 3.41 (s, 2H), 2.80-2.72 (m, 1H), 2.73-2.67 (m, 1H), 2.64-2.55 (m, 2H), 2.46-2.43 (m, 1H), 2.42-2.38 (m, 1H), 2.37-2.34 (m, 1H), 2.22-2.12 (m, 1H), 2.08-1.98 (m, 2H), 1.80-1.71 (m, 1H), 1.65-1.53 (m, 2H), 1.50-1.42 (m, 1H), 1.40-1.31 (m, 1H); MS (ESI): m/z 699.7 (M+H)$^+$.
Example 63
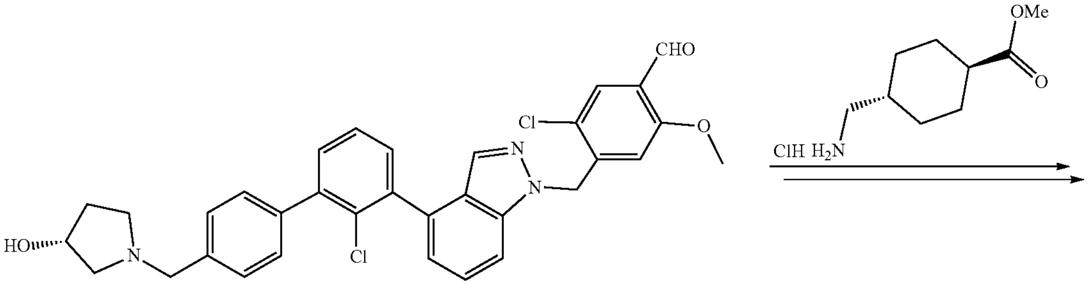
INT-12
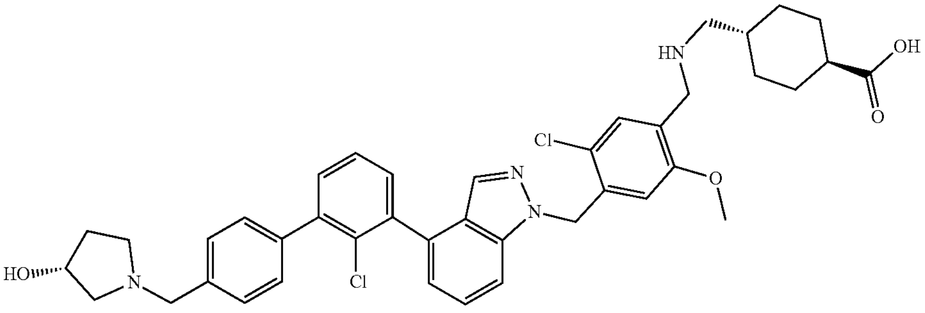
63

Starting from compound INT-12 and methyl 4-aminomethyl-cyclohexanecarboxylate hydrochloride, referring to the synthesis of compound 33, compound 63 is obtained. $^1$H NMR (500 MHz, DMSO-d6) δ 7.89 (s, 1H), 7.76 (d, J=8.5 Hz, 1H), 7.55-7.50 (m, 2H), 7.49-7.45 (m, 4H), 7.42-7.38 (m, 3H), 7.17 (d, J=7.0 Hz, 1H), 6.67 (s, 1H), 5.73 (s, 2H), 4.24-4.18 (m, 1H), 3.64 (d, J=13.0 Hz, 1H), 3.60-3.56 (m, 6H), 2.73-2.67 (m, 1H), 2.64-2.60 (m, 1H), 2.46-2.42 (m, 1H), 2.37-2.34 (m, 1H), 2.31 (d, J=6.5 Hz, 2H), 2.12-2.06 (m, 1H), 2.04-1.98 (m, 1H), 1.89-1.84 (m, 2H), 1.82-1.77 (m, 2H), 1.59-1.52 (m, 1H), 1.39-1.32 (m, 1H), 1.31-1.21 (m, 2H), 0.93-0.83 (m, 2H); MS (ESI): m/z 727.5 (M+H)$^+$.

Example 64

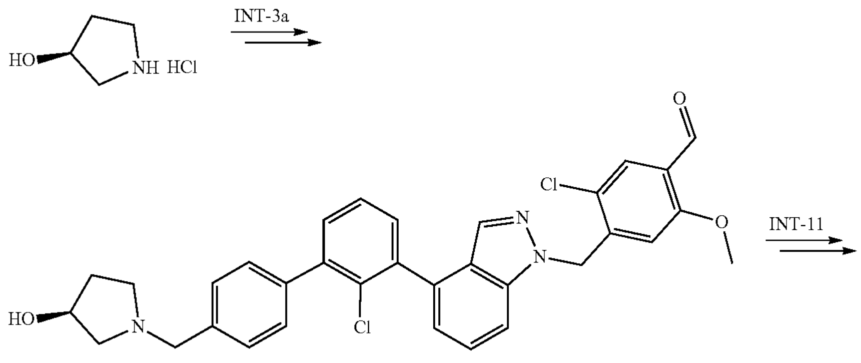

64a

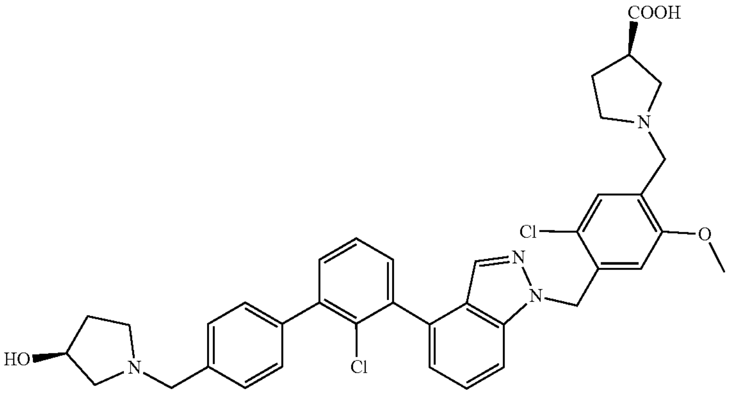

64

Starting from (S)-3-hydroxypyrrolidine hydrochloride and compound INT-3a, referring to the synthesis of compound INT-5 and compound INT-8, compound 64a is obtained. MS (ESI): m/z 586.4 (M+H)$^+$.

Starting from compound 64a and compound INT-11, referring to the synthesis of compound 33, compound 64 is obtained. $^1$H NMR (500 MHz, DMSO-d6) δ 7.88 (s, 1H), 7.75 (d, J=8.5 Hz, 1H), 7.52-7.47 (m, 2H), 7.47-7.42 (m, 4H), 7.39 (s, 1H), 7.37 (d, J=8.0 Hz, 1H), 7.35 (s, 1H), 7.15 (d, J=7.0 Hz, 1H), 6.65 (s, 1H), 5.71 (s, 2H), 4.22-4.15 (m, 1H), 3.64-3.57 (m, 2H), 3.56 (s, 3H), 3.52-3.45 (m, 2H), 2.90-2.82 (m, 1H), 2.70-2.56 (m, 4H), 2.45-2.38 (m, 3H), 2.35-2.30 (m, 1H), 2.02-1.95 (m, 1H), 1.94-1.86 (m, 2H), 1.62-1.50 (m, 1H); MS (ESI): m/z 685.5 (M+H)$^+$.

Example 65

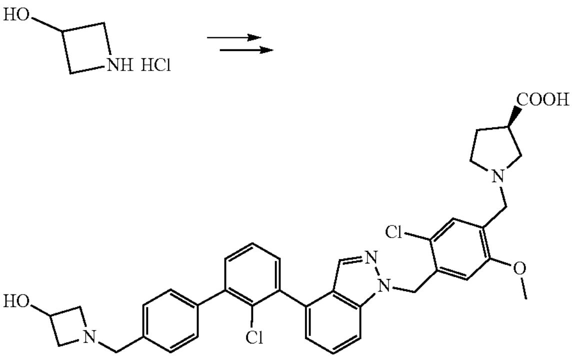

65

Starting from 3-hydroxyl azacyclobutane hydrochloride, referring to the synthesis of compound 64, compound 65 is obtained. $^1$H NMR (500 MHz, DMSO-d6) δ 7.90 (s, 1H), 7.76 (d, J=8.6 Hz, 1H), 7.54-7.50 (m, 2H), 7.49-7.44 (m, 4H), 7.38-7.33 (m, 3H), 7.17 (d, J=7.0 Hz, 1H), 6.67 (s, 1H), 5.73 (s, 2H), 5.34-5.26 (m, 1H), 4.23-4.19 (m, 1H), 3.61 (s, 2H), 3.58 (s, 3H), 3.56-3.46 (m, 6H), 2.94-2.88 (m, 1H), 2.82-2.78 (m, 2H), 2.67-2.64 (m, 2H), 1.97-1.91 (m, 2H); MS (ESI): m/z 671.6 (M+H)$^+$.

Example 66

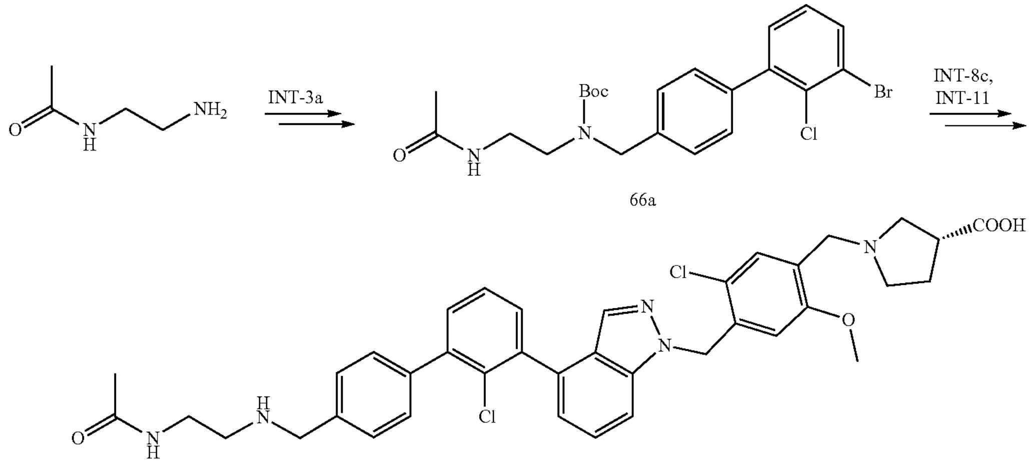

66a

65

Starting from N-acetyl ethylenediamine and compound INT-3a, referring to the synthesis of compound INT-3, compound 66a is obtained. MS (ESI): m/z 481.2 (M+H)$^+$.

Starting from compound 66a, compound INT-8c and compound INT-11, referring to the synthesis of compound INT-8 and compound 33, compound 66 is obtained. $^1$H NMR (500 MHz, DMSO-d6) δ 7.89 (s, 1H), 7.82-7.77 (m, 1H), 7.75 (d, J=8.5 Hz, 1H), 7.53-7.48 (m, 2H), 7.47-7.40 (m, 6H), 7.35 (s, 1H), 7.15 (d, J=7.0 Hz, 1H), 6.65 (s, 1H), 5.71 (s, 2H), 3.73 (s, 2H), 3.56 (s, 3H), 3.52-3.47 (m, 2H), 3.16-3.12 (m, 2H), 2.93-2.84 (m, 1H), 2.67-2.61 (m, 2H), 2.57 (t, J=6.5 Hz, 2H), 2.45-2.42 (m, 2H), 1.96-1.87 (m, 2H), 1.77 (s, 3H); MS (ESI): m/z 700.2 (M+H)$^+$.

Example 67

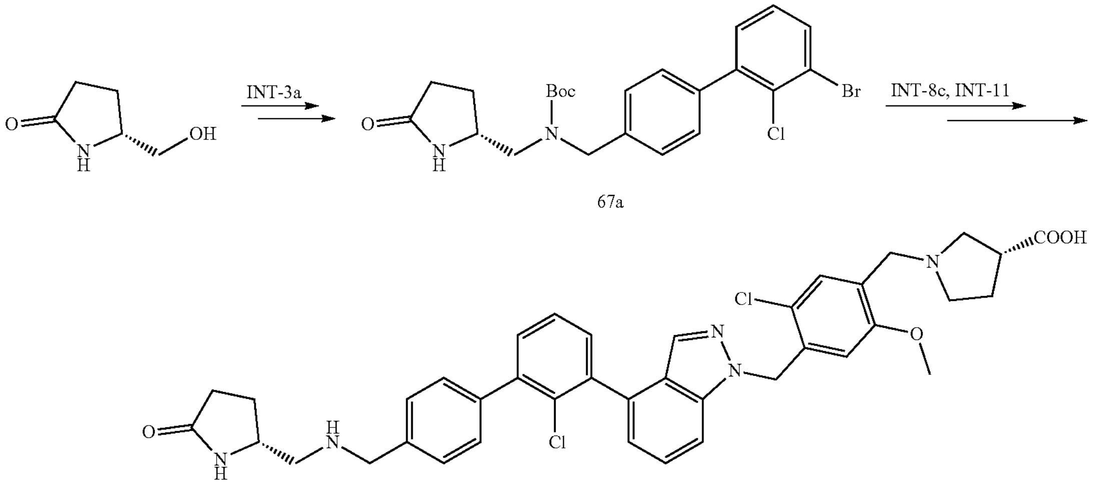

67a

67

Starting from (R)-5-hydroxymethyl-2-pyrrolidone and compound INT-3a, referring to the synthesis of compound INT-2 and compound INT-3, compound 67a is obtained. MS (ESI): m/z 493.2 $(M+H)^+$.

Starting from compound 67a, compound INT-8c and compound INT-11, referring to the synthesis of compound INT-8 and compound 33, compound 67 is obtained. $^1H$ NMR (500 MHz, DMSO-d6) δ 7.88 (s, 1H), 7.74 (d, J=8.5 Hz, 1H), 7.65 (s, 1H), 7.53-7.48 (m, 2H), 7.47-7.39 (m, 6H), 7.35 (s, 1H), 7.15 (d, J=7.0 Hz, 1H), 6.65 (s, 1H), 5.71 (s, 2H), 3.77-3.71 (m, 2H), 3.64-3.59 (m, 1H), 3.56 (s, 3H), 3.52-3.48 (m, 2H), 2.91-2.83 (m, 1H), 2.66-2.60 (m, 2H), 2.55-2.51 (m, 2H), 2.47-2.45 (m, 2H), 2.15-2.04 (m, 3H), 1.95-1.88 (m, 2H), 1.72-1.64 (m, 1H); MS (ESI): m/z 712.6 $(M+H)^+$.

Example 68

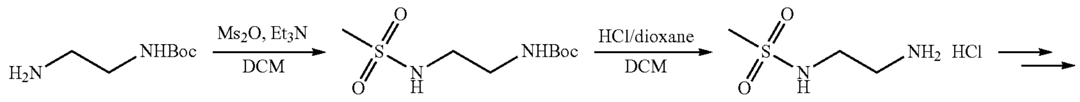

68a 68b

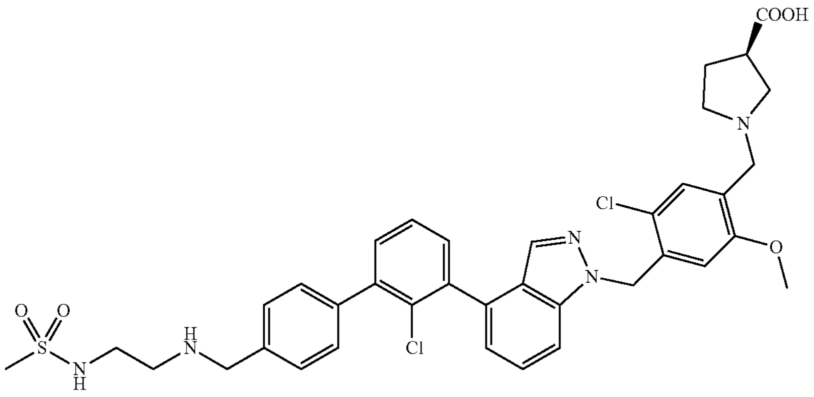

68

Under ice bath conditions, in dichloromethane (3 mL) with N-tert-butoxycarbonyl-1,2-ethylenediamine (99 mg, 0.62 mmol) dissolved methanesulfonic anhydride (135 mg, 0.77 mmol) and triethylamine (102 mg, 1.01 mmol) were sequentially added. The reaction solution under the same conditions was stirred for 1 hour. In the reaction solution saturated sodium bicarbonate solution (20 mL) was added, and the solution was extracted with ethyl acetate (20 mL×2). The combined organic phase was washed with saturated salt solution (30 mL), dried with anhydrous sodium sulfate. The filtrate was concentrated to obtain white solid 68a (160 mg, yield: 86.6%).

In dichloromethane (2 mL) solution with compound 68a (160 mg, 0.67 mmol) dissolved hydrochloric acid (4 M 1,4-dioxane solution, 1.7 mL) was added. The reaction solution at 20° C. was stirred for 16 hours. The reaction solution concentrated to obtain yellow oily matter 68b (90 mg, yield: 76.8%). $^1H$ NMR (500 MHz, DMSO-d6) δ 8.14 (s, 3H), 7.36 (t, J=6.0 Hz, 1H), 3.27-3.16 (m, 2H), 2.94 (s, 3H), 2.92-2.84 (m, 2H).

Starting from compound 68b, referring to the synthesis of compound 64, compound 68 is obtained. $^1H$ NMR (500 MHz, DMSO-d6) δ 7.89 (s, 1H), 7.75 (d, J=8.5 Hz, 1H), 7.53-7.48 (m, 2H), 7.47-7.43 (m, 4H), 7.43-7.40 (m, 2H), 7.35 (s, 1H), 7.15 (d, J=7.0 Hz, 1H), 6.94 (s, 1H), 6.65 (s, 1H), 5.71 (s, 2H), 3.74 (s, 2H), 3.56 (s, 3H), 3.54-3.52 (m, 2H), 3.05 (t, J=6.5 Hz, 2H), 2.92-2.89 (m, 1H), 2.88 (s, 3H), 2.67-2.60 (m, 4H), 2.47-2.45 (m, 2H), 1.95-1.87 (m, 2H); MS (ESI): m/z 736.9 $(M+H)^+$.

Example 69

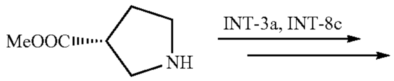

INT-11

-continued

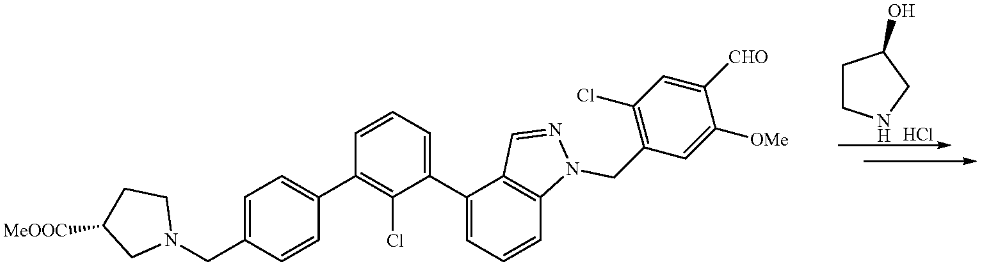

69a

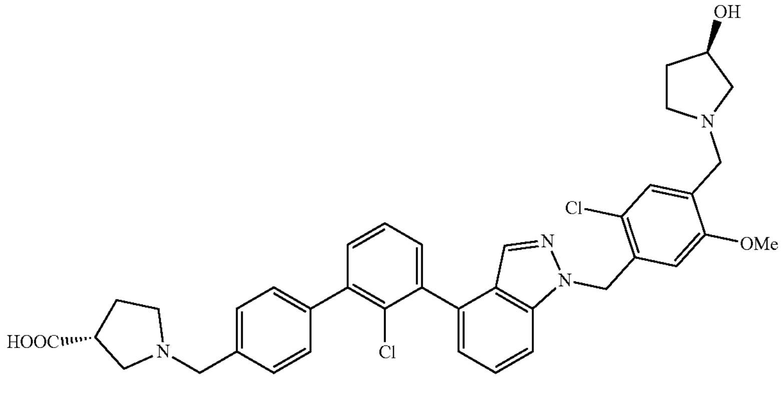

69

Starting from compound INT-11, compound INT-3a and compound INT-8c, referring to the synthesis of compound INT-5 and compound INT-8, compound 69a is obtained. MS (ESI): m/z 628.5 $(M+H)^+$.

Starting from compound 69a and (R)-3-hydroxypyrrolidine hydrochloride, referring to the synthesis of compound 33, compound 69 is obtained. $^1$H NMR (500 MHz, DMSO-d6) δ 7.90 (s, 1H), 7.76 (d, J=8.5 Hz, 1H), 7.55-7.50 (m, 2H), 7.50-7.45 (m, 4H), 7.40 (d, J=8.0 Hz, 2H), 7.37 (s, 1H), 7.17 (d, J=7.0 Hz, 1H), 6.67 (s, 1H), 5.73 (s, 2H), 4.20-4.15 (m, 1H), 3.66-3.59 (m, 2H), 3.58 (s, 3H), 3.53 (d, J=14.5 Hz, 1H), 3.48 (d, J=14.5 Hz, 1H), 2.96-2.91 (m, 1H), 2.74 (t, J=8.5 Hz, 1H), 2.66-2.62 (m, 2H), 2.61-2.58 (m, 1H), 2.42-2.32 (m, 4H), 2.01-1.94 (m, 3H), 1.56-1.49 (m, 1H); MS (ESI): m/z 685.3 $(M+H)^+$.

Example 70

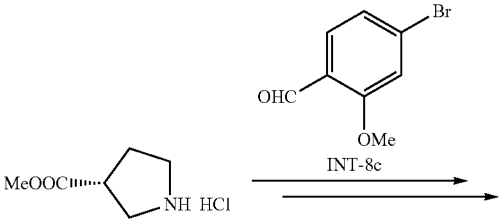

INT-11

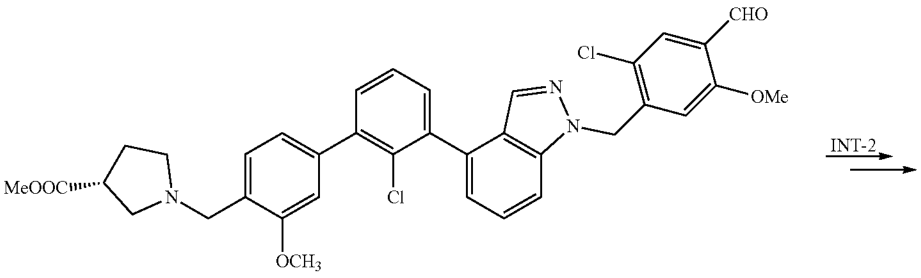

70a

-continued

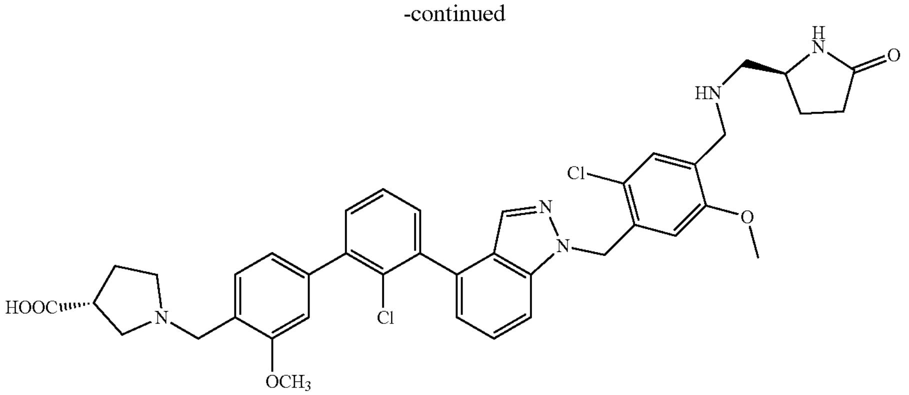

70

Starting from compound INT-11, 4-bromo-2-Methoxy-benzaldehyde and compound INT-8c, referring to the synthesis of compound INT-5 and compound INT-8, compound 70a is obtained. MS (ESI): m/z 658.4 $(M+H)^+$.

Starting from compound 70a and compound INT-2, referring to the synthesis of compound 33, compound 70 is obtained. $^1$H NMR (500 MHz, DMSO-d6) δ 7.89 (s, 1H), 7.75 (d, J=8.5 Hz, 1H), 7.63 (s, 1H), 7.53-7.44 (m, 4H), 7.41 (s, 1H), 7.37 (d, J=8.0 Hz, 1H), 7.15 (d, J=7.0 Hz, 1H), 7.09-7.07 (m, 1H), 7.06-7.02 (m, 1H), 6.67 (s, 1H), 5.71 (s, 2H), 3.80 (s, 3H), 3.62-3.59 (m, 4H), 3.58-3.56 (m, 4H), 2.95-2.89 (m, 1H), 2.77-2.71 (m, 1H), 2.70-2.65 (m, 1H), 2.58-2.52 (m, 2H), 2.47-2.43 (m, 2H), 2.11-2.02 (m, 3H), 1.98-1.92 (m, 2H), 1.67-1.60 (m, 1H); MS (ESI): m/z 742.7 $(M+H)^+$.

Example 71

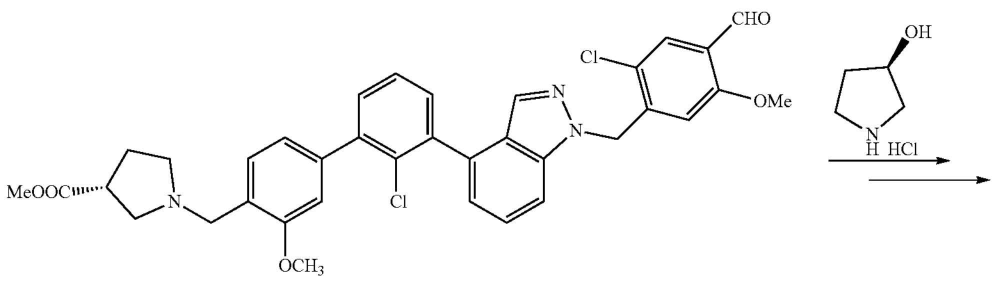

70a

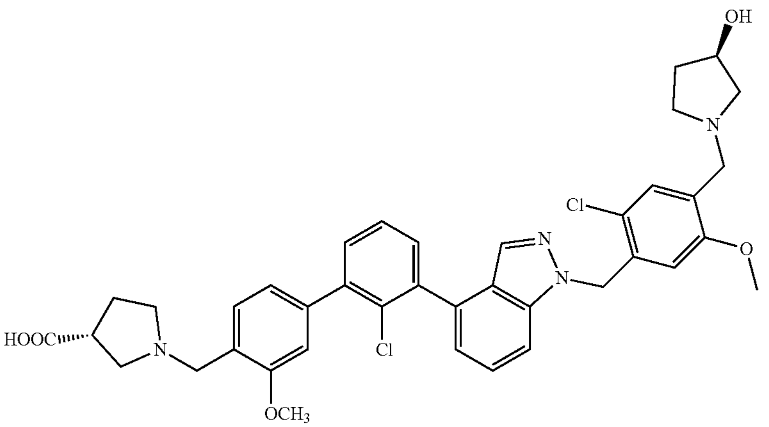

71

Starting from compound 70a and (R)-3-hydroxypyrrolidine hydrochloride, referring to the synthesis of compound 33 compound 71 is obtained. $^1$H NMR (500 MHz, DMSO-d6) δ 7.90 (s, 1H), 7.75 (d, J=8.5 Hz, 1H), 7.52-7.44 (m, 4H), 7.36 (d, J=7.5 Hz, 1H), 7.35 (s, 1H), 7.15 (d, J=7.0 Hz, 1H), 7.09-7.07 (m, 1H), 7.06-7.02 (m, 1H), 6.66 (s, 1H), 5.71 (s, 2H), 4.18-4.11 (m, 1H), 3.80 (s, 3H), 3.61-3.59 (m, 2H), 3.56 (s, 3H), 3.53-3.46 (m, 2H), 2.95-2.87 (m, 1H), 2.78-2.71 (m, 1H), 2.69-2.64 (m, 1H), 2.64-2.53 (m, 4H), 2.41-2.35 (m, 1H), 2.34-2.29 (m, 1H), 1.99-1.92 (m, 3H), 1.55-1.48 (m, 1H); MS (ESI): m/z 715.8 (M+H)$^+$.

Example 72

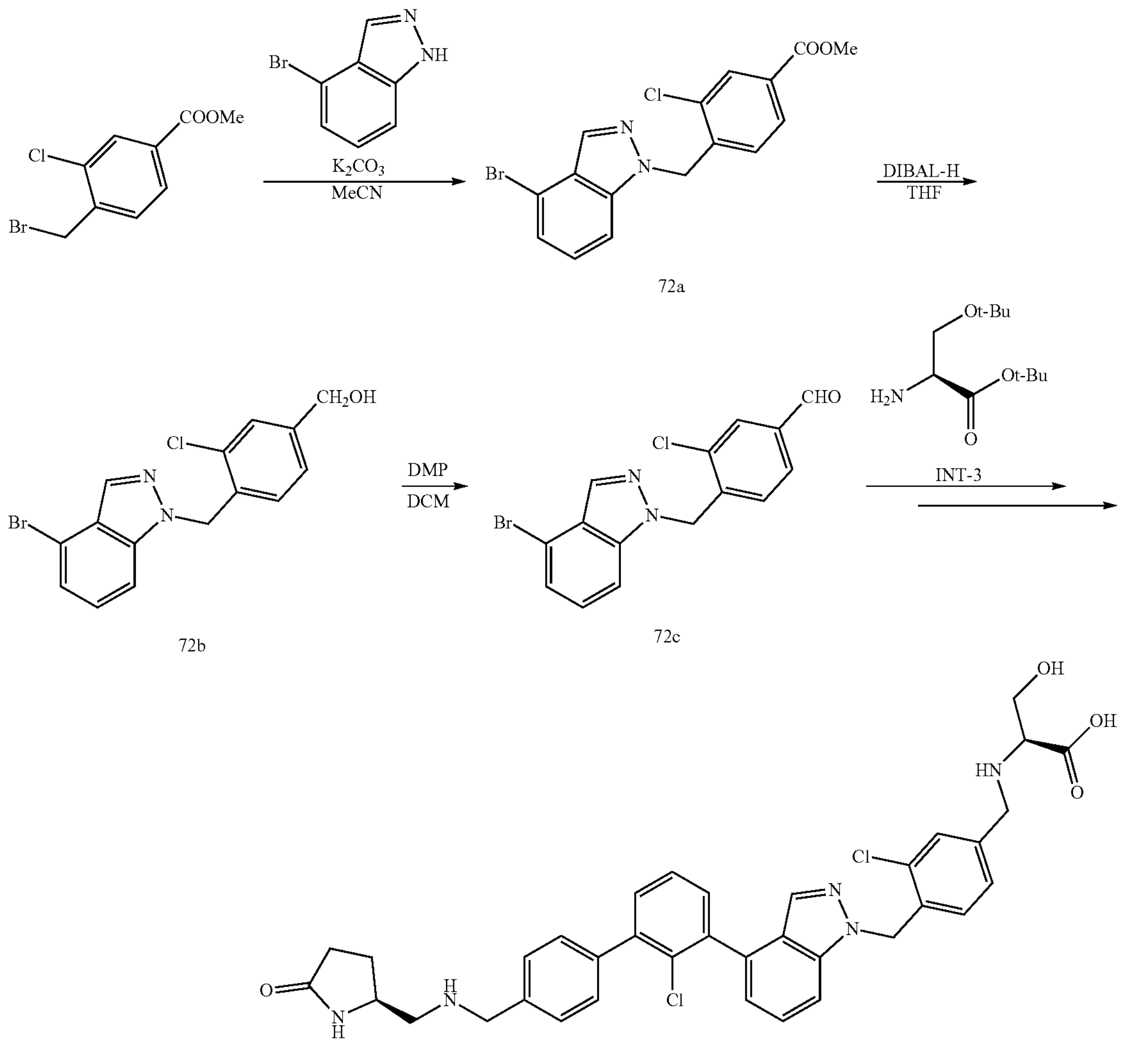

72a

72b

72c

72

In acetonitrile (6 mL) solution with methyl 4-(bromomethyl)-3-chlorobenzoate (200 mg, 0.76 mmol) and 4-bromoindazole (150 mg, 0.76 mmol) dissolved potassium carbonate (231 mg, 1.67 mmol) was added. The reaction solution was at 65° C. condition stirred for 10 hours. The reaction solution was cooled to room temperature. Then the filtrate was concentrated and the thus obtained residue was separated by silica gel column chromatography (petroleum ether/ethyl acetate, v/v=100/0-100/30) to obtain white solid 72a (150 mg, yield: 52.1%). MS (ESI): m/z 379.2 (M+H)$^+$.

At −65° C., in dichloromethane (10 mL) solution with compound 72a (150 mg, 0.40 mmol) dissolved diisobutylaluminum hydride (1.5 M toluene solution, 0.79 mL) was slowly added dropwise. The resulting reaction solution was stirred for half an hour at the same temperature. The reaction solution was then quenched with methanol (2 mL), raised to room temperature, and was rigorously stirred for 2 hours after adding Potassium Sodium Tartrate (10% w/w aqueous solution, 10 mL). In thus obtained mixture dichloromethane (20 mL) was added. Organic phase was further washed with saturated salt solution (30 mL), dried with anhydrous sodium sulfate. The filtrate was concentrated to obtain colorless oily matter 72b (130 mg, yield: 93.6%). MS (ESI): m/z 351.1 $(M+H)^+$.

In dichloromethane (6 mL) solution with compound 72b (130 mg, 0.37 mmol) dissolved Dess-Martin Oxidizer (157 mg, 0.37 mmol) was added. The reaction solution was stirred for 1 hour at 25° C. To the reaction solution saturated sodium bicarbonate solution (20 mL) and dichloromethane (20 mL) were added, thus obtained organic phase was further washed with saturated salt solution (30 mL), dried with anhydrous sodium sulfate. The filtrate was concentrated, and the residue was separated by silica gel column chromatography (petroleum ether/ethyl acetate, v/v=100/0-100/30) to obtain colorless oily matter 72c (120 mg, yield: 92.8%). MS (ESI): m/z 349.1 $(M+H)^+$.

Starting from compound 72c, O-isopropyl-L-serine tert-butyl ester and compound INT-3, referring to the synthesis of compound INT-1 and compound 1, compound 72 is obtained. $^1H$ NMR (500 MHz, DMSO-d6) δ 7.91 (s, 1H), 7.75 (d, J=8.5 Hz, 1H), 7.69 (s, 1H), 7.56 (d, J=1.5 Hz, 1H), 7.52-7.44 (m, 8H), 7.29-7.25 (m, 1H), 7.18 (d, J=7.0 Hz, 1H), 6.92 (d, J=8.0 Hz, 1H), 5.77 (s, 2H), 3.90 (d, J=14.0 Hz, 1H), 3.81-3.76 (m, 3H), 3.65-3.63 (m, 1H), 3.62-3.56 (m, 2H), 3.09 (t, J=5.5 Hz, 1H), 2.57-2.54 (m, 2H), 2.13-2.07 (m, 3H), 1.74-1.67 (m, 1H); MS (ESI): m/z 672.5 $(M+H)^+$.

Example 73

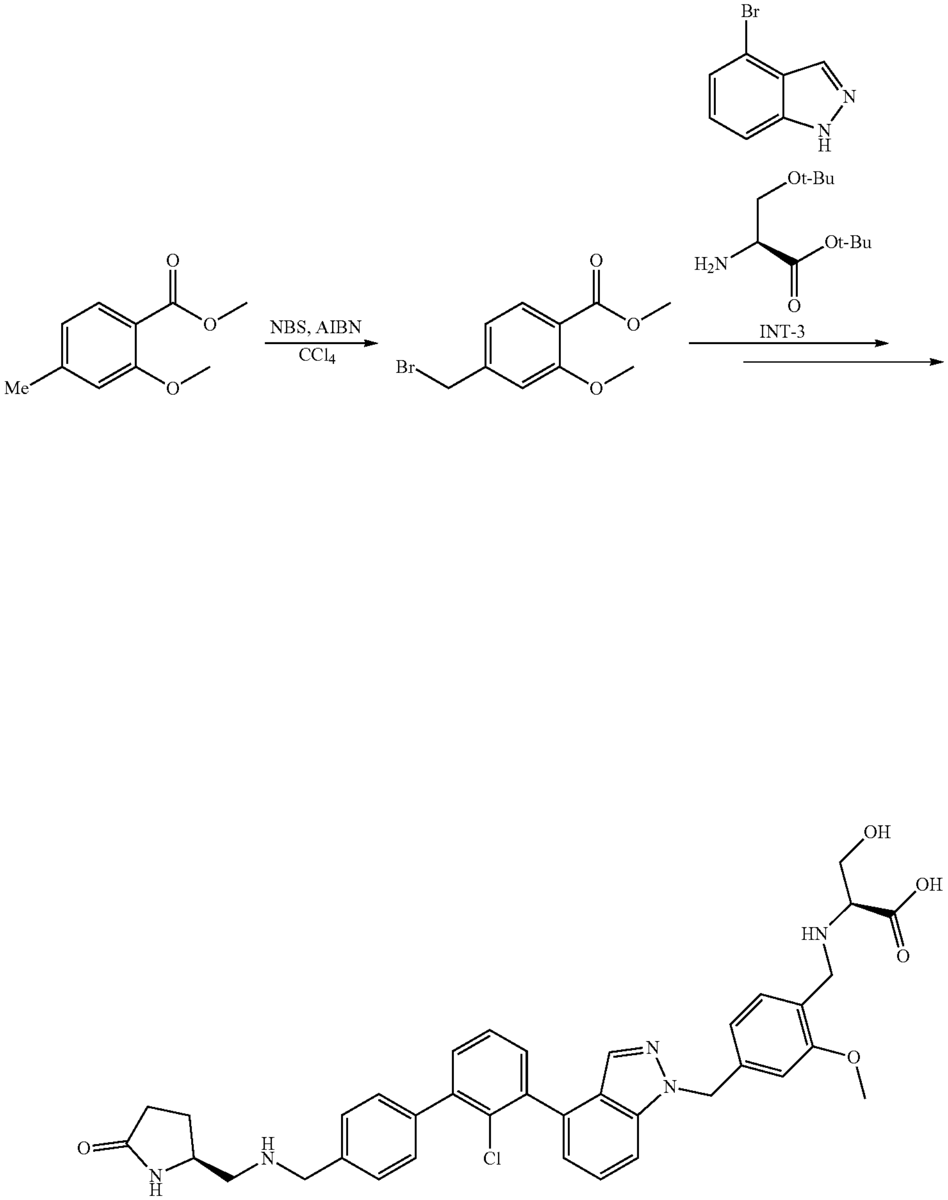

73

In tetrachloromethane (8 mL) solution with methyl 2-methoxy-4-methylbenzoate (250 mg, 1.39 mmol) and N-bromosuccinimide (296 mg, 1.66 mmol) dissolved azobis (isobutyronitrile) (9.4 mg, 0.17 mmol) was added. The reaction solution at 80° C. was stirred for 16 hours. The reaction solution was concentrated, and the residue was separated by silica gel column chromatography (petroleum ether/ethyl acetate, v/v=100/0-100/25) to obtain white solid 73a (204 mg, yield: 34.0%).

Starting from compound 73a, 4-bromoindazole, O-isopropyl-L-serine tert-butyl ester and compound INT-3, referring to the synthesis of compound INT-1 and compound 1, compound 73 is obtained. $^1$H NMR (500 MHz, DMSO-d6) δ 8.18-8.16 (m, 2H), 7.87 (s, 1H), 7.77 (d, J=8.6 Hz, 1H), 7.66 (s, 1H), 7.52-7.49 (m, 1H), 7.48-7.25 (m, 5H), 7.13 (d, J=7.0 Hz, 1H), 7.04 (s, 1H), 6.77 (d, J=7.6 Hz, 1H), 5.68 (s, 2H), 3.96-3.92 (m, 1H), 3.78 (d, J=7.1 Hz, 2H), 3.75 (s, 3H), 3.69-3.61 (m, 2H), 3.60-3.51 (m, 2H), 3.14-3.08 (m, 1H), 2.56 (d, J=6.4 Hz, 2H), 2.12-2.06 (m, 3H), 1.73-1.65 (m, 1H); MS (ESI): m/z 668.7 $(M+H)^+$.

Example 74

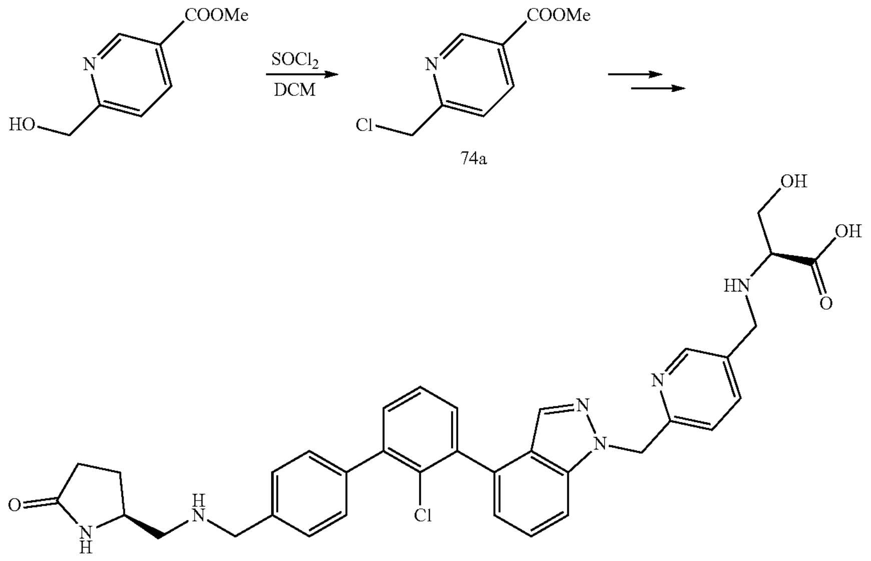

74a

74

In dichloromethane (10 mL) solution with 6-hydroxymethyl methyl nicotinate (470 mg, 2.81 mmol) dissolved thionyl chloride (1.67 g, 14.1 mmol) was added. The reaction solution was stirred for 3 hours at 25° C. The reaction solution was concentrated, and the residue was separated by silica gel column chromatography (ethyl acetate/petroleum ether=0/100-40/100) to obtain white solid 74a (420 mg, yield: 80.5%). MS (ESI): m/z 186.0 $(M+H)^+$.

Starting from compound 74a, referring to the synthesis of compound 73, compound 74 is obtained. $^1$H NMR (500 MHz, DMSO-d6) δ 8.49 (d, J=2.0 Hz, 1H), 8.18 (s, 1H), 7.87 (s, 1H), 7.77-7.69 (m, 2H), 7.67 (s, 1H), 7.51 (d, J=7.5 Hz, 1H), 7.48-7.44 (m, 6H), 7.15 (d, J=7.0 Hz, 1H), 7.05 (d, J=8.0 Hz, 1H), 5.77 (s, 2H), 3.91 (d, J=13.5 Hz, 1H), 3.82-3.73 (m, 3H), 3.66-3.60 (m, 1H), 3.60-3.53 (m, 2H), 3.09 (t, J=5.5 Hz, 1H), 2.55 (d, J=6.0 Hz, 2H), 2.16-2.03 (m, 3H), 1.78-1.61 (m, 1H); MS (ESI): m/z 639.5 $(M+H)^+$.

Example 75

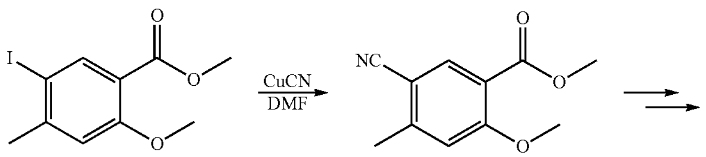

INT-13

75a

-continued

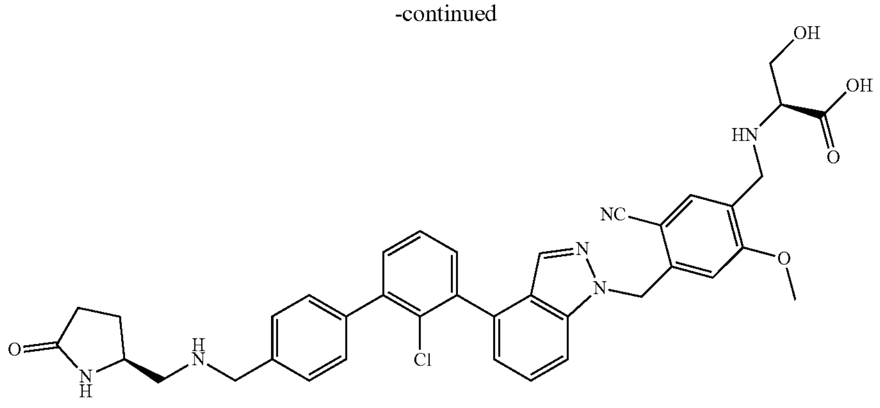

75

In N, N-dimethylformamide (5 mL) solution with compound INT-13 (550 mg, 1.80 mmol) dissolved cuprous cyanide (322 mg, 3.59 mmol) was added. The reaction solution was stirred for 16 hours at 120° C. and nitrogen atmosphere. The reaction solution was filtered, the filtrate was concentrated, and the residue was separated by silica gel column chromatography (petroleum ether/ethyl acetate, v/v=100/0-100/30) to obtain white solid 75a (210 mg, yield: 57.0%).

Starting from compound 75a, referring to the synthesis of compound 73, compound is obtained 75. $^1$H NMR (500 MHz, DMSO-d6) δ 7.91 (s, 1H), 7.84-7.82 (m, 2H), 7.67 (s, 1H), 7.54-7.50 (m, 2H), 7.50-7.42 (m, 6H), 7.18 (d, J=6.9 Hz, 1H), 6.92 (s, 1H), 5.82 (s, 2H), 3.85 (d, J=14.9 Hz, 1H), 3.80-3.73 (m, 3H), 3.71 (s, 3H), 3.64-3.60 (m, 2H), 3.60-3.54 (m, 1H), 3.15-3.11 (m, 1H), 2.55-2.54 (m, 2H), 2.13-2.06 (m, 3H), 1.71-1.67 (m, 1H); MS (ESI): m/z 693.2 $(M+H)^+$.

Example 76

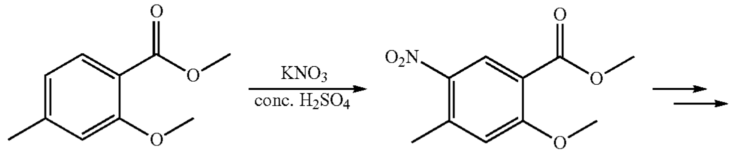

INT-13b 76a

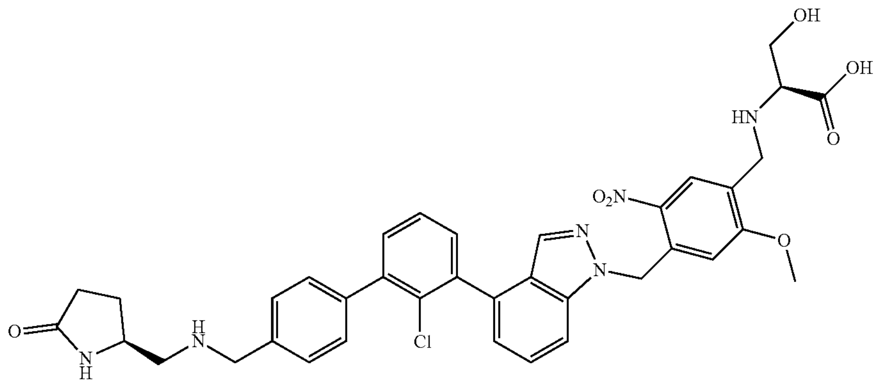

76

Under ice bath conditions, in concentrated sulfuric acid (2 mL) with compound INT-13b (100 mg, 0.55 mmol) dissolved concentrated sulfuric acid (0.5 mL) solution with potassium nitrate (56.1 mg, 0.55 mmol) predissolved was added dropwise. The reaction solution under the same conditions was then stirred for half an hour. In the reaction solution ice water was added, thus precipitated solid was washed with ice water, and dried to obtain white solid 76a (115 mg, yield: 92.0%). $^1$H NMR (500 MHz, DMSO-d6) δ 8.39 (s, 1H), 7.29 (s, 1H), 3.95 (s, 3H), 3.82 (s, 3H), 2.64 (s, 3H).

Starting from compound 76a, referring to the synthesis of compound 73, compound 76 is obtained. $^1$H NMR (500 MHz, DMSO-d6) δ 8.29 (s, 1H), 7.96 (s, 1H), 7.79 (d, J=8.5 Hz, 1H), 7.67 (s, 1H), 7.53 (d, J=7.5 Hz, 1H), 7.51-7.49 (m, 3H), 7.47-7.43 (m, 4H), 7.19 (d, J=7.0 Hz, 1H), 6.13 (s, 1H), 6.11 (s, 1H), 3.87 (d, J=15.4 Hz, 1H), 3.81-3.72 (m, 3H), 3.67-3.57 (m, 3H), 3.51 (s, 3H), 3.15-3.12 (m, 1H), 2.56-2.52 (m, 2H), 2.14-2.08 (m, 3H), 1.72-1.66 (m, 1H); MS (ESI): m/z 713.8 $(M+H)^+$.

Example 77

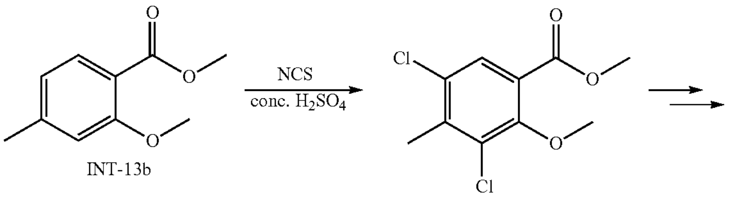

INT-13b

77a

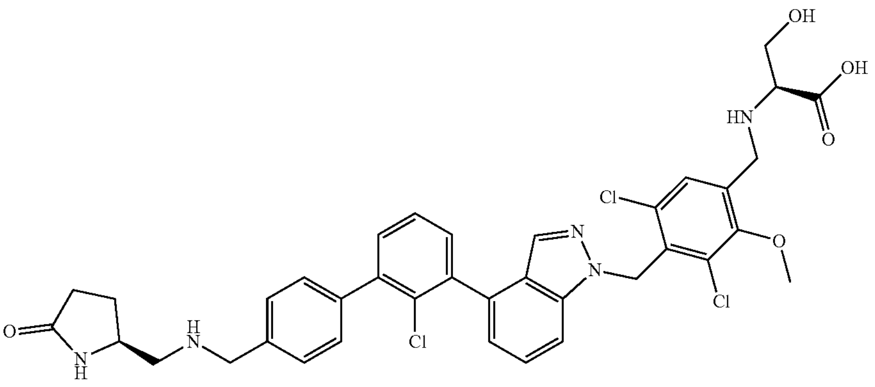

77

In concentrated sulfuric acid (3 mL) with compound INT-13b (300 mg, 1.66 mmol) dissolved N-chlorosuccinimide (467 mg, 3.50 mmol) was added. The reaction solution at 25° C. was stirred for 2 hours. In the reaction solution ice water (25 mL) and ethyl acetate (25 mL) were added. Organic phase was further washed with saturated sodium bicarbonate solution (30 mL) and saturated salt solution (30 mL), and dried by anhydrous sodium sulfate. The filtrate was concentrated to obtain a yellow solid 77a (360 mg, yield: 86.8%). $^1H$ NMR (500 MHz, DMSO-d6) δ 7.74 (s, 1H), 3.84 (s, 3H), 3.80 (s, 3H), 2.45 (s, 3H); MS (ESI): m/z 249.7 $(M+H)^+$.

Starting from compound 77a, referring to the synthesis of compound 73, compound 77 is obtained. $^1H$ NMR (500 MHz, DMSO-d6) δ 7.86 (d, J=8.5 Hz, 1H), 7.80 (s, 1H), 7.67 (s, 1H), 7.65 (s, 1H), 7.56-7.50 (m, 2H), 7.48-7.43 (m, 6H), 7.17 (d, J=7.0 Hz, 1H), 5.81 (s, 2H), 3.95 (d, J=14.5 Hz, 1H), 3.82-3.79 (m, 3H), 3.77 (s, 3H), 3.66-3.59 (m, 3H), 3.20 (t, J=5.1 Hz, 1H), 2.57-2.58 (m, 2H), 2.13-2.07 (m, 3H), 1.74-1.66 (m, 1H); MS (ESI): m/z 736.7 $(M+H)^+$.

Example 78

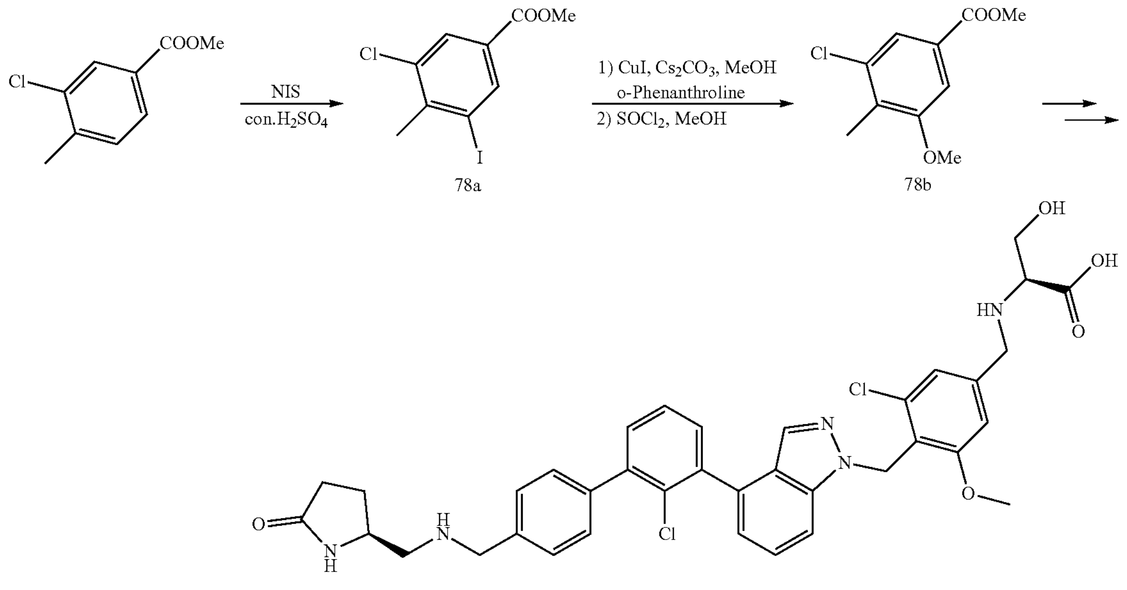

78a 78b

78

Under ice bath conditions, in concentrated sulfuric acid (2 mL) with methyl 3-chloro-4-methylbenzoate (500 mg, 2.71 mmol) dissolved N-iodo succinimide (731 mg, 3.25 mmol) was added. The reaction solution was stirred for 2 hours at 25° C. Adding ice water (50 mL) and ethyl acetate (50 mL) to the reaction solution. The organic phase was further washed with saturated sodium bicarbonate solution (50 mL) and saturated salt solution (50 mL), and dried with anhydrous sodium sulfate. The filtrate was concentrated, and the residue was separated by silica gel column chromatography (petroleum ether/ethyl acetate=100/0-100/15) to obtain a white solid 78a (820 mg, yield: 97.5%).

Under nitrogen atmosphere and 100° C., in methanol (5 mL) solution with compound 78a (1.00 g, 3.22 mmol), cuprous iodide (61.3 mg, 0.32 mmol), 1,10-phenanthroline (116 mg, 0.64 mmol) and cesium carbonate (2.10 g, 6.44 mmol) mixed was stirred for 24 hours. The reaction solution was filtered, and the filtrate was concentrated. The residue was dissolved with methanol (5 mL), and the thionyl chloride (1.4 mL) was added. Thus obtained reaction solution was stirred for 2 hours at 60° C. To the reaction solution ethyl acetate (50 mL) and water (50 mL) were added. The organic phase was further washed with saturated sodium bicarbonate solution (50 mL) and saturated salt solution (50 mL), dried with anhydrous sodium sulfate. The residue was silica gel column chromatography (petroleum ether/ethyl acetate, v/v=100/0-100/5) separated by to obtain a white solid 78b (480 mg, yield: 69.4%). $^1H$ NMR (500 MHz, Chloroform-d) δ 7.67 (d, J=1.6 Hz, 1H), 7.39 (d, J=1.6 Hz, 1H), 3.91 (s, 3H), 3.88 (s, 3H), 2.31 (s, 3H).

Starting from compound 78b, referring to the synthesis of compound 73, compound is obtained 78. $^1H$ NMR (500 MHz, DMSO-d6) δ 8.22 (s, 1H), 7.77 (d, J=8.5 Hz, 1H), 7.74 (s, 1H), 7.66 (s, 1H), 7.52-7.48 (m, 2H), 7.46-7.43 (m, 5H), 7.14-7.11 (m, 3H), 5.67 (s, 2H), 3.94 (d, J=14.2 Hz, 1H), 3.81-3.78 (m, 2H), 3.77 (s, 3H), 3.65-3.61 (m, 4H), 3.15-3.09 (m, 1H), 2.57-2.55 (d, J=6.0 Hz, 2H), 2.13-2.07 (m, 3H), 1.73-1.66 (m, 1H); MS (ESI): m/z 702.7 $(M+H)^+$.

Example 79
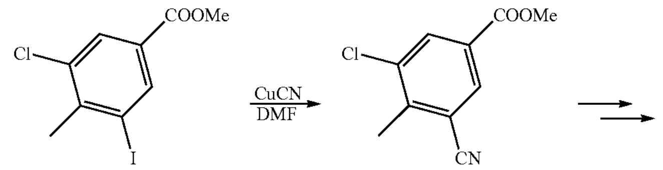
78a 79a
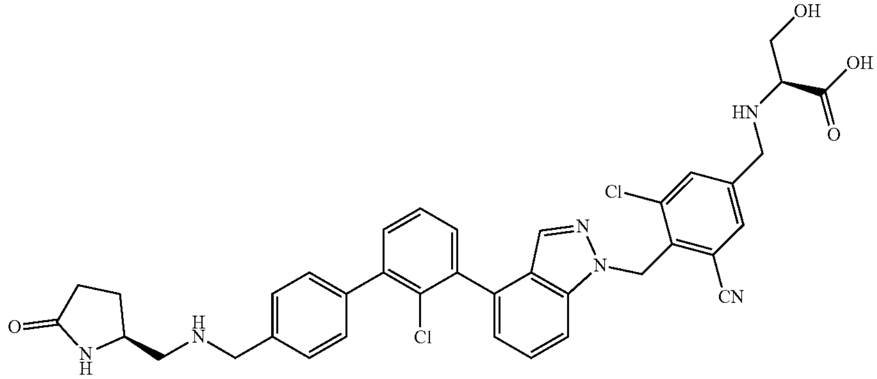
79
Starting from compound 78a, referring to the synthesis of compound 75a, compound 79a is obtained.
Starting from compound 79a, referring to the synthesis of compound 73, compound 79 is obtained. $^{1}H$ NMR (500 MHz, DMSO-d6) δ 8.20 (s, 1H), 7.93 (d, J=1.6 Hz, 1H), 7.90-7.85 (m, 2H), 7.83 (s, 1H), 7.67 (s, 1H), 7.58-7.54 (m, 1H), 7.51 (d, J=7.4 Hz, 1H), 7.48-7.42 (m, 5H), 7.18 (d, J=7.1 Hz, 1H), 5.82 (s, 2H), 3.95 (d, J=14.8 Hz, 1H), 3.81-3.74 (m, 3H), 3.65-3.62 (m, 1H), 3.61-3.56 (m, 2H), 3.12 (t, J=5.3 Hz, 1H), 2.56 (d, J=6.1 Hz, 2H), 2.13-2.07 (m, 3H), 1.72-1.66 (m, 1H); MS (ESI): m/z 697.5 $(M+H)^+$.
Example 80
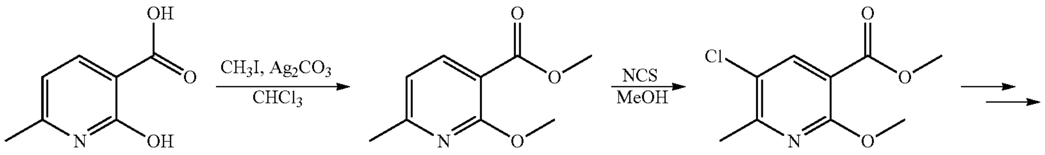
80a 80b
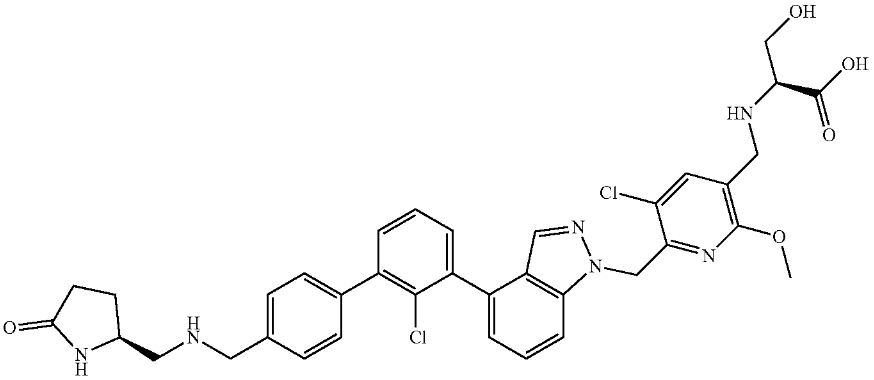
80

In chloroform (35 mL) solution with 2-hydroxy-6-methylnicotinic acid (1.00 g, 6.53 mmol) dissolved iodomethane (3.24 g, 22.9 mmol) and silver carbonate (1.81 g, 6.55 mmol) were added. The reaction solution at 65° C. was stirred for 16 hours. The reaction solution was filtered, and the filtrate was concentrated to obtain colorless oily matter 80a (390 mg, yield: 33.0%). $^1$H NMR (500 MHz, Chloroform-d) δ 8.06 (d, J=7.7 Hz, 1H), 6.77 (d, J=7.7 Hz, 1H), 4.03 (s, 3H), 3.87 (s, 3H), 2.48 (s, 3H); MS (ESI): m/z 182.0 $(M+H)^+$.

In acetonitrile (10 mL) solution with compound 80a (363 mg, 2.00 mmol) dissolved N-chlorosuccinimide (321 mg, 2.40 mmol) was added. The reaction solution at 70° C. condition was stirred for 10 hours. The reaction solution was concentrated, the residue was separated by silica gel column chromatography (petroleum ether/ethyl acetate, v/v=100/0-100/20) to obtain colorless oily matter 80b (420 mg, yield: 97.2%). $^1$H NMR (500 MHz, DMSO-d6) δ 8.09 (s, 1H), 3.91 (s, 3H), 3.80 (s, 3H), 2.51 (s, 3H).

Starting from compound 80b, referring to the synthesis of compound 73, compound 80 is obtained. $^1$H NMR (500 MHz, DMSO-d6) δ 7.86 (s, 1H), 7.84 (s, 1H), 7.79 (d, J=8.4 Hz, 1H), 7.67 (s, 1H), 7.53-7.51 (m, 1H), 7.48-7.44 (m, 7H), 7.14 (d, J=7.0 Hz, 1H), 5.82 (s, 2H), 3.79-3.76 (m, 2H), 3.66-3.55 (m, 5H), 3.38 (s, 3H), 3.13-3.08 (m, 1H), 2.58-2.54 (m, 2H), 2.13-2.08 (m, 3H), 1.73-1.67 (m, 1H); MS (ESI): m/z 703.2 $(M+H)^+$.

Example 81

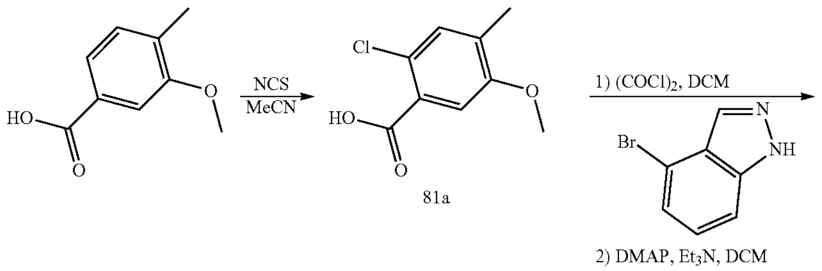

81a

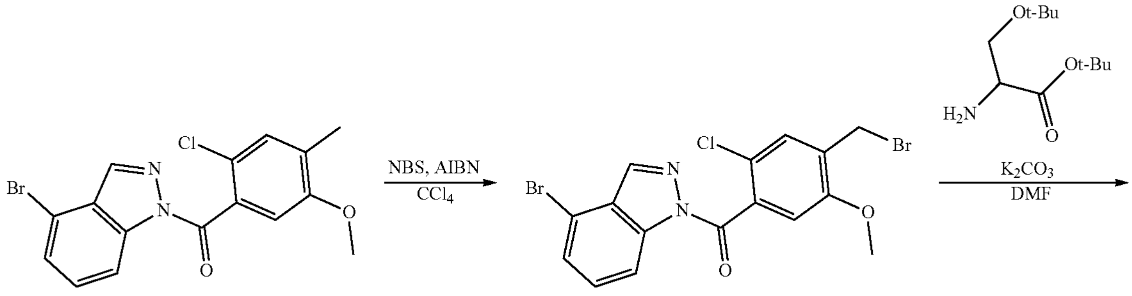

81b

81c

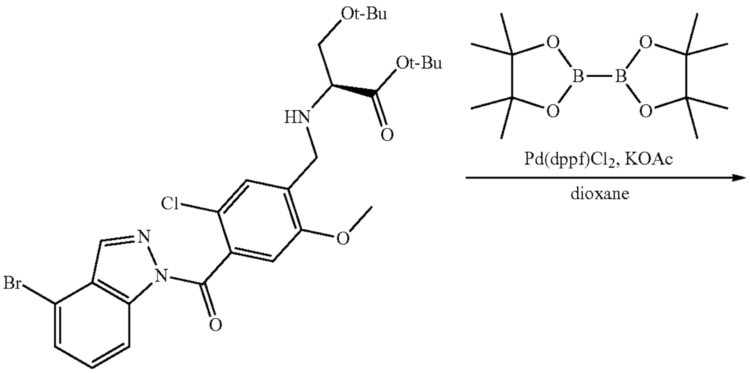

81d

-continued

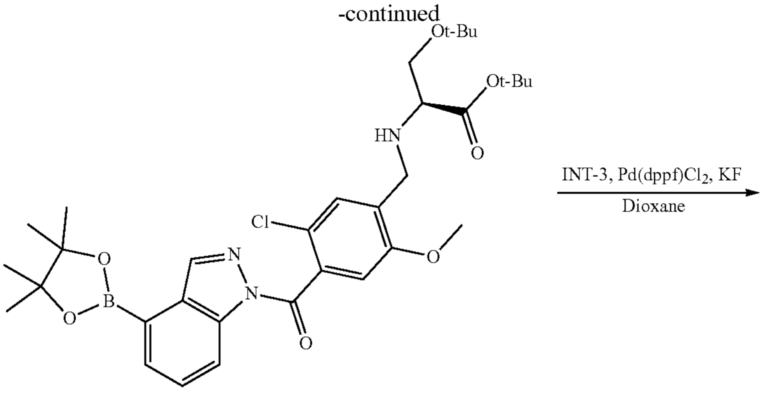

81e

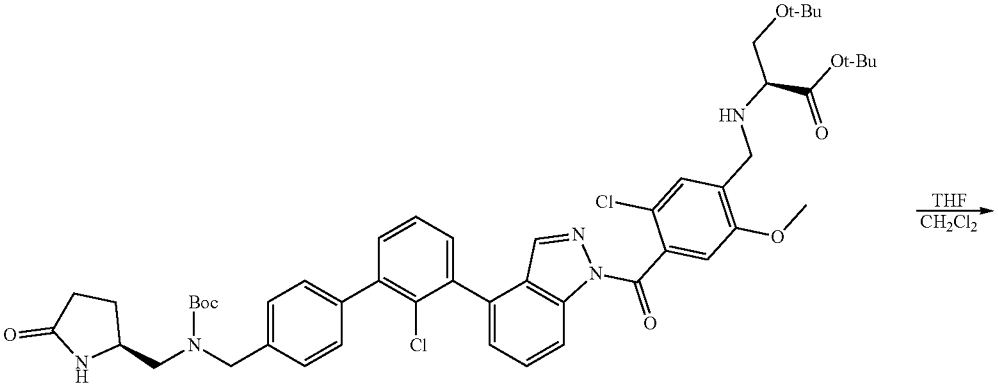

81f

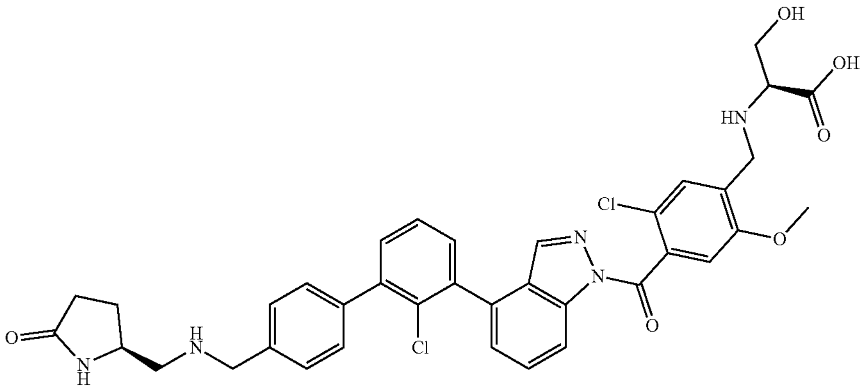

81

Starting from 3-methoxy-4-methylbenzoic acid, referring to the synthesis of compound 80b, compound 81a is obtained. $^1$H NMR (500 MHz, DMSO-d6) δ 13.25 (s, 1H), 7.32 (s, 1H), 7.30 (s, 1H), 3.82 (s, 3H), 2.17 (s, 3H).

In dichloromethane (8 mL) solution with compound 81a (300 mg, 1.50 mmol) dissolved oxalyl chloride (345 mg, 2.72 mmol) and 1 drop N, N-dimethylformamide were added. The reaction solution at 25° C. condition was stirred for 3 hours, subsequently the reaction solution was concentrated. Thus obtained residue was redissolved with dichloromethane (3 mL), then the solution was added to dichloromethane (8 mL) solution with 4-bromoindazole (265 mg, 1.35 mmol), 4-dimethylaminopyridine (18.3 mg, 0.15 mmol) and triethylamine (302 mg, 2.99 mmol) dissolved. The reaction solution was stirred for 16 hours at 25° C. The reaction solution was concentrated, and the residue was separated by silica gel column chromatography (petroleum ether/ethyl acetate, v/v=100/0-100/20) to obtain a white solid 81b (410 mg, yield: 72.2%).

Starting from compound 81b, referring to the synthesis of compound 73a, compound 81c is obtained.

In N'N-dimethylformamide (2 mL) with compound 81c (120 mg, 0.26 mmol) and O-isopropyl-L-serine tert-butyl ester (171 mg, 0.78 mmol) dissolved potassium carbonate (72 mg, 0.52 mmol) was added. The reaction solution was stirred for 1 hour at 25° C. Adding ethyl acetate (20 mL) and water (20 mL) to the reaction solution. Organic phase was further washed with saturated salt solution (20 mL), dried with anhydrous sodium sulfate. The residue was separated by silica gel thin layer chromatography plate (petroleum ether/ethyl acetate, v/v=4/1) to obtain a white solid 81d (70 mg, yield: 45.0%). MS (ESI): m/z 594.4 (M+H)$^+$.

Starting from compound 81d, referring to boron esterification step in the synthesis process of INT-1, compound 81e is obtained. MS (ESI): m/z 642.8 $(M+H)^+$.

At 90° C. and nitrogen atmosphere, 1.4-dioxane (4 mL) solution with compound 81e (35 mg, 0.038 mmol), compound INT-3 (18.9 mg, 0.038 mmol), $Pd(dppf)Cl_2$ (2.8 mg, 0.0038 mmol) and potassium fluoride (6.7 mg, 0.11 mmol) mixed was stirred for 16 hours. The reaction solution was concentrated, and the residue was separated by silica gel thin layer chromatography plate (dichloromethane/methanol, v/v=20/1) to obtain colorless oily matter 81f (20 mg, yield: 36.7%). MS (ESI): m/z 928.2 $(M+H)^+$.

Starting from compound 81f, referring to last step Boc deprotecting group step in the synthesis of compound 1, compound 81 is obtained. $^1$H NMR (500 MHz, DMSO-d6) δ 8.49 (d, J=8.0 Hz, 1H), 8.27 (s, 1H), 7.82 (t, J=8.0 Hz, 1H), 7.65 (s, 1H), 7.57 (s, 1H), 7.55-7.53 (m, 1H), 7.52-7.49 (m, 3H), 7.47-7.40 (m, 5H), 3.79 (s, 3H), 3.76-3.74 (m, 2H), 3.62-3.59 (m, 3H), 3.50-3.48 (m, 2H), 3.12-3.11 (m, 1H), 2.53-2.52 (m, 2H), 2.10-2.06 (m, 3H), 1.69-1.65 (m, 1H); MS (ESI): m/z 716.0 $(M+H)^+$.

Example 82

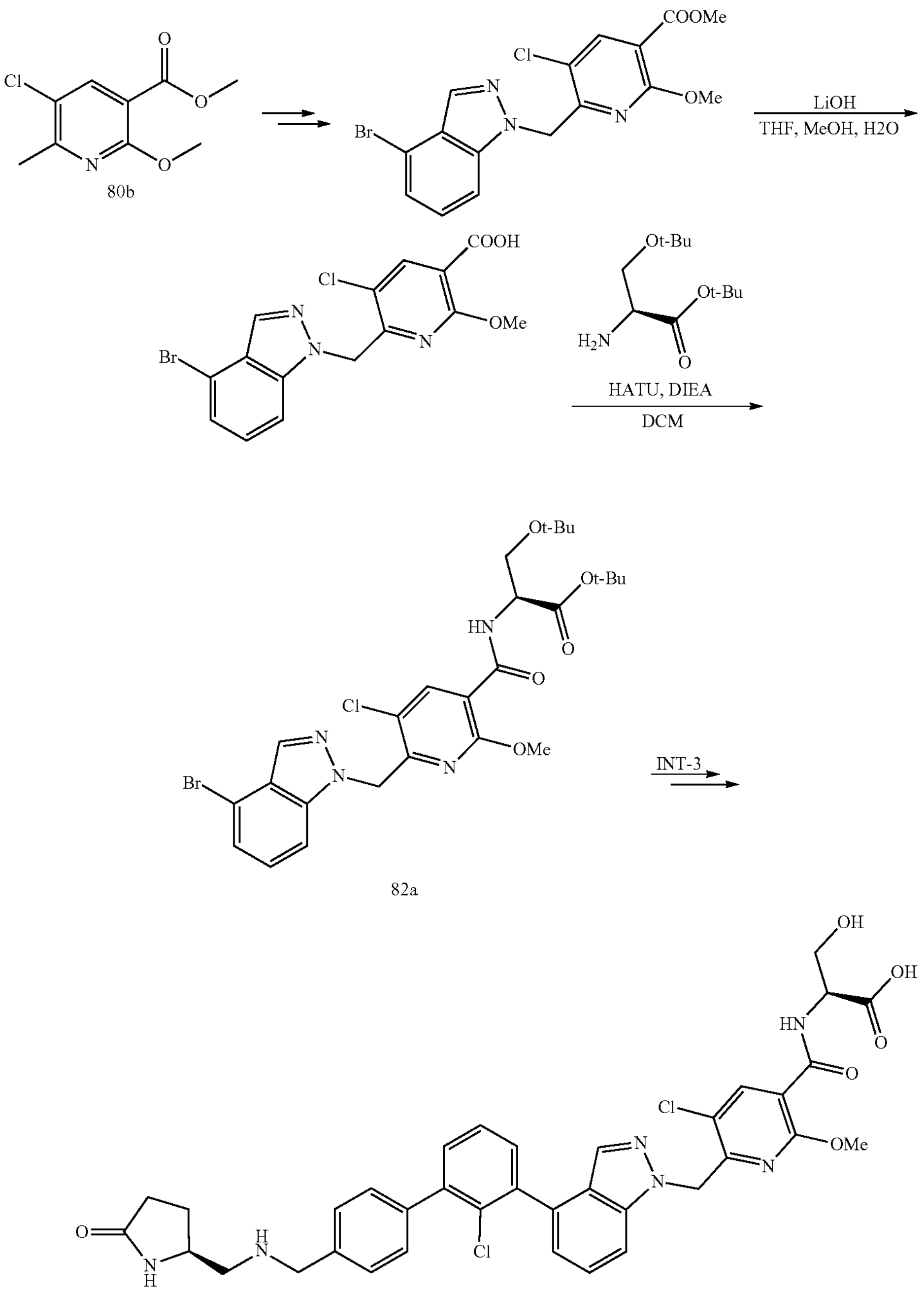

80b

82a

82

Starting from compound 80b, sequentially referring to bromination step of compound 73a, substitution step of compound 72a and ester hydrolysis and acid-amine condensation step in the synthesis process of compound INT-11d, compound 82a is obtained. MS (ESI): m/z 595.4 $(M+H)^+$.

Starting from compound 82a and compound INT-3, referring to last two steps in the synthesis process of compound 81, compound 82 is obtained. $^1$H NMR (500 MHz, DMSO-d6) δ 8.51 (d, J=7.0 Hz, 1H), 8.23 (s, 1H), 7.88 (s, 1H), 7.76 (d, J=8.5 Hz, 1H), 7.68 (s, 1H), 7.55-7.45 (m, 7H), 7.15 (d, J=7.0 Hz, 1H), 5.93 (s, 2H), 4.28-4.26 (m, 1H), 3.85-3.75 (m, 3H), 3.67-3.60 (m, 2H), 3.39 (s, 3H), 2.59 (d, J=6.2 Hz, 2H), 2.14-2.07 (m, 3H), 1.72-1.69 (m, 1H); MS (ESI): m/z 717.2 $(M+H)^+$.

Example 83

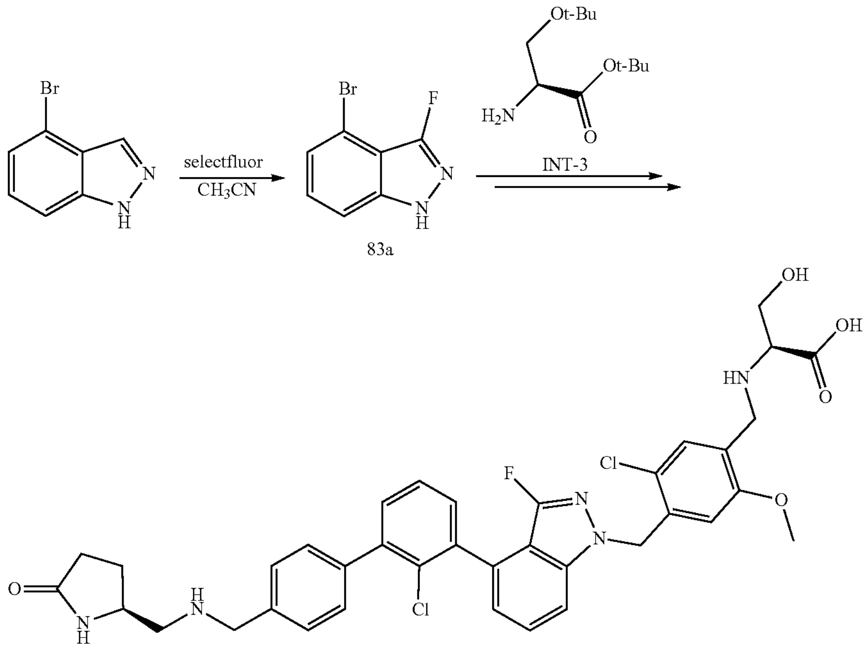

83a

83

At 80° C., acetonitrile (20 mL) solution with 4-bromoindazole (500 mg, 2.54 mmol) and 1-Fluoro-4-methyl-1,4-diazabicyclo[2.2.2]octane tetrafluoroborate (4.49 g, 12.7 mmol) dissolved was stirred for 15 hours. In the reaction solution, ethyl acetate (100 mL) was added, subsequently the solution was washed with water (100 mL) and saturated salt solution (100 mL) and dried with anhydrous sodium sulfate. The residue was separated by silica gel column chromatography to obtain a white solid 83a (231 mg, yield: 42.3%). MS (ESI): m/z 215.1 $(M+H)^+$.

Starting from compound 83a, O-isopropyl-L-serine tert-butyl ester and compound INT-3, referring to the synthesis of compound INT-8 and compound 1, compound 83 is obtained. $^1$H NMR (500 MHz, DMSO-d6) δ 7.84-7.79 (m, 1H), 7.66 (s, 1H), 7.62-7.58 (m, 1H), 7.52-7.43 (m, 8H), 7.17 (d, J=7.0 Hz, 1H), 6.84 (s, 1H), 5.62 (s, 2H), 3.91-3.79 (m, 4H), 3.67 (s, 3H), 3.65-3.56 (m, 3H), 3.17-3.15 (m, 1H), 2.60-2.55 (m, 2H), 2.14-2.09 (m, 3H), 1.73-1.67 (m, 1H); MS (ESI): m/z 720.6 $(M+H)^+$.

Example 84

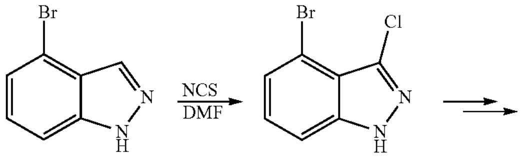

84a

-continued

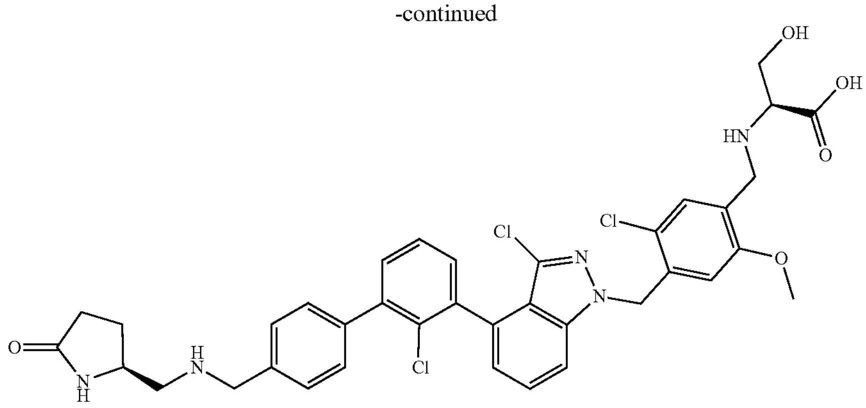

84

At 25° C., N'N-dimethylformamide (3 mL) solution with 4-bromoindazole (200 mg, 1.02 mmol), N-chlorosuccinimide (149 mg, 1.12 mmol) dissolved was stirred for 15 hours. In the reaction solution ethyl acetate (50 mL) was added, subsequently the solution was washed with water (50 mL) and dried with saturated salt solution (50 mL), anhydrous sodium sulfat. The residue was separated by silica gel column chromatography to obtain a white solid 84a (122 mg, yield: 51.9%). MS (ESI): m/z 231.3 $(M+H)^+$.

Starting from compound 84a, referring to the synthesis of compound 83, compound 84 is obtained. $^1H$ NMR (500 MHz, DMSO-d6) δ 7.85 (d, J=8.5 Hz, 1H), 7.65 (s, 1H), 7.59-7.55 (m, 1H), 7.50-7.47 (m, 2H), 7.45-7.39 (m, 6H), 7.11 (d, J=7.0 Hz, 1H), 6.84 (d, J=1.5 Hz, 1H), 5.75-5.68 (m, 1H), 5.70 (s, 1H), 3.89-3.86 (m, 1H), 3.79-3.75 (m, 3H), 3.65 (s, 3H), 3.62-3.59 (m, 3H), 3.14-3.12 (m, 1H), 2.54 (d, J=6.0 Hz, 2H), 2.11-2.06 (m, 3H), 1.70-1.65 (m, 1H); MS (ESI): m/z 736.5 $(M+H)^+$.

Example 85

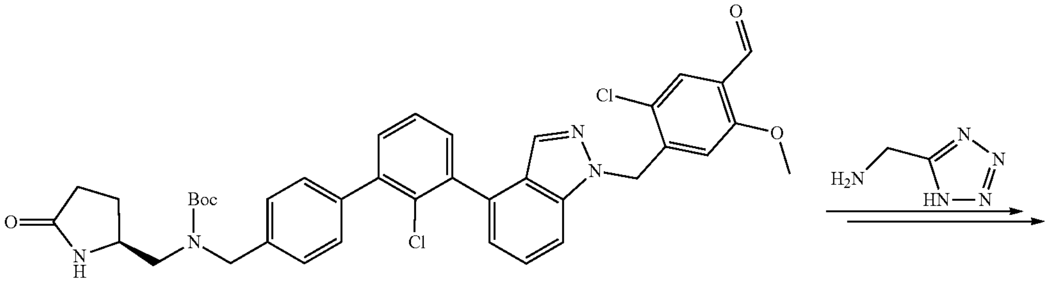

INT-8

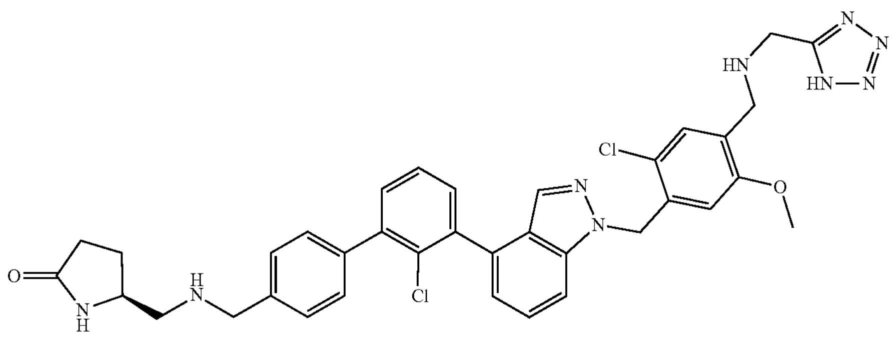

85

Starting from compound INT-8 and 5-aminoethyltetrazolium, referring to the synthesis of compound 22, compound 85 is obtained. $^1$H NMR (500 MHz, DMSO-d6) δ 7.86 (s, 1H), 7.74 (d, J=8.5 Hz, 1H), 7.55-7.38 (m, 9H), 7.14 (d, J=7.0 Hz, 1H), 6.71 (s, 1H), 5.72 (s, 2H), 3.95-3.91 (m, 2H), 3.79-3.71 (m, 4H), 3.65-3.62 (m, 1H), 3.57 (s, 3H), 2.55 (d, J=6.0 Hz, 2H), 2.15-2.04 (m, 3H), 1.72-1.61 (m, 1H); MS (ESI): m/z 696.1 $(M+H)^+$.

Example 86

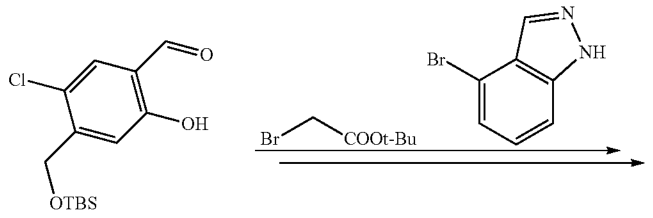

INT-1c

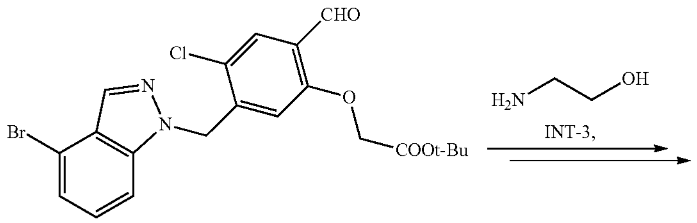

86a

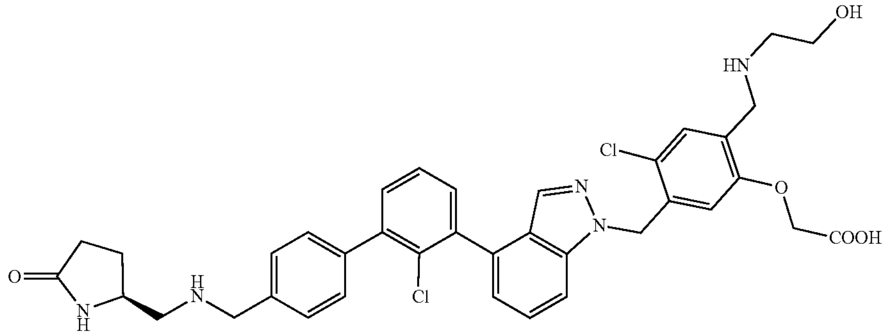

86

Starting from compound INT-1c, tert-butyl bromoacetate, 4-bromoindazole, referring to the synthesis of compound INT-1i, compound 86a is obtained. MS (ESI): m/z 479.4 $(M+H)^+$.

Starting from compound 86a, compound INT-3 and ethanolamine, referring to the synthesis of compound INT-7 and compound 22, compound 86 is obtained. $^1$H NMR (500 MHz, DMSO-d6) δ 7.88 (s, 1H), 7.77 (d, J=8.5 Hz, 1H), 7.67 (s, 1H), 7.53-7.41 (m, 9H), 7.15 (d, J=6.9 Hz, 1H), 6.94 (s, 1H), 5.70 (s, 2H), 4.26 (s, 2H), 4.01 (s, 2H), 3.81-3.72 (m, 2H), 3.67-3.58 (m, 3H), 2.86 (t, J=5.4 Hz, 2H), 2.57-2.50 (m, 2H), 2.13-2.04 (m, 3H), 1.72-1.64 (m, 1H); MS (ESI): m/z 702.4 $(M+H)^+$.

Example 87

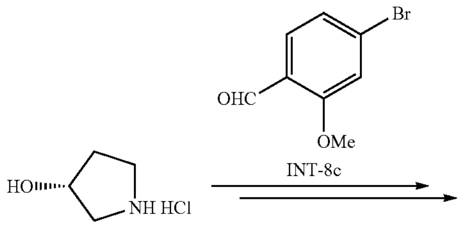

-continued

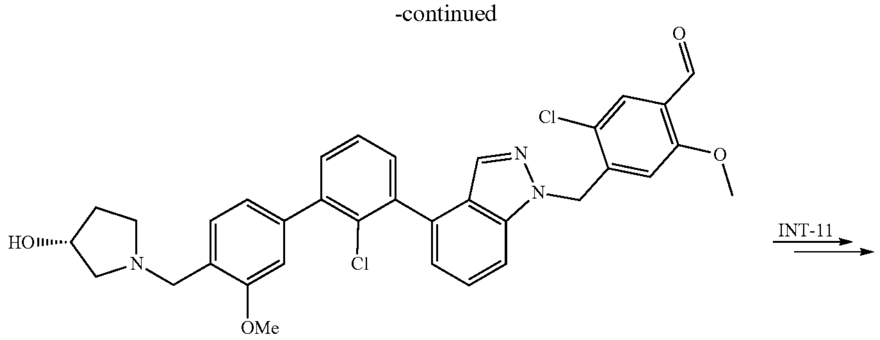

87a

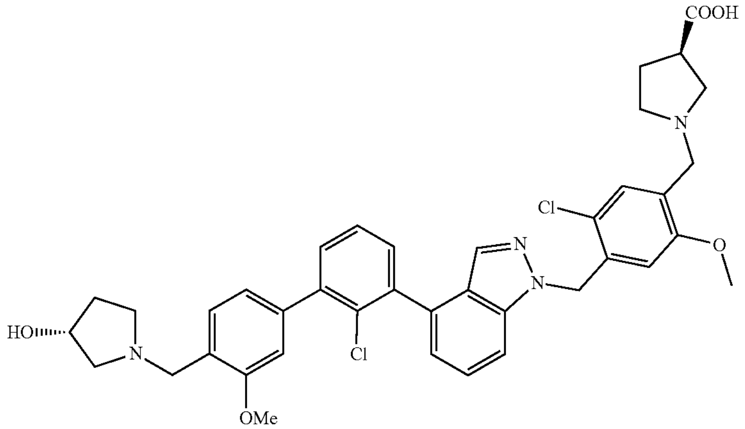

87

Starting from (R)-3-hydroxypyrrolidine hydrochloride, 4-bromo-2-Methoxybenzaldehyde and compound INT-8c, referring to the synthesis of compound INT-5 and compound INT-8, compound 87a is obtained. MS (ESI): m/z 616.4 $(M+H)^+$.

Starting from compound 87a and compound INT-11, referring to the synthesis of compound 33, compound 87 is obtained. $^1$H NMR (500 MHz, DMSO-d6) δ 7.91 (s, 1H), 7.77 (d, J=8.5 Hz, 1H), 7.55-7.47 (m, 4H), 7.39 (d, J=7.5 Hz, 1H), 7.36 (s, 1H), 7.17 (d, J=7.0 Hz, 1H), 7.08 (s, 1H), 7.06 (d, J=7.5 Hz, 1H), 6.68 (s, 1H), 5.73 (s, 2H), 4.23-4.17 (m, 1H), 3.82 (s, 3H), 3.64-3.56 (m, 5H), 3.55-3.47 (m, 2H), 2.88-2.82 (m, 1H), 2.75-2.69 (m, 1H), 2.67-2.61 (m, 3H), 2.47-2.43 (m, 2H), 2.41-2.36 (m, 2H), 2.05-1.97 (m, 1H), 1.95-1.89 (m, 2H), 1.58-1.52 (m, 1H); MS (ESI): m/z 715.7 $(M+H)^+$.

Example 88

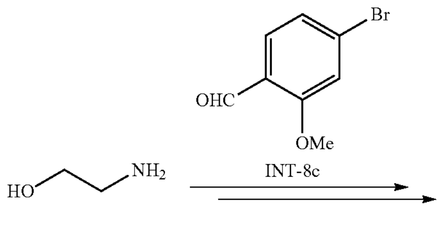

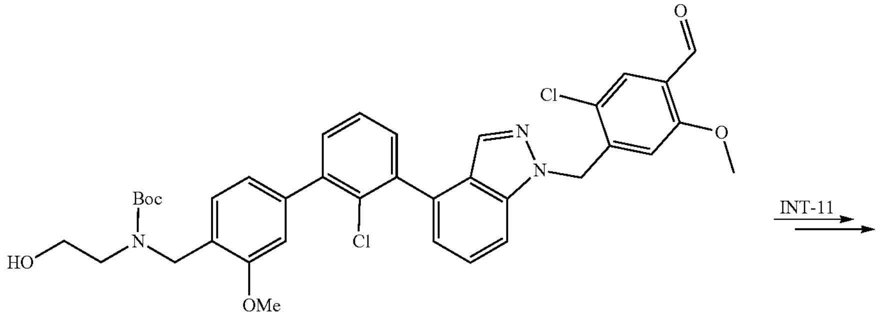

88a

-continued

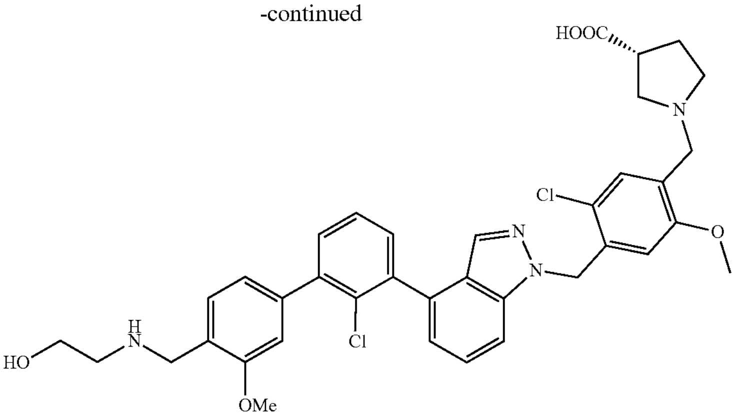

88

Starting from ethanolamine, 4-bromo-2-Methoxybenzaldehyde and compound INT-8c, referring to the synthesis of compound INT-3 and compound INT-8, compound 88a is obtained. MS (ESI): m/z 690.4 $(M+H)^+$.

Starting from compound 88a and compound INT-11, referring to the synthesis of compound 33, compound 88 is obtained. $^1$H NMR (500 MHz, DMSO-d6) δ 7.92 (s, 1H), 7.77 (d, J=8.5 Hz, 1H), 7.55-7.47 (m, 4H), 7.41 (d, J=7.5 Hz, 1H), 7.37 (s, 1H), 7.17 (d, J=7.0 Hz, 1H), 7.11 (s, 1H), 7.09-7.04 (m, 1H), 6.69 (s, 1H), 5.73 (s, 2H), 3.84 (s, 3H), 3.79 (d, J=3.5 Hz, 2H), 3.58 (s, 3H), 3.56-3.47 (m, 4H), 2.94-2.85 (m, 1H), 2.70-2.62 (m, 4H), 2.50-2.48 (m, 2H), 1.96-1.90 (m, 2H); MS (ESI): m/z 689.6 $(M+H)^+$.

Example 89

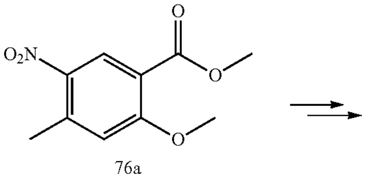

76a

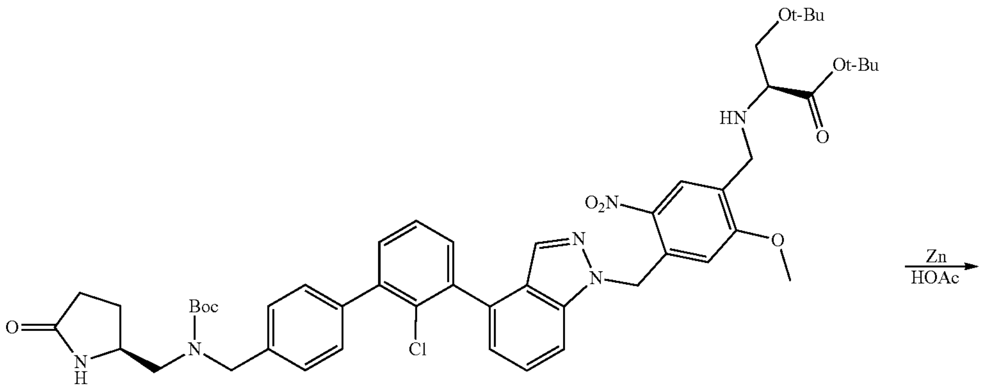

89a

-continued

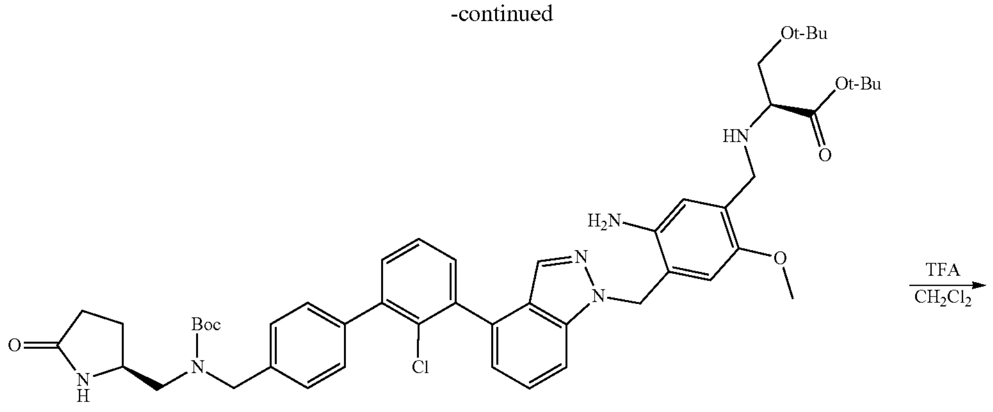

89b

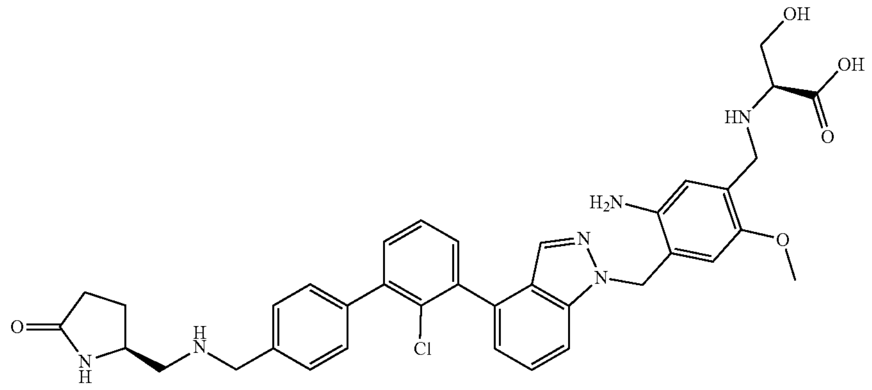

89

Starting from compound 76a, referring to the synthesis of compound 73, compound 89a is obtained. MS (ESI): m/z 925.5 $(M+H)^+$.

In acetic acid (3 mL) solution with compound 89a (150 mg, 0.16 mmol) dissolved Zinc powder (32 mg, 0.49 mmol) was added. The reaction solution was at 70° C. stirred for half an hour. The reaction solution concentrated, and the residue was separated by preparative thin layer chromatography (dichloromethane/methanol, v/v=20/1) to obtain yellow oily matter 89b (30 mg, yield: 20.7%). MS (ESI): m/z 895.9 $(M+H)^+$.

Starting from compound 89b, referring to the last step Boc deprotecting group step in the synthesis process of compound 1, compound 89 is obtained. $^1$H NMR (500 MHz, DMSO-d6) δ 7.88 (s, 1H), 7.84 (d, J=8.6 Hz, 1H), 7.67 (s, 1H), 7.54-7.42 (m, 8H), 7.14 (d, J=6.9 Hz, 1H), 6.80 (s, 1H), 6.68 (s, 1H), 5.55 (s, 2H), 5.00-4.95 (m, 1H), 3.84-3.73 (m, 4H), 3.63 (s, 3H), 3.60-3.51 (m, 3H), 3.04-3.02 (m, 1H), 2.56-2.52 (m, 2H), 2.13-2.06 (m, 3H), 1.73-1.66 (m, 1H); MS (ESI): m/z 683.1 $(M+H)^+$.

Example 90

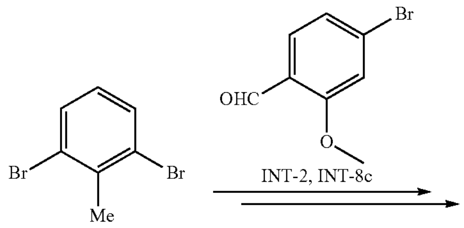

-continued

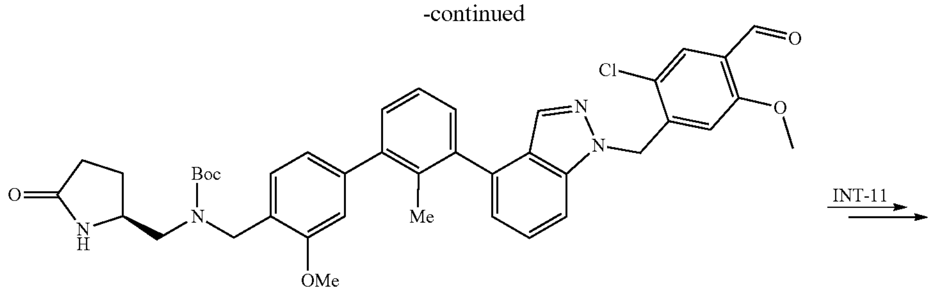

90a

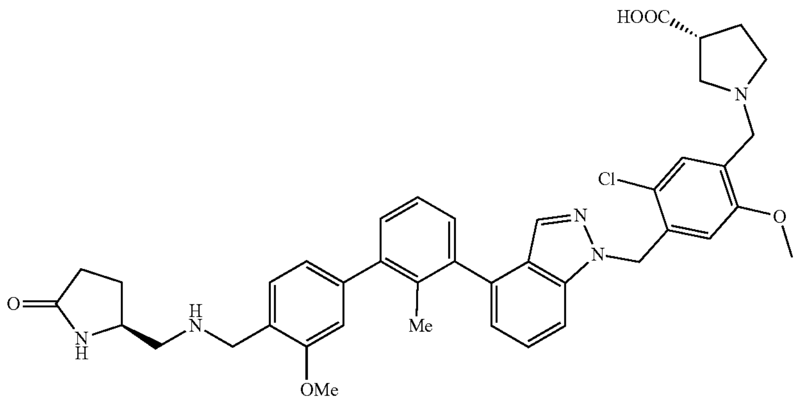

90

Starting from 1,3-dibromo-2-toluene, 4-bromo-2-methoxybenzaldehyde, compound INT-2 and compound INT-8c, referring to the synthesis of compound INT 3 and compound INT 8, compound 90a is obtained. MS (ESI): m/z 723.5 (M+H).

Starting from compound 90a and compound INT-11, referring to the synthesis of compound 33, compound 90 is obtained. $^1$H NMR (500 MHz, DMSO-d6) δ 7.90 (s, 1H), 7.73 (d, J=8.5 Hz, 1H), 7.66 (s, 1H), 7.49 (t, J=8.5 Hz, 1H), 7.43-7.36 (m, 3H), 7.34-7.30 (m, 2H), 7.10 (d, J=7.0 Hz, 1H), 7.03 (s, 1H), 7.00 (d, J=7.0 Hz, 1H), 6.67 (s, 1H), 5.73 (s, 2H), 3.84 (s, 3H), 3.82-3.77 (m, 2H), 3.70-3.65 (m, 1H), 3.58 (s, 3H), 3.53 (d, J=9.0 Hz, 2H), 2.95-2.88 (m, 1H), 2.68-2.62 (m, 4H), 2.53-2.52 (m, 2H), 2.16-2.08 (m, 3H), 2.00 (s, 3H), 1.97-1.91 (m, 2H), 1.75-1.68 (m, 1H); MS (ESI): m/z 722.3 $(M+H)^+$.

Example 91

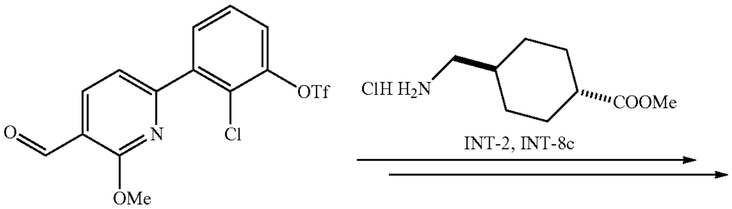

INT-10

-continued
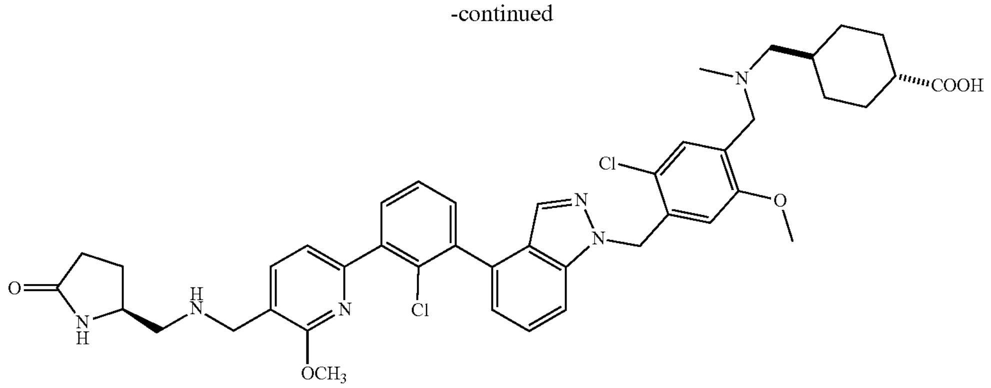
91
Starting from compound INT-10, compound INT-2, compound INT-8c and methyl 4-aminomethyl-cyclohexanecarboxylate hydrochloride, referring to the synthesis of compound INT-3, compound INT 8 and compound 44, compound is obtained 91. H NMR (500 MHz, DMSO-d6) δ 7.88 (s, 1H), 7.86 (d, J=7.4 Hz, 1H), 7.79 (d, J=8.5 Hz, 1H), 7.68-7.64 (m, 2H), 7.59-7.49 (m, 3H), 7.43-7.32 (m, 2H), 7.18 (d, J=7.0 Hz, 1H), 6.71 (s, 1H), 5.74 (s, 2H), 3.94 (s, 3H), 3.91-3.77 (m, 2H), 3.73-3.67 (m, 1H), 3.59 (s, 3H), 3.41-3.35 (m, 2H), 2.82-2.65 (m, 1H), 2.53-2.52 (m, 1H), 2.19-2.01 (m, 9H), 1.91-1.79 (m, 4H), 1.77-1.68 (m, 1H), 1.53-1.40 (m, 1H), 1.34-1.21 (m, 2H), 0.88-0.78 (m, 2H); MS (ESI): m/z 799.7 $(M+H)^+$.
Example 92
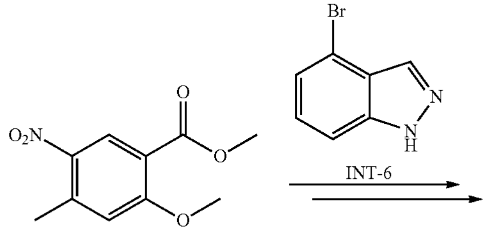
76a
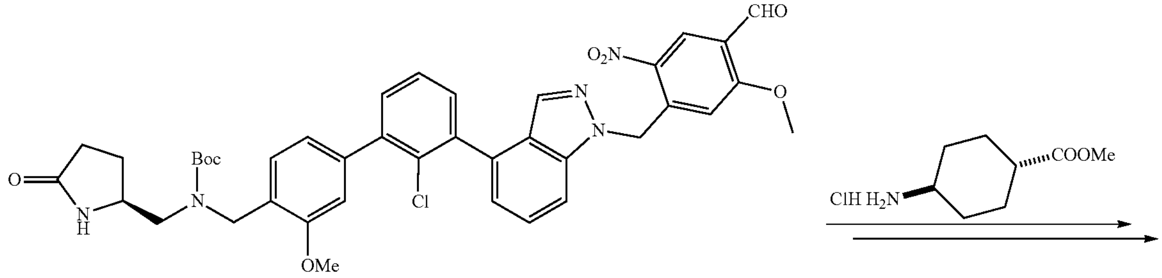
92a -continued

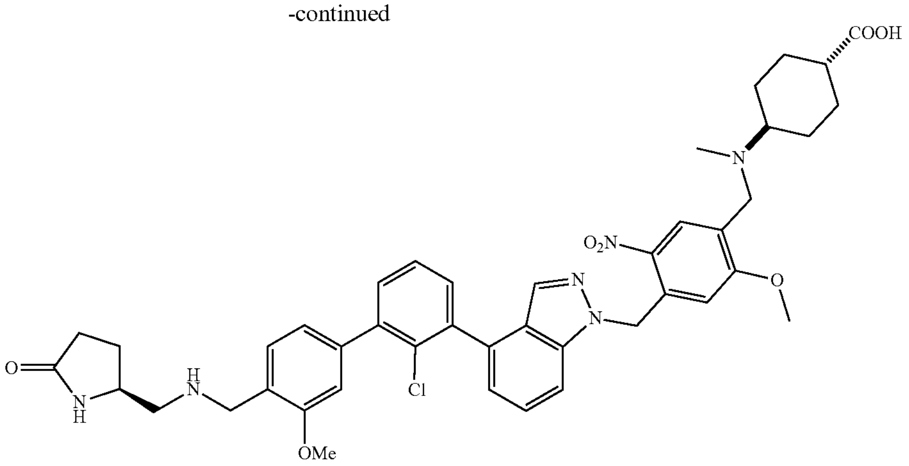

92

Starting from compound 76a, 4-bromoindazole, compound INT-6, referring to the synthesis of compound 73a, compound 82a and compound INT-8, compound 92a is obtained. MS (ESI): m/z 754.5 $(M+H)^+$.

Starting from compound 92a and trans-4-methyl aminocyclohexanate hydrochloride, referring to the synthesis of compound 44, compound 92 is obtained. $^1$H NMR (500 MHz, DMSO-d6) δ 8.18 (s, 1H), 7.96 (s, 1H), 7.78 (d, J=8.5 Hz, 1H), 7.65 (s, 1H), 7.54-7.48 (m, 4H), 7.41 (d, J=7.5 Hz, 1H), 7.17 (d, J=7.0 Hz, 1H), 7.09 (d, J=1.5 Hz, 1H), 7.08-7.04 (m, 1H), 6.11-6.08 (m, 3H), 3.82 (s, 3H), 3.78-3.72 (m, 2H), 3.66-3.62 (m, 1H), 3.51-3.49 (m, 2H), 3.48 (s, 3H), 2.57 (d, J=6.0 Hz, 2H), 2.46-2.36 (m, 2H), 2.13 (s, 3H), 2.11-2.07 (m, 3H), 1.94-1.89 (m, 2H), 1.82-1.77 (m, 2H), 1.72-1.65 (m, 1H), 1.32-1.26 (m, 4H); MS (ESI): m/z 795.7 $(M+H)^+$.

Example 93

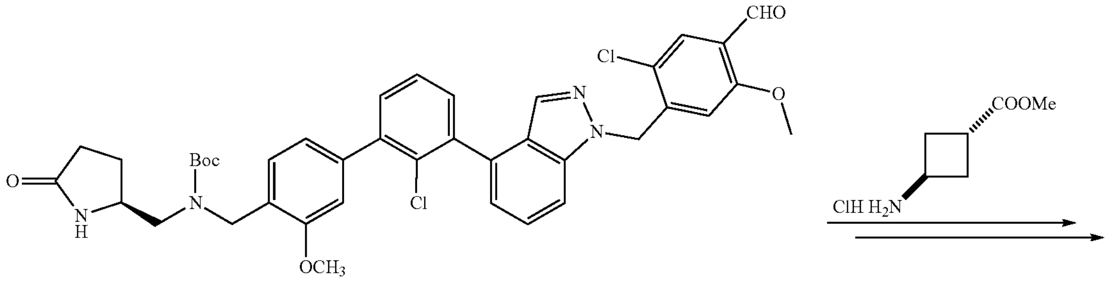

INT-9

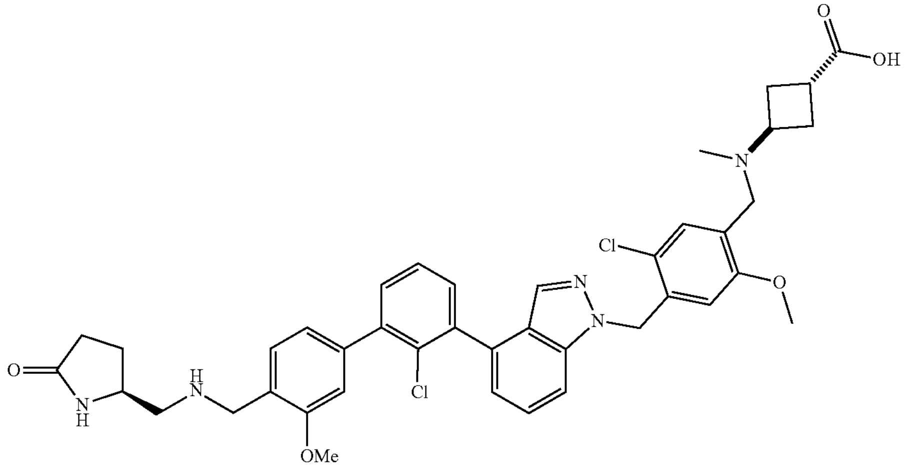

93

Starting from trans-4-methyl aminocyclobutanecarboxylate hydrochloride and compound INT-9, referring to the synthesis of compound 44, compound 93 is obtained. $^{1}$H NMR (500 MHz, DMSO-d6) δ 7.90 (s, 1H), 7.75 (d, J=8.5 Hz, 1H), 7.66 (s, 1H), 7.54-7.44 (m, 4H), 7.40 (d, J=7.5 Hz, 1H), 7.33 (s, 1H), 7.15 (d, J=7.5 Hz, 1H), 7.08-7.06 (m, 1H), 7.05-7.01 (m, 1H), 6.68 (s, 1H), 5.71 (s, 2H), 3.81 (s, 3H), 3.75-3.67 (m, 2H), 3.64-3.60 (m, 1H), 3.57 (s, 3H), 3.30-3.24 (m, 2H), 3.04-2.98 (m, 1H), 2.84-2.79 (m, 1H), 2.55-2.50 (m, 2H), 2.20-2.12 (m, 2H), 2.12-2.03 (m, 5H), 1.91 (s, 3H), 1.70-1.64 (m, 1H); MS (ESI): m/z 756.6 (M+H)$^{+}$.

Example 94

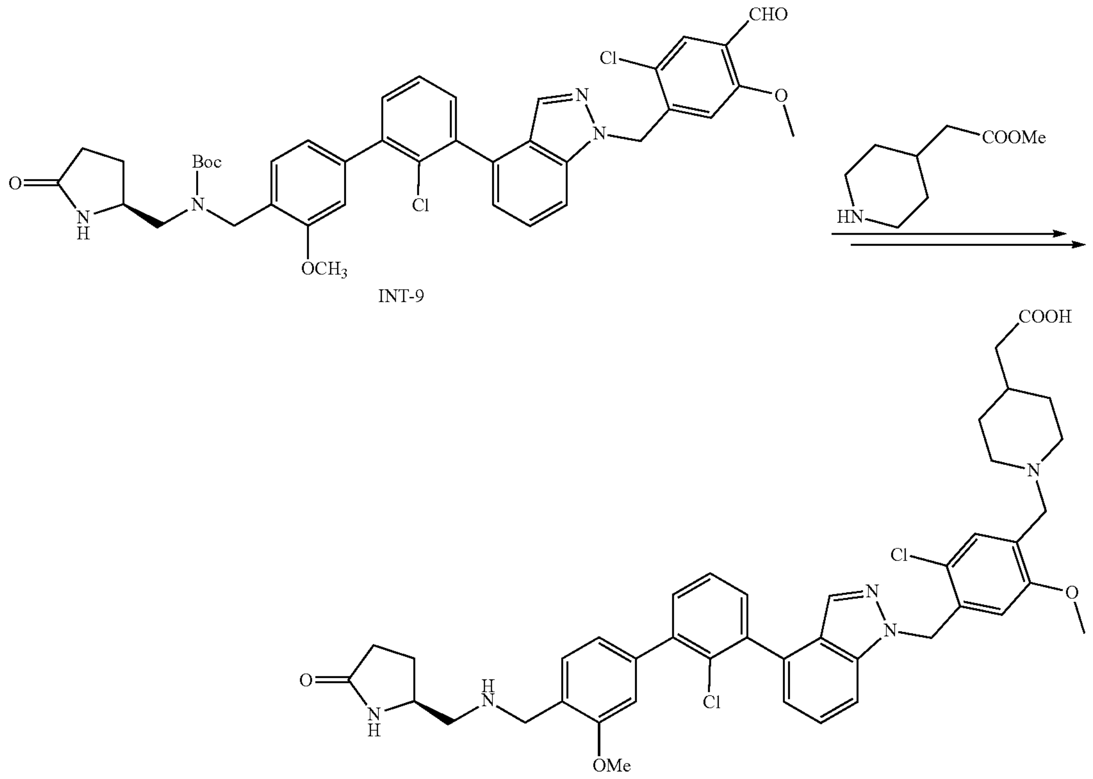

INT-9

94

Starting from methyl (4-piperidine)acetate and compound INT-9, referring to the synthesis of compound 44, compound 94 is obtained. $^{1}$H NMR (500 MHz, DMSO-d6) δ 7.89 (s, 1H), 7.75 (d, J=8.5 Hz, 1H), 7.66 (s, 1H), 7.54-7.44 (m, 4H), 7.40 (d, J=7.5 Hz, 1H), 7.33 (s, 1H), 7.15 (d, J=7.0 Hz, 1H), 7.09-7.06 (m, 1H), 7.05-7.01 (m, 1H), 6.68 (s, 1H), 5.71 (s, 2H), 3.81 (s, 3H), 3.74-3.68 (m, 2H), 3.64-3.59 (m, 1H), 3.56 (s, 3H), 2.76-2.69 (m, 2H), 2.56-2.51 (m, 2H), 2.14-2.03 (m, 5H), 1.96-1.87 (m, 2H), 1.77-1.64 (m, 2H), 1.63-1.54 (m, 2H), 1.22-1.14 (m, 2H); MS (ESI): m/z 770.6 (M+H)$^{+}$.

Example 95

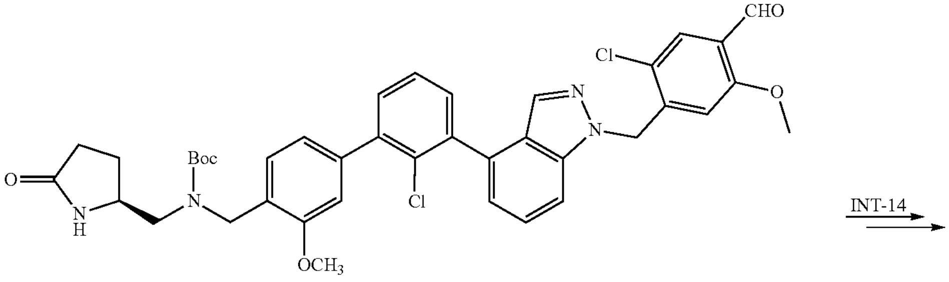

INT-9

-continued
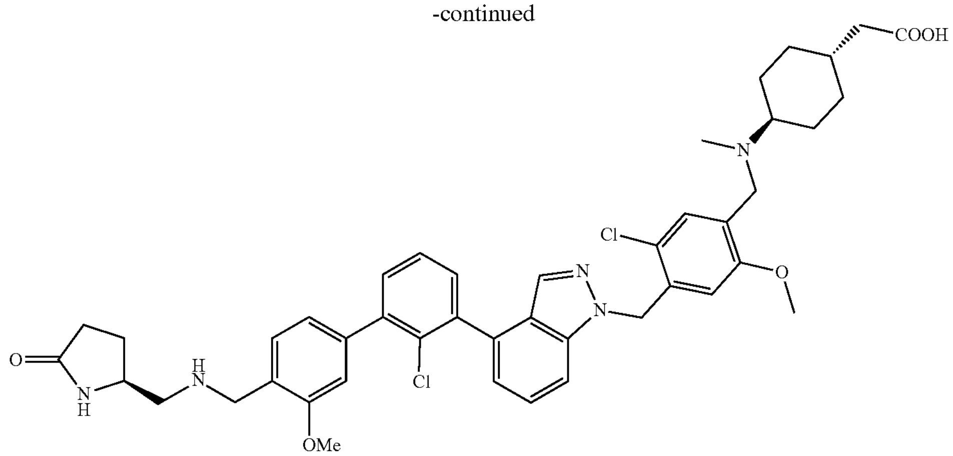
95
Starting from compound INT-9 and compound INT-14, referring to the synthesis of compound 44, compound 95 is obtained. $^1H$ NMR (500 MHz, DMSO-d6) δ 7.89 (s, 1H), 7.75 (d, J=8.5 Hz, 1H), 7.66 (s, 1H), 7.53-7.44 (m, 4H), 7.39 (d, J=7.5 Hz, 1H), 7.36 (s, 1H), 7.15 (d, J=7.0 Hz, 1H), 7.08-7.05 (m, 1H), 7.05-7.01 (m, 1H), 6.67 (s, 1H), 5.70 (s, 2H), 3.81 (s, 3H), 3.72-3.69 (m, 2H), 3.64-3.58 (m, 1H), 3.56 (s, 3H), 3.44-3.35 (m, 2H), 2.54-2.51 (m, 2H), 2.35-2.29 (m, 1H), 2.12-2.10 (m, 1H), 2.09 (s, 3H), 2.07-2.05 (m, 1H), 2.04 (d, J=7.0 Hz, 2H), 1.76-1.71 (m, 4H), 1.69-1.63 (m, 1H), 1.59-1.51 (m, 1H), 1.29-1.20 (m, 2H), 0.99-0.86 (m, 2H); MS (ESI): m/z 798.7 $(M+H)^+$.
Example 96
96
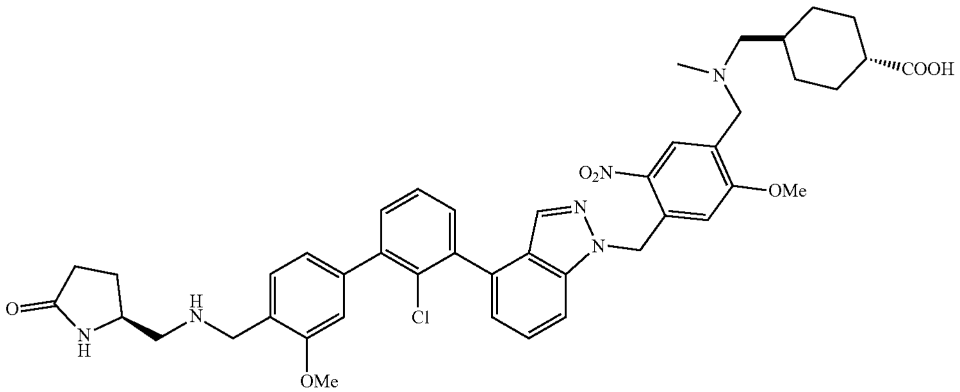

Referring to the synthesis of compound 92, trans-4-methyl aminocyclohexanate hydrochloride is replaced with methyl 4-aminomethyl-cyclohexanecarboxylate hydrochloride, compound 96 is obtained. $^1$H NMR (500 MHz, DMSO-d6) δ 8.21 (s, 1H), 7.98 (s, 1H), 7.80 (d, J=8.5 Hz, 1H), 7.66 (s, 1H), 7.56-7.48 (m, 4H), 7.44-7.43 (m, 1H), 7.19 (d, J=6.9 Hz, 1H), 7.13-7.11 (m, 1H), 7.09-7.07 (m, 1H), 6.13-6.11 (m, 3H), 3.85 (s, 3H), 3.80-3.79 (m, 2H), 3.71-3.64 (m, 1H), 3.49 (s, 3H), 3.41 (s, 2H), 2.64-2.62 (m, 2H), 2.59-2.51 (m, 2H), 2.14 (s, 3H), 2.13-2.07 (m, 4H), 1.89-1.81 (m, 4H), 1.73-1.68 (m, 1H), 1.50-1.45 (m, 1H), 1.33-1.24 (m, 2H), 0.88-0.80 (m, 2H); MS (ESI): m/z 809.8 (M+H).
Example 97
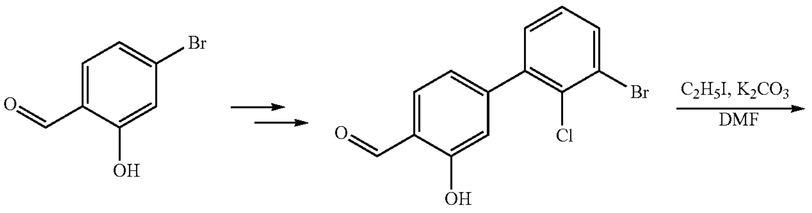
97a
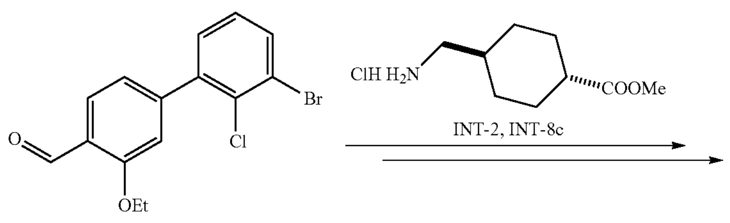
97b
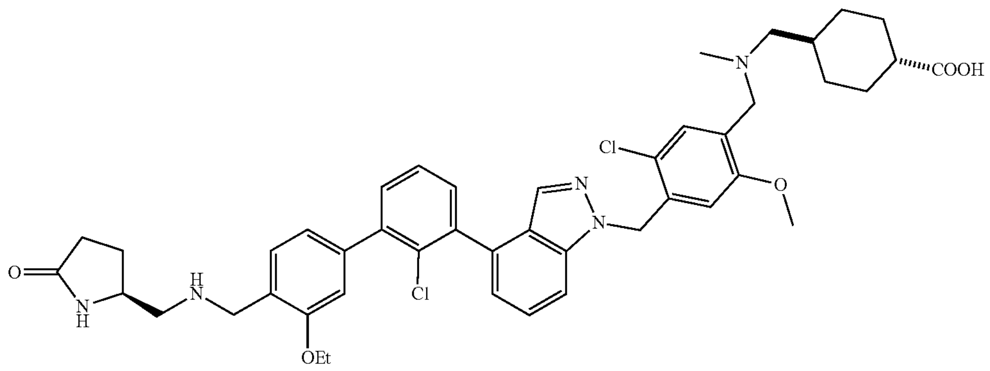
97

Starting from compound 4-bromo-2-hydroxybenzaldehyde, referring to boron esterification of compound INT-7a and the synthesis of compound INT-3a, compound 97a is obtained.

Starting from compound 97a, referring to alkylation reaction step of compound INT-8a compound 97b is obtained. $^1$H NMR (500 MHz, DMSO-d6) δ 10.40 (s, 1H), 7.86-7.82 (m, 1H), 7.74 (d, J=8.0 Hz, 1H), 7.47-7.43 (m, 1H), 7.37 (t, J=8.0 Hz, 1H), 7.24 (d, J=1.4 Hz, 1H), 7.10-7.06 (m, 1H), 4.23 (q, J=7.0 Hz, 2H), 1.38 (t, J=7.0 Hz, 3H).

Starting from compound 97b, compound INT-2, compound INT-8c and methyl 4-aminomethyl-cyclohexanecarboxylate hydrochloride, referring to the synthesis of compound 48, compound 97 is obtained. $^1$H NMR (500 MHz, DMSO-d6) δ 7.90 (s, 1H), 7.75 (d, J=8.5 Hz, 1H), 7.65 (s, 1H), 7.55-7.44 (m, 4H), 7.39 (d, J=7.7 Hz, 1H), 7.36 (s, 1H), 7.15 (d, J=7.0 Hz, 1H), 7.05 (d, J=1.7 Hz, 1H), 7.04-7.00 (m, 1H), 6.67 (s, 1H), 5.71 (s, 2H), 4.08 (q, J=6.9 Hz, 2H), 3.74-3.68 (m, 2H), 3.64-3.59 (m, 1H), 3.56 (s, 3H), 3.34 (s, 2H), 2.55-2.53 (m, 2H), 2.13-2.03 (m, 9H), 1.86-1.75 (m, 4H), 1.72-1.66 (m, 1H), 1.46-1.40 (m, 1H), 1.33 (t, J=6.9 Hz, 3H), 1.27-1.21 (m, 2H), 0.84-0.75 (m, 2H); MS (ESI): m/z 812.8 (M+H).

Example 98

98

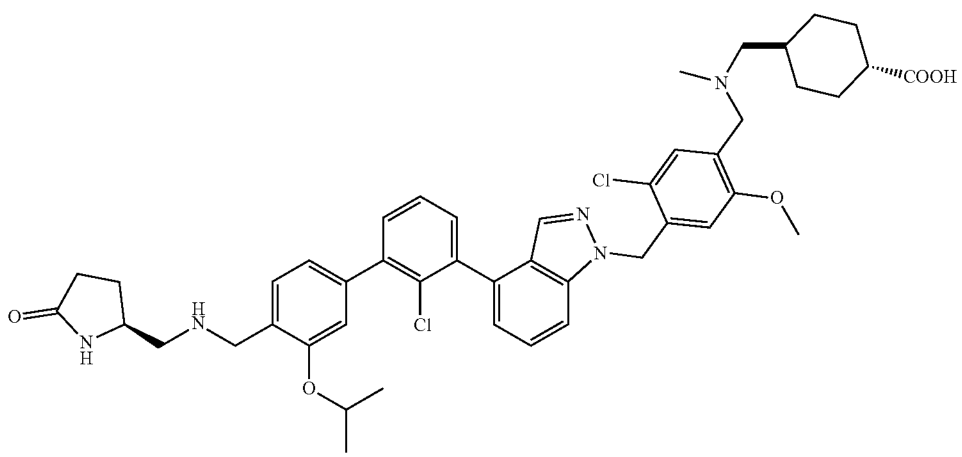

Referring to the synthesis of compound 97, iodoethane is replaced with 2-iodopropane, compound 98 is obtained. $^1$H NMR (500 MHz, DMSO-d6) δ 7.91 (s, 1H), 7.76 (d, J=8.5 Hz, 1H), 7.64 (s, 1H), 7.55-7.43 (m, 4H), 7.39 (d, J=7.7 Hz, 1H), 7.36 (s, 1H), 7.15 (d, J=7.0 Hz, 1H), 7.07 (d, J=1.6 Hz, 1H), 7.01-6.97 (m, 1H), 6.67 (s, 1H), 5.71 (s, 2H), 4.70-4.62 (m, 1H), 3.74-3.66 (m, 2H), 3.64-3.60 (m, 1H), 3.56 (s, 3H), 3.34 (s, 2H), 2.54-2.52 (m, 2H), 2.13-2.03 (m, 9H), 1.89-1.78 (m, 4H), 1.71-1.65 (m, 1H), 1.48-1.39 (m, 1H), 1.29-1.26 (m, 6H), 1.26-1.20 (m, 2H), 0.86-0.74 (m, 2H); MS (ESI): m/z 826.7 (M+H).

Example 99

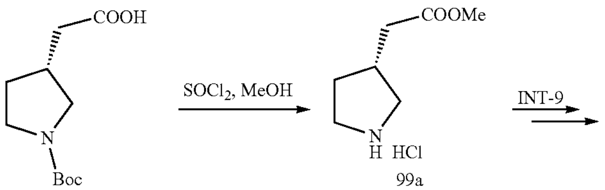

99a

-continued

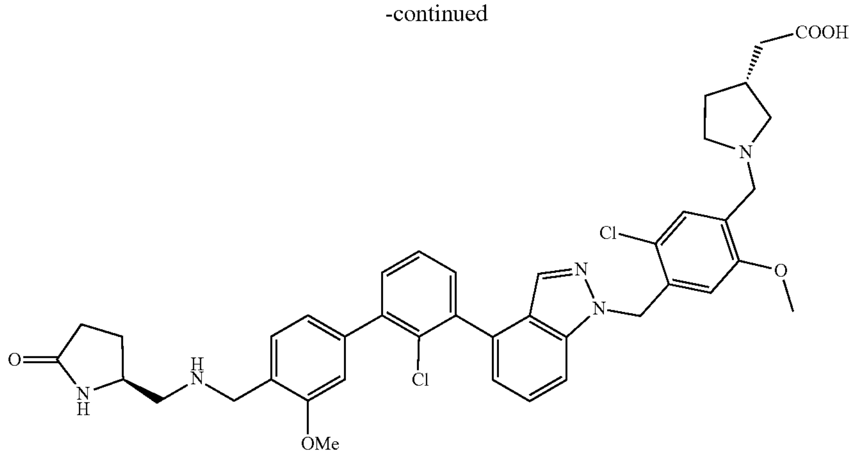

99

Starting from (R)—N-Boc-3-tetrahydropyrroleacetic acid, referring to the synthesis of compound INT-14, compound 99a is obtained. $^{1}$H NMR (500 MHz, DMSO-d6) δ 9.27-8.91 (m, 2H), 3.59 (s, 3H), 3.32-3.26 (m, 1H), 3.23-3.15 (m, 1H), 3.13-3.02 (m, 1H), 2.80-2.71 (m, 1H), 2.55-2.49 (m, 3H), 2.10-2.02 (m, 1H), 1.55-1.48 (m, 1H).

Starting from compound 99a and compound INT-9, referring to the synthesis of compound 44, compound 99 is obtained. $^{1}$H NMR (500 MHz, DMSO-d6) δ 7.90 (s, 1H), 7.75 (d, J=8.5 Hz, 1H), 7.66 (s, 1H), 7.54-7.45 (m, 4H), 7.40 (d, J=7.5 Hz, 1H), 7.33 (s, 1H), 7.15 (d, J=7.0 Hz, 1H), 7.08-7.06 (m, 1H), 7.05-7.02 (m, 1H), 6.67 (s, 1H), 5.71 (s, 2H), 3.81 (s, 3H), 3.75-3.68 (m, 2H), 3.64-3.60 (m, 1H), 3.56 (s, 3H), 3.48 (s, 2H), 2.68-2.62 (m, 1H), 2.55-2.51 (m, 2H), 2.47-2.42 (m, 2H), 2.40-2.34 (m, 1H), 2.28-2.23 (m, 2H), 2.15-2.05 (m, 4H), 1.97-1.89 (m, 1H), 1.72-1.64 (m, 1H), 1.37-1.29 (m, 1H); MS (ESI): m/z 756.7 (M+H).

Example 100

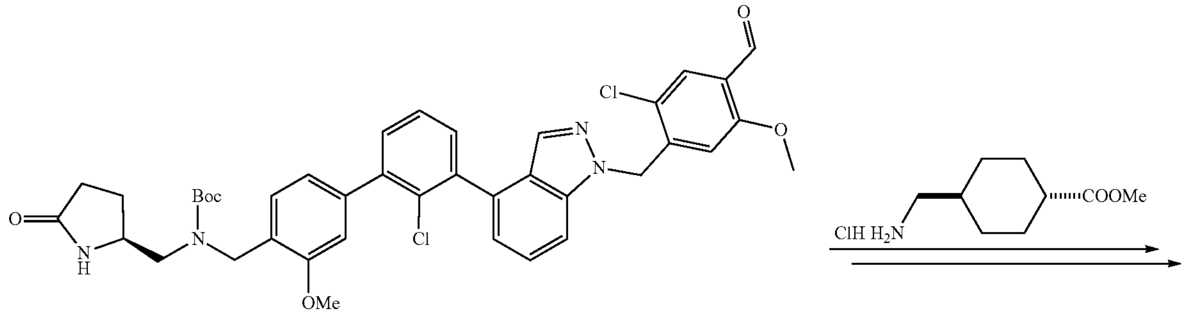

INT-9

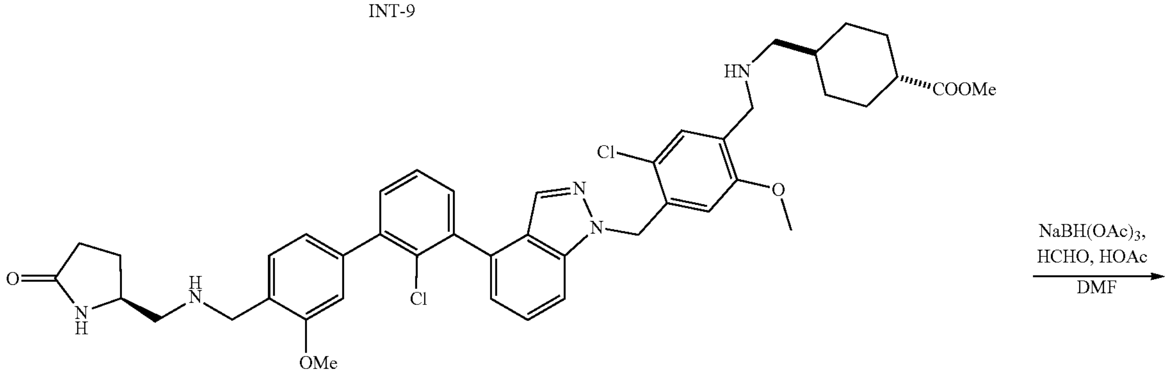

100a

-continued

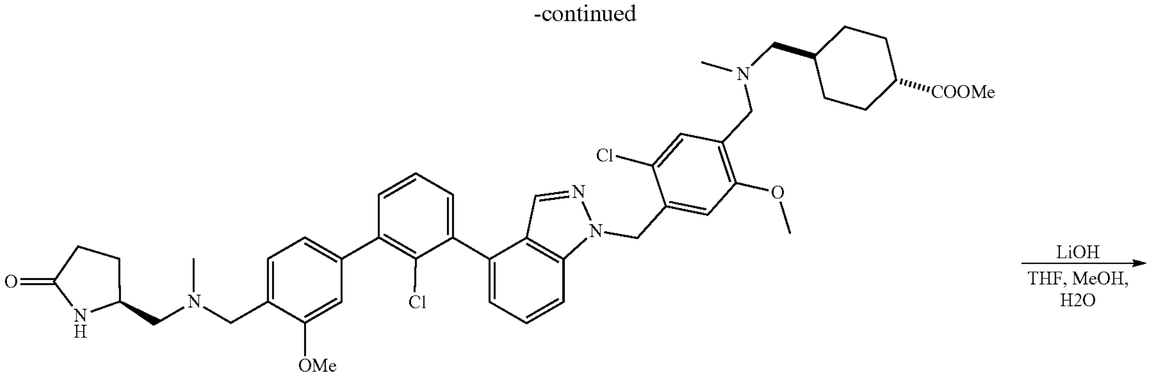

100b

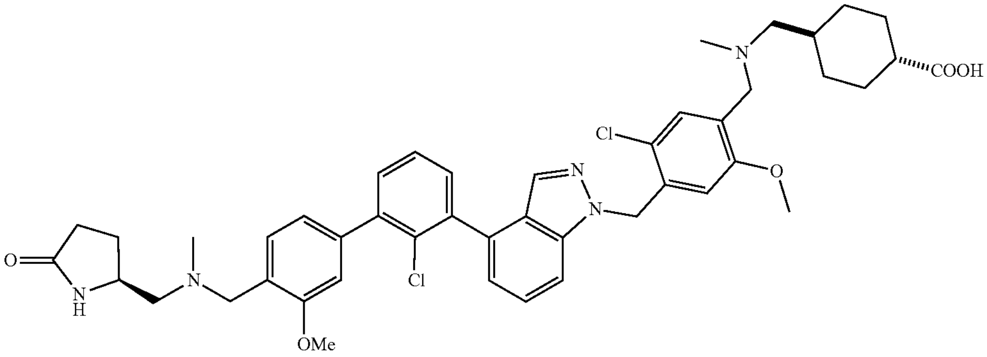

100

Starting from compound INT-9 and methyl 4-aminomethyl-cyclohexanecarboxylate hydrochloride, referring to the synthesis of compound INT-5 and last step Boc deprotecting step in the synthesis of compound 1, compound 100a is obtained. MS (ESI): m/z 798.7 (M+H).

In N,N-dimethylformamide (2 mL) with compound 100a (40 mg, 0.050 mmol) dissolved formaldehyde (34% aqueous solution, 0.10 mL), acetic acid (6.0 mg, 0.10 mmol) and sodium triacetate borohydride (42 mg, 0.20 mmol) were added. The reaction solution was at 25° C. stirred for 2 hours. To the reaction solution saturated sodium bicarbonate solution (20 mL) was added, and the solution was extracted with ethyl acetate (20 mL×2). The combined organic phase was washed with saturated salt solution (30 mL), dried with anhydrous sodium sulfate, and concentrated to obtain brown oily matter 100b (35 mg, yield: 84.5%). MS (ESI): m/z 826.7 (M+H).

Starting from compound 100b, referring to compound 33 in the synthesis process of ester hydrolysis step compound is obtained 100. $^{1}$H NMR (500 MHz, DMSO-d6) δ 7.90 (s, 1H), 7.75 (d, J=8.5 Hz, 1H), 7.55-7.45 (m, 5H), 7.44 (d, J=7.5 Hz, 1H), 7.36 (s, 1H), 7.15 (d, J=7.0 Hz, 1H), 7.09-7.07 (m, 1H), 7.06-7.03 (m, 1H), 6.67 (s, 1H), 5.71 (s, 2H), 3.80 (s, 3H), 3.74-3.68 (m, 1H), 3.56 (s, 3H), 3.53-3.49 (m, 2H), 3.36 (s, 2H), 2.44-2.39 (m, 1H), 2.36-2.30 (m, 1H), 2.17 (s, 3H), 2.11-2.05 (m, 9H), 1.87-1.78 (m, 4H), 1.70-1.64 (m, 1H), 1.48-1.40 (m, 1H), 1.32-1.21 (m, 2H), 0.86-0.76 (m, 2H); MS (ESI): m/z 812.7 (M+H).

Example 101

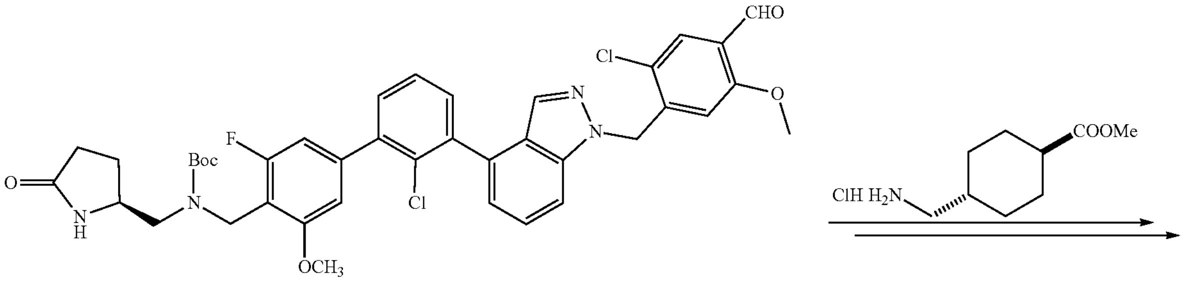

INT-16

-continued
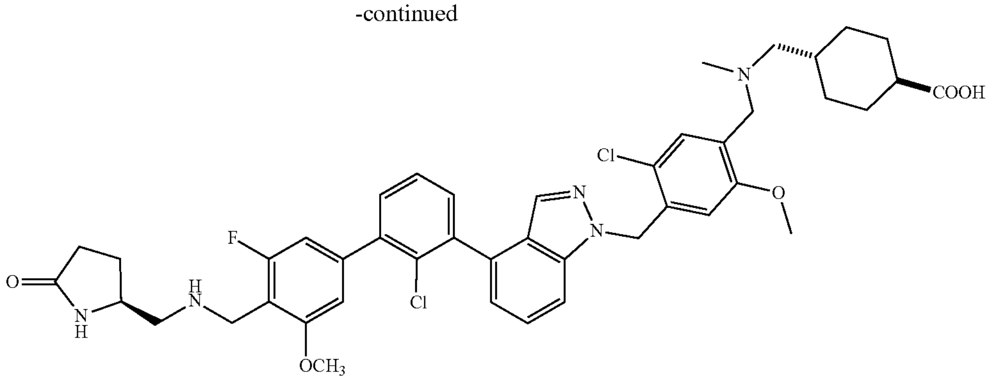
101
Starting from compound INT-16 and methyl 4-aminomethyl-cyclohexanecarboxylate hydrochloride, referring to the synthesis of compound 44, compound 101 is obtained. $^1$H NMR (500 MHz, DMSO-d6) δ 7.95 (s, 1H), 7.78 (d, J=8.5 Hz, 1H), 7.65 (s, 1H), 7.57-7.49 (m, 4H), 7.38 (s, 1H), 7.17 (d, J=7.0 Hz, 1H), 7.00-6.96 (m, 2H), 6.69 (s, 1H), 5.73 (s, 2H), 3.87 (s, 3H), 3.79-3.71 (m, 2H), 3.61-3.59 (m, 1H), 3.58 (s, 3H), 3.36 (s, 2H), 2.53-2.51 (m, 2H), 2.13-2.03 (m, 6H), 2.09 (s, 3H), 1.88-1.78 (m, 4H), 1.70-1.62 (m, 1H), 1.49-1.41 (m, 1H), 1.32-1.22 (m, 2H), 0.87-0.76 (m, 2H); MS (ESI): m/z 816.3 (M+H).
Example 102
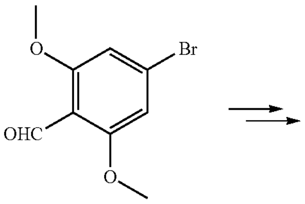
INT-15b
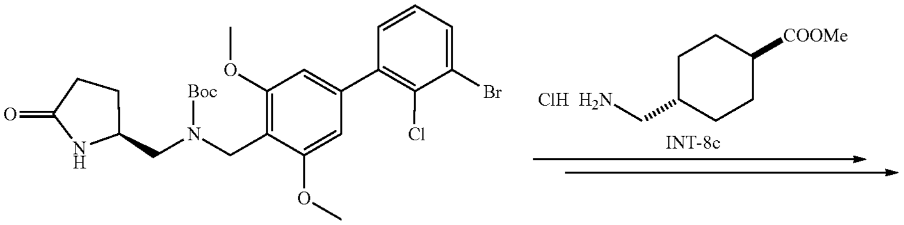
102a
INT-8c
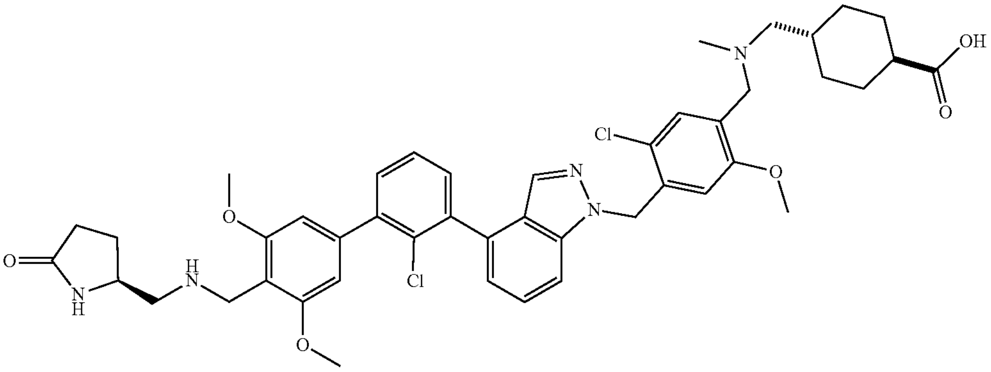
102

Starting from compound INT-15b, referring to the synthesis of compound INT-3, compound 102a is obtained. MS (ESI): m/z 553.6 (M+H).

Starting from compound 102a, compound INT-8c and methyl 4-aminomethyl-cyclohexanecarboxylate hydrochloride, referring to the synthesis of compound INT-8 and compound 44, compound 102 is obtained. $^1$H NMR (500 MHz, DMSO-d6) δ 7.93 (s, 1H), 7.78 (d, J=8.5 Hz, 1H), 7.63 (s, 1H), 7.56-7.48 (m, 4H), 7.38 (s, 1H), 7.17 (d, J=7.0 Hz, 1H), 6.77 (s, 2H), 6.70 (s, 1H), 5.73 (s, 2H), 3.82 (s, 6H), 3.76-3.70 (m, 2H), 3.60-3.56 (m, 4H), 3.36 (s, 2H), 2.53-2.52 (m, 2H), 2.13-2.04 (m, 9H), 1.89-1.79 (m, 4H), 1.70-1.61 (m, 1H), 1.50-1.42 (m, 1H), 1.32-1.23 (m, 2H), 0.87-0.77 (m, 2H); MS (ESI): m/z 828.5 (M+H).

Example 103

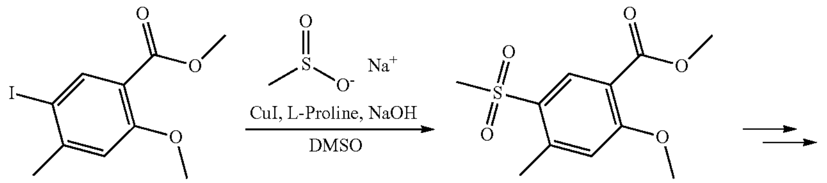

INT-13

103a

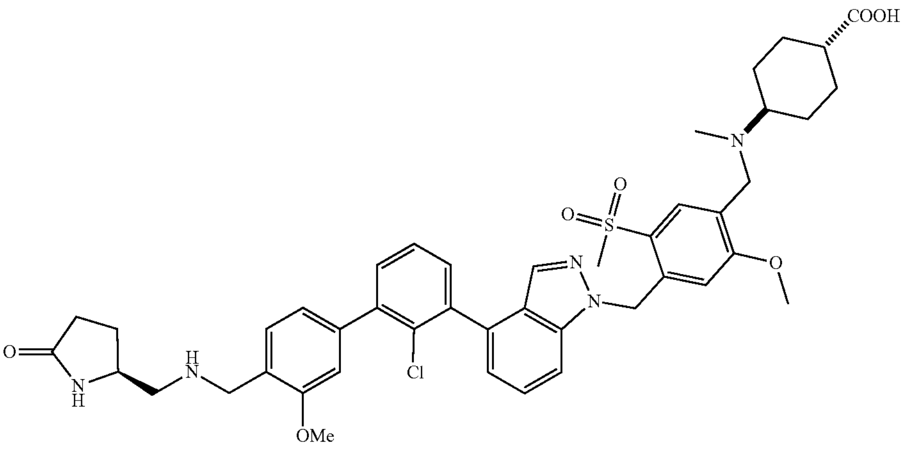

103

At 25° C., dimethyl sulfoxide (5 mL) solution with L-proline (132 mg, 1.14 mmol), sodium hydroxide (46 mg, 1.14 mmol) dissolved was stirred for 1 hour. Subsequently compound INT-13 (350 mg, 1.14 mmol), sodium methanesulfinate (1.17 g, 11.4 mmol) and cuprous iodide (218 mg, 1.14 mmol) were added. The resulting reaction solution was replaced with nitrogen for 3 times and was stirred for 2 hours under nitrogen atmosphere and 120° C. conditions. The reaction solution was diluted with water (50 mL) and was extracted with ethyl acetate (50 mL×2). The combined organic phase was saturated salt solution (100 mL) washed with, dried with anhydrous sodium sulfate, and concentrated. The residue was silica gel column chromatography (petroleum ether/ethyl acetate, v/v=1/1) separated by to obtain a white solid 103a (232 mg, yield: 94.5%). $^1$H NMR (500 MHz, Chloroform-d) δ 8.48 (s, 1H), 6.89 (s, 1H), 3.98 (s, 3H), 3.89 (s, 3H), 3.07 (s, 3H), 2.74 (s, 3H); MS (ESI): m/z 259.1 (M+H).

Starting from compound 103a, referring to the synthesis of compound 92, compound 103 is obtained. $^1$H NMR (500 MHz, DMSO-d6) δ 7.98 (s, 1H), 7.96 (s, 1H), 7.78 (d, J=8.5 Hz, 1H), 7.66 (s, 1H), 7.56-7.47 (m, 4H), 7.40 (d, J=7.6 Hz, 1H), 7.18 (d, J=7.0 Hz, 1H), 7.07 (d, J=1.6 Hz, 1H), 7.06-7.02 (m, 1H), 6.31 (s, 1H), 6.14 (s, 2H), 3.82 (s, 3H), 3.76-3.67 (m, 2H), 3.64-3.59 (m, 1H), 3.48 (s, 2H), 3.47 (s, 3H), 3.21 (s, 3H), 2.56-2.52 (m, 2H), 2.39-2.33 (m, 1H), 2.11 (s, 3H), 2.11-2.07 (m, 3H), 2.07-2.04 (m, 1H), 1.94-1.87 (m, 2H), 1.82-1.76 (m, 2H), 1.71-1.64 (m, 1H), 1.32-1.23 (m, 4H); MS (ESI): m/z 828.2 (M+H).

Example 104
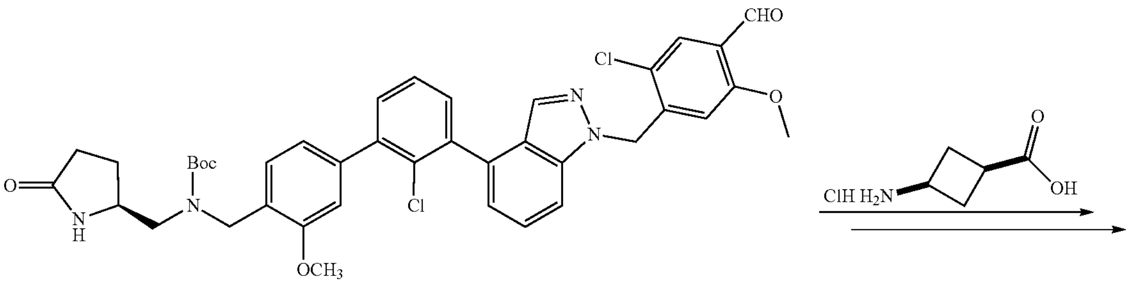
INT-9
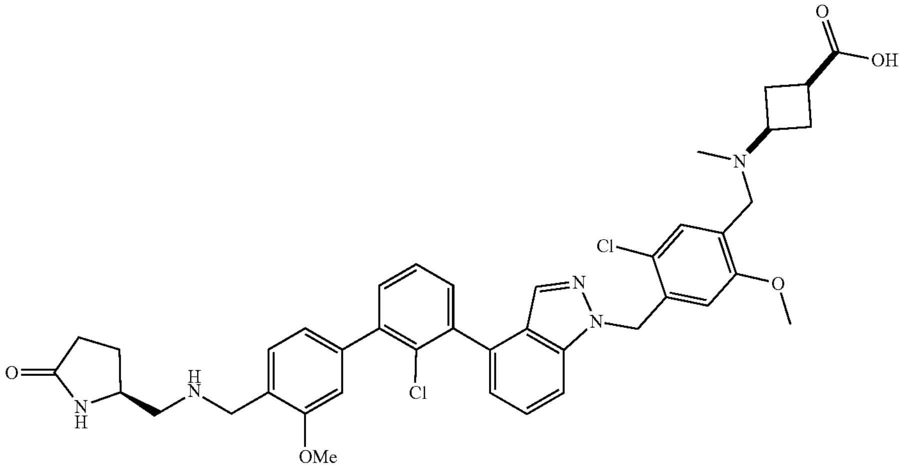
104
Starting from compound INT-9 and cis-3-Methyl amino-cyclobutanecarboxylate hydrochloride, referring to the synthesis of compound 44, compound 104 is obtained. $^1H$ NMR (500 MHz, DMSO-d6) δ 7.90 (s, 1H), 7.75 (d, J=8.0 Hz, 1H), 7.66 (s, 1H), 7.52-7.47 (m, 4H), 7.40 (d, J=7.5 Hz, 1H), 7.32 (s, 1H), 7.15 (d, J=7.0 Hz, 1H), 7.07 (s, 1H), 7.04 (d, J=7.5 Hz, 1H), 6.68 (s, 1H), 5.72 (s, 2H), 3.81 (s, 3H), 3.75-3.68 (m, 2H), 3.64-3.60 (m, 1H), 3.57 (s, 3H), 3.26 (s, 2H), 2.82-2.75 (m, 1H), 2.67-2.60 (m, 1H), 2.57-2.52 (m, 2H), 2.23-2.17 (m, 2H), 2.14-2.04 (m, 3H), 1.94-1.87 (m, 2H), 1.92 (s, 3H), 1.71-1.64 (m, 1H); MS (ESI): m/z 755.9 (M+H).
Example 105
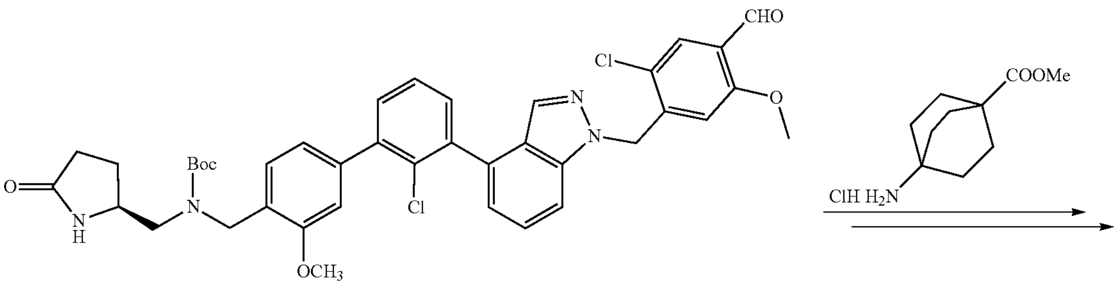
INT-9

-continued
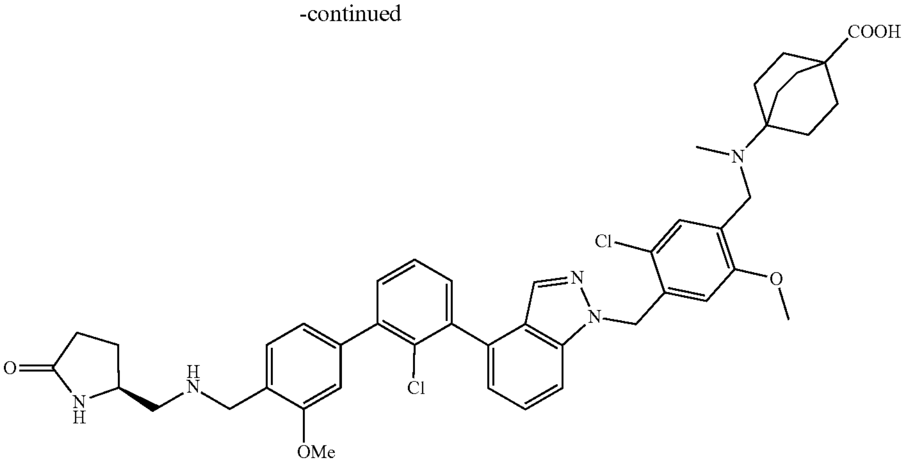
105
Starting from compound INT-9 and 4-aminobicyclo [2.2.2]octane-1-carboxylic acid methyl ester hydrochloride, referring to the synthesis of compound 44, compound 105 is obtained. $^1$H NMR (500 MHz, DMSO-d6) δ 7.89 (s, 1H), 7.75 (d, J=8.5 Hz, 1H), 7.66 (s, 1H), 7.54-7.43 (m, 4H), 7.40 (d, J=7.5 Hz, 1H), 7.38 (s, 1H), 7.15 (d, J=7.0 Hz, 1H), 7.07 (d, J=1.5 Hz, 1H), 7.05-7.02 (m, 1H), 6.66 (s, 1H), 5.70 (s, 2H), 3.81 (s, 3H), 3.74-3.68 (m, 2H), 3.64-3.59 (m, 1H), 3.57 (s, 3H), 3.41 (s, 2H), 2.56-2.52 (m, 2H), 2.14-2.04 (m, 3H), 1.99 (s, 3H), 1.75-1.66 (m, 7H), 1.60-1.49 (m, 6H); MS (ESI): m/z 810.2 (M+H).
Example 106
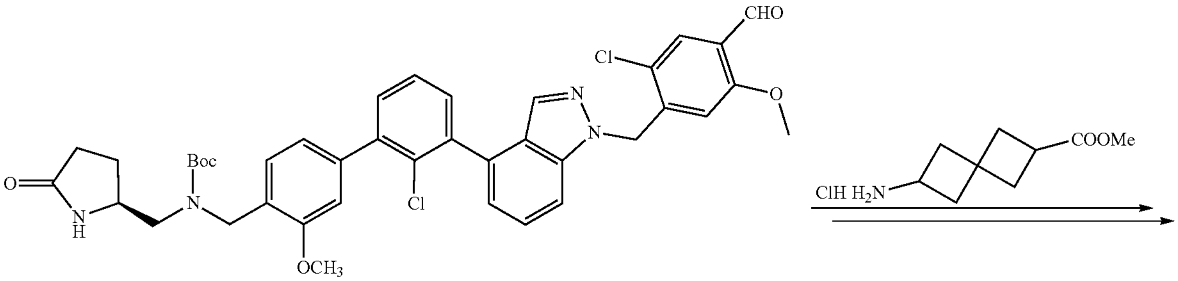
INT-9
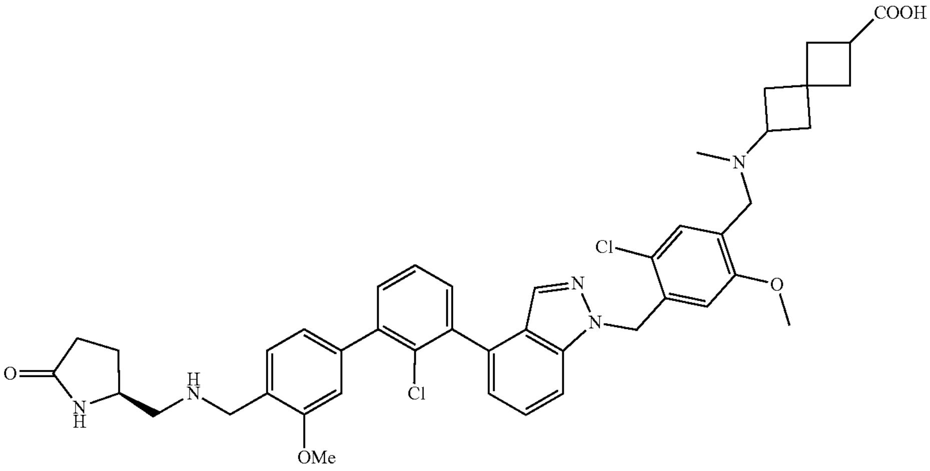
106

Starting from compound INT-9 and methyl 6-aminospiro[3.3]heptane-2-carboxylate hydrochloride, referring to the synthesis of compound 44, compound 106 is obtained. $^1$H NMR (500 MHz, DMSO-d6) δ 7.90 (s, 1H), 7.75 (d, J=8.5 Hz, 1H), 7.66 (s, 1H), 7.54-7.44 (m, 4H), 7.40 (d, J=7.5 Hz, 1H), 7.30 (s, 1H), 7.15 (d, J=7.0 Hz, 1H), 7.08-7.06 (m, 1H), 7.05-7.02 (m, 1H), 6.67 (s, 1H), 5.71 (s, 2H), 3.81 (s, 3H), 3.75-3.67 (m, 2H), 3.64-3.59 (m, 1H), 3.56 (s, 3H), 3.21 (s, 2H), 2.93-2.86 (m, 1H), 2.74-2.68 (m, 1H), 2.55-2.52 (m, 2H), 2.20-1.98 (m, 9H), 1.88 (s, 3H), 1.80-1.74 (m, 1H), 1.72-1.65 (m, 2H); MS (ESI): m/z 796.2 (M+H).
Example 107
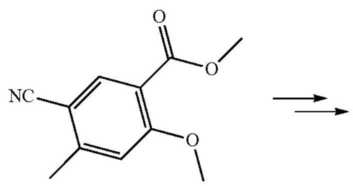
75a
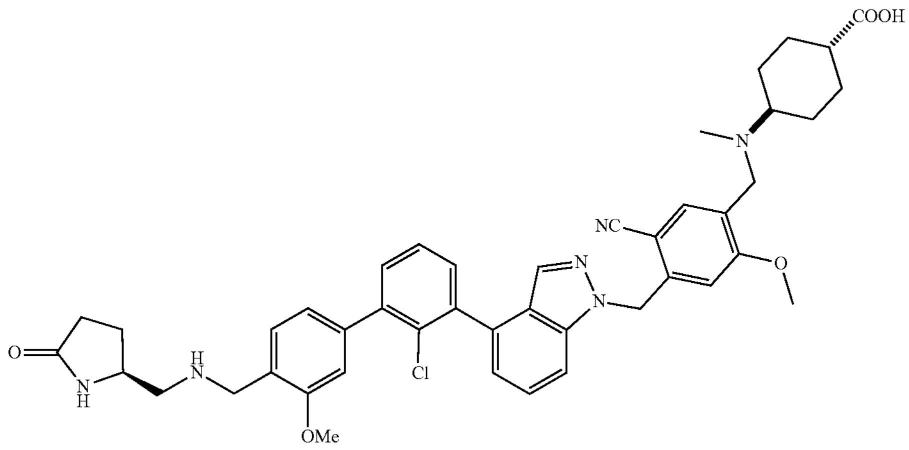
107

Starting from compound 75a, referring to the synthesis of compound 92, compound 107 is obtained. $^1$H NMR (500 MHz, DMSO-d6) δ 7.91 (s, 1H), 7.82 (d, J=8.5 Hz, 1H), 7.70 (s, 1H), 7.65 (s, 1H), 7.53-7.46 (m, 4H), 7.40 (d, J=7.5 Hz, 1H), 7.17 (d, J=7.0 Hz, 1H), 7.07 (d, J=1.5 Hz, 1H), 7.06-7.02 (m, 1H), 6.90 (s, 1H), 5.80 (s, 2H), 3.81 (s, 3H), 3.71 (d, J=3.0 Hz, 2H), 3.69 (s, 3H), 3.63-3.60 (m, 1H), 3.47 (s, 2H), 2.54-2.52 (m, 2H), 2.39-2.36 (m, 1H), 2.12-2.06 (m, 4H), 2.10 (s, 3H), 1.93-1.88 (m, 2H), 1.81-1.76 (m, 2H), 1.70-1.66 (m, 1H), 1.30-1.25 (m, 4H); MS (ESI): m/z 775.3 (M+H).

Example 108

108

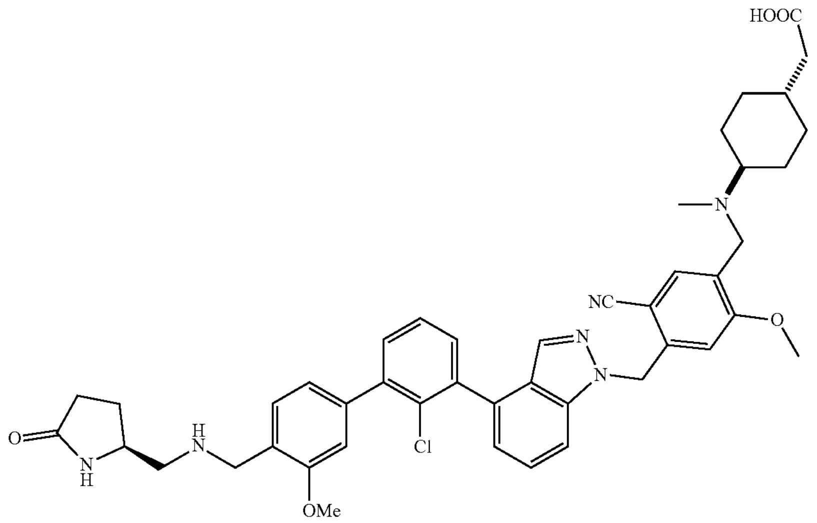

Referring to the synthesis of compound 107, trans-4-methyl aminocyclohexanate hydrochloride is replaced with compound INT-14, compound 108 is obtained. $^1$H NMR (500 MHz, DMSO-d6) δ 7.91 (s, 1H), 7.83 (d, J=8.5 Hz, 1H), 7.71 (s, 1H), 7.63 (s, 1H), 7.54-7.46 (m, 4H), 7.42 (d, J=7.5 Hz, 1H), 7.17 (d, J=7.0 Hz, 1H), 7.11 (s, 1H), 7.07 (d, J=7.5 Hz, 1H), 6.92 (s, 1H), 5.80 (s, 2H), 3.87-3.78 (m, 2H), 3.83 (s, 3H), 3.71-3.66 (m, 1H), 3.70 (s, 3H), 3.51-3.45 (m, 2H), 2.54-2.52 (m, 2H), 2.14-2.04 (m, 8H), 1.78-1.68 (m, 5H), 1.59-1.53 (m, 1H), 1.31-1.21 (m, 2H), 0.98-0.90 (m, 2H); MS (ESI): m/z 789.1 (M+H).

Example 109

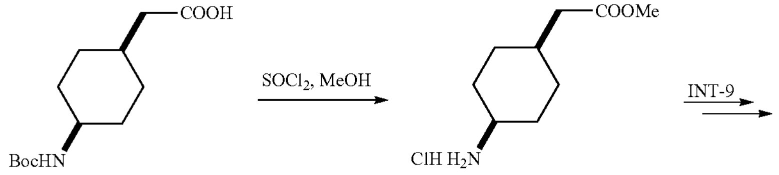

109a

-continued

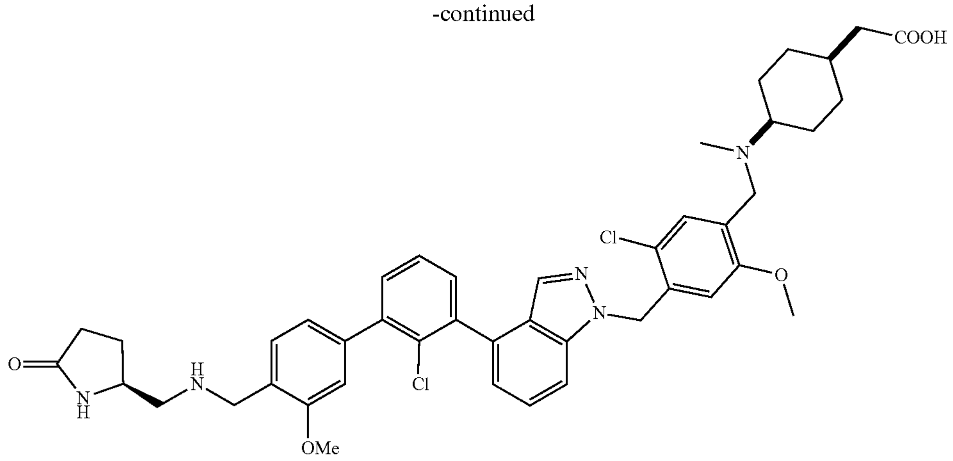

109

Starting from cis-(N-BOC-4-aminocyclohexyl) acetic acid, referring to the synthesis of compound INT-14, compound 109a is obtained. $^1$H NMR (500 MHz, DMSO-d6) δ 7.95 (brs, 3H), 3.57 (s, 3H), 3.18-3.08 (m, 1H), 2.27 (d, J=7.5 Hz, 2H), 1.95-1.86 (m, 1H), 1.69-1.56 (m, 4H), 1.54-1.38 (m, 4H).

Starting from compound 109a and compound INT-9, referring to the synthesis of compound 44, compound 109 is obtained. $^1$H NMR (500 MHz, DMSO-d6) δ 7.90 (s, 1H), 7.76 (d, J=8.5 Hz, 1H), 7.65 (s, 1H), 7.54-7.46 (m, 4H), 7.40 (d, J=7.5 Hz, 1H), 7.37 (s, 1H), 7.15 (d, J=7.0 Hz, 1H), 7.08-7.06 (m, 1H), 7.05-7.02 (m, 1H), 6.67 (s, 1H), 5.71 (s, 2H), 3.81 (s, 3H), 3.71 (d, J=3.0 Hz, 2H), 3.64-3.59 (m, 1H), 3.57 (s, 3H), 3.43 (s, 2H), 2.56-2.52 (m, 2H), 2.36-2.31 (m, 1H), 2.21-2.16 (m, 2H), 2.13-2.04 (m, 3H), 2.07 (s, 3H), 1.98-1.91 (m, 1H), 1.72-1.66 (m, 1H), 1.61-1.53 (m, 2H), 1.51-1.39 (m, 6H); MS (ESI): m/z 798.3 (M+H).

Example 110

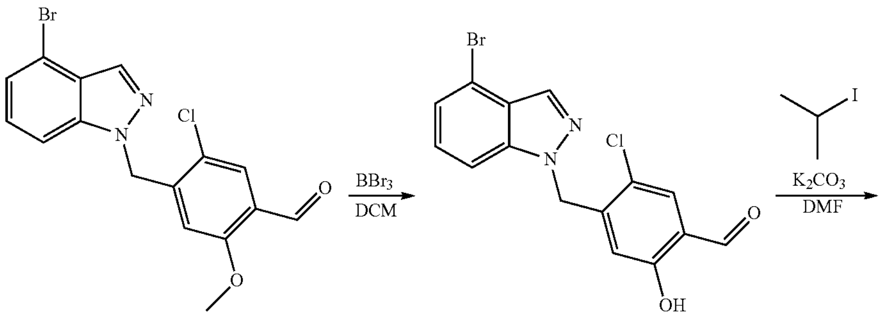

INT-8b 110a

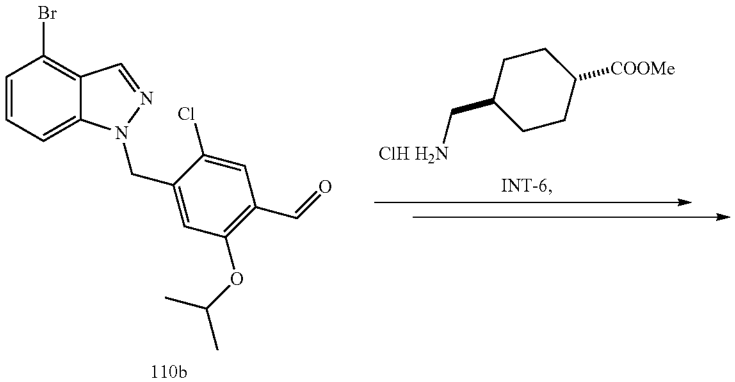

110b

-continued

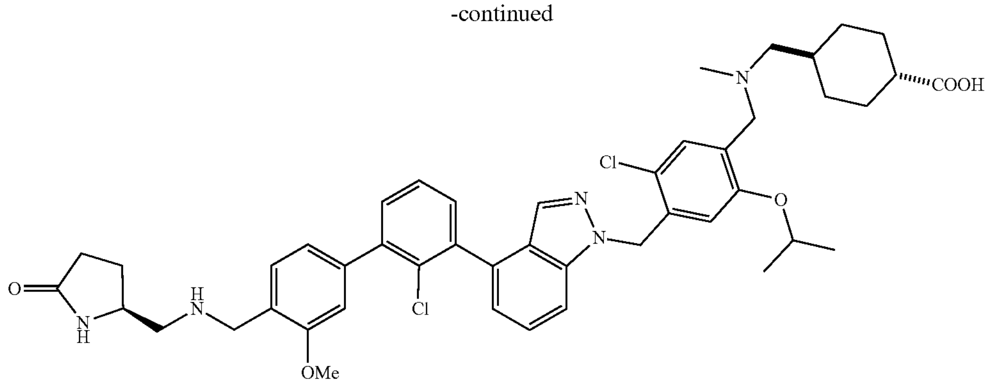

110

Under ice bath conditions, to dichloromethane (10 mL) solution with compound INT-8b (500 mg, 1.32 mmol) dissolved boron tribromide (IM in dichloromethane solution, 3.95 mL) was added dropwise. The reaction solution under the same conditions stirred for 1 hour. The reaction solution was quenched with ice water (30 mL), the resulting mixture was further stirred for half an hour. Aqueous phase was extracted (50 mL×2) with dichloromethane. The combined organic phase was washed with saturated salt solution (100 mL), dried with anhydrous sodium sulfate, and concentrated. The residue was separated by silica gel column chromatography to obtain white solid 110a (370 mg, yield: 76.8%). MS (ESI): m/z 365.2 (M+H).

Starting from compound 110a, referring to alkylation reaction step of compound INT-8[a], compound 110b is obtained. $^1$H NMR (500 MHz, DMSO-d6) δ 10.21 (s, 1H), 8.13 (s, 1H), 7.79 (d, J=8.3 Hz, 1H), 7.48-7.24 (m, 2H), 6.80 (s, 1H), 5.78 (s, 2H), 4.55-4.32 (m, 1H), 1.19 (d, J=6.0 Hz, 6H).

Starting from compound 110b, compound INT-6 and methyl 4-aminomethyl-cyclohexanecarboxylate hydrochloride, referring to compound INT-8 and compound 44 the synthesis of compound is obtained 110. $^1$H NMR (500 MHz, DMSO-d6) δ 7.92 (s, 1H), 7.74 (d, J=8.5 Hz, 1H), 7.64 (s, 1H), 7.54-7.45 (m, 4H), 7.43 (d, J=8.0 Hz, 1H), 7.35 (s, 1H), 7.15 (d, J=7.0 Hz, 1H), 7.12 (s, 1H), 7.08 (d, J=7.5 Hz, 1H), 6.41 (s, 1H), 5.72 (s, 2H), 4.20-4.12 (m, 1H), 3.86-3.82 (m, 2H), 3.84 (s, 3H), 3.71-3.66 (m, 1H), 3.33 (s, 2H), 2.73-2.63 (m, 2H), 2.14-2.06 (m, 9H), 1.87-1.77 (m, 4H), 1.72-1.68 (m, 1H), 1.48-1.39 (m, 1H), 1.30-1.22 (m, 2H), 1.05 (d, J=6.0 Hz, 6H), 0.86-0.76 (m, 2H); MS (ESI): m/z 826.3 (M+H).

Example 111

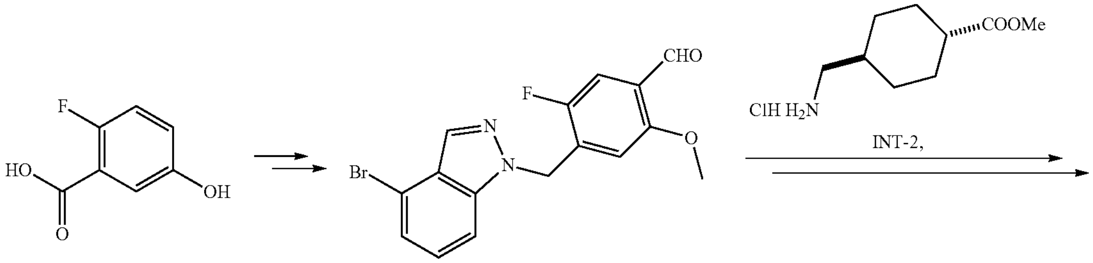

111a

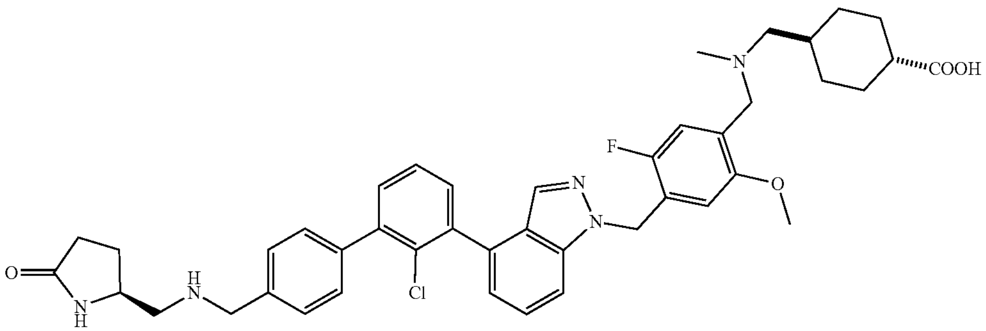

111

Starting from 2-fluoro-5-hydroxy benzoic acid, referring to the synthesis of compound INT-1c and compound INT-8b, compound 111a is obtained. MS (ESI): m/z 363.1 (M+H).

Starting from compound 111a, compound INT-2 and methyl 4-aminomethyl-cyclohexanecarboxylate hydrochloride, referring to compound INT-8 and compound 44 the synthesis of compound is obtained 111. $^1$H NMR (500 MHz, DMSO-d6) δ 7.86 (s, 1H), 7.79 (d, J=8.5 Hz, 1H), 7.67 (s, 1H), 7.53-7.49 (m, 2H), 7.48-7.42 (m, 6H), 7.18-7.12 (m, 2H), 6.88 (d, J=6.0 Hz, 1H), 5.69 (s, 2H), 3.80-3.72 (m, 2H), 3.66-3.60 (m, 1H), 3.65 (s, 3H), 3.36 (s, 2H), 2.56-2.53 (m, 2H), 2.14-2.07 (m, 6H), 2.09 (s, 3H), 1.89-1.78 (m, 4H), 1.73-1.66 (m, 1H), 1.50-1.40 (m, 1H), 1.31-1.22 (m, 2H), 0.85-0.76 (m, 2H); MS (ESI): m/z 752.3 (M+H).

Example 112

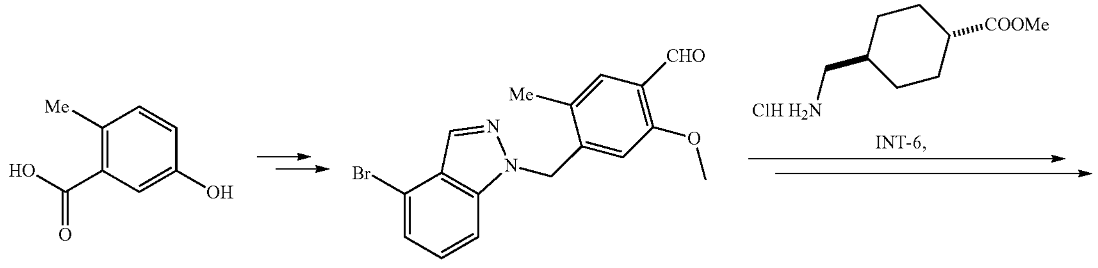

112a

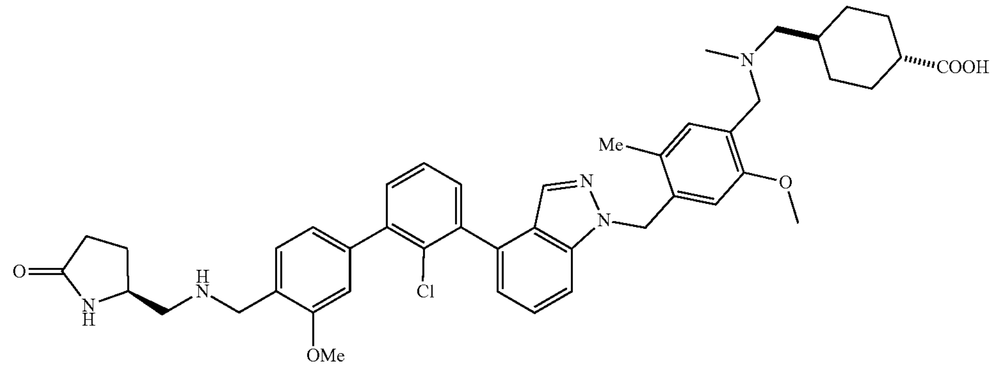

112

Starting from 5-hydroxy-2-methylbenzoic acid, referring to the synthesis of compound INT-1c and compound INT-8b, compound 112a is obtained. MS (ESI): m/z 359.2 (M+H).

Starting from compound 112a, compound INT-6 and methyl 4-aminomethyl-cyclohexanecarboxylate hydrochloride, referring to the synthesis of compound INT-8 and compound 44, compound 112 is obtained. $^1$H NMR (500 MHz, DMSO-d6) δ 7.89 (s, 1H), 7.75 (d, J=8.5 Hz, 1H), 7.66 (s, 1H), 7.55-7.46 (m, 4H), 7.44 (d, J=7.5 Hz, 1H), 7.15 (d, J=7.0 Hz, 1H), 7.12 (s, 2H), 7.09 (d, J=7.5 Hz, 1H), 6.60 (s, 1H), 5.66 (s, 2H), 3.88-3.82 (m, 2H), 3.85 (s, 3H), 3.72-3.67 (m, 1H), 3.57 (s, 3H), 3.43-3.40 (m, 2H), 2.67 (d, J=6.0 Hz, 2H), 2.25 (s, 3H), 2.18-2.04 (m, 9H), 1.89-1.80 (m, 4H), 1.76-1.68 (m, 1H), 1.55-1.45 (m, 1H), 1.32-1.23 (m, 2H), 0.86-0.75 (m, 2H); MS (ESI): m/z 778.4 (M+H).

Example 113

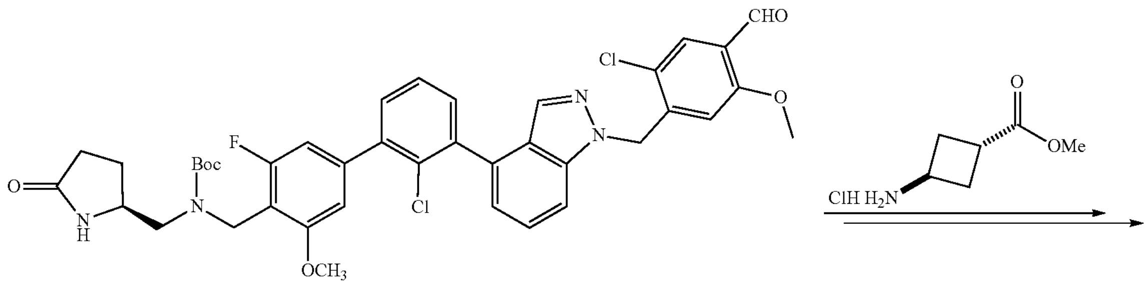

INT-16

-continued
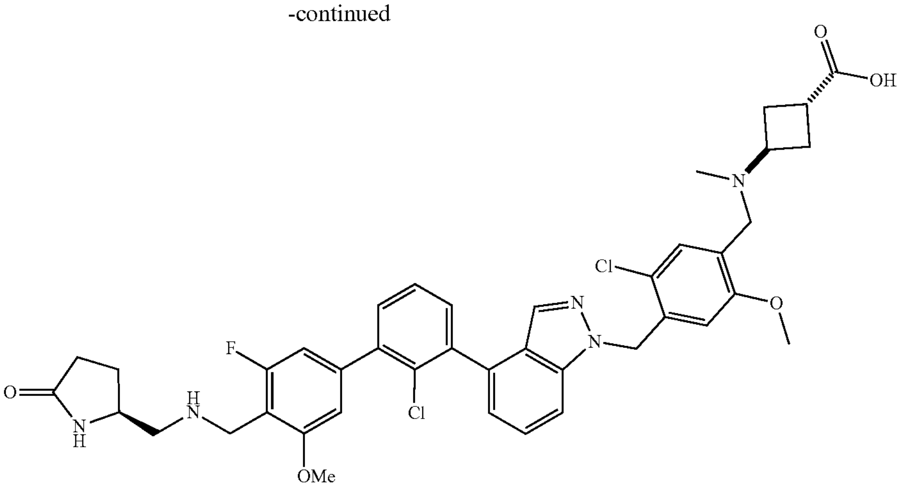
113
Starting from compound INT-16 and methyl trans-4-aminocyclobutanecarboxylate hydrochloride, referring to the synthesis of compound 101, compound 113 is obtained. $^1$H NMR (500 MHz, DMSO-d6) δ 7.93 (s, 1H), 7.76 (d, J=8.5 Hz, 1H), 7.62 (s, 1H), 7.56-7.45 (m, 4H), 7.34 (s, 1H), 7.15 (d, J=7.0 Hz, 1H), 7.02-6.93 (m, 2H), 6.68 (s, 1H), 5.72 (s, 2H), 3.86 (s, 3H), 3.83-3.72 (m, 2H), 3.62-3.58 (m, 1H), 3.57 (s, 3H), 3.27-3.25 (m, 2H), 3.06-2.97 (m, 1H), 2.87-2.78 (m, 1H), 2.56-2.52 (m, 2H), 2.22-2.15 (m, 2H), 2.14-1.99 (m, 5H), 1.92 (s, 3H), 1.69-1.60 (m, 1H); MS (ESI): m/z 774.2 (M+H).
Example 114
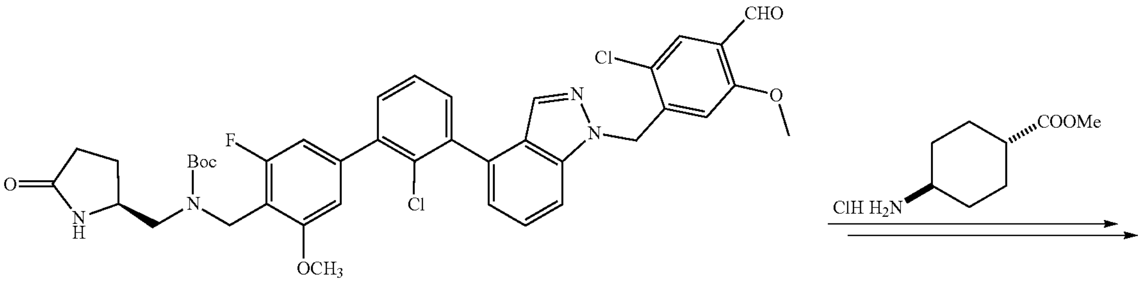
INT-16
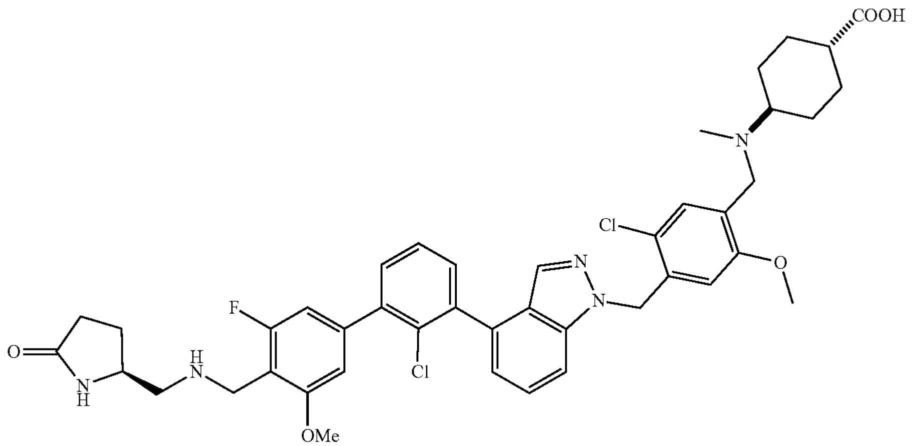
114

Starting from compound INT-16 and trans-4-methyl aminocyclohexanate hydrochloride, referring to the synthesis of compound 101, compound 114 is obtained. $^1$H NMR (500 MHz, DMSO-d6) δ 7.92 (s, 1H), 7.76 (d, J=8.5 Hz, 1H), 7.63 (s, 1H), 7.55-7.47 (m, 4H), 7.36 (s, 1H), 7.15 (d, J=7.0 Hz, 1H), 6.98-6.93 (m, 2H), 6.67 (s, 1H), 5.71 (s, 2H), 3.86 (s, 3H), 3.77-3.70 (m, 2H), 3.60-3.56 (m, 1H), 3.57 (s, 3H), 3.45 (brs, 2H), 2.52-2.50 (m, 2H), 2.40-2.35 (m, 1H), 2.12-2.03 (m, 7H), 1.94-1.87 (m, 2H), 1.81-1.75 (m, 2H), 1.69-1.60 (m, 1H), 1.32-1.23 (m, 4H); MS (ESI): m/z 802.2 (M+H).
Example 115
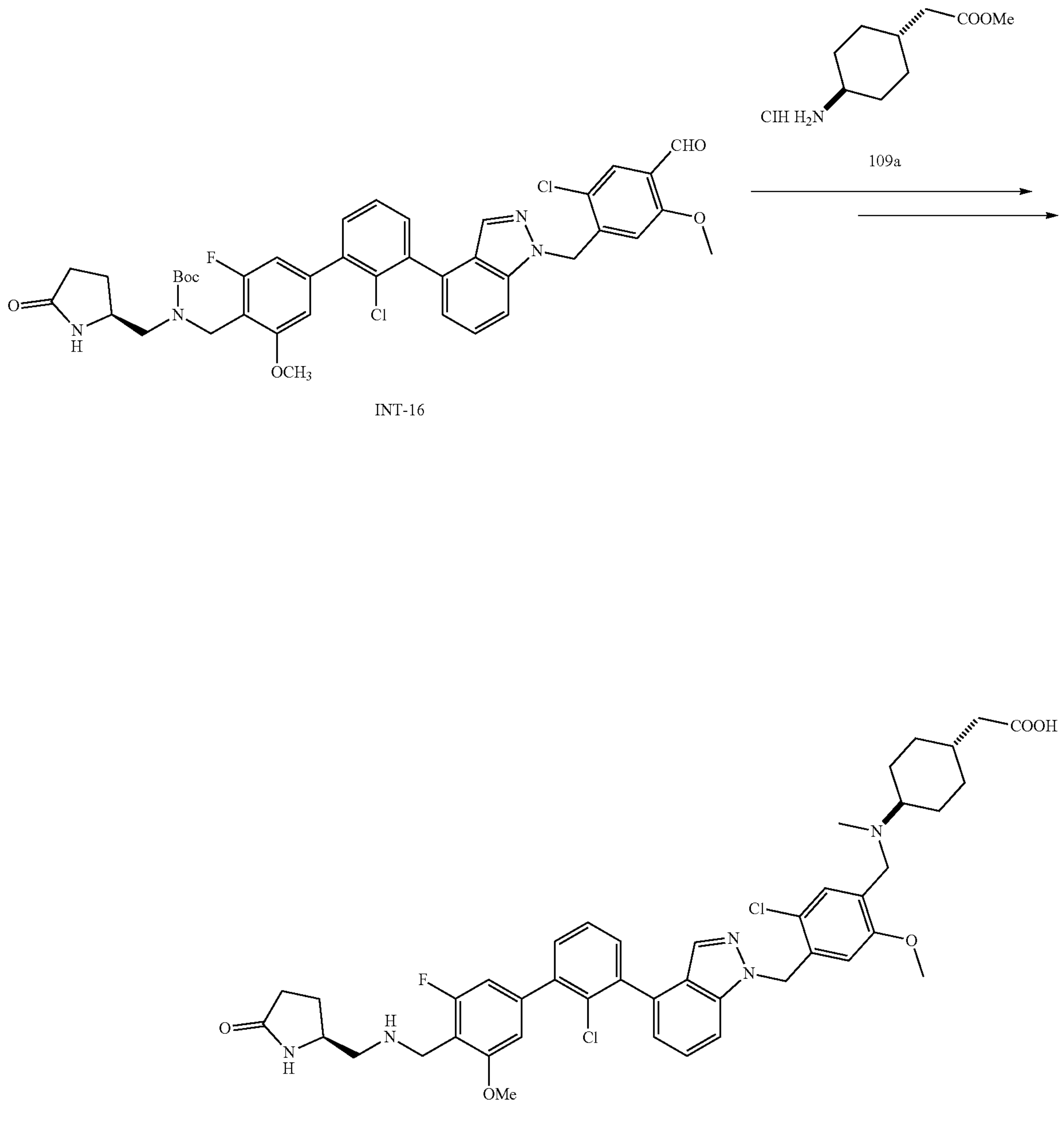
INT-16
109a
115

Starting from compound INT-16 and compound 109a, referring to the synthesis of compound 101, compound 115 is obtained. $^1$H NMR (500 MHz, DMSO-d6) δ 7.92 (s, 1H), 7.76 (d, J=8.5 Hz, 1H), 7.63 (s, 1H), 7.55-7.45 (m, 4H), 7.36 (s, 1H), 7.15 (d, J=7.0 Hz, 1H), 6.99-6.93 (m, 2H), 6.67 (s, 1H), 5.71 (s, 2H), 3.86 (s, 3H), 3.78-3.69 (m, 2H), 3.60-3.58 (m, 1H), 3.57 (s, 3H), 3.45 (s, 2H), 2.53-2.50 (m, 2H), 2.36-2.31 (m, 1H), 2.09 (s, 3H), 2.07-2.02 (m, 5H), 1.78-1.70 (m, 4H), 1.68-1.60 (m, 1H), 1.59-1.50 (m, 1H), 1.31-1.18 (m, 2H), 0.98-0.86 (m, 2H); MS (ESI): m/z 816.2 (M+H).

Example 116

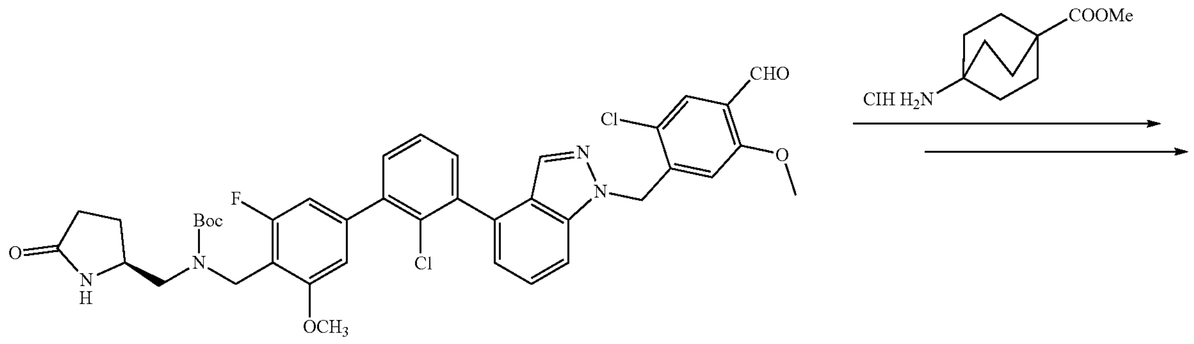

INT-16

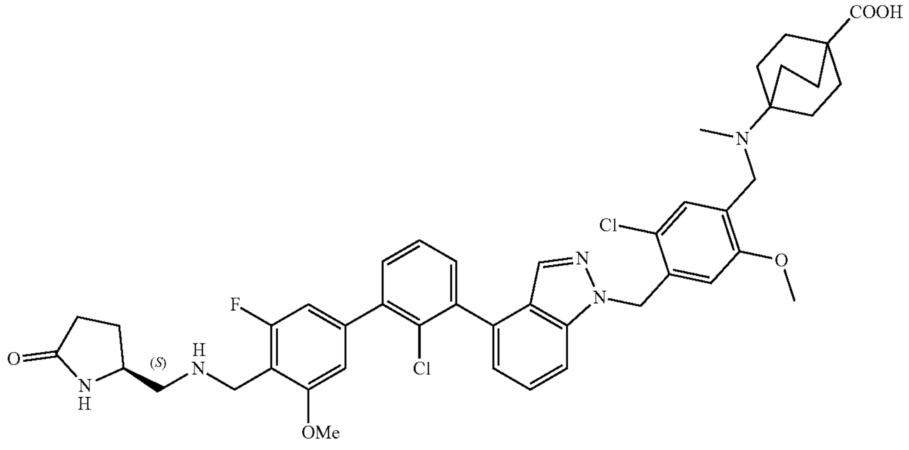

116

Starting from compound INT-16 and 4-aminobicyclo[2.2.2]octane-1-carboxylic acid methyl ester hydrochloride, referring to the synthesis of compound 101 compound 116 is obtained. $^1$H NMR (500 MHz, DMSO-d6) δ 7.97-7.88 (m, 1H), 7.76 (d, J=8.5 Hz, 1H), 7.63 (s, 1H), 7.55-7.47 (m, 4H), 7.38 (s, 1H), 7.15 (d, J=7.0 Hz, 1H), 6.98-6.94 (m, 2H), 6.66 (s, 1H), 5.70 (s, 2H), 3.85 (s, 3H), 3.77-3.69 (m, 2H), 3.65-3.59 (m, 1H), 3.57 (s, 3H), 3.41 (s, 2H), 2.60-2.54 (m, 2H), 2.14-2.03 (m, 3H), 1.99 (s, 3H), 1.76-1.69 (m, 6H), 1.67-1.61 (m, 1H), 1.58-1.52 (m, 6H); MS (ESI): m/z 828.1 (M+H).

Example 117

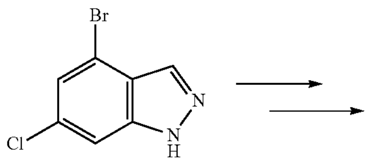

-continued
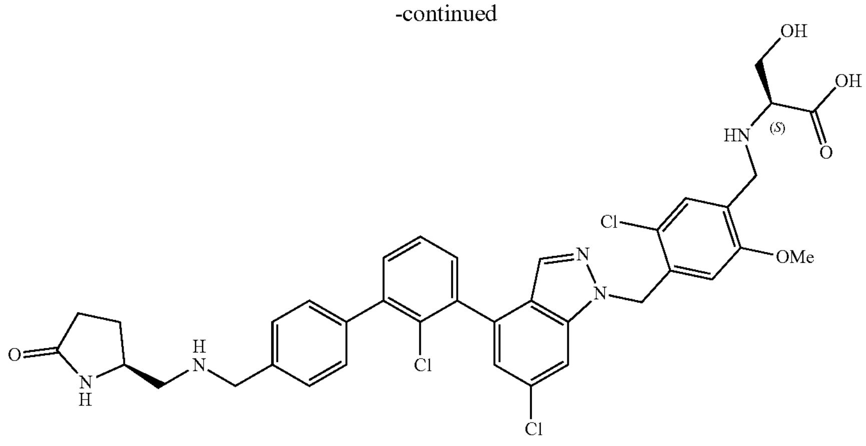
117
Starting from 4-bromo-6-chloro indazole, referring to the synthesis of compound INT-8 and compound 30, compound 117 is obtained. $^1$H NMR (500 MHz, DMSO-d6) δ 8.03 (s, 1H), 7.93 (s, 1H), 7.66 (s, 1H), 7.55-7.44 (m, 8H), 7.24 (s, 1H), 6.78 (s, 1H), 5.74 (brs, 2H), 3.91-3.85 (m, 1H), 3.79-3.76 (m, 2H), 3.69-3.57 (m, 7H), 3.15-3.08 (m, 1H), 2.57-2.55 (m, 2H), 2.15-2.07 (m, 3H), 1.74-1.66 (m, 1H); MS (ESI): m/z 736.0 (M+H).
Example 118
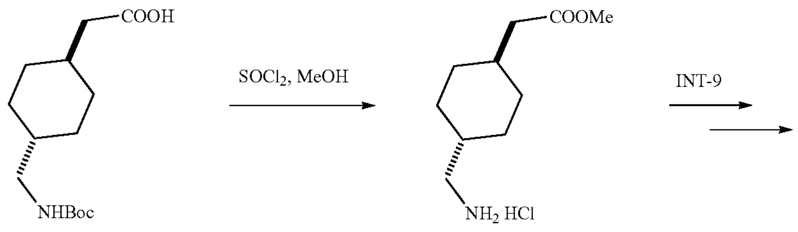
118a 118b
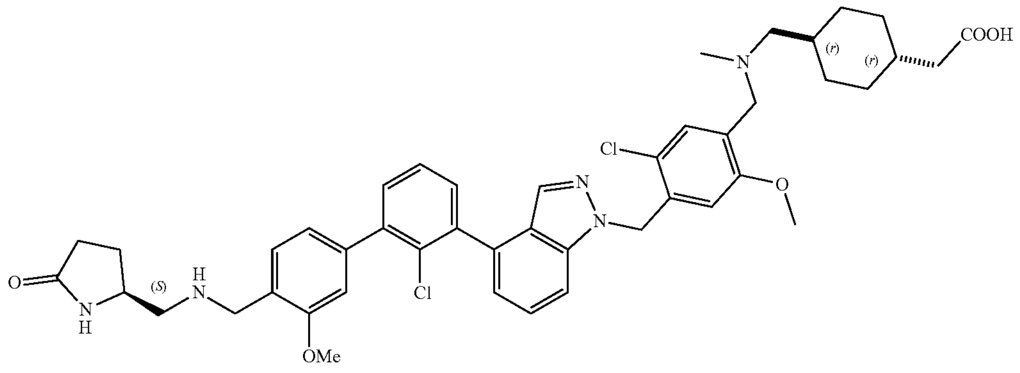
118

Starting from compound 118a, referring to the synthesis of compound INT-14, compound 118b is obtained.

Starting from compound 118b and compound INT-9, referring to the synthesis of compound 44, compound 118 is obtained. $^{1}H$ NMR (500 MHz, DMSO-d6) δ 7.90 (s, 1H), 7.75 (d, J=8.5 Hz, 1H), 7.65 (s, 1H), 7.53-7.45 (m, 4H), 7.40 (d, J=7.5 Hz, 1H), 7.36 (s, 1H), 7.15 (d, J=7.5 Hz, 1H), 7.08-7.06 (m, 1H), 7.04 (d, J=8.5 Hz, 1H), 6.67 (s, 1H), 5.71 (s, 2H), 3.81 (s, 3H), 3.75-3.67 (m, 2H), 3.65-3.59 (m, 1H), 3.56 (s, 3H), 3.34 (s, 2H), 2.56-2.52 (m, 2H), 2.14-2.03 (m, 10H), 1.80-1.73 (m, 2H), 1.72-1.65 (m, 3H), 1.58-1.53 (m, 1H), 1.44-1.36 (m, 1H), 0.97-0.86 (m, 2H), 0.83-0.75 (m, 2H); MS (ESI): m/z 812.2 (M+H).

Example 119

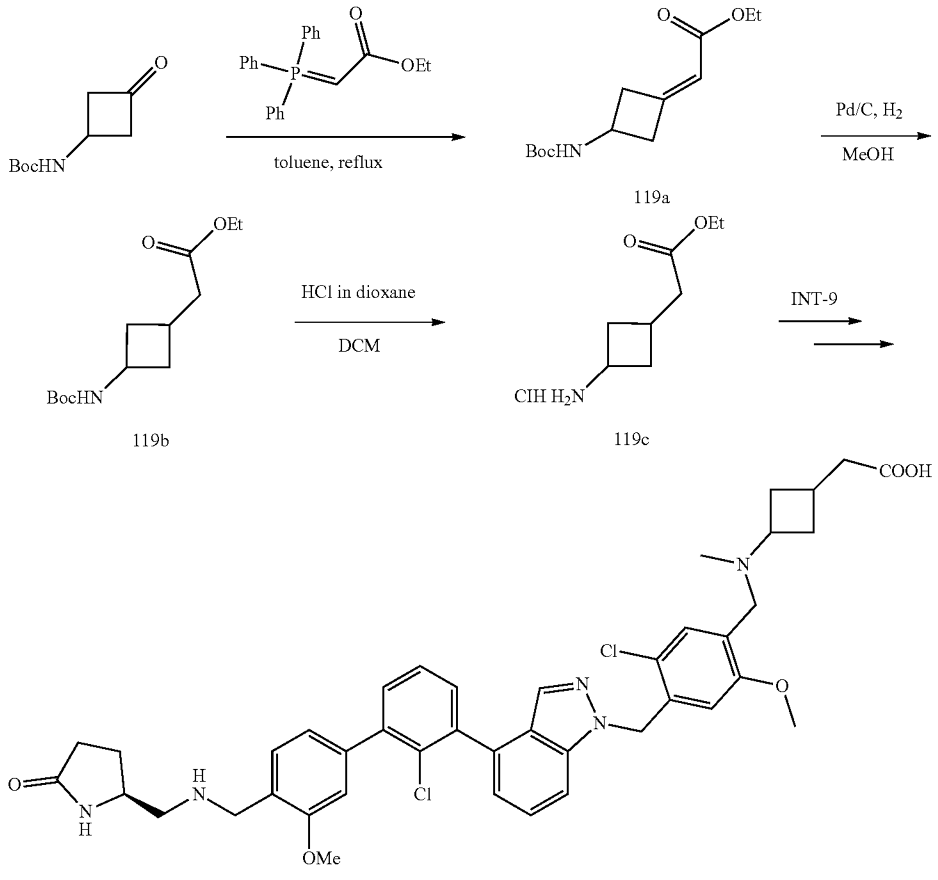

119a

119b

119c

119

In a nitrogen atmosphere, toluene (15 mL) solution with tert-butyl 3-oxocyclobutylcarbamate (1.0 g, 5.4 mmol) and ethoxyformylmethylenetriphenylphosphine (2.1 g, 5.9 mmol) dissolved was stirred for 6 hours at 110° C. To the reaction solution water (100 mL) and ethyl acetate (100 mL) were added. The water phase was further extracted with ethyl acetate (100 mL×2). The combined organic phase was washed with saturated salt solution (200 mL), dried with anhydrous sodium sulfate, and concentrated. The residue was silica gel column chromatography to obtain white solid 119a (1.1 g, yield: 79.8%). MS (ESI): m/z 256.3 (M+H).

Under hydrogen atmosphere, methanol (15 mL) solution with compound 119a (1.1 g, 4.3 mmol), Pd (10% w/w adsorbed on activated carbon, 150 mg) mixed was stirred overnight at 25° C. The reaction solution was filtered, The filtrate concentrated to obtain white solid 119b (1.1 g, yield: 99.8%). MS (ESI): m/z 258.3 (M+H).

In dichloromethane (15 mL) solution with compound 119b (1.1 g, 4.3 mmol) dissolved hydrochloric acid (4M in 1, 4-dioxane, 5.4 mL) were added. The resulting reaction solution at room temperature was stirred for 2 hours. The reaction solution was concentrated to obtain colorless oily matter 119c (0.83 g, yield: 99.5%).

Starting from compound 119c and compound INT-9, referring to the synthesis of compound 44, compound 119 is obtained (Judging from NMR, the compound should be a mixture of cis and trans isomers in a ratio of 6:4). $^{1}H$ NMR (500 MHz, DMSO-d6) δ 7.92 (s, 1H), 7.77 (d, J=8.5 Hz, 1H), 7.68 (s, 1H), 7.55-7.47 (m, 4H), 7.42 (d, J=7.0 Hz, 1H), 7.34 (d, J=8.5 Hz, 1H), 7.17 (d, J=7.0 Hz, 1H), 7.09 (d, J=1.5 Hz, 1H), 7.06 (dd, J=7.5, 1.5 Hz, 1H), 6.69 (s, 1H), 5.73 (s, 2H), 3.83 (s, 3H), 3.77-3.69 (m, 2H), 3.66-3.61 (m, 1H), 3.58 (s, 3H), 3.25 (s, 2H), 3.03-2.95 (m, 0.4H), 2.74-2.69 (m, 0.6H), 2.58-2.54 (m, 2H), 2.43-2.35 (m, 1H), 2.31-2.27 (m, 1.2H), 2.23-2.06 (m, 5H), 2.04-1.97 (m, 0.8H), 1.91 (s, 3H), 1.80-1.73 (m, 0.8H), 1.72-1.64 (m, 1H), 1.51-1.41 (m, 1.2H); MS (ESI): m/z 770.0 (M+H).
Example 120
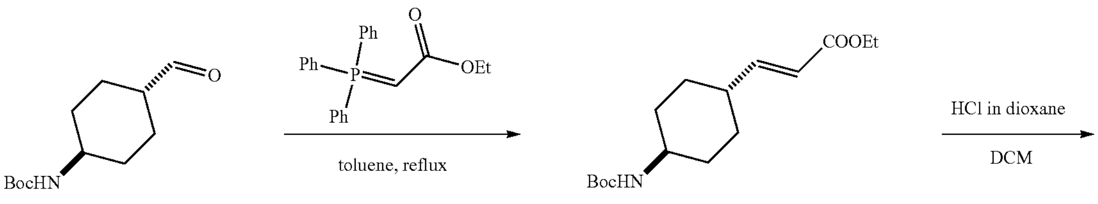
120a
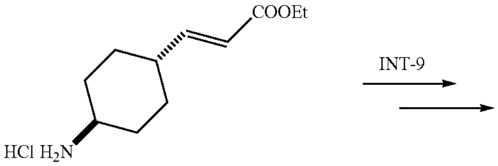
120b
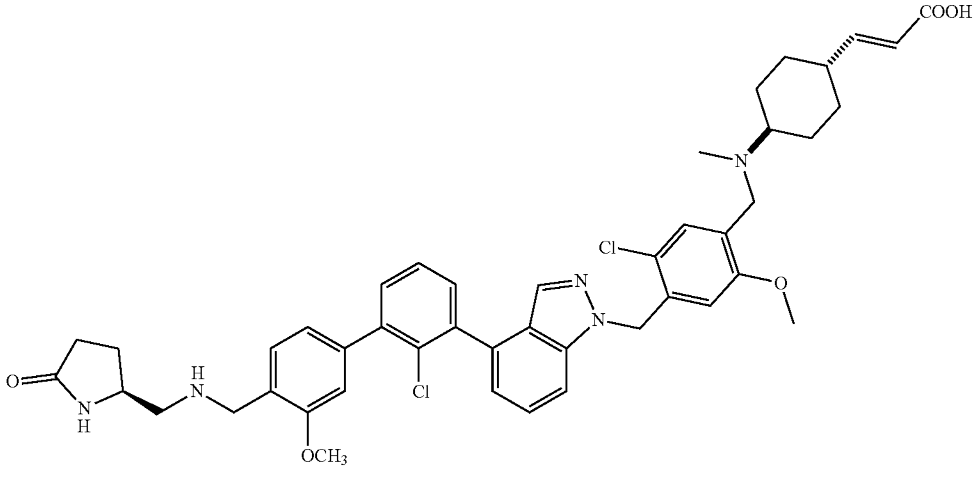
120

Starting from trans-4-(Boc-amino)cyclohexylcarbaldehyde, referring to compound 119a and compound 119c the synthesis of compound is obtained 120b. MS (ESI): m/z 198.6 (M+H).

Starting from compound 120b and compound INT-9, referring to the synthesis of compound 44, compound 120 is obtained. $^1$H NMR (500 MHz, DMSO-d6) δ 7.91 (s, 1H), 7.78 (d, J=8.5 Hz, 1H), 7.66 (s, 1H), 7.56-7.47 (m, 4H), 7.42 (d, J=7.7 Hz, 1H), 7.39 (s, 1H), 7.17 (d, J=7.0 Hz, 1H), 7.10 (s, 1H), 7.09-7.05 (m, 1H), 6.77-6.71 (m, 1H), 6.69 (s, 1H), 5.73 (s, 2H), 5.72-5.66 (m, 1H), 3.84 (s, 3H), 3.82-3.73 (m, 2H), 3.68-3.63 (m, 1H), 3.59 (s, 3H), 3.53-3.42 (m, 2H), 2.61-2.56 (m, 2H), 2.44-2.36 (m, 1H), 2.17-2.06 (m, 7H), 1.86-1.75 (m, 4H), 1.75-1.66 (m, 1H), 1.40-1.27 (m, 2H), 1.18-1.08 (m, 2H); MS (ESI): m/z 810.2 (M+H).

Example 121

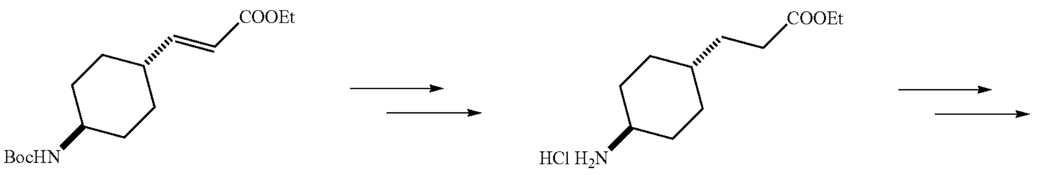

120a

121a

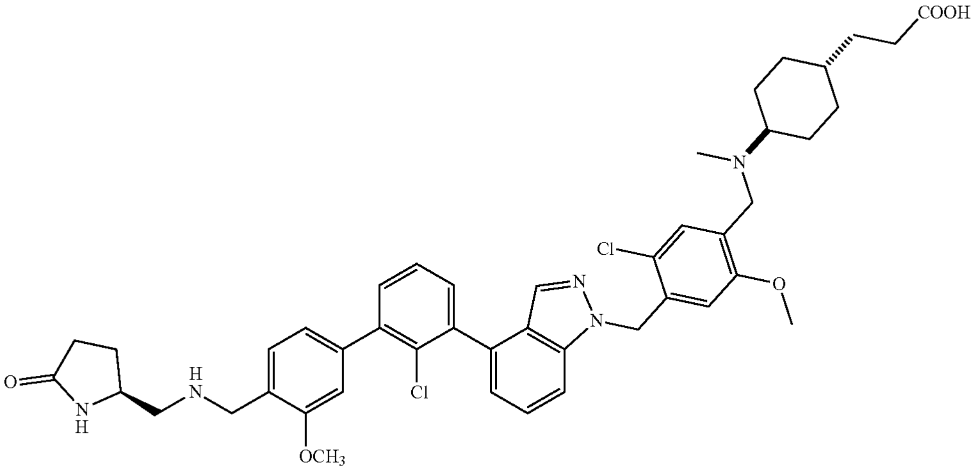

121

Starting from compound 120a, referring to the synthesis of compound 119, compound 121 is obtained. $^{1}$H NMR (500 MHz, DMSO-d6) δ 7.91 (s, 1H), 7.77 (d, J=8.5 Hz, 1H), 7.67 (s, 1H), 7.56-7.46 (m, 4H), 7.41 (d, J=7.7 Hz, 1H), 7.38 (s, 1H), 7.17 (d, J=7.0 Hz, 1H), 7.08 (d, J=1.7 Hz, 1H), 7.08-7.04 (m, 1H), 6.68 (s, 1H), 5.72 (s, 2H), 3.83 (s, 3H), 3.77-3.69 (m, 2H), 3.66-3.61 (m, 1H), 3.58 (s, 3H), 3.46 (brs, 2H), 2.57-2.54 (m, 2H), 2.38-2.30 (m, 1H), 2.18 (t, J=7.5 Hz, 2H), 2.15-2.05 (m, 6H), 1.81-1.65 (m, 5H), 1.38 (t, J=7.5 Hz, 2H), 1.29-1.17 (m, 2H), 1.17-1.08 (m, 1H), 0.92-0.82 (m, 2H); MS (ESI): m/z 812.2 (M+H).
Example 122 and 123
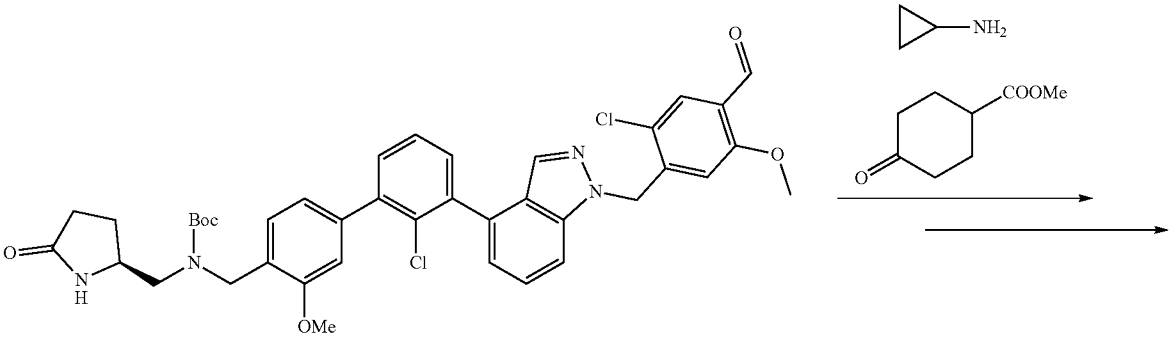
INT-9
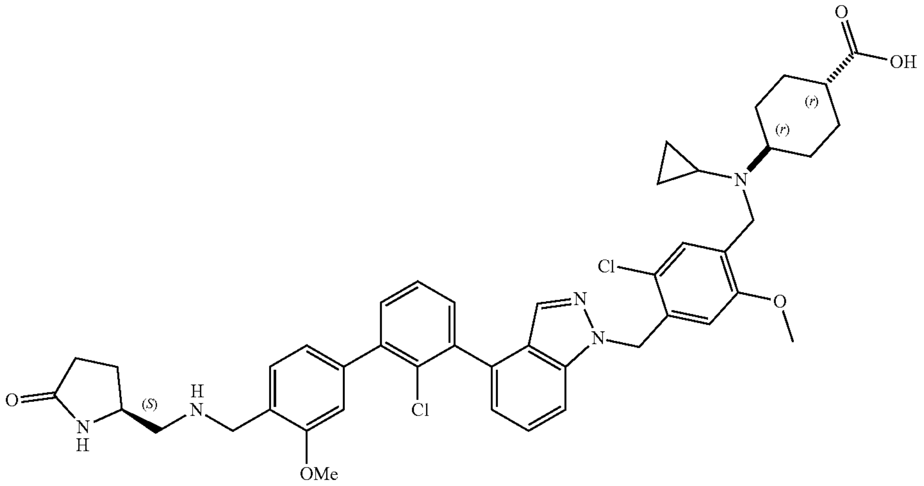
122
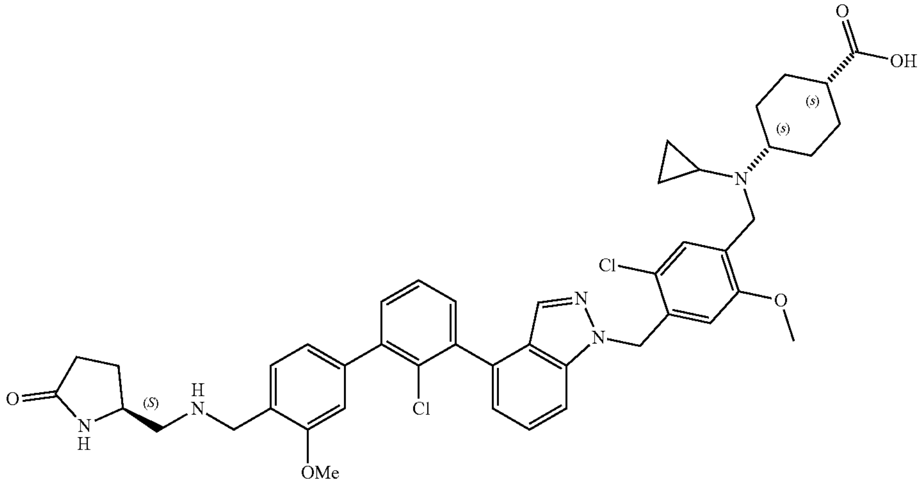
123

Starting from compound INT-9, cyclopropylamine and methyl 4-oxocyclohexanecarboxylate, referring to the synthesis of compound 44, compound 122 and compound 123 are obtained.

Compound 122: $^1$H NMR (500 MHz, DMSO-d6) δ 7.91 (s, 1H), 7.76 (d, J=8.5 Hz, 1H), 7.67 (s, 1H), 7.55-7.45 (m, 4H), 7.41 (d, J=7.5 Hz, 1H), 7.31 (s, 1H), 7.17 (d, J=7.0 Hz, 1H), 7.09-7.07 (m, 1H), 7.07-7.03 (m, 1H), 6.66 (s, 1H), 5.71 (s, 2H), 3.83 (s, 3H), 3.73-3.72 (m, 2H), 3.68 (s, 2H), 3.65-3.60 (m, 1H), 3.59 (s, 3H), 2.56-2.53 (m, 2H), 2.46-2.42 (m, 1H), 2.14-2.03 (m, 5H), 1.93-1.87 (m, 2H), 1.83-1.78 (m, 2H), 1.72-1.67 (m, 1H), 1.38-1.30 (m, 2H), 1.26-1.20 (m, 2H), 0.40-0.35 (m, 2H), 0.26-0.17 (m, 2H); MS (ESI): m/z 810.2 (M+H).

Compound 123: $^1$H NMR (500 MHz, DMSO-d6) δ 7.89 (s, 1H), 7.74 (d, J=8.5 Hz, 1H), 7.65 (s, 1H), 7.52-7.45 (m, 4H), 7.40 (d, J=7.5 Hz, 1H), 7.29 (s, 1H), 7.15 (d, J=7.0 Hz, 1H), 7.07-7.06 (m, 1H), 7.05-7.02 (m, 1H), 6.63 (s, 1H), 5.70 (s, 2H), 3.81 (s, 3H), 3.72-3.70 (m, 2H), 3.68-3.66 (m, 1H), 3.64 (s, 2H), 3.57 (s, 3H), 2.55-2.52 (m, 2H), 2.45-2.42 (m, 1H), 2.13-2.03 (m, 5H), 1.70-1.65 (m, 1H), 1.60-1.55 (m, 2H), 1.47-1.40 (m, 2H), 1.31-1.25 (m, 4H), 0.37-0.32 (m, 2H), 0.22-0.17 (m, 2H); MS (ESI): m/z 810.2 (M+H).

Example 124

124

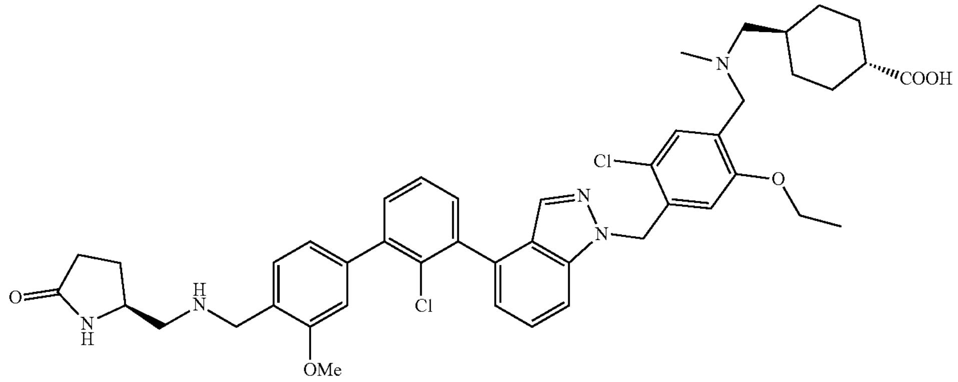

Referring to the synthesis of compound 110, isopropyl iodide is replaced with iodoethane, compound 124 is obtained. $^1$H NMR (500 MHz, DMSO-d6) δ 7.92 (s, 1H), 7.76 (d, J=8.5 Hz, 1H), 7.68 (s, 1H), 7.55-7.47 (m, 4H), 7.42 (d, J=7.7 Hz, 1H), 7.37 (s, 1H), 7.17 (d, J=7.0 Hz, 1H), 7.09 (d, J=1.6 Hz, 1H), 7.08-7.05 (m, 1H), 6.59 (s, 1H), 5.73 (s, 2H), 3.83 (s, 3H), 3.78 (q, J=7.0 Hz, 2H), 3.75-3.71 (m, 2H), 3.65-3.61 (m, 1H), 3.36 (brs, 2H), 2.56-2.53 (m, 2H), 2.14-2.03 (m, 6H), 2.08 (s, 3H), 1.89-1.80 (m, 4H), 1.72-1.66 (m, 1H), 1.50-1.42 (m, 1H), 1.29-1.24 (m, 2H), 1.18 (t, J=7.0 Hz, 3H), 0.85-0.79 (m, 2H); MS (ESI): m/z 812.2 (M+H).

Example 125

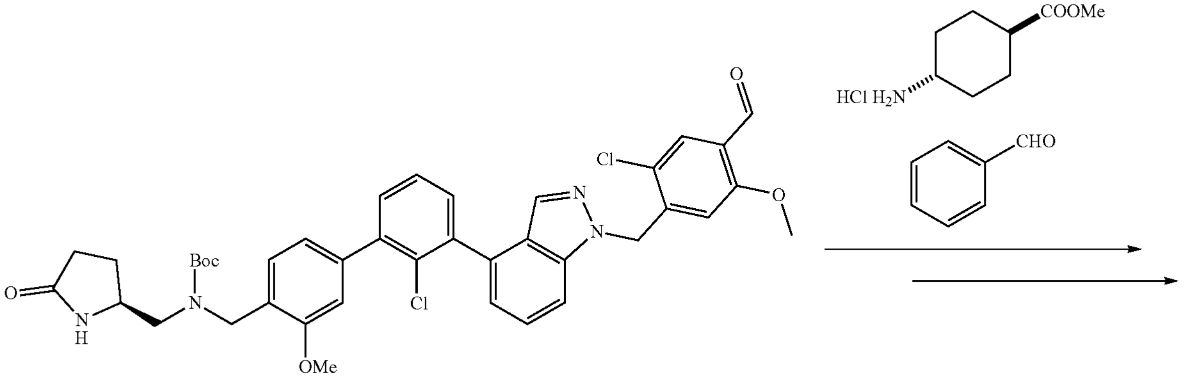

INT-9

-continued
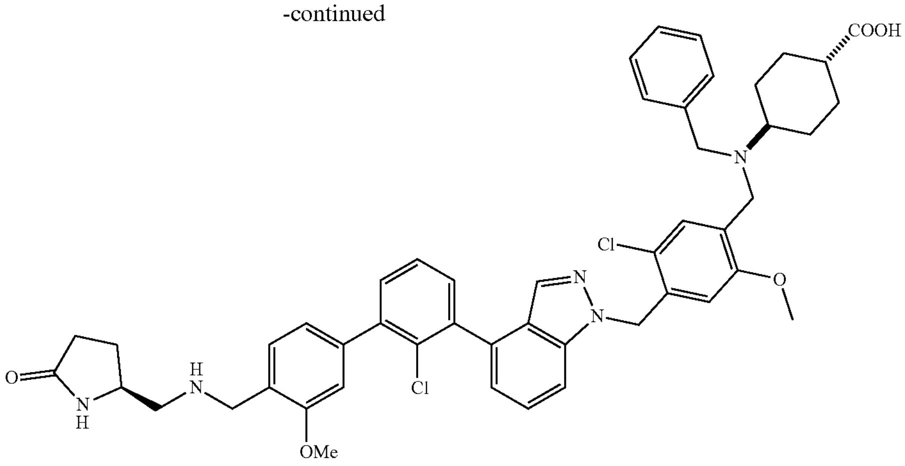
125
Starting from compound INT-9, trans-4-methyl aminocyclohexanate hydrochloride and benzaldehyde, referring to the synthesis of compound 44, compound 125 is obtained. $^1$H NMR (500 MHz, DMSO-d6) δ 7.88 (s, 1H), 7.74 (d, J=8.5 Hz, 1H), 7.65 (s, 1H), 7.53-7.43 (m, 4H), 7.44 (s, 1H), 7.40 (d, J=7.5 Hz, 1H), 7.30-7.23 (m, 4H), 7.22-7.13 (m, 2H), 7.08-7.06 (m, 1H), 7.05-7.02 (m, 1H), 6.62 (s, 1H), 5.68 (s, 2H), 3.81 (s, 3H), 3.77-3.70 (m, 2H), 3.66-3.61 (m, 1H), 3.57 (s, 2H), 3.54 (s, 3H), 3.51 (s, 2H), 2.59-2.54 (m, 2H), 2.41-2.36 (m, 1H), 2.14-2.04 (m, 4H), 1.94-1.87 (m, 2H), 1.84-1.79 (m, 2H), 1.71-1.65 (m, 1H), 1.41-1.32 (m, 2H), 1.20-1.11 (m, 2H); MS (ESI): m/z 860.1 (M+H).
Example 126
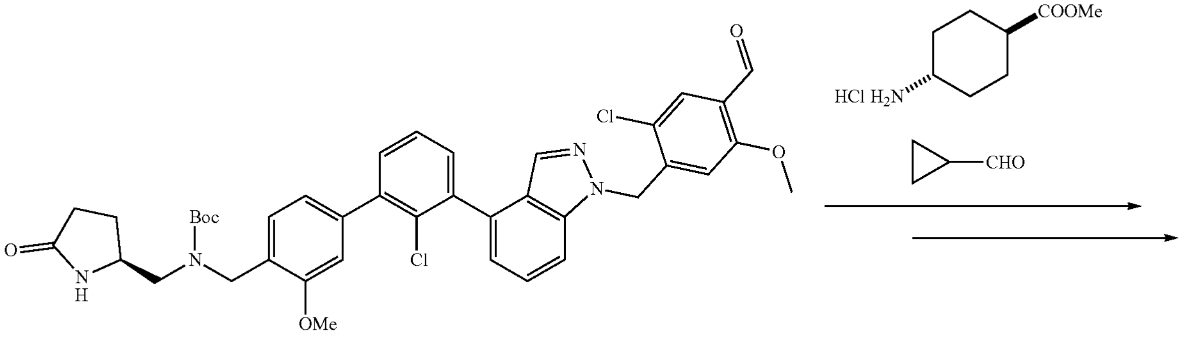
INT-9
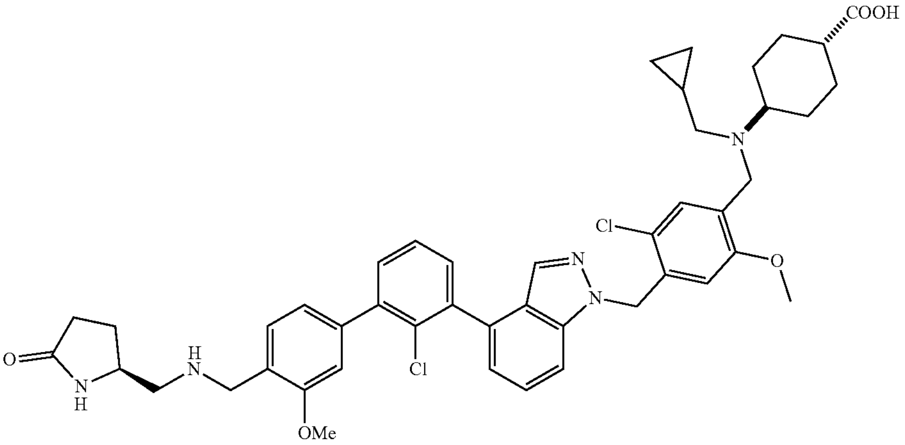
126

Starting from compound INT-9, trans-4-methyl aminocyclohexanate hydrochloride and cyclopropanecarbaldehyde, referring to the synthesis of compound 44, compound 126 is obtained. $^1$H NMR (500 MHz, DMSO-d6) δ 7.91 (s, 1H), 7.77 (d, J=8.5 Hz, 1H), 7.67 (s, 1H), 7.56 (s, 1H), 7.55-7.46 (m, 4H), 7.41 (d, J=7.5 Hz, 1H), 7.17 (d, J=7.0 Hz, 1H), 7.10-7.08 (m, 1H), 7.08-7.03 (m, 1H), 6.67 (s, 1H), 5.72 (s, 3H), 3.83 (s, 3H), 3.76-7.68 (m, 2H), 3.66-3.62 (m, 1H), 3.59 (s, 3H), 3.55 (s, 2H), 2.56-2.53 (m, 2H), 2.32 (d, J=6.0 Hz, 2H), 2.15-2.05 (m, 4H), 1.93-1.88 (m, 2H), 1.80-1.73 (m, 2H), 1.72-1.66 (m, 1H), 1.30-1.21 (m, 5H), 0.75-0.69 (m, 1H), 0.37-0.31 (m, 2H), 0.03-0.00 (m, 2H); MS (ESI): m/z 824.1 (M+H).

Example 127

127

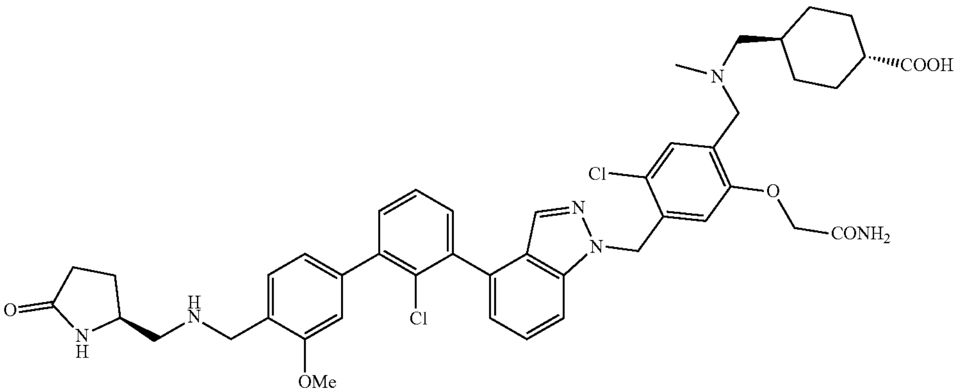

Referring to the synthesis of compound 110, isopropyl iodide is replaced with 2-bromoacetamide, compound 127 is obtained. $^1$H NMR (500 MHz, DMSO-d6) δ 7.87 (d, J=1.0 Hz, 1H), 7.73 (d, J=8.5 Hz, 1H), 7.65 (s, 1H), 7.54 (s, 1H), 7.51-7.47 (m, 4H), 7.40 (d, J=7.5 Hz, 1H), 7.37 (s, 1H), 7.34 (s, 1H), 7.15 (d, J=7.0 Hz, 1H), 7.07 (d, J=1.5 Hz, 1H), 7.06-7.02 (m, 1H), 6.79 (s, 1H), 5.68 (s, 2H), 4.28 (s, 2H), 3.81 (s, 3H), 3.72 (d, J=3.0 Hz, 2H), 3.64-3.61 (m, 1H), 3.43 (s, 2H), 2.58-2.55 (m, 2H), 2.15-2.09 (m, 6H), 2.08 (s, 3H), 1.83-1.76 (m, 4H), 1.69-1.66 (m, 1H), 1.46-1.43 (m, 1H), 1.26-1.22 (m, 2H), 0.83-0.78 (m, 2H); MS (ESI): m/z 841.2 (M+H).

Example 128

128

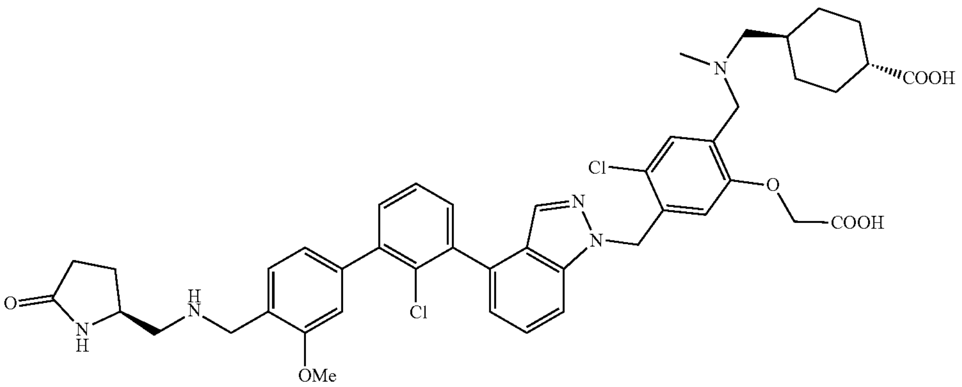

Referring to the synthesis of compound 110, isopropyl iodide is replaced with 2-bromoacetic acid tert-butyl ester, compound 128 is obtained. $^1$H NMR (500 MHz, DMSO-d6) δ 7.87 (s, 1H), 7.73 (d, J=8.5 Hz, 1H), 7.67 (s, 1H), 7.51-7.46 (m, 4H), 7.42-7.37 (m, 2H), 7.14 (d, J=7.0 Hz, 1H), 7.07 (d, J=1.5 Hz, 1H), 7.06-7.01 (m, 1H), 6.79 (s, 1H), 5.65 (s, 2H), 4.09 (brs, 2H), 3.81 (s, 3H), 3.73-3.69 (m, 2H), 3.63-3.60 (m, 1H), 3.41 (s, 2H), 2.54-2.52 (m, 2H), 2.33-2.28 (m, 1H), 2.20 (s, 3H), 2.12-2.05 (m, 5H), 1.86-1.80 (m, 4H), 1.71-1.66 (m, 1H), 1.59-1.50 (m, 1H), 1.29-1.23 (m, 2H), 0.87-0.80 (m, 2H); MS (ESI): m/z 843.2 (M+H).
Example 129
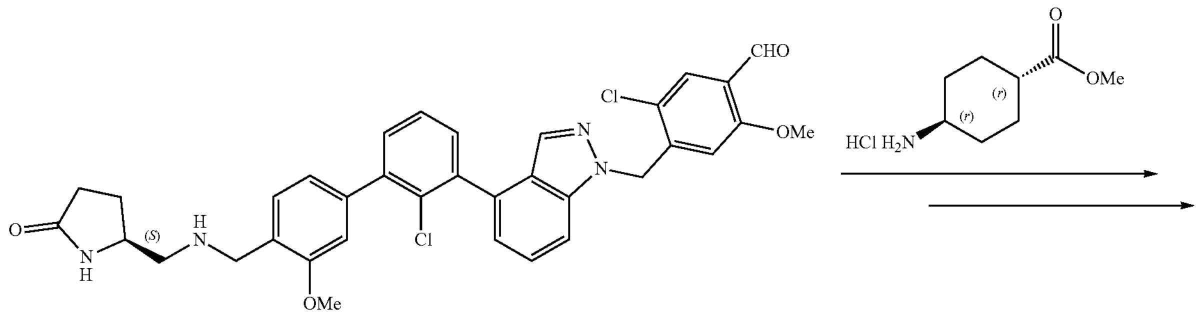
INT-9
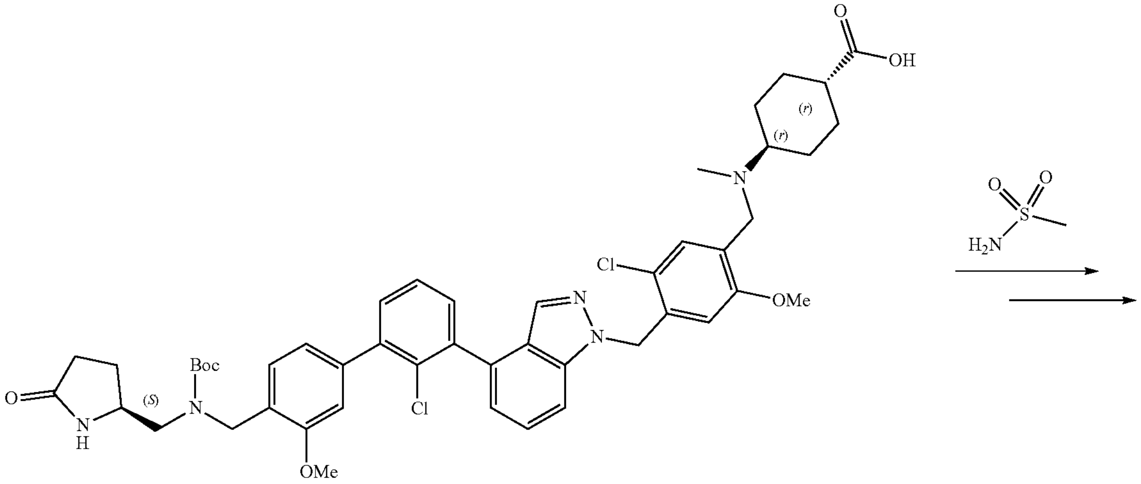
129a
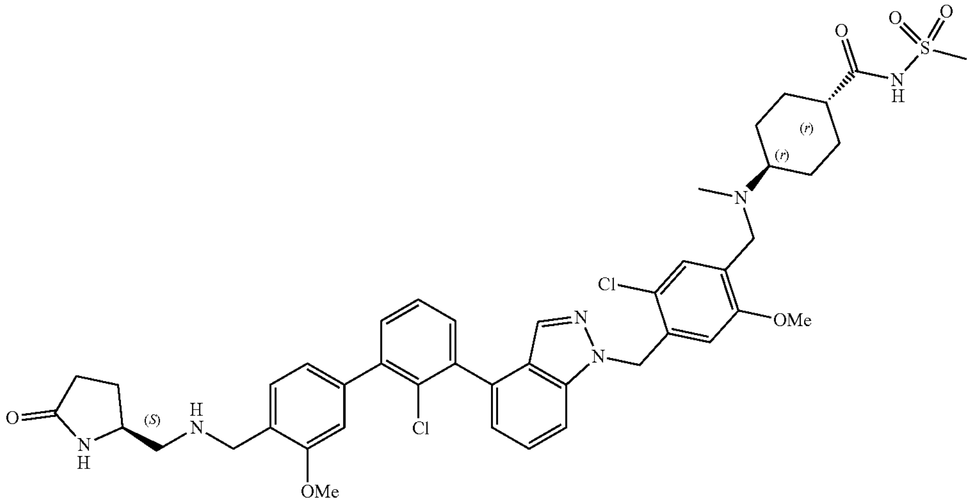
129

Starting from compound INT-9 and trans-4-methyl aminocyclohexanate hydrochloride, referring to the synthesis of compound 44 (last step Boc deprotection not included), compound 129a is obtained. MS (ESI): m/z 883.6 (M+H).

Starting from compound 129a and methanesulfonamide, referring to condensation conditions of acid and amine in the synthesis of compound 82a and last step Boc deprotecting step of compound 1, compound 129 is obtained. $^1$H NMR (500 MHz, DMSO-d6) δ 7.92 (s, 1H), 7.78 (d, J=8.5 Hz, 1H), 7.67 (s, 1H), 7.56-7.47 (m, 4H), 7.44 (d, J=7.5 Hz, 1H), 7.41 (s, 1H), 7.17 (d, J=7.0 Hz, 1H), 7.12 (s, 1H), 7.08 (d, J=7.5 Hz, 1H), 6.70 (s, 1H), 5.73 (s, 2H), 3.85 (s, 3H), 3.84-3.79 (m, 2H), 3.71-3.65 (m, 1H), 3.59 (s, 3H), 3.53 (s, 2H), 3.05 (s, 3H), 2.65 (d, J=6.0 Hz, 2H), 2.46-2.40 (m, 1H), 2.15 (s, 3H), 2.14-2.05 (m, 4H), 1.88-1.78 (m, 4H), 1.75-1.68 (m, 1H), 1.35-1.22 (m, 4H); MS (ESI): m/z 861.3 (M+H).

Example 130

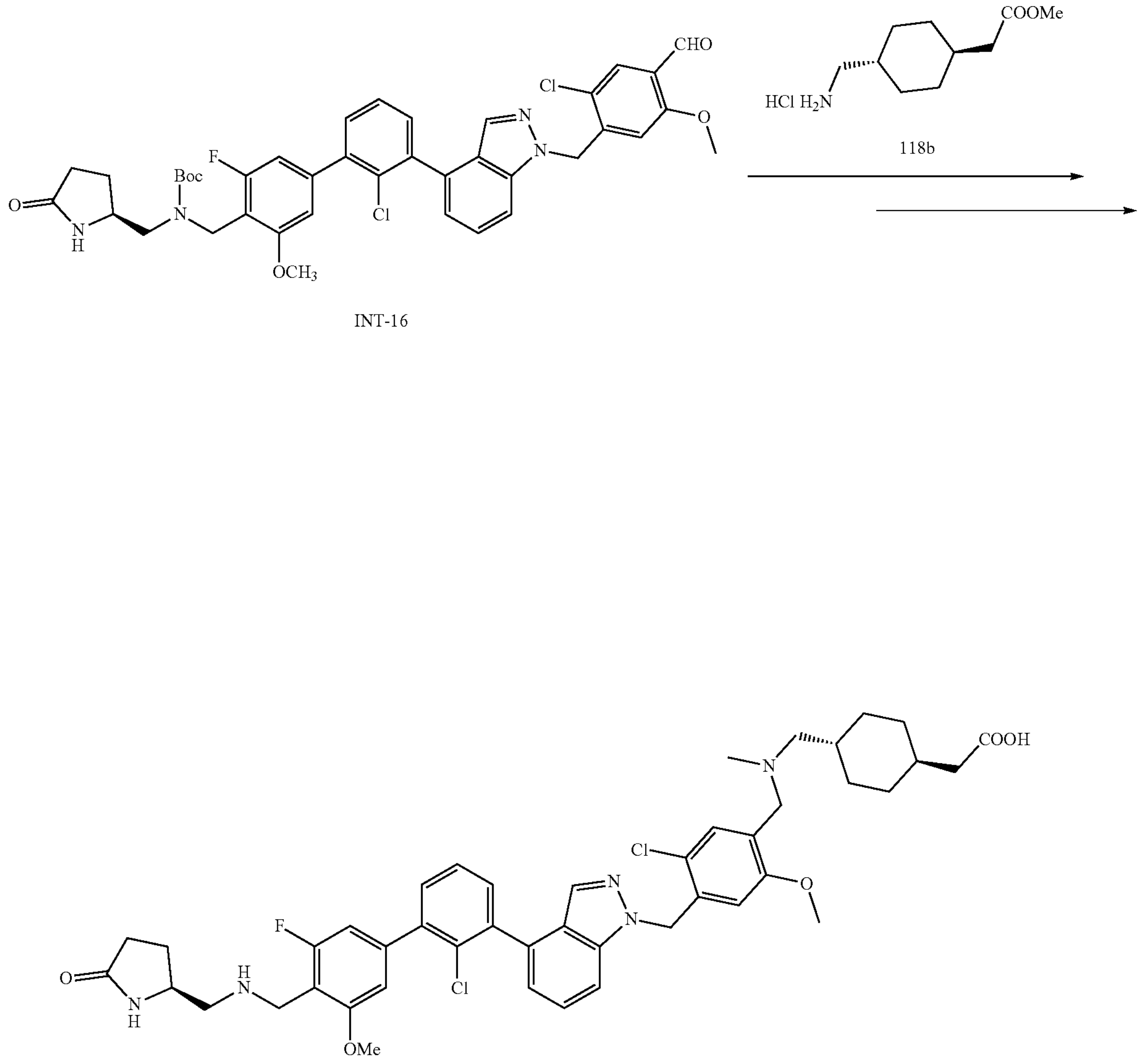

INT-16

118b

130

Starting from compound INT-16 and compound 118b, referring to the synthesis of compound 101, compound 130 is obtained. $^1$H NMR (500 MHz, DMSO-d6) δ 7.93 (s, 1H), 7.75 (d, J=8.5 Hz, 2H), 7.63 (s, 1H), 7.54-7.48 (m, 4H), 7.36 (s, 1H), 7.15 (d, J=7.0 Hz, 1H), 6.99-6.93 (m, 2H), 6.67 (s, 1H), 5.71 (s, 2H), 3.85 (s, 3H), 3.76-3.70 (m, 2H), 3.60-3.57 (m, 1H), 3.56 (s, 3H), 3.34 (s, 2H), 2.53-2.50 (m, 2H), 2.11-2.02 (m, 10H), 1.79-1.74 (m, 2H), 1.71-1.66 (m, 2H), 1.65-1.60 (m, 1H), 1.58-1.51 (m, 1H), 1.44-1.36 (m, 1H), 0.95-0.87 (m, 2H), 0.83-0.74 (m, 2H); MS (ESI): m/z 830.1 (M+H).
Example 131
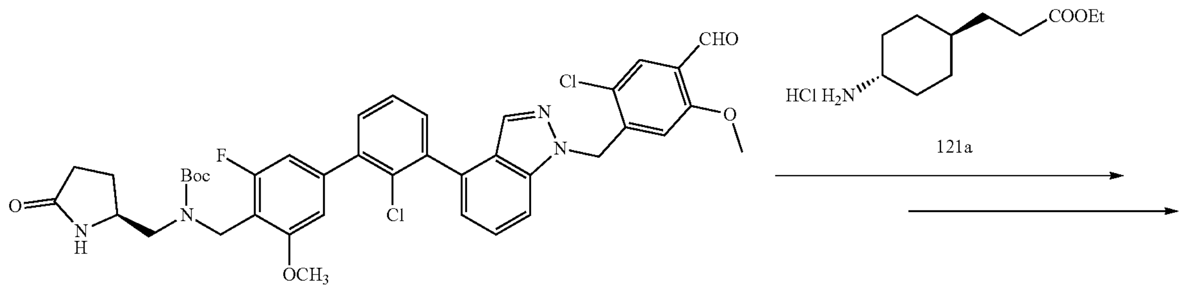
121a
INT-16
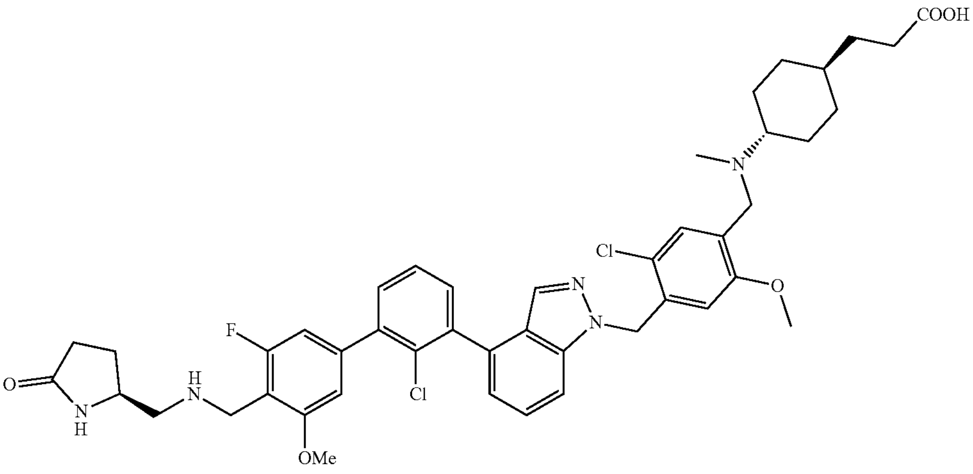
131

Starting from compound INT-16 and compound 121a, referring to the synthesis of compound 101, compound 131 is obtained. $^1$H NMR (500 MHz, DMSO-d6) δ 7.92 (s, 1H), 7.76 (d, J=8.5 Hz, 1H), 7.63 (s, 1H), 7.55-7.47 (m, 4H), 7.36 (s, 1H), 7.15 (d, J=7.0 Hz, 1H), 6.98-6.92 (m, 2H), 6.66 (s, 1H), 5.71 (s, 2H), 3.85 (s, 3H), 3.77-3.69 (m, 2H), 3.62-3.59 (m, 1H), 3.56 (s, 3H), 3.44 (s, 2H), 2.55-2.52 (m, 2H), 2.36-2.31 (m, 1H), 2.19-2.14 (m, 2H), 2.09 (s, 3H), 2.07-2.02 (m, 3H), 1.77-1.69 (m, 4H), 1.66-1.60 (m, 1H), 1.39-1.33 (m, 2H), 1.24-1.17 (m, 2H), 1.13-1.08 (m, 1H), 0.89-0.82 (m, 2H); MS (ESI): m/z 830.1 (M+H).
Example 132
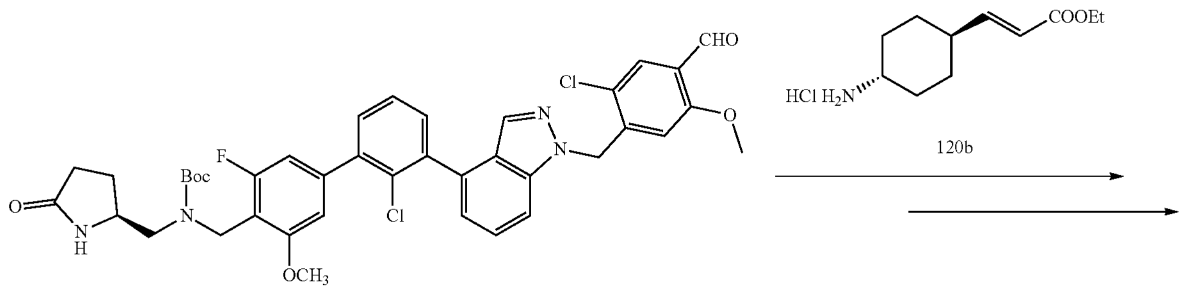
INT-16
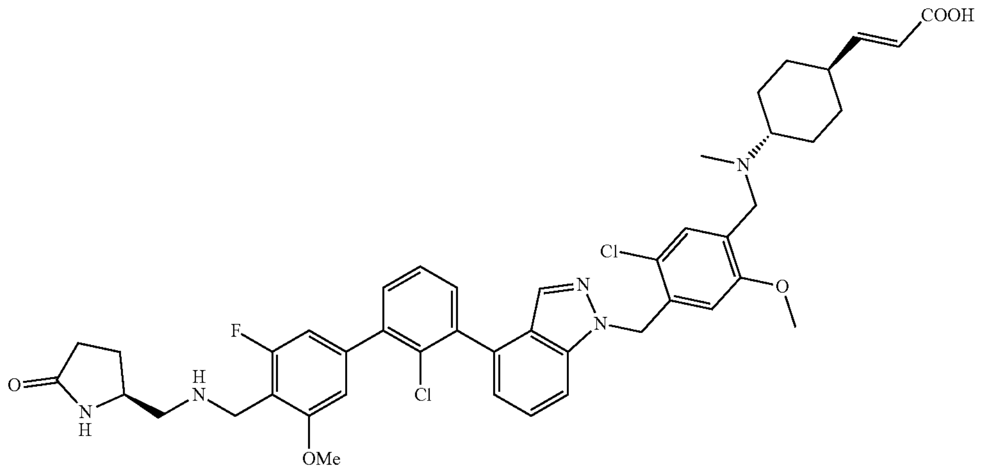
132

Starting from compound INT-16 and compound 120b, referring to the synthesis of compound 101, compound 132 is obtained. $^1$H NMR (500 MHz, DMSO-d6) δ 7.92 (s, 1H), 7.76 (d, J=8.5 Hz, 1H), 7.63 (s, 1H), 7.54-7.47 (m, 4H), 7.37 (s, 1H), 7.15 (d, J=7.0 Hz, 1H), 6.99-6.94 (m, 2H), 6.76-6.69 (m, 1H), 6.67 (s, 1H), 5.71 (s, 2H), 5.69-5.64 (m, 1H), 3.86 (s, 3H), 3.77-3.71 (m, 2H), 3.61-3.58 (m, 1H), 3.57 (s, 3H), 3.46 (s, 2H), 2.52-2.50 (m, 2H), 2.14-2.02 (m, 8H), 1.84-1.74 (m, 4H), 1.69-1.60 (m, 1H), 1.34-1.24 (m, 2H), 1.16-1.07 (m, 2H); MS (ESI): m/z 828.1 (M+H).

Example 133

133

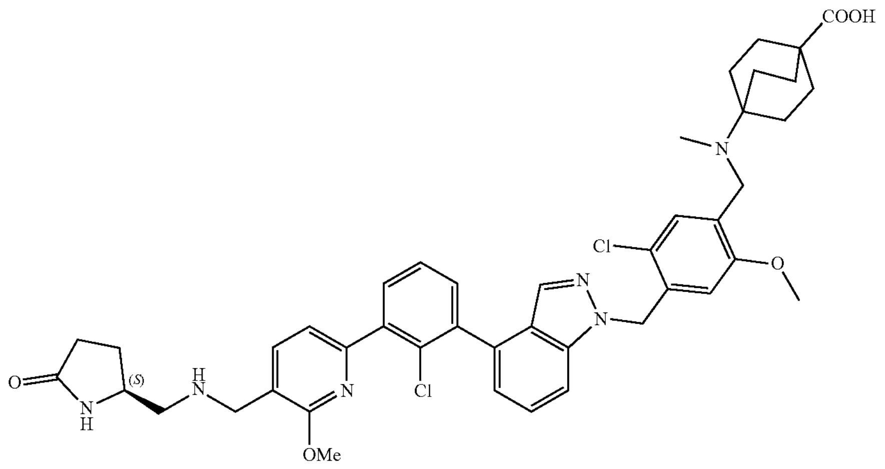

Referring to the synthesis of compound 91, methyl 4-aminomethyl-cyclohexanecarboxylate hydrochloride is replaced with 4-aminobicyclo[2.2.2]octane-1-carboxylic acid methyl ester hydrochloride, compound 133 is obtained. $^1$H NMR (500 MHz, DMSO-d6) δ 7.87 (s, 1H), 7.82 (d, J=7.5 Hz, 1H), 7.78 (d, J=8.6 Hz, 1H), 7.68-7.64 (m, 2H), 7.58-7.49 (m, 3H), 7.40 (s, 1H), 7.32 (d, J=7.5 Hz, 1H), 7.17 (d, J=7.0 Hz, 1H), 6.69 (s, 1H), 5.72 (s, 2H), 3.92 (s, 3H), 3.76-3.68 (m, 2H), 3.66-3.62 (m, 1H), 3.59 (s, 3H), 3.43 (s, 2H), 2.60-2.54 (m, 2H), 2.16-2.07 (m, 3H), 2.01 (s, 3H), 1.77-1.65 (m, 7H), 1.61-1.54 (m, 6H); MS (ESI): m/z 811.1 (M+H).

Example 134

134

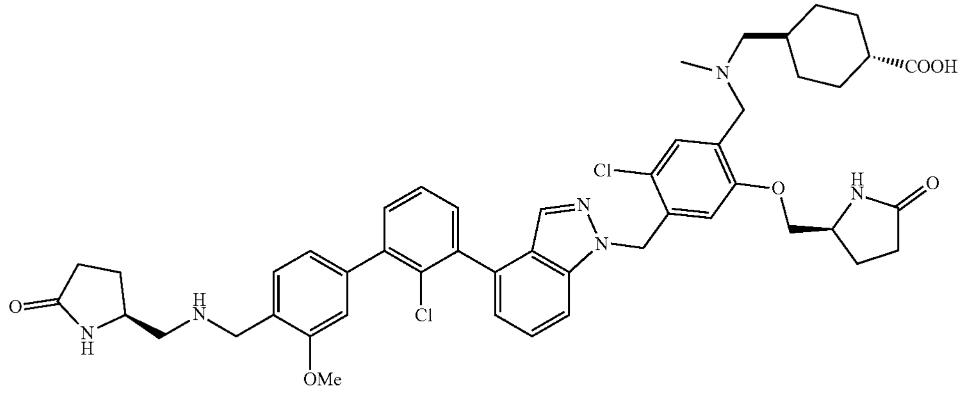

Referring to the synthesis of compound 110, isopropyl iodide is replaced with (S)-5-bromomethyl-2-pyrrolidone, compound 134 is obtained. $^{1}H$ NMR (500 MHz, DMSO-d6) δ 7.89 (s, 1H), 7.78-7.73 (m, 2H), 7.66 (s, 1H), 7.52-7.46 (m, 4H), 7.40 (d, J=7.5 Hz, 1H), 7.37 (s, 1H), 7.15 (d, J=7.0 Hz, 1H), 7.07 (s, 1H), 7.04 (d, J=7.5 Hz, 1H), 6.72 (s, 1H), 5.70 (s, 2H), 3.81 (s, 3H), 3.80-3.76 (m, 1H), 3.75-3.72 (m, 1H), 3.72-3.70 (m, 2H), 3.66-3.60 (m, 2H), 3.40-3.35 (m, 2H), 2.57-2.52 (m, 2H), 2.17 (d, J=11.0 Hz, 1H), 2.12-2.08 (m, 6H), 2.08 (s, 3H), 2.06-2.04 (m, 1H), 1.87-1.75 (m, 5H), 1.70-1.64 (m, 1H), 1.47-1.40 (m, 1H), 1.30-1.20 (m, 3H), 0.85-0.77 (m, 2H); MS (ESI): m/z 881.2 (M+H).
Example 135
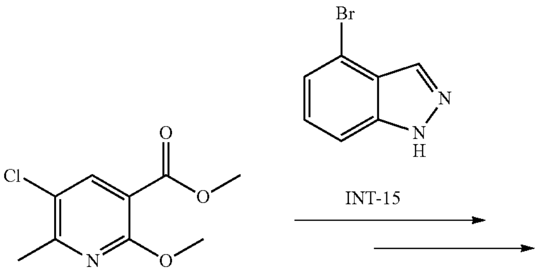
80b
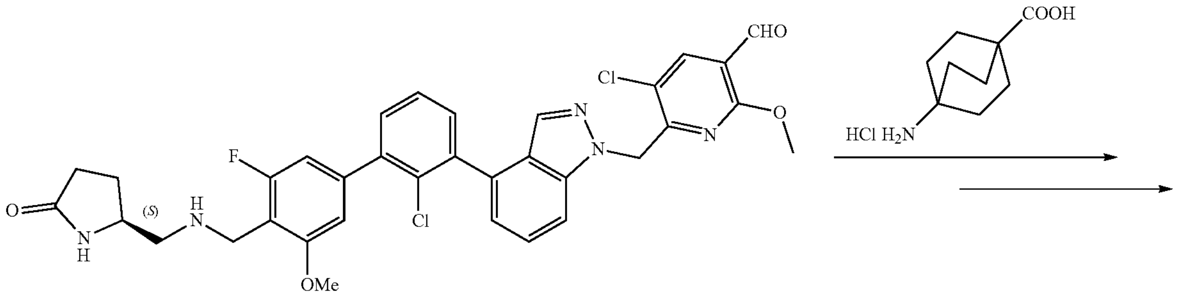
135a
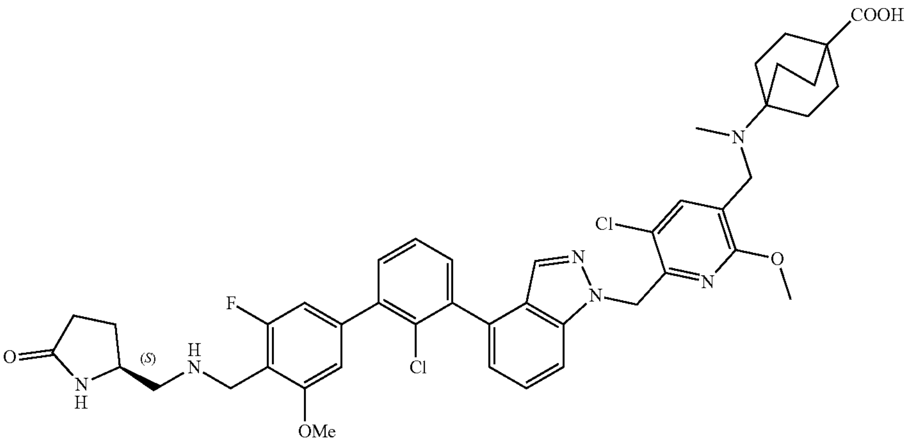
135

Starting from compound 80b, 4-bromoindazole and compound INT-15, referring to the synthesis of compound 73a and compound INT-16, compound 135a is obtained. MS (ESI): m/z 661.4 (M+H).

Starting from compound 135a and 4-aminobicyclo[2.2.2] octane-1-carboxylic acid methyl ester hydrochloride, referring to the synthesis of compound 101, compound 135 is obtained. $^1$H NMR (500 MHz, DMSO-d6) δ 7.85 (s, 1H), 7.79 (d, J=8.5 Hz, 1H), 7.69 (s, 1H), 7.63 (s, 1H), 7.57-7.43 (m, 4H), 7.12 (d, J=7.0 Hz, 1H), 6.96 (s, 1H), 6.94 (d, J=8.5 Hz, 1H), 5.78 (s, 2H), 3.85 (s, 3H), 3.74-3.73 (m, 2H), 3.58-3.56 (m, 3H), 3.37 (s, 3H), 2.51-2.50 (m, 2H), 2.10-2.03 (m, 3H), 1.99 (s, 3H), 1.70-1.67 (m, 6H), 1.64-1.62 (m, 1H), 1.54-1.51 (m, 6H); MS (ESI): m/z 829.2 (M+H).

Example 136

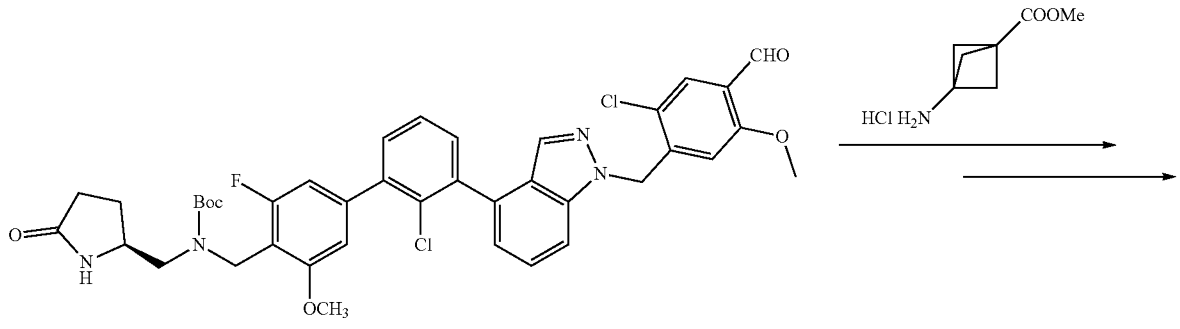

INT-16

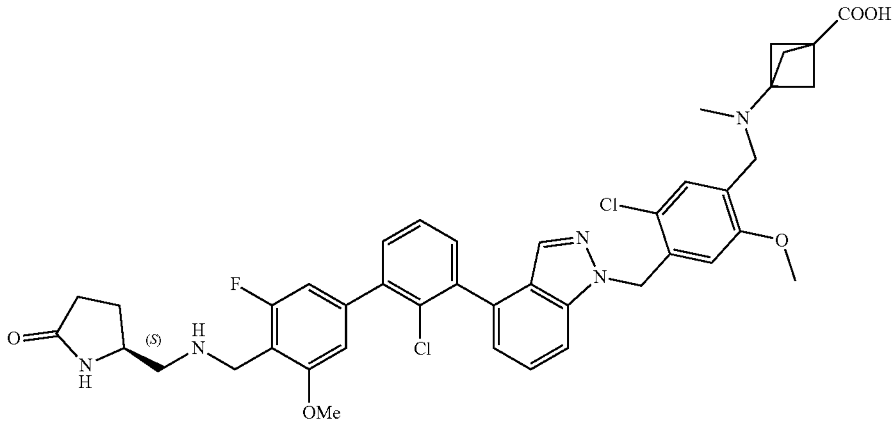

136

Starting from compound INT-16 and 3-aminobicyclo [1.1.1]pentane-1-carboxylate methyl ester hydrochloride, referring to the synthesis of compound 101, compound 136 is obtained. $^{1}$H NMR (500 MHz, DMSO-d6) δ 7.93 (s, 1H), 7.75 (d, J=8.5 Hz, 1H), 7.63 (s, 1H), 7.56-7.46 (m, 4H), 7.33 (s, 1H), 7.15 (d, J=7.0 Hz, 1H), 7.00-6.94 (m, 2H), 6.67 (s, 1H), 5.72 (s, 2H), 3.86 (s, 3H), 3.78-3.70 (m, 2H), 3.57 (s, 3H), 3.56-3.52 (m, 1H), 3.40 (s, 2H), 2.55-2.52 (m, 2H), 2.10-2.03 (m, 6H), 1.89 (s, 6H), 1.68-1.60 (m, 1H); MS (ESI): m/z 786.0 (M+H).
Example 137
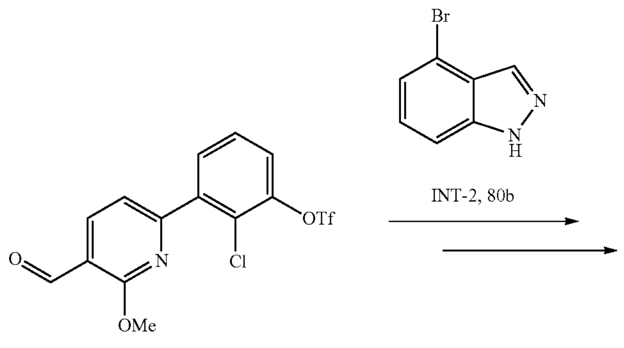
INT-10
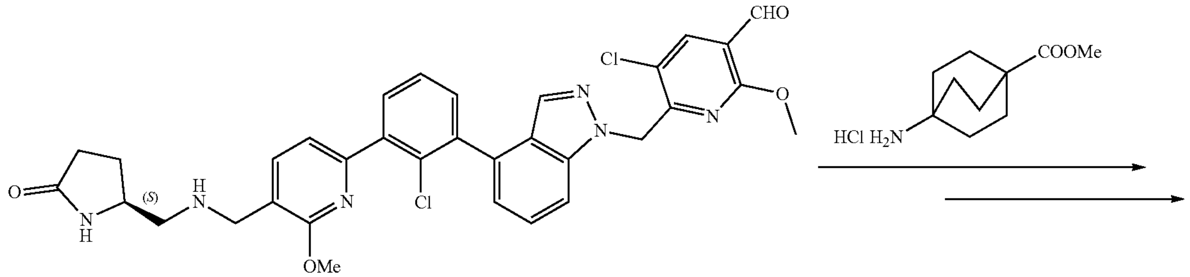
137a
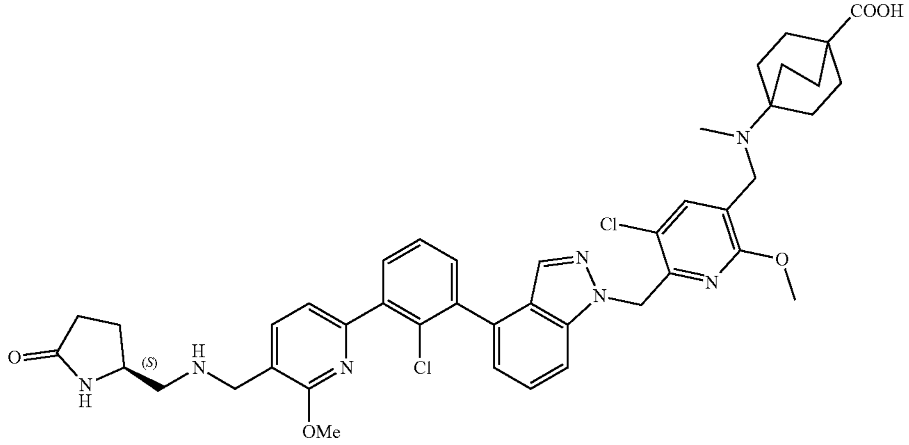
137

Starting from compound INT-10, compound INT-2, compound 80b and 4-bromoindazole, referring to the synthesis of compound INT-3, compound 73a and compound 16, compound 137a is obtained. MS (ESI): m/z 644.3 (M+H).

Starting from compound 137a and 4-Aminobicyclo[2.2.2] octane-1-carboxylic acid methyl ester hydrochloride, referring to the synthesis of compound 101, compound 137 is obtained. $^{1}$H NMR (500 MHz, DMSO-d6) δ 7.83-7.80 (m, 3H), 7.70-7.65 (m, 3H), 7.55 (t, J=7.5 Hz, 1H), 7.50-7.47 (m, 2H), 7.31 (d, J=7.4 Hz, 1H), 7.14 (d, J=7.0 Hz, 1H), 5.80 (s, 2H), 3.92 (s, 3H), 3.73-3.71 (m, 2H), 3.65-3.63 (m, 1H), 3.39 (s, 3H), 3.36 (brs, 2H), 2.56 (d, J=6.0 Hz, 2H), 2.14-2.07 (m, 3H), 2.00 (s, 3H), 1.72-1.68 (m, 7H), 1.56-1.52 (m, 6H); MS (ESI): m/z 812.1 (M+H).

Example 138

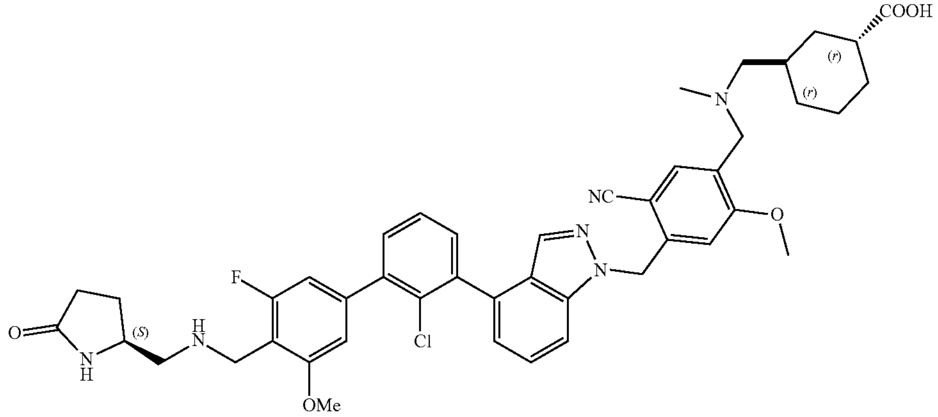

138

Referring to the synthesis of compound 107, compound INT-6 is replaced with compound INT-15, compound 138 is obtained. $^{1}$H NMR (500 MHz, DMSO-d6) δ 7.96 (s, 1H), 7.84 (d, J=8.6 Hz, 1H), 7.71 (s, 1H), 7.65 (s, 1H), 7.56-7.50 (m, 4H), 7.18 (d, J=7.0 Hz, 1H), 6.99-6.97 (m, 2H), 6.92 (s, 1H), 5.82 (s, 2H), 3.87 (s, 3H), 3.76-3.73 (m, 2H), 3.71 (s, 3H), 3.62-3.58 (m, 1H), 3.49 (s, 2H), 2.60-2.55 (m, 2H), 2.45-2.35 (m, 1H), 2.12 (s, 3H), 2.10-2.04 (m, 3H), 1.94-1.92 (m, 2H), 1.81-1.79 (m, 2H), 1.69-1.62 (m, 1H), 1.34-1.23 (m, 5H); MS (ESI): m/z 793.0 (M+H).

Example 139

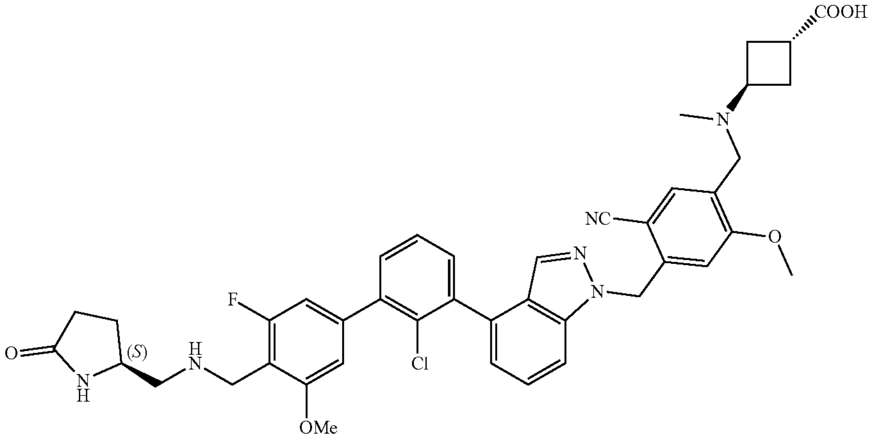

139

Referring to the synthesis of compound 138, trans-4-methyl aminocyclohexanate hydrochloride is replaced with trans-4-methyl aminocyclobutanecarboxylate hydrochloride, compound 139 is obtained. $^1$H NMR (500 MHz, DMSO-d6) δ 7.94 (s, 1H), 7.82 (d, J=8.5 Hz, 1H), 7.69 (s, 1H), 7.63 (s, 1H), 7.55-7.48 (m, 4H), 7.17 (d, J=7.1 Hz, 1H), 6.99-6.95 (m, 2H), 6.91 (s, 1H), 5.80 (s, 2H), 3.85 (s, 3H), 3.73 (d, J=4.2 Hz, 2H), 3.69 (s, 3H), 3.58-3.56 (m, 1H), 3.26 (brs, 2H), 3.03-3.01 (m, 1H), 2.80-2.76 (m, 1H), 2.51-2.48 (m, 2H), 2.20-2.15 (m, 2H), 2.09-2.02 (m, 5H), 1.92 (s, 3H), 1.66-1.62 (m, 1H); MS (ESI): m/z 765.1 (M+H).

Example 140

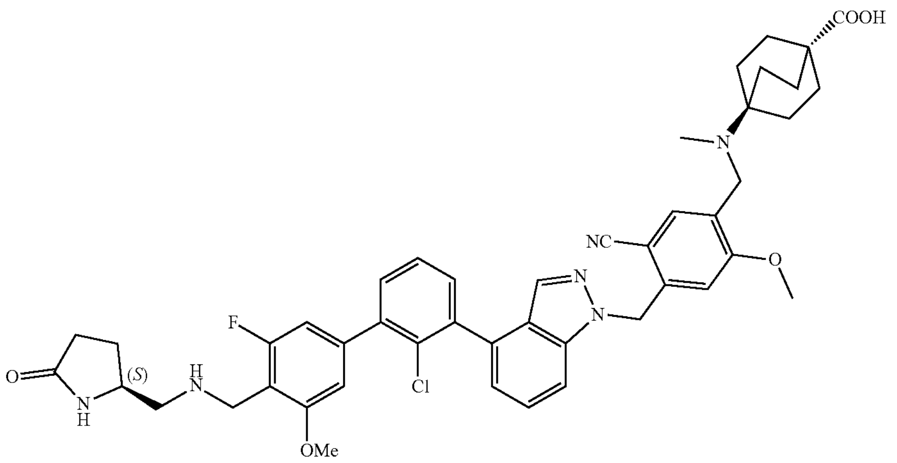

140

Referring to the synthesis of compound 138, trans-4-methyl aminocyclohexanate hydrochloride is replaced with 4-aminobicyclo[2.2.2]octane-1-carboxylic acid methyl ester hydrochloride, compound 140 is obtained. $^1$H NMR (500 MHz, DMSO-d6) δ 7.95 (s, 1H), 7.84 (d, J=8.5 Hz, 1H), 7.73 (s, 1H), 7.65 (s, 1H), 7.56-7.49 (m, 4H), 7.18 (d, J=7.0 Hz, 1H), 7.00-6.97 (m, 2H), 6.91 (s, 1H), 5.81 (s, 2H), 3.87 (s, 3H), 3.75 (d, J=4.5 Hz, 2H), 3.70 (s, 3H), 3.62-3.56 (m, 1H), 3.45 (s, 2H), 2.54-2.52 (m, 2H), 2.09-2.05 (m, 3H), 2.02 (s, 3H), 1.75-1.72 (m, 6H), 1.68-1.63 (m, 1H), 1.59-1.56 (m, 6H); MS (ESI): m/z 819.0 (M+H).

Example 141

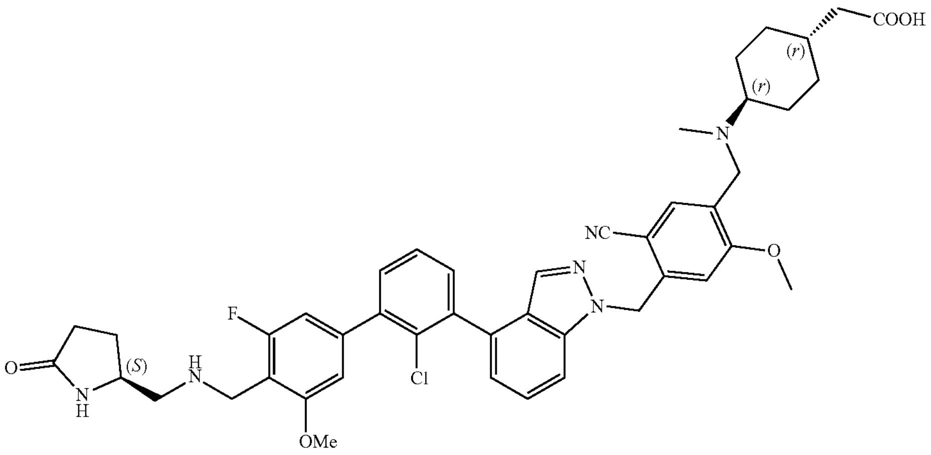

141

Referring to the synthesis of compound 138, trans-4-methyl aminocyclohexanate hydrochloride is replaced with compound INT-14, compound 141 is obtained. $^1H$ NMR (500 MHz, DMSO-d6) δ 7.94 (s, 1H), 7.82 (d, J=8.5 Hz, 1H), 7.69 (s, 1H), 7.63 (s, 1H), 7.56-7.48 (m, 4H), 7.17 (d, J=7.0 Hz, 1H), 6.97-6.95 (m, 2H), 6.90 (s, 1H), 5.80 (s, 2H), 3.85 (s, 3H), 3.73 (d, J=4.1 Hz, 2H), 3.69 (s, 3H), 3.58-3.55 (m, 1H), 3.46 (s, 2H), 2.52-2.49 (m, 2H), 2.36-2.33 (m, 1H), 2.10 (s, 3H), 2.08-2.01 (m, 5H), 1.77-1.70 (m, 4H), 1.66-1.61 (m, 1H), 1.58-1.52 (m, 1H), 1.29-1.22 (m, 2H), 0.96-0.89 (m, 2H); MS (ESI): m/z 807.1 (M+H).

Example 142

142

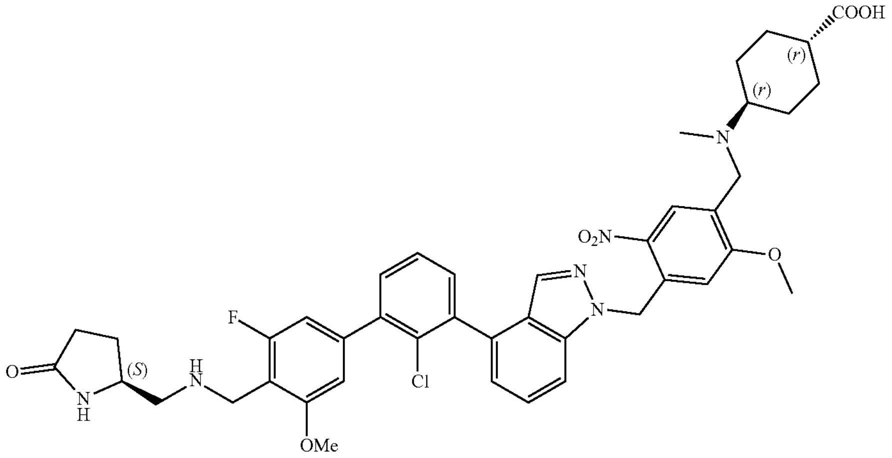

Referring to the synthesis of compound 92, compound INT-6 is replaced with compound INT-15, compound is obtained 142. $^1H$ NMR (500 MHz, DMSO-d6) δ 8.17 (s, 1H), 7.99 (s, 1H), 7.78 (d, J=8.5 Hz, 1H), 7.64 (s, 1H), 7.57-7.46 (m, 4H), 7.17 (d, J=7.0 Hz, 1H), 7.00-6.95 (m, 2H), 6.10 (s, 1H), 6.09 (s, 2H), 3.86 (s, 3H), 3.73 (d, J=4.5 Hz, 2H), 3.59-3.55 (m, 1H), 3.49 (s, 2H), 3.48 (s, 3H), 2.53-2.51 (m, 2H), 2.43-2.37 (m, 1H), 2.13 (s, 3H), 2.11-2.01 (m, 4H), 1.95-1.86 (m, 2H), 1.84-1.75 (m, 2H), 1.68-1.59 (m, 1H), 1.33-1.23 (m, 4H); MS (ESI): m/z 813.3 (M+H).

Example 143

143

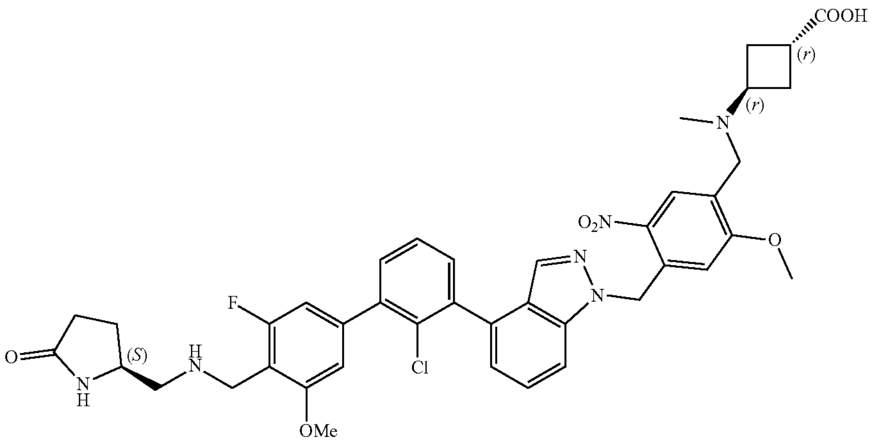

Referring to the synthesis of compound 142, trans-4-methyl aminocyclohexanate hydrochloride is replaced with trans-4-methyl aminocyclobutanecarboxylate hydrochloride, compound 143 is obtained. $^1$H NMR (500 MHz, DMSO-d6) δ 8.13 (s, 1H), 7.99 (s, 1H), 7.79 (d, J=8.5 Hz, 1H), 7.63 (s, 1H), 7.55-7.48 (m, 4H), 7.17 (d, J=6.5 Hz, 1H), 7.00-6.96 (m, 2H), 6.12 (s, 1H), 6.09 (s, 2H), 3.86 (s, 3H), 3.77-3.70 (m, 2H), 3.59-3.55 (m, 1H), 3.48 (s, 3H), 3.32-3.30 (m, 2H), 3.09-3.02 (m, 1H), 2.87-2.78 (m, 1H), 2.52-2.48 (m, 2H), 2.21-2.16 (m, 2H), 2.12-2.02 (m, 5H), 1.95 (s, 3H), 1.67-1.60 (m, 1H); MS (ESI): m/z 785.3 (M+H).

Example 144

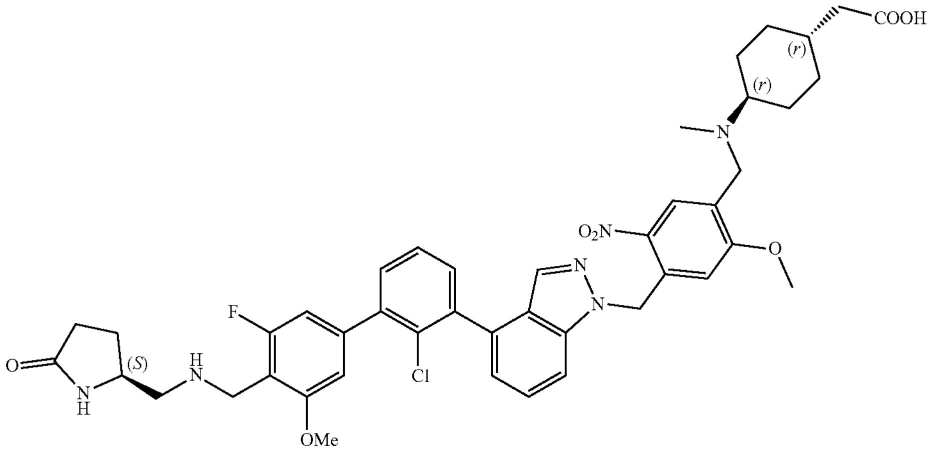

144

Referring to the synthesis of compound 142, trans-4-methyl aminocyclohexanate hydrochloride is replaced with compound INT-14, compound 144 is obtained. $^1$H NMR (500 MHz, DMSO-d6) δ 8.17 (s, 1H), 7.98 (s, 1H), 7.78 (d, J=8.5 Hz, 1H), 7.63 (s, 1H), 7.57-7.47 (m, 4H), 7.17 (d, J=6.5 Hz, 1H), 7.00-6.95 (m, 2H), 6.09 (s, 1H), 6.09 (s, 2H), 3.86 (s, 3H), 3.77-3.70 (m, 2H), 3.59-3.55 (m, 1H), 3.49 (s, 2H), 3.48 (s, 3H), 2.54-2.50 (m, 2H), 2.36-2.33 (m, 1H), 2.13 (s, 3H), 2.10-2.02 (m, 5H), 1.78-1.70 (m, 4H), 1.67-1.64 (m, 1H), 1.57-1.52 (m, 1H), 1.32-1.21 (m, 2H), 0.98-0.88 (m, 2H); MS (ESI): m/z 827.1 (M+H).

Example 145

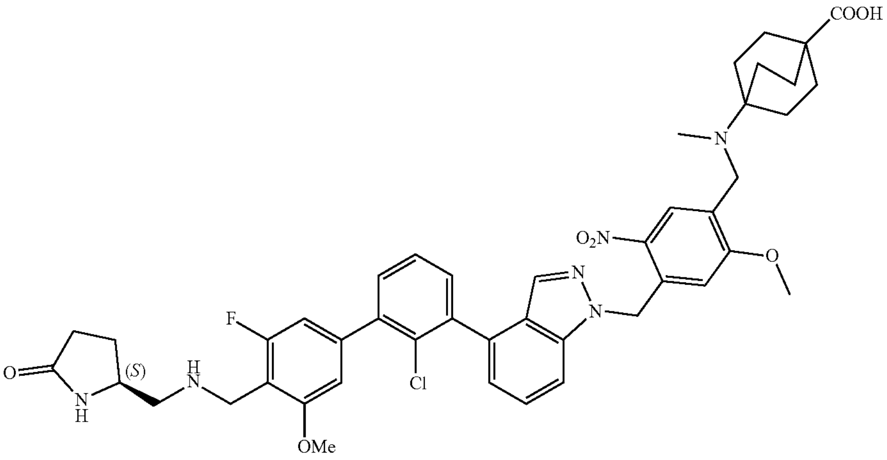

145

Referring to the synthesis of compound 142, methyl trans-4-aminocyclohexanate hydrochloride is replaced with 4-aminobicyclo[2.2.2]octane-1-carboxylic acid methyl ester hydrochloride, compound 145 is obtained. $^1$H NMR (500 MHz, DMSO-d6) δ 8.18 (s, 1H), 7.98 (s, 1H), 7.78 (d, J=8.5 Hz, 1H), 7.63 (s, 1H), 7.56-7.47 (m, 4H), 7.17 (d, J=7.0 Hz, 1H), 7.00-6.95 (m, 2H), 6.09 (s, 1H), 6.08 (s, 2H), 3.86 (s, 3H), 3.77-3.70 (m, 2H), 3.59-3.55 (m, 1H), 3.48 (s, 3H), 3.45 (s, 2H), 2.54-2.50 (m, 2H), 2.10-2.04 (m, 3H), 2.03 (s, 3H), 1.74-1.69 (m, 6H), 1.68-1.62 (m, 1H), 1.60-1.55 (s, 6H); MS (ESI): m/z 839.1 (M+H).

Example 146

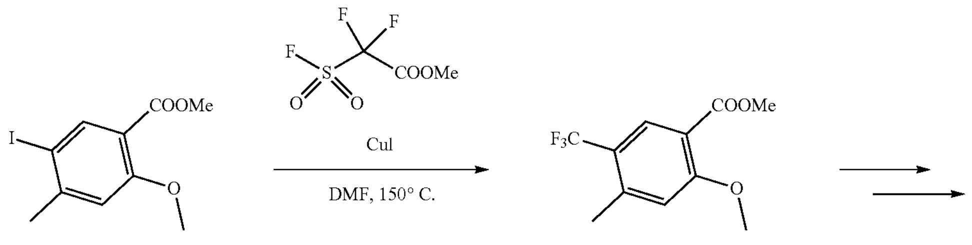

INT-13

146a

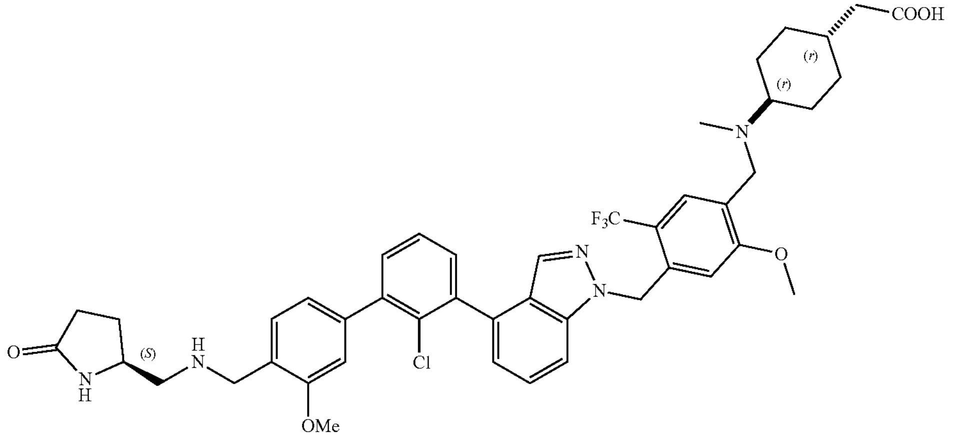

146

In N,N-dimethylformamide (2 mL) solution with compound INT-13 (50 mg, 0.16 mmol) and methyl fluorosulfonyl difluoroacetate (314 mg, 1.6 mmol) mixed cuprous iodide (156 mg, 0.82 mmol) was added. Thus obtained mixture as at 150 degree condition stirred for 4 hours. The reaction solution was filtered, and a mixture of ethyl acetate and water (100 mL, v/v=1/1) was added to the filtrate. Thus obtained organic phase was washed with saturated salt solution (50 mL), dried with anhydrous sodium sulfate, and concentrated. The residue was separated by silica gel column chromatography to obtain white solid 146a (40 mg, yield: 98.7%). $^1$H NMR (500 MHz, DMSO-d6) δ 7.92 (s, 1H), 7.27 (s, 1H), 3.90 (s, 3H), 3.80 (s, 3H); MS (ESI): m/z 249.0 (M+H).

Starting from compound 146a, referring to the synthesis of compound 92, wherein trans-4-methyl aminocyclohexanate hydrochloride is replaced with compound INT-14, compound 146 is obtained. $^1$H NMR (500 MHz, DMSO-d6) δ 7.95 (s, 1H), 7.70 (s, 1H), 7.67-7.62 (m, 2H), 7.54-7.46 (m, 4H), 7.40 (d, J=7.7 Hz, 1H), 7.17 (d, J=7.0 Hz, 1H), 7.07 (d, J=1.6 Hz, 1H), 7.04 (dd, J=7.5, 1.6 Hz, 1H), 6.32 (s, 1H), 5.82 (s, 2H), 3.82 (s, 3H), 3.71 (d, J=3.0 Hz, 2H), 3.65-3.59 (m, 1H), 3.48 (s, 2H), 3.46 (s, 3H), 2.55-2.53 (m, 2H), 2.37-2.33 (m, 1H), 2.12-2.06 (m, 6H), 2.02 (d, J=7.1 Hz, 2H), 1.76-1.67 (m, 5H), 1.58-1.51 (m, 1H), 1.29-1.21 (m, 2H), 0.97-0.87 (m, 2H); MS (ESI): m/z 832.2 (M+H).

Example 147
147
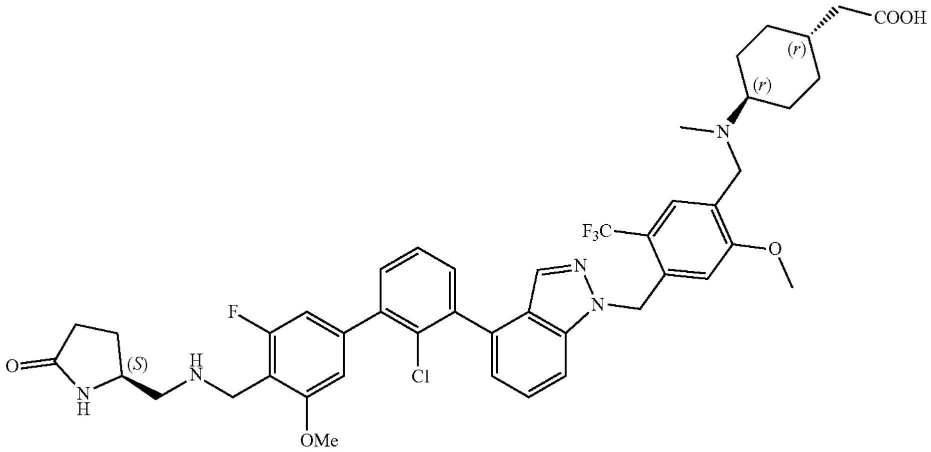
Referring to the synthesis of compound 146, compound INT-6 is replaced with compound INT-15, compound 147 is obtained. $^1$H NMR (500 MHz, DMSO-d6) δ 7.98 (s, 1H), 7.70 (s, 1H), 7.68-7.61 (m, 2H), 7.57-7.47 (m, 4H), 7.17 (d, J=7.0 Hz, 1H), 7.01-6.94 (m, 2H), 6.33 (s, 1H), 5.82 (s, 2H), 3.86 (s, 3H), 3.78-3.70 (m, 2H), 3.62-3.54 (m, 1H), 3.48 (s, 2H), 3.46 (s, 3H), 2.55-2.50 (m, 2H), 2.36-2.31 (m, 1H), 2.10 (s, 3H), 2.09-2.01 (m, 5H), 1.77-1.69 (m, 4H), 1.67-1.61 (m, 1H), 1.59-1.52 (m, 1H), 1.31-1.24 (m, 2H), 0.97-0.88 (m, 2H); MS (ESI): m/z 850.1 (M+H).
Example 148
148
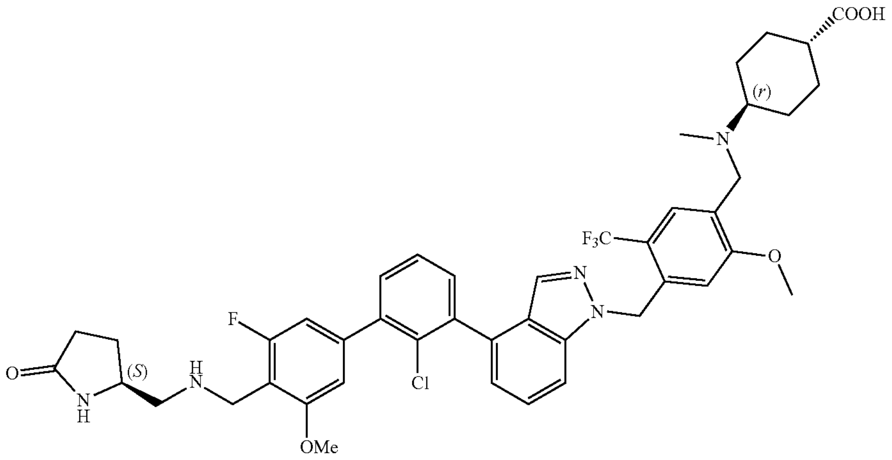

Referring to the synthesis of compound 147, 将 compound INT-14 is replaced with trans-4-methyl aminocyclohexanate hydrochloride, compound 148 is obtained $^1$H NMR (500 MHz, DMSO-d6) δ7.98 (s, 1H), 7.70 (s, 1H), 7.69-7.61 (m, 2H), 7.57-7.46 (m, 4H), 7.17 (d, J=7.0 Hz, 1H), 7.00-6.95 (m, 2H), 6.33 (s, 1H), 5.82 (s, 2H), 3.86 (s, 3H), 3.78-3.68 (m, 2H), 3.61-3.55 (m, 1H), 3.48 (s, 2H), 3.46 (s, 3H), 2.56-2.50 (m, 2H), 2.39-2.33 (m, 1H), 2.10 (s, 3H), 2.09-2.02 (m, 4H), 1.94-1.87 (m, 2H), 1.82-1.74 (m, 2H), 1.68-1.60 (m, 1H), 1.34-1.24 (m, 4H); MS (ESI): m/z 836.1 (M+H).

Example 149

149

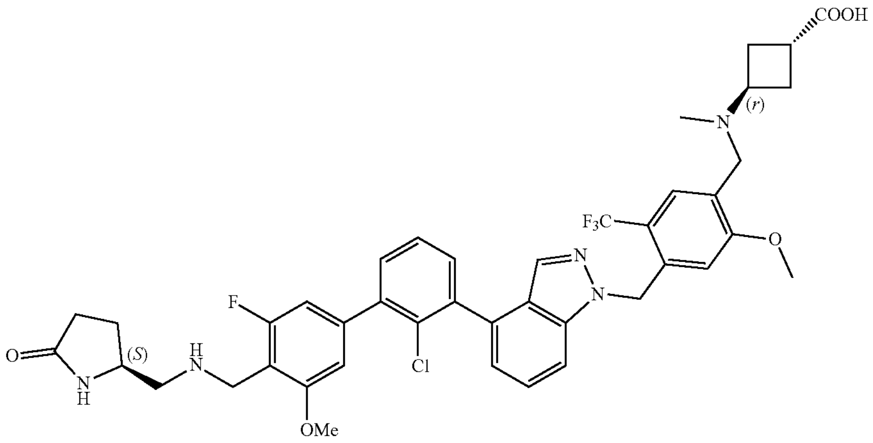

Referring to the synthesis of compound 147, 将 compound INT-14 is replaced with trans-4-methyl aminocyclohexanate hydrochloride, compound 149 is obtained. $^1$H NMR (500 MHz, DMSO-d6) δ 7.99 (s, 1H), 7.69-7.62 (m, 3H), 7.57-7.47 (m, 4H), 7.17 (d, J=6.9 Hz, 1H), 7.04-6.92 (m, 2H), 6.34 (s, 1H), 5.83 (s, 2H), 3.86 (s, 3H), 3.79-3.70 (m, 2H), 3.61-3.54 (m, 1H), 3.46 (s, 3H), 3.29 (s, 2H), 3.06-2.97 (m, 1H), 2.83-2.75 (m, 1H), 2.56-2.52 (m, 2H), 2.19-2.14 (m, 2H), 2.11-2.01 (m, 5H), 1.91 (s, 3H), 1.68-1.61 (m, 1H); MS (ESI): m/z 808.1 (M+H).

Example 150

150

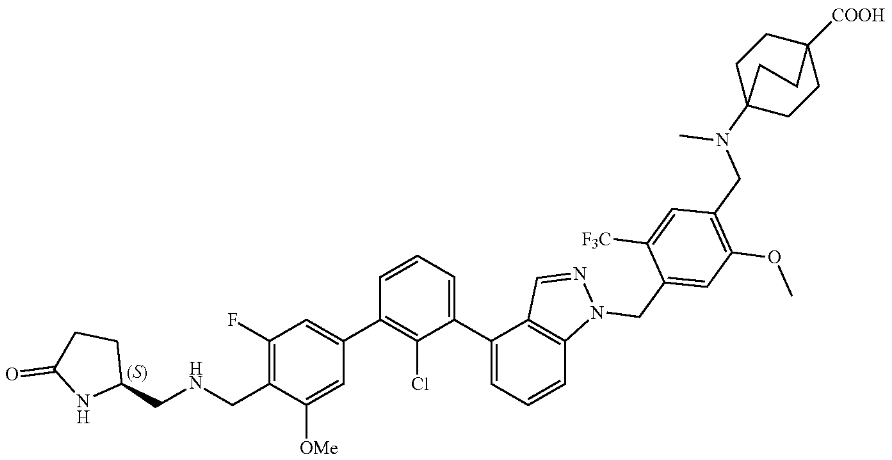

Referring to the synthesis of compound 147, compound INT-14 is replaced with 4-aminobicyclo[2.2.2]octane-1-carboxylic acid methyl ester hydrochloride, compound 150 is obtained. $^1$H NMR (500 MHz, DMSO-d6) δ 7.98 (s, 1H), 7.72 (s, 1H), 7.67-7.61 (m, 2H), 7.58-7.47 (m, 4H), 7.17 (d, J=7.0 Hz, 1H), 7.05-6.94 (m, 2H), 6.32 (s, 1H), 5.82 (s, 2H), 3.86 (s, 3H), 3.78-3.70 (m, 2H), 3.61-3.55 (m, 1H), 3.46 (s, 3H), 3.44 (s, 2H), 2.60-2.54 (m, 2H), 2.10-2.02 (m, 3H), 1.99 (s, 3H), 1.74-1.68 (m, 6H), 1.66-1.62 (m, 1H), 1.59-1.53 (m, 6H); MS (ESI): m/z 862.1 (M+H).

Example 151

151

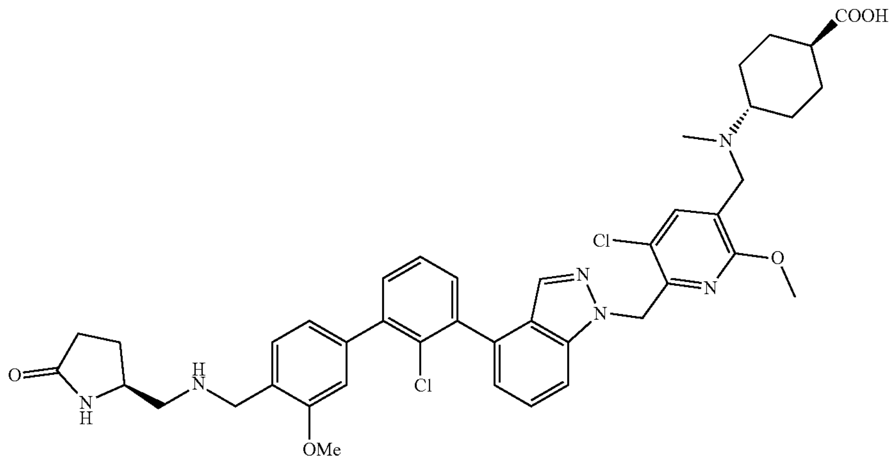

Referring to the synthesis of compound 137, 4-Aminobicyclo[2.2.2]octane-1-carboxylic acid methyl ester hydrochloride is replaced with trans-4-methyl aminocyclohexanate hydrochloride, compound 151 is obtained. $^1$H NMR (500 MHz, DMSO-d6) δ 7.83-7.78 (m, 3H), 7.72-7.63 (m, 3H), 7.54 (t, J=7.5 Hz, 1H), 7.50-7.45 (m, 2H), 7.30 (d, J=7.5 Hz, 1H), 7.13 (d, J=7.0 Hz, 1H), 5.80 (s, 2H), 3.90 (s, 3H), 3.70 (d, J=3.5 Hz, 2H), 3.65-3.60 (m, 1H), 3.39 (s, 2H), 3.37 (s, 3H), 2.55-2.53 (m, 2H), 2.37-2.33 (m, 1H), 2.12-2.05 (m, 4H), 2.08 (s, 3H), 1.93-1.87 (m, 2H), 1.78-1.73 (m, 2H), 1.71-1.66 (m, 1H), 1.29-1.23 (m, 4H); MS (ESI): m/z 786.0 (M+H).

Example 152

152

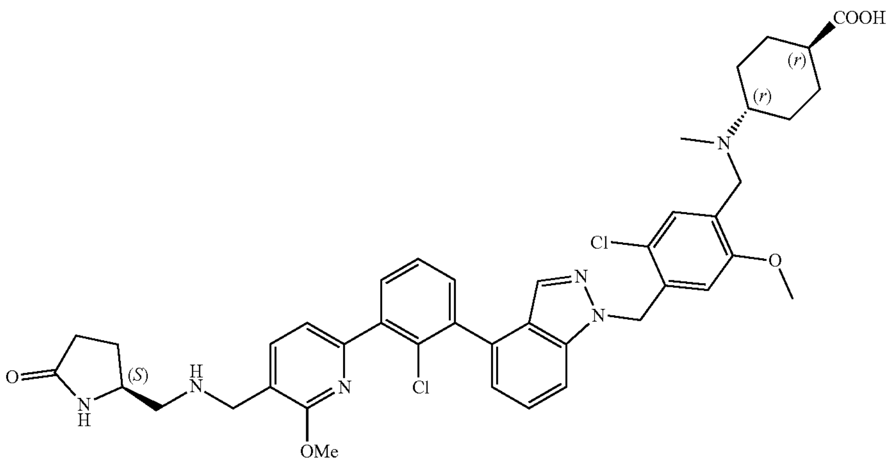

Referring to the synthesis of compound 91, methyl 4-aminomethyl-cyclohexanecarboxylate hydrochloride is replaced with trans-4-methyl aminocyclohexanate hydrochloride, compound 152 is obtained. $^1$H NMR (500 MHz, DMSO-d6) δ 7.88 (s, 1H), 7.83 (d, J=7.5 Hz, 1H), 7.78 (d, J=8.5 Hz, 1H), 7.70-7.65 (m, 2H), 7.59-7.49 (m, 3H), 7.38 (s, 1H), 7.32 (d, J=7.4 Hz, 1H), 7.18 (d, J=7.0 Hz, 1H), 6.69 (s, 1H), 5.73 (s, 2H), 3.92 (s, 3H), 3.76-3.70 (m, 2H), 3.66-3.61 (m, 1H), 3.59 (s, 3H), 3.46 (s, 2H), 2.56-2.55 (m, 2H), 2.42-2.35 (m, 1H), 2.16-2.06 (m, 4H), 2.12 (s, 3H), 1.96-1.88 (m, 2H), 1.83-1.76 (m, 2H), 1.74-1.66 (m, 1H), 1.34-1.23 (m, 4H); MS (ESI): m/z 784.8 (M+H).

Example 153

153

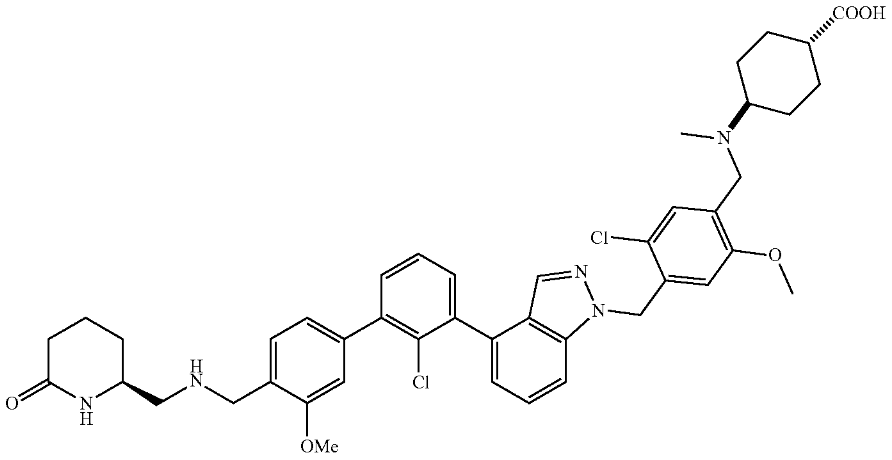

Referring to the synthesis of compound 57, compound INT-2 is replaced with compound INT-17, compound 153 is obtained. $^1$H NMR (500 MHz, DMSO-d6) δ 7.91 (s, 1H), 7.77 (d, J=8.5 Hz, 1H), 7.54-7.48 (m, 4H), 7.41 (d, J=8.0 Hz, 1H), 7.38 (s, 1H), 7.19-7.14 (m, 2H), 7.10 (brs, 1H), 7.07-7.03 (m, 1H), 6.68 (s, 1H), 5.73 (s, 2H), 3.83 (s, 3H), 3.76-3.66 (m, 2H), 3.58 (s, 3H), 3.46 (s, 2H), 3.41-3.36 (m, 1H), 2.61-2.58 (m, 2H), 2.16-2.05 (m, 3H), 2.13 (s, 3H), 1.95-1.89 (m, 2H), 1.83-1.74 (m, 4H), 1.63-1.54 (m, 1H), 1.36-1.23 (m, 6H); MS (ESI): m/z 799.1 (M+H).

Example 154

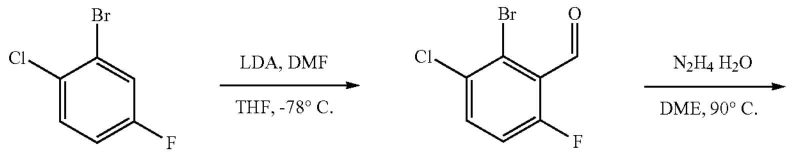

154a

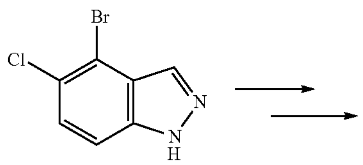

154b

-continued

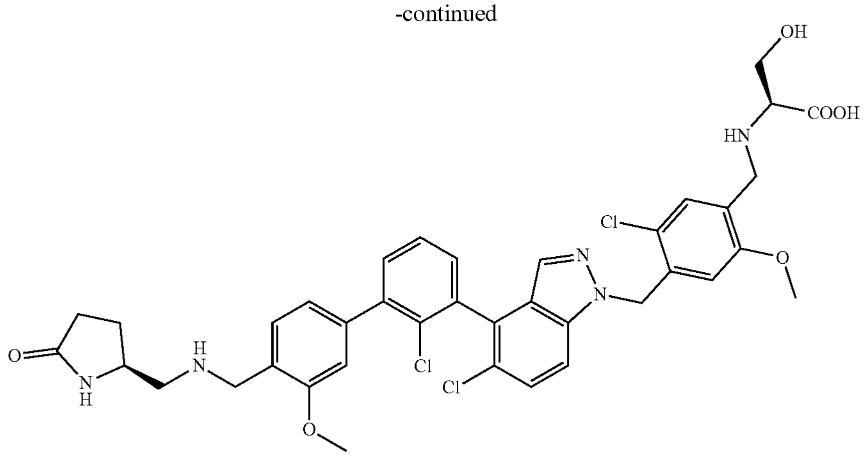

154

At −78° C., lithium diisopropylamide (2.0 M in tetrahydrofuran solution, 2.6 mL) was added to tetrahydrofuran (6 mL) solution with 1-chloro-2-bromo-4-fluorobenzene (1.0 g, 4.8 mmol) dissolved. The resulting reaction solution at the same temperature was stirred for 1 hour. Subsequently N,N-dimethylformamide (1.7 g, 24 mmol) was added to the reaction solution. The resulting mixture was further stirred for 1 hour at −78° C. The reaction solution was quenched with ammonium chloride aqueous solution (40 mL, 5% w/w). The aqueous phase was extracted with ethyl acetate (30 mL×3). The combined organic phase was washed with saturated salt solution (100 mL), dried with anhydrous sodium sulfate, filtered, and concentrated. The residue was separated by silica gel column chromatography (ethyl acetate/petroleum ether=10/1) to obtain a white solid 154a (830 mg, yield: 73.2%). MS (ESI): m/z 237.1 (M+H).

At 90° C., ethylene glycol dimethyl ether (5 mL) with compound 154a (830 mg, 3.5 mmol), hydrazine hydrate (2.0 mL, 85% analytical purity) mixed was stirred for 3 hours. After the reaction cooled down, ethyl acetate (50 mL) and water (50 mL) were added to the reaction solution. The organic phase was washed with saturated salt solution (50 mL), dried with anhydrous sodium sulfate, filtered, and concentrated. The residue was separated by silica gel column chromatography (ethyl acetate/petroleum ether=10/1) to obtain a light yellow solid 154b (725 mg, yield: 89.6%). MS (ESI): m/z 231.0 (M+H).

Starting from compound 154b, referring to the synthesis of compound INT-9 and compound 30, compound 154 is obtained. $^1$H NMR (500 MHz, DMSO-d6) δ 7.83 (d, J=9.0 Hz, 1H), 7.71 (s, 1H), 7.65 (s, 1H), 7.57 (d, J=9.0 Hz, 1H), 7.55-7.53 (m, 2H), 7.48 (s, 1H), 7.43-7.39 (m, 2H), 7.07-7.02 (m, 2H), 6.75 (s, 1H), 5.73 (s, 2H), 3.88-3.84 (m, 1H), 3.82 (s, 3H), 3.79-3.73 (m, 3H), 3.65-3.64 (m, 1H), 3.62 (s, 3H), 3.60-3.55 (m, 2H), 3.13-3.11 (m, 1H), 2.59-2.54 (m, 2H), 2.11-2.06 (m, 3H), 1.71-1.65 (m, 1H); MS (ESI): m/z 765.9 (M+H).

Example 155

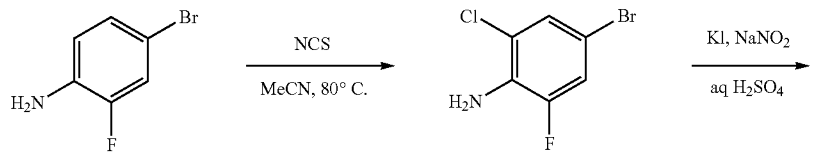

155a

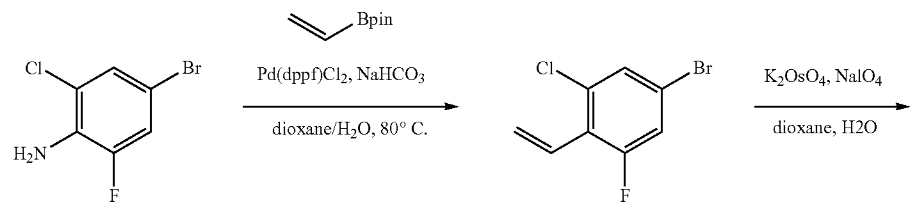

155b

155c

-continued

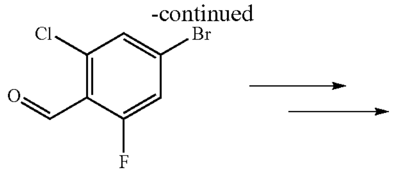

155d

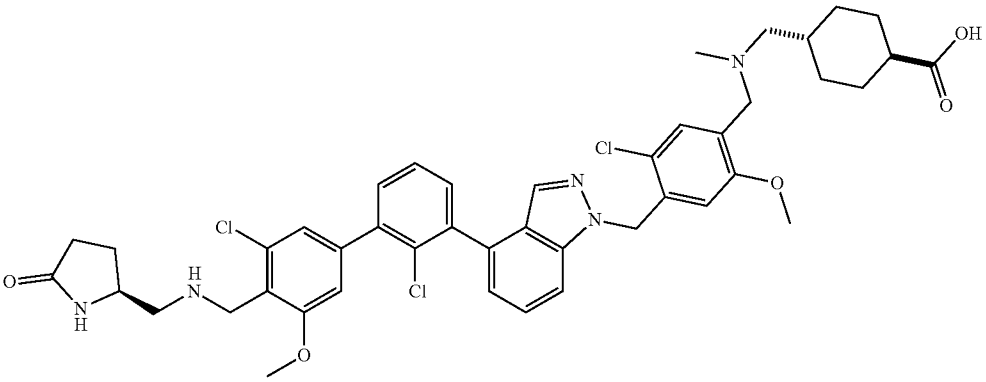

155

In acetonitrile (10 mL) solution with 4-bromo-2-fluoroaniline (1.0 g, 5.3 mmol) dissolved N-chlorosuccinimide (843 mg, 6.3 mmol) was in batches added. The reaction solution stirred for 2 hours under reflux conditions. After the reaction solution was cooled down, 5% potassium carbonate aqueous solution (50 mL) was added. The obtained aqueous phase was extracted with dichloromethane (50 mL×2). The combined organic phase was washed with saturated salt solution (100 mL), dried with anhydrous sodium sulfate, filtered, and concentrated. The residue was separated by silica gel column chromatography (petroleum ether as eluent) to obtain a white solid 155a (1.0 g, yield: 84.6%). $^1$H NMR (500 MHz, Chloroform-d) δ 7.21 (t, J=2.0 Hz, 1H), 7.09 (dd, J=10.0, 2.0 Hz, 1H), 4.04 (brs, 2H).

At room temperature, sulfuric acid aqueous solution (25% w/w) with compound 155a (1.0 g, 4.5 mmol) dissolved was stirred for half an hour, subsequently was cooled to −5° C. and aqueous (5 mL) solution with sodium nitrite (369 mg, 5.4 mmol) dissolved was slowly added. The reaction solution was further stirred for 1 hour at −5° C. A mixed solution of ethyl acetate and water (50 mL, v/v=3/2) with potassium iodide (1.5 g, 8.9 mmol) dissolved was at the same temperature slowly added dropwise. The resulting reaction solution at room temperature reaction 1 hours. After the stratification of the reaction solution, the water phase was further extracted with ethyl acetate (30 mL×2). The combined organic phase was washed with saturated salt solution (100 mL), dried with anhydrous sodium sulfate, filtered, and concentrated. The residue was separated by silica gel column chromatography (petroleum ether as eluent) to obtain colorless oily matter 155b (800 mg, yield: 53.6%). $^1$H NMR (500 MHz, Chloroform-d) δ 7.45 (t, J=2.0 Hz, 1H), 7.13 (dd, J=7.0, 2.0 Hz, 1H).

Under nitrogen atmosphere and 80° C., a mixed solution of 1,4-dioxane and water (11 mL, v/v=10/1) with compound 155b (1.0 g, 3.0 mmol), vinyl borate pinacol ester (1.4 g, 9.0 mmol), Pd(dppf)$Cl_2$ (109 mg, 0.15 mmol) and sodium bicarbonate (504 mg, 6.0 mmol) mixed was stirred for 16 hours. The reaction solution was filtered with diatomaceous earth, The filtrate concentrated, The residue was separated by silica gel column chromatography (petroleum ether as eluent) to obtain colorless oily matter 155c (550 mg, yield: 58.7%).

At room temperature, a mixed solution of 1,4-dioxane and water (6 mL, v/v=1/1) with compound 155c (520 mg, 2.2 mmol) mixed potassium osmate dihydrate (8.1 mg, 0.02 mmol) and sodium periodate (1.4 g, 6.6 mmol) were added. The reaction solution at the same temperature stirred for 2 hours. To the reaction solution water (30 mL) was added, and the solution was extracted with ethyl acetate (30 mL×2). The combined organic phase was washed with saturated salt solution (100 mL), dried with anhydrous sodium sulfate, filtered, and concentrated. The residue was separated by silica gel column chromatography (petroleum ether/ethyl acetate, v/v=10/1) to obtain colorless oily matter 155d (400 mg, yield: 76.3%). $^1$H NMR (500 MHz, Chloroform-d) δ 10.40 (brs, 1H), 7.48 (d, J=1.5 Hz, 1H), 7.33-7.29 (m, 1H).

Starting from compound 155d, referring to the synthesis of compound INT-16 and compound 101, compound is obtained 155. $^1$H NMR (500 MHz, DMSO-d6) δ 7.93 (s, 1H), 7.76 (d, J=8.5 Hz, 1H), 7.63 (s, 1H), 7.55-7.48 (m, 4H), 7.36 (s, 1H), 7.19-7.17 (m, 1H), 7.15 (d, J=7.0 Hz, 1H), 7.11-7.09 (m, 1H), 6.67 (s, 1H), 5.71 (s, 2H), 3.85 (s, 3H), 3.85-3.83 (m, 2H), 3.62-3.57 (m, 1H), 3.56 (s, 3H), 3.34 (s, 2H), 2.54-2.51 (m, 2H), 2.11-2.04 (m, 8H), 1.86-1.77 (m, 4H), 1.67-1.61 (m, 1H), 1.48-1.39 (m, 1H), 1.27-1.19 (m, 3H), 0.85-0.75 (m, 2H); MS (ESI): m/z 832.2 (M+H).

Example 156

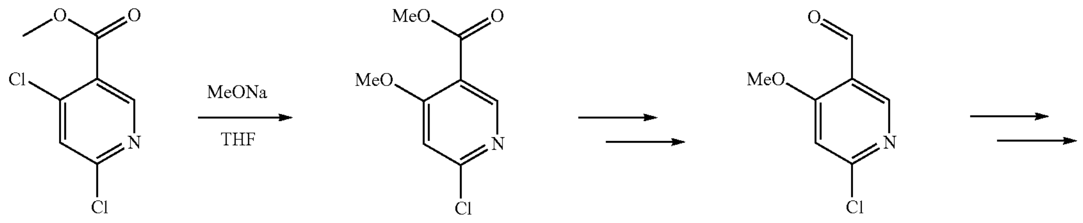

156a 156b

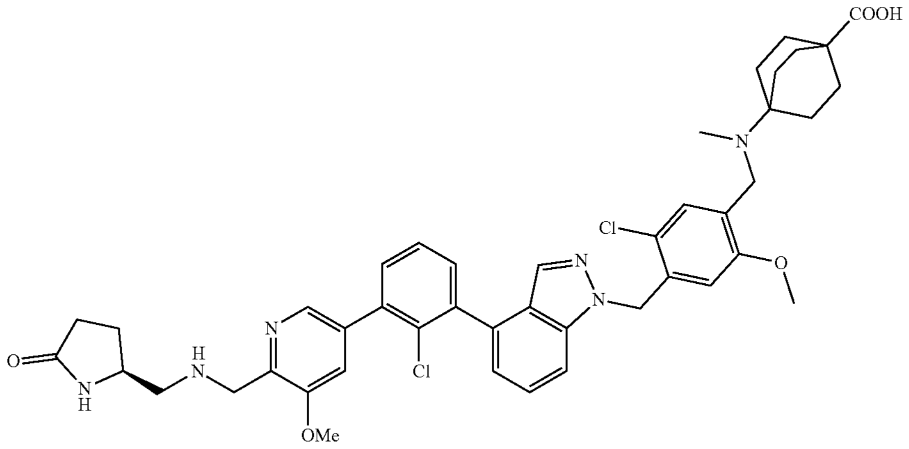

156

Sodium methoxide (1.8 g, 33.5 mmol) was added to tetrahydrofuran (40 mL) solution with methyl 4,6-dichloronicotinate (4.6 g, 22.3 mmol) dissolved. The resulting reaction solution at 50° C. was stirred for 16 hours. To the reaction solution water (100 mL) was added, and the solution was extracted with ethyl acetate (100 mL×2). The combined organic phase was saturated salt solution (150 mL) washed with, dried with anhydrous sodium sulfate, filtered, concentrated. The residue was separated by silica gel column chromatography to obtain a white solid 156a (2.8 g, yield: 62.2%). MS (ESI): m/z 202.1 (M+H).

Starting from compound 156a, referring to the synthesis of compound 72c, compound 156b is obtained. MS (ESI): m/z 172.1 (M+H).

Starting from compound 156b, referring to the synthesis of compound INT-10 and compound 133, compound 156 is obtained. $^1$H NMR (500 MHz, DMSO-d6) δ 8.24 (d, J=1.7 Hz, 1H), 7.94 (s, 1H), 7.78 (d, J=8.5 Hz, 1H), 7.68 (s, 1H), 7.61-7.48 (m, 5H), 7.40 (s, 1H), 7.18 (d, J=7.0 Hz, 1H), 6.68 (s, 1H), 5.72 (s, 2H), 3.88 (s, 3H), 3.86 (s, 2H), 3.65-3.60 (m, 1H), 3.58 (s, 3H), 3.43 (s, 2H), 2.66-2.56 (m, 2H), 2.15-2.05 (m, 3H), 2.00 (s, 3H), 1.77-1.67 (m, 7H), 1.61-1.52 (m, 6H); MS (ESI): m/z 811.1 (M+H).

Example 157

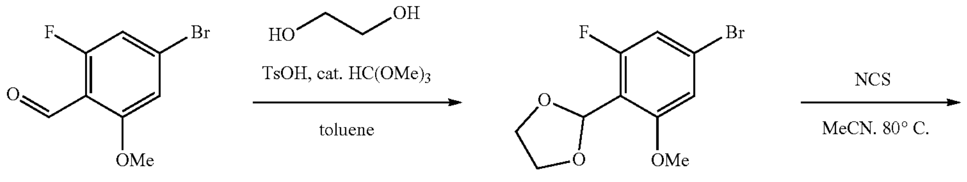

INT-15a 157a

-continued

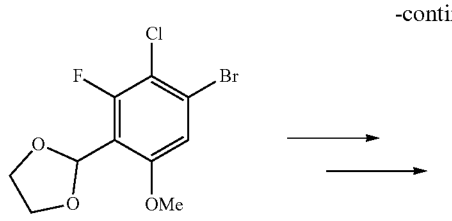

157b

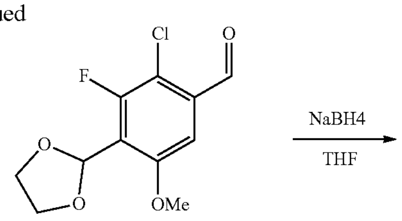

157c

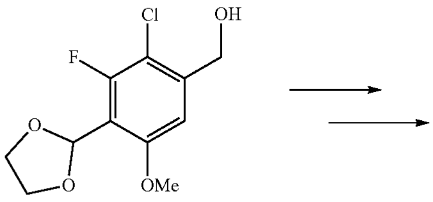

157d

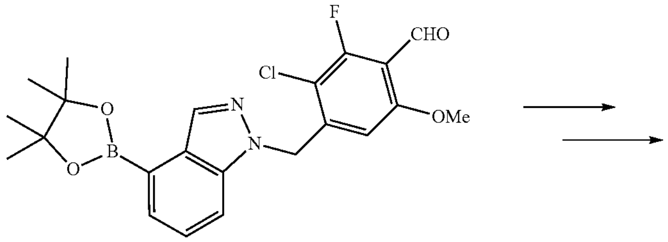

157e

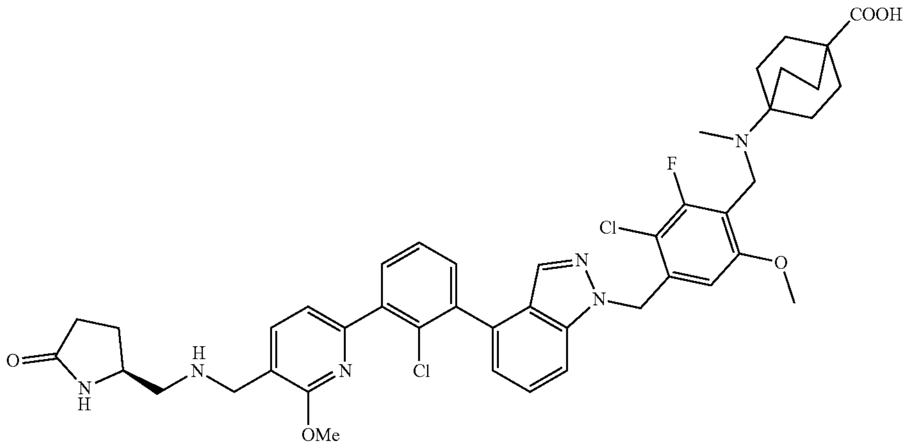

157

Starting from compound INT-15a, referring to the synthesis of compound INT-1e, compound 157a is obtained. MS (ESI): m/z 276.8 (M+H).

Starting from compound 157a, referring to the synthesis of 155c, compound 157c is obtained. $^{1}$H NMR (500 MHz, DMSO-d6) δ 10.27 (s, 1H), 7.31 (d, J=1.5 Hz, 1H), 6.19 (d, J=1.5 Hz, 1H), 4.11-4.07 (m, 2H), 3.96-3.92 (m, 2H), 3.90 (s, 3H).

At 0° C., sodium borohydride (29 mg, 0.77 mmol) was added to tetrahydrofuran (20 mL) solution with compound 157c (400 mg, 1.53 mmol) dissolved. The reaction solution was subsequently at room temperature stirred for half an hour. In the reaction solution saturated sodium bicarbonate (20 mL) solution was added, and the solution was extracted with ethyl acetate (20 mL×2). The combined organic phase was saturated salt solution (50 mL) washed with, dried with anhydrous sodium sulfate, filtered, and concentrated to obtain yellow solid 157d (400 mg, yield: 99.2%). MS (ESI): m/z 263.3 (M+H).

Starting from compound 157d, referring to the synthesis of compound INT-8c and compound INT-1i, compound 157e is obtained. MS (ESI): m/z 445.5 (M+H).

Starting from compound 157e, referring to the synthesis of compound 133, compound 157 is obtained. $^{1}$H NMR (500 MHz, DMSO-d6) δ 7.87 (s, 1H), 7.81 (d, J=7.5 Hz, 1H), 7.78 (d, J=8.5 Hz, 1H), 7.68-7.63 (m, 2H), 7.56-7.49 (m, 3H), 7.30 (d, J=7.5 Hz, 1H), 7.17 (d, J=7.0 Hz, 1H), 6.58 (s, 1H), 5.76 (s, 2H), 3.90 (s, 3H), 3.70 (d, J=3.5 Hz, 2H), 3.64-3.61 (m, 1H), 3.60 (s, 3H), 3.45 (s, 2H), 2.54 (d, J=6.0 Hz, 2H), 2.14-2.05 (m, 3H), 1.89 (s, 3H), 1.74-1.69 (m, 6H), 1.69-1.64 (m, 1H), 1.62-1.57 (m, 6H); MS (ESI): m/z 829.3 (M+H).

Example 158
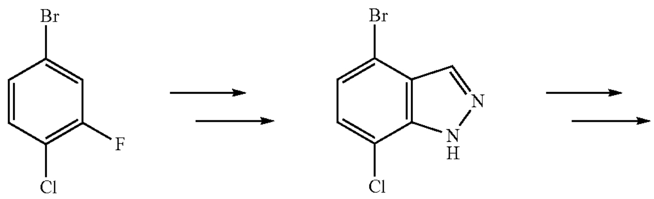
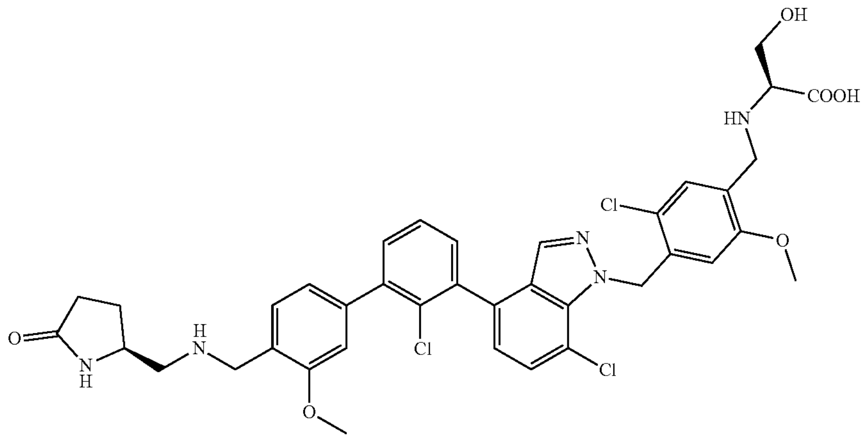
158
Starting from 1-chloro-2-fluoro-4-bromo benzene, referring to the synthesis of compound 154, compound 158 is obtained. $^1$H NMR (500 MHz, DMSO-d6) δ 8.05 (s, 1H), 7.66 (s, 1H), 7.56-7.49 (m, 4H), 7.45-7.39 (m, 2H), 7.16 (d, J=7.6 Hz, 1H), 7.08 (d, J=1.6 Hz, 1H), 7.05 (dd, J=7.6, 1.6 Hz, 1H), 6.04-6.00 (m, 3H), 3.81 (s, 3H), 3.73-3.69 (m, 2H), 3.66-3.56 (m, 3H), 3.45-3.41 (m, 2H), 3.38 (s, 3H), 3.25-3.22 (m, 1H), 2.55-2.50 (m, 2H), 2.11-2.05 (m, 3H), 1.71-1.65 (m, 1H); MS (ESI): m/z 766.0 (M+H).
Example 159
159
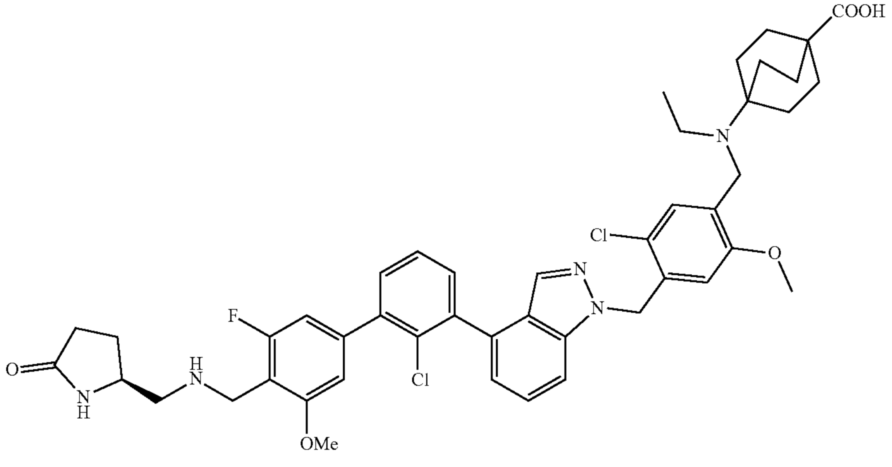

Referring to the synthesis of compound 116, formaldehyde used in reductive amination is replaced with acetaldehyde, thus compound 159 is obtained. $^1$H NMR (500 MHz, DMSO-d6) δ 7.92 (s, 1H), 7.76 (d, J=8.5 Hz, 1H), 7.63 (s, 1H), 7.55 (s, 1H), 7.54-7.47 (m, 4H), 7.15 (d, J=7.0 Hz, 1H), 7.00-6.95 (m, 2H), 6.64 (s, 1H), 5.70 (s, 2H), 3.86 (s, 3H), 3.77-3.71 (m, 2H), 3.62-3.57 (m, 1H), 3.60 (s, 3H), 3.56 (s, 2H), 2.57-2.50 (m, 4H), 2.10-2.03 (m, 3H), 1.72-1.66 (m, 6H), 1.65-1.61 (m, 1H), 1.56-1.51 (m, 6H), 0.78 (t, J=7.0 Hz, 3H); MS (ESI): m/z 842.1 (M+H).

Example 160

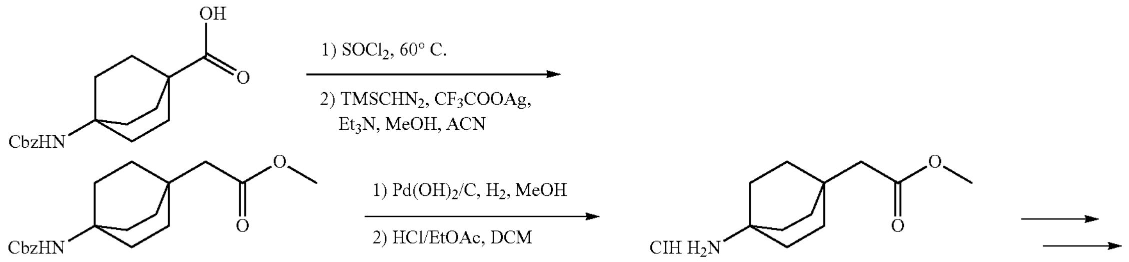

160a

160b

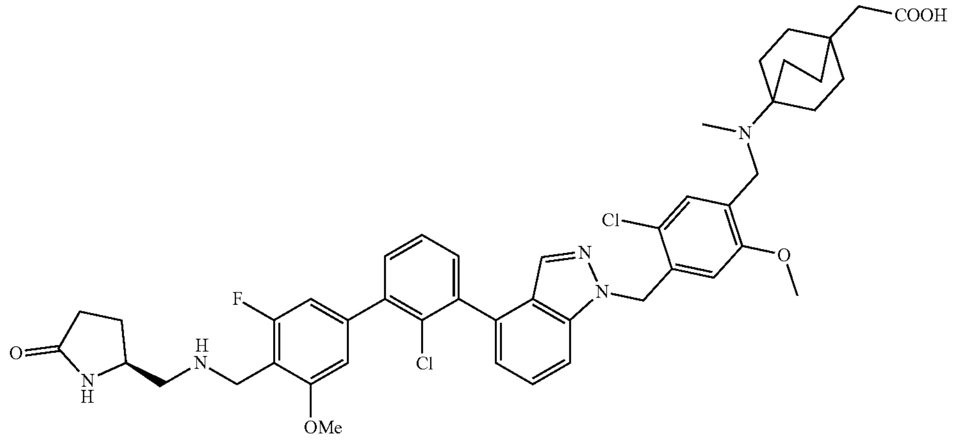

160

At 60° C., thionyl chloride (2 mL) solution with 4-(((benzyloxy)carbonyl)amino)bicyclo[2.2.2]octane-1-carboxylic acid (150 mg, 0.49 mmol) dissolved was stirred for 2 hours. After the reaction solution was concentrated, the residue was dissolved with acetonitrile (3 mL), and trimethylsilylated diazomethane (2 M in n-hexane, 0.24 mL) were added. The resulting reaction solution at room temperature was stirred for 2 hours. Subsequently at 0° C. in the above solution triethylamine (0.13 mL), silver trifluoroacetate (154 mg, 0.70 mmol) and methanol (1 mL) were added. The resulting reaction solution at room temperature was stirred for 16 hours. The reaction solution was filtered. The filtrate was concentrated. The residue was separated by silica gel column chromatography to obtain a white solid 160a (50 mg, yield: 32.4%). $^1$H NMR (500 MHz, DMSO-d6) δ 7.37-7.26 (m, 5H), 6.87 (s, 1H), 4.92 (s, 2H), 3.53 (s, 3H), 2.05 (s, 2H), 1.75-1.66 (m, 6H), 1.55-1.42 (m, 6H); MS (ESI): m/z 332.4 (M+H).

At room temperature and hydrogen atmosphere, methanol (3 mL) solution with compound 160a (100 mg, 0.30 mmol) and palladium hydroxide (10% w/w adsorbed on activated carbon, 20 mg) dissolved was stirred for 1 hour. The reaction solution was filtered with diatomaceous earth, The filtrate was concentrated and the residue was dissolved with dichloromethane (2 mL), and hydrochloric acid (4 M in ethyl acetate, 0.15 mL) was added dropwise. The resulting reaction solution was stirred for half an hour at room temperature. The reaction solution was concentrated to obtain solid residue, and was washed by ethyl acetate to obtain white solid 160b (60 mg, yield: 85.1%). MS (ESI): m/z 198.5 (M+H).

Starting from compound INT-16 and compound 160b, referring to the synthesis of compound 101, compound 160 is obtained. $^1$H NMR (500 MHz, DMSO-d6) δ 7.93 (s, 1H), 7.76 (d, J=8.5 Hz, 1H), 7.63 (s, 1H), 7.55-7.47 (m, 4H), 7.40 (s, 1H), 7.16 (d, J=7.0 Hz, 1H), 6.98-6.95 (m, 2H), 6.67 (s, 1H), 5.72 (s, 2H), 3.87 (s, 3H), 3.79-3.71 (m, 2H), 3.65-3.59 (m, 1H), 3.58 (s, 3H), 3.41 (s, 2H), 2.60-2.54 (m, 2H), 2.14-2.03 (m, 3H), 1.99 (s, 3H), 1.96 (s, 2H), 1.76-1.69 (m, 1H), 1.60-1.46 (m, 12H); MS (ESI): m/z 842.3 (M+H).

Example 161
161
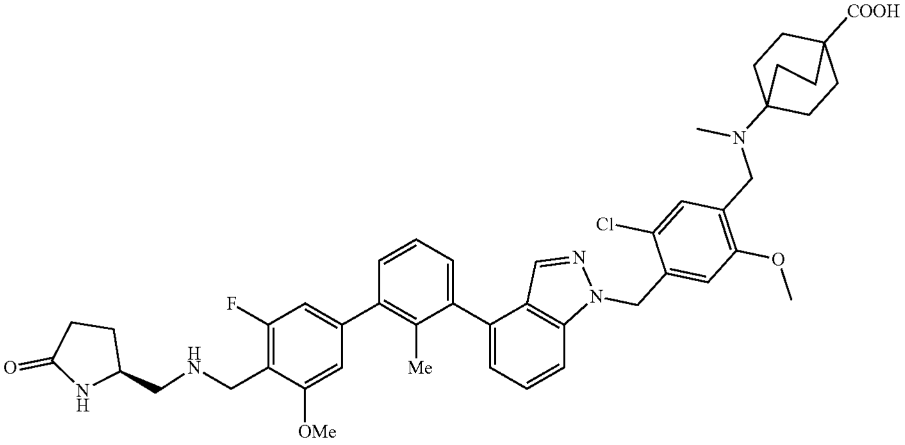
Referring to the synthesis of compound 116, 2-chloro-1,3-dibromobenzene is replaced with 2-methyl-1,3-dibromobenzene, compound 161 is obtained. $^1$H NMR (500 MHz, DMSO-d6) δ 7.92 (d, J=1.5 Hz, 1H), 7.73 (d, J=8.5 Hz, 1H), 7.65 (s, 1H), 7.52-7.47 (m, 1H), 7.40-7.36 (m, 2H), 7.35-7.31 (m, 2H), 7.09 (d, J=7.0 Hz, 1H), 6.93-6.88 (m, 2H), 6.65 (s, 1H), 5.72 (s, 2H), 3.87 (s, 3H), 3.78-3.71 (m, 2H), 3.64-3.60 (m, 1H), 3.57 (s, 3H), 3.42 (s, 2H), 2.56-2.53 (m, 2H), 2.13-2.06 (m, 3H), 2.03 (s, 3H), 2.00 (s, 3H), 1.76-1.68 (m, 6H), 1.69-1.63 (m, 1H), 1.60-1.53 (m, 6H); MS (ESI): m/z 808.1 (M+H).
Example 162
162
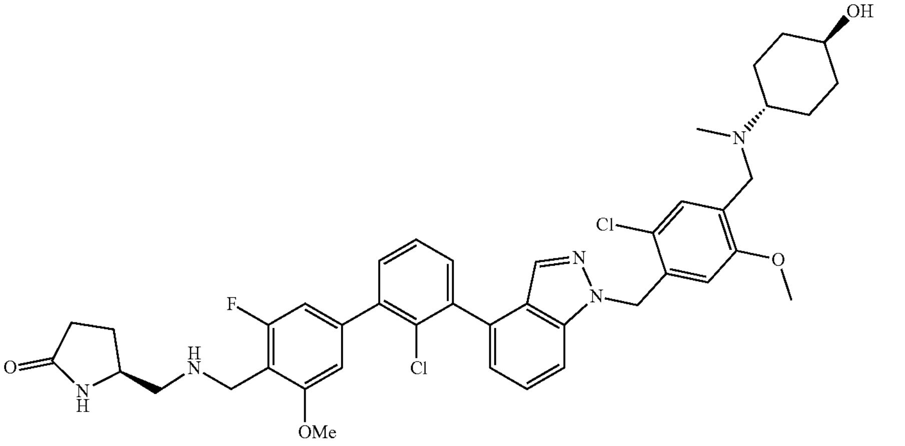

Starting from compound INT-16 and trans-4-aminocyclohexanol, referring to the synthesis of compound 101, compound 162 is obtained. $^{1}$H NMR (500 MHz, DMSO-d6) δ 7.93 (d, J=1.0 Hz, 1H), 7.76 (d, J=8.5 Hz, 1H), 7.64 (s, 1H), 7.54-7.48 (m, 4H), 7.35 (s, 1H), 7.15 (d, J=7.0 Hz, 1H), 6.98-6.94 (m, 2H), 6.67 (s, 1H), 5.71 (s, 2H), 4.43 (d, J=4.5 Hz, 1H), 3.85 (s, 3H), 3.77-3.70 (m, 2H), 3.62-3.60 (m, 1H), 3.56 (s, 3H), 3.42 (s, 2H), 3.35-3.32 (m, 1H), 2.55-2.52 (m, 1H), 2.36-2.33 (m, 1H), 2.10-2.04 (m, 6H), 1.84-1.78 (m, 2H), 1.72-1.67 (m, 2H), 1.65-1.59 (m, 1H), 1.31-1.20 (m, 2H), 1.14-1.06 (m, 2H); MS (ESI): m/z 774.1 (M+H).

Example 163

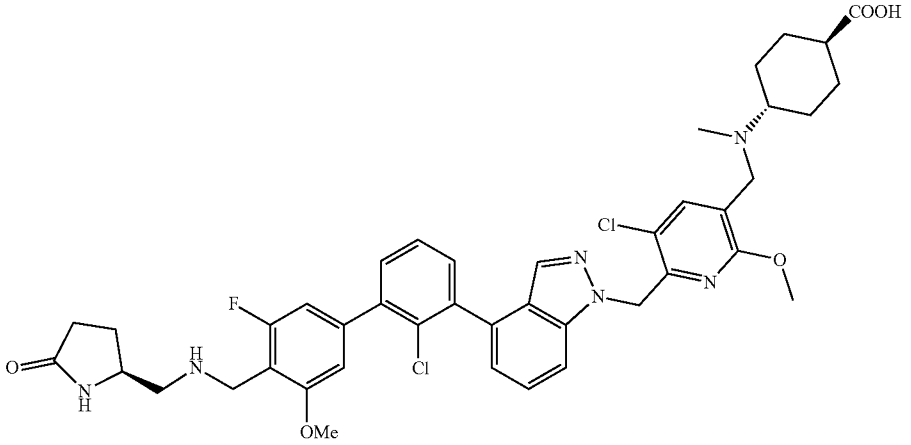

163

Referring to the synthesis of compound 135, 4-aminobicyclo[2.2.2]octane-1-carboxylic acid methyl ester hydrochloride is replaced with trans-4-methyl aminocyclohexanate hydrochloride, compound 163 is obtained. $^{1}$H NMR (500 MHz, DMSO-d6) δ 7.88-7.83 (m, 1H), 7.81-7.75 (m, 1H), 7.71-7.61 (m, 2H), 7.55-7.44 (m, 4H), 7.15-7.09 (m, 1H), 6.99-6.92 (m, 2H), 5.83-5.76 (m, 2H), 3.88-3.83 (m, 3H), 3.76-3.70 (m, 2H), 3.59-3.54 (m, 1H), 3.40-3.38 (m, 2H), 3.37-3.36 (m, 3H), 2.51-2.50 (m, 2H), 2.35-2.30 (m, 1H), 2.10-2.03 (m, 6H), 1.90-1.81 (m, 3H), 1.76-1.69 (m, 2H), 1.68-1.61 (m, 1H), 1.24-1.16 (m, 4H); MS (ESI): m/z 803.1 (M+H).

Example 164

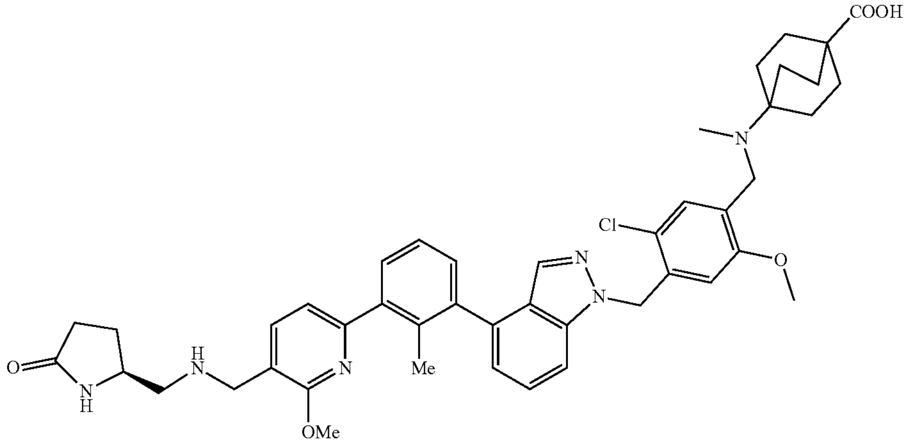

164

Referring to the synthesis of compound 133, 2-chloro-1,3-dibromobenzene is replaced with 2-methyl-1,3-dibromobenzene, compound 164 is obtained. $^1$H NMR (500 MHz, DMSO-d6) δ 7.81-7.77 (m, 2H), 7.72 (d, J=8.5 Hz, 1H), 7.67 (s, 1H), 7.50-7.44 (m, 2H), 7.40-7.35 (m, 2H), 7.34-7.30 (m, 1H), 7.18 (d, J=7.4 Hz, 1H), 7.08 (d, J=7.0 Hz, 1H), 6.65 (s, 1H), 5.70 (s, 2H), 3.88 (s, 3H), 3.75-3.68 (m, 2H), 3.66-3.59 (m, 1H), 3.57 (s, 3H), 3.41 (s, 2H), 2.54 (d, J=6.0 Hz, 2H), 2.15-2.05 (m, 3H), 2.09 (s, 3H), 1.99 (s, 3H), 1.75-1.69 (m, 6H), 1.69-1.65 (m, 1H), 1.59-1.52 (m, 6H); MS (ESI): m/z 791.0 (M+H).

Example 165

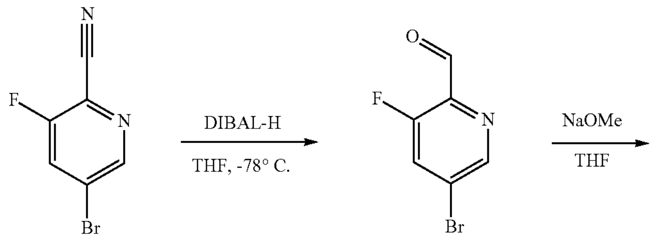

165a

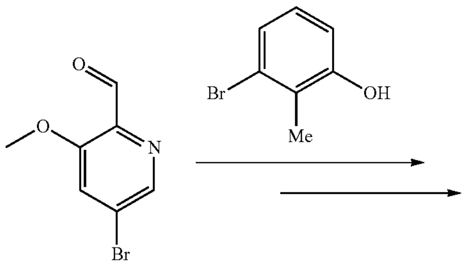

165b

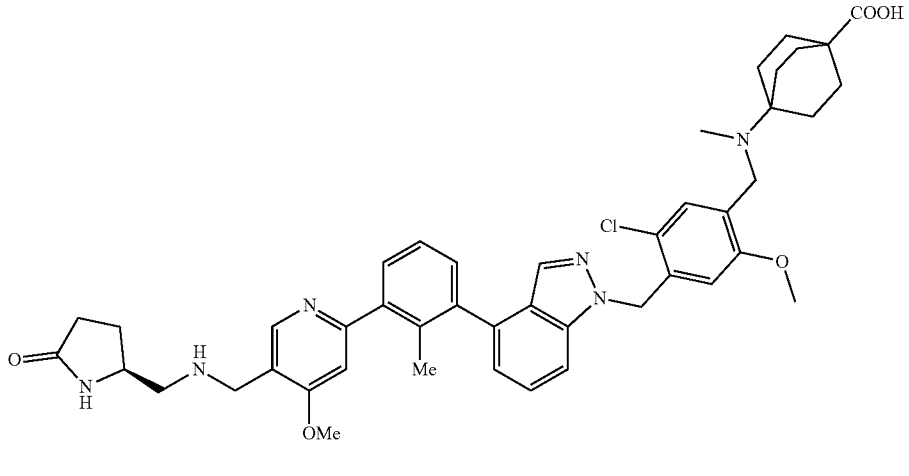

165

At −78° C. and nitrogen atmosphere, diisobutylaluminum hydride (1 M in toluene, 30.6 mL) was slowly added dropwise to tetrahydrofuran (40 mL) solution with 5-bromo-3-fluoro-2-pyridinecarbonitrile (4.1 g, 20.4 mmol) dissolved. The reaction solution was then at the same temperature stirred for 2 hours. Then in the reaction solution water (50 mL) was added, and the solution was filtered with diatomaceous earth. The resulting filtrate was extracted with ethyl acetate (50 mL×2). The combined organic phase was saturated salt solution (100 mL) washed with, dried with anhydrous sodium sulfate, filtered, concentrated. The residue was separated by silica gel column chromatography by to obtain a white solid 165a (2.7 g, yield: 64.9%). MS (ESI): m/z 204.0 (M+H).

Starting from compound 165a, referring to the synthesis of compound 156a, compound 165b is obtained. MS (ESI): m/z 216.3 (M+H).

Starting from compound 165b and 3-bromo-2-methylphenol, referring to the synthesis of compound INT-10 and compound 133, compound 165 is obtained. $^1$H NMR (500

MHz, DMSO-d6) δ 8.44 (s, 1H), 7.83 (s, 1H), 7.74 (d, J=8.5 Hz, 1H), 7.68 (s, 1H), 7.52-7.48 (m, 1H), 7.46-7.43 (m, 1H), 7.42-7.38 (m, 2H), 7.37-7.33 (m, 1H), 7.19 (s, 1H), 7.09 (d, J=6.9 Hz, 1H), 6.66 (s, 1H), 5.72 (s, 2H), 3.92 (s, 3H), 3.78-3.69 (m, 2H), 3.67-3.60 (m, 1H), 3.58 (s, 3H), 3.43-3.38 (m, 2H), 2.55 (d, J=6.0 Hz, 2H), 2.15-2.06 (m, 3H), 2.05 (s, 3H), 2.01 (s, 3H), 1.77-1.71 (m, 6H), 1.71-1.65 (m, 1H), 1.61-1.54 (m, 6H); MS (ESI): m/z 791.0 (M+H).
Example 166
166
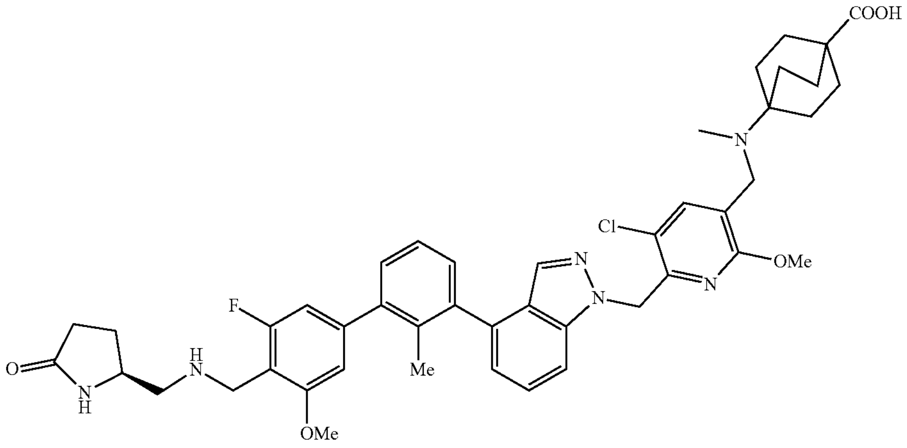
Referring to the synthesis of compound 135, 2-chloro-1,3-dibromobenzene is replaced with 2-methyl-1,3-dibromobenzene, compound 166 is obtained. $^1$H NMR (500 MHz, DMSO-d6) δ 7.87 (d, J=1.0 Hz, 1H), 7.79-7.75 (m, 1H), 7.72 (s, 1H), 7.67 (s, 1H), 7.50-7.46 (m, 1H), 7.41-7.37 (m, 1H), 7.36-7.29 (m, 2H), 7.09-7.05 (m, 1H), 6.95-6.89 (m, 2H), 5.82 (s, 2H), 3.88 (s, 3H), 3.80-3.72 (m, 2H), 3.65-3.55 (m, 1H), 3.38 (s, 3H), 3.35-3.30 (m, 2H), 2.54-2.50 (m, 2H), 2.13-2.05 (m, 3H), 2.02 (s, 6H), 1.76-1.70 (m, 6H), 1.69-1.64 (m, 1H), 1.60-1.53 (m, 6H); MS (ESI): m/z 809.1 (M+H).
Example 167
167
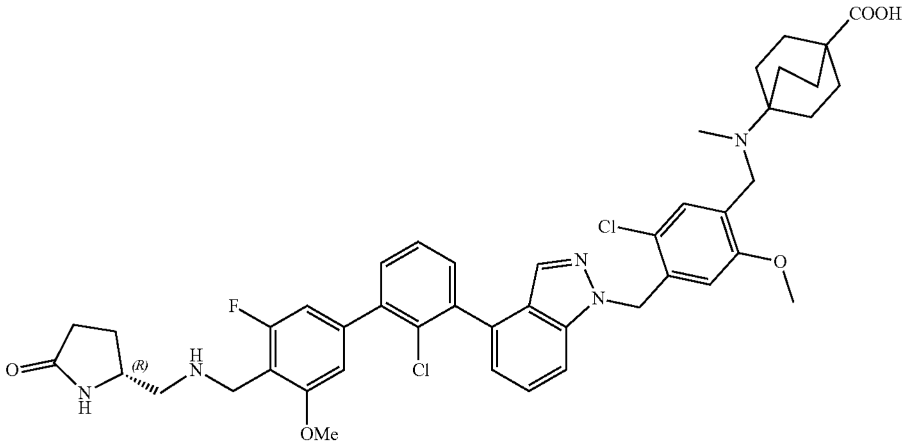

Referring to the synthesis of compound 133, compound INT-2 is replaced with compound 67a, compound 167 is obtained. $^1H$ NMR (500 MHz, DMSO-d6) δ 7.94 (s, 1H), 7.78 (d, J=8.5 Hz, 1H), 7.69 (s, 1H), 7.57-7.49 (m, 4H), 7.39 (s, 1H), 7.16 (d, J=7.0 Hz, 1H), 7.05-6.97 (m, 2H), 6.69 (s, 1H), 5.72 (s, 2H), 3.87 (s, 3H), 3.78-3.71 (m, 2H), 3.59-3.53 (m, 1H), 3.58 (s, 3H), 3.42 (s, 2H), 2.54-2.53 (m, 2H), 2.11-2.04 (m, 3H), 2.00 (s, 3H), 1.75-1.70 (m, 6H), 1.67-1.63 (m, 1H), 1.60-1.54 (m, 6H); MS (ESI): m/z 828.1 (M+H).

Example 168

168

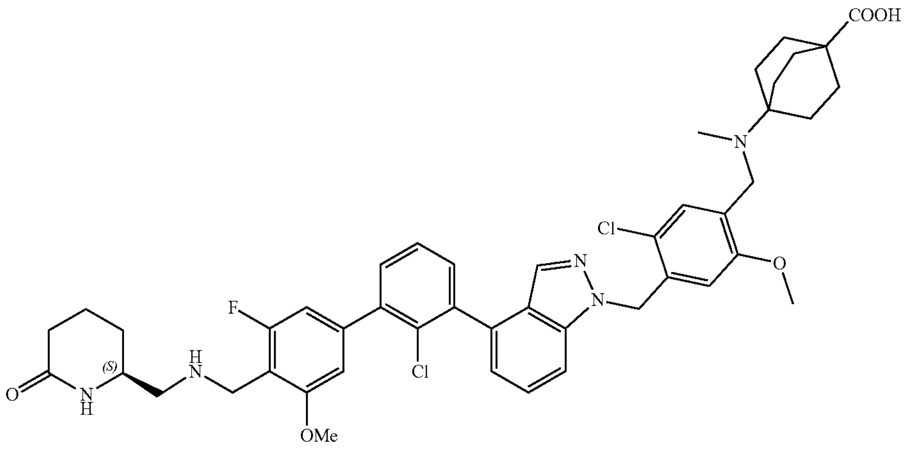

Referring to the synthesis of compound 133, wherein compound INT-2 is replaced with compound INT-18, compound 168 is obtained. $^1H$ NMR (500 MHz, DMSO-d6) δ 7.94 (s, 1H), 7.78 (d, J=8.7 Hz, 1H), 7.55-7.50 (m, 4H), 7.39 (s, 1H), 7.19-7.11 (m, 2H), 7.01-6.97 (m, 2H), 6.69 (s, 1H), 5.72 (s, 2H), 3.87 (s, 3H), 3.75-3.70 (m, 2H), 3.58 (s, 3H), 3.42 (s, 2H), 3.36-3.35 (m, 1H), 2.53-2.52 (m, 2H), 2.12-2.07 (m, 2H), 2.00 (s, 3H), 1.76-1.70 (m, 8H), 1.58-1.54 (m, 7H), 1.34-1.27 (m, 1H); MS (ESI): m/z 842.1 (M+H).

Example 169

169

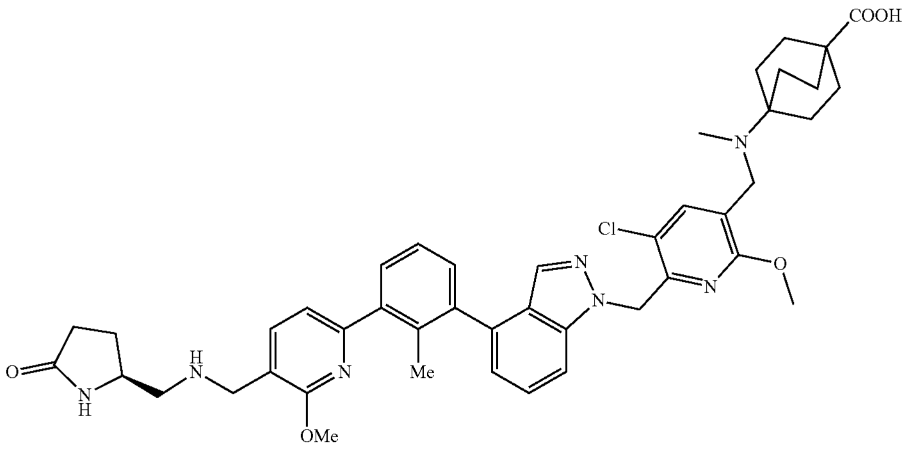

Referring to the synthesis of compound 137, wherein 2-chloro-1,3-dibromobenzene is replaced with 2-methyl-1,3-dibromobenzene, compound 169 is obtained. $^1H$ NMR (500 MHz, DMSO-d6) δ 7.81 (d, J=7.5 Hz, 1H), 7.79-7.74 (m, 2H), 7.73-7.69 (m, 2H), 7.51-7.44 (m, 2H), 7.42-7.37 (m, 1H), 7.35-7.29 (m, 1H), 7.20 (d, J=7.5 Hz, 1H), 7.07 (d, J=7.5 Hz, 1H), 5.81 (s, 2H), 3.90 (s, 3H), 3.75-3.67 (m, 2H), 3.66-3.59 (m, 1H), 3.37 (s, 3H), 3.35 (s, 2H), 2.58-2.54 (m, 2H), 2.14-2.06 (m, 3H), 2.10 (s, 3H), 2.00 (s, 3H), 1.75-1.66 (m, 7H), 1.61-1.44 (m, 6H); MS (ESI): m/z 792.2 (M+H).

Example 170

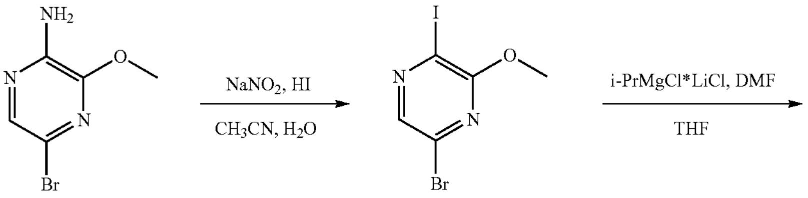

170a

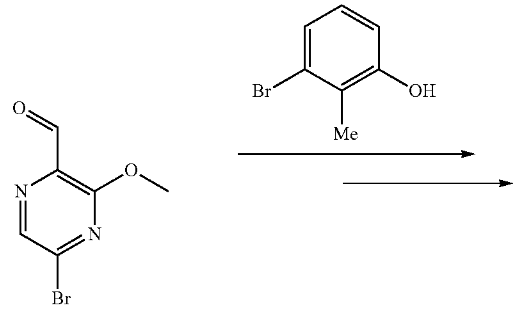

170b

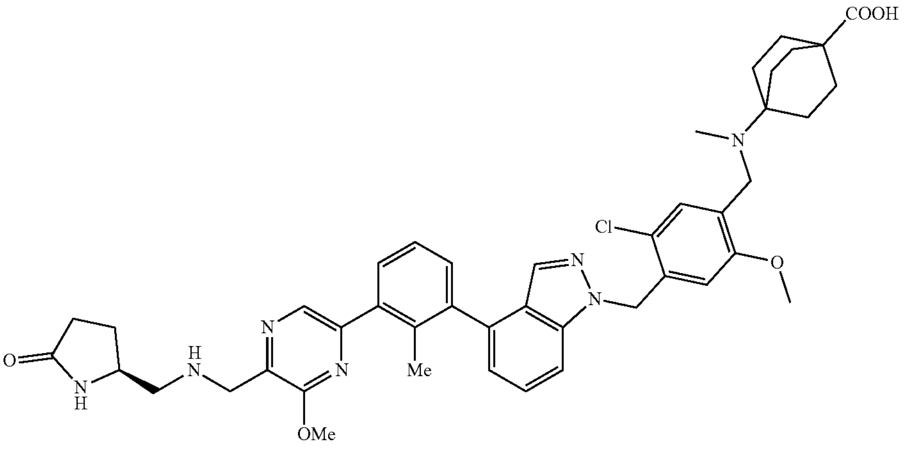

170

At 0° C., a solution of water (50 mL) with sodium nitrite (10 g, 147 mmol) dissolved was slowly added dropwise to a mixed solution of acetonitrile and water (250 mL, v/v=3/2) with 2-amino-5-bromo-3-methoxy pyrazine (2 g, 9.8 mmol) and hydroiodic acid (57% w/w, 50 mL) predissolved. The reaction solution was heated to 50° C. while stirring, and reacted under the same condition for 16 hours. The reaction solution was neutralized with 20% sodium hydroxide aqueous solution and was extracted with ethyl acetate (100 mL×2). The combined organic phase was washed with saturated sodium thiosulfate solution and saturated salt solution (each 150 mL), dried with anhydrous sodium sulfate, filtered, and concentrated. The residue was separated by silica gel column chromatography to obtain brown solid 170a (1.55 g, yield: 50.2%).

At nitrogen atmosphere and −40° C., isopropyl magnesium chloride-lithium chloride (1.3 M in tetrahydrofuran solution, 1.83 mL) was slowly added dropwise to tetrahydrofuran (10 mL) solution with compound 170a (500 mg, 1.6 mmol) dissolved. The reaction solution was further stirred under the same conditions for half an hour, subsequently heated to 15° C. and then N, N-dimethylformamide (1.2 mL) was slowly added. The resulting reaction solution was further stirred for 2 hours at 15° C. The reaction solution was neutralized with citric acid and extracted with ethyl acetate (50 mL×2). The combined organic phase was saturated salt solution (100 mL) washed with, dried with anhydrous sodium sulfate, filtered, concentrated. The residue was separated by silica gel column chromatography separated to obtain a light yellow solid 170b (300 mg, yield: 87.1%). MS (ESI): m/z 217.0 (M+H).

Starting from compound 165b and 3-bromo-2-methylphenol, referring to the synthesis of compound INT-10 and compound 133, compound 170 is obtained. $^1$H NMR (500 MHz, DMSO-d6) δ 8.38 (s, 1H), 7.81 (s, 1H), 7.74 (d, J=8.4 Hz, 1H), 7.67 (s, 1H), 7.53 (d, J=7.4 Hz, 1H), 7.51-7.46 (m, 1H), 7.44-7.37 (m, 3H), 7.09 (d, J=7.0 Hz, 1H), 6.66 (s, 1H), 5.70 (s, 2H), 3.95 (s, 3H), 3.87 (s, 2H), 3.63-3.60 (m, 1H), 3.57 (s, 3H), 3.41 (s, 2H), 2.60-2.57 (m, 2H), 2.11 (s, 3H), 2.10-2.02 (m, 3H), 1.99 (s, 3H), 1.73-1.67 (m, 7H), 1.58-1.53 (m, 6H); MS (ESI): m/z 792.1 (M+H).

Example 171

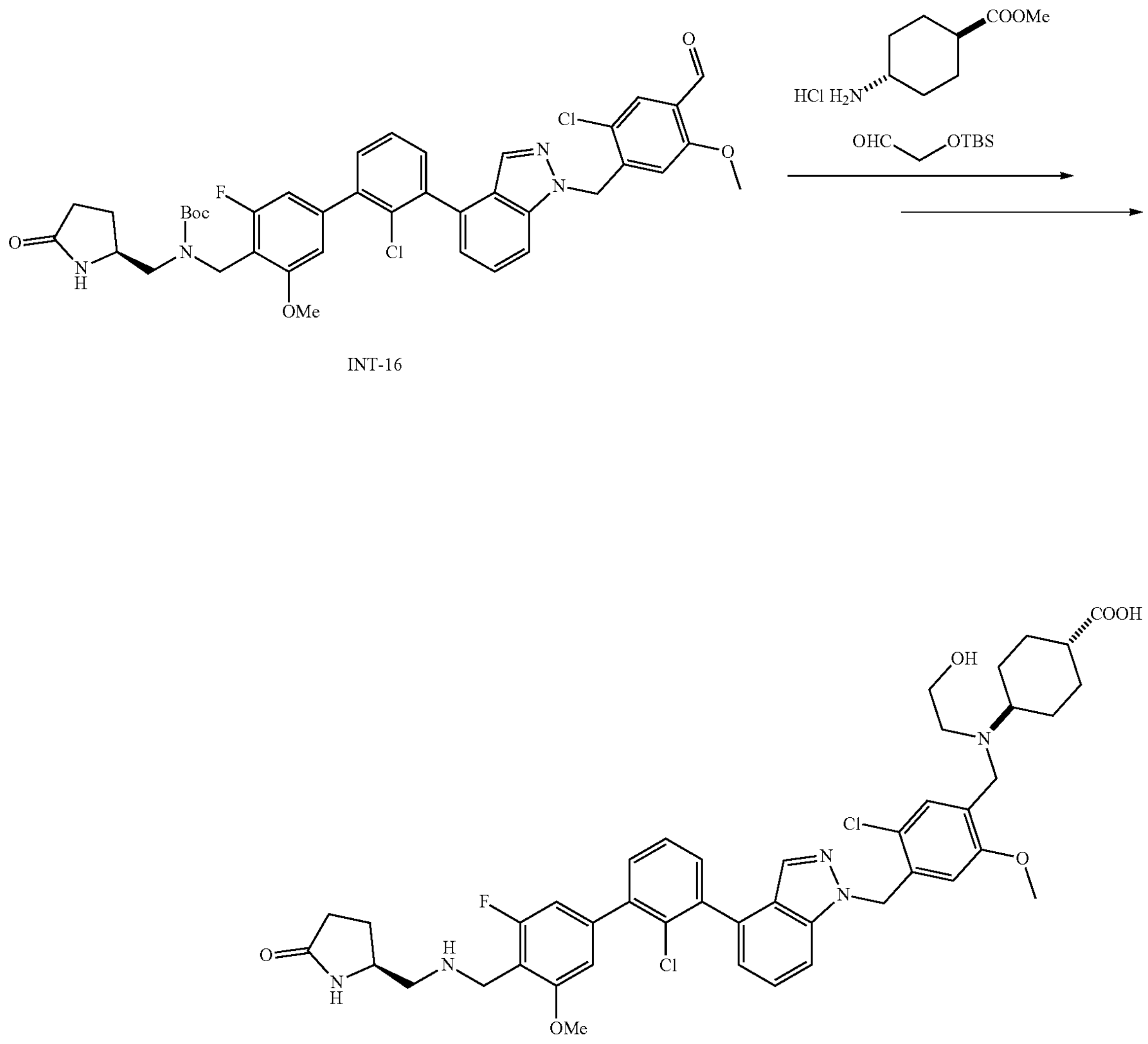

INT-16

171

Starting from compound INT-16, trans-4-methyl amino-cyclohexanate hydrochloride and tert-butyldimethylsiloxane acetaldehyde, referring to the synthesis of compound 125, compound 171 is obtained. $^1$H NMR (500 MHz, DMSO-d6) δ 7.96 (s, 1H), 7.80 (d, J=8.5 Hz, 1H), 7.69 (s, 1H), 7.60-7.50 (m, 5H), 7.17 (d, J=7.1 Hz, 1H), 7.09-6.99 (m, 2H), 6.69 (s, 1H), 5.73 (s, 2H), 3.89 (s, 3H), 3.85-3.80 (m, 2H), 3.78-3.47 (m, 5H), 3.60 (s, 3H), 2.56-2.53 (m, 2H), 2.16-2.04 (m, 5H), 1.94-1.87 (m, 2H), 1.81-1.65 (m, 4H), 1.63-1.53 (m, 1H), 1.31-1.20 (m, 4H); MS (ESI): m/z 832.0 (M+H).

Example 172

172

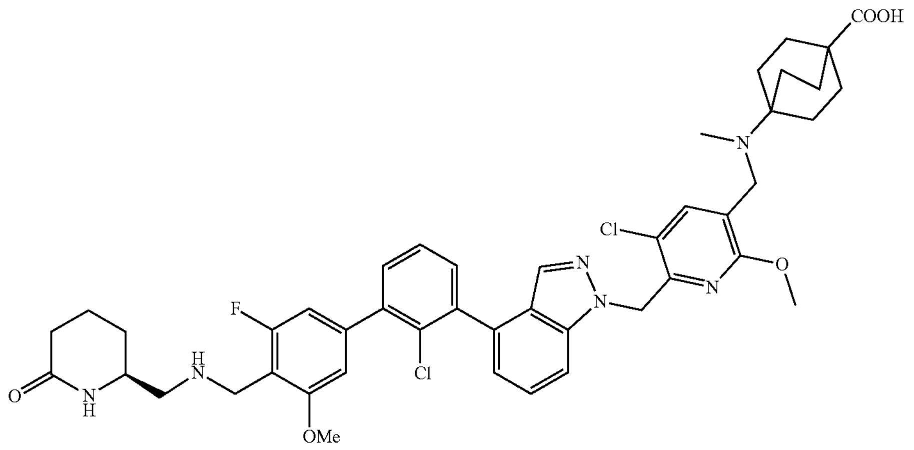 [SMILES: COc1cc(-c2cccc(-c3cccc4c3cnn4Cc3nc(OC)c(CN(C)C45CCC(C(=O)O)(CC4)CC5)cc3Cl)c2C)cc(F)c1CNC[C@@H]1CCCC(=O)N1]

Referring to the synthesis of compound 135, compound INT-2 is replaced with compound INT-18, compound 172 is obtained. $^1$H NMR (500 MHz, DMSO-d6) δ 7.88 (s, 1H), 7.81 (d, J=8.5 Hz, 1H), 7.71 (s, 1H), 7.57-7.47 (m, 4H), 7.17-7.12 (m, 2H), 7.01-6.96 (m, 2H), 5.81 (s, 2H), 3.88 (s, 3H), 3.76-3.69 (m, 2H), 3.38 (s, 3H), 3.36-3.29 (m, 3H), 2.57-2.53 (m, 2H), 2.15-2.05 (m, 2H), 2.00 (s, 3H), 1.79-1.68 (m, 8H), 1.60-1.52 (m, 7H), 1.35-1.28 (m, 1H); MS (ESI): m/z 843.1 (M+H).

Example 173

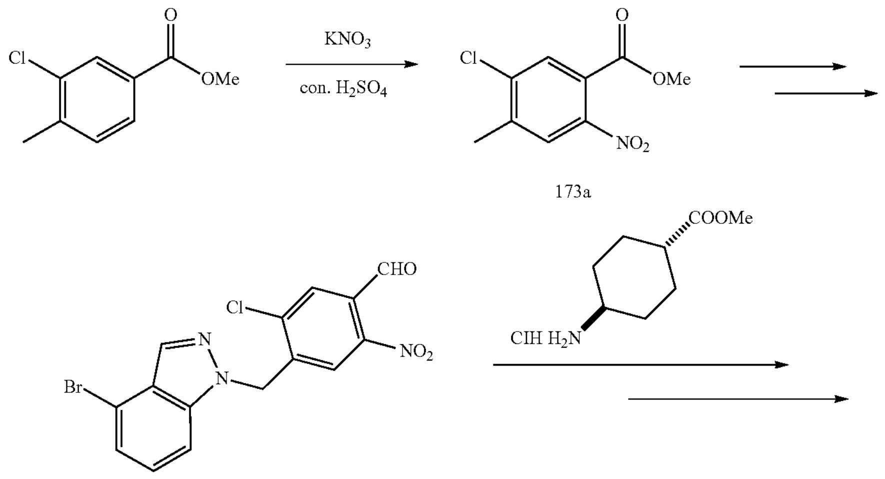

173a

173b

-continued

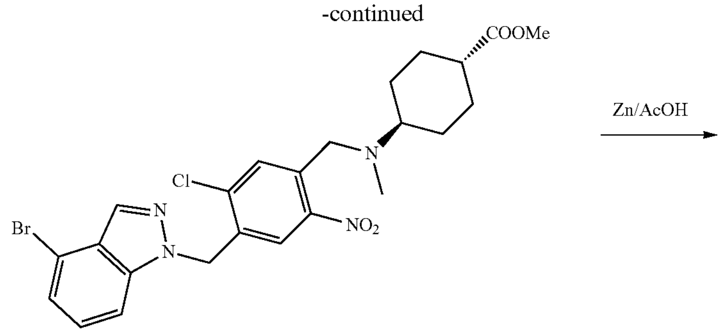

173c

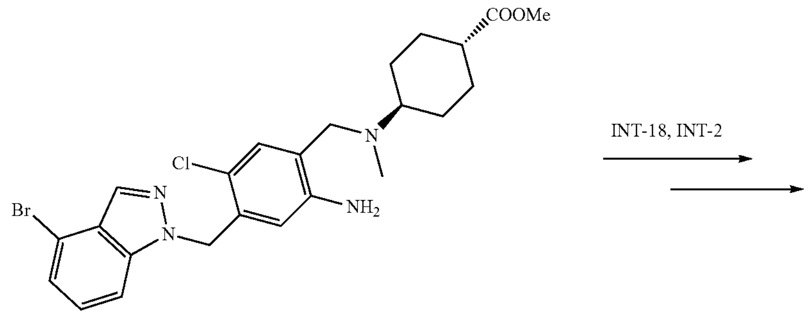

173d

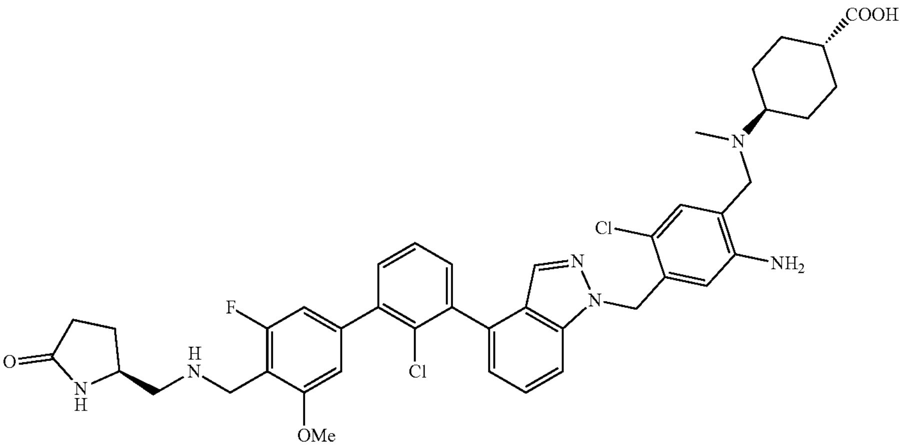

173

At 0° C., concentrated sulfuric acid (1 mL) with potassium nitrate (55 mg, 0.54 mmol) dissolved was added dropwise to concentrated sulfuric acid (2 mL) with methyl 3-chloro-4-methylbenzoate (100 mg, 0.54 mmol) predissolved. The reaction solution under the same conditions was stirred for half an hour. The reaction solution was subsequently poured into ice water and was extracted with ethyl acetate (15 mL×2). The combined organic phase was washed with saturated salt solution (30 mL), dried with anhydrous sodium sulfate, filtered, and concentrated. The residue was separated by silica gel column chromatography (petroleum ether/ethyl acetate=10/1, v/v) to obtain colorless oily matter 173a (100 mg, yield: 80.4%). $^1H$ NMR (500 MHz, DMSO-d6) δ 8.13 (s, 1H), 7.93 (s, 1H), 3.83 (s, 3H), 2.44 (s, 3H).

Starting from compound 173a and trans-4-methyl aminocyclohexanate hydrochloride, referring to the synthesis of compound 72c and reductive amination of compound 44, compound 173c is obtained. MS (ESI): m/z 549.0 (M+H).

Zinc powder (44 mg, 0.67 mmol) was added to acetic acid (4 mL) solution with compound 173c (74 mg, 0.13 mmol) dissolved. The resulting reaction solution was heated at 60° C. and stirred for 2 hours. The reaction solution was concentrated and then ethyl acetate (20 mL) and saturated sodium bicarbonate solution (20 mL) were added. Organic phase was dried by anhydrous sodium sulfate, concentrated thus compound 173d is obtained. MS (ESI): m/z 519.0 (M+H).

Starting from compound 173d, compound INT-18 and compound INT-2, sequentially referring to Suzuki reaction of compound INT-7, reductive amination reaction of compound INT-3b and ester hydrolysis reaction of compound 33, compound 173 is obtained. $^1H$ NMR (500 MHz, DMSO-d6) δ 7.92 (s, 1H), 7.69 (d, J=8.6 Hz, 1H), 7.64 (s, 1H), 7.55-7.46 (m, 4H), 7.15 (d, J=7.0 Hz, 1H), 7.04 (s, 1H), 6.98-6.96 (m, 2H), 6.23 (s, 1H), 5.60 (s, 2H), 5.38 (s, 2H), 3.86 (s, 3H), 3.73 (d, J=4.3 Hz, 2H), 3.58-3.56 (m, 1H), 3.42 (s, 2H), 2.53-2.50 (m, 2H), 2.34-2.30 (m, 1H), 2.23 (brs, 1H), 2.10-1.95 (m, 3H), 2.03 (s, 3H), 1.92-1.86 (m, 2H), 1.77-1.71 (m, 2H), 1.66-1.61 (m, 1H), 1.32-1.18 (m, 4H); MS (ESI): m/z 787.8 (M+H).

Test Example

Detection of Biological Activity of PD-1/PD-L1 Signaling Inhibition at the Cellular Level This detection method is used for evaluating the biological activity of the compounds described in the present invention at the cellular level.

Experimental Principle

This detection method uses the luciferase reporter gene method to detect the biological activity of the compound on the inhibition of PD-1/PD-L1 signal at the cellular level. PD-1/NFAT—Reporter—Jurkat cells stably express human PD-1 and express the luciferase reporter gene regulated by NFAT elements; TCR activator/PD-L1-CHO cells stably express human PD-L1 and TCR activator elements. When the two cell lines were co-cultured, the binding of PD-1/PD-L1 inhibited the TCR signaling pathway, thereby inhibiting the expression of the downstream NFAT-controlled luciferase reporter gene. When PD-1/PD-L1 antibody or inhibitor is added, this inhibitory effect is reversed and luciferase is expressed, so that the effect of PD-1/PD-L1 inhibitor on luciferase activity can be detected.

Experimental Materials and Equipment

PD-1/NFAT—Reporter—Jurkat cell (Cat: 60535) and TCR activator/PD-L1-CHO cell (Cat: 60536) were purchased from BPS Bioscience. Anti-human PD-L1 antibody (Atezolizumab, Cat: A2004) was purchased from Selleck; luciferase reporter gene expression detection kit (ONE-Glo™ Luciferase Assay System, Cat: E6120) was purchased from Promega; multifunction plate reader (SpectraMax i3x) was purchased from Molecular Devices.

Main Procedures of the Experiment

The PD-1/NFAT—Reporter—Jurkat cells and TCR activator/PD-L1-CHO cells were cultured according to the routine cell culture protocol.

TCR activator/PD-L1-CHO cells were harvested and seeded into a 96-well culture plate at 35,000 cells/well in a medium volume of 100 μl and incubated overnight at 37° C. The next day, the medium was discarded, compound was added and incubated for 30 minutes, while a solvent control (dimethyl sulfoxide, DMSO, final concentration of 0.1%) and PD-L1 antibody (Atezolizumab, final concentration of about 10 nM) as positive controls were set. PD-1/NFAT-reporter-Jurkat cells were then added. After culturing for 6 hours, the luciferase activity was detected according to the instructions of the luciferase detection reagent.

Using PD-L1 antibody as a positive control, calculate the inhibition rate of PD-1/PD-L1 binding of the test compound (%)=(chemiluminescence value of compound treated wells/average value of chemiluminescence value of solvent control wells−1)/(average value of chemiluminescence value of PD-L1 antibody well/average value of chemiluminescence value of solvent control well−1)×100%.

According to the above detection method, the compounds of the present invention were evaluated for their biological activity at the cellular level, and the activity results are shown in the following table.

| Compound No. | EC50 NFAT Luciferase (nM) | Compound No. | EC50 NFAT Luciferase (nM) |
|---|---|---|---|
| 1 | 83 | 2 | 85 |
| 3 | 395 | 4 | 206 |
| 5 | 58 | 6 | 228 |
| 7 | 161 | 8 | 31 |
| 9 | 591 | 10 | 82 |
| 11 | 112 | 12 | 255 |
| 13 | 116 | 14 | 339 |
| 18 | 562 | 19 | 510 |
| 22 | 89 | 23 | 512 |
| 24 | 54 | 25 | 128 |
| 26 | 86 | 27 | 133 |
| 28 | 110 | 29 | 66 |
| 30 | 82 | 31 | 82 |
| 32 | 244 | 33 | 511 |
| 34 | 488 | 35 | 859 |
| 36 | 459 | 37 | 977 |
| 38 | 809 | 39 | 298 |
| 40 | 213 | 41 | 295 |
| 42 | 348 | 43 | 537 |
| 47 | 499 | 48 | 654 |
| 49 | 850 | | |
| 51 | 692 | 52 | 92 |
| 53 | 24 | 54 | 38 |
| 55 | 66 | 56 | 50 |
| 57 | 38 | 58 | 69 |
| 59 | 37 | 60 | 33 |
| 63 | 950 | 69 | 805 |
| 70 | 222 | 71 | 693 |
| 75 | 142 | 76 | 49 |
| 80 | 302 | 83 | 92 |
| 85 | 469 | 86 | 395 |
| 87 | 692 | 88 | 80 |
| 89 | 1110 | 90 | 150 |
| 91 | 92 | 92 | 15 |
| 93 | 21 | 94 | 142 |
| 95 | 15 | 96 | 45 |
| 97 | 273 | 98 | 520 |
| 99 | 62 | 100 | 745 |
| 101 | 87 | 102 | 735 |
| 103 | 208 | 104 | 46 |
| 105 | 20 | 106 | 43 |
| 107 | 20 | 108 | 63 |
| 109 | 44 | 110 | 495 |
| ill | 1043 | 112 | 185 |
| 113 | 15 | 114 | 14 |
| 115 | 16 | 116 | 16 |
| 117 | 537 | 118 | 53 |
| 119 | 152 | 120 | 32 |
| 121 | 34 | 122 | 320 |
| 123 | 520 | 124 | 91 |
| 125 | 680 | 126 | 103 |
| 127 | 160 | 128 | 391 |
| 129 | 29 | 130 | 134 |
| 131 | 40 | 132 | 23 |
| 133 | 81 | 134 | 68 |
| 135 | 25 | 136 | 240 |
| 137 | 41 | 138 | 15 |
| 139 | 15 | 140 | 25 |
| 141 | 40 | 142 | 37 |
| 143 | 31 | 144 | 40 |
| 145 | 51 | 146 | 28 |
| 147 | 32 | 148 | 34 |
| 149 | 28 | 150 | 30 |
| 151 | 63 | 152 | 56 |
| 153 | 94 | 154 | 393 |
| 155 | 145 | 156 | 133 |
| 157 | 90 | 158 | 1011 |
| 159 | 37 | 160 | 46 |
| 161 | 75 | 162 | 44 |
| 163 | 26 | 164 | 105 |
| 165 | 98 | 166 | 49 |
| 167 | 53 | 168 | 69 |
| 169 | 59 | 170 | 265 |
| 171 | 40 | 172 | 32 |
| 173 | 222 | Ref compound[1] | 85 |

Ref compound is from the Example 40260 of patent US20180057455, and was internally synthesized to obtain It can be seen from the above results that the compound of the present invention can effectively inhibit PD-1/PD-L1 and has good PD-1/PD-L1 inhibitory activity.

The invention claimed is:

1. A compound of formula (I) or a pharmaceutically acceptable salt thereof,

Formula (I)

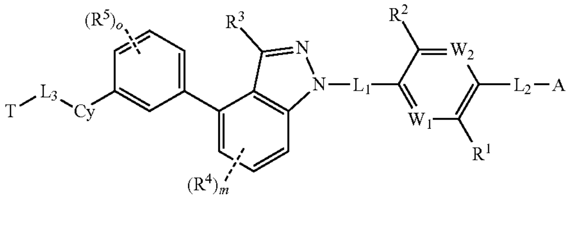

wherein $L_1$ is selected from —$CR^AR^B$— and —C(O)—;

$L_2$, $L_3$ is selected from —$(CR^CR^D)_p$, —$(CR^CR^D)_p$—$NR^a$—$(CR^CR^D)_q$—, —$(CR^CR^D)_p$—O—$(CR^CR^D)_q$— and —C(O)—;

$W_1$, $W_2$ each independently represent $CR^L$ or N;

$R^1$ each independently represent hydrogen, halogen, nitro, cyano or —$NR^aR^b$ or $C_1$-$C_6$ alkyl, $C_3$-$C_6$ cycloalkyl, —O($C_1$-$C_6$ alkyl), —O($C_0$-$C_6$ alkylene)($C_3$-$C_6$ cycloalkyl) or —O($C_0$-$C_6$ alkylene)(3-6 membered heterocycloalkyl) substituted with 0, 1, 2 or 3 substituents; wherein the substituents are selected from —$OR^a$, cyano, oxo, halogen, $C_1$-$C_6$ alkyl, —($C_1$-$C_6$ alkylene) $OR^a$, cyano $C_1$-$C_6$ alkyl, $C_1$-$C_6$ haloalkyl, $C_3$-$C_8$ cycloalkyl, —C(O)$R^a$, —($C_1$-$C_6$ alkylene)C(O)$R^a$, —C(O)$OR^a$, —($C_1$-$C_6$ alkyl)C(O)$OR^a$, —$NR^aR^b$, —($C_1$-$C_6$ alkylene)$NR^aR^b$, —C(O)$NR^aR^b$, —$SO_2R^a$, —C(O)$NR^aSO_2R^b$ and —$NR^a$C(O)$R^b$, wherein the 3-6 membered heterocycloalkyl contain 1, 2 or 3 heteroatoms selected from N, O and S;

$R^2$ and $R^3$ each independently represent hydrogen, halogen, nitro, cyano, —$NR^aR^b$, —$SO_2R^a$, —S(O)$R^a$, —P(O)$R^aR^b$, $C_1$-$C_6$ alkyl, —O($C_1$-$C_6$ alkyl), —O($C_3$-$C_6$ cycloalkyl), halo($C_1$-$C_6$ alkyl) or $C_3$-$C_6$ cycloalkyl;

$R^4$ and $R^5$ each independently represent halogen, nitro, cyano, —$NR^aR^b$, —$SO_2R^a$, —S(O)$R^a$, —P(O)$R^aR^b$, $C_1$-$C_6$ alkyl, —O($C_1$-$C_6$ alkyl), —O($C_3$-$C_6$ cycloalkyl), halo($C_1$-$C_6$ alkyl) or $C_3$-$C_6$ cycloalkyl;

Cy represents phenylene or six-membered heteroaryl substituted by 0, 1, 2 or 3 $R^6$, wherein the six-membered heteroaryl may optionally contain 1 or 2 nitrogen atoms; wherein the $R^6$ represents hydrogen, halogen, nitro, cyano, —$NR^aR^b$, —$SO_2R^a$, —S(O)$R^a$ or —P(O) $R^aR^b$ or $C_1$-$C_6$ alkyl, $C_3$-$C_6$ cycloalkyl, —O($C_1$-$C_6$ alkyl), —O($C_0$-$C_6$ alkylene)($C_5$-$C_{10}$ aryl), —O($C_0$-$C_6$ alkylene)(5-10 membered heteroaryl), —O($C_0$-$C_6$ alkylene)($C_3$-$C_6$ cycloalkyl) or —O($C_0$-$C_6$ alkylene) (3-6 membered heterocycloalkyl) substituted with 0, 1, 2 or 3 substituents; wherein the substituents are selected from —$OR^a$, cyano, oxo, halogen, $C_1$-$C_6$ alkyl, —($C_1$-$C_6$ alkylene)$OR^a$, cyano $C_1$-$C_6$ alkyl, $C_1$-$C_6$ haloalkyl, $C_3$-$C_8$ cycloalkyl, —C(O)$R^a$, —($C_1$-$C_6$ alkylene)C(O)$R^a$, —C(O)$OR^a$, —($C_1$-$C_6$ alkylene) C(O)$OR^a$, —$NR^aR^b$, —($C_1$-$C_6$ alkylene)$NR^aR^b$, —C(O)$NR^aR^b$, —$SO_2R^a$, —C(O)$NR^aSO_2R^b$ or —$NR^a$C(O)$R^b$, wherein the six-membered heteroaryl contains 1, 2, 3 or 4 heteroatoms independently selected from N, O and S, and the 3-6 membered heterocycloalkyl contain 1, 2 or 3 heteroatoms selected from N, O and S;

wherein $R^L$ represents hydrogen, $C_1$-$C_6$ alkyl, —O($C_1$-$C_6$ alkyl), —O($C_3$-$C_6$ cycloalkyl), halogen, nitro, cyano, —$NR^aR^b$, halo($C_1$-$C_6$ alkyl) or $C_3$-$C_6$ cycloalkyl;

T, A each independently represent —($C_1$-$C_6$ alkyl), —($C_0$-$C_6$ alkylene)-($C_3$-$C_{12}$ cycloalkyl), —($C_0$-$C_6$ alkylene)-(3-12 membered heterocycloalkyl), —($C_0$-$C_6$ alkylene)-($C_6$-$C_{10}$ aryl) or —($C_0$-$C_6$ alkylene)-(5-10 membered heteroaryl) substituted with 0, 1, 2 or 3 substituents, wherein the substituents are selected from: cyano, oxo, halogen, $C_1$-$C_6$ alkyl, —($C_0$-$C_6$ alkylene) $OR^a$, cyano $C_1$-$C_6$ alkyl, halo($C_1$-$C_6$ alkyl), $C_3$-$C_8$ cycloalkyl, —($C_0$-$C_6$ alkylene)C(O)$R^a$, —($C_0$-$C_6$ alkylene)C(O)$OR^a$, —($C_0$-$C_6$ alkenyl)C(O)$OR^a$, —($C_0$-$C_6$ alkylene)$NR^aR^b$, —C(O)$NR^aR^b$, —$NR^aSO_2R^b$, —C(O)$NR^aSO_2R^b$ and —$NR^a$C(O)$R^b$, wherein the 3-12 membered heterocycle is a heteroaryl or a heterocycloalkyl which contains 1, 2 or 3 heteroatoms selected from N, O and S, and the 5-10 membered heteroaryl contains 1, 2, 3 or 4 heteroatoms independently selected from N, O and S;

wherein $R^A$, $R^B$ each independently represent hydrogen, $C_1$-$C_6$ alkyl, —($C_0$-$C_3$ alkylene)($C_3$-$C_{12}$ cycloalkyl), —($C_0$-$C_3$ alkylene)(3-12 membered heterocycloalkyl), halo($C_1$-$C_6$ alkyl) or halogen, or $R^A$ and $R^B$ together with their co-attached carbon atoms form a 3-6 membered ring, wherein the 3-12 membered heterocycle is a heteroaryl or a heterocycloalkyl which contains 1, 2 or 3 heteroatoms selected from N, O and S; and the 3-6 membered ring contains a carbon atom and a heteroatom selected from N, O and S;

$R^C$, $R^D$ each independently represent: hydrogen, $C_1$-$C_6$ alkyl, —($C_0$-$C_3$ alkylene)($C_3$-$C_{12}$ cycloalkyl), —($C_0$-$C_3$ alkylene)(3-12 membered heterocycloalkyl), halo ($C_1$-$C_6$ alkyl) or halogen, or $R^C$ and $R^D$ together with their co-attached carbon atom form a 3-6 membered ring, wherein the 3-12 membered heterocycle is a heteroaryl or a heterocycloalkyl which contains 1, 2 or 3 heteroatoms selected from N, O and S, and the 3-6 membered ring contains a carbon atom and a heteroatom selected from N, O and S;

$R^a$, $R^b$ each independently represent hydrogen, $C_1$-$C_6$ alkyl, halo($C_1$-$C_6$ alkyl), —($C_0$-$C_6$ alkylene)OH, —($C_0$-$C_3$ alkylene)($C_3$-$C_{12}$ cycloalkyl), —($C_0$-$C_3$ alkylene)(3-12 membered heterocycloalkyl), —($C_0$-$C_3$ alkylene)($C_6$-$C_{10}$ aryl), —($C_0$-$C_3$ alkylene)(5-10 membered heteroaryl) or halo($C_1$-$C_6$ alkyl), or $R^a$ and $R^b$ together with their co-attached atom form a 3-6 membered ring, wherein the 3-12 membered heterocycle is a heteroaryl or a heterocycloalkyl which contains 1, 2 or 3 heteroatoms selected from N, O and S, the 5-10 membered heteroaryl contains 1, 2, 3 or 4 heteroatoms independently selected from N, O and S, and the 3-6 membered ring contains a carbon atom and a heteroatom selected from N, O and S;

wherein m, o each independently represent 0, 1 or 2; and wherein p, q each independently represent 0, 1, 2 or 3.

2. The compound of Formula (I) or a pharmaceutically acceptable salt thereof according to claim 1, wherein the compound of Formula (I) having the following structure of Formula (II):

Formula (II)

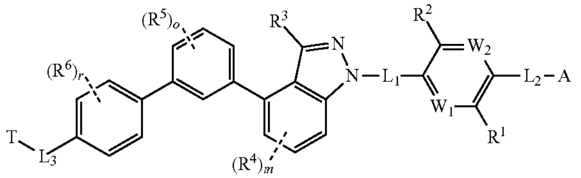

wherein r represents 0, 1, 2 or 3.

3. The compound of Formula (I) or a pharmaceutically acceptable salt thereof according to claim 1, wherein the compound of Formula (I) having the following structure of Formula (III):

Formula (III)

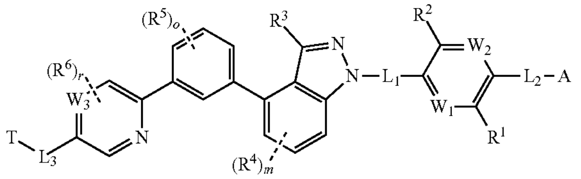

wherein $W_3$ represents $CR^M$ or N;

wherein $R^M$ represents hydrogen, $C_1$-$C_6$ alkyl, —O($C_1$-$C_6$ alkyl), —O($C_3$-$C_6$ cycloalkyl), halogen, nitro, cyano, —$NR^aR^b$, halo($C_1$-$C_6$ alkyl) or $C_3$-$C_6$ cycloalkyl;

wherein r represents 0, 1 or 2.

4. The compound according to claim 3, wherein $W_3$ represents CH or N.

5. The compound according to claim 1, wherein $L_1$ is selected from —$CR^AR^B$—, and wherein $R^A$ and $R^B$ are each independently selected from hydrogen, halogen, $C_1$-$C_6$ alkyl and halo($C_1$-$C_6$ alkyl).

6. The compound according to claim 1, wherein $L_2$ and $L_3$ are each independently selected from —$CR^CR^D$— and —$CR^CR^D$—$NR^a$—$(CR^CR^D)_q$—, wherein q is selected from 0, 1 or 2, and wherein $R^C$, $R^D$ are each independently selected from hydrogen, halogen, $C_1$-$C_6$ alkyl and halo($C_1$-$C_6$ alkyl).

7. The compound according to claim 1, wherein $W_1$, $W_2$ each independently represents CH or N.

8. The compound according to claim 1, wherein T, A each independently represent —($C_1$-$C_6$ alkyl), —($C_0$-$C_6$ alkylene)-($C_3$-$C_{12}$ cycloalkyl) or —($C_0$-$C_6$ alkylene)-(3-12 membered heterocycle) substituted with 0, 1, 2 or 3 substituents, and wherein the substituents are selected from oxo, halogen, $C_1$-$C_6$ alkyl, —($C_0$-$C_6$ alkylene)$OR^a$, halo($C_1$-$C_6$ alkyl), $C_3$-$C_8$ cycloalkyl, —($C_0$-$C_6$ alkylene)C(O)$R^a$, —($C_0$-$C_6$ alkylene)C(O)$OR^a$, —($C_0$-$C_6$ alkenyl)C(O)$OR^a$, —($C_0$-C6 alkylene)$NR^aR^b$, —C(O)$NR^aR^b$, —$NR^aSO_2R^b$, —C(O)$NR^aSO_2R^b$ and —$NR^a$C(O)$R^b$;

or wherein T, A each independently represents $C_1$-$C_6$ alkyl, $C_3$-$C_{12}$ cycloalkyl or 3-12 membered heterocycle substituted with 0, 1 or 2 substituents, wherein the substituents are selected from oxo, —$OR^a$, —($C_0$-$C_6$ alkylene)C(O)$OR^a$, —($C_0$-$C_6$ alkenyl)C(O)$OR^a$, —$NR^aSO_2R^b$, —C(O)$NR^aSO_2R^b$ and —$NR^a$C(O)$R^b$.

9. The compound according to claim 8, wherein T represents: —($C_1$-$C_6$ alkyl), —($C_0$-$C_6$ alkylene)-($C_3$-$C_{12}$ cycloalkyl) or —($C_0$-$C_6$ alkylene)-(3-12 membered heterocycloalkyl) substituted with 0, 1, 2 or 3 substituents, and wherein the substituents are selected from oxo, —($C_0$-$C_6$ alkylene)$OR^a$, —($C_0$-$C_6$ alkylene)C(O)$OR^a$, —($C_0$-$C_6$ alkylene)$NR^aR^b$, —C(O)$NR^aR^b$, —$NR^aSO_2R^b$ and —$NR^a$C(O)$R^b$.

10. The compound of claim 1, wherein T, A each independently represents the following groups:

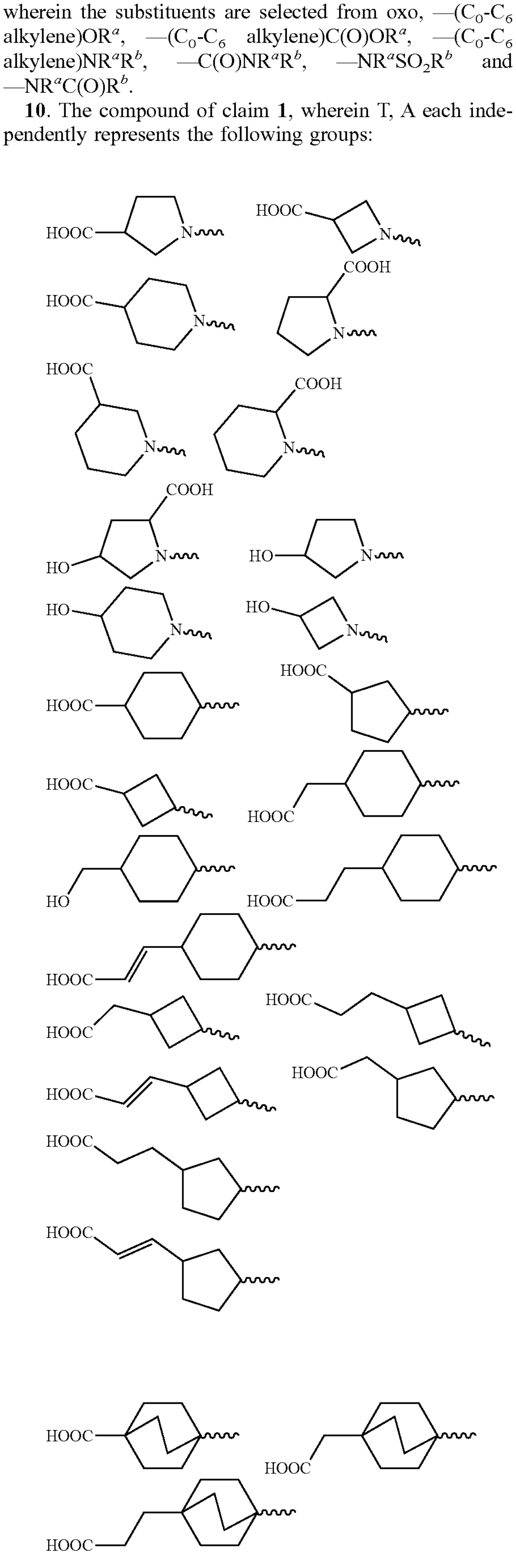

-continued

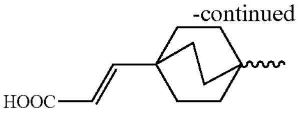
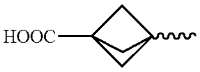
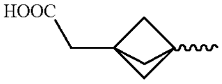
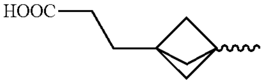
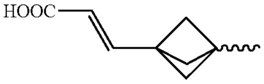
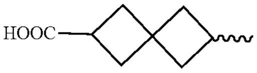
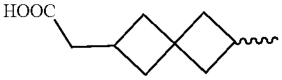
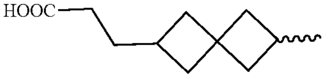
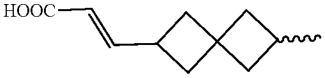
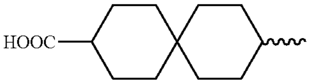
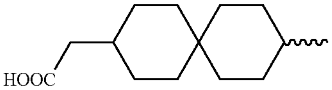
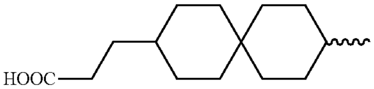
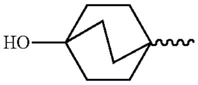
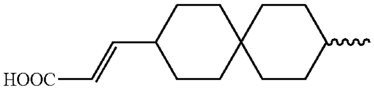
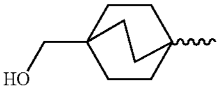
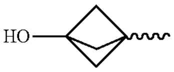
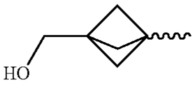
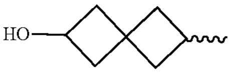

-continued

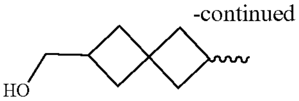
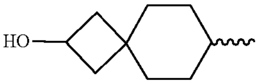
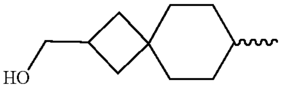
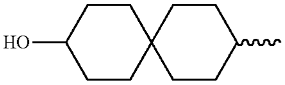
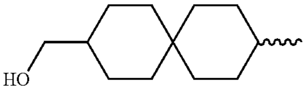

11. The compound according to claim 1, wherein $R^1$ represents —O($C_1$-$C_6$ alkyl), —O($C_0$-$C_6$ alkylene)($C_3$-$C_6$ cycloalkyl) or —O($C_0$-$C_6$ alkylene)(3-6 membered heterocycloalkyl) substituted with 0, 1, 2 or 3 substituents; wherein the substituents are selected from: cyano, oxo, halogen, cyano $C_1$-$C_6$ alkyl and $C_1$-$C_6$ haloalkyl.

12. The compound according to claim 1, wherein $R^2$ represents hydrogen, halogen, nitro, cyano, —$SO_2R^a$, $C_1$-$C_6$ alkyl, halo($C_1$-$C_6$ alkyl) or $C_3$-$C_6$ cycloalkyl.

13. The compound according to claim 1, wherein $R^3$, $R^4$ each independently represent hydrogen or halogen.

14. The compound according to claim 1, wherein $R^5$ represents hydrogen, halogen, nitro, cyano, $C_1$-$C_6$ alkyl, halo($C_1$-$C_6$ alkyl) or $C_3$-$C_6$ cycloalkyl.

15. The compound according to claim 1, wherein $R^6$ represents hydrogen, halogen, $C_1$-$C_6$ alkyl, halo($C_1$-$C_6$ alkyl) or $C_3$-$C_6$ cycloalkyl or —O($C_1$-$C_6$ alkyl), —O($C_0$-$C_6$ alkylene)($C_3$-$C_6$ cycloalkyl) or —O($C_0$-$C_6$ alkylene)(3-6 membered heterocycloalkyl) substituted with 0, 1, 2 or 3 substituents; wherein the substituents are selected from: cyano, oxo, halogen, cyano $C_1$-$C_6$ alkyl and $C_1$-$C_6$ haloalkyl.

16. The compound according to claim 15, wherein the substituents are selected from halogen.

17. The compound according to claim 1, $R^L$ represents hydrogen or halogen.

18. The compound according to claim 1, selected from the group consisting of:

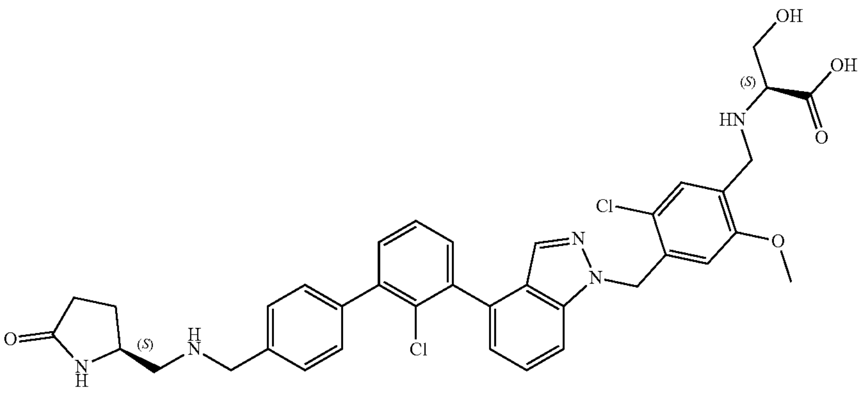

-continued
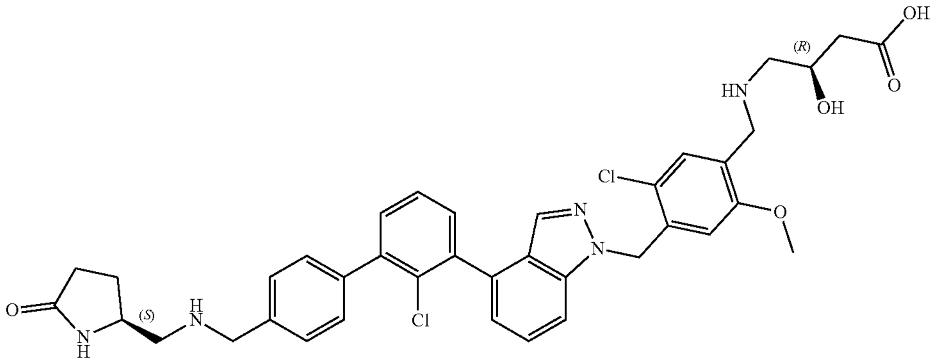
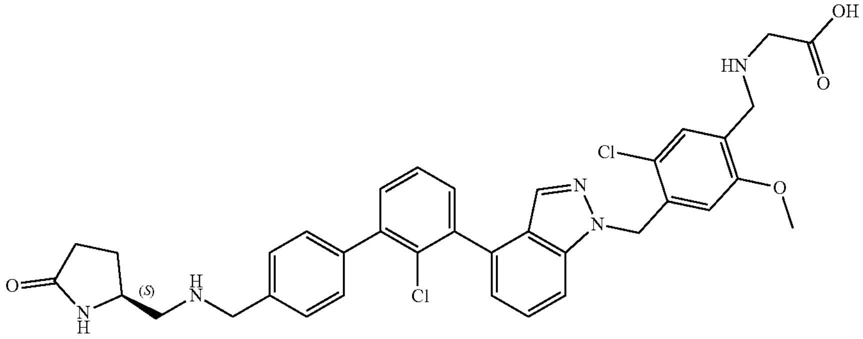
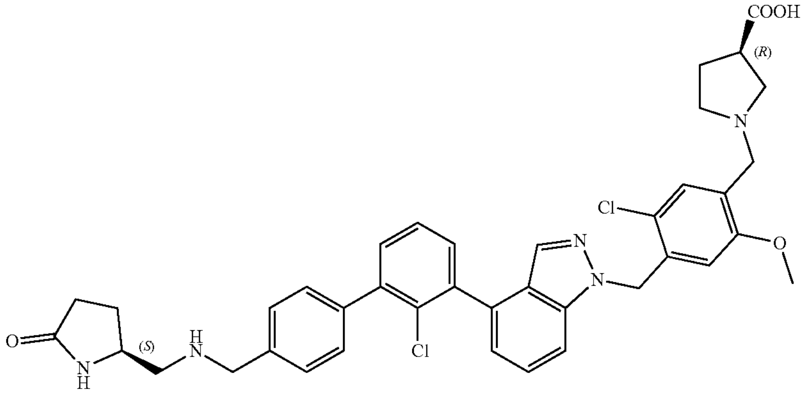
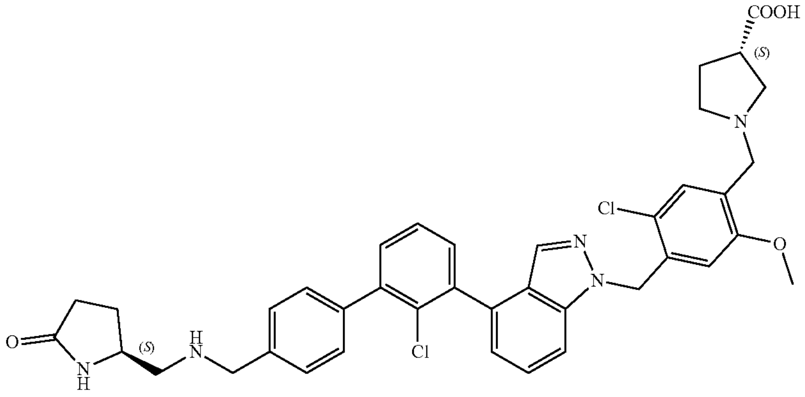

-continued
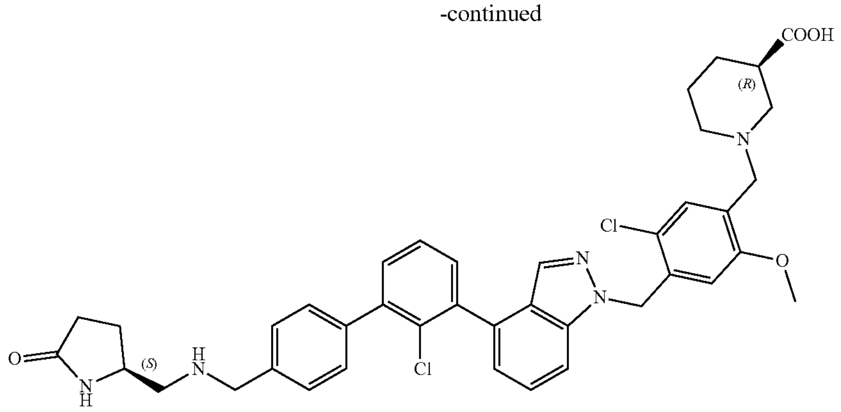
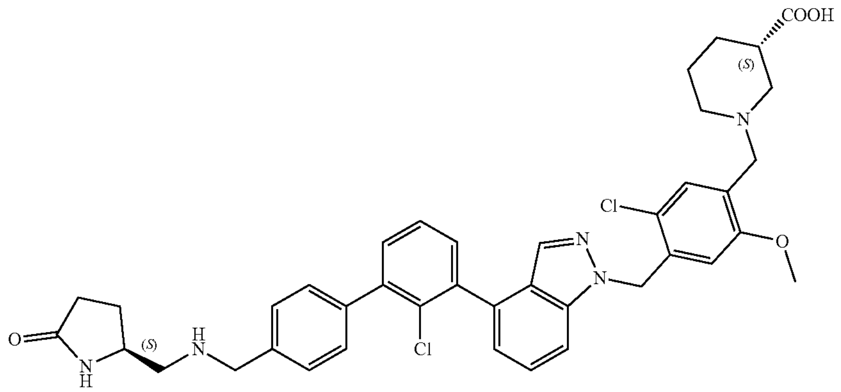
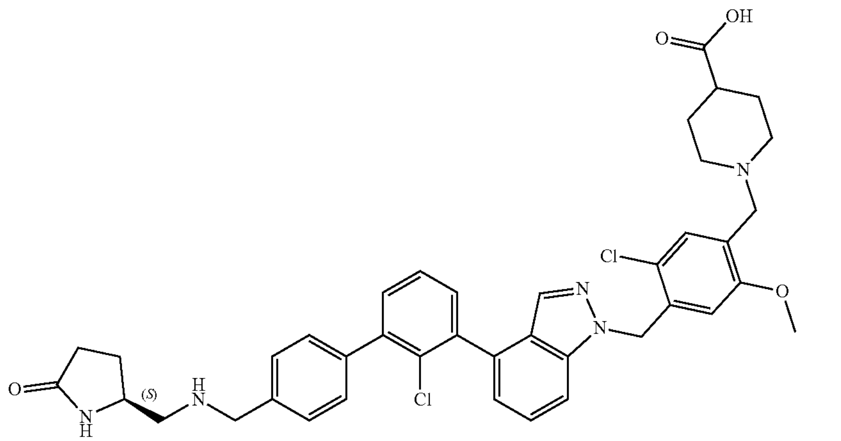
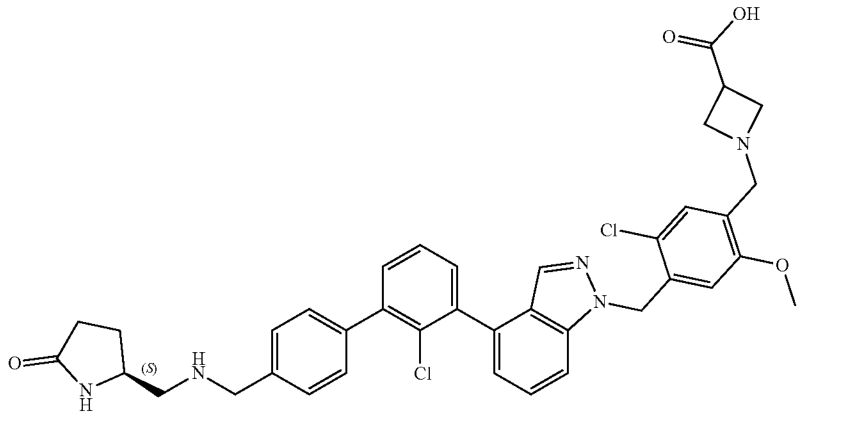

-continued
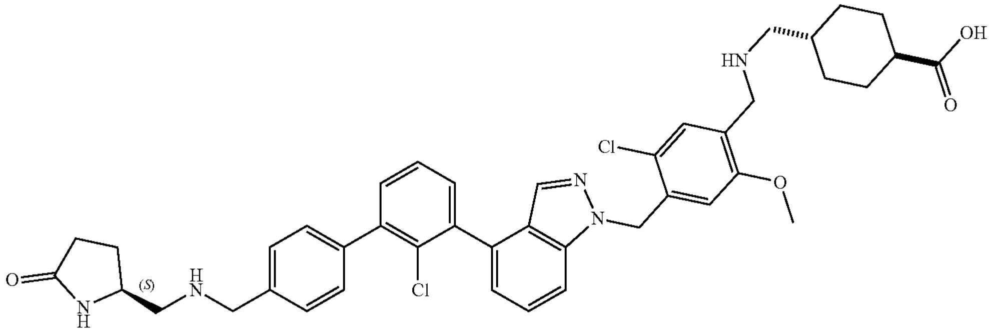
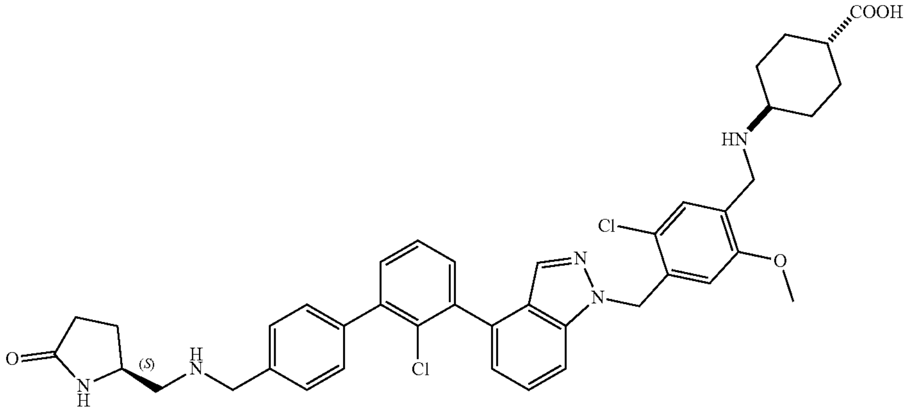
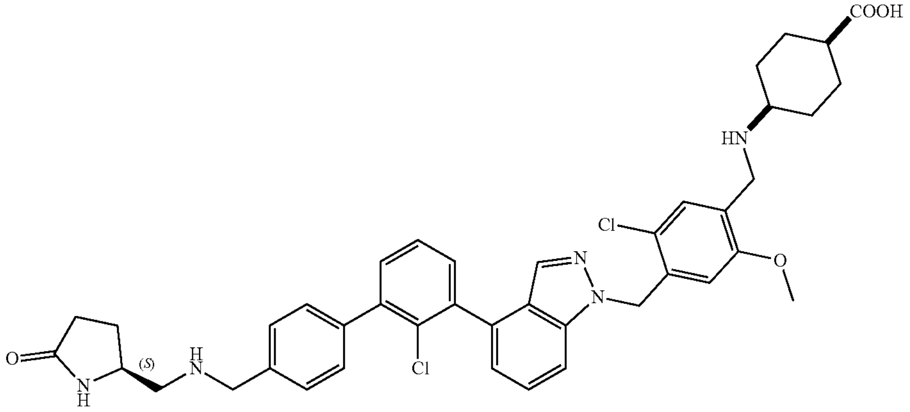
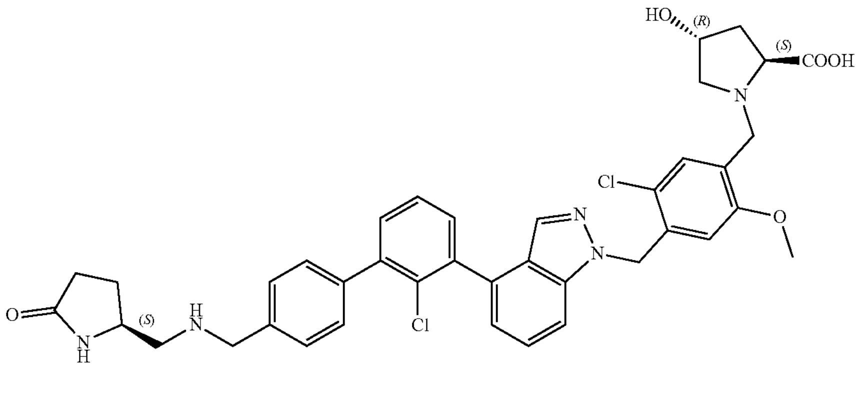

-continued
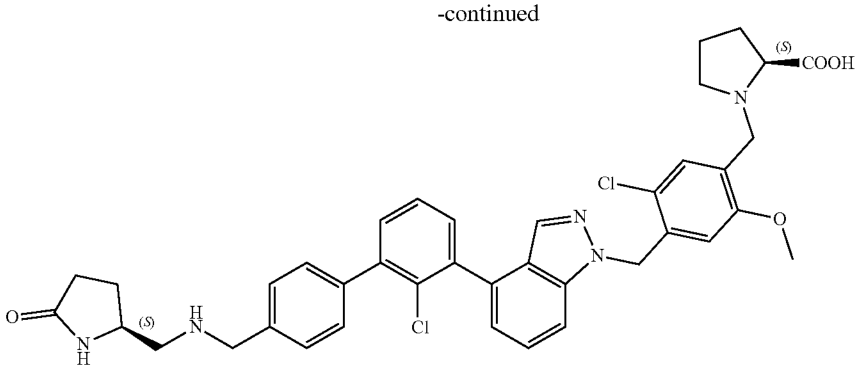
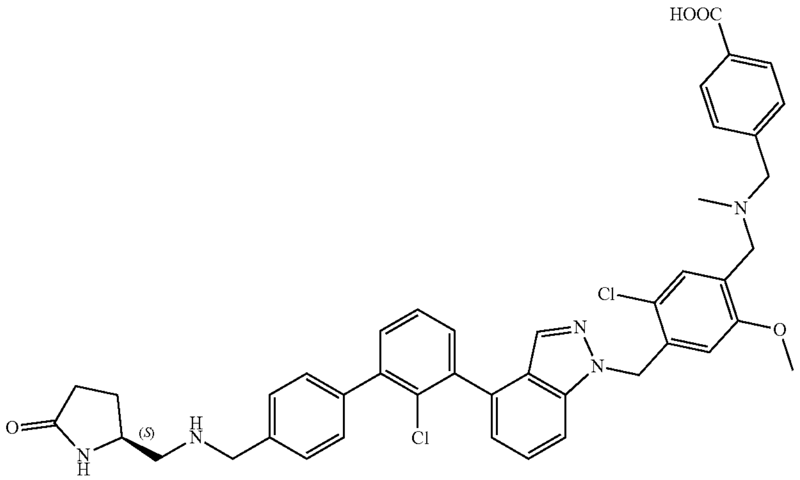
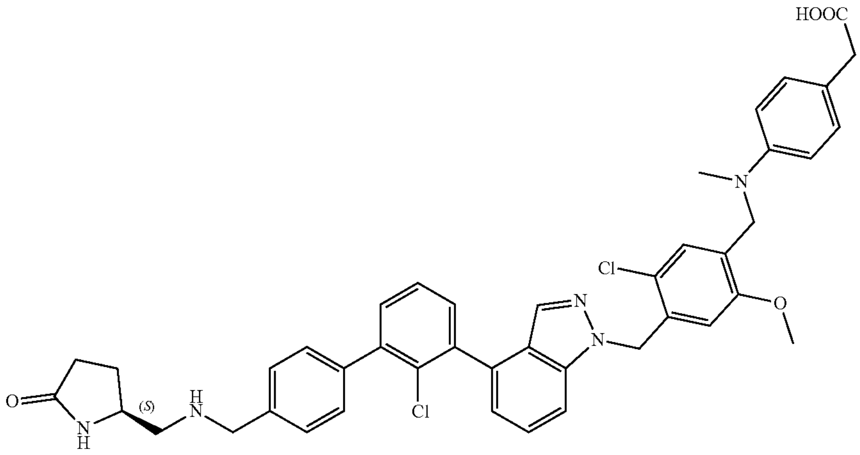
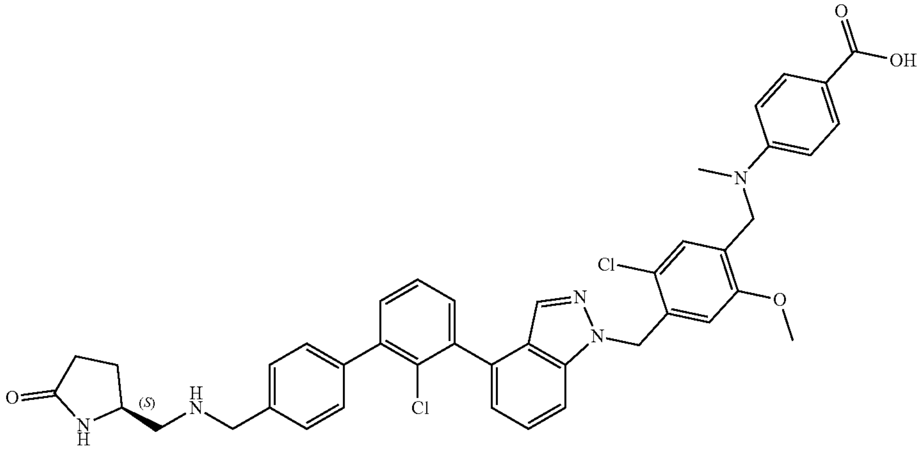

-continued
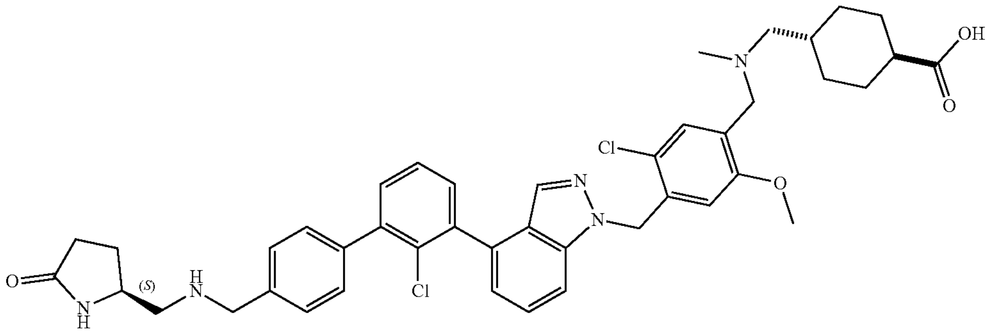
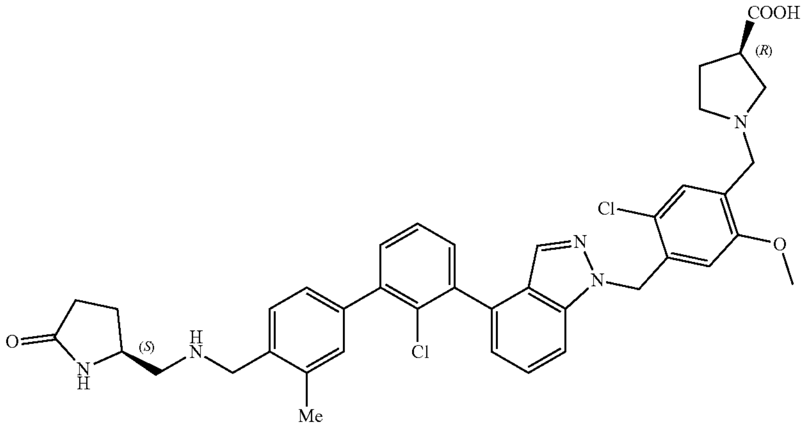
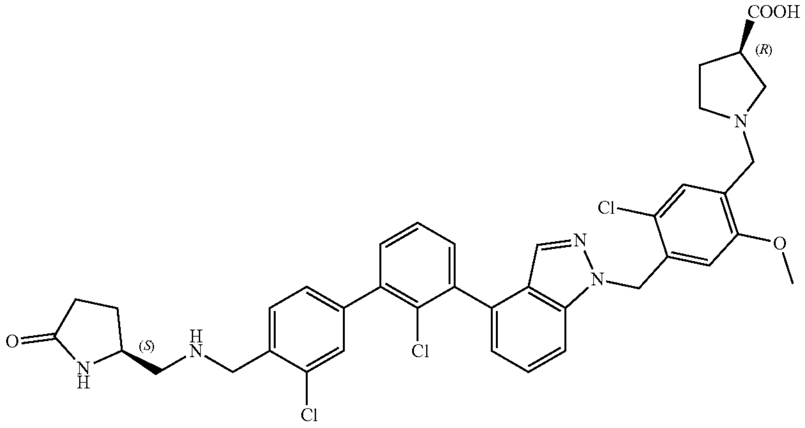
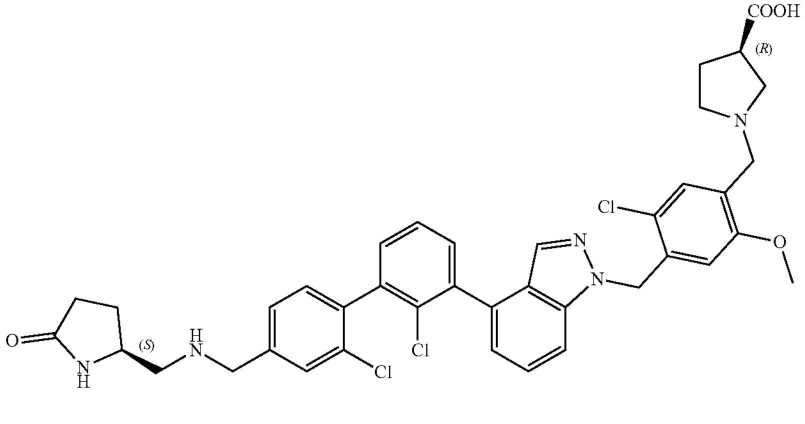

-continued
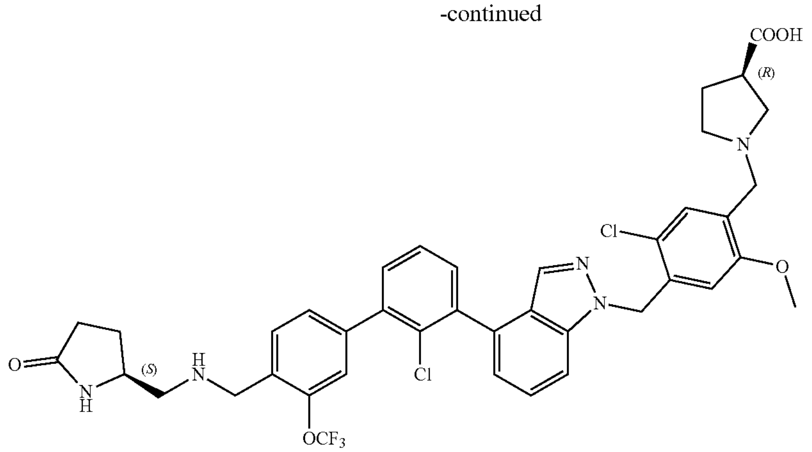
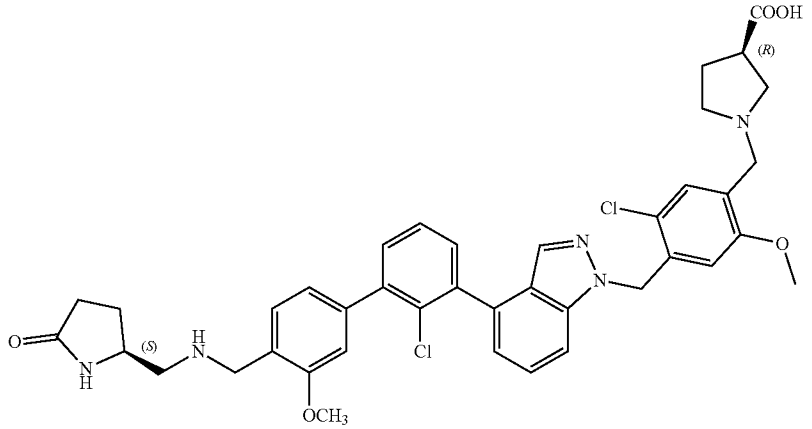
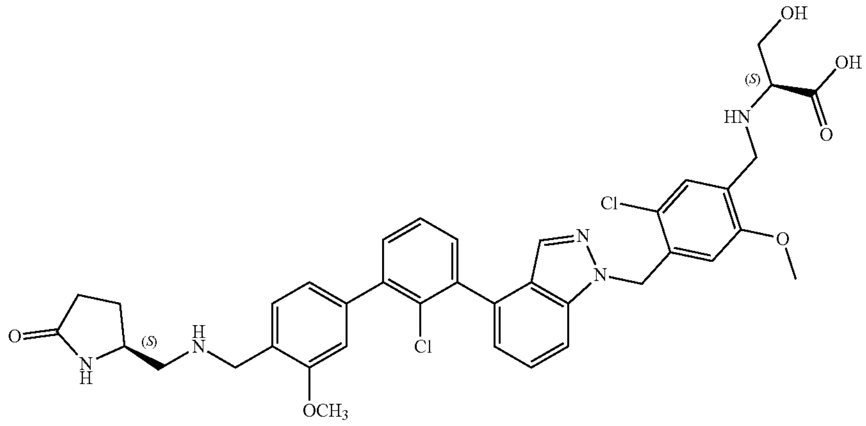 [SMILES: COc1cc(C(=O)n2ncc3c(-c4cccc(-c5ccc(CNC[C@@H]6CCC(=O)N6)cc5)c4Cl)cccc32)c(Cl)cc1CN[C@@H](CO)C(=O)O]
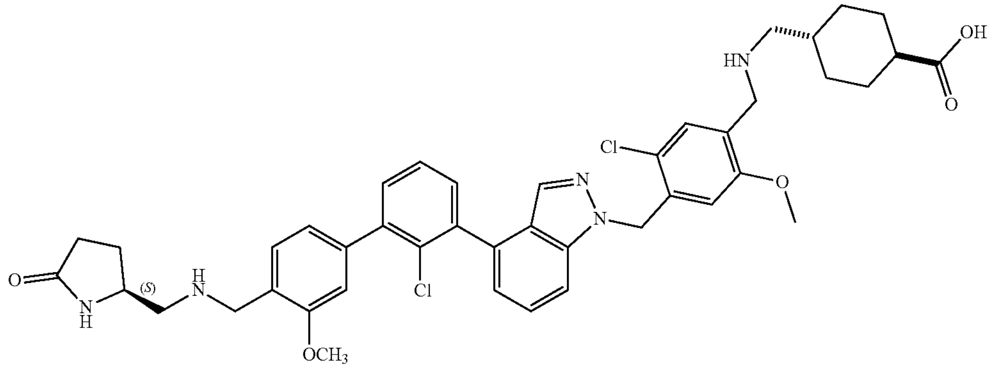

-continued
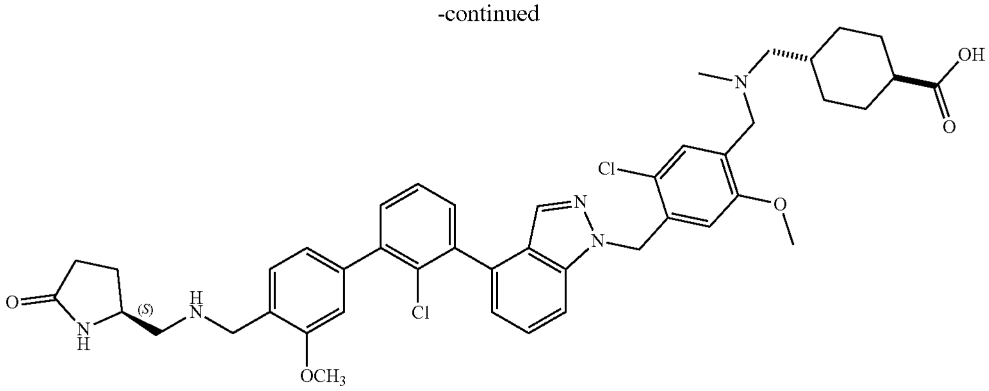
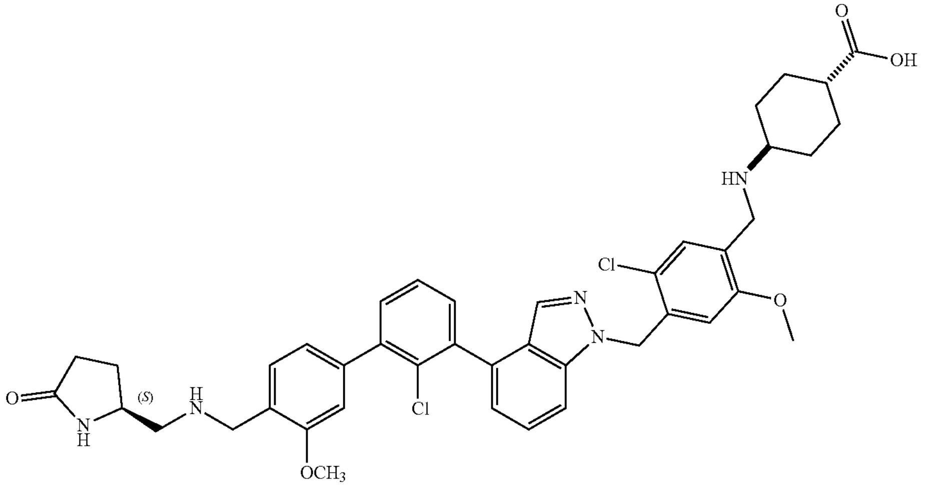
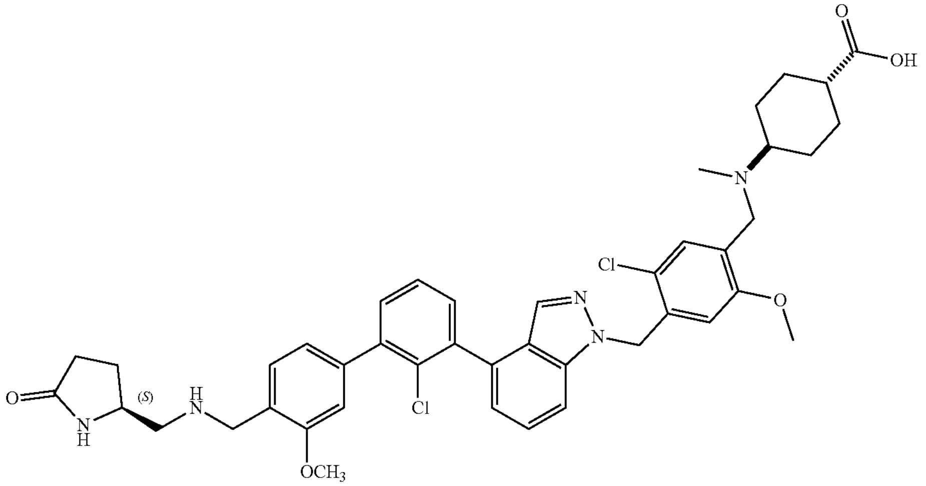
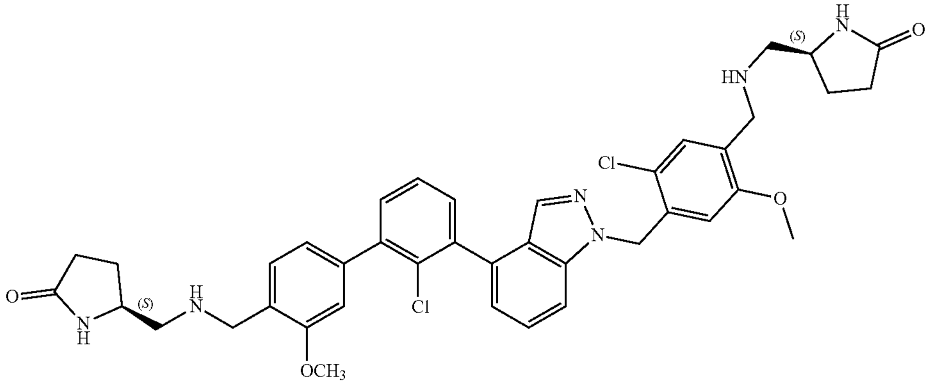

-continued
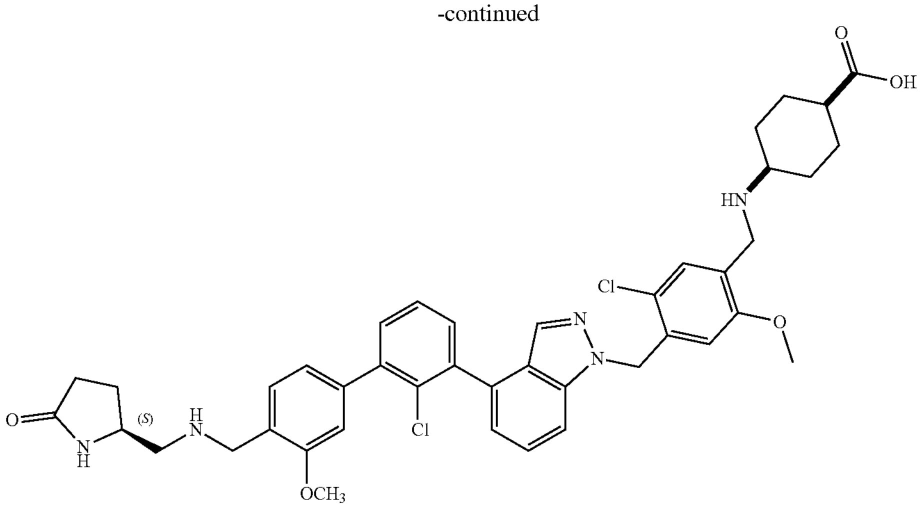
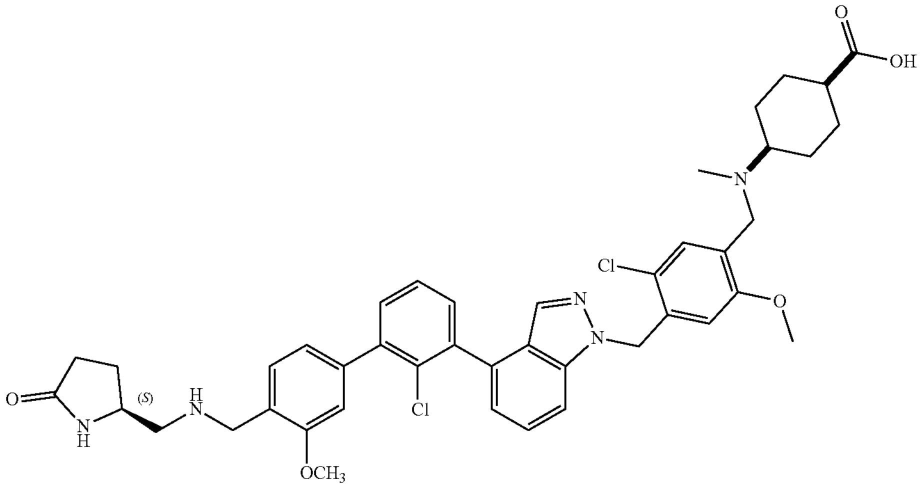
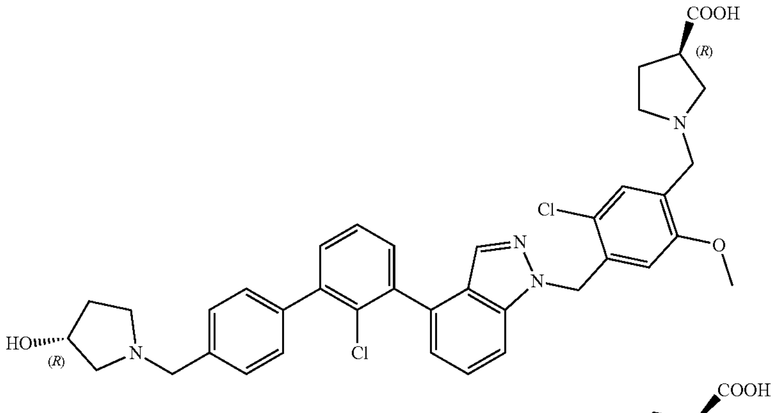
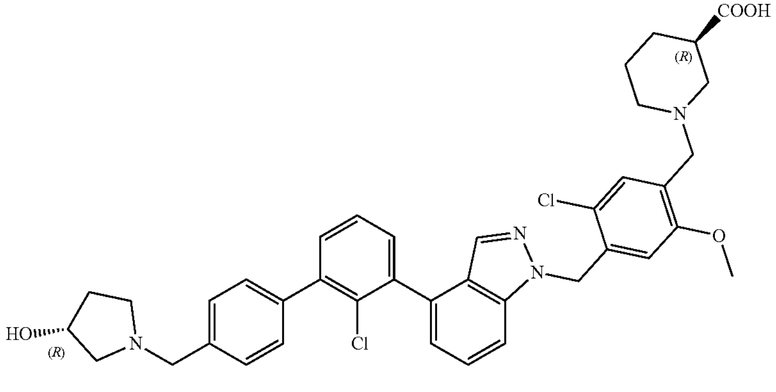

-continued
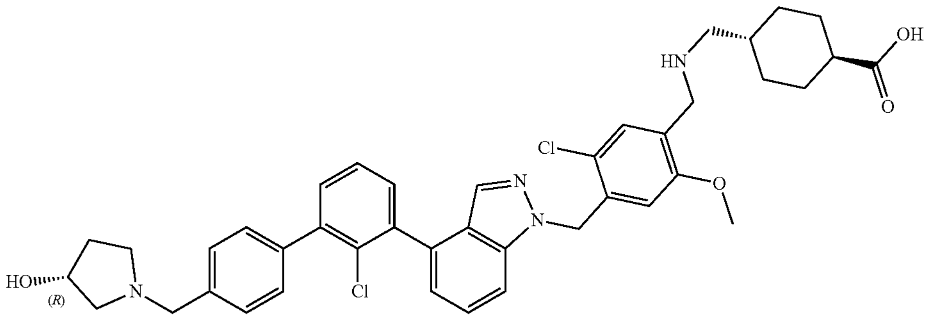
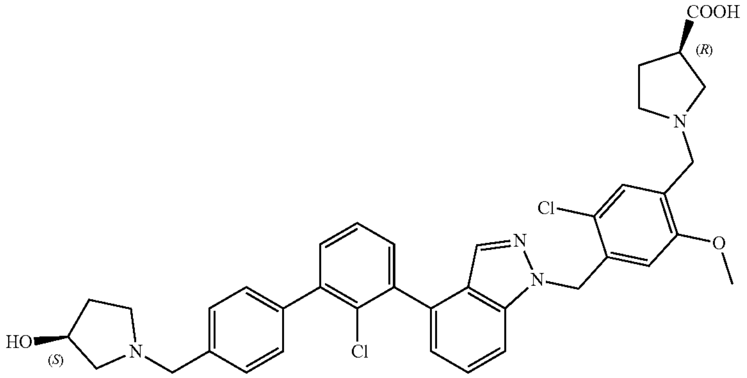
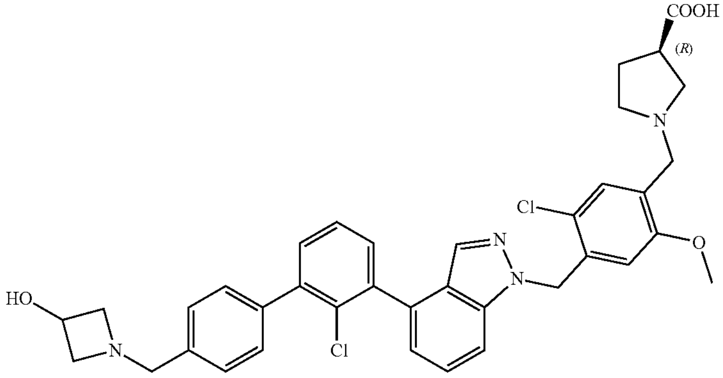
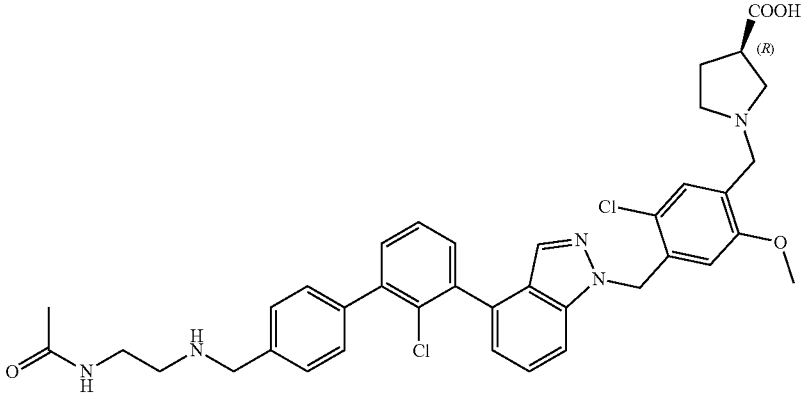

-continued
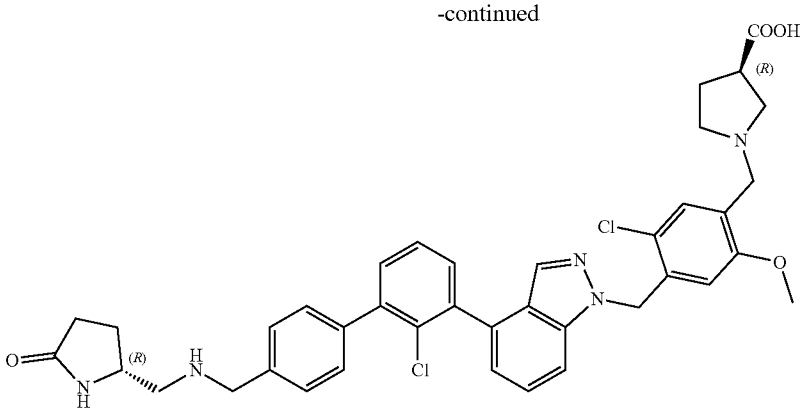
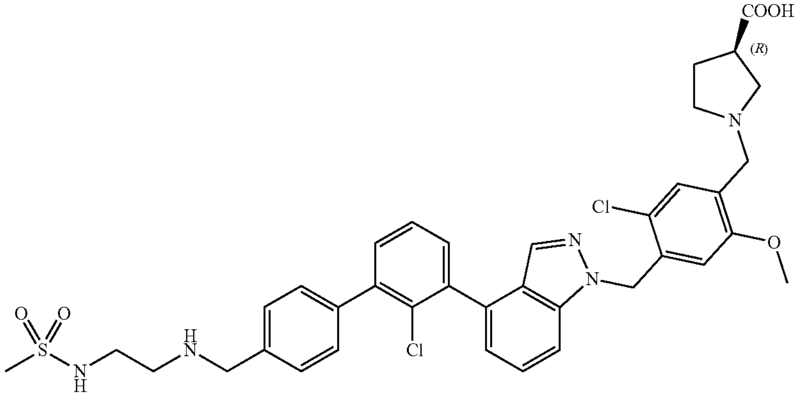
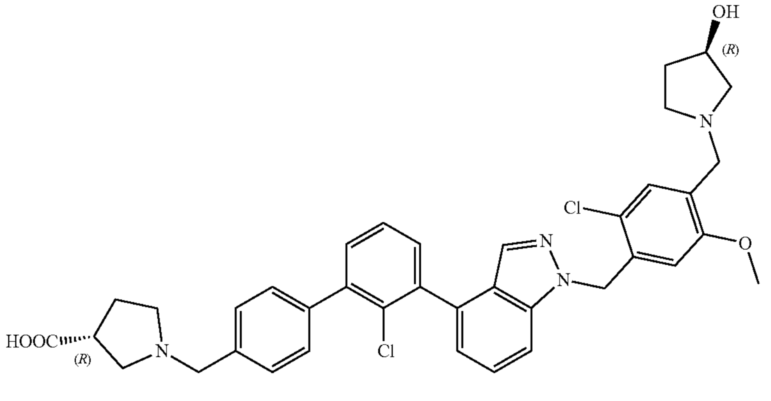
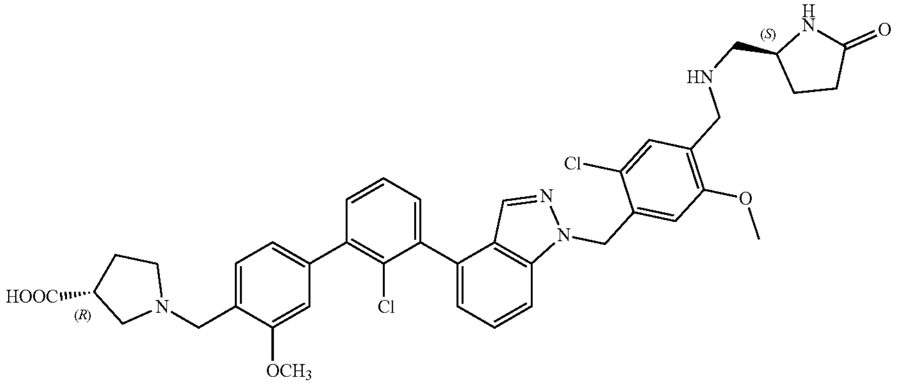

-continued
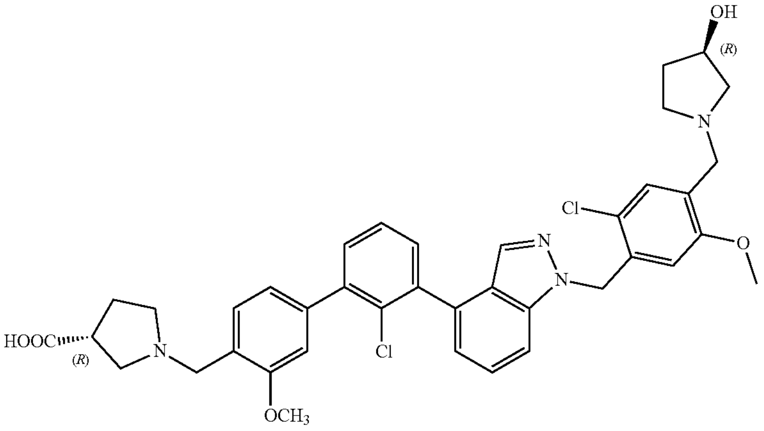
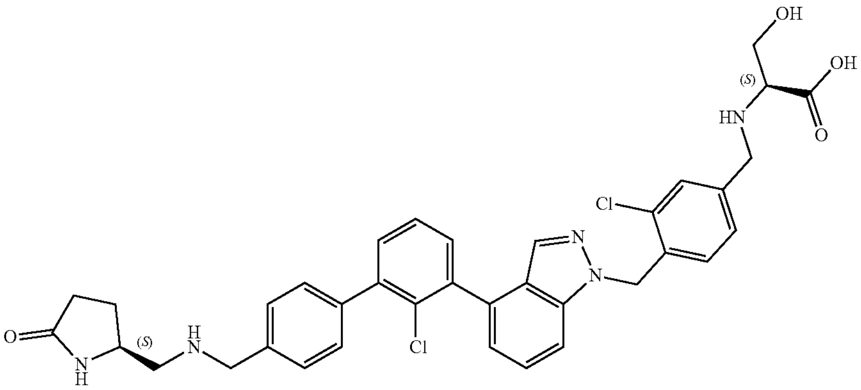
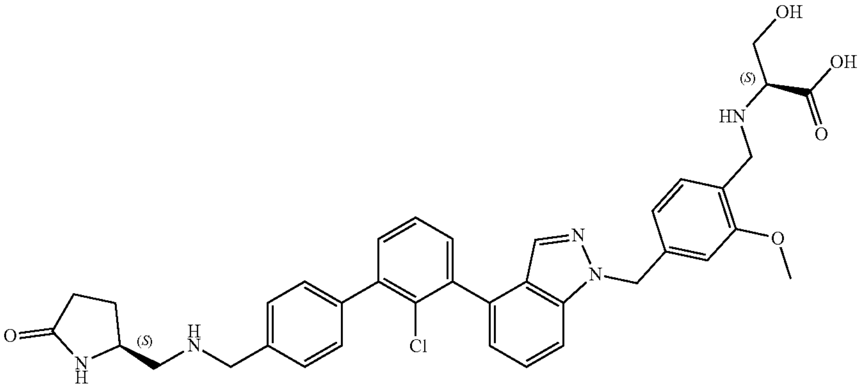
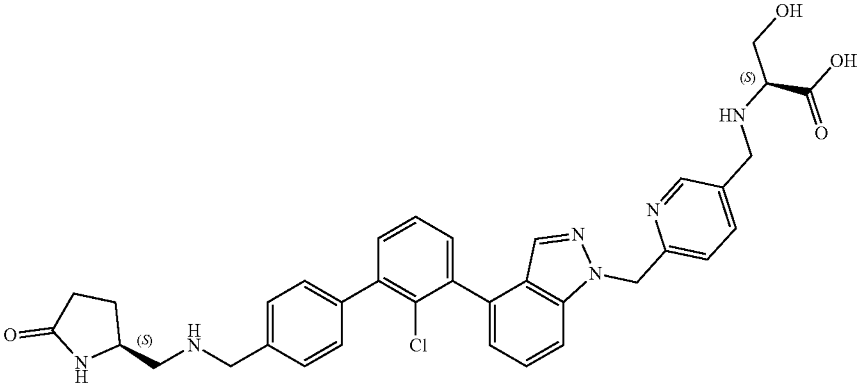

-continued
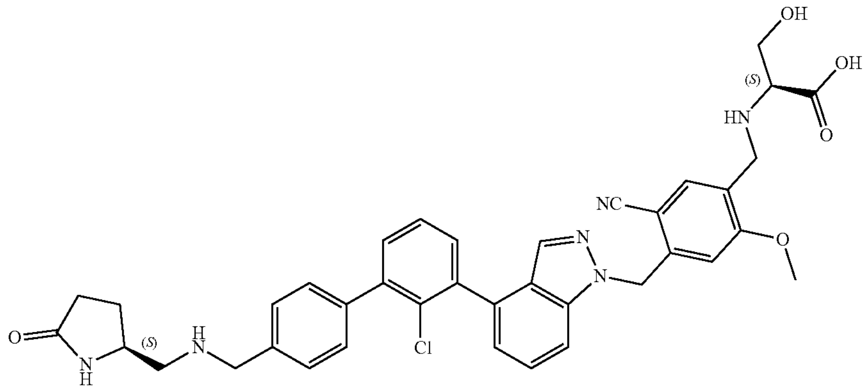
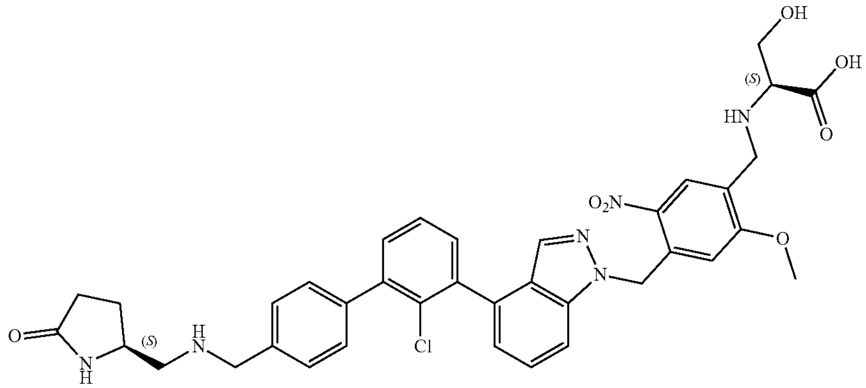
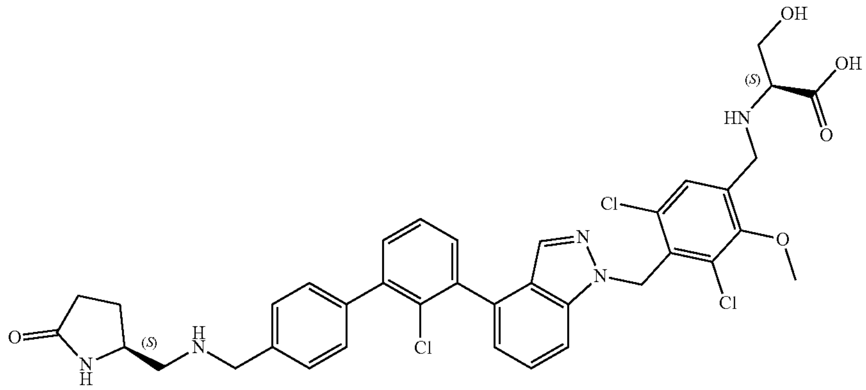
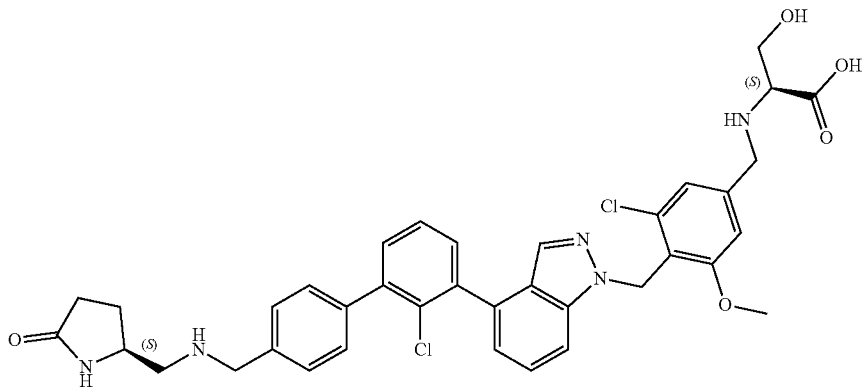

-continued
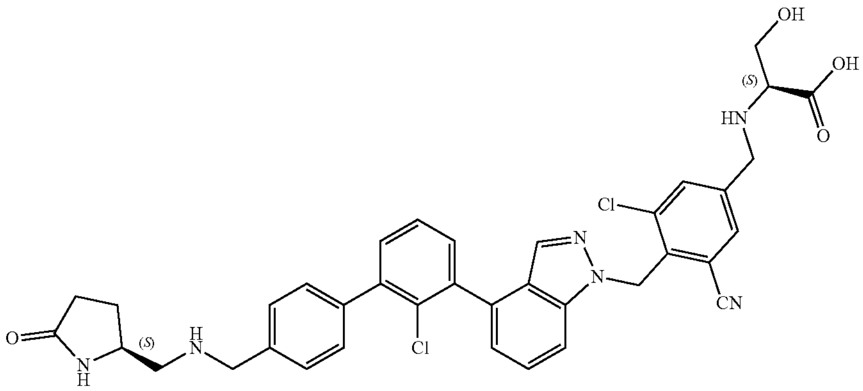
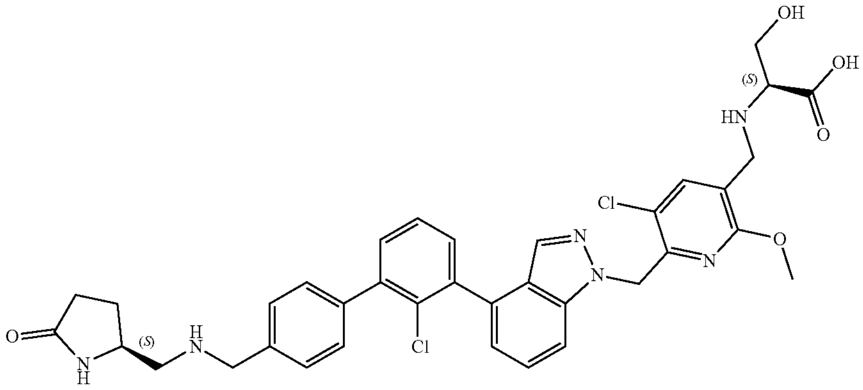
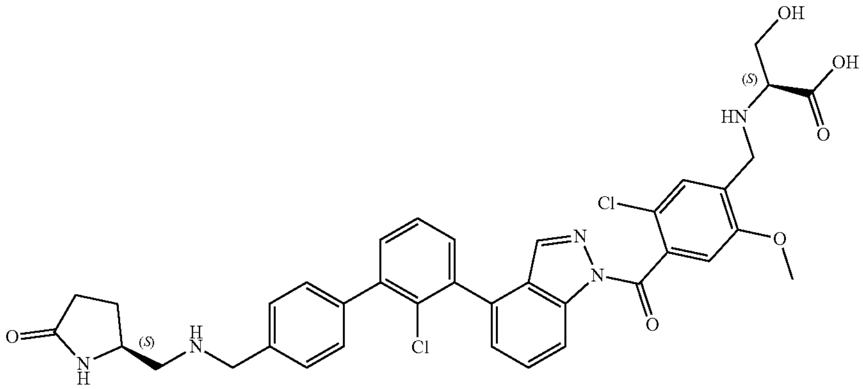
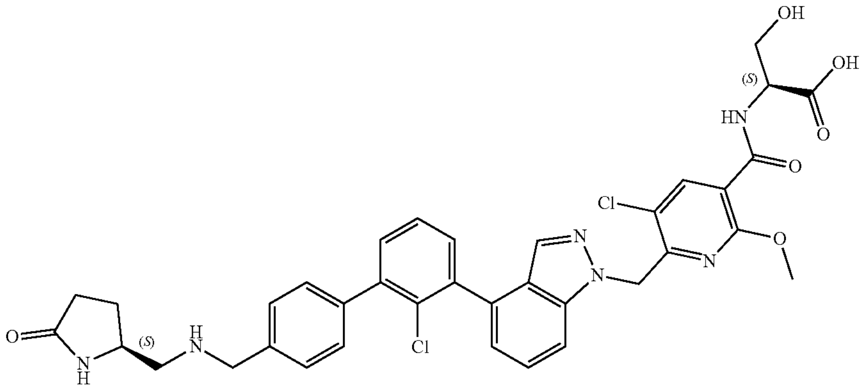

-continued
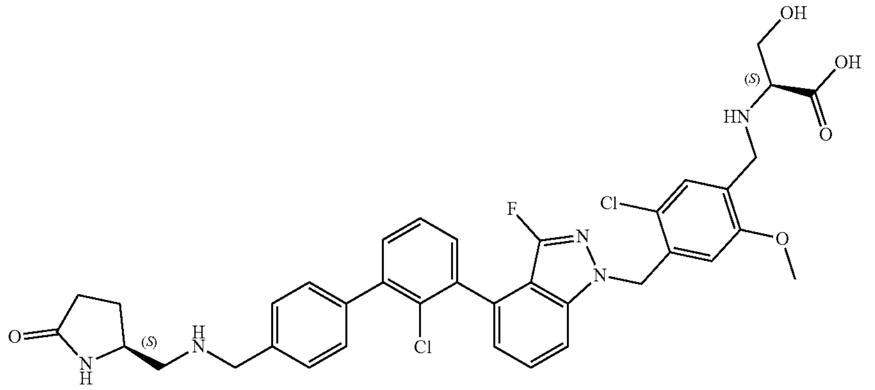
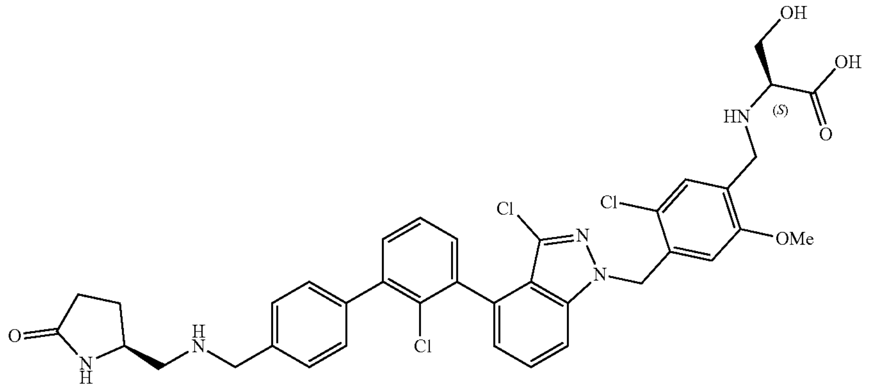
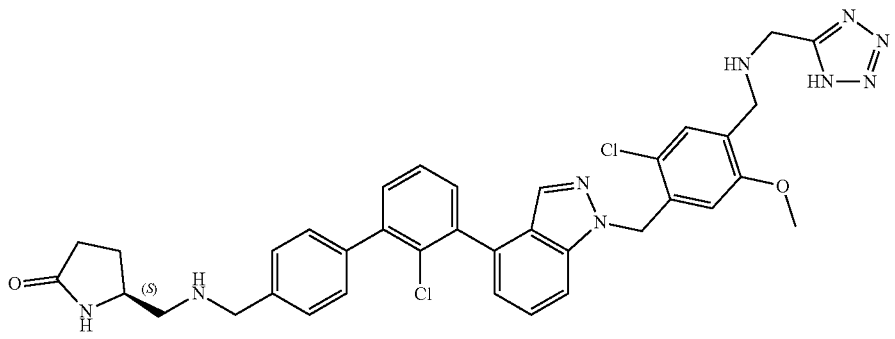
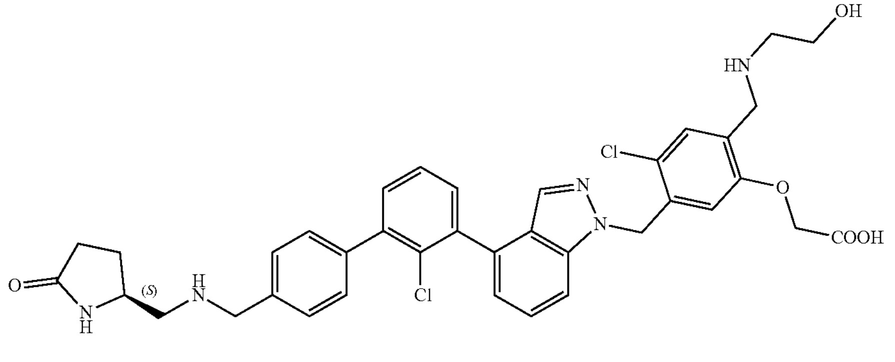

-continued
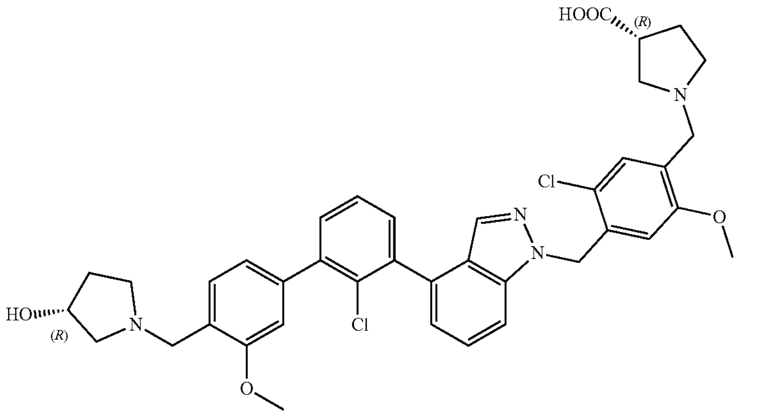
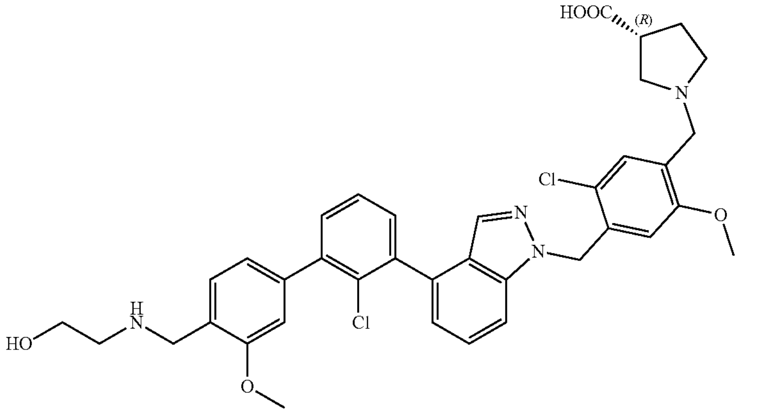
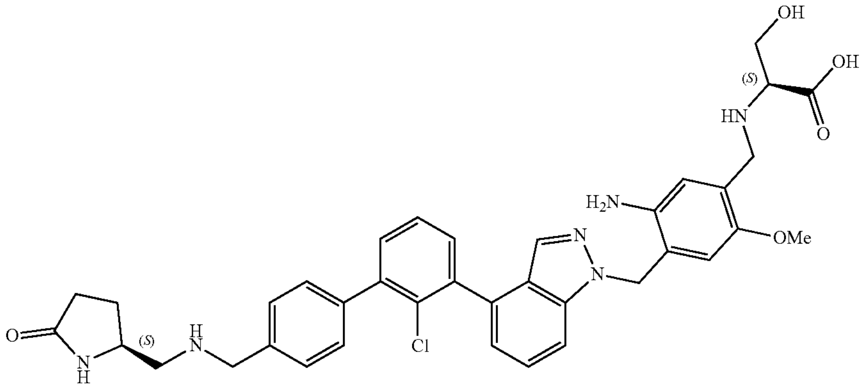
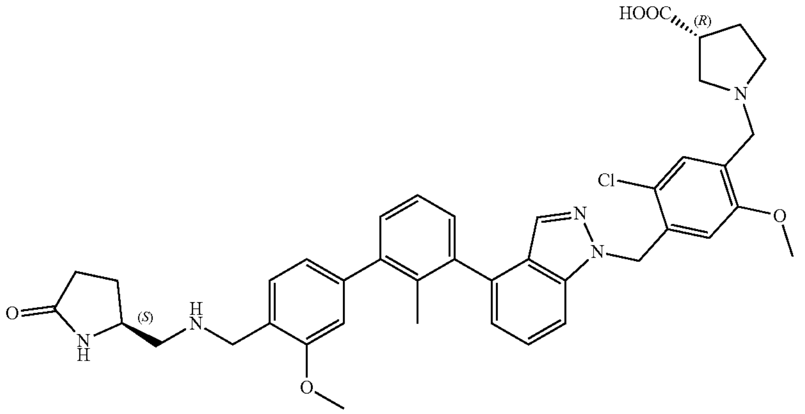

-continued
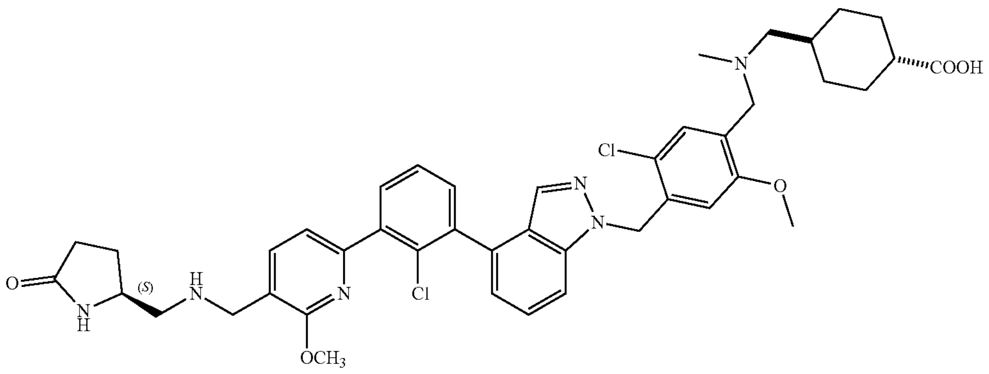
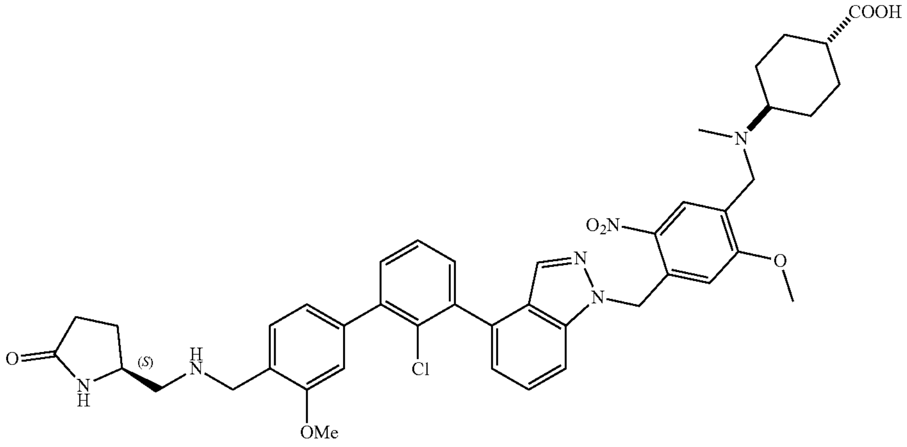
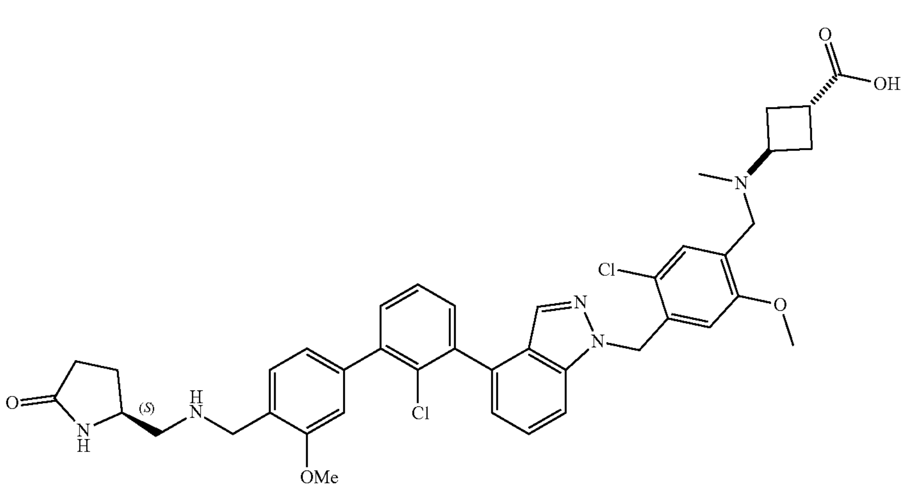

-continued
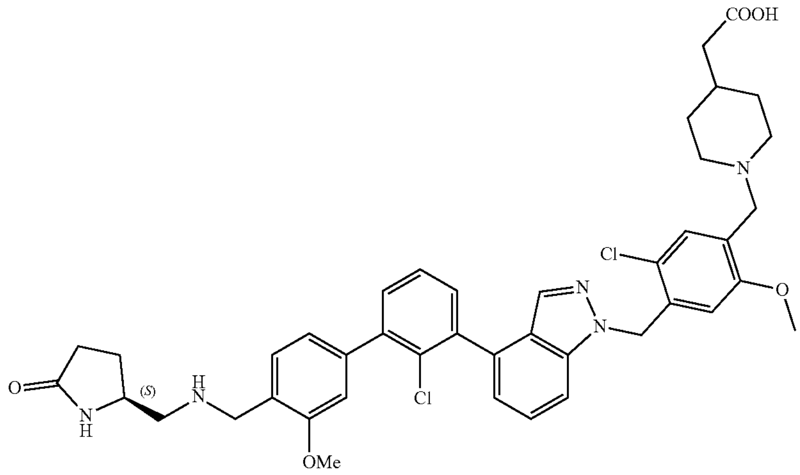
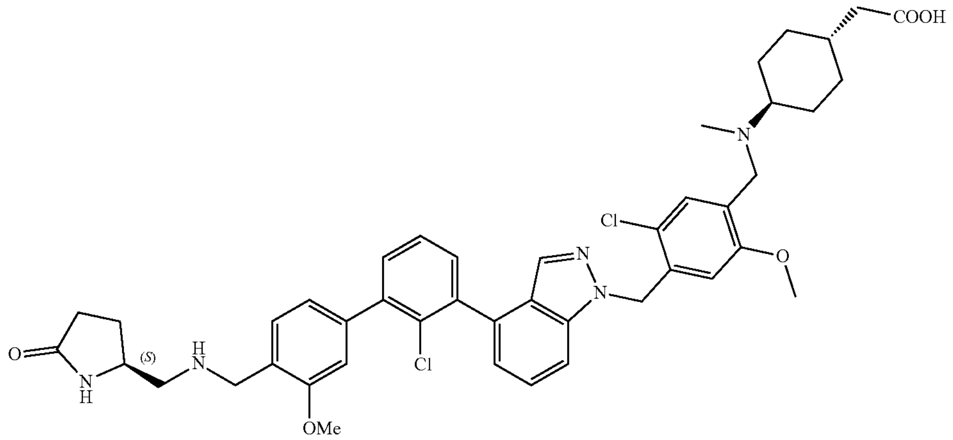
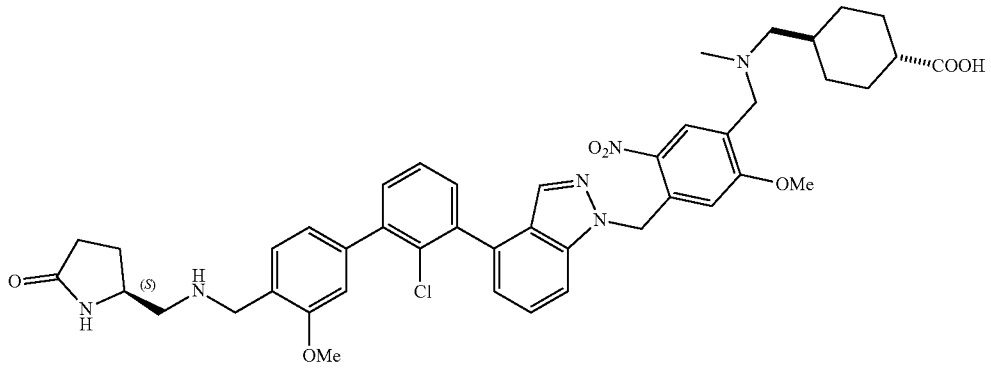
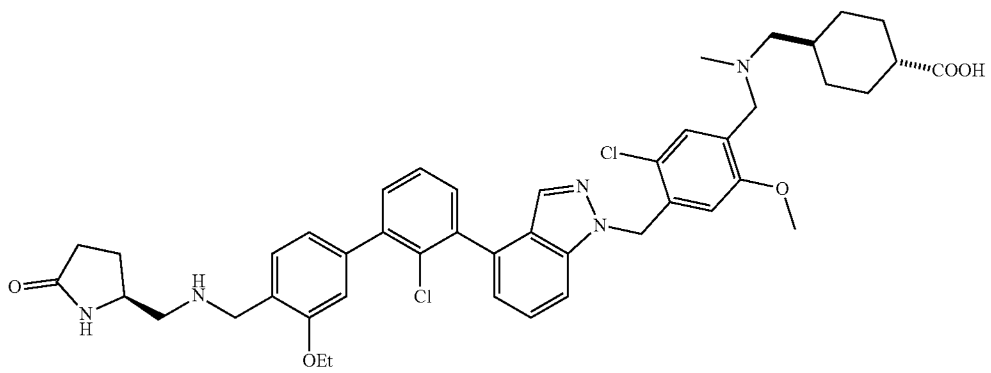

-continued
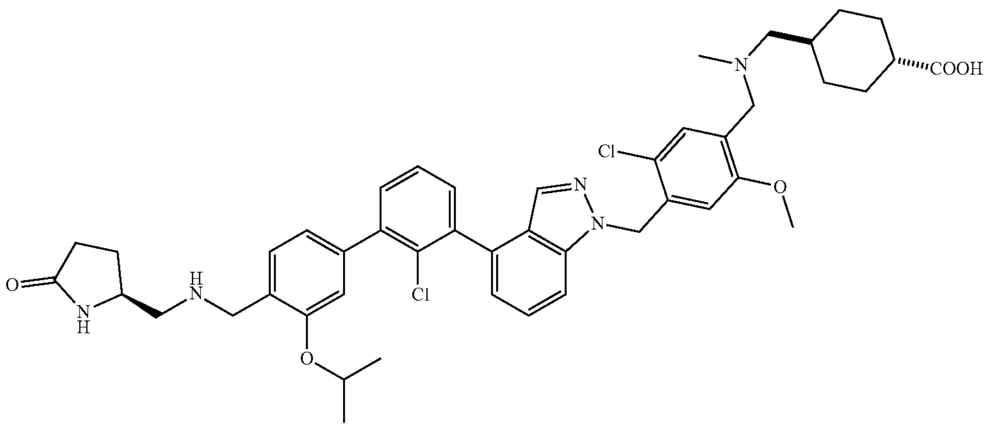
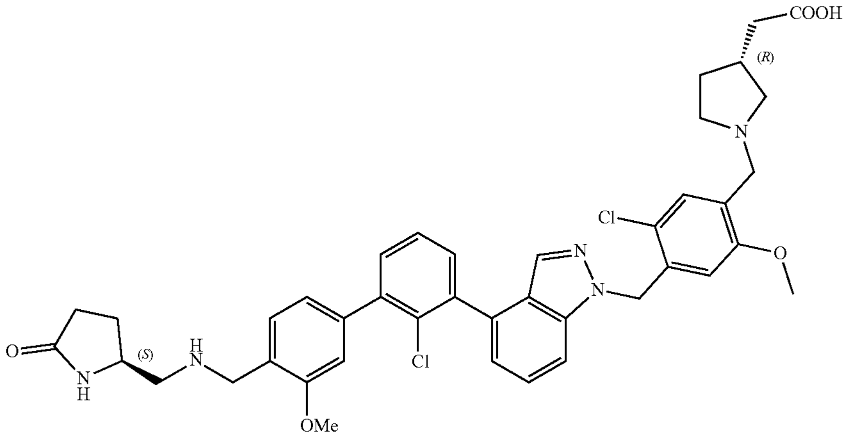
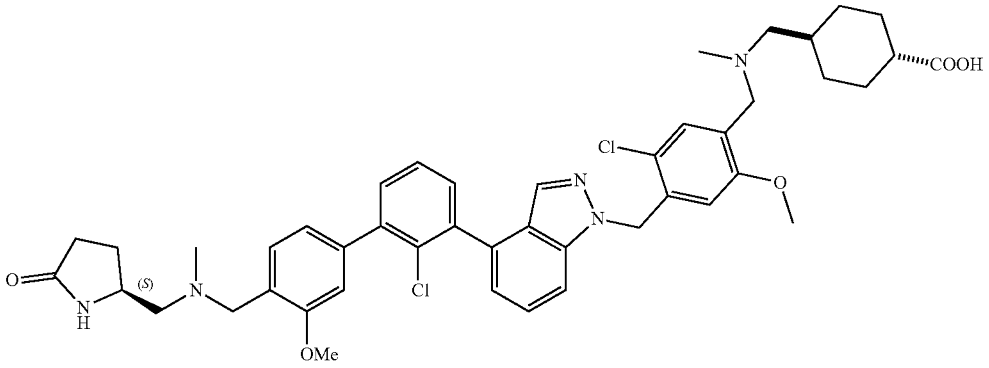
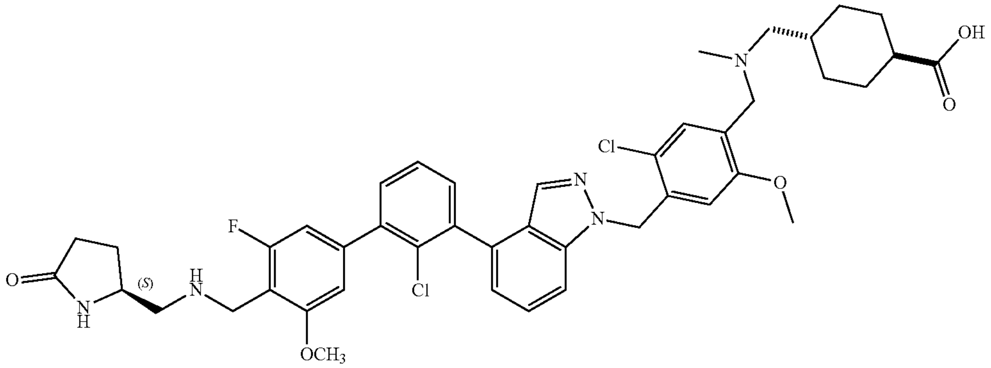

-continued
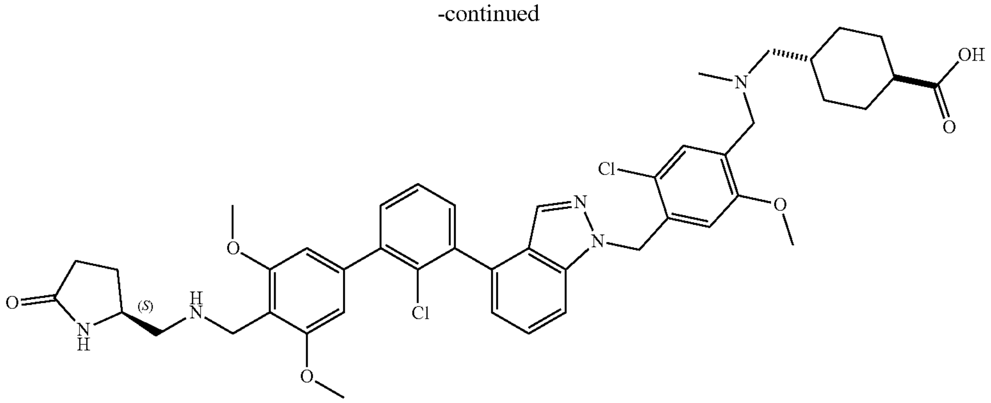
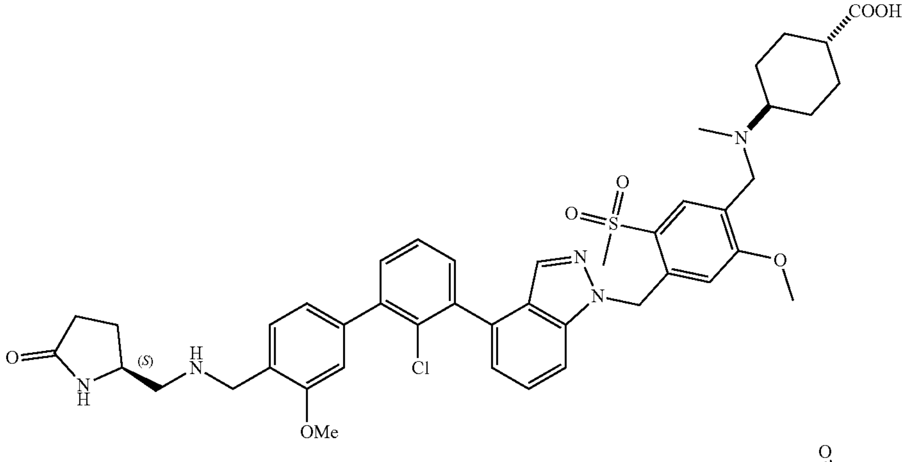
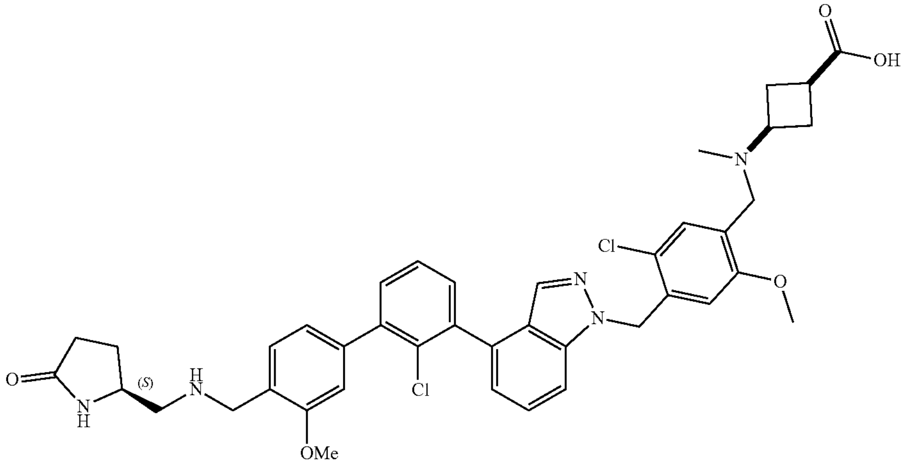
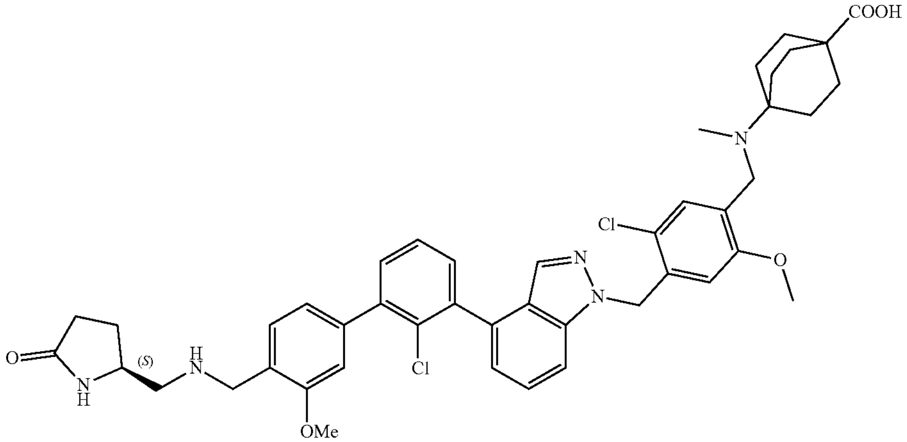

-continued
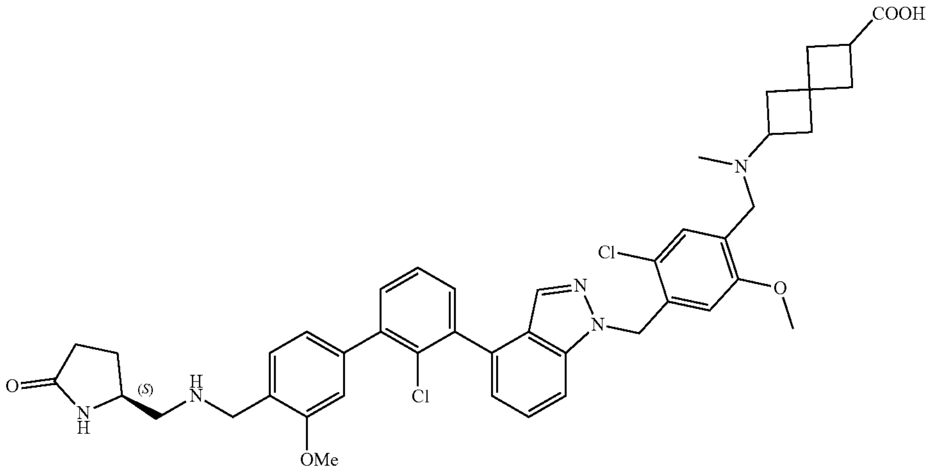
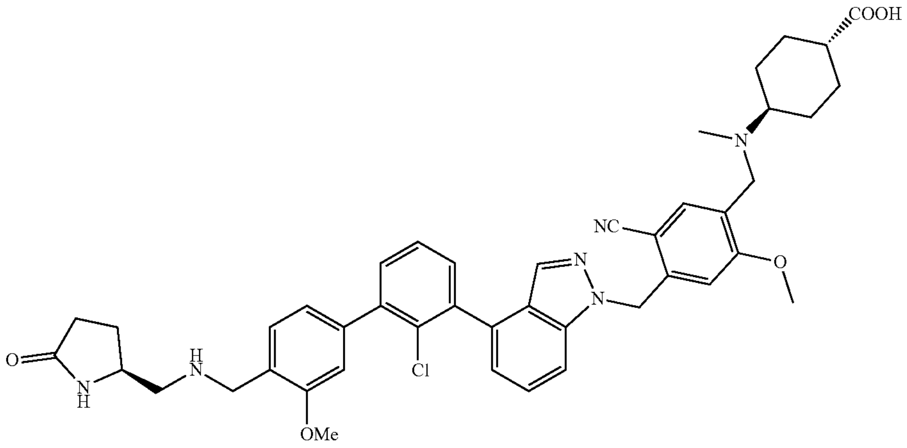
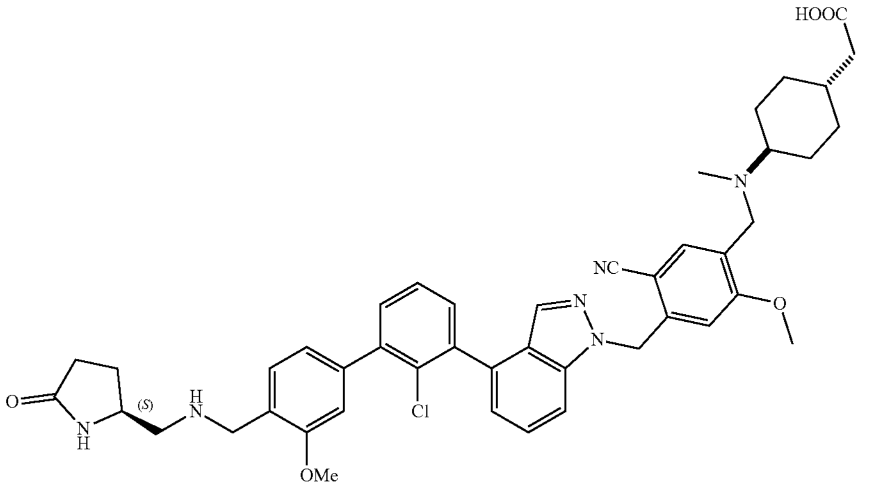

-continued
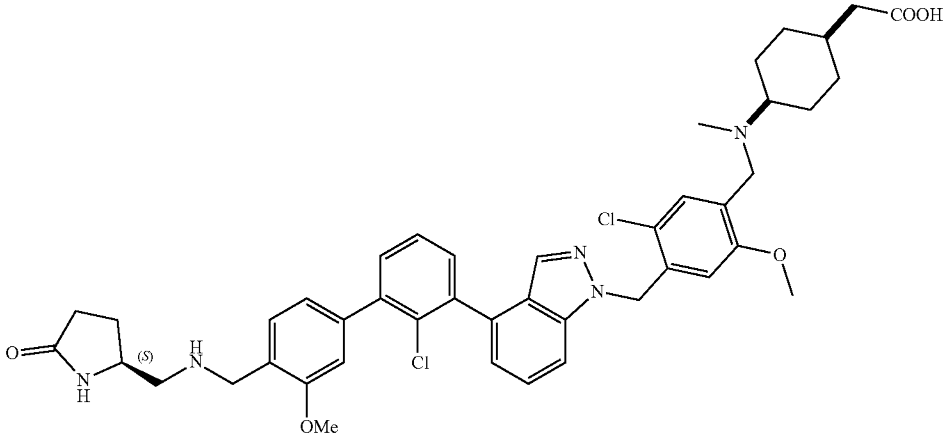
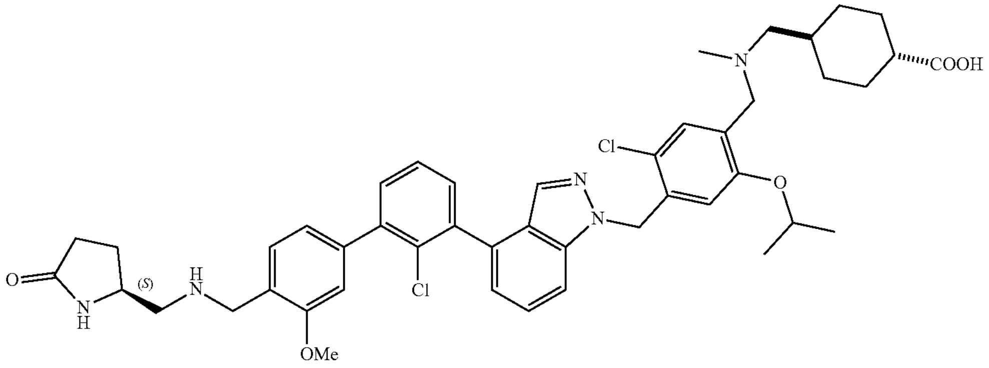
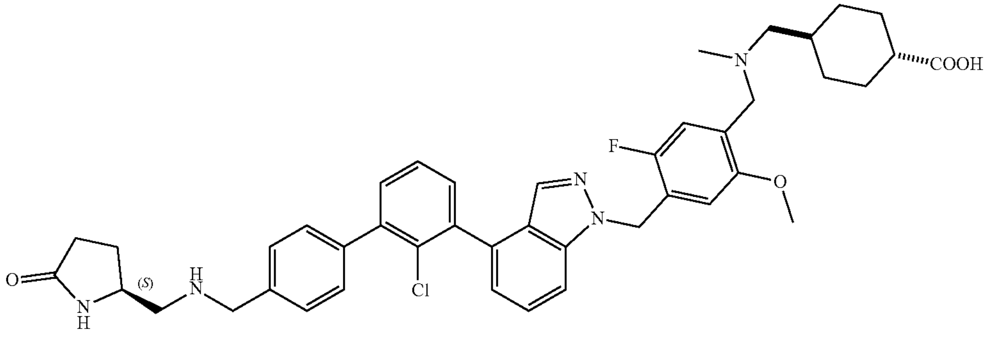
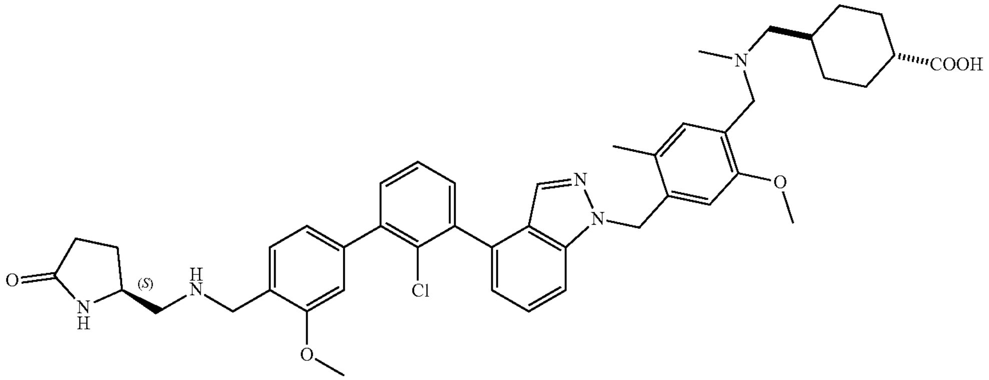

-continued
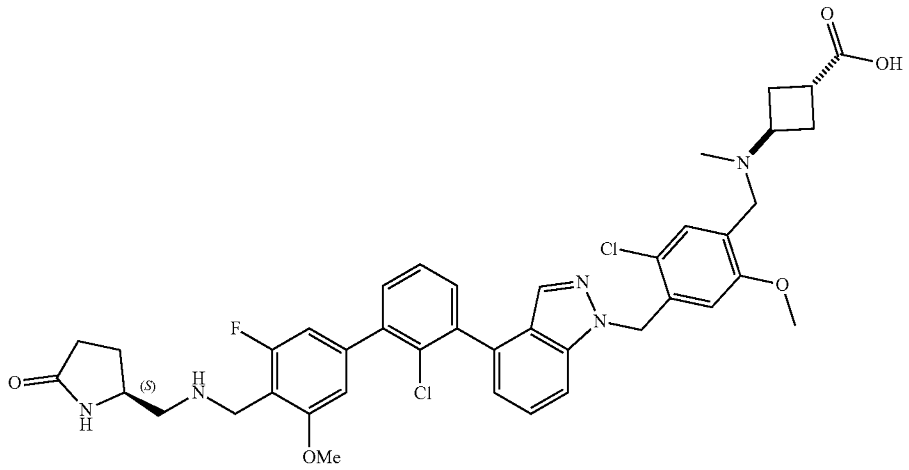
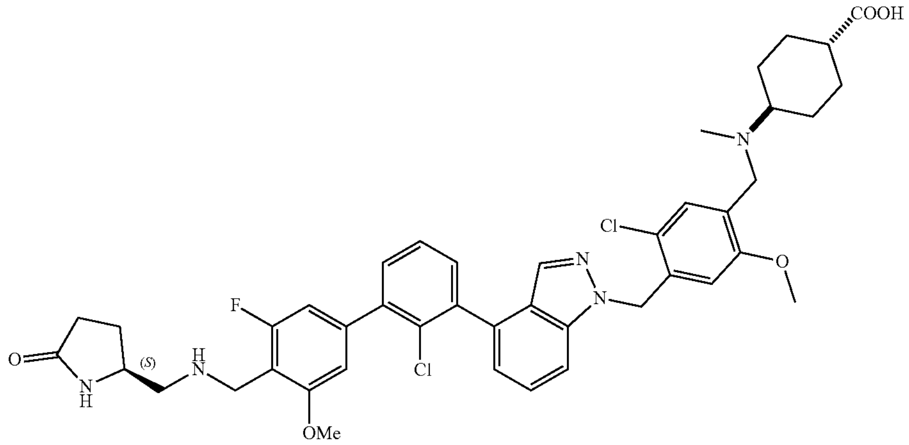
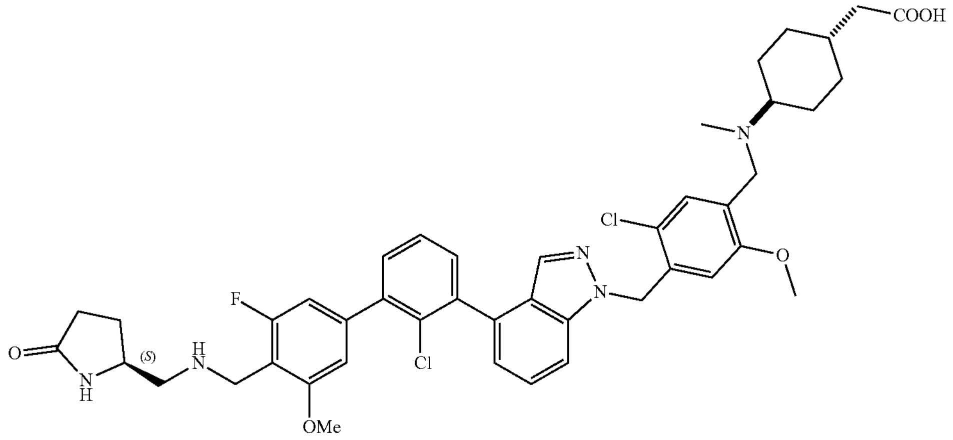

-continued
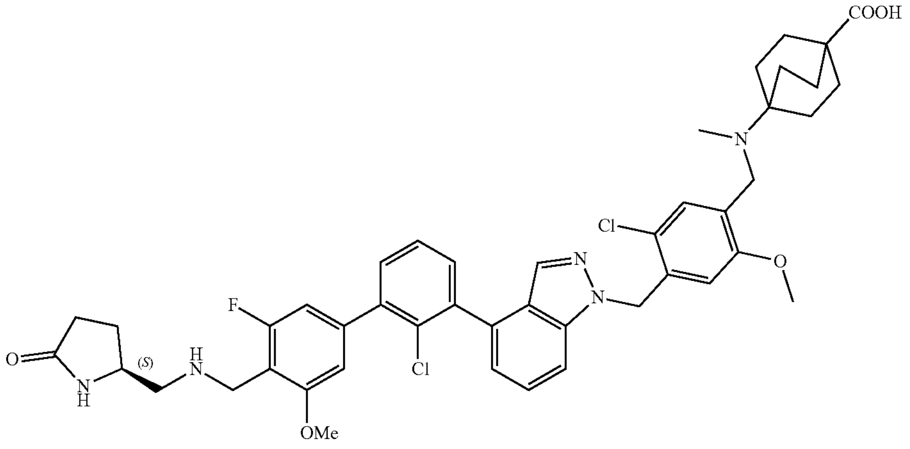
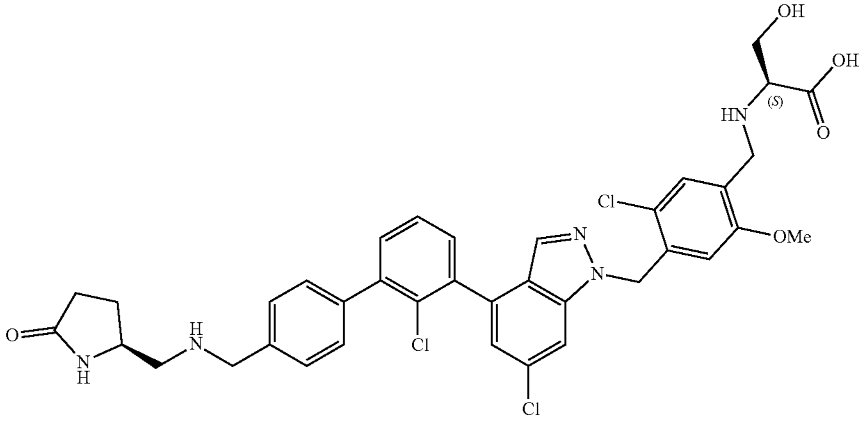
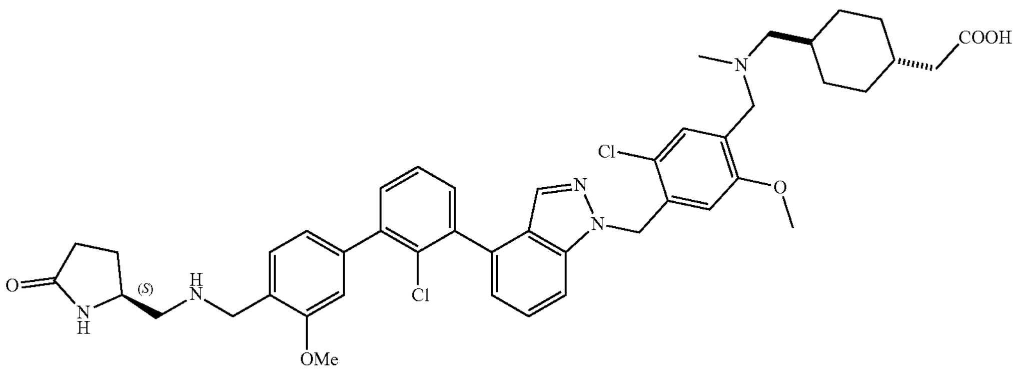
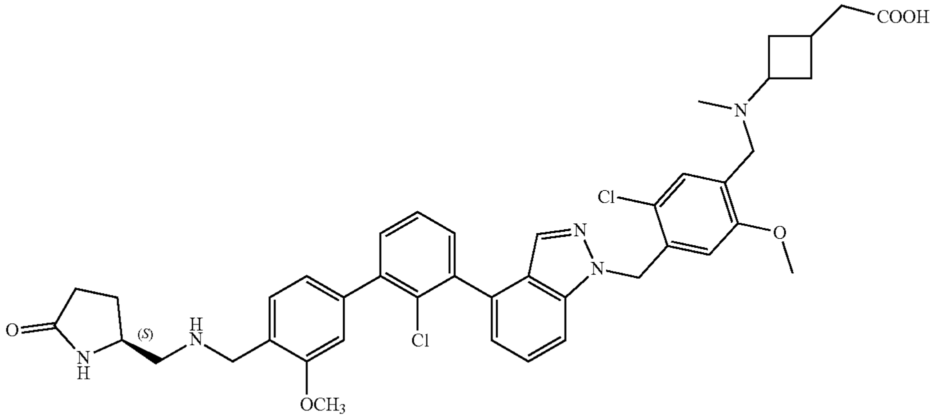

-continued
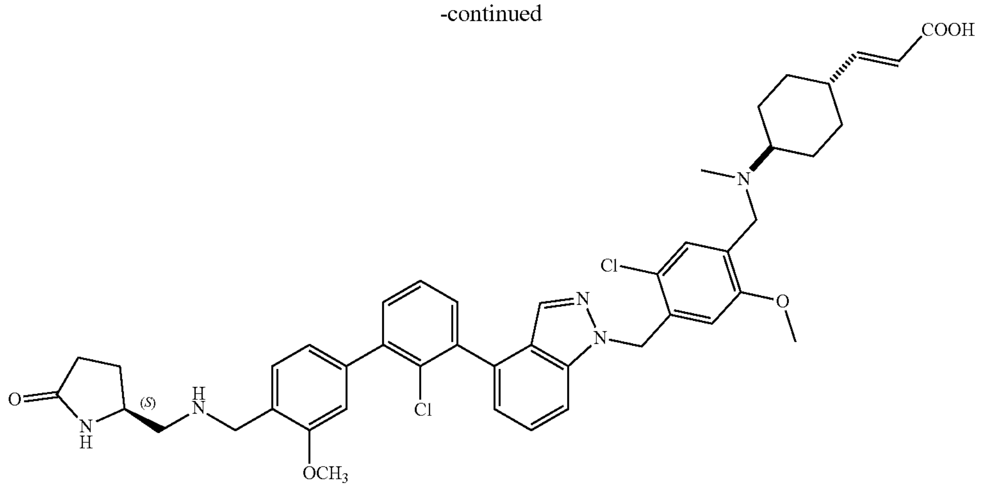
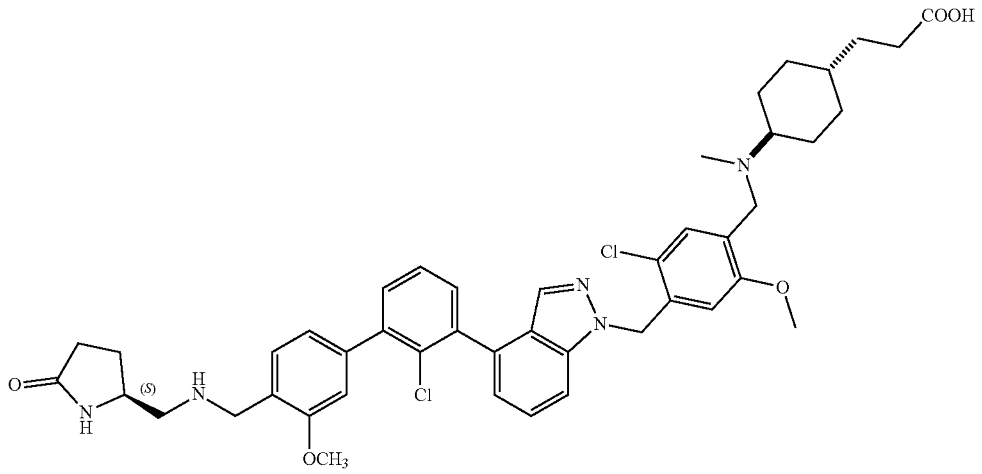
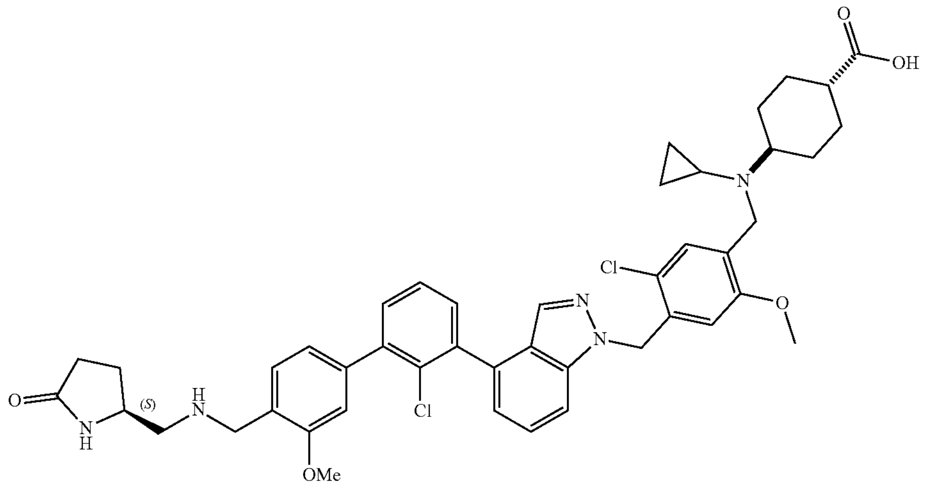

-continued
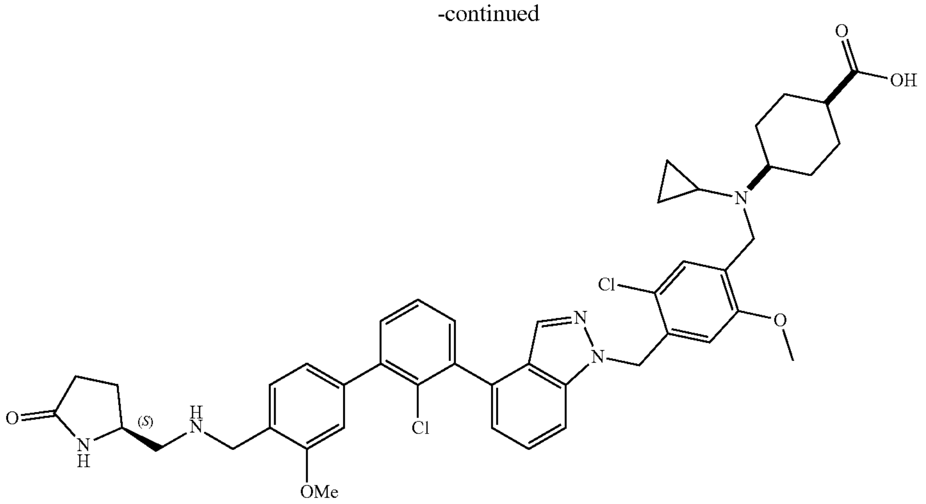
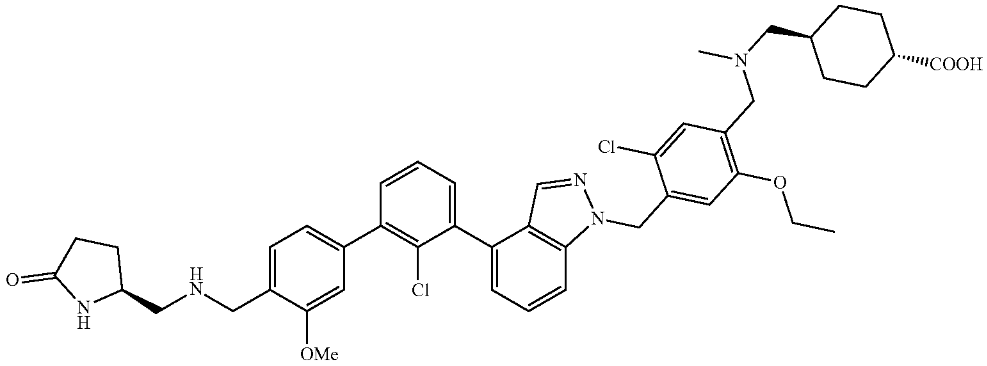
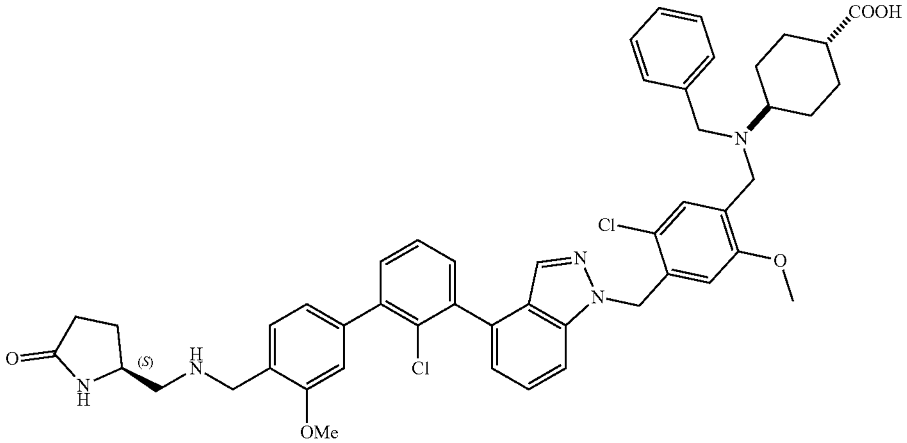
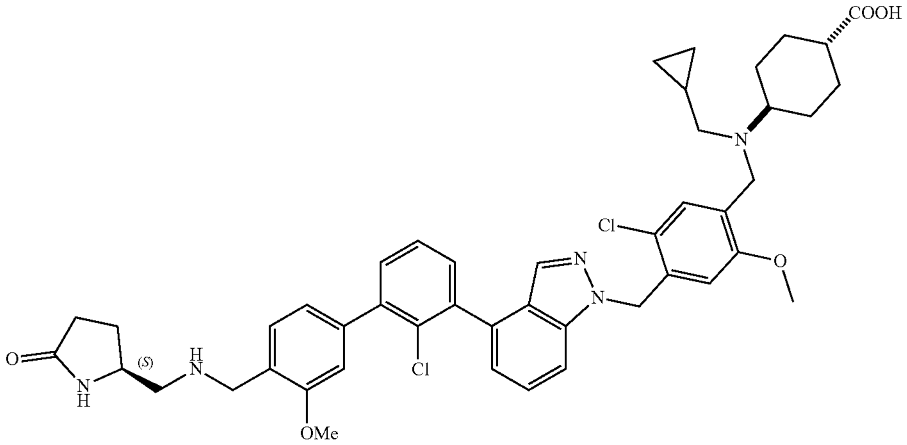

-continued
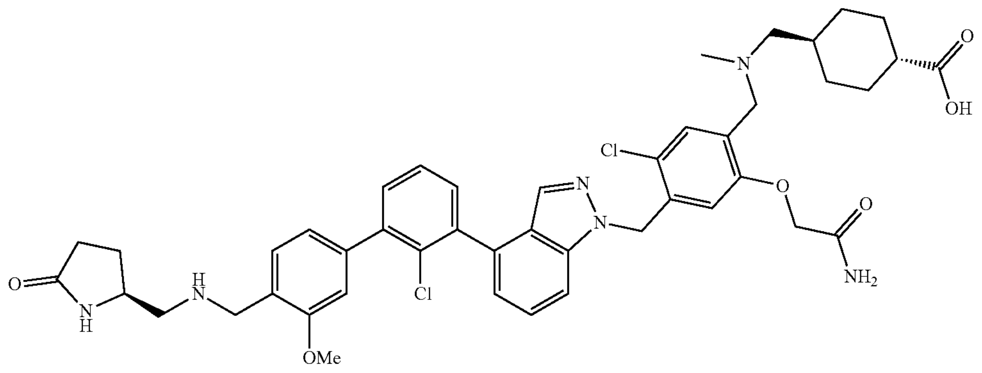
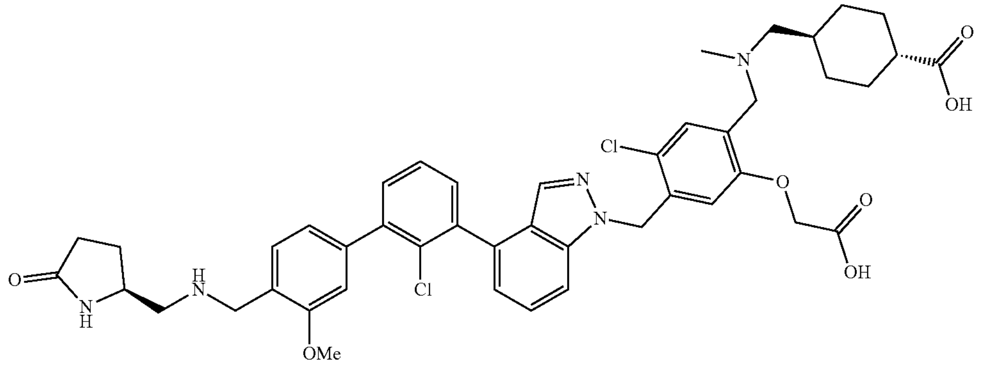
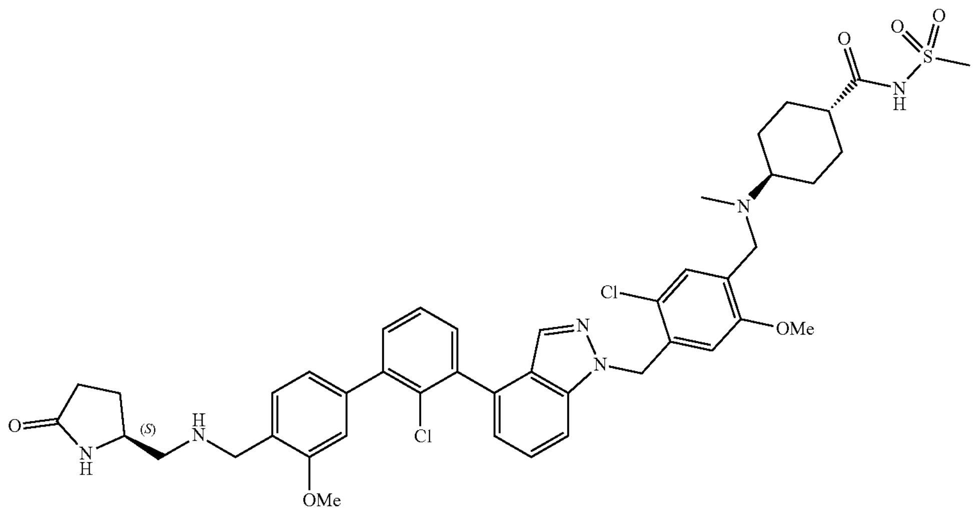
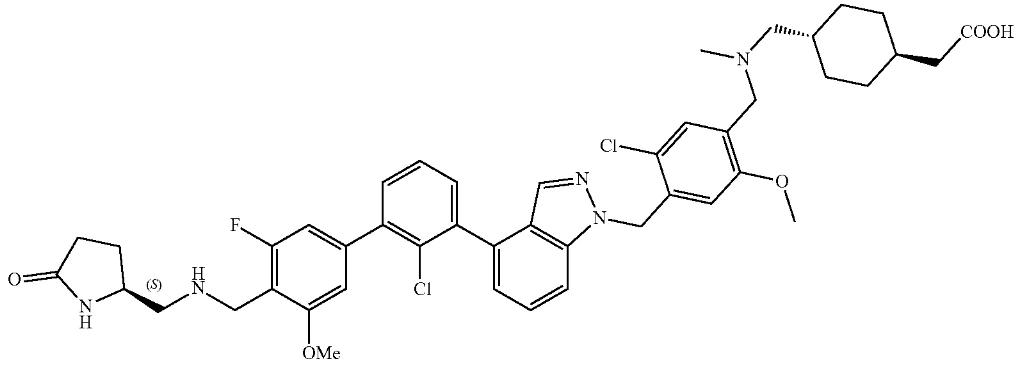

-continued
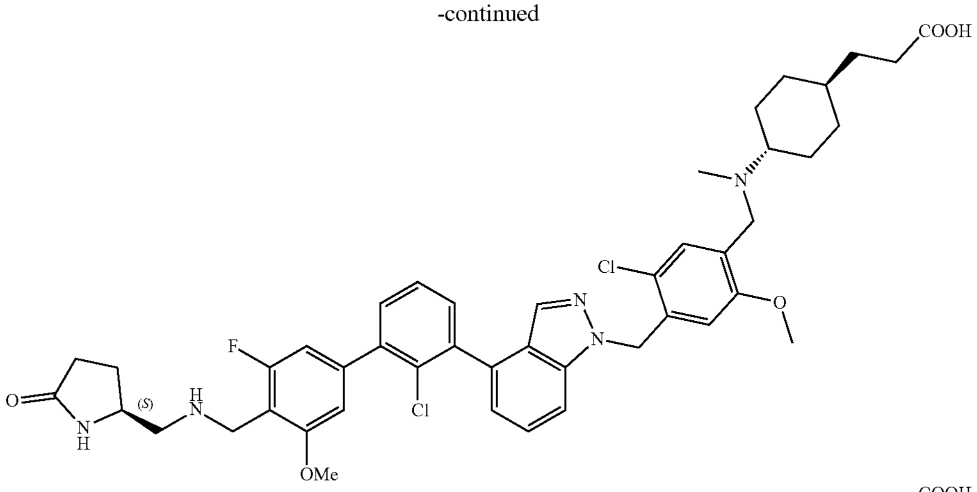
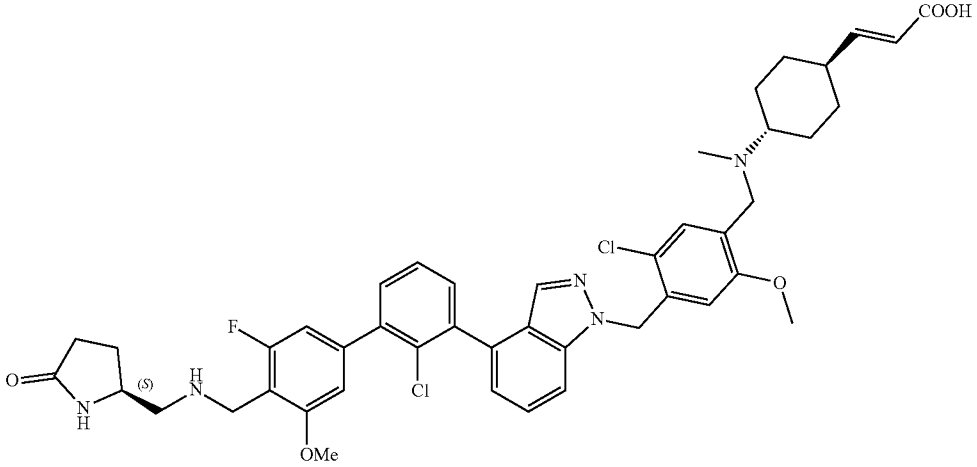
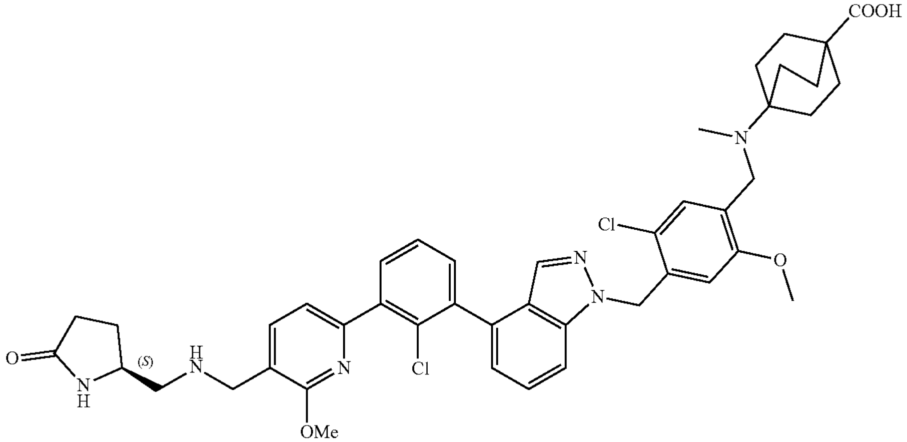
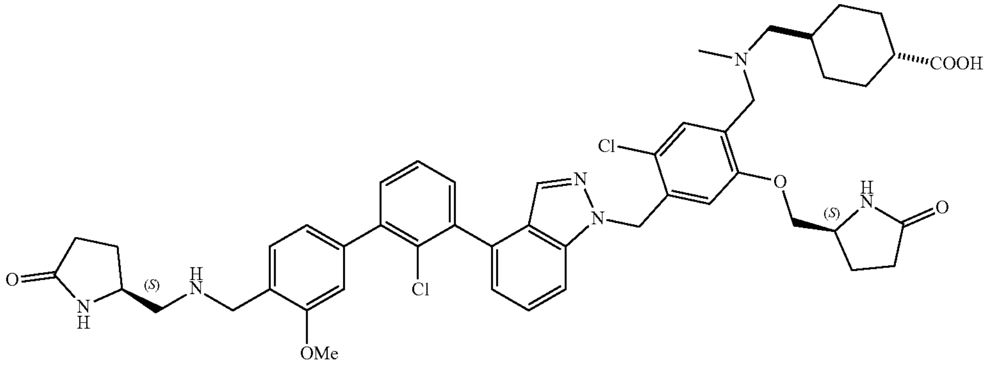

-continued
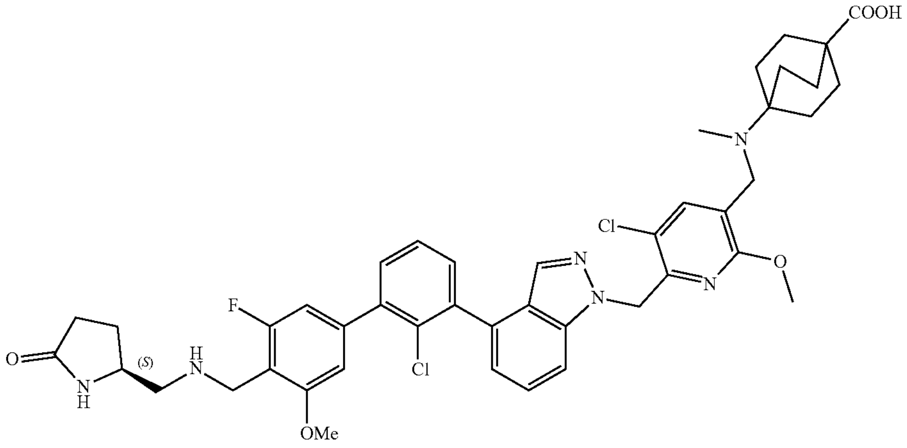
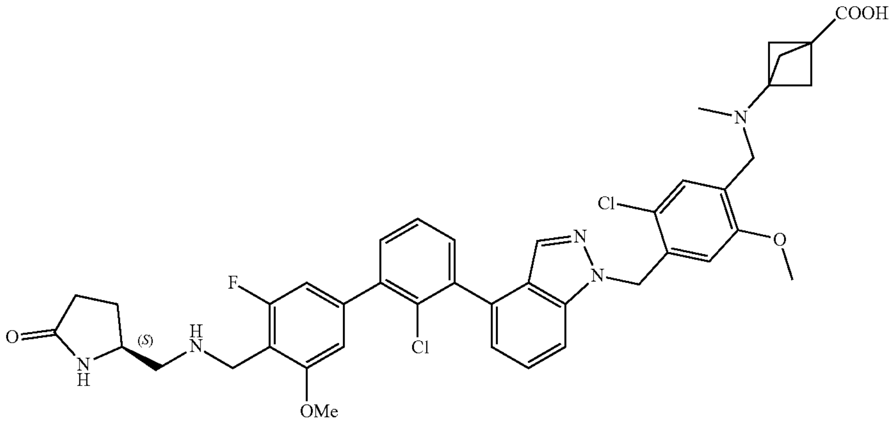
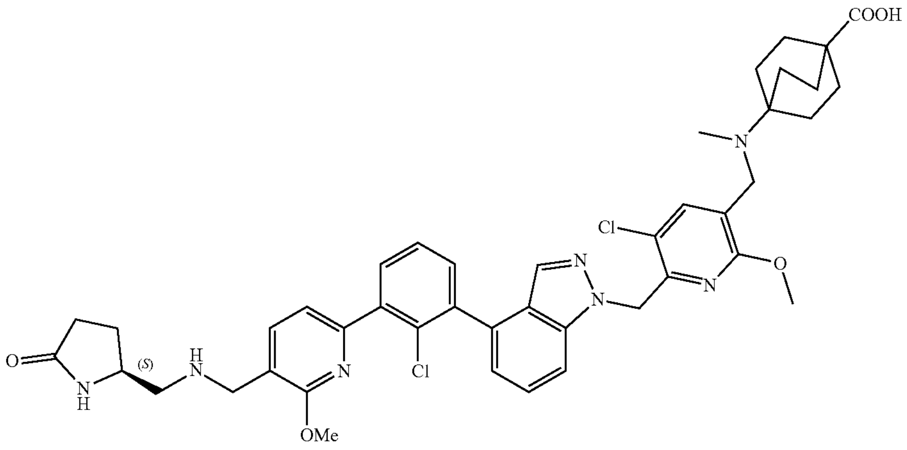

-continued
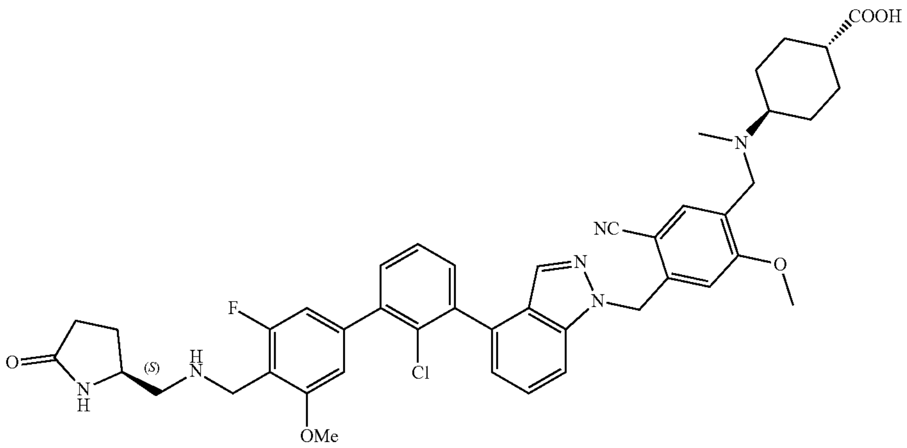
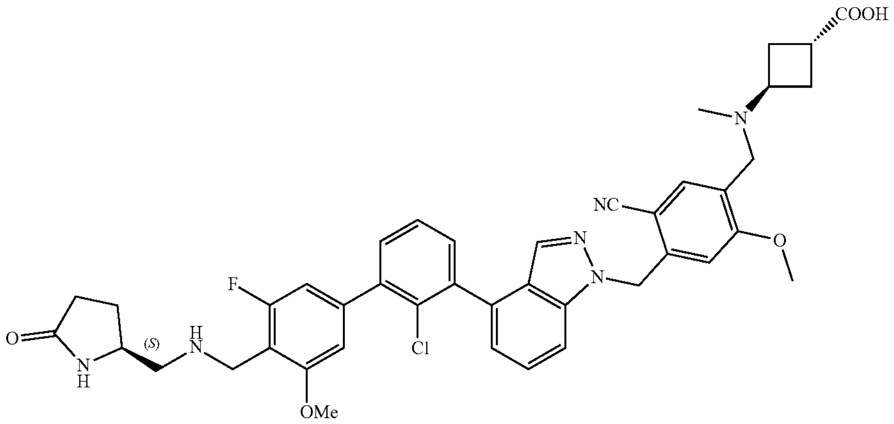
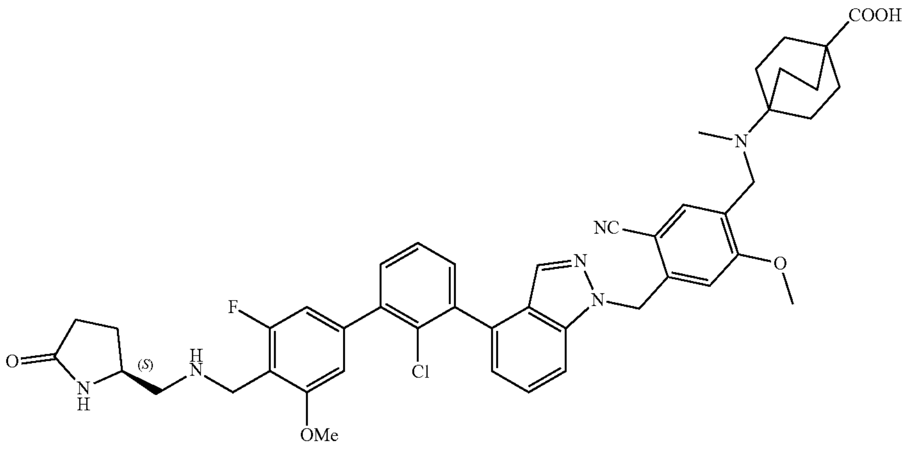

-continued
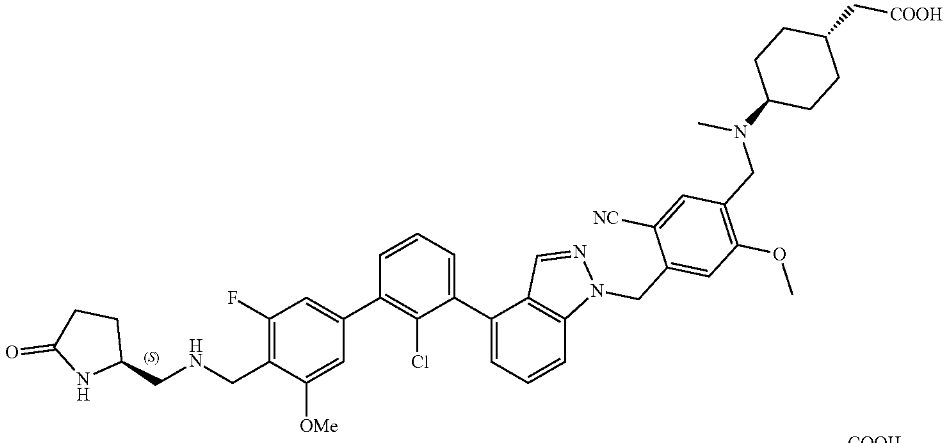
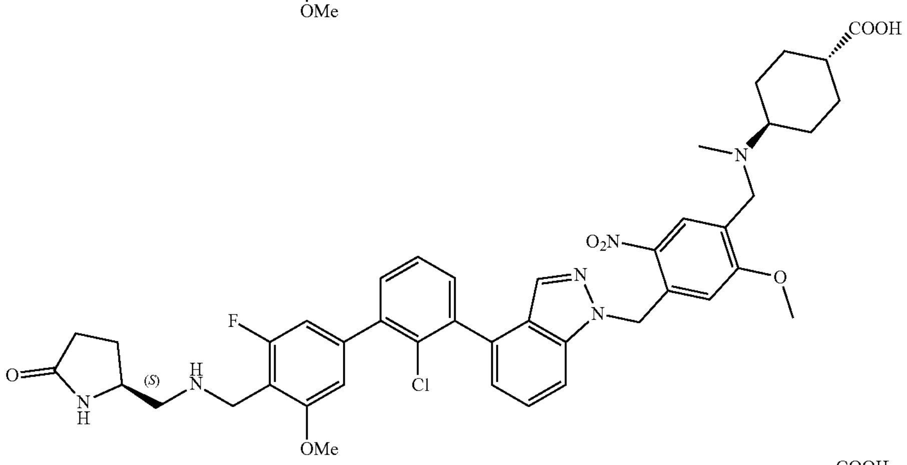
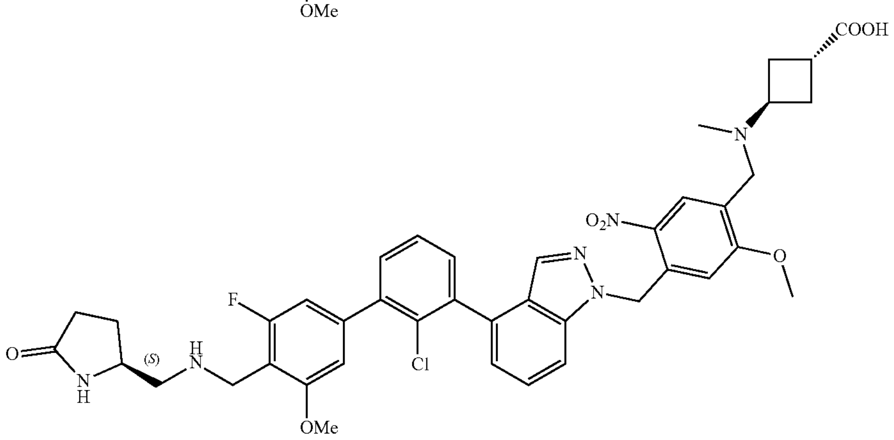
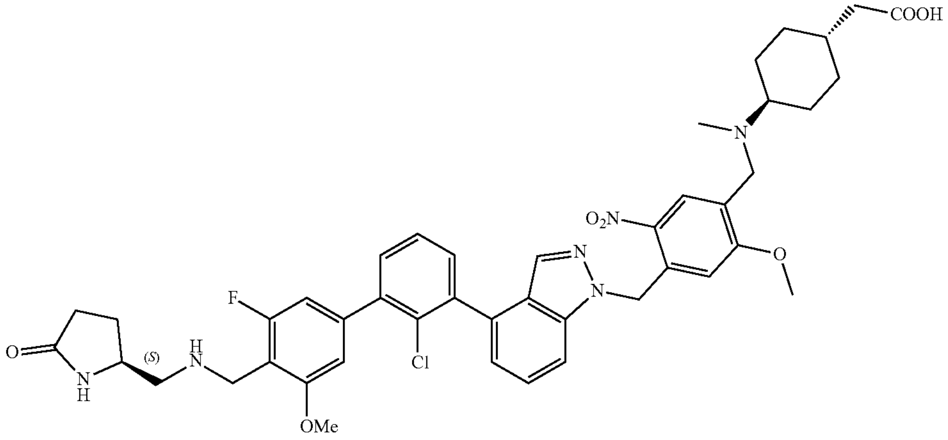

-continued
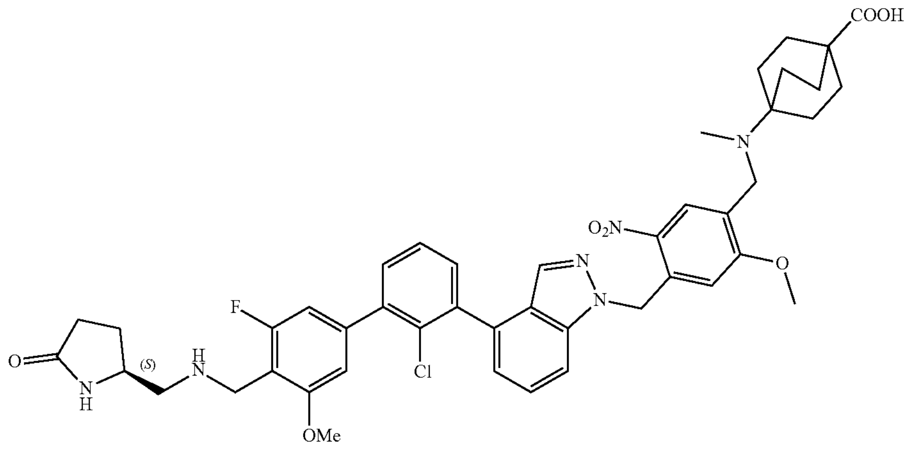
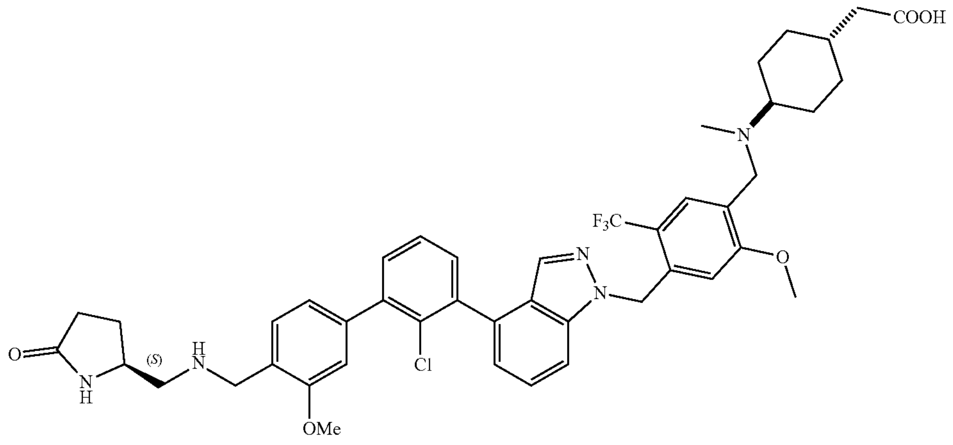
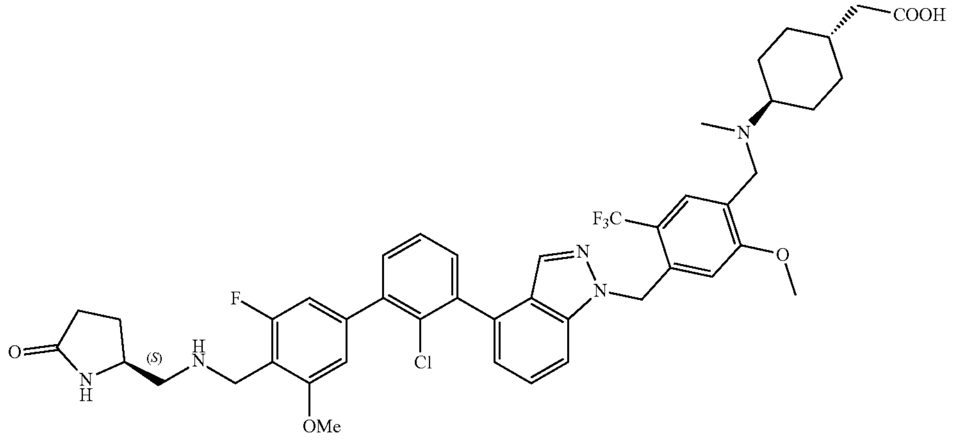

-continued
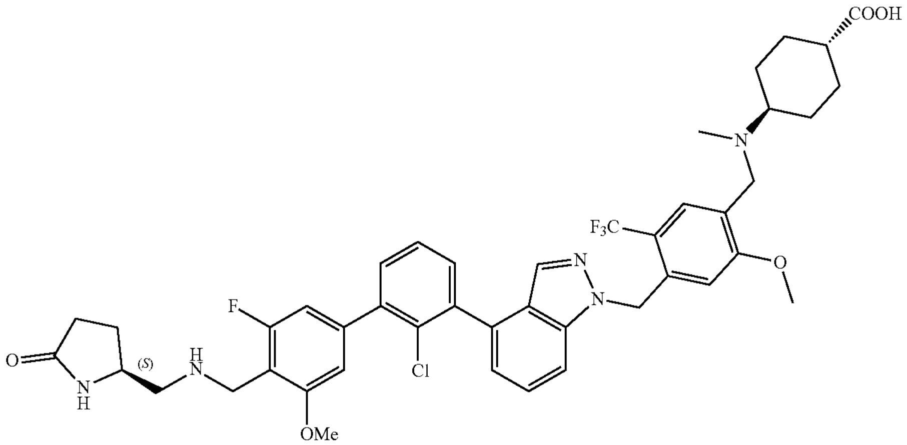
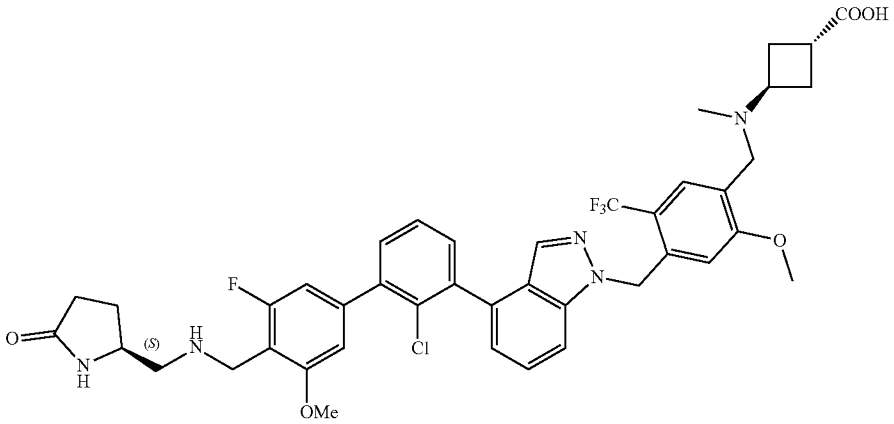
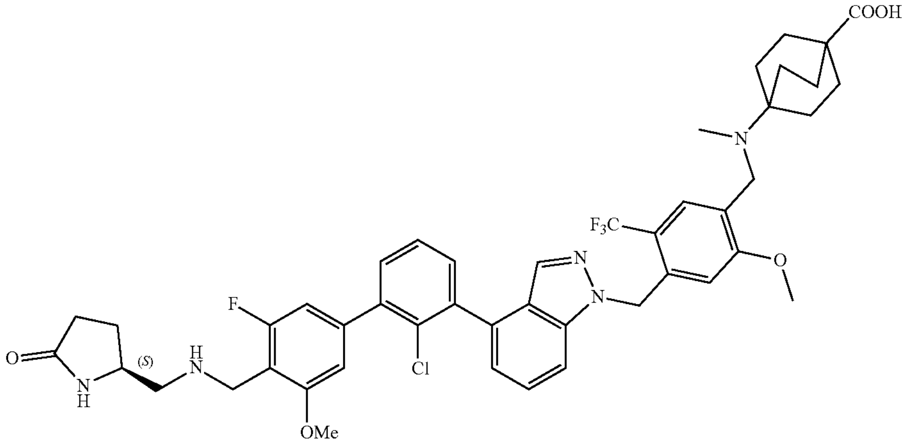

-continued
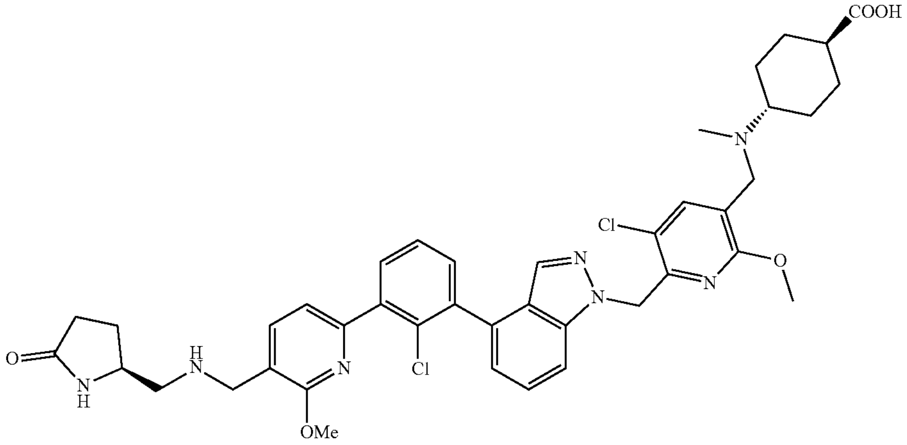
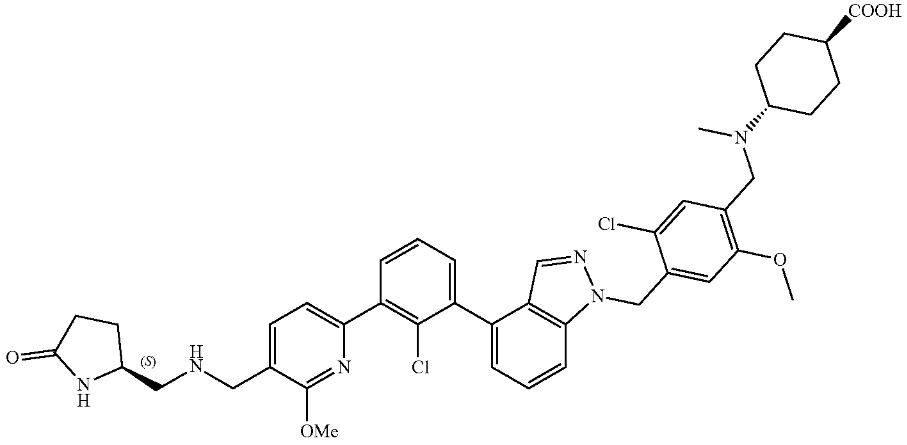
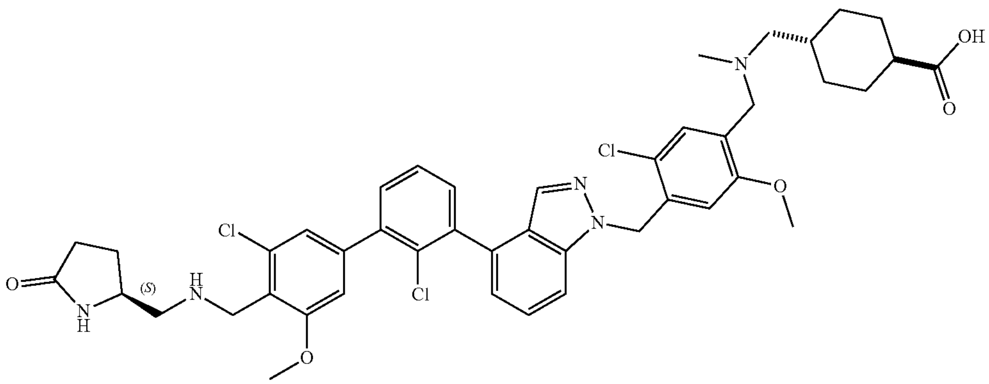
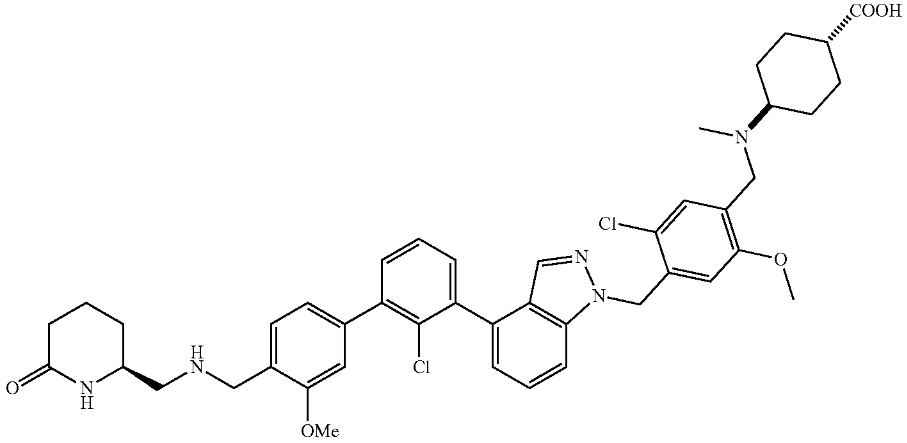

-continued
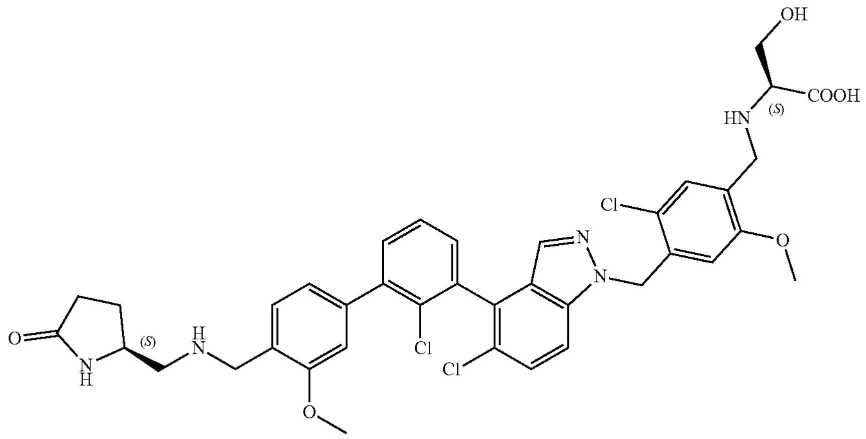
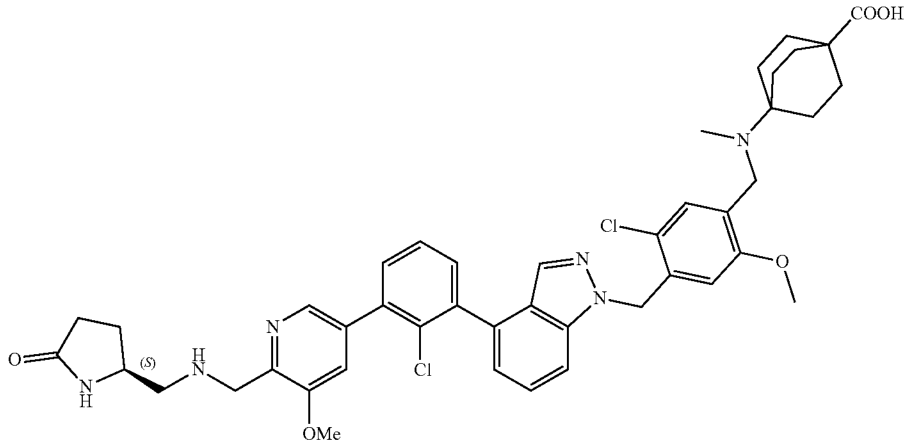
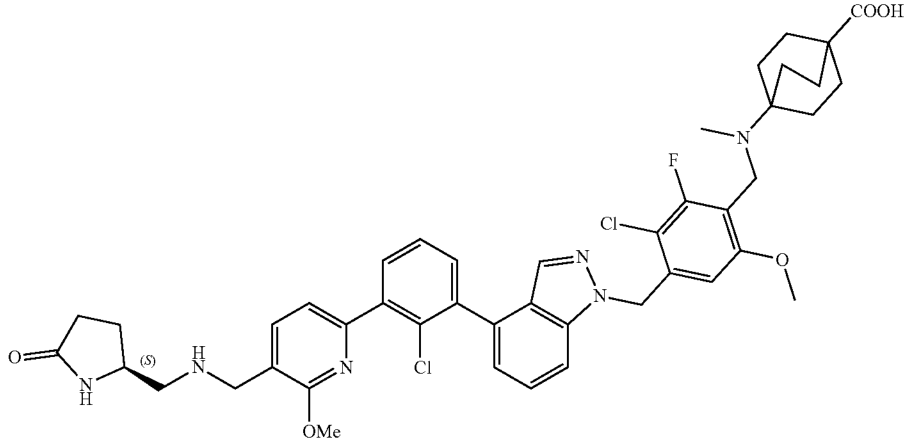

-continued
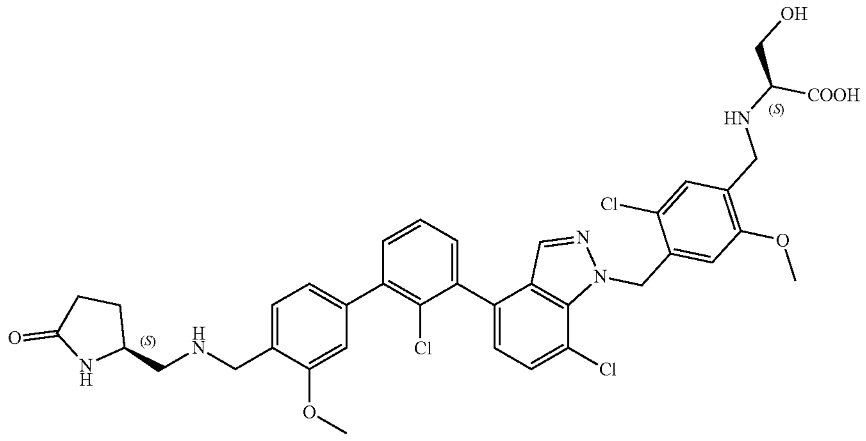
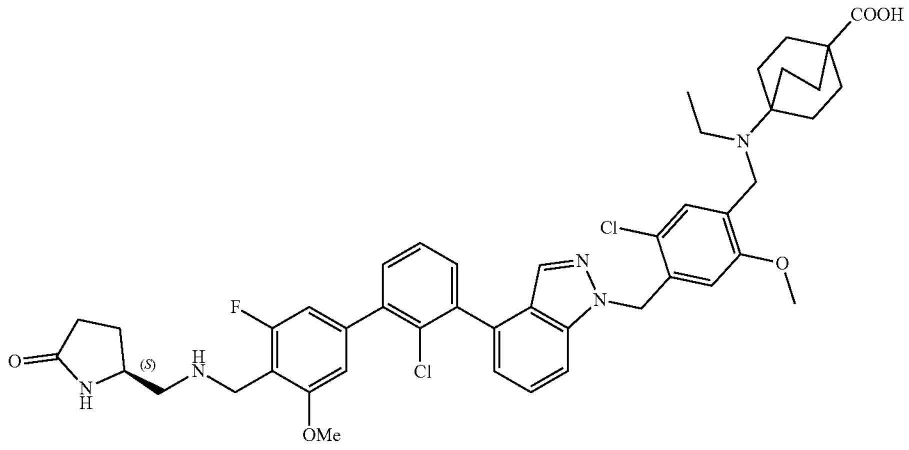
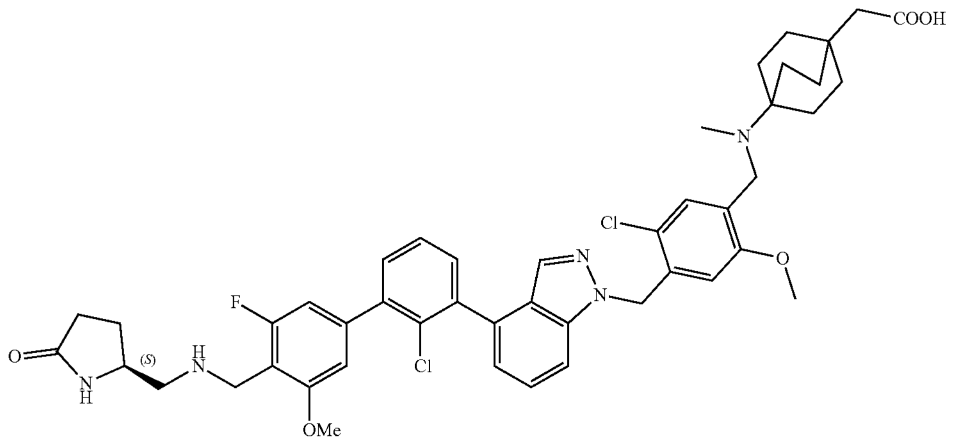

-continued
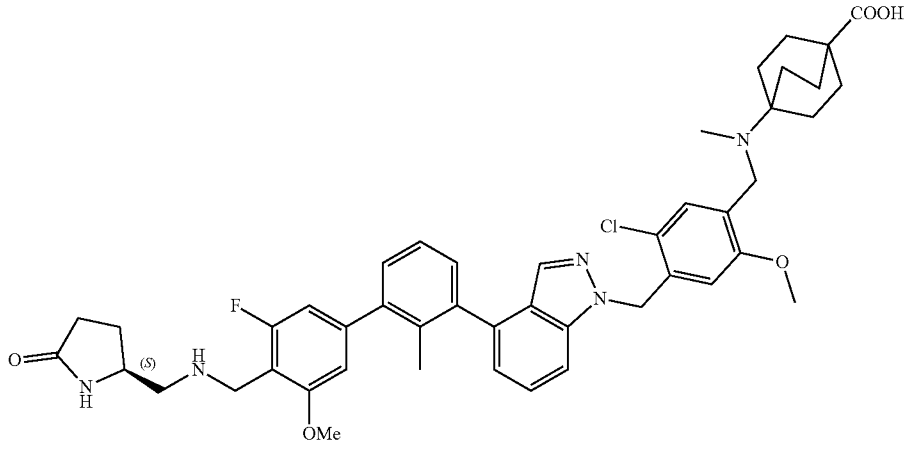
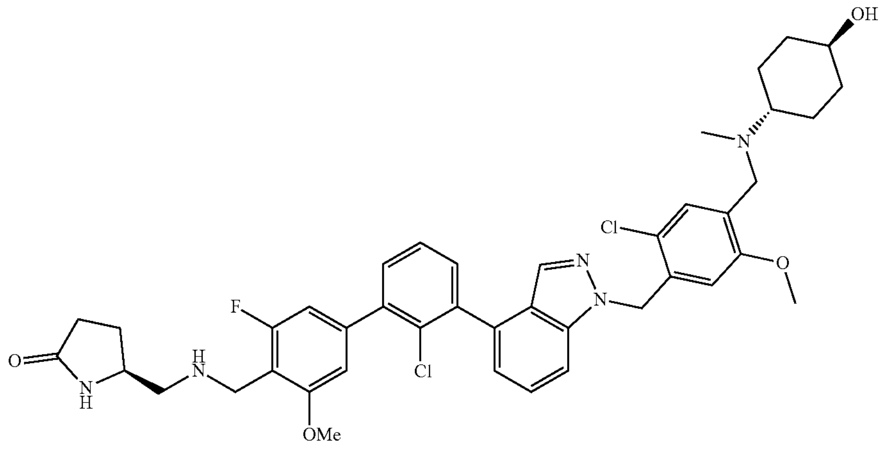
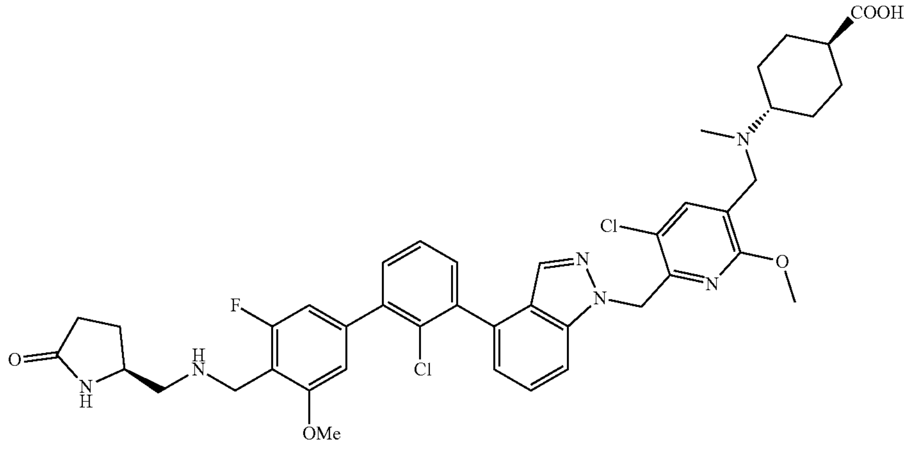

-continued
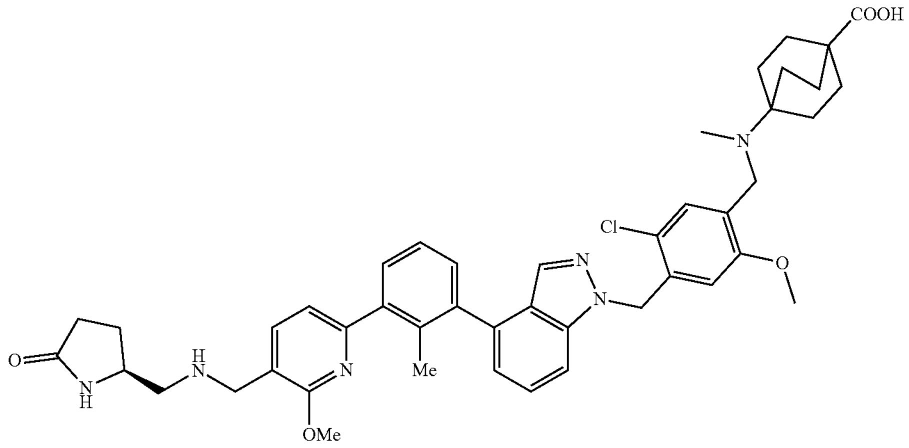
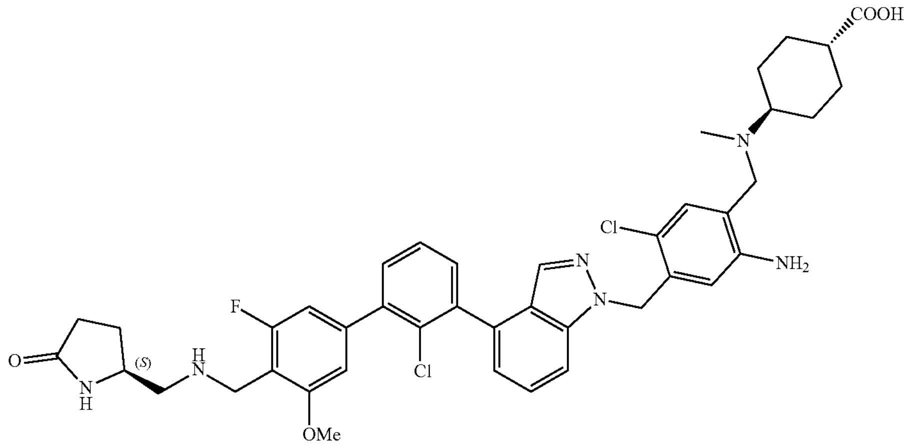
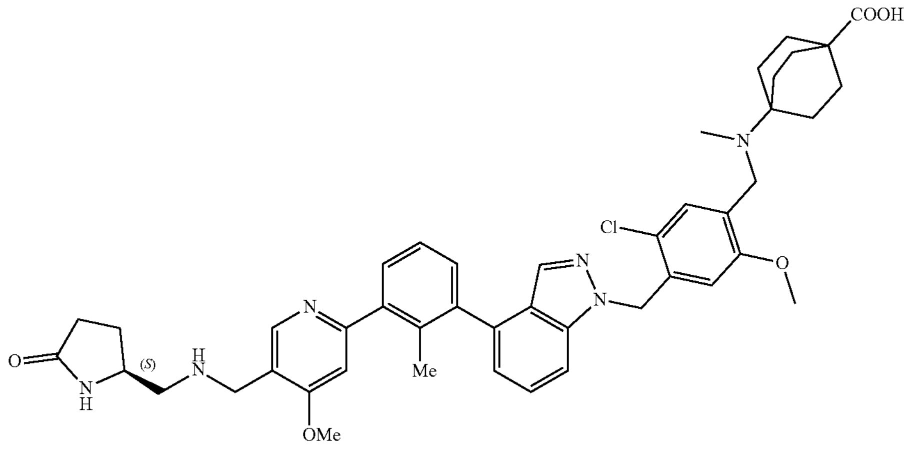

-continued
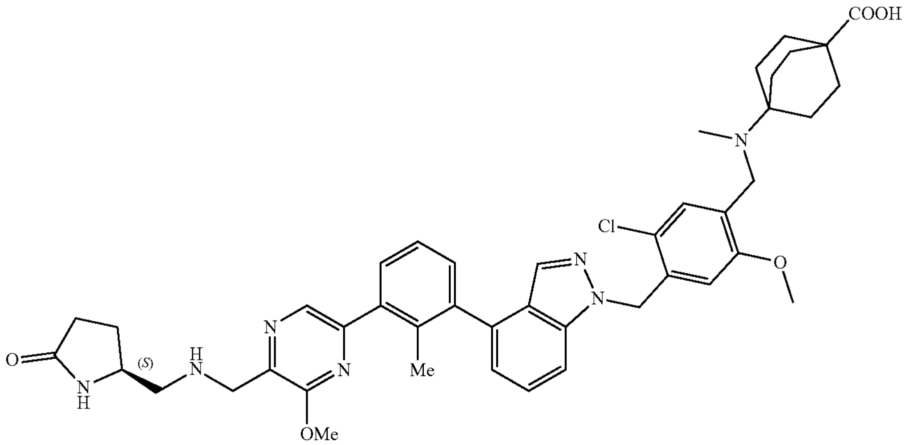
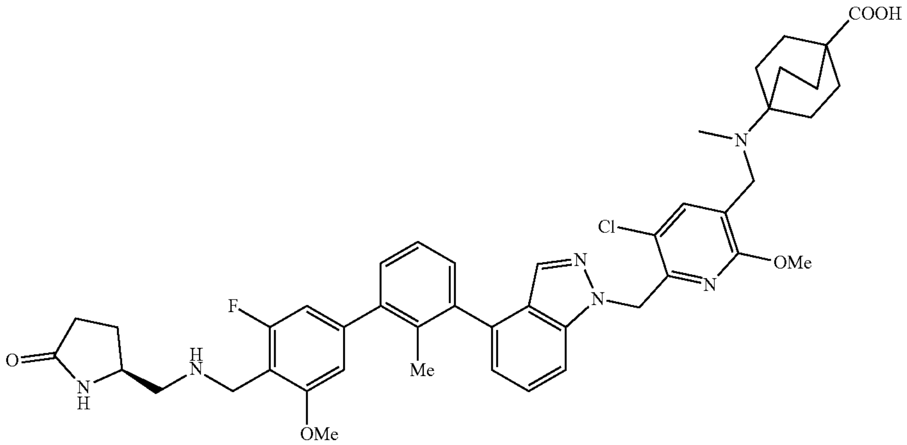
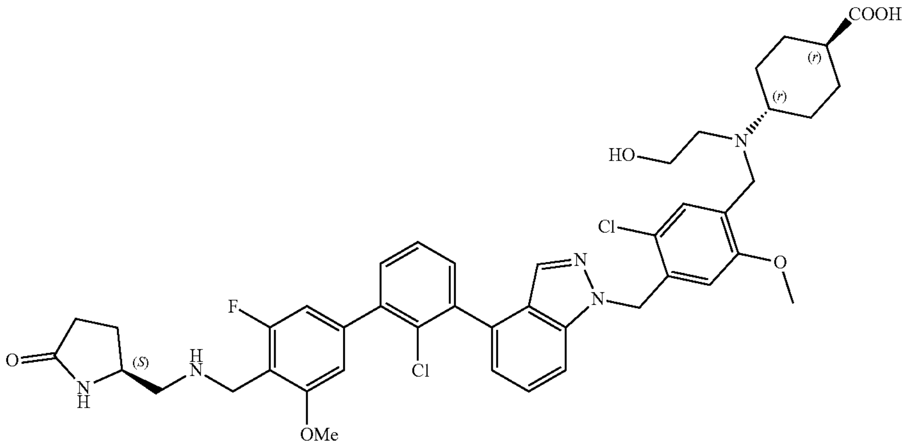

-continued
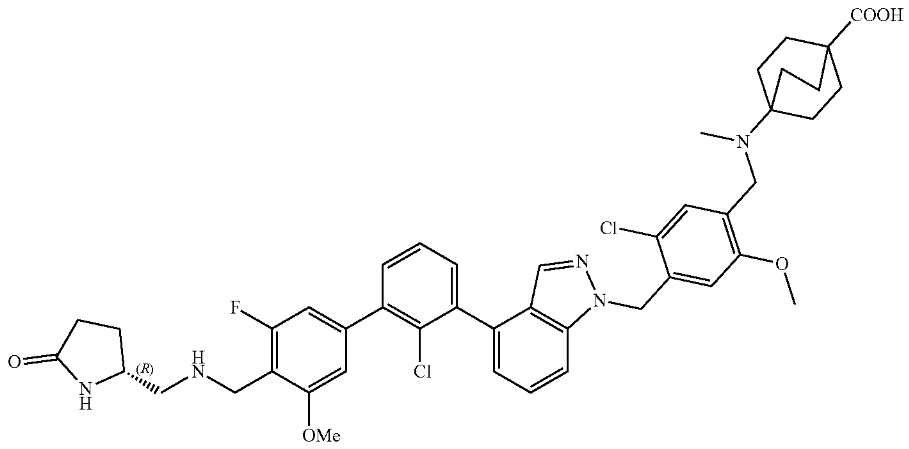
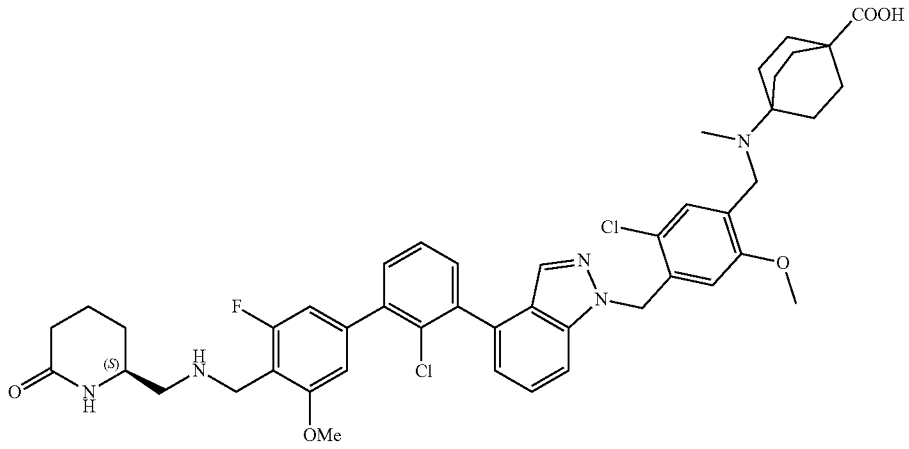

-continued
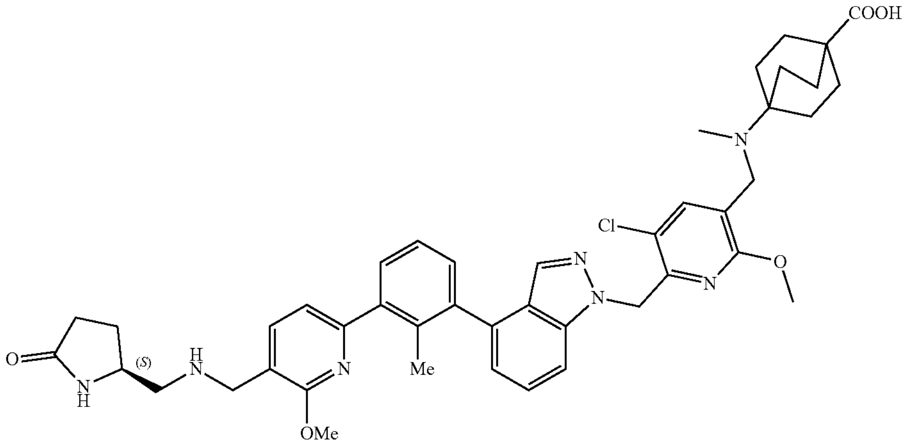
, and
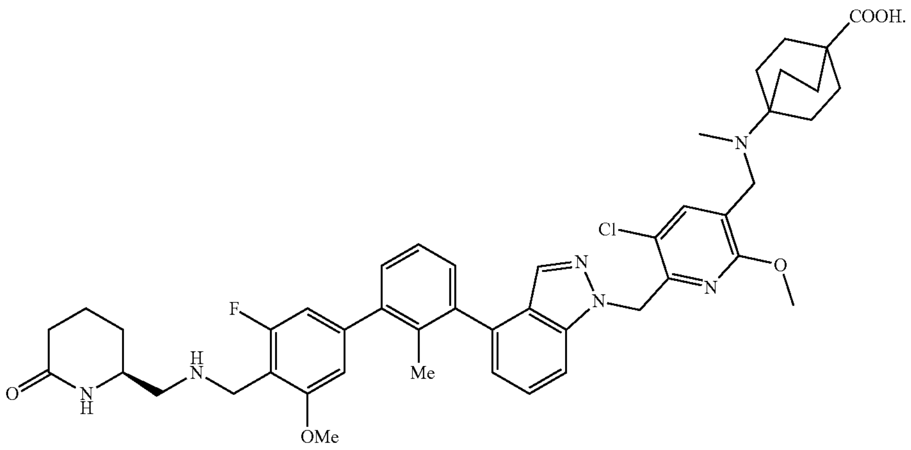 [SMILES: COc1cc(-c2cccc(-c3cccc4c3cnn4Cc3nc(OC)c(CN(C)C45CCC(C(=O)O)(CC4)CC5)cc3Cl)c2C)cc(F)c1CNC[C@@H]1CCCC(=O)N1]
.

19. A pharmaceutical composition, comprising an effective amount of a compound according to claim 1 and optionally a pharmaceutically acceptable carrier.

* * * * *